US012195805B2

(12) United States Patent
Faruki et al.

(10) Patent No.: US 12,195,805 B2
(45) Date of Patent: Jan. 14, 2025

(54) METHODS FOR SUBTYPING OF BLADDER CANCER

(71) Applicants: GeneCentric Therapeutics, Inc., Durham, NC (US); The University of North Carolina at Chapel Hill, Chapel Hill, NC (US)

(72) Inventors: Hawazin Faruki, Durham, NC (US); Greg Mayhew, Durham, NC (US); Myla Lai-Goldman, Durham, NC (US); Charles Perou, Carrboro, NC (US)

(73) Assignees: GeneCentric Therapeutics, Inc., Durham, NC (US); University of North Carolina at Chapel Hill, Chapel Hill, NC (US)

( * ) Notice: Subject to any disclaimer, the term of this patent is extended or adjusted under 35 U.S.C. 154(b) by 1079 days.

(21) Appl. No.: 16/969,304

(22) PCT Filed: Feb. 13, 2019

(86) PCT No.: PCT/US2019/017799
§ 371 (c)(1),
(2) Date: Aug. 12, 2020

(87) PCT Pub. No.: WO2019/160914
PCT Pub. Date: Aug. 22, 2019

(65) Prior Publication Data

US 2021/0054464 A1 Feb. 25, 2021

Related U.S. Application Data

(60) Provisional application No. 62/629,975, filed on Feb. 13, 2018.

(51) Int. Cl.
*C12Q 1/68* (2018.01)
*C12P 19/34* (2006.01)
*C12Q 1/6869* (2018.01)
*C12Q 1/6886* (2018.01)

(52) U.S. Cl.
CPC ......... *C12Q 1/6886* (2013.01); *C12Q 1/6869* (2013.01); *C12Q 2600/158* (2013.01)

(58) Field of Classification Search
CPC ................ C12Q 1/6869; C12Q 1/6886; C12Q 2600/112; C12Q 600/158
See application file for complete search history.

(56) References Cited

U.S. PATENT DOCUMENTS

| | | | |
|---|---|---|---|
| 4,483,155 | A | 11/1984 | Stiles |
| 4,683,202 | A | 7/1987 | Mullis |
| 5,384,261 | A | 1/1995 | Winkler et al. |
| 5,445,934 | A | 8/1995 | Fodor et al. |
| 5,677,195 | A | 10/1997 | Winkler et al. |
| 5,708,153 | A | 1/1998 | Dower et al. |
| 5,744,305 | A | 4/1998 | Fodor et al. |
| 5,770,358 | A | 6/1998 | Dower et al. |
| 5,770,722 | A | 6/1998 | Lockhart et al. |
| 5,789,162 | A | 8/1998 | Dower et al. |
| 5,800,992 | A | 9/1998 | Fodor et al. |
| 5,854,033 | A | 12/1998 | Lizardi |
| 5,856,174 | A | 1/1999 | Lipshutz et al. |
| 5,874,219 | A | 2/1999 | Rava et al. |
| 5,922,591 | A | 7/1999 | Anderson et al. |
| 6,020,135 | A | 2/2000 | Levine et al. |
| 6,033,860 | A | 3/2000 | Lockhart et al. |
| 6,040,138 | A | 3/2000 | Lockhart et al. |
| 6,040,193 | A | 3/2000 | Winkler et al. |
| 6,344,316 | B1 | 2/2002 | Lockhart et al. |
| 7,473,767 | B2 | 1/2009 | Dimitrov |
| 8,492,094 | B2 | 7/2013 | Dimitrov et al. |
| 2011/0143959 | A1 | 6/2011 | Nativ et al. |
| 2014/0295416 | A1 | 10/2014 | Zarbl et al. |
| 2015/0292030 | A1 | 10/2015 | McConkey et al. |
| 2016/0115551 | A1 | 4/2016 | Cowens |
| 2017/0044618 | A1 | 2/2017 | Ellis et al. |

FOREIGN PATENT DOCUMENTS

| | | | |
|---|---|---|---|
| WO | WO 2015/073949 | A1 | 5/2015 |
| WO | WO2017/201164 | A1 | 11/2017 |
| WO | WO2017/201165 | A1 | 11/2017 |

OTHER PUBLICATIONS

Wolfgang Enard, et al. "Intra- and Interspecific Variation in Primate Gene Expression Patterns" Science. Apr. 12, 2002; 296(5566):340-3. (Year: 2002).*
Extended European Search Report issued by the European Patent Office for Application No. 19755024.7, dated Oct. 27, 2021, 9 pages.
Mcconkey et al., Genetic subtypes of invasive bladder cancer, Curr Opin Urol 25(5):449-458 (2015).
Bibikova et al., "Quantitative gene expression profiling in formalin-fixed, paraffin-embedded tissues using universal bead arrays," Am J. Pathol 165:1799-1807 (2004).
Bindea et al., "Spatiotemporal dynamics of intratumoral immune cells reveal the immune landscape in human cancer," Immunity 39(4); 782-795 (2013).
Bolstad et al., "A comparison of normalization methods for high density oligonucleotide array data based on variance and bias," Bioinformatics Bioinformatics 19(2):185-193 (2003).
Brenner et al., "Gene expression analysis by massively parallel signature sequencing (MPSS) on microbead arrays," Nat. Biotech. 18:630-634 (2000).

(Continued)

*Primary Examiner* — Stephen T Kapushoc
(74) *Attorney, Agent, or Firm* — COOLEY LLP

(57) ABSTRACT

Methods and compositions are provided for determining a subtype of Muscle Invasive Bladder Cancer (MIBC) in an individual by detecting the expression level of at least one classifier biomarker selected from a group of gene signatures for MIBC. Also provided herein are methods and compositions for determining the response of an individual with a MIBC subtype to a therapy such as immunotherapy.

13 Claims, 27 Drawing Sheets

Specification includes a Sequence Listing.

(56) References Cited

OTHER PUBLICATIONS

Broomhead DS, Jones R, King GP., "Comment on Singular-value decomposition and embedding dimension," Phys Rev A Gen Phys. Jun. 15;37(12):5004-5005 (1988).
Carter, S. L. et al., "Absolute quantification of somatic DNA alterations in human cancer," Nat. Biotechnol. 30:413-421 (2012).
Charoentong, P., et al., "Pan-cancer Immunogenomic Analyses Reveal Genotype-Immunophenotype Relationships and Predictors of Response to Checkpoint Blockade," Cell Reports 18(1): 248-262 (2017).
Clark et al., "Suppression of nonspecific binding of avidin-biotin complex (ABC) to proteins electroblotted to nitrocellulose paper," J Histochem Cytochem 34:1509-1512 (1986).
Cronin et al., "Measurement of gene expression in archival paraffin-embedded tissues: development and performance of a 92-gene reverse transcriptase-polymerase chain reaction assay," Am. J Pathol. 164(1):35-42 (2004).
Dabney AR ClaNC: Point-and-click software for classifying microarrays to nearest centroids. Bioinformatics. 2006;22: 122-123.
Dabney, "Classification of microarrays to nearest centroids," Bioinformatics 21(22):4148-4154 (2005).
Faruki et al., "Lung Adenocarcinoma and Squamous Cell Carcinoma Gene Expression Subtypes Demonstrate Significant Differences in Tumor Immune Landscape," Journal of Thoracic Oncology 12(6):943-953 (2017).
Fishel and Kaufman et al., "Meta-analysis of gene expression data: a predictor-based approach," Bioinformatics 23(13): 1599-1606 (2007).
Fox et al., "Formaldehyde Fixation," J Histochem Cytochem 33:845-853 (1985).
Friedman et al., "Regularization Paths for Generalized Linear Models via Coordinate Descent," Journal of statistical software 33(1): 1-22 (2010).
Geiss et al., "Direct multiplexed measurement of gene expression with color-coded probe pairs," Nat. Biotechnol. 26:317-325 (2008).
Glaser et al. "APOBEC-mediated mutagenesis in urothelial carcinoma is associated with improved survival, mutations in DNA damage response genes, and immune response," Oncotarget 9(4):4537-4548 (2017).
Guatelli et al., "Isothermal, in vitro amplification of nucleic acids by a multienzyme reaction modeled after retroviral replication," Proc. Natl. Acad. Sci. USA 87:1874-1878 (1990).
Hoadley et al, "Cell-of-Origin Patterns Dominate the Molecular Classification of 10,000 Tumors from 33 Types of Cancer," Cell 173(2):291-304 (2018).
International Search Report and Written Opinion issued by the International Searching Authority for Application No. PCT/US2019/017799, dated Jul. 3, 2019, 12 pages.
Irizarry et al., "Exploration, normalization, and summaries of high density oligonucleotide array probe level data," Biostatistics April 4(2): 249-64 (2003).
Krupenko et al. "Chapter 11: ALDH1L1 and ALDH1L2 Folate Regulatory Enzymes in Cancer," AEMB:Alcohol and Cancer 103:127-143 (2018).
Kwoh et al., "Transcription-based amplification system and detection of amplified human immunodeficiency virus type 1 with a bead-based sandwich hybridization format," Proc. Natl. Acad. Sci. USA 86:1173-77 (1989).
Landergren et al., "A Ligase-Mediated Gene Detection Technique," Science 241:1077-1080 (1988).
Martin, M., et al., "PAM50 proliferation score as a predictor of weekly paclitaxel benefit in breast cancer," Breast Cancer Res Treat 138:457-466 (2013).
Mayhew et al. "Abstract 4538: Bladder cancer gene expression subtypes (60 gene signature) to define prognosis, differential immune response, and biomarker associations," Journal of Clinical Oncology 36(15):4538-4838 (2018).
McGhee and von Hippel, "Formaldehyde as a probe of DNA structure. II. Reaction with endocyclic amino groups of DNA bases," Biochemistry 14:1281-1296 (1975).
Mullins et al., "Agreement in breast cancer classification between microarray and quantitative reverse transcription PCR from fresh-frozen and formalin-fixed, paraffin-embedded tissues," Clin Chem. 53(7):1273-1279 (2007).
Paolillo et al., "Small molecule integrin antagonists in cancer therapy," Mini Rev Med Chem 12:1439-1446 (2009).
Parzen, "On Estimation of a Probability Density Function and Mode," Stanford University, 1065-1076 (1962).
Quinlan, "Induction of Decision Trees," Machine Learning 1(1):81-106 (1986).
Robertson, AG, et al., "Comprehensive molecular characterization of muscle invasive bladder cancer," Cell, 171(3): 540-556 (2017).
Robin et al., "pROC: an open source package for R and S+ to analyze and compare ROC curves," BMC bioinformatic 12:77 (2011), 8 pages.
Rouskin et al., "Genome-wide probing of RNA structure reveals active unfolding of mRNA structures in vivo," Nature 505, pp. 701-705 (2014).
Seiler, R., et al., "Impact of Molecular Subtypes in Muscle-invasive Bladder Cancer on Predicting Response and Survival after Neoadjuvant Chemotherapy," Eur Urol 72(4):544-554 (2017).
Sjodahl, G., et al., "A Molecular Taxonomy for Urothelial Carcinoma," Clin Cancer Res, 18(12):3377-3386 (2012).
Smyth, G. K., Limma: linear models for microarray data. In: Bioinformatics and Computational Biology Solutions using Rand Bioconductor, R. Gentleman, V. Carey, S. Dudoit, R.Irizarry, W. Huber (eds.), Springer, New York, pp. 397-420 (2005).
Smyth, G. K., "Linear Models and Empirical Bayes Methods for Assessing Differential Expression in Microarray Experiments," Stat. Appl. Genet. Mol. Biol. 3: Article 3 (2004), 28 pages.
Suykens JAK, Vandewalle J., "Least Squares Support Vector Machine Classifiers," Neural Processing Letters 9(3): 293-300 (1999).
Szumilas, "Explaining odds ratios," J. Can. Acad. Child Adolesc. Psychiatry 19(3): 227-229 (2010).
The Cancer Genome Atlas Research Network, "Comprehensive molecular characterization of urothelial bladder carcinoma," Nature, 507(492): 315-22 (2014).
Thorsson, V. et al., "The immune landscape of cancer," Immunity, 48(4), pp. 812-830 (2018).
Tibshirani et al., "Diagnosis of multiple cancer types by shrunken centroids of gene expression," Proc. Natl. Acad. Sci. USA 99(10):6576-6572 (2002).
Trapnell et al., "TopHat: discovering splice junctions with RNA-Seq.," Bioinformatics 25(9):1105-1111 (2009).
Velculescu et al., "Serial analysis of gene expression," Science 270(5235):484-487 (1995).
Wold, et al., "Genome expression and mRNA maturation at late stages of productive adenovirus type 2 infection," J Virol. Nov. 1976;20(2):465-77.
Wu and Wallace, "The ligation amplification reaction (LAR)—amplification of specific DNA sequences using sequential rounds of template dependent ligation.," Genomics, 4(4):560-569 (1989).

* cited by examiner

FIG. 1
Gold standard (GS) subtype distribution (n=408)
| I | II | III | IV | Sum |
|---|---|---|---|---|
| 132 | 95 | 110 | 71 | 408 |
GS sil vs GS subtype (n=408), solid when sample is in 2014 data used to fit gold standard subtyper
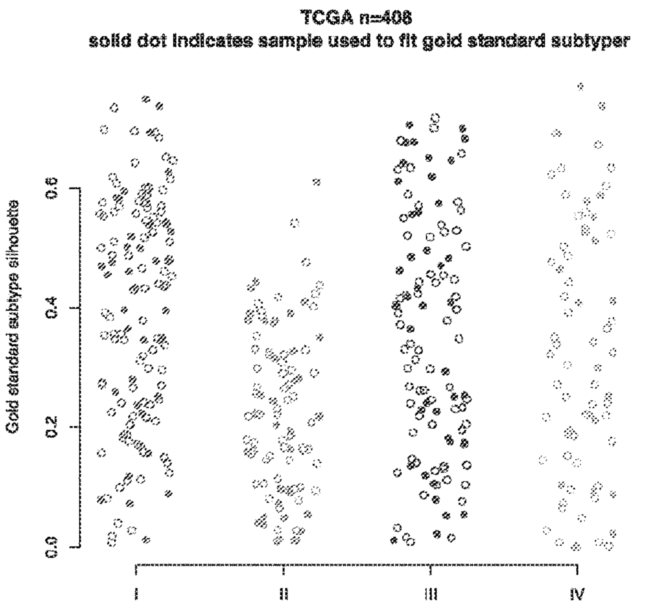
Nature 2014 cluster assignment (rows) vs gold standard subtype (columns), (n=129) agreement: 0.87
| | I | II | III | IV | Sum |
|---|---|---|---|---|---|
| I | 35 | 1 | 5 | 0 | 41 |
| II | 2 | 31 | 5 | 4 | 42 |
| III | 0 | 0 | 31 | 0 | 31 |
| IV | 0 | 0 | 0 | 15 | 15 |
| Sum | 37 | 32 | 41 | 19 | 129 |
GS sil vs GS subtype (n=129), solid when doesn't match Nature 2014 cluster assignment
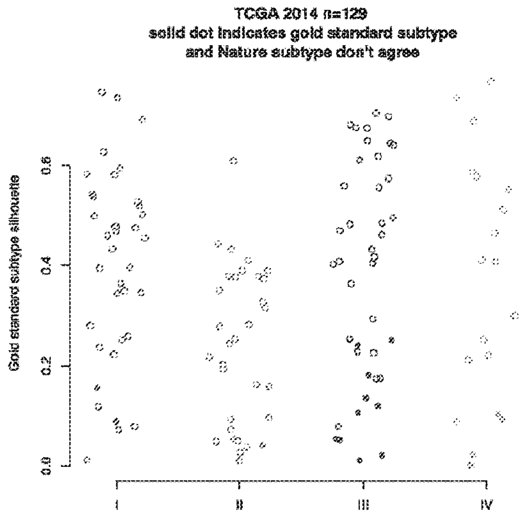

Gold Standard subtype (rows) vs. clanc (60) subtype (columns), agreement: 0.87

| | I | II | III | IV | Sum |
|---|---|---|---|---|---|
| I | 121 | 8 | 3 | 0 | 132 |
| II | 10 | 72 | 5 | 8 | 95 |
| III | 1 | 0 | 106 | 3 | 110 |
| IV | 0 | 6 | 11 | 54 | 71 |
| Sum | 132 | 86 | 125 | 65 | 408 |

TCGA 2017 n=408
Solid dot indicates gold standard subtype and clanc subtype don't agree

FIG. 6

| | I | II | III | IV | | | I | II | III | IV |
|---|---|---|---|---|---|---|---|---|---|---|
| ALDH1L2 | -2.95 | 0.51 | 0.59 | 1.31 | | LMOD1 | -1.31 | 2.77 | -0.22 | 0.96 |
| ANXA6 | -2.00 | 0.64 | 0.09 | 1.66 | | LOC100188947 | 3.20 | 2.48 | -3.88 | -4.38 |
| ARSI | -3.67 | 0.42 | 1.72 | 1.23 | | MRVI1 | -1.19 | 1.65 | -0.15 | 0.54 |
| BCAS1 | 1.88 | 1.10 | -3.83 | -5.58 | | NRP2 | -2.34 | 0.40 | 0.62 | 1.43 |
| BNC1 | -1.48 | -0.57 | 7.97 | 2.24 | | PDLIM3 | -2.49 | 1.95 | 0.33 | 1.51 |
| C10orf99 | 1.69 | 1.15 | -1.26 | -7.80 | | PLA2G4F | 1.13 | 0.24 | -0.66 | -4.12 |
| C17orf28 | 0.80 | 0.61 | -3.52 | -2.18 | | PODN | -3.54 | 1.82 | -0.72 | 1.20 |
| CAPN5 | 1.17 | 1.17 | -2.49 | -1.86 | | POSTN | -4.38 | 1.37 | 0.46 | 1.42 |
| CCDC80 | -3.08 | 1.14 | 0.43 | 1.87 | | PRRX1 | -3.33 | 0.94 | 0.50 | 2.06 |
| COL6A2 | -2.25 | 1.10 | 0.36 | 2.02 | | PVRL4 | 0.49 | 0.36 | -0.39 | -2.97 |
| CPXM2 | -2.14 | 1.78 | -0.13 | 1.70 | | RAPGEFL1 | 1.01 | 0.10 | -0.43 | -3.66 |
| CTHRC1 | -3.30 | 0.61 | 0.64 | 1.15 | | RHOU | 0.59 | 1.22 | -2.78 | -1.70 |
| DSG3 | -2.16 | -1.59 | 7.87 | -1.24 | | RHOV | -0.17 | 0.20 | 0.89 | -2.93 |
| EMILIN1 | -1.96 | 1.86 | -0.20 | 1.84 | | SCUBE2 | 1.29 | 3.00 | -3.51 | -1.86 |
| EPN3 | 0.61 | 0.45 | -0.73 | -2.60 | | SDC1 | 0.39 | 0.13 | -0.01 | -2.41 |
| EVPL | 0.51 | 0.48 | -0.65 | -2.53 | | SERPINB13 | -0.64 | -2.10 | 5.68 | -2.94 |
| FAP | -3.87 | 0.94 | 0.84 | 1.46 | | SFRP2 | -6.65 | 2.50 | 0.68 | 1.68 |
| FBN1 | -2.47 | 1.02 | 0.22 | 1.82 | | SFRP4 | -5.67 | 3.09 | 0.38 | 2.19 |
| FGF7 | -2.23 | 1.98 | 0.12 | 1.44 | | SLC30A2 | 2.17 | 3.26 | -4.60 | -3.18 |
| FMO9P | 2.37 | 3.22 | -3.99 | -5.26 | | SMOC2 | -1.41 | 2.14 | -0.44 | 1.00 |
| FNDC1 | -4.02 | 2.05 | 0.42 | 2.44 | | SNX31 | 1.40 | 2.05 | -6.48 | -7.24 |
| GABBR2 | 0.63 | 5.25 | -2.87 | -0.72 | | SPRR2A | -1.49 | -0.32 | 5.64 | -1.95 |
| GFPT2 | -4.37 | 0.83 | 0.74 | 1.95 | | SSC5D | -2.38 | 1.82 | 0.09 | 1.78 |
| GGT6 | 1.18 | 0.33 | -2.23 | -5.61 | | TBX3 | 1.48 | 0.55 | -3.24 | -2.08 |
| GREM1 | -5.82 | 1.63 | 0.66 | 0.80 | | TLE2 | 0.96 | 0.69 | -2.92 | -1.06 |
| GRHL3 | 1.02 | 1.46 | -1.39 | -6.23 | | TOX3 | 2.44 | 2.08 | -6.52 | -5.74 |
| IL20RB | -0.89 | -0.97 | 4.28 | -0.59 | | UPK1A | 1.94 | 2.82 | -5.92 | -6.97 |
| KRT6A | -2.15 | -2.48 | 7.61 | -0.59 | | UPK2 | 1.85 | 2.45 | -5.94 | -6.04 |
| KRT6B | -1.53 | -2.24 | 7.55 | -0.39 | | UPK3A | 1.88 | 3.61 | -5.63 | -4.89 |
| KRT6C | -1.76 | -2.57 | 7.25 | -1.05 | | ZNF750 | -0.07 | 0.52 | 0.82 | -3.97 |

FIG. 14

| subtype (rows) vs mutation.in.RB1 (columns) | | | |
|---|---|---|---|
| | no | yes | Sum |
| I | 122(0.92) | 10(0.08) | 132(1) |
| II | 72(0.84) | 14(0.16) | 86(1) |
| III | 98(0.78) | 27(0.22) | 125(1) |
| IV | 46(0.71) | 19(0.29) | 65(1) |
| Sum | 338(0.83) | 70(0.17) | 408(1) |
| Fisher test p-value: 0.0005 | | | |

| subtype (rows) vs mutation.in.FGFR3 (columns) | | | |
|---|---|---|---|
| | no | yes | Sum |
| I | 93(0.7) | 39(0.3) | 132(1) |
| II | 81(0.94) | 5(0.06) | 86(1) |
| III | 114(0.91) | 11(0.09) | 125(1) |
| IV | 63(0.97) | 2(0.03) | 65(1) |
| Sum | 351(0.86) | 57(0.14) | 408(1) |
| Fisher test p-value: 1e-05 | | | |

| subtype (rows) vs mutation.in.ERBB2 (columns) | | | |
|---|---|---|---|
| | no | yes | Sum |
| I | 116(0.88) | 16(0.12) | 132(1) |
| II | 80(0.93) | 6(0.07) | 86(1) |
| III | 107(0.86) | 18(0.14) | 125(1) |
| IV | 56(0.86) | 9(0.14) | 65(1) |
| Sum | 359(0.88) | 49(0.12) | 408(1) |
| Fisher test p-value: 0.38 | | | |

| subtype (rows) vs focal.deletion.in.RB1 (columns) | | | | |
|---|---|---|---|---|
| | . | Del | Loss | Sum |
| I | 106(0.81) | 8(0.06) | 17(0.13) | 131(1) |
| II | 75(0.88) | 3(0.04) | 7(0.08) | 85(1) |
| III | 105(0.85) | 6(0.05) | 12(0.1) | 123(1) |
| IV | 54(0.83) | 1(0.02) | 10(0.15) | 65(1) |
| Sum | 340(0.84) | 18(0.04) | 46(0.11) | 404(1) |
| Fisher test p-value: 0.6 | | | | |

| subtype (rows) vs focal.amplification.in.FGFR3 (columns) | | | | |
|---|---|---|---|---|
| | . | Amp | Gain | Sum |
| I | 121(0.92) | 5(0.04) | 5(0.04) | 131(1) |
| II | 85(1) | 0(0) | 0(0) | 85(1) |
| III | 123(1) | 0(0) | 0(0) | 123(1) |
| IV | 65(1) | 0(0) | 0(0) | 65(1) |
| Sum | 394(0.98) | 5(0.01) | 5(0.01) | 404(1) |
| Fisher test p-value: 0.0016 | | | | |

| subtype (rows) vs focal.amplification.in.ERBB2 (columns) | | | | |
|---|---|---|---|---|
| | . | Amp | Gain | Sum |
| I | 121(0.92) | 6(0.05) | 4(0.03) | 131(1) |
| II | 79(0.93) | 6(0.07) | 0(0) | 85(1) |
| III | 120(0.98) | 2(0.02) | 1(0.01) | 123(1) |
| IV | 63(0.97) | 1(0.02) | 1(0.02) | 65(1) |
| Sum | 383(0.95) | 15(0.04) | 6(0.01) | 404(1) |
| Fisher test p-value: 0.18 | | | | |

FIG. 15

| subtype (rows) vs mutation.in.TP53 (columns) | | | |
|---|---|---|---|
| | | | |
| | no | yes | Sum |
| I | 91(0.69) | 41(0.31) | 132(1) |
| II | 37(0.43) | 49(0.57) | 86(1) |
| III | 55(0.44) | 70(0.56) | 125(1) |
| IV | 29(0.45) | 36(0.55) | 65(1) |
| Sum | 212(0.52) | 196(0.48) | 408(1) |
| | | | |
| Fisher test p-value: 4e-05 | | | |

Seiler

Gold standard subtype (rows) vs clanc (60) subtype (colum

Agreement: 0.81

| | I | II | III | IV | Sum |
|---|---|---|---|---|---|
| I | 91 | 5 | 3 | 1 | 100 |
| II | 16 | 50 | 2 | 8 | 76 |
| III | 1 | 0 | 75 | 7 | 83 |
| IV | 1 | 0 | 14 | 31 | 46 |
| Sum | 109 | 55 | 94 | 47 | 305 |

Sjodahl

Gold standard subtype (rows) vs clanc (60) subtype (colum

Agreement: 0.72

| | I | II | III | IV | Sum |
|---|---|---|---|---|---|
| I | 84 | 11 | 22 | 7 | 124 |
| II | 15 | 39 | 1 | 8 | 63 |
| III | 1 | 1 | 52 | 5 | 59 |
| IV | 0 | 12 | 3 | 47 | 62 |
| Sum | 100 | 63 | 78 | 67 | 308 |

FIG. 20

| 5-typer (rows) vs 60-gene subtype (columns) | I | II | III | IV | Sum |
|---|---|---|---|---|---|
| Basal_squamous | 3 | 1 | 99 | 39 | 142 |
| Luminal | 6 | 19 | 0 | 1 | 26 |
| Luminal_infiltrated | 1 | 52 | 10 | 15 | 78 |
| Luminal_papillary | 122 | 10 | 10 | 0 | 142 |
| Neuronal | 0 | 4 | 6 | 10 | 20 |
| Sum | 132 | 86 | 125 | 65 | 408 |

Gold standard subtype (rows) vs clanc5050 (56) subtype (columns), agreement: 0.88

| | I | II | III | IV | Sum |
|---|---|---|---|---|---|
| I | 119 | 10 | 3 | 0 | 132 |
| II | 4 | 80 | 7 | 4 | 95 |
| III | 0 | 0 | 110 | 0 | 110 |
| IV | 0 | 6 | 15 | 50 | 71 |
| Sum | 123 | 96 | 135 | 54 | 408 |

TCGA 2017 n=408
Solid dot indicates gold standard subtype and clanc subtype don't agree

FIG. 22

| | I | II | III | IV | | I | II | III | IV |
|---|---|---|---|---|---|---|---|---|---|
| LOC100188947 | 3.200446 | 2.47801 | -3.8801 | -4.37765 | TSSK2 | 0 | 0 | 0 | 0 |
| UPK3A | 1.882588 | 3.610797 | -5.65419 | -4.8912 | ADORA2B | -0.04243 | -1.99523 | 1.175231 | -0.55327 |
| KRT6B | -1.5279 | -2.2406 | 7.549432 | -0.39285 | RHOU | 0.587884 | 1.217374 | -2.77856 | -1.69619 |
| ANXA6 | -1.99651 | 0.642773 | 0.093877 | 1.662346 | GRHL3 | 1.022277 | 1.45992 | -1.39229 | -6.231 |
| FER1L4 | 1.710085 | 0.684431 | -3.29832 | -3.09831 | GFPT2 | -4.37252 | 0.832095 | 0.740754 | 1.949319 |
| UPK1A | 1.938255 | 2.816538 | -5.91898 | -6.9682 | KRT6C | -1.75746 | -2.5669 | 7.254879 | -1.05224 |
| DSG3 | -2.16488 | -1.58563 | 7.867258 | -1.23773 | C17orf28 | 0.801032 | 0.605037 | -3.52447 | -2.18042 |
| EMP3 | -1.88941 | 0.343301 | 0.700897 | 2.157498 | SDC1 | 0.390035 | 0.130128 | -0.01364 | -2.41266 |
| TBX3 | 1.480683 | 0.549164 | -3.24421 | -2.07565 | ALDH1L2 | -2.94616 | 0.513865 | 0.585891 | 1.307414 |
| SNX31 | 1.396561 | 2.04992 | -6.47583 | -7.24402 | KRT6A | -2.14698 | -2.4806 | 7.610361 | -0.58897 |
| BNC1 | -1.48301 | -0.5707 | 7.967862 | 2.237664 | CAPN5 | 1.168725 | 1.167339 | -2.49187 | -1.86401 |
| CMKLR1 | -2.01308 | 0.542859 | 0.300845 | 2.383412 | GGT6 | 1.184901 | 0.334371 | -2.22912 | -5.6065 |
| PPFIBP2 | 1.217493 | 0.728831 | -1.84142 | -2.19674 | SFRP2 | -6.64573 | 2.503393 | 0.675616 | 1.67583 |
| SFRP4 | -5.6671 | 3.091055 | 0.381761 | 2.186904 | CA9 | 0.703749 | -4.00206 | 1.431651 | -1.18965 |
| IL20RB | -0.8862 | -0.97047 | 4.280383 | -0.59347 | TOX3 | 2.43787 | 2.076916 | -6.52131 | -5.74298 |
| VSIG4 | -2.65714 | 0.592793 | 0.580961 | 2.608184 | RAPGEFL1 | 1.008142 | 0.104638 | -0.42977 | -3.65996 |
| FAM174B | 1.460997 | 0.570248 | -3.02958 | -1.94295 | CCDC80 | -3.07843 | 1.135826 | 0.432487 | 1.874276 |
| UPK2 | 1.848754 | 2.449998 | -5.94129 | -6.03892 | E2F7 | -0.19117 | -1.11786 | 0.991805 | 0.355714 |
| SERPINB13 | -0.63778 | -2.09682 | 5.682929 | -2.9445 | TLE2 | 0.958556 | 0.687707 | -2.918 | -1.05654 |
| CD163 | -2.94862 | 0.752134 | 0.398723 | 2.642102 | ZNF750 | -0.0658 | 0.518628 | 0.823911 | -3.96537 |
| C1orf126 | 1.653253 | 0.175782 | -1.38005 | -1.99388 | ARSI | -3.66852 | 0.424043 | 1.722501 | 1.228148 |
| MRVI1 | -1.19127 | 1.648828 | -0.14507 | 0.544091 | SERPINB4 | -1.12424 | -3.5076 | 5.840766 | -1.61832 |
| SPRR2A | -1.49003 | -0.31559 | 5.642145 | -1.94896 | SARM1 | 0.516351 | 0.468972 | -1.87233 | -0.35696 |
| SLC7A7 | -2.04585 | 0.370701 | 0.465131 | 2.010601 | PVRL4 | 0.494431 | 0.363084 | -0.39383 | -2.9725 |
| HMGCS2 | 3.624373 | 2.43858 | -6.28311 | -6.90542 | CTHRC1 | -3.30083 | 0.60929 | 0.643421 | 1.148149 |
| EMILIN1 | -1.95999 | 1.856179 | -0.19675 | 1.837401 | SERPINB3 | -0.98946 | -4.25249 | 5.934203 | -2.2102 |
| CD109 | -2.26195 | -0.3247 | 2.615978 | 1.522168 | TBX2 | 1.539893 | 1.508642 | -2.76057 | -1.55403 |
| PIK3AP1 | -1.83069 | 0.185984 | 0.500394 | 2.183511 | RHOV | -0.17371 | 0.204546 | 0.887872 | -2.9274 |

METHODS FOR SUBTYPING OF BLADDER CANCER

CROSS-REFERENCE TO RELATED APPLICATIONS

This application is a U.S. national stage application of International Application No. PCT/US2019/017799, filed Feb. 13, 2019, which claims the benefit of priority to U.S. Provisional Application Ser. No. 62/629,975, filed Feb. 13, 2018, each of which is herein incorporated by reference in its entirety for all purposes.

FIELD

The present invention relates to methods for determining a muscle invasive bladder cancer (MIBC) subtype and for predicting the prognosis of a patient inflicted with specific subtypes of bladder cancer.

STATEMENT REGARDING SEQUENCE LISTING

The Sequence Listing associated with this application is provided in text format in lieu of a paper copy, and is hereby incorporated by reference into the specification. The name of the text file containing the Sequence Listing is GNCN_014_01WO_SeqList_ST25.txt. The text file is ≈401 KB, was created on Feb. 13, 2019, and is being submitted electronically via EFS-Web.

BACKGROUND

Bladder cancer is comprised of cancers arising from the tissues of the urinary bladder. The most common type of bladder cancer is transitional cell carcinoma, which begins in urothelial cells that line the inside of the bladder. Urothelial cells are transitional cells, which are able to change shape and stretch when the bladder is full. This type of cancer is also called urothelial carcinoma. Other types of bladder cancer include squamous cell carcinoma (cancer that begins in thin, flat cells lining the bladder) and adenocarcinoma (cancer that begins in cells that make and release mucus and other fluids). More than 90% of bladder cancers are urothelial cell carcinoma and about 5% are squamous cell carcinoma. The most significant known risk factors for bladder cancer include tobacco use, age, diet, consumption of alcohol, chronic inflammation, obesity, and the exposure to cancer-causing substances.

Common detection and diagnosis methods of bladder cancer include cystoscopy, non-invasive urine bound markers, and molecular bladder cancer detection assays. However, a challenge in clinical practice is that the pathologic assessment can be uncertain, and therefore, lacks accuracy.

The present disclosure addresses the limitations of the current methods and other needs in the field for an efficient method for improved bladder cancer tumor classification that may inform prognosis and patient management based on underlying genomic and biologic tumor characteristics.

SUMMARY

The methods disclosed herein include determination of a bladder cancer (e.g., MIBC) subtype, treatment of muscle invasive bladder cancer, prediction of overall survival of bladder cancer (e.g., MIBC) patients, and application of an algorithm for categorization of bladder cancer (e.g., MIBC)

tumors into one of 4 subtypes (Type I: luminal, Type II: luminal infiltrated, Type III: basal, and Type IV: basal infiltrated/neuronal)). The algorithm can be a classification to the nearest centroid (CLaNC) algorithm.

In one aspect, provided herein is a method for determining a bladder cancer subtype of a bladder cancer sample obtained from a patient, the method comprising detecting an expression level of at least one classifier biomarker of Table 1 or Table 2, wherein the detection of the expression level of the classifier biomarker specifically identifies a luminal, luminal infiltrated, basal or basal infiltrated/neuronal bladder cancer subtype. In some cases, the method further comprises comparing the detected levels of expression of the at least one classifier biomarker of Table 1 or Table 2 to the expression of the at least one classifier biomarker of Table 1 or Table 2 in at least one sample training set(s), wherein the at least one sample training set(s) comprises expression data of the at least one classifier biomarker of Table 1 or Table 2 from a reference bladder cancer luminal sample, expression data of the at least one classifier biomarker of Table 1 or Table 2 from a reference bladder cancer luminal infiltrated sample, expression data of the at least one classifier biomarker of Table 1 or Table 2 from a reference bladder cancer basal sample, expression data of the at least one classifier biomarker of Table 1 or Table 2 from a reference bladder cancer basal infiltrated/neuronal sample or a combination thereof; and classifying the sample as luminal, luminal infiltrated, basal or basal infiltrated/neuronal subtype based on the results of the comparing step. In some cases, the comparing step comprises applying a statistical algorithm which comprises determining a correlation between the expression data obtained from the sample and the expression data from the at least one training set(s); and classifying the sample as a luminal, luminal infiltrated, basal or basal infiltrated/neuronal subtype based on the results of the statistical algorithm. In some cases, the expression level of the classifier biomarker is detected at the nucleic acid level. In some cases, the nucleic acid level is RNA or cDNA. In some cases, the detecting an expression level comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing RNAseq. In some cases, the detection of the expression level comprises using at least one pair of oligonucleotide primers specific for at least one classifier biomarker of Table 1 or Table 2. In some cases, the sample is a formalin-fixed, paraffin-embedded (FFPE) bladder tissue sample, a fresh or a frozen tissue sample, an exosome, wash fluids, cell pellets, or a bodily fluid obtained from the patient. In some cases, the bodily fluid is blood or fractions thereof, urine, saliva, or sputum. In some cases, the at least one classifier biomarker comprises a plurality of classifier biomarkers. In some cases, the plurality of classifier biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, or at least 60 classifier biomarkers of Table 1. In some cases, the plurality of classifier biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, or at least 56 classifier biomarkers of Table 2. In some cases, the at least one classifier biomarker comprises, consists essentially of or consists of all the classifier biomarkers of Table 1 or Table 2.

In another aspect, provided herein is a method for determining a muscle invasive bladder cancer (MIBC) subtype of a bladder cancer sample obtained from a patient, the method comprising detecting an expression level of at least one classifier biomarker of Table 1 or Table 2, wherein the detection of the expression level of the classifier biomarker specifically identifies a luminal, luminal infiltrated, basal or basal infiltrated/neuronal bladder cancer subtype. In some cases, the method further comprises comparing the detected levels of expression of the at least one classifier biomarker of Table 1 or Table 2 to the expression of the at least one classifier biomarker of Table 1 or Table 2 in at least one sample training set(s), wherein the at least one sample training set comprises expression data of the at least one classifier biomarker of Table 1 or Table 2 from a reference bladder cancer luminal sample, expression data of the at least one classifier biomarker of Table 1 or Table 2 from a reference bladder cancer luminal infiltrated sample, expression data of the at least one classifier biomarker of Table 1 or Table 2 from a reference bladder cancer basal sample, expression data of the at least one classifier biomarker of Table 1 or Table 2 from a reference bladder cancer basal infiltrated/neuronal sample or a combination thereof; and classifying the sample as luminal, luminal infiltrated, basal or basal infiltrated/neuronal subtype based on the results of the comparing step. In some cases, the comparing step comprises applying a statistical algorithm which comprises determining a correlation between the expression data obtained from the sample and the expression data from the at least one training set(s); and classifying the sample as a luminal, luminal infiltrated, basal or basal infiltrated/neuronal subtype based on the results of the statistical algorithm. In some cases, the expression level of the classifier biomarker is detected at the nucleic acid level. In some cases, the nucleic acid level is RNA or cDNA. In some cases, the detecting an expression level comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing RNAseq. In some cases, the detection of the expression level comprises using at least one pair of oligonucleotide primers specific for at least one classifier biomarker of Table 1 or Table 2. In some cases, the sample is a formalin-fixed, paraffin-embedded (FFPE) bladder tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the at least one classifier biomarker comprises a plurality of classifier biomarkers. In some cases, the plurality of classifier biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers or at least 60 classifier biomarkers of Table 1. In some cases, the plurality of classifier biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, or at least 56 classifier biomarkers of Table 2. In some cases, the at least one classifier biomarker comprises, consists essentially of or consist of all the classifier biomarkers of Table 1 or Table 2.

In yet another aspect, provided herein is a method of detecting a biomarker in a bladder cancer sample obtained from a patient, the method comprising measuring the expression level of a plurality of classifier biomarker nucleic acids selected from Table 1 or Table 2 using an amplification, hybridization and/or sequencing assay. In some cases, the bladder cancer sample was previously diagnosed as being muscle invasive bladder cancer (MIBC). In some cases, the previous diagnosis was by histological examination. In some cases, the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing RNAseq. In some cases, the detection of the expression level comprises using at least one pair of oligonucleotide primers per each of the plurality of biomarker nucleic acids selected from Table 1 or Table 2. In some cases, the sample is a formalin-fixed, paraffin-embedded (FFPE) bladder tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the plurality of biomarker nucleic acids comprises, consists essentially of or consists of at least two biomarker nucleic acids, at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers or at least 60 classifier biomarker nucleic acids of Table 1. In some cases, the plurality of classifier biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, or at least 56 classifier biomarkers of Table 2. In some cases, the plurality of biomarker nucleic acids comprises, consists essentially of or consists of all the classifier biomarker nucleic acids of Table 1 or Table 2.

In still another aspect, provided herein is a method of treating muscle invasive bladder cancer (MIBC) in a subject, the method comprising: measuring the expression level of at least one biomarker nucleic acid in a MIBC sample obtained from the subject, wherein the at least one biomarker nucleic acid is selected from a set of biomarkers listed in Table 1 or Table 2, wherein the presence, absence and/or level of the at least one biomarker indicates a subtype of the MIBC; and administering a therapeutic agent based on the subtype of the MIBC. In some cases, the at least one biomarker nucleic acid selected from the set of biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers or at least 60 classifier biomarker nucleic acids of Table 1. In some cases, the at least one biomarker nucleic acid selected from the set of biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, or at least 56 classifier biomarkers of Table 2. In some cases, the at least one biomarker nucleic acid selected from the set of biomarkers comprises, consists essentially of or consists of all the classifier biomarker nucleic acids of Table 1 or Table 2. In some cases, the method further comprises measuring the expression of at least one biomarker from an additional set of biomarkers. In some cases, the additional set of biomarkers comprises BIRC5, CCNB1, CDC20, CDCA1, CEP55, KNTC2, MK167, PTTG1, RRM2, TYMS, UBE2C, TP53, RB1, FGFR2, FGFR3 and ERBB2. In some cases, the additional set of biomarkers comprise genes selected from Gene Expression Omnibus Dataset GSE87304, Gene Expression Omnibus Dataset GSE32894 or a combination thereof. In some cases, the additional set of biomarkers comprises at least an immune cell signature, a cell proliferation signature, or drug target genes. In some cases, the measuring the expression level is conducted using an amplification, hybridization and/or sequencing assay. In some cases, the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing qRT-PCR. In some cases, the sample is a formalin-fixed, paraffin-embedded (FFPE) bladder tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the subject's MIBC subtype is selected from luminal, luminal infiltrated, basal, and basal infiltrated/neuronal. In some cases, the at least one biomarker nucleic acid is a plurality of biomarker nucleic acids, wherein the plurality of biomarker nucleic acids comprises at least one biomarker nucleic acid listed in Table 1 or Table 2 in combination with one or more biomarker nucleic acids from a publically available bladder cancer dataset, wherein the presence, absence and/or level of the plurality of biomarker nucleic acids indicates a subtype of the MIBC. In some cases, the at least one biomarker nucleic acid is a plurality of biomarker nucleic acids, wherein the plurality of biomarker nucleic acids comprises all of the biomarker nucleic acids listed in Table 1 or Table 2, all of the biomarker nucleic acids listed in claim 45 or claim 46, in combination with one or more biomarker nucleic acids from a publically available bladder cancer dataset, wherein the presence, absence and/or level of the plurality of biomarker nucleic acids indicates a subtype of the bladder cancer. In some cases, the publically available bladder cancer dataset is TCGA bladder cancer RNAseq dataset.

In a still further aspect, provided herein is a method of predicting overall survival in a muscularly invasive bladder cancer (MIBC) patient, the method comprising detecting an expression level of at least one classifier biomarker of Table 1 or Table 2 in a MIBC sample obtained from a patient, wherein the detection of the expression level of the at least one classifier biomarker specifically identifies a luminal, luminal infiltrated, basal, and basal infiltrated/neuronal subtype, and wherein identification of the subtype is predictive of the overall survival in the patient. In some cases, the method further comprises comparing the detected levels of expression of the at least one classifier biomarker of Table 1 or Table 2 to the expression of the at least one classifier biomarker of Table 1 or Table 2 in at least one sample training set(s), wherein the at least one sample training set comprises expression data of the at least one classifier biomarker of Table 1 or Table 2 from a reference bladder cancer luminal sample, expression data of the at least one classifier biomarker of Table 1 or Table 2 from a reference bladder cancer luminal infiltrated sample, expression data of the at least one classifier biomarkers of Table 1 or Table 2 from a reference bladder cancer basal sample, expression data of the at least one classifier biomarker of Table 1 or Table 2 from a reference bladder cancer basal infiltrated/neuronal sample or a combination thereof; and classifying the sample as luminal, luminal infiltrated, basal or basal infiltrated/neuronal subtype based on the results of the comparing step. In some cases, the comparing step comprises applying a statistical algorithm which comprises determining a correlation between the expression data obtained from the sample and the expression data from the at least one training set(s); and classifying the sample as a luminal, luminal infiltrated, basal or basal infiltrated/neuronal subtype based on the results of the statistical algorithm. In some cases, the expression level of the classifier biomarker is detected at the nucleic acid level. In some cases, the nucleic acid level is RNA or cDNA. In some cases, the detecting an expression level comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing qRT-PCR. In some cases, the detection of the expression level comprises using at least one pair of oligonucleotide primers specific for at least one classifier biomarker of Table 1 or Table 2. In some cases, the sample is a formalin-fixed, paraffin-embedded (FFPE) bladder tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the at least one classifier biomarker comprises a plurality of classifier biomarkers. In some cases, the plurality of classifier biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, or at least 60 classifier biomarkers of Table 1. In some cases, the plurality of classifier biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, or at least 56 classifier biomarkers of Table 2. In some cases, the at least one classifier biomarker comprises, consists essentially of or consists of all the classifier biomarkers of Table 1 or Table 2.

BRIEF DESCRIPTION OF THE DRAWINGS

FIG. 1 illustrates the bladder cancer subtype distribution for the 408 unique primary solid tumor samples described in Robertson, A G, et al., Cell, 171(3): 540-556 (2017) (dataset referred to herein as "Gold standard," "GS," or "TCGA-2017") (upper left panel). FIG. 1 also provides the cluster assignment for the 129 tumor samples described in Cancer Genome Atlas Research Network, Nature, 507(492): 315-22 (2014) (dataset described herein as TCGA-2014) (upper right panel). The GS subtype silhouette is shown for the TCGA-2017 dataset (n=408) (bottom left panel). A solid dot indicates that a sample used to fit the GS standard subtyper was present in the TCGA-2014 dataset. Also, the GS subtype silhouette is shown for the 129 TCGA-2014 samples (bottom right panel). A solid dot indicates that the GS subtype and the TCGA-2014 subtype do not agree. Type I: Luminal; Type II: Luminal Infiltrated; Type III: Basal; Type IV: basal infiltrated/neuronal.

FIG. 6 lists the 60 gene centroids selected for use in subtyping, and their corresponding gene expression levels (i.e., centroid classifier coefficients) by subtype.

FIG. 12 also provides boxplots showing expression of potential treatment targets FGFR2, FGFR3, and ERBB2 by subtype.

FIG. 14 illustrates tumor driver (R131, FGFR3, ERBB2) gene mutation frequencies across subtypes.

FIG. 15 illustrates frequency of TP53 tumor suppressor mutations across subtypes.

FIG. 20 presents a comparison of the subtyping of the TCGA-2017 bladder cancer dataset (n=408) samples based on the 5-type classification system described in Roberston, et al. (2017), and the 4-type classification system based on the 60 gene subtype described herein.

FIG. 22 lists the 56 gene centroids selected for use in subtyping, and their corresponding gene expression levels (i.e., centroid classifier coefficients) by subtype.

DETAILED DESCRIPTION

Overview

Figure 2:
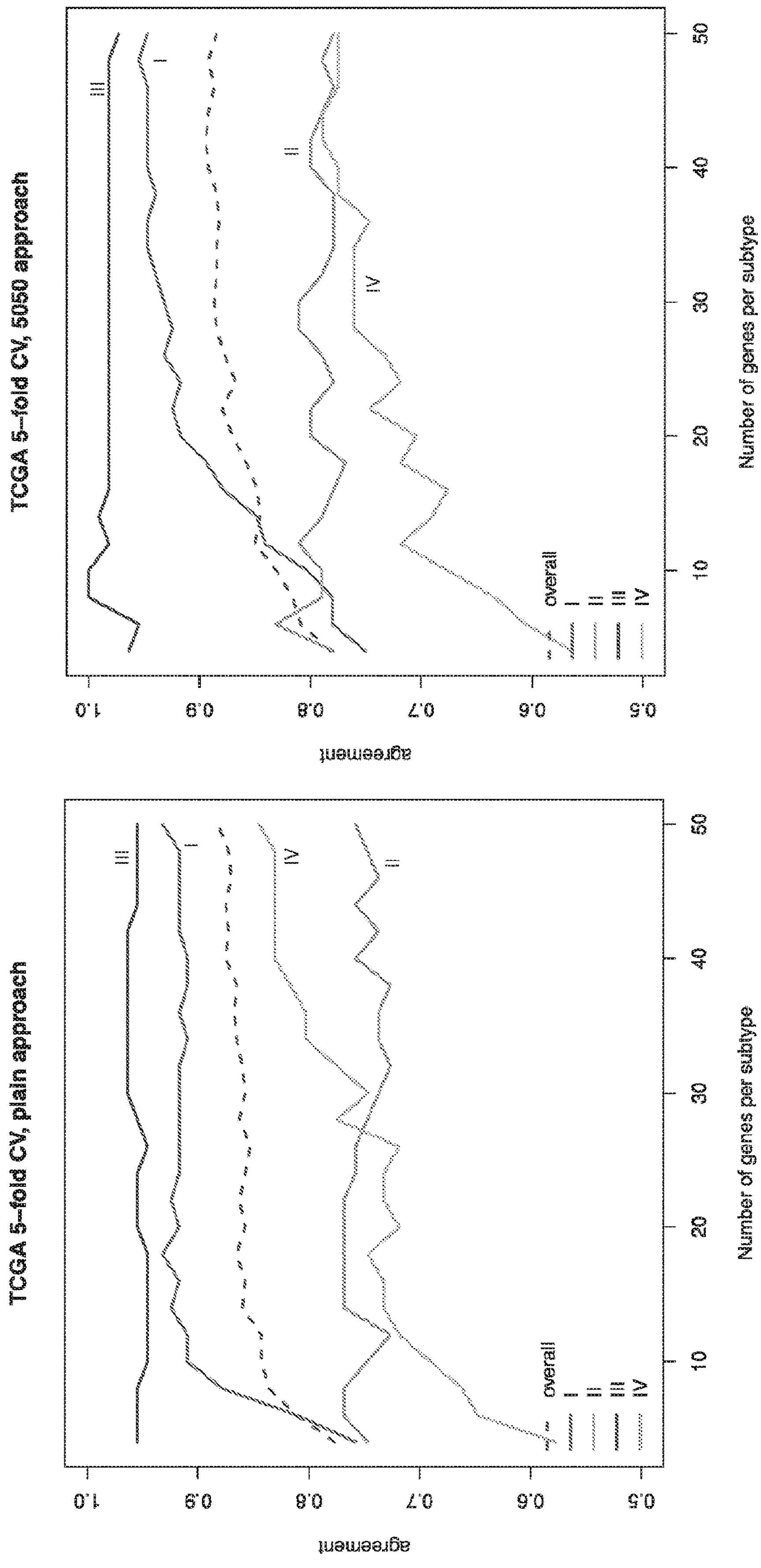
FIG. 2 illustrates five-fold cross validation curves using a Clanc plain (left panel) and Clanc 50:50 high:low (right panel) approach on the TCGA-2017 dataset (n=408) to guide the selection of the number of genes per subtype to include in the signature for bladder cancer subtyping provided herein.

The present invention provides kits, compositions and methods for identifying or diagnosing bladder cancer. That is, the methods can be useful for molecularly defining subsets of bladder cancer. The bladder cancer can be a muscle invasive bladder cancer (MIBC). The methods provide a classification of bladder cancer that can be prognostic and predictive for therapeutic response. The therapeutic response can include chemotherapy, immunotherapy, surgical intervention and radiotherapy. The methods can be also provide a prognosis of overall survival for bladder cancer patients according to their subtypes (e.g., luminal, luminal infiltrated, basal or basal infiltrated/neuronal).

While a useful term for epidemiologic purposes, "bladder cancer" can refer to cancers arising from the tissues of the urinary bladder that includes urothelial carcinoma, squamous cell carcinoma and adenocarcinoma. Bladder cancer can be described as cancers that are non-muscle invasive, muscle invasive, and transitional cell carcinoma. As used herein, bladder cancer can also refer to MIBC. Subtypes of these types of cancer as defined by underlying genomic features can have varied cell of origin, tumor drivers, proliferation, immune responses, and prognosis.

"Determining a bladder cancer subtype" can include, for example, diagnosing or detecting the presence and sub-type of bladder cancer, monitoring the progression of the disease, and identifying or detecting cells or samples that are indicative of subtypes.

In one embodiment, bladder cancer status is assessed through the evaluation of expression patterns, or profiles, of a plurality of classifier biomarkers or biomarkers in one or more subject samples. The term subject, or subject sample, may refer to an individual regardless of health and/or disease status. A subject can be a subject, a study participant, a control subject, a screening subject, or any other class of individual from whom a sample is obtained and assessed in the context of the methods, compositions and kits provided herein. Accordingly, a subject can be diagnosed with bladder cancer (including subtypes, or grades thereof), can present with one or more symptoms of bladder cancer, or a predisposing factor, such as a family (genetic) or medical history (medical) factor, for bladder cancer, can be undergoing treatment or therapy for bladder cancer, or the like. Alternatively, a subject can be healthy with respect to any of the aforementioned factors or criteria. It will be appreciated that the term "healthy" as used herein, is relative to bladder cancer status, as the term "healthy" cannot be defined to correspond to any absolute evaluation or status. Thus, an individual defined as healthy with reference to any specified disease (e.g., bladder cancer) or disease criterion, can in fact be diagnosed with any other one or more diseases, or exhibit any other one or more disease criterion, including one or more other cancers.

As used herein, an "expression profile" or a "biomarker profile" or "gene signature" comprises one or more values corresponding to a measurement of the relative abundance, level, presence, or absence of expression of a discriminative or classifier biomarker or biomarker. An expression profile can be derived from a subject prior to or subsequent to a diagnosis of bladder cancer, can be derived from a biological sample collected from a subject at one or more time points prior to or following treatment or therapy, can be derived from a biological sample collected from a subject at one or more time points during which there is no treatment or therapy (e.g., to monitor progression of disease or to assess development of disease in a subject diagnosed with or at risk for bladder cancer), or can be collected from a healthy subject. The term subject can be used interchangeably with patient. The patient can be a human patient. The one or more biomarkers of the biomarker profiles provided herein are selected from one or more biomarkers of Table 1, Table 2 and/or any additional set of biomarker classifiers disclosed herein.

As used herein, the term "determining an expression level" or "determining an expression profile" or "detecting an expression level" or "detecting an expression profile" as used in reference to a biomarker or classifier means the application of a biomarker specific reagent such as a probe, primer or antibody and/or a method to a sample, for example a sample of the subject or patient and/or a control sample, for ascertaining or measuring quantitatively, semi-quantitatively or qualitatively the amount of a biomarker or biomarkers, for example the amount of biomarker polypeptide or mRNA (or cDNA derived therefrom). For example, a level of a biomarker can be determined by a number of methods including for example immunoassays including for example immunohistochemistry, ELISA, Western blot, immunoprecipitation and the like, where a biomarker detection agent such as an antibody for example, a labeled antibody, specifically binds the biomarker and permits for example relative or absolute ascertaining of the amount of polypeptide biomarker, hybridization and PCR protocols where a probe or primer or primer set are used to ascertain the amount of nucleic acid biomarker, including for example probe based and amplification based methods including for example microarray analysis, RT-PCR such as quantitative RT-PCR (qRT-PCR), serial analysis of gene expression (SAGE), Northern Blot, digital molecular barcoding technology, for example Nanostring Counter Analysis, and TaqMan quantitative PCR assays. Other methods of mRNA detection and quantification can be applied, such as mRNA in situ hybridization in formalin-fixed, paraffin-embedded (FFPE) tissue samples or cells. This technology is currently offered by the QuantiGene ViewRNA (Affymetrix), which uses probe sets for each mRNA that bind specifically to an amplification system to amplify the hybridization signals; these amplified signals can be visualized using a standard fluorescence microscope or imaging system. This system for example can detect and measure transcript levels in heterogeneous samples; for example, if a sample has normal and tumor cells present in the same tissue section. As mentioned, TaqMan probe-based gene expression analysis (PCR-based) can also be used for measuring gene expression levels in tissue samples, and this technology has been shown to be useful for measuring mRNA levels in FFPE samples. In brief, TaqMan probe-based assays utilize a probe that hybridizes specifically to the mRNA target. This probe contains a quencher dye and a reporter dye (fluorescent molecule) attached to each end, and fluorescence is emitted only when specific hybridization to the mRNA target occurs.

During the amplification step, the exonuclease activity of the polymerase enzyme causes the quencher and the reporter dyes to be detached from the probe, and fluorescence emission can occur. This fluorescence emission is recorded and signals are measured by a detection system; these signal intensities are used to calculate the abundance of a given transcript (gene expression) in a sample.

In one embodiment, the “expression profile” or a “biomarker profile” or “gene signature” associated with the gene signatures or classifier biomarkers described herein (e.g., Table 1, Table 2 and/or any additional set of biomarker classifiers as disclosed herein) can be useful for distinguishing between normal and tumor samples. In another embodiment, the tumor samples are bladder cancer. In another embodiment, the bladder cancer can be further classified as luminal, luminal infiltrated, basal, or basal infiltrated/neuronal based upon an expression profile determined using the methods provided herein. In some embodiments, the bladder cancer is MIBC. Expression profiles using the classifier biomarkers disclosed herein (e.g., Table 1, Table 2 and any additional set of biomarker classifiers as disclosed herein) can provide valuable molecular tools for specifically identifying bladder cancer subtypes, and for treating bladder cancer. Accordingly, the invention provides methods for screening and classifying a subject for molecular bladder cancer subtypes.

In some instances, a single classifier biomarker or a plurality of classifier bio markers provided herein is capable of identifying subtypes of bladder cancer with a predictive success of at least about 70%, at least about 71%, at least about 72%, at least about 73%, at least about 74%, at least about 75%, at least about 76%, at least about 77%, at least about 78%, at 1 east about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, up to 100%, inclusive of all ranges and subranges therebetween.

In some instances, a single classifier biomarker or a plurality of classifier bio markers as provided herein is capable of determining bladder cancer subtypes with a sensitivity or specificity of at least about 70%, at least about 71%, at least about 72%, at least about 73%, at least about 74%, at least about 75%, at least about 76%, at least about 77%, at least about 78%, at 1 east about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, up to 100%, inclusive of all ranges and subranges therebetween.

The present invention also encompasses a system capable of distinguishing various subtypes of bladder cancer not detectable using current methods. This system can be capable of processing a large number of subjects and subject variables such as expression profiles and other diagnostic criteria. The expression profile can be used in combination with other diagnostic methods including histochemical, immunohistochemical, cytologic, immunocytologic, and visual diagnostic methods including histologic or morphometric evaluation of bladder tissue.

In various embodiments, the expression profile derived from a subject is compared to a reference expression profile. A “reference expression profile” or “control expression profile” can be a profile derived from the subject prior to treatment or therapy; can be a profile produced from the subject sample at a particular time point (usually prior to or following treatment or therapy, but can also include a particular time point prior to or following diagnosis of bladder cancer); or can be derived from a healthy individual or a pooled reference from healthy individuals. A reference expression profile can be generic for bladder cancer or can be specific to different subtypes of bladder cancer. The bladder cancer reference expression profile can be from any tissues of the urinary bladder.

The reference expression profile can be compared to a test expression profile. A “test expression profile” can be derived from the same subject as the reference expression profile except at a subsequent time point (e.g., one or more days, weeks or months following collection of the reference expression profile) or can be derived from a different subject. In summary, any test expression profile of a subject can be compared to a previously collected profile from a subject that has a luminal, luminal infiltrated, basal, basal infiltrated/neuronal bladder cancer subtype.

The classifier biomarkers of the invention can include nucleic acids (RNA, cDNA, and DNA) and proteins, and variants and fragments thereof. Such biomarkers can include DNA comprising the entire or partial sequence of the nucleic acid sequence encoding the biomarker, or the complement of such a sequence. The biomarkers described herein can include RNA comprising the entire or partial sequence of any of the nucleic acid sequences of interest, or their non-natural cDNA products, obtained synthetically in vitro in a reverse transcription reaction. The biomarker nucleic acids can also include any expression product or portion thereof of the nucleic acid sequences of interest. A biomarker protein can be a protein encoded by or corresponding to a DNA biomarker as provided herein. A biomarker protein can comprise the entire or partial amino acid sequence of any of the biomarker proteins or polypeptides. The biomarker nucleic acid can be extracted from a cell or can be cell free or extracted from an extracellular vesicular entity such as an exosome.

A “classifier biomarker” or “biomarker” or “classifier gene” can be any gene or protein whose level of expression in a tissue or cell is altered compared to that of a normal or healthy cell or tissue. For example, a “classifier biomarker” or “biomarker” or “classifier gene” can be any gene or protein whose level of expression in a tissue or cell is altered in a specific bladder cancer subtype. The detection of the biomarkers as provided herein can permit the determination of the specific subtype. The “classifier biomarker” or “biomarker” or “classifier gene” may be one that is up-regulated (e.g. expression is increased) or down-regulated (e.g. expression is decreased) relative to a reference or control as provided herein. The reference or control can be any reference or control as provided herein. In some embodiments, the expression values of genes that are up-regulated or down-regulated in a particular subtype of bladder cancer can be pooled into one gene signature. The overall expression level of each gene in each gene signature is referred to herein as the “expression profile” and is used to classify a test sample according to the subtype of bladder cancer. However, it is understood that independent evaluation of expression for each of the genes disclosed herein can be used to classify tumor subtypes without the need to group up-regulated and down-regulated genes into one or more gene signatures. In some cases, as shown in Table 1, a total of 60 biomarkers can be used for bladder cancer subtype determination. For each bladder cancer subtype, for example, 30 of the 60 biomarkers can be negatively correlated genes, while 30 of the 60 biomarkers can be positively correlated genes which can be selected as the gene signature of a specific bladder cancer subtype. In some cases, as shown in Table 2, a total of 56 biomarkers can be used for bladder cancer subtype determination.

The classifier biomarkers as provided herein can include any gene or protein that is selectively expressed in bladder cancer, as defined herein above. Sample biomarker genes are listed in Table 1 or Table 2, below. In Table 1, the first column of the table represents the biomarker list selected for distinguishing luminal subtype. The second column of the table represents the biomarker list selected for distinguishing luminal infiltrated subtype. The third column of the table represents the biomarker list selected for distinguishing basal subtype. The last column of the table represents the biomarker list selected for distinguishing basal infiltrated/neuronal subtype. In Table 2, the first column of the table represents the biomarker list selected for distinguishing luminal subtype. The second column of the table represents the biomarker list selected for distinguishing luminal infiltrated subtype. The third column of the table represents the biomarker list selected for distinguishing basal subtype. The last column of the table represents the biomarker list selected for distinguishing basal infiltrated/neuronal subtype.

The relative gene expression levels as represented by the centroid coefficients as described herein of the classifier biomarkers for 60-gene bladder cancer subtyping are shown in Table 1. In one embodiment, the gene centroids including gene expression levels (i.e., centroid coefficients) of the classifier biomarkers for bladder cancer subtyping are shown in Table 1. The relative gene expression levels as represented by the centroid coefficients as described herein of the classifier biomarkers for 56-gene bladder cancer subtyping are shown in Table 2. In one embodiment, the gene centroids including gene expression levels (i.e., centroid coefficients) of the classifier biomarkers for bladder cancer subtyping are shown in Table 2.

TABLE 1

Gene Centroids of 60 Classifier Biomarkers for the Bladder Cancer Subtypes

| Gene Symbol | Gene Name | I (Luminal) | II (Luminal Infiltrated) | III (Basal) | IV (Neuronal/Basal Infiltrated) | SEQ ID NO: | GenBank Accession Number* |
|---|---|---|---|---|---|---|---|
| ALDH1L2 | aldehyde dehydrogenase 1 family member L2 | −2.95 | 0.51 | 0.59 | 1.31 | 1 | NM_001034173 |
| ANXA6 | annexin A6 | −2.00 | 0.64 | 0.09 | 1.66 | 2 | NM_001155 |
| ARSI | arylsulfatase family member I | −3.67 | 0.42 | 1.72 | 1.23 | 3 | NM_001012301 |
| BCAS1 | breast carcinoma amplified sequence 1 | 1.88 | 1.10 | −3.83 | −5.58 | 4 | NM_003657 |
| BNC1 | basonuclin 1 | −1.48 | −0.57 | 7.97 | 2.24 | 5 | NM_001717 |
| C10orf99 | chromosome 10 open reading frame 99 | 1.69 | 1.15 | −1.26 | −7.80 | 6 | NM_207373 |
| C17orf28 | HID1 domain containing | 0.80 | 0.61 | −3.52 | −2.18 | 7 | NM_030630 |
| CAPN5 | calpain 5 | 1.17 | 1.17 | −2.49 | −1.86 | 8 | NM_004055 |
| CCDC80 | coiled-coil domain containing 80 | −3.08 | 1.14 | 0.43 | 1.87 | 9 | NM_199511 |
| COL6A2 | collagen type VI alpha 2 chain | −2.25 | 1.10 | 0.36 | 2.02 | 10 | NM_058174 |
| CPXM2 | carboxypeptidase X, M14 family member 2 | −2.14 | 1.78 | −0.13 | 1.70 | 11 | NM_198148 |
| CTHRC1 | collagen triple helix repeat containing 1 | −3.30 | 0.61 | 0.64 | 1.15 | 12 | NM_138455 |
| DSG3 | desmoglein 3 | −2.16 | −1.59 | 7.87 | −1.24 | 13 | NM_001944 |
| EMILIN1 | elastin microfibril interfacer 1 | −1.96 | 1.86 | −0.20 | 1.84 | 14 | NM_007046 |
| EPN3 | epsin 3 | 0.61 | 0.45 | −0.73 | −2.60 | 15 | NM_017957 |
| EVPL | envoplakin | 0.51 | 0.48 | −0.65 | −2.53 | 16 | NM_001320747 |
| FAP | fibroblast activation protein alpha | −3.87 | 0.94 | 0.84 | 1.46 | 17 | NM_004460 |
| FBN1 | fibrillin 1 | −2.47 | 1.02 | 0.22 | 1.82 | 18 | NM_000138 |
| FGF7 | fibroblast growth factor 7 | −2.23 | 1.98 | 0.12 | 1.44 | 19 | NM_002009 |
| FMO9P | flavin containing monooxygenase 9 pseudogene | 2.37 | 3.22 | −3.99 | −5.26 | 20 | NR_002925 |
| FNDC1 | fibronectin type III domain containing 1 | −4.02 | 2.05 | 0.42 | 2.44 | 21 | NM_032532 |
| GABBR2 | gamma-ammobutyric acid type B receptor subunit 2 | 0.63 | 5.25 | −2.87 | −0.72 | 22 | NM_005458 |

TABLE 1-continued

Gene Centroids of 60 Classifier Biomarkers for the Bladder Cancer Subtypes

| Gene Symbol | Gene Name | I (Luminal) | II (Luminal Infiltrated) | III (Basal) | IV (Neuronal/Basal Infiltrated) | SEQ ID NO: | GenBank Accession Number* |
|---|---|---|---|---|---|---|---|
| GFPT2 | glutamine-fructose-6-phosphate transaminase 2 | −4.37 | 0.83 | 0.74 | 1.95 | 23 | NM_005110 |
| GGT6 | gamma-glutamyltransferase 6 | 1.18 | 0.33 | −2.23 | −5.61 | 24 | NM_001122890 |
| GREM1 | gremlin 1, DAN family BMP antagonist | −5.82 | 1.63 | 0.66 | 0.50 | 25 | NM_013372 |
| GRHL3 | grainyhead like transcription factor 3 | 1.02 | 1.46 | −1.39 | −6.23 | 26 | NM_021180 |
| IL20RB | interleukin 20 receptor subunit beta | −0.89 | −0.97 | 4.28 | −0.59 | 27 | NM_144717 |
| KRT6A | keratin 6A | −2.15 | −2.48 | 7.61 | −0.59 | 28 | NM_005554 |
| KRT6B | keratin 6B | −1.53 | −2.24 | 7.55 | −0.39 | 29 | NM_005555 |
| KRT6C | keratin 6C | −1.76 | −2.57 | 7.25 | −1.05 | 30 | NM_173086 |
| LMOD1 | leiomodin 1 | −1.31 | 2.77 | −0.22 | 0.96 | 31 | NM_012134 |
| LOC100188947 | HECTD2 antisense RNA 1 | 3.20 | 2.48 | −3.88 | −4.38 | 32 | NR_024467 |
| MRVI1 | murine retrovirus integration site 1 homolog | −1.19 | 1.65 | −0.15 | 0.54 | 33 | NM_001098579 |
| NRP2 | neuropilin 2 | −2.34 | 0.40 | 0.62 | 1.43 | 34 | NM_201266 |
| PDLIM3 | PDZ and LIM domain 3 | −2.49 | 1.95 | 0.33 | 1.51 | 35 | NM_014476. |
| PLA2G4F | phospholipase A2 group IVF | 1.13 | 0.24 | −0.66 | −4.12 | 36 | NM_213600 |
| PODN | podocan | −1.54 | 1.82 | −0.72 | 1.20 | 37 | NM_153703 |
| POSTN | periostin | −4.38 | 1.37 | 0.46 | 1.42 | 38 | NM_006475 |
| PRRX1 | paired related homeobox 1 | −3.33 | 0.94 | 0.50 | 2.06 | 39 | NM_006902 |
| PVRL4 | nectin cell adhesion molecule 4 | 0.49 | 0.36 | −0.39 | −2.97 | 40 | NM_030916 |
| RAPGEFL1 | Rap guanine nucleotide exchange factor like 1 | 1.01 | 0.10 | −0.43 | −3.66 | 41 | NM_001303533 |
| RHOU | ras homolog family member U | 0.59 | 1.22 | −2.78 | −1.70 | 42 | NM_021205 |
| RHOV | ras homolog family member V | −0.17 | 0.20 | 0.89 | −2.93 | 43 | NM_133639 |
| SCUBE2 | signal peptide, CUB domain and EGF like domain containing 2 | 1.29 | 3.00 | −3.51 | −1.86 | 44 | NM_020974 |
| SDC1 | syndecan 1 | 0.39 | 0.13 | −0.01 | −2.41 | 45 | NM_001006946 |
| SERPINB13 | serpin family B member 13 | −0.64 | −2.10 | 5.68 | −2.94 | 46 | NM_001307923 |
| SFRP2 | secreted frizzled related protein 2 | −6.65 | 2.50 | 0.68 | 1.68 | 47 | NM_003013 |
| SFRP4 | secreted frizzled related protein 4 | −5.67 | 3.09 | 0.38 | 2.19 | 48 | NM_003014 |
| SLC30A2 | solute carrier family 30 member 2 | 2.17 | 3.26 | −4.60 | −3.18 | 49 | NM_001004434 |
| SMOC2 | SPARC related modular calcium binding 2 | −1.41 | 2.14 | −0.44 | 1.00 | 50 | NM_022138 |
| SNX31 | sorting nexin 31 | 1.40 | 2.05 | −6.48 | −7.24 | 51 | NM_152628 |
| SPRR2A | small proline rich protein 2A | −1.49 | −0.32 | 5.64 | −1.95 | 52 | NM_005988 |
| SSC5D | scavenger receptor cysteine rich family member with 5 domains | −2.38 | 1.82 | 0.09 | 1.78 | 53 | NM_001144950 |
| TBX3 | T-box 3 | 1.48 | 0.55 | −3.24 | −2.08 | 54 | NM_005996 |
| TLE2 | transducin like enhancer of split 2 | 0.96 | 0.69 | −2.92 | −1.06 | 55 | NM_003260 |
| TOX3 | TOX high mobility group box family member 3 | 2.44 | 2.08 | −6.52 | −5.74 | 56 | NM_001080430 |

TABLE 1-continued

Gene Centroids of 60 Classifier Biomarkers for the Bladder Cancer Subtypes

| Gene Symbol | Gene Name | I (Luminal) | II (Luminal Infiltrated) | III (Basal) | IV (Neuronal/Basal Infiltrated) | SEQ ID NO: | GenBank Accession Number* |
|---|---|---|---|---|---|---|---|
| UPK1A | uroplakin 1A | 1.94 | 2.82 | −5.92 | −6.97 | 57 | NM_007000 |
| UPK2 | uroplakin 2 | 1.85 | 2.45 | −5.94 | −6.04 | 58 | NM_006760 |
| UPK3A | uroplakin 3A | 1.88 | 3.61 | −5.65 | −4.89 | 59 | NM_006953 |
| ZNF750 | zinc finger protein 750 | −0.07 | 0.52 | 0.82 | −3.97 | 60 | NM_024702 |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 2

Gene Centroids of 56 Classifier Biomarkers for the Bladder Cancer Subtypes

| Gene Symbol | Gene Name | I (Luminal) | II (Luminal Infiltrated) | III (Basal) | IV (Basal infiltrated/ neuronal) | SEQ ID NO. | GenBank Accession Number* |
|---|---|---|---|---|---|---|---|
| ALDH1L2 | aldehyde dehydrogenase 1 family member L2 | −2.95 | 0.51 | 0.59 | 1.31 | 1 | NM_001034173 |
| ANXA6 | annexin A6 | −2.00 | 0.64 | 0.09 | 1.66 | 2 | NM_001155 |
| ARSI | arylsulfatase family member I | −3.67 | 0.42 | 1.72 | 1.23 | 3 | NM_001012301 |
| BNC1 | basonuclin 1 | −1.48 | −0.57 | 7.97 | 2.24 | 5 | NM_001717 |
| C17orf28 | HID1 domain containing | 0.80 | 0.61 | −3.52 | −2.18 | 7 | NM_030630 |
| C1orf126 | TMEM51 antisense RNA 1 | 1.65 | 0.18 | −1.38 | −1.99 | 61 | NR_027136 |
| CA9 | carbonic anhydrase 9 | 0.70 | −4.00 | 1.43 | −1.19 | 62 | NM_001216 |
| CAPN5 | calpain 5 | 1.17 | 1.17 | −2.49 | −1.86 | 8 | NM_004055 |
| CCDC80 | coiled-coil domain containing 80 | −3.08 | 1.14 | 0.43 | 1.87 | 9 | NM_199511 |
| CD109 | CD109 molecule | −2.26 | −0.32 | 2.62 | 1.52 | 63 | NM_133493 |
| CD163 | CD163 molecule | −2.95 | 0.75 | 0.40 | 2.64 | 64 | NM_004244 |
| CMKLR1 | chemerin chemokine-like receptor 1 | −2.01 | 0.54 | 0.30 | 2.38 | 65 | NM_001142343 |
| CTHRC1 | collagen triple helix repeat containing 1 | −3.30 | 0.61 | 0.64 | 1.15 | 12 | NM_138455 |
| DSG3 | desmoglein 3 | −2.16 | −1.59 | 7.87 | −1.24 | 13 | NM_001944 |
| E2F7 | E2F transcription factor 7 | −0.19 | −1.12 | 0.99 | 0.36 | 66 | NM_203394 |
| EMILIN1 | elastin microfibril interfacer 1 | −1.96 | 1.86 | −0.20 | 1.84 | 14 | NM_007046 |
| EMP3 | epithelial membrane protein 3 | −1.89 | 0.34 | 0.70 | 2.16 | 67 | NM_001425 |
| FAM174B | family with sequence similarity 174 member B | 1.46 | 0.57 | −3.03 | −1.94 | 68 | NM_207446 |
| FER1L4 | fer-1 like family member 4, pseudogene | 1.71 | 0.68 | −3.30 | −3.10 | 69 | NR_119376 |
| GFPT2 | glutamine-fructose-6-phosphate transaminase 2 | −4.37 | 0.83 | 0.74 | 1.95 | 23 | NM_005110 |
| GGT6 | gamma-glutamyltransferase 6 | 1.18 | 0.33 | −2.23 | −5.61 | 24 | NM_001122890 |

TABLE 2-continued

Gene Centroids of 56 Classifier Biomarkers for the Bladder Cancer Subtypes

| Gene Symbol | Gene Name | I (Luminal) | II (Luminal Infiltrated) | III (Basal) | IV (Basal infiltrated/ neuronal) | SEQ ID NO. | GenBank Accession Number* |
|---|---|---|---|---|---|---|---|
| GRHL3 | grainyhead like transcription factor 3 | 1.02 | 1.46 | −1.39 | −6.23 | 26 | NM_021180 |
| HMGCS2 | 3-hydroxy-3-methylglutaryl-CoA synthase 2 | 3.62 | 2.44 | −6.28 | −6.91 | 70 | NM_005518 |
| IL20RB | interleukin 20 receptor subunit beta | −0.89 | −0.97 | 4.28 | −0.59 | 27 | NM_144717 |
| KRT6A | keratin 6A | −2.15 | −2.48 | 7.61 | −0.59 | 28 | NM_005554 |
| KRT6B | keratin 6B | −1.53 | −2.24 | 7.55 | −0.39 | 29 | NM_005555 |
| KRT6C | keratin 6C | −1.76 | −2.57 | 7.25 | −1.05 | 30 | NM_173086 |
| LOC100188947 | HECTD2 antisense RNA 1 | 3.20 | 2.48 | −3.88 | −4.38 | 32 | NR_024467 |
| MRVI1 | murine retroyirus integration site 1 homolog | −1.19 | 1.65 | −0.15 | 0.54 | 33 | NM_001098579 |
| PIK3AP1 | phosphoinositide-3-kinase adaptor protein 1 | −1.83 | 0.19 | 0.50 | 2.18 | 71 | NM_152309 |
| PPFIBP2 | PPFIA binding protein 2 | 1.22 | 0.73 | −1.84 | −2.20 | 72 | NM_003621 |
| PVRL4 | nectin cell adhesion molecule 4 | 0.49 | 0.36 | −0.39 | −2.97 | 40 | NM_030916 |
| RAPGEFL1 | Rap guanine nucleotide exchange factor like 1 | 1.01 | 0.10 | −0.43 | −3.66 | 41 | NM_001303533 |
| RHOU | ras homolog family member U | 0.59 | 1.22 | −2.78 | −1.70 | 42 | NM_021205 |
| RHOV | ras homolog family member V | −0.17 | 0.20 | 0.89 | −2.93 | 43 | NM_133639 |
| SARM1 | sterile alpha and TIR motif containing 1 | 0.52 | 0.47 | −1.87 | −0.36 | 73 | NM_015077 |
| SDC1 | syndecan 1 | 0.39 | 0.13 | −0.01 | −2.41 | 45 | NM_001006946 |
| SERPINB13 | serpin family B member 13 | −0.64 | −2.10 | 5.68 | −2.94 | 46 | NM_001307923 |
| SERPINB3 | serpin family B member 3 | −0.99 | −4.25 | 5.93 | −2.21 | 74 | NM_006919 |
| SERPINB4 | serpin family B member 4 | −1.12 | −3.51 | 5.84 | −1.62 | 75 | NM_002974 |
| SFRP2 | secreted frizzled related protein 2 | −6.65 | 2.50 | 0.68 | 1.68 | 47 | NM_003013 |
| SFRP4 | secreted frizzled related protein 4 | −5.67 | 3.09 | 0.38 | 2.19 | 48 | NM_003014 |
| SLC7A7 | solute carrier family 7 member 7 | −2.05 | 0.37 | 0.47 | 2.01 | 76 | NR_040448 |
| SNX31 | sorting nexin 31 | 1.40 | 2.05 | −6.48 | −7.24 | 51 | NM_152628 |
| SPRR2A | small proline rich protein 2A | −1.49 | −0.32 | 5.64 | −1.95 | 52 | NM_005988 |
| TBX2 | T-box 2 | 1.54 | 1.51 | −2.76 | −1.55 | 77 | NM_005994 |
| TBX3 | T-box 3 | 1.48 | 0.55 | −3.24 | −2.08 | 54 | NM_005996 |
| TLE2 | transducin like enhancer of split 2 | 0.96 | 0.69 | −2.92 | −1.06 | 55 | NM_003260 |
| TOX3 | TOX high mobility group box family member 3 | 2.44 | 2.08 | −6.52 | −5.74 | 56 | NM_001080430 |
| TSSK2 | testis specific serine kinase 2 | 0.00 | 0.00 | 0.00 | 0.00 | 78 | NM_053006 |
| UPK1A | uroplakin 1A | 1.94 | 2.82 | −5.92 | −6.97 | 57 | NM_007000 |
| UPK2 | uroplakin 2 | 1.85 | 2.45 | −5.94 | −6.04 | 58 | NM_006760 |

TABLE 2-continued

Gene Centroids of 56 Classifier Biomarkers for the Bladder Cancer Subtypes

| Gene Symbol | Gene Name | I (Luminal) | II (Luminal Infiltrated) | III (Basal) | IV (Basal infiltrated/ neuronal) | SEQ ID NO. | GenBank Accession Number* |
|---|---|---|---|---|---|---|---|
| UPK3A | uroplakin 3A | 1.88 | 3.61 | −5.65 | −4.89 | 59 | NM_006953 |
| VSIG4 | V-set and inununoglobulin domain containing 4 | −2.66 | 0.59 | 0.58 | 2.61 | 79 | NM_007268 |
| ZNF750 | zinc finger protein 750 | −0.07 | 0.52 | 0.82 | −3.97 | 60 | NM_024702 |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

In one embodiment, the relative gene expression levels (e.g., centroid classifier coefficients) of the classifier biomarkers for bladder cancer subtyping are shown in Table 1 or Table 2. In one embodiment, all 60 genes of Table 1, or all 56 genes of Table 2, can be used to classify the subtypes of bladder cancer. In one embodiment, all 60 genes of Table 1, or all 56 genes of Table 2, can be used to classify the subtypes of MIBC. In some embodiments, the up-regulation of a classifier biomarker (e.g. expression is increased) can refer to an expression value that is positive (i.e., higher than zero) relative to a reference or control as provided herein. In some embodiments, the down-regulation of a classifier biomarker (e.g. expression is decreased) can refer to an expression value that is negative (i.e., lower than zero) relative to a reference or control as provided herein. In some embodiments, a classifier biomarker may have no specific effects on a certain bladder cancer subtype when the expression level equals to zero. For example, ALDH1L2 is down-regulated in the luminal subtype, whereas it is up-regulated in luminal infiltrated, basal, and basal infiltrated/neuronal subtypes. In another example, BCAS1 is up-regulated in both luminal and luminal infiltrated subtypes, whereas it is down-regulated in both basal and basal infiltrated/neuronal subtypes.

In some embodiments, determining bladder cancer (e.g., MIBC) subtypes can further include measuring the expression of at least one biomarker from an additional set of biomarker classifiers. In some embodiments, an additional set of biomarker classifiers can include an 11 gene signature comprising BIRC5, CCNB1, CDC20, CDCA1, CEP55, KNTC2, MKI67, PTTG1, RRM2, TYMS, and UBE2C (Martin M. et al., Breast Cancer Res Treat, 138: 457-466 (2013), which is herein incorporated by reference). In one embodiment, the 11 gene signature is related to the signature of cell proliferation. In some embodiments, an additional set of biomarker classifiers can include an 18 gene signature found in US2016115551, which is herein incorporated by reference. In one embodiment, the 18 gene signature is related to the signature of cell proliferation. In some embodiments, an additional set of biomarker classifiers can include a 26 gene signature found in U.S. 62/789,668 filed Jan. 8, 2019, which is herein incorporated by reference. In one embodiment, the 26 gene signature is related to the signature of cell proliferation. In some embodiments, an additional set of biomarker classifiers can include a 5 gene signature comprising tumor driver genes such as TP53 and RB1, and receptor tyrosine kinases including FGFR2, FGFR3, and ERBB2. In one embodiment, the 5 gene signature is related to the signature of tumor driver genes. In some embodiments, the biomarker classifiers can also include immune cell signatures that are known in the art such as the signatures found in Thorsson, V. et al., 2018, The immune landscape of cancer. *Immunity,* 48(4), pp. 812-830. Bindea G. et al., Immunity, 39(4), 782-95 (2013), Faruki H. et al., JTO, 12(6): 943-953 (2017), Charoentong P. et al., Cell reports, 18, 248-262 (2017) and/or WO2017/201165 and WO2017/201164, each of which is herein incorporated by reference). In some embodiments, an additional set of biomarker classifiers can include assessing tumor purity ABSOLUTE derived from the TCGA supplementary data. In some embodiments, an additional set of biomarker classifiers can include the bladder cancer biomarker signature described in Gene Expression Omnibus (GEO) dataset: GSE87304, Seiler R. et al., Eur Urol, 72(4):544-554 (2017); Gene Expression Omnibus (GEO) dataset: GSE32894, Sjödahl G. et al., Clin Cancer Res, 18(12):3377-86 (2012), each of which is herein incorporated by reference).

In some embodiments, determining bladder cancer subtypes can further include assessing tumor mutation burden (TMB) and/or TMB rate. In one embodiment, the TMB value and/or rate can be calculated using any method known in the art. In one embodiment, the TMB value and/or rate can be calculated from RNA (e.g., via transcriptome profiling or RNA sequencing)) as provided in U.S. 62/771,702 filed Nov. 27, 2018 and U.S. 62/743,257 filed Oct. 9, 2018, which is herein incorporated by reference herein.

In some embodiments, determining bladder cancer (e.g., MIBC) subtypes can further include determining a cell of origin subtype of the bladder cancer sample. In one embodiment, cell of origin subtype is determined using any method known in the art such as, for example, as provided in Hoadley et al, Cell. 2018 Apr. 5; 173(2):291-304, which is herein incorporated by reference herein.

Diagnostic Uses

In one embodiment, the methods and compositions provided herein allow for the differentiation of the four subtypes of bladder cancer, or MIBC: (I) luminal, (II) luminal infiltrated, (III) basal, and (IV) basal infiltrated/neuronal.

In general, the methods provided herein are used to classify a bladder cancer sample as a particular bladder cancer subtype (e.g. subtype of bladder cancer). In one embodiment, the method comprises measuring, detecting or determining an expression level of at least one of the classifier biomarkers of any publically available bladder cancer expression dataset. In one embodiment, the method comprises detecting or determining an expression level of at least one of the classifier biomarkers of Table 1, Table 2 or any additional set of biomarker classifiers as disclosed herein in a bladder cancer sample obtained from a patient or a subject. The bladder cancer sample for the detection or differentiation methods described herein can be a sample previously determined or diagnosed as an MIBC sample. The previous diagnosis can be based on a histological analysis. The histological analysis can be performed by one or more pathologists.

In one embodiment, the measuring or detecting step is at the nucleic acid level by performing RNA-seq, a reverse transcriptase polymerase chain reaction (RT-PCR) or a hybridization assay with oligonucleotides that are substantially complementary to portions of cDNA molecules of the at least one classifier biomarker (such as the classifier biomarkers of Table 1, Table 2 or any additional set of biomarker classifiers as disclosed herein) under conditions suitable for RNA-seq, RT-PCR or hybridization and obtaining expression levels of the at least one classifier biomarkers based on the detecting step. The expression levels of the at least one of the classifier biomarkers are then compared to reference expression levels of the at least one of the classifier biomarkers (such as the classifier biomarkers of Table 1, Table 2 or any additional set of biomarker classifiers as disclosed herein) from at least one sample training set. The at least one sample training set can comprise, (i) expression levels of the at least one biomarker from a sample that overexpresses the at least one biomarker, (ii) expression levels from a reference luminal, luminal infiltrated, basal, and basal infiltrated/neuronal sample, or (iii) expression levels from MIBC sample, and classifying the bladder cancer sample as a luminal, luminal infiltrated, basal, or basal infiltrated/neuronal subtype based on the results of the comparing step. In one embodiment, the comparing step can comprise applying a statistical algorithm which comprises determining a correlation between the expression data obtained from the bladder tissue or cancer sample and the expression data from the at least one training set(s); and classifying the bladder tissue or cancer sample as a luminal, luminal infiltrated, basal, or basal infiltrated/neuronal sample subtype based on the results of the statistical algorithm. In one embodiment, the statistical algorithm for the comparing step can be an algorithm that comprises determining a correlation between the expression data obtained from the bladder tissue or cancer sample and centroids constructed from the expression levels or profiles measured or detected for the at least one classifier biomarkers (such as the classifier biomarkers of Table 1, Table 2 or any additional set of biomarker classifiers as disclosed herein) from the at least one training set. The subtype for the bladder cancer sample can then be assigned by finding the centroid to which it is nearest from the centroids constructed from the expression data from the at least one training set, using any distance measure e.g. Euclidean distance or correlation. The centroids can be constructed using any method known in the art for generating centroids such as, for example, those found in Mullins et al. (2007) Clin Chem. 53(7):1273-9 or Dabney (2005) Bioinformatics 21(22):4148-4154 Subtype can then be assigned to the bladder cancer sample obtained from subject based on the use of a classification to the nearest centroid (CLaNC) algorithm as applied to the expression data generated from the bladder cancer sample and the centroid(s) constructed for the at least one training set. The CLaNC algorithm for use in the methods, compositions and kits provided herein can be the CLaNC algorithm implemented by the CLaNC software found in Dabney A R. ClaNC: Point-and-click software for classifying microarrays to nearest centroids. Bioinformatics. 2006; 22: 122-123 or equivalents or derivatives thereof.

In one embodiment, the method comprises probing the levels of at least one of the classifier biomarkers provided herein, such as the classifier biomarkers of Table 1, Table 2 or any additional set of biomarker classifiers disclosed herein, at the nucleic acid level, in a bladder cancer sample obtained from the patient. The bladder cancer sample can be a sample previously determined or diagnosed as a MIBC sample. The previous diagnosis can be based on a histological analysis. The histological analysis can be performed by one or more pathologists. The probing step, in one embodiment, comprises mixing the sample with one or more oligonucleotides that are substantially complementary to portions of cDNA molecules of the at least one classifier biomarkers provided herein, such as the classifier biomarkers of Table 1, Table 2 or any additional set of biomarker classifiers disclosed herein under conditions suitable for hybridization of the one or more oligonucleotides to their complements or substantial complements; detecting whether hybridization occurs between the one or more oligonucleotides to their complements or substantial complements; and obtaining hybridization values of the at least one classifier biomarkers based on the detecting step. The hybridization values of the at least one classifier biomarkers are then compared to reference hybridization value(s) from at least one sample training set. The bladder cancer sample is classified, for example, as luminal, luminal infiltrated, basal, or basal infiltrated/neuronal based on the results of the comparing step. In one embodiment, the hybridization values of the bladder cancer sample can be compared to centroids constructed from the hybridization values obtained for the training set.

The bladder tissue sample can be any sample isolated from a human subject or patient. For example, in one embodiment, the analysis is performed on bladder biopsies that are embedded in paraffin wax. In one embodiment, the sample can be a fresh frozen bladder tissue sample. In another embodiment, the sample can be a bodily fluid obtained from the patient. The bodily fluid can be blood or fractions thereof (i.e., serum, plasma), urine, saliva, sputum or cerebrospinal fluid (CSF). The sample can contain cellular as well as extracellular sources of nucleic acid for use in the methods provided herein. The extracellular sources can be cell-free DNA and/or exosomes. In one embodiment, the sample can be a cell pellet or a wash. This aspect provides a means to improve current diagnostics by accurately identifying the major histological types, even from small biopsies. The methods as provided herein, including the RT-PCR methods, are sensitive, precise and have multianalyte capability for use with paraffin-embedded samples. See, for example, Cronin et al. (2004) *Am. J Pathol.* 164 (1):35-42, herein incorporated by reference.

Formalin fixation and tissue embedding in paraffin wax is a universal approach for tissue processing prior to light microscopic evaluation. A major advantage afforded by formalin-fixed paraffin-embedded (FFPE) specimens is the preservation of cellular and architectural morphologic detail in tissue sections. (Fox et al. (1985) J Histochem Cytochem 33:845-853). The standard buffered formalin fixative in which biopsy specimens are processed is typically an aqueous solution containing 37% formaldehyde and 10-15% methyl alcohol. Formaldehyde is a highly reactive dipolar compound that results in the formation of protein-nucleic acid and protein-protein crosslinks in vitro (Clark et al. (1986) J Histochem Cytochem 34:1509-1512; McGhee and von Hippel (1975) Biochemistry 14:1281-1296, each incorporated by reference herein).

In one embodiment, the sample used herein is obtained from an individual, and comprises formalin-fixed paraffin-embedded (FFPE) tissue. However, other tissue and sample types are amenable for use herein. In one embodiment, the other tissue and sample types can be fresh frozen tissue, wash fluids, or cell pellets, or the like. In one embodiment, the sample can be a bodily fluid obtained from the individual. The bodily fluid can be blood or fractions thereof (e.g., serum, plasma), urine, sputum, saliva or cerebrospinal fluid (CSF). A biomarker nucleic acid as provided herein can be extracted from a cell or can be cell free or extracted from an extracellular vesicular entity such as an exosome.

Methods are known in the art for the isolation of RNA from FFPE tissue. In one embodiment, total RNA can be isolated from FFPE tissues as described by Bibikova et al. (2004) American Journal of Pathology 165:1799-1807, herein incorporated by reference. Likewise, the High Pure RNA Paraffin Kit (Roche) can be used. Paraffin is removed by xylene extraction followed by ethanol wash. RNA can be isolated from sectioned tissue blocks using the MasterPure Purification kit (Epicenter, Madison, Wis.); a DNase I treatment step is included. RNA can be extracted from frozen samples using Trizol reagent according to the supplier's instructions (Invitrogen Life Technologies, Carlsbad, Calif.). Samples with measurable residual genomic DNA can be resubjected to DNaseI treatment and assayed for DNA contamination. All purification, DNase treatment, and other steps can be performed according to the manufacturer's protocol. After total RNA isolation, samples can be stored at −80° C. until use.

General methods for mRNA extraction are well known in the art and are disclosed in standard textbooks of molecular biology, including Ausubel et al., ed., Current Protocols in Molecular Biology, John Wiley & Sons, New York 1987-1999. Methods for RNA extraction from paraffin embedded tissues are disclosed, for example, in Rupp and Locker (Lab Invest. 56:A67, 1987) and De Andres et al. (Biotechniques 18:42-44, 1995). In particular, RNA isolation can be performed using a purification kit, a buffer set and protease from commercial manufacturers, such as Qiagen (Valencia, Calif.), according to the manufacturer's instructions. For example, total RNA from cells in culture can be isolated using Qiagen RNeasy mini-columns. Other commercially available RNA isolation kits include MasterPure™. Complete DNA and RNA Purification Kit (Epicentre, Madison, Wis.) and Paraffin Block RNA Isolation Kit (Ambion, Austin, Tex.). Total RNA from tissue samples can be isolated, for example, using RNA Stat-60 (Tel-Test, Friendswood, Tex.). RNA prepared from a tumor can be isolated, for example, by cesium chloride density gradient centrifugation. Additionally, large numbers of tissue samples can readily be processed using techniques well known to those of skill in the art, such as, for example, the single-step RNA isolation process of Chomczynski (U.S. Pat. No. 4,843,155, incorporated by reference in its entirety for all purposes).

In one embodiment, a sample comprises cells harvested from a bladder tissue sample, for example, a MIBC sample. Cells can be harvested from a biological sample using standard techniques known in the art. For example, in one embodiment, cells are harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract nucleic acid, e.g., messenger RNA. All samples obtained from a subject, including those subjected to any sort of further processing, are considered to be obtained from the subject.

The sample, in one embodiment, is further processed before the detection of the biomarker levels of the combination of biomarkers set forth herein. For example, mRNA in a cell or tissue sample can be separated from other components of the sample. The sample can be concentrated and/or purified to isolate mRNA in its non-natural state, as the mRNA is not in its natural environment. For example, studies have indicated that the higher order structure of mRNA in vivo differs from the in vitro structure of the same sequence (see, e.g., Rouskin et al. (2014). Nature 505, pp. 701-705, incorporated herein in its entirety for all purposes).

mRNA from the sample in one embodiment, is hybridized to a synthetic DNA probe, which in some embodiments, includes a detection moiety (e.g., detectable label, capture sequence, barcode reporting sequence). Accordingly, in these embodiments, a non-natural mRNA-cDNA complex is ultimately made and used for detection of the biomarker. In another embodiment, mRNA from the sample is directly labeled with a detectable label, e.g., a fluorophore. In a further embodiment, the non-natural labeled-mRNA molecule is hybridized to a cDNA probe and the complex is detected.

In one embodiment, once the mRNA is obtained from a sample, it is converted to complementary DNA (cDNA) prior to the hybridization reaction or is used in a hybridization reaction together with one or more cDNA probes. cDNA does not exist in vivo and therefore is a non-natural molecule. Furthermore, cDNA-mRNA hybrids are synthetic and do not exist in vivo. Besides cDNA not existing in vivo, cDNA is necessarily different than mRNA, as it includes deoxyribonucleic acid and not ribonucleic acid. The cDNA is then amplified, for example, by the polymerase chain reaction (PCR) or other amplification method known to those of ordinary skill in the art. For example, other amplification methods that may be employed include the ligase chain reaction (LCR) (Wu and Wallace, Genomics, 4:560 (1989), Landegren et al., Science, 241:1077 (1988), incorporated by reference in its entirety for all purposes, transcription amplification (Kwoh et al., *Proc. Natl. Acad. Sci. USA,* 86:1173 (1989), incorporated by reference in its entirety for all purposes), self-sustained sequence replication (Guatelli et al., *Proc. Nat. Acad. Sci. USA,* 87:1874 (1990), incorporated by reference in its entirety for all purposes), incorporated by reference in its entirety for all purposes, and nucleic acid based sequence amplification (NASBA). Guidelines for selecting primers for PCR amplification are known to those of ordinary skill in the art. See, e.g., McPherson et al., PCR Basics: From Background to Bench, Springer-Verlag, 2000, incorporated by reference in its entirety for all purposes. The product of this amplification reaction, i.e., amplified cDNA is also necessarily a non-natural product. First, as mentioned above, cDNA is a non-natural molecule. Second, in the case of PCR, the amplification process serves to create hundreds of millions of cDNA copies for every individual cDNA molecule of starting material. The numbers of copies generated are far removed from the number of copies of mRNA that are present in vivo.

In one embodiment, cDNA is amplified with primers that introduce an additional DNA sequence (e.g., adapter, reporter, capture sequence or moiety, barcode) onto the fragments (e.g., with the use of adapter-specific primers), or mRNA or cDNA biomarker sequences are hybridized directly to a cDNA probe comprising the additional sequence (e.g., adapter, reporter, capture sequence or moiety, barcode). Amplification and/or hybridization of mRNA to a cDNA probe therefore serves to create non-natural double stranded molecules from the non-natural single stranded cDNA, or the mRNA, by introducing additional sequences and forming non-natural hybrids. Further, as known to those of ordinary skill in the art, amplification procedures have error rates associated with them. Therefore, amplification introduces further modifications into the cDNA molecules. In one embodiment, during amplification with the adapter-specific primers, a detectable label, e.g., a fluorophore, is added to single strand cDNA molecules. Amplification therefore also serves to create DNA complexes that do not occur in nature, at least because (i) cDNA does not exist in vivo, (i) adapter sequences are added to the ends of cDNA molecules to make DNA sequences that do not exist in vivo, (ii) the error rate associated with amplification further creates DNA sequences that do not exist in vivo, (iii) the disparate structure of the cDNA molecules as compared to what exists in nature, and (iv) the chemical addition of a detectable label to the cDNA molecules.

In some embodiments, the expression of a biomarker of interest is detected at the nucleic acid level via detection of non-natural cDNA molecules.

In some embodiments, the method for bladder cancer subtyping includes detecting expression levels of a classifier biomarker set in a sample obtained from a subject. The method can further comprise detecting expression levels of said classifier biomarker set in one or more control or reference samples. The one or more control or reference samples can be selected from a normal or bladder cancer-free sample, a bladder cancer luminal sample, a bladder cancer luminal infiltrated sample, a bladder cancer basal sample, a bladder cancer basal infiltrated/neuronal sample, or any combination thereof. In some embodiments, the detecting includes all of the classifier biomarkers of Table 1, Table 2 or any additional set of biomarker classifiers as disclosed herein at the nucleic acid level or protein level. In some embodiments, the detecting includes all of the classifier biomarkers of Table 1 or Table 2 at the nucleic acid level or protein level. In another embodiment, a single or a subset or a plurality of the classifier biomarkers of Table 1 are detected, for example, from about 1 to about 5, from about 5 to about 15, from about 15 to about 30, from about 30 to about 45, from about 45 to about 60 of the biomarkers in Table 1 are detected in a method to determine the bladder cancer luminal subtype. In another embodiment, each of the biomarkers from Table 1 is detected in a method to determine the bladder cancer subtype. In another embodiment, any of 60 of the biomarkers from Table 1 are selected as the gene signatures for a specific bladder cancer subtype. In another embodiment, a single or a subset or a plurality of the classifier biomarkers of Table 2 are detected, for example, from about 1 to about 5, from about 5 to about 15, from about 15 to about 30, from about 30 to about 45, from about 45 to about 56 of the biomarkers in Table 2 are detected in a method to determine the bladder cancer luminal subtype. In another embodiment, each of the biomarkers from Table 2 is detected in a method to determine the bladder cancer subtype. In another embodiment, any of 60 of the biomarkers from Table 2 are selected as the gene signatures for a specific bladder cancer subtype. In some embodiments, the detecting includes all of the classifier biomarkers of Table 2 at the nucleic acid level or protein level. In another embodiment, a single or a subset or a plurality of the classifier biomarkers of Table 2 are detected, for example, from about 5 to about 10, from about 10 to about 20, from about 20 to about 34, from about 30 to about 56, of the biomarkers in Table 2 are detected in a method to determine the bladder cancer subtype. In another embodiment, each of the biomarkers from Table 2 is detected in a method to determine the bladder cancer subtype. In another embodiment, any of 56 of the biomarkers from Table 2 are selected as the gene signatures for a specific bladder cancer subtype. The detecting can be performed by any suitable technique including, but not limited to, RNA-seq, a reverse transcriptase polymerase chain reaction (RT-PCR), a microarray hybridization assay, or another hybridization assay, e.g., a NanoString assay for example, with primers and/or probes specific to the classifier biomarkers, and/or the like. In some cases, the primers useful for the amplification methods (e.g., RT-PCR or qRT-PCR) are any forward and reverse primers suitable for binding to a classifier biomarker provided herein, such as the classifier biomarkers of Table 1, Table 2 or any additional set of biomarker classifiers as disclosed herein.

The biomarkers described herein include RNA comprising the entire or partial sequence of any of the nucleic acid sequences of interest, or their non-natural cDNA product, obtained synthetically in vitro in a reverse transcription reaction. The term "fragment" is intended to refer to a portion of the polynucleotide that generally comprise at least 10, 15, 20, 50, 75, 100, 150, 200, 250, 300, 350, 400, 450, 500, 550, 600, 650, 700, 800, 900, 1,000, 1,200, or 1,500 contiguous nucleotides, or up to the number of nucleotides present in a full-length biomarker polynucleotide disclosed herein. A fragment of a biomarker polynucleotide will generally encode at least 15, 25, 30, 50, 100, 150, 200, or 250 contiguous amino acids, or up to the total number of amino acids present in a full-length biomarker protein as provided herein.

In some embodiments, overexpression, such as of an RNA transcript or its expression product, is determined by normalization to the level of reference RNA transcripts or their expression products, which can be all measured transcripts (or their products) in the sample or a particular reference set of RNA transcripts (or their non-natural cDNA products). Normalization is performed to correct for or normalize away both differences in the amount of RNA or cDNA assayed and variability in the quality of the RNA or cDNA used. Therefore, an assay typically measures and incorporates the expression of certain normalizing genes, including well known housekeeping genes, such as, for example, GAPDH and/or (3-Actin. Alternatively, normalization can be based on the mean or median signal of all of the assayed biomarkers or a large subset thereof (global normalization approach).

Isolated mRNA can be used in hybridization or amplification assays that include, but are not limited to, Southern or Northern analyses, PCR analyses and probe arrays, NanoString Assays. One method for the detection of mRNA levels involves contacting the isolated mRNA or synthesized cDNA with a nucleic acid molecule (probe) that can hybridize to the mRNA encoded by the gene being detected. The nucleic acid probe can be, for example, a cDNA, or a portion thereof, such as an oligonucleotide of at least 7, 15, 30, 50, 100, 250, or 500 nucleotides in length and sufficient to specifically hybridize under stringent conditions to the non-natural cDNA or mRNA biomarker.

As explained above, in one embodiment, once the mRNA is obtained from a sample, it is converted to complementary DNA (cDNA) in a hybridization reaction. Conversion of the mRNA to cDNA can be performed with oligonucleotides or primers comprising sequence that is complementary to a portion of a specific mRNA. Conversion of the mRNA to cDNA can be performed with oligonucleotides or primers comprising random sequence. Conversion of the mRNA to cDNA can be performed with oligonucleotides or primers comprising sequence that is complementary to the poly(A) tail of an mRNA. cDNA does not exist in vivo and therefore is a non-natural molecule. In a further embodiment, the cDNA is then amplified, for example, by the polymerase chain reaction (PCR) or other amplification method known to those of ordinary skill in the art. PCR can be performed with the forward and/or reverse primers comprising sequence complementary to at least a portion of a classifier biomarker provided herein, such as the classifier biomarkers of Table 1, Table 2 or any additional set of biomarker classifiers as disclosed herein. The product of this amplification reaction, i.e., amplified cDNA is necessarily a non-natural product. As mentioned above, cDNA is a non-natural molecule. Second, in the case of PCR, the amplification process serves to create hundreds of millions of cDNA copies for every individual cDNA molecule of starting material. The number of copies generated is far removed from the number of copies of mRNA that are present in vivo.

In one embodiment, cDNA is amplified with primers that introduce an additional DNA sequence (adapter sequence) onto the fragments (with the use of adapter-specific primers). The adaptor sequence can be a tail, wherein the tail sequence is not complementary to the cDNA. For example, the forward and/or reverse primers comprising sequence complementary to at least a portion of a classifier biomarker provided herein, such as the classifier biomarkers of Table 1, Table 2 or any additional set of biomarker classifiers as disclosed herein can comprise tail sequence. Amplification therefore serves to create non-natural double stranded molecules from the non-natural single stranded cDNA, by introducing barcode, adapter and/or reporter sequences onto the already non-natural cDNA. In one embodiment, during amplification with the adapter-specific primers, a detectable label, e.g., a fluorophore, is added to single strand cDNA molecules. Amplification therefore also serves to create DNA complexes that do not occur in nature, at least because (i) cDNA does not exist in vivo, (ii) adapter sequences are added to the ends of cDNA molecules to make DNA sequences that do not exist in vivo, (iii) the error rate associated with amplification further creates DNA sequences that do not exist in vivo, (iv) the disparate structure of the cDNA molecules as compared to what exists in nature, and (v) the chemical addition of a detectable label to the cDNA molecules.

In one embodiment, the synthesized cDNA (for example, amplified cDNA) is immobilized on a solid surface via hybridization with a probe, e.g., via a microarray. In another embodiment, cDNA products are detected via real-time polymerase chain reaction (PCR) via the introduction of fluorescent probes that hybridize with the cDNA products. For example, in one embodiment, biomarker detection is assessed by quantitative fluorogenic RT-PCR (e.g., with TaqMan® probes). For PCR analysis, well known methods are available in the art for the determination of primer sequences for use in the analysis.

Biomarkers provided herein in one embodiment, are detected via a hybridization reaction that employs a capture probe and/or a reporter probe. For example, the hybridization probe is a probe derivatized to a solid surface such as a bead, glass or silicon substrate. In another embodiment, the capture probe is present in solution and mixed with the patient's sample, followed by attachment of the hybridization product to a surface, e.g., via a biotin-avidin interaction (e.g., where biotin is a part of the capture probe and avidin is on the surface). The hybridization assay, in one embodiment, employs both a capture probe and a reporter probe. The reporter probe can hybridize to either the capture probe or the biomarker nucleic acid. Reporter probes e.g., are then counted and detected to determine the level of biomarker(s) in the sample. The capture and/or reporter probe, in one embodiment contain a detectable label, and/or a group that allows functionalization to a surface.

For example, the nCounter gene analysis system (see, e.g., Geiss et al. (2008) Nat. Biotechnol. 26, pp. 317-325, incorporated by reference in its entirety for all purposes, is amenable for use with the methods provided herein.

Hybridization assays described in U.S. Pat. Nos. 7,473,767 and 8,492,094, the disclosures of which are incorporated by reference in their entireties for all purposes, are amenable for use with the methods provided herein, i.e., to detect the biomarkers and biomarker combinations described herein.

Biomarker levels may be monitored using a membrane blot (such as used in hybridization analysis such as Northern, Southern, dot, and the like), or microwells, sample tubes, gels, beads, or fibers (or any solid support comprising bound nucleic acids). See, for example, U.S. Pat. Nos. 5,770,722, 5,874,219, 5,744,305, 5,677,195 and 5,445,934, each incorporated by reference in their entireties.

In one embodiment, microarrays are used to detect biomarker levels. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning hybridization intensities for each probe on the array are determined and converted to a quantitative value representing relative gene expression levels. See, for example, U.S. Pat. Nos. 6,040,138, 5,800,992 and 6,020,135, 6,033,860, and 6,344,316, each incorporated by reference in their entireties. High-density oligonucleotide arrays are particularly useful for determining the gene expression profile for a large number of RNAs in a sample.

Techniques for the synthesis of these arrays using mechanical synthesis methods are described in, for example, U.S. Pat. No. 5,384,261. Although a planar array surface is generally used, the array can be fabricated on a surface of virtually any shape or even a multiplicity of surfaces. Arrays can be nucleic acids (or peptides) on beads, gels, polymeric surfaces, fibers (such as fiber optics), glass, or any other appropriate substrate. See, for example, U.S. Pat. Nos. 5,770,358, 5,789,162, 5,708,153, 6,040,193 and 5,800,992, each incorporated by reference in their entireties. Arrays can be packaged in such a manner as to allow for diagnostics or other manipulation of an all-inclusive device. See, for example, U.S. Pat. Nos. 5,856,174 and 5,922,591, each incorporated by reference in their entireties.

Serial analysis of gene expression (SAGE) in one embodiment is employed in the methods described herein. SAGE is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. See, Velculescu et al. Science 270:484-87, 1995; Cell 88:243-51, 1997, incorporated by reference in its entirety.

An additional method of biomarker level analysis at the nucleic acid level is the use of a sequencing method, for example, RNAseq, next generation sequencing, and massively parallel signature sequencing (MPSS), as described by Brenner et al. (Nat. Biotech. 18:630-34, 2000, incorporated by reference in its entirety). This is a sequencing approach that combines non-gel-based signature sequencing with in vitro cloning of millions of templates on separate 5 μm diameter microbeads. First, a microbead library of DNA templates is constructed by in vitro cloning. This is followed by the assembly of a planar array of the template-containing microbeads in a flow cell at a high density (typically greater than $3.0\times10^6$ microbeads/$cm^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

Another method of biomarker level analysis at the nucleic acid level is the use of an amplification method such as, for example, RT-PCR or quantitative RT-PCR (qRT-PCR). Methods for determining the level of biomarker mRNA in a sample may involve the process of nucleic acid amplification, e.g., by RT-PCR (the experimental embodiment set forth in Mullis, 1987, U.S. Pat. No. 4,683,202), ligase chain reaction (Barany (1991) Proc. Natl. Acad. Sci. USA 88:189-193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques well known to those of skill in the art. Numerous different PCR or qRT-PCR protocols are known in the art and can be directly applied or adapted for use using the presently described compositions for the detection and/or quantification of expression of discriminative genes in a sample. See, for example, Fan et al. (2004) Genome Res. 14:878-885, herein incorporated by reference. Generally, in PCR, a target polynucleotide sequence is amplified by reaction with at least one oligonucleotide primer or pair of oligonucleotide primers. The primer(s) hybridize to a complementary region of the target nucleic acid and a DNA polymerase extends the primer(s) to amplify the target sequence. Under conditions sufficient to provide polymerase-based nucleic acid amplification products, a nucleic acid fragment of one size dominates the reaction products (the target polynucleotide sequence which is the amplification product). The amplification cycle is repeated to increase the concentration of the single target polynucleotide sequence. The reaction can be performed in any thermocycler commonly used for PCR.

Quantitative RT-PCR (qRT-PCR) (also referred as real-time RT-PCR) is preferred under some circumstances because it provides not only a quantitative measurement, but also reduced time and contamination. As used herein, “quantitative PCR” (or “real time qRT-PCR”) refers to the direct monitoring of the progress of a PCR amplification as it is occurring without the need for repeated sampling of the reaction products. In quantitative PCR, the reaction products may be monitored via a signaling mechanism (e.g., fluorescence) as they are generated and are tracked after the signal rises above a background level but before the reaction reaches a plateau. The number of cycles required to achieve a detectable or “threshold” level of fluorescence varies directly with the concentration of amplifiable targets at the beginning of the PCR process, enabling a measure of signal intensity to provide a measure of the amount of target nucleic acid in a sample in real time. A DNA binding dye (e.g., SYBR green) or a labeled probe can be used to detect the extension product generated by PCR amplification. Any probe format utilizing a labeled probe comprising sequence complementary to the sequences as provided herein may be used.

Immunohistochemistry methods are also suitable for detecting the levels of the biomarkers. Samples can be frozen for later preparation or immediately placed in a fixative solution. Tissue samples can be fixed by treatment with a reagent, such as formalin, gluteraldehyde, methanol, or the like and embedded in paraffin. Methods for preparing slides for immunohistochemical analysis from formalin-fixed, paraffin-embedded tissue samples are well known in the art.

In one embodiment, the levels of the biomarkers provided herein, such as the classifier biomarkers of Table 1 (or subsets thereof, for example 1 to 5, 5 to 15, 15 to 30, 30 to 45, 45 to 60 of the biomarkers biomarkers) or Table 2 (or subsets thereof, for example 1 to 5, 5 to 15, 15 to 30, 30 to 45, 45 to 56 of the biomarkers biomarkers), are normalized against the expression levels of all RNA transcripts or their non-natural cDNA expression products, or protein products in the sample, or of a reference set of RNA transcripts or a reference set of their non-natural cDNA expression products, or a reference set of their protein products in the sample. In one embodiment, the levels of the biomarkers provided herein, such as any of the additional set of classifier biomarkers disclosed herein are normalized against the expression levels of all RNA transcripts or their non-natural cDNA expression products, or protein products in the sample, or of a reference set of RNA transcripts or a reference set of their non-natural cDNA expression products, or a reference set of their protein products in the sample. The reference set of RNA transcripts or the reference set of their non-natural cDNA expression products, or the reference set of their protein products in the sample can be one or more housekeeping genes or their protein products.

In one embodiment, bladder cancer subtypes can be evaluated using levels of protein expression of one or more of the classifier biomarkers provided herein, such as the classifier biomarkers of Table 1, Table 2 or any additional set of biomarker classifiers disclosed herein. The level of protein expression can be measured using an immunological detection method. Immunological detection methods which can be used herein include, but are not limited to, competitive and non-competitive assay systems using techniques such as Western blots, radioimmunoassays, ELISA (enzyme linked immunosorbent assay), “sandwich” immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and the like. Such assays are routine and well known in the art (see, e.g., Ausubel et al, eds, 1994, *Current Protocols in Molecular Biology*, Vol. I, John Wiley & Sons, Inc., New York, which is incorporated by reference herein in its entirety).

In one embodiment, antibodies specific for biomarker proteins are utilized to detect the expression of a biomarker protein in a body sample. The method comprises obtaining a body sample from a patient or a subject, contacting the body sample with at least one antibody directed to a biomarker that is selectively expressed in bladder cancer cells, and detecting antibody binding to determine if the biomarker is expressed in the patient sample. In one embodiment, provided herein is an immunocytochemistry technique for diagnosing bladder cancer subtypes. One of skill in the art will recognize that the immunocytochemistry method described herein may be performed manually or in an automated fashion.

As provided throughout, the methods set forth herein provide a method for determining the bladder cancer subtype of a patient. Once the biomarker levels are determined, for example by measuring non-natural cDNA biomarker levels or non-natural mRNA-cDNA biomarker complexes, the biomarker levels are compared to reference values or a reference sample as provided herein, for example with the use of statistical methods or direct comparison of detected levels, to make a determination of the bladder cancer molecular subtype. Based on the comparison, the patient's bladder cancer sample is classified, e.g., as luminal, luminal infiltrated, basal, or basal infiltrated/neuronal. As provided herein, the statistical methods utilized in the methods provided herein can be centroid based statistical methods as described herein and/or known in the art.

In one embodiment, expression level values of the at least one classifier biomarkers provided herein, such as the classifier biomarkers of Table 1 or Table 2 are compared to reference expression level value(s) from at least one sample training set, wherein the at least one sample training set comprises expression level values from a reference sample(s). In a further embodiment, the at least one sample training set comprises expression level values of the at least one classifier biomarkers provided herein, such as the classifier biomarkers of Table 1, Table 2 or any additional set of biomarker classifiers disclosed herein from a bladder cancer luminal subtype, bladder cancer luminal infiltrated subtype, bladder cancer basal subtype, bladder cancer basal infiltrated/neuronal subtype, or bladder cancer-free sample or a combination thereof.

In a separate embodiment, hybridization values of the at least one classifier biomarkers provided herein, such as the classifier biomarkers of Table 1, Table 2 or any additional set of biomarker classifiers disclosed herein are compared to reference hybridization value(s) from at least one sample training set, wherein the at least one sample training set comprises hybridization values from a reference sample(s). In a further embodiment, the at least one sample training set comprises hybridization values of the at least one classifier biomarker provided herein, such as the classifier biomarkers of Table 1, Table 2 or any additional set of biomarker classifiers disclosed herein from a bladder cancer luminal subtype, bladder cancer luminal infiltrated subtype, bladder cancer basal subtype, bladder cancer basal infiltrated/neuronal subtype, or bladder cancer-free sample, or a combination thereof. Methods for comparing detected levels of biomarkers to reference values and/or reference samples are provided herein. Based on this comparison, in one embodiment a correlation or distance measure (e.g., Euclidean distance) between the biomarker levels obtained from the subject's sample and the reference values is obtained. An assessment of the bladder cancer subtype is then made.

Various statistical methods can be used to aid in the comparison of the biomarker levels obtained from the patient and reference biomarker levels, for example, from at least one sample training set.

In one embodiment, a supervised pattern recognition method is employed. Examples of supervised pattern recognition methods can include, but are not limited to, the nearest centroid methods (Dabney (2005) Bioinformatics 21(22):4148-4154 and Tibshirani et al. (2002) Proc. Natl. Acad. Sci. USA 99(10):6576-6572); soft independent modeling of class analysis (SIMCA) (see, for example, Wold, 1976); partial least squares analysis (PLS) (see, for example, Wold, 1966; Joreskog, 1982; Frank, 1984; Bro, R., 1997); linear discriminant analysis (LDA) (see, for example, Nillson, 1965); K-nearest neighbor analysis (KNN) (sec, for example, Brown et al., 1996); artificial neural networks (ANN) (see, for example, Wasserman, 1989; Anker et al., 1992; Hare, 1994); probabilistic neural networks (PNNs) (see, for example, Parzen, 1962; Bishop, 1995; Speckt, 1990; Broomhead et al., 1988; Patterson, 1996); rule induction (RI) (see, for example, Quinlan, 1986); and, Bayesian methods (see, for example, Bretthorst, 1990a, 1990b, 1988). In one embodiment, the classifier for identifying tumor subtypes based on gene expression data is used in a centroid based method as described in Mullins et al. (2007) Clin Chem. 53(7):1273-9, which is incorporated herein by reference in its entirety. In another embodiment, the classifier for identifying tumor subtypes based on gene expression data is used in a nearest centroid based method as described in Dabney (2005) Bioinformatics 21(22):4148-4154, which is incorporated herein by reference in its entirety. The nearest centroid based method can be performed using CLaNC software as described in Dabney A R. ClaNC: Point-and-click software for classifying microarrays to nearest centroids. Bioinformatics. 2006; 22: 122-123 or equivalents or derivatives thereof.

In other embodiments, an unsupervised training approach is employed, and therefore, no training set is used.

Referring to sample training sets for supervised learning approaches again, in some embodiments, a sample training set(s) can include expression data of a plurality or all of the classifier biomarkers (e.g., all the classifier biomarkers of Table 1 or Table 2, or any additional set of biomarker classifiers disclosed herein) from a bladder cancer sample. The plurality of classifier biomarkers can comprise at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, or at least 60 classifier biomarkers of Table 1. In some embodiments, the plurality of classifier biomarkers comprises all 60 biomarkers of Table 1. The plurality of classifier biomarkers can comprise at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, or at least 56 classifier biomarkers of Table 2. In some embodiments, the plurality of classifier biomarkers comprises all 56 biomarkers of Table 2. In some embodiments, the sample training set(s) are normalized to remove sample-to-sample variation.

In some embodiments, comparing can include applying a statistical algorithm, such as, for example, any suitable multivariate statistical analysis model, which can be parametric or non-parametric. In some embodiments, applying the statistical algorithm can include determining a correlation between the expression data obtained from the human bladder tissue sample and the expression data from the bladder cancer training set(s). In some embodiments, cross-validation is performed, such as (for example), leave-one-out cross-validation (LOOCV). In some embodiments, integrative correlation is performed. In some embodiments, a Spearman correlation is performed. In some embodiments, a centroid based method based on gene expression data is employed for the statistical algorithm. The centroids can be constructed using any method known in the art for generating centroids such as, for example, those found in Mullins et al. (2007) Clin Chem. 53(7):1273-9 or the nearest centroid method found in Dabney (2005) Bioinformatics 21(22): 4148-4154, which is herein incorporated by reference in its entirety. In one embodiment, a correlation analysis is performed on the expression data obtained from the human bladder tissue sample and the centroid(s) constructed on the expression data from the bladder cancer training set(s). The correlation analysis can be a Spearman correlation or a Pearson correlation. In one embodiment, a distance measure analysis (e.g., Euclidean distance) is performed on the expression data obtained from the human bladder tissue sample and the centroid(s) constructed on the expression data from the bladder cancer training set(s).

Results of the gene expression analysis performed on a sample (e.g., bladder sample as provided herein) from a subject (test sample) may be compared to a biological sample(s) or data derived (e.g., expression data or levels from at least one classifier biomarker provided herein, e.g., Table 1 or 2) from a biological sample(s) that is known or suspected to be normal ("reference sample" or "normal sample", e.g., non-bladder cancer sample). In some embodiments, a reference sample or reference gene expression data (e.g., for at least one classifier biomarkers provided herein such as, for example, Table 1 or Table 2) is obtained or derived from an individual known to have a particular molecular subtype of bladder cancer, i.e., luminal, luminal infiltrated, basal or basal infiltrated/neuronal. In one embodiment, the gene expression levels or profile for the at least one classifier biomarker provided herein (e.g., Table 1 or 2) measured or detected in the test sample may be compared to centroids constructed from the gene expression performed on the reference or normal sample. The centroids can be constructed using any of the methods provided herein such as, for example, using the ClaNC software described in Dabney A R. ClaNC: Point-and-click software for classifying microarrays to nearest centroids. Bioinformatics. 2006; 22: 122-123 or equivalents or derivatives related thereto. Classification or determination of the subtype of the test sample can then be ascertained by determining the nearest centroid from the reference or normal sample to which the expression levels or profile from said test sample is nearest based on a distance measure or correlation. The distance measure can be a Euclidean distance.

The reference sample may be assayed at the same time, or at a different time from the test sample (e.g., bladder tissue sample obtained from a subject suffering from or suspected of suffering from bladder cancer). Alternatively, the biomarker level information from a reference sample may be stored in a database or other means for access at a later date.

The biomarker level results of an assay on the test sample may be compared to the results of the same assay on a reference sample. In some cases, the results of the assay on the reference sample are from a database, or a reference value(s). In some cases, the results of the assay on the reference sample are a known or generally accepted value or range of values by those skilled in the art. In some cases, the comparison is qualitative. In other cases, the comparison is quantitative. In some cases, qualitative or quantitative comparisons may involve but are not limited to one or more of the following: comparing expression levels of a test sample to gene centroids constructed from expression level data from a reference sample (e.g., constructed from expression level data for one or a plurality of genes from Table 1 or Table 2), fluorescence values, spot intensities, absorbance values, chemiluminescent signals, histograms, critical threshold values, statistical significance values, expression levels of the genes described herein, mRNA copy numbers.

In one embodiment, an odds ratio (OR) is calculated for each biomarker level panel measurement. Here, the OR is a measure of association between the measured biomarker values for the patient and an outcome, e.g., bladder cancer subtype. For example, see, *J. Can. Acad. Child Adolesc. Psychiatry* 2010; 19(3): 227-229, which is incorporated by reference in its entirety for all purposes.

In one embodiment, a specified statistical confidence level may be determined in order to provide a confidence level regarding the bladder cancer subtype. For example, it may be determined that a confidence level of greater than 90% may be a useful predictor of the bladder cancer subtype. In other embodiments, more or less stringent confidence levels may be chosen. For example, a confidence level of about or at least about 50%, 60%, 70%, 75%, 80%, 85%, 90%, 95%, 97.5%, 99%, 99.5%, or 99.9% may be chosen. The confidence level provided may in some cases be related to the quality of the sample, the quality of the data, the quality of the analysis, the specific methods used, and/or the number of gene expression values (i.e., the number of genes) analyzed. The specified confidence level for providing the likelihood of response may be chosen on the basis of the expected number of false positives or false negatives. Methods for choosing parameters for achieving a specified confidence level or for identifying markers with diagnostic power include but are not limited to Receiver Operating Characteristic (ROC) curve analysis, binormal ROC, principal component analysis, odds ratio analysis, partial least squares analysis, singular value decomposition, least absolute shrinkage and selection operator analysis, least angle regression, and the threshold gradient directed regularization method.

Determining the bladder cancer subtype in some cases can be improved through the application of algorithms designed to normalize and or improve the reliability of the gene expression data. In some embodiments, the data analysis utilizes a computer or other device, machine or apparatus for application of the various algorithms described herein due to the large number of individual data points that are processed. A "machine learning algorithm" refers to a computational-based prediction methodology, also known to persons skilled in the art as a "classifier," employed for characterizing a gene expression profile or profiles, e.g., to determine the bladder cancer subtype. The biomarker levels, determined by, e.g., microarray-based hybridization assays, sequencing assays, NanoString assays, etc., are in one embodiment subjected to the algorithm in order to classify the profile. Supervised learning generally involves "training" a classifier to recognize the distinctions among subtypes such as luminal positive, luminal infiltrated positive, basal positive or basal infiltrated/neuronal positive, and then "testing" the accuracy of the classifier on an independent test set. Therefore, for new, unknown samples the classifier can be used to predict, for example, the class (e.g., luminal vs. luminal infiltrated vs. basal vs. basal infiltrated/neuronal) in which the samples belong. The machine learning algorithm can be a CLaNC algorithm as provided herein.

In some embodiments, a robust multi-array average (RMA) method may be used to normalize raw data. The RMA method begins by computing background-corrected intensities for each matched cell on a number of microarrays. In one embodiment, the background corrected values are restricted to positive values as described by Irizarry et al. (2003). Biostatistics April 4 (2): 249-64, incorporated by reference in its entirety for all purposes. After background correction, the base-2 logarithm of each background corrected matched-cell intensity is then obtained. The background corrected, log-transformed, matched intensity on each microarray is then normalized using the quantile normalization method in which for each input array and each probe value, the array percentile probe value is replaced with the average of all array percentile points, this method is more completely described by Bolstad et al. Bioinformatics 2003, incorporated by reference in its entirety. Following quantile normalization, the normalized data may then be fit to a linear model to obtain an intensity measure for each probe on each microarray. Tukey's median polish algorithm (Tukey, J. W., Exploratory Data Analysis. 1977, incorporated by reference in its entirety for all purposes) may then be used to determine the log-scale intensity level for the normalized probe set data.

Various other software programs may be implemented. In certain methods, feature selection and model estimation may be performed by logistic regression with lasso penalty using glmnet (Friedman et al. (2010). *Journal of statistical software* 33(1): 1-22, incorporated by reference in its entirety). Raw reads may be aligned using TopHat (Trapnell et al. (2009). *Bioinformatics* 25(9): 1105-11, incorporated by reference in its entirety). In methods, top features (N ranging from 10 to 200) are used to train a linear support vector machine (SVM) (Suykens J A K, Vandewalle J. Least Squares Support Vector Machine Classifiers. *Neural Processing Letters* 1999; 9(3): 293-300, incorporated by reference in its entirety) using the e1071 library (Meyer D. Support vector machines: the interface to libsvm in package e1071. 2014, incorporated by reference in its entirety). Confidence intervals, in one embodiment, are computed using the pROC package (Robin X, Turck N, Hainard A, et al. pROC: an open-source package for R and S+ to analyze and compare ROC curves. *BMC bioinformatics* 2011; 12: 77, incorporated by reference in its entirety).

In addition, data may be filtered to remove data that may be considered suspect. In one embodiment, data derived from microarray probes that have fewer than about 4, 5, 6, 7 or 8 guanosine+cytosine nucleotides may be considered to be unreliable due to their aberrant hybridization propensity or secondary structure issues. Similarly, data deriving from microarray probes that have more than about 12, 13, 14, 15, 16, 17, 18, 19, 20, 21, or 22 guanosine+cytosine nucleotides may in one embodiment be considered unreliable due to their aberrant hybridization propensity or secondary structure issues.

In some embodiments, data from probe-sets may be excluded from analysis if they are not identified at a detectable level (above background).

In some embodiments, probe-sets that exhibit no, or low variance may be excluded from further analysis. Low-variance probe-sets are excluded from the analysis via a Chi-Square test. In one embodiment, a probe-set is considered to be low-variance if its transformed variance is to the left of the 99 percent confidence interval of the Chi-Squared distribution with (N−1) degrees of freedom. (N−1)*Probe-set Variance/(Gene Probe-set Variance). Chi-Sq(N−1) where N is the number of input CEL files, (N−1) is the degrees of freedom for the Chi-Squared distribution, and the "probe-set variance for the gene" is the average of probe-set variances across the gene. In some embodiments, probe-sets for a given mRNA or group of mRNAs may be excluded from further analysis if they contain less than a minimum number of probes that pass through the previously described filter steps for GC content, reliability, variance and the like. For example, in some embodiments, probe-sets for a given gene or transcript cluster may be excluded from further analysis if they contain less than about 1, 2, 3, 4, 5, 6, 7, 8, 9, 10, 11, 12, 13, 14, 15, or less than about 20 probes.

Methods of biomarker level data analysis in one embodiment, further include the use of a feature selection algorithm as provided herein. In some embodiments, feature selection is provided by use of the LIMMA software package (Smyth, G. K. (2005). Limma: linear models for microarray data. In: Bioinformatics and Computational Biology Solutions using R and Bioconductor, R. Gentleman, V. Carey, S. Dudoit, R. Irizarry, W. Huber (eds.), Springer, New York, pages 397-420, incorporated by reference in its entirety for all purposes).

Methods of biomarker level data analysis, in one embodiment, include the use of a pre-classifier algorithm. For example, an algorithm may use a specific molecular fingerprint to pre-classify the samples according to their composition and then apply a correction/normalization factor. This data/information may then be fed in to a final classification algorithm that would incorporate that information to aid in the final diagnosis.

Methods of biomarker level data analysis, in one embodiment, further include the use of a classifier algorithm as provided herein. In one embodiment, a diagonal linear discriminant analysis, k-nearest neighbor algorithm, support vector machine (SVM) algorithm, linear support vector machine, random forest algorithm, or a probabilistic model-based method or a combination thereof is provided for classification of microarray data. In some embodiments, identified markers that distinguish samples (e.g., of varying biomarker level profiles, and/or varying molecular subtypes of bladder cancer (e.g., luminal, luminal infiltrated, basal, basal infiltrated/neuronal)) are selected based on statistical significance of the difference in biomarker levels between classes of interest. In some cases, the statistical significance is adjusted by applying a Benjamin Hochberg or another correction for false discovery rate (FDR).

In some cases, the classifier algorithm may be supplemented with a meta-analysis approach such as that described by Fishel and Kaufman et al. 2007 Bioinformatics 23(13): 1599-606, incorporated by reference in its entirety for all purposes. In some cases, the classifier algorithm may be supplemented with a meta-analysis approach such as a repeatability analysis.

Methods for deriving and applying posterior probabilities to the analysis of biomarker level data are known in the art and have been described for example in Smyth, G. K. 2004 *Stat. Appi. Genet. Mol. Biol.* 3: Article 3, incorporated by reference in its entirety for all purposes. In some cases, the posterior probabilities may be used in the methods provided herein to rank the markers provided by the classifier algorithm.

A statistical evaluation of the results of the biomarker level profiling may provide a quantitative value or values indicative of one or more of the following: molecular subtype of bladder cancer (e.g., luminal, luminal infiltrated, basal, basal infiltrated/neuronal); the likelihood of the success of a particular therapeutic intervention, e.g., angiogenesis inhibitor therapy, chemotherapy, or immunotherapy. In one embodiment, the data is presented directly to the physician in its most useful form to guide patient care, or is used to define patient populations in clinical trials or a patient population for a given medication. The results of the molecular profiling can be statistically evaluated using a number of methods known to the art including, but not limited to: the students T test, the two sided T test, Pearson rank sum analysis, hidden Markov model analysis, analysis of q-q plots, principal component analysis, one way ANOVA, two way ANOVA, LIMMA and the like.

In some cases, accuracy may be determined by tracking the subject over time to determine the accuracy of the original diagnosis. In other cases, accuracy may be established in a deterministic manner or using statistical methods. For example, receiver operator characteristic (ROC) analysis may be used to determine the optimal assay parameters to achieve a specific level of accuracy, specificity, positive predictive value, negative predictive value, and/or false discovery rate.

In some cases, the results of the biomarker level profiling assays, are entered into a database for access by representatives or agents of a molecular profiling business, the individual, a medical provider, or insurance provider. In some cases, assay results include sample classification, identification, or diagnosis by a representative, agent or consultant of the business, such as a medical professional. In other cases, a computer or algorithmic analysis of the data is provided automatically. In some cases, the molecular profiling business may bill the individual, insurance provider, medical provider, researcher, or government entity for one or more of the following: molecular profiling assays performed, consulting services, data analysis, reporting of results, or database access.

In some embodiments, the results of the biomarker level profiling assays are presented as a report on a computer screen or as a paper record. In some embodiments, the report may include, but is not limited to, such information as one or more of the following: the levels of biomarkers (e.g., as reported by copy number or fluorescence intensity, etc.) as compared to the reference sample or reference value(s); the likelihood the subject will respond to a particular therapy, based on the biomarker level values and the bladder cancer subtype and proposed therapies.

In one embodiment, the results of the gene expression profiling may be classified into one or more of the following: luminal positive, luminal infiltrated positive, basal positive or basal infiltrated/neuronal positive, luminal negative, luminal infiltrated negative, basal negative or basal infiltrated/neuronal negative or a combination thereof.

In some embodiments, results are classified using a trained algorithm. Trained algorithms include algorithms that have been developed using a reference set of known gene expression values and/or normal samples, for example, samples from individuals diagnosed with a particular molecular subtype of bladder cancer. In some cases, a reference set of known gene expression values are obtained from individuals who have been diagnosed with a particular molecular subtype of bladder cancer. In some cases, a reference set of known gene expression values are obtained from individuals who have been diagnosed with a particular molecular subtype of bladder cancer, and are also known to possess certain immune cell signature. In some cases, a reference set of known gene expression values are obtained from individuals who have been diagnosed with a particular molecular subtype of bladder cancer, and are also known to have certain expression of tumor driver genes.

Algorithms suitable for categorization of samples include but are not limited to k-nearest neighbor algorithms, support vector machines, linear discriminant analysis, centroid algorithms (e.g., CLaNC), diagonal linear discriminant analysis, updown, naive Bayesian algorithms, neural network algorithms, hidden Markov model algorithms, genetic algorithms, or any combination thereof.

When a binary classifier is compared with actual true values (e.g., values from a biological sample), there are typically four possible outcomes. If the outcome from a prediction is p (where "p" is a positive classifier output, such as the presence of a deletion or duplication syndrome) and the actual value is also p, then it is called a true positive (TP); however if the actual value is n then it is said to be a false positive (FP). Conversely, a true negative has occurred when both the prediction outcome and the actual value are n (where "n" is a negative classifier output, such as no deletion or duplication syndrome), and false negative is when the prediction outcome is n while the actual value is p. In one embodiment, consider a test that seeks to determine whether a person is likely or unlikely to respond to angiogenesis inhibitor therapy. A false positive in this case occurs when the person tests positive, but actually does respond. A false negative, on the other hand, occurs when the person tests negative, suggesting they are unlikely to respond, when they actually are likely to respond. The same holds true for classifying a bladder cancer subtype.

The positive predictive value (PPV), or precision rate, or post-test probability of disease, is the proportion of subjects with positive test results who are correctly diagnosed as likely or unlikely to respond, or diagnosed with the correct bladder cancer subtype, or a combination thereof. It reflects the probability that a positive test reflects the underlying condition being tested for. Its value does however depend on the prevalence of the disease, which may vary. In one example the following characteristics are provided: FP (false positive); TN (true negative); TP (true positive); FN (false negative). False positive rate ($\alpha$)=FP/(FP+TN)−specificity; False negative rate ($\beta$)=FN/(TP+FN)−sensitivity; Power=sensitivity=1−$\beta$; Likelihood-ratio positive=sensitivity/(1−specificity); Likelihood-ratio negative=(1−sensitivity)/specificity. The negative predictive value (NPV) is the proportion of subjects with negative test results who are correctly diagnosed.

In some embodiments, the results of the biomarker level analysis of the subject methods provide a statistical confidence level that a given diagnosis is correct. In some embodiments, such statistical confidence level is at least about, or more than about 85%, 90%, 91%, 92%, 93%, 94%, 95%, 96%, 97%, 98%, 99% 99.5%, or more.

In some embodiments, the method further includes classifying the bladder tissue sample as a particular bladder cancer subtype based on the comparison of biomarker levels in the sample and reference biomarker levels, for example present in at least one training set. In some embodiments, the bladder tissue sample is classified as a particular subtype if the results of the comparison meet one or more criterion such as, for example, a minimum percent agreement, a value of a statistic calculated based on the percentage agreement such as (for example) a kappa statistic, a minimum correlation (e.g., Pearson's correlation) and/or the like.

It is intended that the methods described herein can be performed by software (stored in memory and/or executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including Unix utilities, C, C++, Java™, Ruby, SQL, SAS®, the R programming language/software environment, Visual Basic™, and other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Some embodiments described herein relate to devices with a non-transitory computer-readable medium (also can be referred to as a non-transitory processor-readable medium or memory) having instructions or computer code thereon for performing various computer-implemented operations and/or methods disclosed herein. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

In some embodiments, a single biomarker, or from about 1 to about 5, from about 5 to about 15, from about 15 to about 30, from about 30 to about 45, from about 45 to about 56, from about 45 to about 60 (e.g., as disclosed in Table 1 or Table 2) is capable of classifying subtypes of bladder cancer with a predictive success of at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, up to 100%, and all values in between. In some embodiments, any combination of biomarkers disclosed herein (e.g., in Table 1, Table 2) can be used to obtain a predictive success of at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, up to 100%, and all values in between.

In some embodiments, a single biomarker, or any of the biomarkers as herein disclosed as the additional set of biomarker classifiers is capable of classifying subtypes of bladder cancer with a predictive success of at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, up to 100%, and all values in between. In some embodiments, any combination of biomarkers disclosed herein (e.g., as herein disclosed as the additional set of biomarker classifiers) can be used to obtain a predictive success of at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, up to 100%, and all values in between.

In some embodiments, a single biomarker, or from about 1 to about 5, from about 5 to about 15, from about 15 to about 30, from about 30 to about 45, from about 45 to about 56, from about 45 to about 60 biomarkers (e.g., as disclosed in Table 1 or Table 2) is capable of classifying subtypes of bladder cancer with a sensitivity or specificity of at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, up to 100%, and all values in between. In some embodiments, any combination of biomarkers disclosed herein can be used to obtain a sensitivity or specificity of at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, up to 100%, and all values in between.

In some embodiments, a single biomarker, as herein disclosed such as the additional set of biomarker classifiers is capable of classifying subtypes of bladder cancer with a sensitivity or specificity of at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, up to 100%, and all values in between. In some embodiments, any combination of biomarkers disclosed herein can be used to obtain a sensitivity or specificity of at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, up to 100%, and all values in between.

Classifier Biomarker Selection

Figure 3:
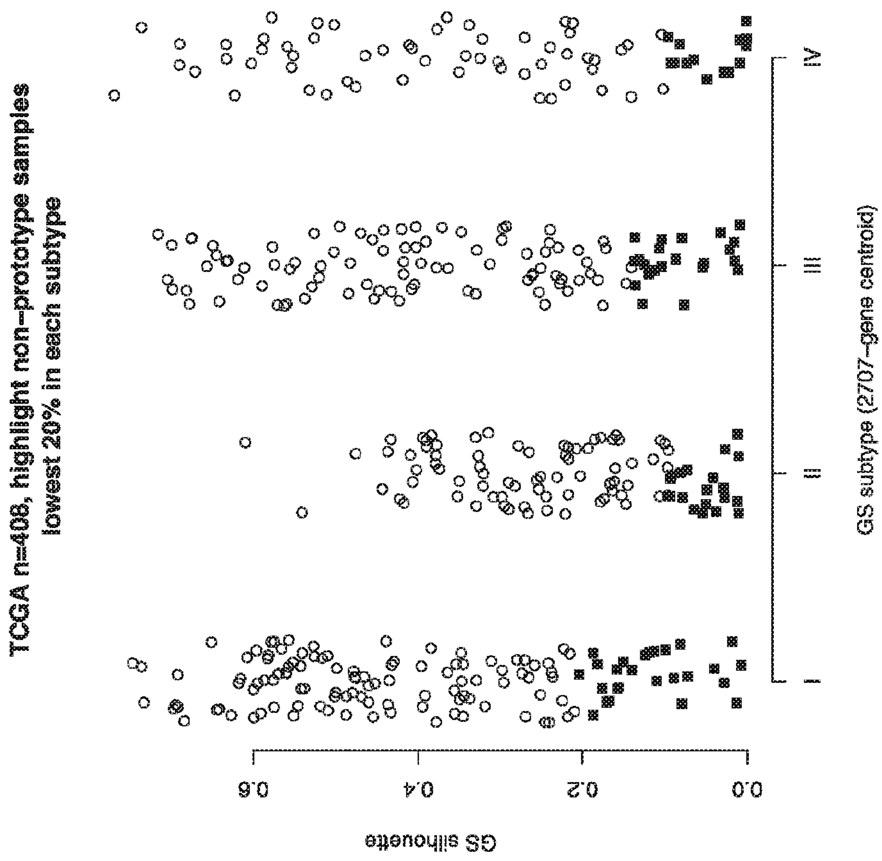
FIG. 3 illustrates the GS subtype silhouette for the TCGA-2017 dataset (n=408), wherein non-prototype samples are shown with a solid dot. The non-prototype samples represent the bottom ~20% of each subtype, and due to their low predictive strength, were excluded from gene selection.

In one embodiment, the methods and compositions provided herein are useful for determining the bladder cancer subtype of a sample (e.g., bladder tissue sample) from a patient by analyzing the expression of a set of biomarkers, whereby the set of biomarkers comprise a fewer number of biomarkers that methods known in the art for molecularly classifying bladder cancer subtype. In some cases, the set of biomarkers is less than 250, 240, 230, 220, 210, 200, 150, 100, 90, 80, 70, or 65 biomarkers. In some cases, the set of biomarkers is between 10 and 60 biomarkers. In some cases, the set of biomarkers is the set of 60 biomarkers listed in Table 1. In some cases, the set of biomarkers is a sub-set of biomarkers listed Table 1 such as, for example, 5, 10, 15, 20, 25, 30, 35, 40, 45, 50, 55, 56, 57, 58, or 59 of the biomarkers listed in Table 1. In some cases, the set of biomarkers is between 10 and 56 biomarkers. In some cases, the set of biomarkers is the set of 56 biomarkers listed in Table 2. In some cases, the set of biomarkers is a sub-set of biomarkers listed Table 2 such as, for example, 5, 10, 15, 20, 25, 30, 35, 40, 45, 50, 51, 52, 53, 54, 55, or 56 of the biomarkers listed in Table 2. The biomarkers or classifier biomarkers useful in the methods and compositions provided herein can be selected from one or more bladder cancer datasets from one or more databases. The databases can be public databases. In one embodiment, classifier biomarkers (e.g., one or more genes listed in Table 1 and Table 2) useful in the methods and compositions provided herein for detecting or diagnosing bladder cancer subtypes were selected from a bladder cancer dataset from The Cancer Genome Atlas (TCGA). See Robertson, A G, et al., Cell, 171(3): 540-556 (2017); Cancer Genome Atlas Research Network, Nature, 507(492): 315-22 (2014), both of which are incorporated by reference in their entireties. In one embodiment, classifier biomarkers useful for the methods and compositions provided herein such as those in Table 1 (or Table 2) are selected by subjecting a large set of classifier biomarkers to an in silico based process in order to determine the minimum number of genes whose expression profile can be used to determine an bladder cancer subtype of sample obtained from a subject. In some cases, the large set of classifier biomarkers can be a bladder cancer dataset such as, for example, from TCGA. In some cases, the large set of classifier biomarkers can be 2708-gene classifier described herein, whereby the 2708-gene classifier can serve to define gold standard (GS) subtype. The in silico process for selecting a gene signature as provided herein for determining bladder cancer subtype of a sample from a patient can comprise, applying or using a Classification to Nearest Centroid (CLaNC) algorithm with modification on the standard 2708 classifier biomarkers to choose an equal number of negatively and positively correlated genes for each subtype. For determination of the optimal number of genes (e.g., 60 per subtype as shown in Table 1, or 56 per subtype as shown in Table 2) to include in the signature, the process can further comprise performing a 5-fold cross validation using TCGA bladder cancer dataset as provided herein to produce cross-validation curves as shown in FIG. 2. To get the final list of gene classifiers, the method can further comprise applying the Classification to Nearest Centroid (CLaNC) to the entire TCGA data set minus 20% of samples with the lowest gold standard subtype prediction strength (for example, as shown in FIG. 3), and removing an equal number from each subtype.

In one embodiment, the method further comprises validating the gene classifiers. Validation can comprise testing the expression of the classifiers in several fresh frozen publicly available array and RNAseq datasets and calling the subtype based on said expression levels and subsequently comparing the expression with the gold standard subtype calls as defined by the previously published 2708-gene signature. In other words, validation can comprise calling the subtypes of the several fresh frozen publicly available array and RNAseq test datasets using their expression levels and the CLaNC algorithm as described herein and comparing the subtype calls with the gold standard subtype calls as defined by the previously published 2708-gene signature. Final validation of the gene signature (e.g., Table 1 or Table 2) can then be performed in a newly collected dataset of archived formalin-fixed paraffin-embedded (FFPE) bladder cancer samples to assure comparable performance in the FFPE samples. In one embodiment, the classifier biomarkers of Table 1 were selected based on the in silico CLaNC process described herein. The gene symbols and official gene names are listed in Table 1. In one embodiment, the classifier biomarkers of Table 2 were selected based on the in silico CLaNC process described herein. The gene symbols and official gene names are listed in Table 2. Further to the above embodiments, the in silico CLaNC process can entail use of the CLaNC process described in Dabney (2005) Bioinformatics 21(22):4148-4154. In one embodiment, the in silico CLaNC process can entail use of CLaNC software described in Dabney A R. ClaNC: Point-and-click software for classifying microarrays to nearest centroids. Bioinformatics. 2006; 22: 122-123 or equivalents or derivatives related thereto.

In one embodiment, the methods as provided herein require the detection of at least 1, at least 2, at least 3, at least 4, at least 5, at least 6, at least 7, at least 8, at least 9, at least 10, at least 11, at least 12, at least 13, at least 14, at least 15, at least 16, at least 18, at least 20, at least 22, at least 24, at least 26, at least 28, at least 30, at least 32, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, up to 60 classifier biomarkers in a bladder cancer cell sample obtained from a patient which expression is altered in order to identify a luminal, luminal infiltrated, basal, or basal infiltrated/neuronal bladder cancer subtype. The same applies for other classifier biomarker expression datasets as provided herein.

In another embodiment, the methods as provided herein require the detection of a total of at least 1, at least 2, at least 5, at least 8, at least 10, at least 18, at least 36, at least 54, at least 55, at least 56, at least 57, at least 58, at least 59, or up to 60 classifier biomarkers out of the 60 gene biomarkers of Table 1 (or Table 2) in a bladder cancer cell sample obtained from a patient in order to identify a luminal, luminal infiltrated, basal, or basal infiltrated/neuronal bladder cancer subtype. In another embodiment, the methods as provided herein require the detection of a total of at least 1, at least 2, at least 5, at least 10, at least 20, at least 40, at least 50 or up to 60 classifier biomarkers out of the 60 gene biomarkers of Table 1 (or Table 2) in a bladder cancer cell sample obtained from a patient in order to identify a luminal, luminal infiltrated, basal, or basal infiltrated/neuronal bladder cancer subtype. The same applies for other classifier biomarker expression datasets as provided herein.

In one embodiment, at least 1, at least 2, at least 3, at least 4, at least 5, at least 6, at least 7, at least 8, at least 10, at least 18, at least 36, at least 54, at least 55, at least 56, at least 57, at least 58, at least 59, or up to 60 classifier biomarkers out of the 60 gene biomarkers of Table 1 (or Table 2) are "up-regulated" in a specific subtype of bladder cancer. In another embodiment, at least 1, at least 2, at least 3, at least 4, at least 5, at least 6, at least 7, at least 8, at least 10, at least 18, at least 36, at least 54, at least 55, at least 56, at least 57, at least 58, at least 59, or up to 60 classifier biomarkers out of the 60 gene biomarkers of Table 1 (or Table 2) are "down-regulated" in a specific subtype of bladder cancer. The same applies for other classifier biomarker expression datasets as provided herein.

In one embodiment, the expression level of an "up-regulated" biomarker as provided herein is increased by about 0.5-fold, about 1-fold, about 1.5-fold, about 2-fold, about 2.5-fold, about 3-fold, about 3.5-fold, about 4-fold, about 4.5-fold, about 5-fold, and any values in between. In another embodiment, the expression level of a "down-regulated" biomarker as provided herein is decreased by about 0.8-fold, about 1.4-fold, about 2-fold, about 2.6-fold, about 3.2-fold, about 3.6-fold, about 4-fold, and any values in between.

It is recognized that additional genes or proteins can be used in the practice of methods, compositions and kits provided herein. In general, genes useful in classifying the subtypes of bladder cancer, include those that are independently capable of distinguishing between normal versus tumor, or between different classes or grades of bladder cancer. A gene is considered to be capable of reliably distinguishing between subtypes if the area under the receiver operator characteristic (ROC) curve is approximately 1.

Clinical/Therapeutic Uses

In one embodiment, a method is provided herein for determining a disease outcome or prognosis for a patient suffering from bladder cancer. In some cases, the bladder cancer is Muscle Invasive Bladder Cancer (MIBC). The disease outcome or prognosis can be measured by examining the overall survival for a period of time or intervals (e.g., 0 to 36 months or 0 to 60 months). In one embodiment, survival is analyzed as a function of bladder cancer subtype (e.g., luminal, luminal infiltrated, basal, basal infiltrated/neuronal). In one embodiment, survival is analyzed as a function of MIBC subtype (e.g., luminal, luminal infiltrated, basal, basal infiltrated/neuronal). The bladder cancer subtype (e.g., MIBC subtype) can be determined using the methods provided herein such as, for example, determining the expression of all or subsets of the genes in Table 1 or Table 2. Relapse-free and overall survival can be assessed using standard Kaplan-Meier plots as well as Cox proportional hazards modeling.

In one embodiment, the methods and compositions as provided herein for determining a bladder cancer (e.g., MIBC) subtype of a patient suffering or suspected of suffering from bladder cancer is used to determine whether or not said patient is a candidate for treatment with a specific type or types of cancer therapy. The sample can be any type of sample obtained from the patient as provided herein. In one embodiment, determining the bladder cancer (e.g., MIBC) subtype is one of a number of methods that can be employed to characterize the sample obtained from the patient such that the determining the bladder cancer (e.g., MIBC) subtype alone or in combination with one or more of the number of methods can be used to determine whether or not said patient is a candidate for treatment with a specific type or types of cancer therapy. In addition to assessing or determining a bladder cancer (e.g., MIBC) subtype, the number of methods for characterizing the sample can entail determining a proliferation score, the tumor mutation burden (TMB), the level of immune activation, the cell of origin subtype or any combination thereof. In one embodiment, one or all of the methods for characterizing the sample can be performed on RNA sequencing data obtained from the sample.

In one embodiment, in addition to assessing the bladder cancer (e.g., MIBC) subtype as provided herein, the characterization entails determining proliferation or proliferation score. In one embodiment, proliferation or the proliferation score is determined using any method known in the art such as, for example, as provided in U.S. 62/789,668 filed Jan. 8, 2019, which is herein incorporated by reference herein.

In one embodiment, in addition to assessing the bladder cancer (e.g., MIBC) subtype as provided herein, the characterization entails determining the cell of origin subtype. In one embodiment, cell of origin subtype is determined using any method known in the art such as, for example, as provided in Hoadley et al, Cell. 2018 Apr. 5; 173(2):291-304, which is herein incorporated by reference herein.

In one embodiment, in addition to determining the bladder cancer (e.g., MIBC) subtype as provided herein, the characterization entails calculating a TMB value and/or rate. The TMB value and/or rate can be calculated using any method known in the art. In one embodiment, the TMB value and/or rate can be calculated from RNA (e.g., via transcriptome profiling or RNA sequencing)) as provided in U.S. 62/771,702 filed Nov. 27, 2018 and U.S. 62/743,257 filed Oct. 9, 2018, which is herein incorporated by reference herein.

The determination of whether or not said patient is a candidate for treatment with a specific type or types of cancer therapy can be based on the bladder cancer (e.g., MIBC) subtype alone or in combination with other methods known in the art for characterizing a sample obtained from a patient suffering from or suspected of suffering from cancer. The other methods for characterizing said sample can be histologically based methods, gene expression based methods or a combination thereof. The histologically based methods can include histological cancer subtyping by one or more trained pathologists as well as the histological based methods of assessing proliferation such as, for example, determining the mitotic activity index. The gene expression based methods can include bladder cancer subtyping, assessment of TMB, assessment of cell of origin subtype, immune subtyping or any combination thereof. The gene expression based methods can be assessed from DNA, RNA or a combination thereof. In one embodiment, the characterization of the sample obtained from the patient suffering from or suspected of suffering from cancer is performed on RNA obtained or isolated from the sample.

The gene expression based tissue of origin cancer subtyping can be determined using gene signatures known in the art for specific types of cancer. In one embodiment, cell of origin subtype is determined using any method known in the art such as, for example, as provided in Hoadley et al, Cell. 2018 Apr. 5; 173(2):291-304, which is herein incorporated by reference herein.

The gene expression based immune subtyping or immune cell activation can be determined using immune expression signatures known in the art such as, for example, the gene signatures found in Thorsson, V., Gibbs, D. L., Brown, S. D., Wolf, D., Bortone, D. S., Yang, T. H. O., Porta-Pardo, E., Gao, G. F., Plaisier, C. L., Eddy, J. A. and Ziv, E., 2018, The immune landscape of cancer. *Immunity,* 48(4), pp. 812-830, which is herein incorporated by reference in its entirety. In one embodiment, immune cell activation is determined by monitoring the immune cell signatures of Bindea et al (Immunity 2013; 39(4); 782-795), the contents of which are herein incorporated by reference in its entirety. In one embodiment, the method further comprises measuring single gene immune biomarkers, such as, for example, CTLA4, PDCD1 and CD274 (PD-LI), PDCDLG2(PD-L2) and/or IFN gene signatures. In one embodiment, the level of immune cell activation is determined by measuring gene expression signatures of immunomarkers. The immunomarkers can be measured in the same and/or different sample used to determine the bladder cancer (e.g., MIBC) subtype as described herein. The immunomarkers can be those found in WO2017/201165, and WO2017/201164, each of which is herein incorporated by reference in their entirety.

The gene expression based method for calculating a TMB value and/or rate can be any method known in the art. In one embodiment, the TMB value and/or rate can be calculated from RNA (e.g., via transcriptome profiling or RNA sequencing)) as provided in U.S. 62/771,702 filed Nov. 27, 2018 and U.S. 62/743,257 filed Oct. 9, 2018, which is herein incorporated by reference herein.

In one embodiment, upon determining a patient's bladder cancer subtype (e.g., by measuring the expression of all or subsets of the genes in Table 1 or Table 2), the patient is selected for suitable therapy, for example, radiotherapy (radiation therapy), surgical intervention, target therapy, chemotherapy or drug therapy with an angiogenesis inhibitor or immunotherapy or combinations thereof. In some embodiments, the suitable treatment can be any treatment or therapeutic method that can be used for a bladder cancer patient. In one embodiment, upon determining a patient's bladder cancer subtype, the patient is administered a suitable therapeutic agent, for example chemotherapeutic agent(s) or an angiogenesis inhibitor or immunotherapeutic agent(s). In one embodiment, the therapy is immunotherapy, and the immunotherapeutic agent is a checkpoint inhibitor, monoclonal antibody, biological response modifier, therapeutic vaccine or cellular immunotherapy. In some embodiments, the determination of a suitable treatment can identify treatment responders. In some embodiments, the determination of a suitable treatment can identify treatment non-responders. In some embodiments, upon determining a patient's bladder cancer subtype, the bladder cancer patient can be selected for any combination of suitable therapies. For example, chemotherapy or drug therapy with a radiotherapy, a tumor dissection with an immunotherapy or a chemotherapeutic agent with a radiotherapy. In some embodiments, immunotherapy, or immunotherapeutic agent can be a checkpoint inhibitor, monoclonal antibody, biological response modifier, therapeutic vaccine or cellular immunotherapy.

The methods of present invention are also useful for evaluating clinical response to therapy, as well as for endpoints in clinical trials for efficacy of new therapies. The extent to which sequential diagnostic expression profiles move towards normal can be used as one measure of the efficacy of the candidate therapy.

In one embodiment, the methods as provided herein also find use in predicting response to different lines of therapies based on the subtype of bladder cancer (e.g., MIBC). For example, chemotherapeutic response can be improved by more accurately assigning tumor subtypes. Likewise, treatment regimens can be formulated based on the tumor subtype. In one embodiment, a bladder cancer (i.e., MIBC) sample obtained from a subject is determined to have a luminal subtype using the methods provided herein and is selected for treatment with FGFR inhibitors (e.g., FGFR3 inhibitors). The FGFR inhibitors can be tyrosine kinase inhibitors of FGFR3. In one embodiment, a bladder cancer (i.e., MIBC) sample obtained from a subject is determined to have a luminal-infiltrated subtype using the methods provided herein and is selected for immunotherapy. The immunotherapy can be immune checkpoint therapy. The checkpoint inhibitor can be PD-1, PD-LI, CTLA-4 checkpoint inhibitors or a combination thereof. The PD-1, PD-LI, CTLA-4 checkpoint inhibitors can be any PD-1, PD-L1, CTLA-4 checkpoint inhibitors known in the art and/or provided herein. In one embodiment, the checkpoint inhibitor can be a PD-1/PD-L1 checkpoint inhibitor such as, for example, atezolizumab. In one embodiment, a bladder cancer (i.e., MIBC) sample obtained from a subject is determined to have a basal subtype using the methods provided herein and is selected for chemotherapy (e.g., cisplatin-based neoadjuvant chemotherapy) and/or immunotherapy. The immunotherapy can be immune checkpoint therapy. The checkpoint inhibitor can be PD-1, PD-L1, CTLA-4 checkpoint inhibitors or a combination thereof. The PD-1, PD-L1, CTLA-4 checkpoint inhibitors can be any PD-1, PD-L1, CTLA-4 checkpoint inhibitors known in the art and/or provided herein. In one embodiment, a bladder cancer (i.e., MIBC) sample obtained from a subject is determined to have a basal-infiltrated/neuronal subtype using the methods provided herein and is selected for chemotherapy. The chemotherapy can be etoposide-cisplatin therapy.

In one embodiment, determination of a specific subtype of bladder cancer (e.g., MIBC) using the methods provided herein can serve as a negative predictor for use of specific treatments for subjects with said bladder cancer (e.g., MIBC) subtype. For example, a bladder cancer (i.e., MIBC) sample obtained from a subject is determined to have a luminal subtype or a luminal infiltrated subtype using the methods provided herein and thus may not be selected for treatment with chemotherapy such as, cisplatin-based neoadjuvant chemotherapy. Accordingly, validation of the luminal or luminal-infiltrated subtype of a bladder cancer (e.g., MIBC) sample obtained from a subject using the methods provided herein can serve as negative predictors for treatment with chemotherapeutic agents and thus suggest exploration of alternative treatment strategies including, for example, targeted therapies (e.g., immunotherapy).

Immunotherapy

In one embodiment, provided herein is a method for determining whether a bladder cancer patient is likely to respond to immunotherapy by determining the subtype of bladder cancer of a sample obtained from the patient and, based on the bladder cancer subtype, assessing whether the patient is likely to respond to immunotherapy. In another embodiment, provided herein is a method of selecting a patient suffering from bladder cancer for immunotherapy by determining a bladder cancer subtype of a sample from the patient and, based on the bladder cancer subtype, selecting the patient for immunotherapy. The determination of the bladder cancer subtype of the sample obtained from the patient can be performed using any method for subtyping bladder cancer known in the art. The determination of the bladder cancer subtype of the sample obtained from the patient can be performed using any method for subtyping bladder cancer provided herein. In one embodiment, the sample obtained from the patient has been previously diagnosed as being bladder cancer, and the methods provided herein are used to determine the bladder cancer subtype of the sample. The previous diagnosis can be based on a histological analysis. The histological analysis can be performed by one or more pathologists. In one embodiment, the bladder cancer has been diagnosed to be MIBC. In one embodiment, the bladder cancer subtyping is performed via gene expression analysis of a set or panel of biomarkers or subsets thereof in order to generate an expression profile. The gene expression analysis can be performed on a bladder cancer sample obtained from a patient in order to determine the presence, absence or level of expression of one or more biomarkers selected from a publically available bladder cancer database described herein and/or Tables 1 or 2 provided herein. The bladder cancer subtype (e.g., MIBC subtype) can be selected from the group consisting of luminal, luminal infiltrated, basal, and basal infiltrated/neuronal. The immunotherapy can be any immunotherapy provided herein. In one embodiment, the immunotherapy comprises administering one or more checkpoint inhibitors. The checkpoint inhibitors can be any checkpoint inhibitor provided herein such as, for example, a checkpoint inhibitor that targets PD-1, PD-LI or CTLA4.

As disclosed herein, the biomarkers panels, or subsets thereof, can be those disclosed in any publically available liver cancer gene expression dataset or datasets. In one embodiment, the biomarker panel or subset thereof is, for example, the cancer genome atlas bladder cancer gene expression dataset (n=412). See Robertson, A G, et al., Cell, 171(3): 540-556 (2017), the contents of which are herein incorporated by reference in its entirety. In one embodiment, the biomarker panel or subset thereof is, for example, the bladder cancer gene expression dataset (n=305) disclosed in Seiler et al. Eur Urol 72(4):544-554 (2017), the contents of which are herein incorporated by reference in its entirety. In one embodiment, the biomarker panel or subset thereof is, for example, the bladder cancer gene expression dataset (n=308) disclosed in Sjodahl, G., et al, Clin Cancer Res, 18(12):3377-86 (2012), the contents of which are herein incorporated by reference in its entirety. In one embodiment, the biomarker panel or subset thereof is, for example, the bladder cancer gene expression dataset disclosed in Table 1 or Table 2 in combination with one or more biomarkers from a publically available bladder cancer expression dataset.

In one embodiment, from about 1 to about 5, about 5 to about 10, from about 5 to about 15, from about 5 to about 20, from about 5 to about 25, from about 5 to about 30, from about 5 to about 35, from about 5 to about 40, from about 5 to about 45, from about 5 to about 50, from about 5 to about 55, from about 5 to about 60, of the biomarkers in any of the bladder cancer gene expression datasets provided herein, including, for example, Table 1 (or Table 2) for an bladder cancer sample are detected in a method to determine the bladder cancer subtype as provided herein. In another embodiment, each of the biomarkers from any one of the bladder cancer gene expression datasets provided herein, including, for example, Table 1 (or Table 2) for a bladder cancer sample are detected in a method to determine the bladder cancer subtype as provided herein.

In one embodiment, the methods provided herein further comprise determining the presence, absence or level of immune activation in a bladder cancer subtype. The presence or level of immune cell activation can be determined by creating an expression profile or detecting the expression of one or more biomarkers associated with innate immune cells and/or adaptive immune cells associated with each bladder cancer subtype in a sample obtained from a patient. In one embodiment, immune cell activation associated with a bladder cancer subtype is determined by monitoring the immune cell signatures of Bindea et al (Immunity 2013; 39(4); 782-795), Faruki H. et al., JTO, 12(6): 943-953 (2017), Charoentong P. et al., Cell reports, 18, 248-262 (2017), Thorsson, V. et al., 2018, The immune landscape of cancer. *Immunity,* 48(4), pp. 812-830, and/or WO2017/201165 and WO2017/201164, the contents of each of which are herein incorporated by reference in its entirety. In one embodiment, the method further comprises measuring single gene immune biomarkers, such as, for example, CTLA4, PDCD1 and CD274 (PD-LI), PDCDLG2(PD-L2) and/or IFN gene signatures. In one embodiment, immune subtyping or immune cell activation can be determined using the gene signatures found in Thorsson, V., Gibbs, D. L., Brown, S. D., Wolf, D., Bortone, D. S., Yang, T. H. O., Porta-Pardo, E., Gao, G. F., Plaisier, C. L., Eddy, J. A. and Ziv, E., 2018, The immune landscape of cancer. *Immunity,* 48(4), pp. 812-830, which is herein incorporated by reference in its entirety. The presence or a detectable level of immune activation (Innate and/or Adaptive) associated with a bladder cancer subtype can indicate or predict that a patient with said bladder cancer subtype may be amendable to immunotherapy. The immunotherapy can be treatment with a checkpoint inhibitor as provided herein. In one embodiment, a method is provided herein for detecting the expression of at least one classifier biomarker provided herein in a sample (e.g., bladder cancer sample) obtained from a patient further comprises administering an immunotherapeutic agent following detection of immune activation as provided herein in said sample.

In one embodiment, the method comprises determining a subtype of a bladder cancer sample and subsequently determining a level of immune cell activation of said sub-type. In one embodiment, the subtype is determined by determining the expression levels of one or more classifier biomarkers using sequencing (e.g., RNASeq), amplification (e.g., qRT-PCR) or hybridization assays (e.g., microarray analysis) as described herein. The one or more biomarkers can be selected from a publically available database (e.g., TCGA bladder cancer gene expression datasets or any other publically available bladder cancer gene expression datasets provided herein). In some embodiments, the biomarkers of Table 1 or Table 2 can be used to specifically determine the subtype of a bladder cancer sample obtained from a patient. In one embodiment, the level of immune cell activation is determined by measuring gene expression signatures of immunomarkers. The immunomarkers can be measured in the same and/or different sample used to subtype the bladder cancer sample as described herein. The immunomarkers that can be measured can comprise, consist of, or consistently essentially of innate immune cell (IIC) and/or adaptive immune cell (AIC) gene signatures, interferon (IFN) gene signatures, individual immunomarkers, major histocompatibility complex class II (MHC class II) genes or a combination thereof. The gene expression signatures for IICs, AICs, IFN and MHC class II can be any known gene signatures for said cell types or genes known in the art. For example, the immune gene signatures can be those from Bindea et al. (Immunity 2013; 39(4); 782-795), Faruki H. et al., JTO, 12(6): 943-953 (2017), Charoentong P. et al., Cell reports, 18, 248-262 (2017) and/or WO2017/201165 and WO2017/201164. The individual immunomarkers can be those found in Faruki H. et al., JTO, 12(6): 943-953 (2017), Charoentong P. et al., Cell reports, 18, 248-262 (2017) and/or WO2017/201165 and WO2017/201164. In one embodiment, the individual immunomarkers can be CTLA4 (e.g., NM_005214 (SEQ ID NO. 80), PDCD1 (e.g., NM_005018; SEQ ID NO. 81), PDL2 (e.g., AY254343; SEQ ID NO. 82) and CD274 (PD-L1; e.g., NM_014143; SEQ ID NO. 83). In one embodiment, immune subtyping or immune cell activation can be determined using the gene signatures found in Thorsson, V., Gibbs, D. L., Brown, S. D., Wolf, D., Bortone, D. S., Yang, T. H. O., Porta-Pardo, E., Gao, G. F., Plaisier, C. L., Eddy, J. A. and Ziv, E., 2018, The immune landscape of cancer. *Immunity,* 48(4), pp. 812-830.

In one embodiment, upon determining a patient's bladder cancer subtype using any of the methods and classifier biomarkers panels or subsets thereof as provided herein, the patient is selected for treatment with or administered an immunotherapeutic agent. The immunotherapeutic agent can be a checkpoint inhibitor, monoclonal antibody, biological response modifiers, therapeutic vaccine or cellular immunotherapy.

In another embodiment, the immunotherapeutic agent is a checkpoint inhibitor. In some cases, a method for determining the likelihood of response to one or more checkpoint inhibitors is provided. In one embodiment, the checkpoint inhibitor is a PD-1/PD-LI checkpoint inhibitor. The PD-1/PD-LI checkpoint inhibitor can be nivolumab, pembrolizumab, atezolizumab, durvalumab, lambrolizumab, or avelumab. In one embodiment, the checkpoint inhibitor is a CTLA-4 checkpoint inhibitor. The CTLA-4 checkpoint inhibitor can be ipilimumab or tremelimumab. In one embodiment, the checkpoint inhibitor is a combination of checkpoint inhibitors such as, for example, a combination of one or more PD-1/PD-LI checkpoint inhibitors used in combination with one or more CTLA-4 checkpoint inhibitors.

In one embodiment, the immunotherapeutic agent is a monoclonal antibody. In some cases, a method for determining the likelihood of response to one or more monoclonal antibodies is provided. The monoclonal antibody can be directed against tumor cells or directed against tumor products. The monoclonal antibody can be panitumumab, matuzumab, necitumunab, trastuzumab, amatuximab, bevacizumab, ramucirumab, bavituximab, patritumab, rilotumumab, cetuximab, immu-132, or demcizumab.

In yet another embodiment, the immunotherapeutic agent is a therapeutic vaccine. In some cases, a method for determining the likelihood of response to one or more therapeutic vaccines is provided. The therapeutic vaccine can be a peptide or tumor cell vaccine. The vaccine can target MAGE-3 antigens, NY-ESO-1 antigens, p53 antigens, survivin antigens, or MUC1 antigens. The therapeutic cancer vaccine can be GVAX (GM-CSF gene-transfected tumor cell vaccine), belagenpumatucel-L (allogeneic tumor cell vaccine made with four irradiated NSCLC cell lines modified with TGF-beta2 antisense plasmid), MAGE-A3 vaccine (composed of MAGE-A3 protein and adjuvant AS15), (1)-BLP-25 anti-MUC-1 (targets MUC-1 expressed on tumor cells), CimaVax EGF (vaccine composed of human recombinant Epidermal Growth Factor (EGF) conjugated to a carrier protein), WT1 peptide vaccine (composed of four Wilms' tumor suppressor gene analogue peptides), CRS-207 (live-attenuated *Listeria monocytogenes* vector encoding human mesothelin), Bec2/BCG (induces anti-GD3 antibodies), GV1001 (targets the human telomerase reverse transcriptase), TG4010 (targets the MUC1 antigen), racotumomab (anti-idiotypic antibody which mimicks the NGcGM3 ganglioside that is expressed on multiple human cancers), tecemotide (liposomal BLP25; liposome-based vaccine made from tandem repeat region of MUC1) or DRibbles (a vaccine made from nine cancer antigens plus TLR adjuvants).

In one embodiment, the immunotherapeutic agent is a biological response modifier. In some cases, a method for determining the likelihood of response to one or more biological response modifiers is provided. The biological response modifier can trigger inflammation such as, for example, PF-3512676 (CpG 7909) (a toll-like receptor 9 agonist), CpG-ODN 2006 (downregulates Tregs), *Bacillus* Calmette-Guerin (BCG), *mycobacterium* vaccae (SRL172) (nonspecific immune stimulants now often tested as adjuvants). The biological response modifier can be cytokine therapy such as, for example, IL-2+ tumor necrosis factor alpha (TNF-alpha) or interferon alpha (induces T-cell proliferation), interferon gamma (induces tumor cell apoptosis), or Mda-7 (IL-24) (Mda-7/IL-24 induces tumor cell apoptosis and inhibits tumor angiogenesis). The biological response modifier can be a colony-stimulating factor such as, for example granulocyte colony-stimulating factor. The biological response modifier can be a multi-modal effector such as, for example, multi-target VEGFR: thalidomide and analogues such as lenalidomide and pomalidomide, cyclophosphamide, cyclosporine, denileukin diftitox, talactoferrin, trabecetedin or all-trans-retinmoic acid.

In one embodiment, the immunotherapy is cellular immunotherapy. In some cases, a method for determining the likelihood of response to one or more cellular therapeutic agents. The cellular immunotherapeutic agent can be dendritic cells (DCs) (ex vivo generated DC-vaccines loaded with tumor antigens), T-cells (ex vivo generated lymphokine-activated killer cells; cytokine-induce killer cells; activated T-cells; gamma delta T-cells), or natural killer cells.

In some cases, specific subtypes of bladder cancer have different levels of immune activation (e.g., innate immunity and/or adaptive immunity) such that subtypes with elevated or detectable immune activation (e.g., innate immunity and/or adaptive immunity) are selected for treatment with one or more immunotherapeutic agents described herein. In some cases, specific subtypes of bladder cancer have high or elevated levels of immune activation. In some cases, the luminal, luminal infiltrated, basal, and/or basal infiltrated/neuronal subtype has elevated levels of immune activation (e.g., innate immunity and/or adaptive immunity) as compared to other bladder cancer subtypes. In some cases, the luminal, luminal infiltrated, basal, and/or basal infiltrated/neuronal subtype has reduced levels of immune activation (e.g., innate immunity and/or adaptive immunity) as compared to other bladder cancer subtypes. In one embodiment, bladder cancer subtypes with low levels of or no immune activation (e.g., innate immunity and/or adaptive immunity) are not selected for treatment with one or more immunotherapeutic agents described herein.

Angiogenesis Inhibitors

In one embodiment, upon determining a patient's or subject's bladder cancer (e.g., MIBC) subtype alone or in combination with other characterization methods as described herein (e.g., determining cell of origin cancer subtype, proliferation signature or score, immune subtype and/or TMB status, etc.), the patient is selected for drug therapy with an angiogenesis inhibitor.

In one embodiment, the angiogenesis inhibitor is a vascular endothelial growth factor (VEGF) inhibitor, a VEGF receptor inhibitor, a platelet derived growth factor (PDGF) inhibitor or a PDGF receptor inhibitor.

In general, methods of determining whether a patient is likely to respond to angiogenesis inhibitor therapy, or methods of selecting a patient for angiogenesis inhibitor therapy are provided herein. In one embodiment, the method comprises determining a bladder cancer (e.g., MIBC) subtype alone or in combination with other characterization methods as described herein (e.g., determining cell of origin cancer subtype, proliferation signature or score, immune subtype and/or TMB status, etc.) and probing a sample from the patient for the levels of at least five hypoxia biomarkers selected from the group consisting of RRAGD, FABP5, UCHL1, GAL, PLOD, DDIT4, VEGF, ADM, ANGPTL4, NDRG1, NP, SLC16A3, and C14ORF58 (see Table A) at the nucleic acid level. In a further embodiment, the probing step comprises mixing the sample with five or more oligonucleotides that are substantially complementary to portions of nucleic acid molecules of the at least five biomarkers under conditions suitable for hybridization of the five or more oligonucleotides to their complements or substantial complements, detecting whether hybridization occurs between the five or more oligonucleotides to their complements or substantial complements; and obtaining hybridization values of the sample based on the detecting steps. The hybridization values of the sample are then compared to reference hybridization value(s) from at least one sample training set, wherein the at least one sample training set comprises (i) hybridization value(s) of the at least five biomarkers from a sample that overexpresses the at least five biomarkers, or overexpresses a subset of the at least five biomarkers, (ii) hybridization values of the at least five biomarkers from a reference bladder cancer (e.g., MIBC) sample, or (iii) hybridization values of the at least five biomarkers from a non-bladder cancer (e.g., MIBC) sample. A determination of whether the patient is likely to respond to angiogenesis inhibitor therapy, or a selection of the patient for angiogenesis inhibitor is then made based upon (i) the patient's bladder cancer (e.g., MIBC) subtype alone or in combination with other characterization methods as described herein (e.g., determining cell of origin cancer subtype, proliferation signature or score, immune subtype and/or TMB status, etc.) and (ii) the results of comparison.

TABLE A

Biomarkers for hypoxia profile

| Name | Abbreviation | GenBank Accession No. |
|---|---|---|
| RRAGD | Ras-related GTP binding D | BC003088 |
| FABP5 | fatty acid binding protein 5 | M94856 |
| UCHL1 | ubiquitin carboxyl-terminal esterase L1 | NM_004181 |
| GAL | Galanin | BC030241 |
| PLOD | procollagen-lysine, 2-oxoglutarate 5-dioxygenase lysine hydroxylase | M98252 |
| DDIT4 | DNA-damage-inducible transcript 4 | NM_019058 |
| VEGF | vascular endothelial growth factor | M32977 |
| ADM | Adrenomedullin | NM_001124 |
| ANGPTL4 | angiopoietin-like 4 | AF202636 |
| NDRG1 | N-myc downstream regulated gene 1 | NM_006096 |
| NP | nucleoside phosphorylase | NM 000270 |
| SLC16A3 | solute carrier family 16 monocarboxylic acid transporters, member 3 | NM_004207 |
| C14ORF58 | chromosome 14 open reading frame 58 | AK000378 |

The aforementioned set of thirteen biomarkers, or a subset thereof, is also referred to herein as a "hypoxia profile".

In one embodiment, the method provided herein includes determining the levels of at least five biomarkers, at least six biomarkers, at least seven biomarkers, at least eight biomarkers, at least nine biomarkers, or at least ten biomarkers, or five to thirteen, six to thirteen, seven to thirteen, eight to thirteen, nine to thirteen or ten to thirteen biomarkers selected from RRAGD, FABP5, UCHL1, GAL, PLOD, DDIT4, VEGF, ADM, ANGPTL4, NDRG1, NP, SLC16A3, and C14ORF58 in a sample obtained from a subject. Biomarker expression in some instances may be normalized against the expression levels of all RNA transcripts or their expression products in the sample or against a reference set of RNA transcripts or their expression products. The reference set as explained throughout, may be an actual sample that is tested in parallel with the sample, or may be a reference set of values from a database or stored dataset. Levels of expression, in one embodiment, are reported in number of copies, relative fluorescence value or detected fluorescence value. The level of expression of the biomarkers of the hypoxia profile together with the bladder cancer (e.g., MIBC) subtype alone or in combination with other characterization methods as described herein (e.g., determining cell of origin cancer subtype, proliferation signature or score, immune subtype and/or TMB status, etc.) as determined using the methods provided herein can be used in the methods described herein to determine whether a patient is likely to respond to angiogenesis inhibitor therapy.

In one embodiment, the levels of expression of the thirteen biomarkers (or subsets thereof, as described above, e.g., five or more, from about five to about 13), are normalized against the expression levels of all RNA transcripts or their non-natural cDNA expression products, or protein products in the sample, or of a reference set of RNA transcripts or a reference set of their non-natural cDNA expression products, or a reference set of their protein products in the sample.

In one embodiment, angiogenesis inhibitor treatments include, but are not limited to an integrin antagonist, a selectin antagonist, an adhesion molecule antagonist, an antagonist of intercellular adhesion molecule (ICAM)-1, ICAM-2, ICAM-3, platelet endothelial adhesion molecule (PCAM), vascular cell adhesion molecule (VCAM)), lymphocyte function-associated antigen 1 (LFA-1), a basic fibroblast growth factor antagonist, a vascular endothelial growth factor (VEGF) modulator, a platelet derived growth factor (PDGF) modulator (e.g., a PDGF antagonist).

In one embodiment of determining whether a subject is likely to respond to an integrin antagonist, the integrin antagonist is a small molecule integrin antagonist, for example, an antagonist described by Paolillo et al. (Mini Rev Med Chem, 2009, volume 12, pp. 1439-1446, incorporated by reference in its entirety), or a leukocyte adhesion-inducing cytokine or growth factor antagonist (e.g., tumor necrosis factor-α (TNF-α), interleukin-1β (IL-1β), monocyte chemotactic protein-1 (MCP-1) and a vascular endothelial growth factor (VEGF)), as described in U.S. Pat. No. 6,524,581, incorporated by reference in its entirety herein.

The methods provided herein are also useful for determining whether a subject is likely to respond to one or more of the following angiogenesis inhibitors: interferon gamma 1(3, interferon gamma 113 (Actimmune®) with pirfenidone, ACUHTR028, αVβ5, aminobenzoate potassium, amyloid P, ANG1122, ANG1170, ANG3062, ANG3281, ANG3298, ANG4011, anti-CTGF RNAi, Aplidin, *Astragalus membranaceus* extract with *salvia* and *Schisandra chinensis*, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, a galectin-3 inhibitor, GKT137831, GMCT01, GMCT02, GRMD01, GRMD02, GRN510, Heberon Alfa R, interferon α-2β, ITMN520, JKB119, JKB121, JKB122, KRX168, LPA1 receptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 fusion protein, RXI109, secretin, STX100, TGF-β Inhibitor, transforming growth factor, β-receptor 2 oligonucleotide, VA999260, XV615 or a combination thereof.

In another embodiment, a method is provided for determining whether a subject is likely to respond to one or more endogenous angiogenesis inhibitors. In a further embodiment, the endogenous angiogenesis inhibitor is endostatin, a 20 kDa C-terminal fragment derived from type XVIII collagen, angiostatin (a 38 kDa fragment of plasmin), a member of the thrombospondin (TSP) family of proteins. In a further embodiment, the angiogenesis inhibitor is a TSP-1, TSP-2, TSP-3, TSP-4 and TSP-5. Methods for determining the likelihood of response to one or more of the following angiogenesis inhibitors are also provided a soluble VEGF receptor, e.g., soluble VEGFR-1 and neuropilin 1 (NPR1), angiopoietin-1, angiopoietin-2, vasostatin, calreticulin, platelet factor-4, a tissue inhibitor of metalloproteinase (TIMP) (e.g., TIMP1, TIMP2, TIMP3, TIMP4), cartilage-derived angiogenesis inhibitor (e.g., peptide troponin I and chrondomodulin I), a disintegrin and metalloproteinase with thrombospondin motif 1, an interferon (IFN), (e.g., IFN-α, IFN-β, IFN-γ), a chemokine, e.g., a chemokine having the C-X-C motif (e.g., CXCL10, also known as interferon gamma-induced protein 10 or small inducible cytokine B10), an interleukin cytokine (e.g., IL-4, IL-12, IL-18), prothrombin, antithrombin III fragment, prolactin, the protein encoded by the TNFSF15 gene, osteopontin, maspin, canstatin, proliferin-related protein.

In one embodiment, a method for determining the likelihood of response to one or more of the following angiogenesis inhibitors is provided is angiopoietin-1, angiopoietin-2, angiostatin, endostatin, vasostatin, thrombospondin, calreticulin, platelet factor-4, TIMP, CDAI, interferon α, interferon β, vascular endothelial growth factor inhibitor (VEGI) meth-1, meth-2, prolactin, VEGI, SPARC, osteopontin, maspin, canstatin, proliferin-related protein (PRP), restin, TSP-1, TSP-2, interferon gamma 1β, ACUHTR028, αVβ5, aminobenzoate potassium, amyloid P, ANG1122, ANG1170, ANG3062, ANG3281, ANG3298, ANG4011, anti-CTGF RNAi, Aplidin, *Astragalus membranaceus* extract with *salvia* and *Schisandra chinensis*, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, a galectin-3 inhibitor, GKT137831, GMCT01, GMCT02, GRMD01, GRMD02, GRN510, Heberon Alfa R, interferon α-2β, ITMN520, JKB119, JKB121, JKB122, KRX168, LPA1 receptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 fusion protein, RXI109, secretin, STX100, TGF-β Inhibitor, transforming growth factor, β-receptor 2 oligonucleotide, VA999260, XV615 or a combination thereof.

In yet another embodiment, the angiogenesis inhibitor can include pazopanib (Votrient), sunitinib (Sutent), sorafenib (Nexavar), axitinib (Inlyta), ponatinib (Iclusig), vandetanib (Caprelsa), cabozantinib (Cometrig), ramucirumab (Cyramza), regorafenib (Stivarga), ziv-aflibercept (Zaltrap), motesanib, or a combination thereof. In another embodiment, the angiogenesis inhibitor is a VEGF inhibitor. In a further embodiment, the VEGF inhibitor is axitinib, cabozantinib, aflibercept, brivanib, tivozanib, ramucirumab or motesanib. In yet a further embodiment, the angiogenesis inhibitor is motesanib.

In one embodiment, the methods provided herein relate to determining a subject's likelihood of response to an antagonist of a member of the platelet derived growth factor (PDGF) family, for example, a drug that inhibits, reduces or modulates the signaling and/or activity of PDGF-receptors (PDGFR). For example, the PDGF antagonist, in one embodiment, is an anti-PDGF aptamer, an anti-PDGF antibody or fragment thereof, an anti-PDGFR antibody or fragment thereof, or a small molecule antagonist. In one embodiment, the PDGF antagonist is an antagonist of the PDGFR-α or PDGFR-β. In one embodiment, the PDGF antagonist is the anti-PDGF-β aptamer E10030, sunitinib, axitinib, sorefenib, imatinib, imatinib mesylate, nintedanib, pazopanib HCl, ponatinib, MK-2461, dovitinib, pazopanib, crenolanib, PP-121, telatinib, imatinib, KRN 633, CP 673451, TSU-68, Ki8751, amuvatinib, tivozanib, masitinib, motesanib diphosphate, dovitinib dilactic acid, linifanib (ABT-869).

Upon making a determination of whether a patient is likely to respond to angiogenesis inhibitor therapy, or selecting a patient for angiogenesis inhibitor therapy, in one embodiment, the patient is administered the angiogenesis inhibitor. The angiogenesis in inhibitor can be any of the angiogenesis inhibitors described herein.

Radiotherapy

In one embodiment, provided herein is a method for determining whether a patient is likely to respond to radiotherapy by determining the bladder cancer (e.g., MIBC) subtype alone or in combination with other characterization methods as described herein (e.g., determining cell of origin cancer subtype, proliferation signature or score, immune subtype and/or TMB status, etc.) of a sample obtained from the patient and, based on the bladder cancer (e.g., MIBC) subtype alone or in combination with other characterization methods as described herein (e.g., cell of origin cancer subtype, proliferation signature or score, immune subtype and/or TMB status, etc.), assessing whether the patient is likely to respond to or benefit from radiotherapy. In another embodiment, provided herein is a method of selecting a patient suffering from cancer for radiotherapy by determining a bladder cancer (e.g., MIBC) subtype alone or in combination with other characterization methods as described herein (e.g., determining cell of origin cancer subtype, proliferation signature or score, immune subtype and/or TMB status, etc.) of a sample from the patient and, based on the bladder cancer (e.g., MIBC) subtype alone or in combination with other characterization methods as described herein (e.g., determining cell of origin cancer subtype, proliferation signature or score, immune subtype and/or TMB status, etc.), selecting the patient for radiotherapy.

In some embodiments, the radiotherapy can include but are not limited to proton therapy and external-beam radiation therapy. In some embodiments, the radiotherapy can include any types or forms of treatment that is suitable for patients with specific types of cancer.

In some embodiments, a patient with a specific type of cancer can have or display resistance to radiotherapy. Radiotherapy resistance in any cancer or subtype thereof can be determined by measuring or detecting the expression levels of one or more genes known in the art and/or provided herein associated with or related to the presence of radiotherapy resistance. Genes associated with radiotherapy resistance can include NFE2L2, KEAP1 and CUL3. In some embodiments, radiotherapy resistance can be associated with the alterations of KEAP1 (Kelch-like ECH-associated protein 1)/NRF2 (nuclear factor E2-related factor 2) pathway. Association of a particular gene to radiotherapy resistance can be determined by examining expression of said gene in one or more patients known to be radiotherapy non-responders and comparing expression of said gene in one or more patients known to be radiotherapy responders.

Surgical Intervention

In one embodiment, provided herein is a method for determining whether a bladder cancer (e.g., MIBC) cancer patient is likely to respond to surgical intervention by determining the bladder cancer (e.g., MIBC) subtype alone or in combination with other characterization methods as described herein (e.g., determining cell of origin cancer subtype, proliferation signature or score, immune subtype and/or TMB status, etc.) of a sample obtained from the patient and, based on the bladder cancer (e.g., MIBC) subtype alone or in combination with other characterization methods as described herein (e.g., determining cell of origin cancer subtype, proliferation signature or score, immune subtype and/or TMB status, etc.), assessing whether the patient is likely to respond to or benefit from surgery. In another embodiment, provided herein is a method of selecting a patient suffering from cancer for surgery by determining a bladder cancer (e.g., MIBC) subtype alone or in combination with other characterization methods as described herein (e.g., determining cell of origin cancer subtype, proliferation signature or score, immune subtype and/or TMB status, etc.) of a sample from the patient and, based on the bladder cancer (e.g., MIBC) subtype alone or in combination with other characterization methods as described herein (e.g., determining cell of origin cancer subtype, proliferation signature or score, immune subtype and/or TMB status, etc.), selecting the patient for surgery. In some embodiments, the surgery can include laser technology, excision, dissection, and reconstructive surgery.

Prediction of Overall Survival Rate and Metastasis for Bladder Cancer Patients

The present disclosure provides methods for predicting overall survival rate for a bladder cancer patient. In some embodiments, the prediction of overall survival rate can involve obtaining a bladder tissue sample for a bladder cancer patient. In some embodiments, the bladder cancer patients can have various stages of cancers. In some embodiments, the overall survival rate can be determined by detecting the expression level of at least one subtype classifier of a publically available bladder cancer database or dataset. In some embodiments, an overall survival rate can be determined by detecting the expression level (e.g., protein and/or nucleic acid) of any subtype classifiers that are relevant to bladder cancer. In one embodiment, the subtype classifiers can be all or a subset of classifiers from Table 1 or Table 2.

In some embodiments, the present disclosure further provides methods of predicting overall survival in bladder cancer from specific areas of the bladder. In some embodiments, the prediction includes detecting an expression level of at least one gene from a bladder cancer dataset (e.g., Table 1 or Table 2) in a bladder tissue sample obtained from a patient. In some embodiments, the detection of the expression level of a subtype classifier from a bladder cancer dataset (e.g., Table 1 or Table 2) using the methods provided herein specifically identifies a luminal, luminal infiltrated, basal, or basal infiltrated/neuronal subtype. In some embodiments, the identification of the subtype is indicative of the overall survival in the patient. For example, a basal-infiltrated/neuronal subtype or a luminal-infiltrated subtype of bladder cancer (e.g., MIBC) is indicative of a poor overall survival.

The present disclosure provides methods for predicting nodal metastasis for a bladder cancer patient. In some embodiments, the prediction of nodal metastasis can involve obtaining a bladder tissue sample for a patient. In some embodiments, the patients can have various stages of cancers. In some embodiments, the nodal metastasis can be determined by detecting the expression level of at least one subtype classifier from a bladder gene set. The bladder gene set can be a publically available bladder database or a bladder gene set provided herein (e.g. Table 1 or Table 2) or a combination thereof. The publically available bladder gene set can be a TCGA bladder cancer gene set. In one embodiment, nodal metastasis of bladder cancer can be determined by detecting the expression level of all the subtype classifiers or subsets thereof of the classifiers found in Table 1 or Table 2.

In some embodiments, the luminal, luminal infiltrated, basal, or basal infiltrated/neuronal subtype of bladder cancer can be more likely to be associated with nodal metastasis compared with other subtypes. In some embodiments, the luminal, luminal infiltrated, basal, or basal infiltrated/neuronal subtype can be most likely associated with positive lymph node metastasis compared with other subtypes. In some embodiments, the luminal, luminal infiltrated, basal, or basal infiltrated/neuronal subtype can be at least about 0.1 times, at least about 0.2 times, at least about 0.3 times, at least about 0.4 times, at least about 0.5 times, at least about 0.6 times, at least about 0.7 times, at least about 0.8 times, at least about 0.9 times, at least about 1 time, at least about 1.2 times, at least about 1.5 times, at least about 1.7 times, at least about 2.0 times, at least about 2.2 times, at least about 2.5 times, at least about 2.7 times, at least about 3.0 times, at least about 3.2 times, at least about 3.5 times, at least about 3.7 times, at least about 4.0 times, at least about 4.2 times, at least about 4.5 times, at least about 4.7 times, at least about 5.0 times, inclusive of all ranges and subranges therebetween more likely to have occult nodal metastasis compared to other bladder cancer subtypes.

Detection Methods

In one embodiment, the methods and compositions provided herein allow for the detection of at least one biomarker in a bladder cancer sample obtained from a subject. The at least one biomarker can be a classifier biomarker provided herein. The detection can be at the nucleic acid level or protein level. In one embodiment, the detection is at the nucleic acid level and the detection can be by using any amplification, hybridization and/or sequencing assay disclosed herein. In one embodiment, the at least one biomarker detected using the methods and compositions provided herein is selected from Table 1 or Table 2. Further to the above embodiment, the detection of the at least one biomarker selected from Table 1 or Table 2 is at the nucleic acid level. In one embodiment, the methods of detecting the nucleic acid(s) (e.g., classifier biomarkers) in the bladder cancer sample obtained from the subject comprises, consists essentially of, or consists of measuring the expression level of at least one or a plurality of biomarkers using any of the methods provided herein. The biomarkers can be selected from Table 1 or Table 2. In some cases, the plurality of biomarker nucleic acids comprises, consists essentially of or consists of at least two biomarker nucleic acids, at least 18 biomarker nucleic acids, at least 36 biomarker nucleic acids, at least 54 biomarker nucleic acids, or all 60 biomarkers nucleic acids of Table 1. In some cases, the plurality of biomarker nucleic acids comprises, consists essentially of or consists of at least two biomarker nucleic acids, at least 10 biomarker nucleic acids, at least 20 biomarker nucleic acids, at least 30 biomarker nucleic acids, at least 40 biomarker nucleic acids, at least 50 biomarker nucleic acids, at least 55 biomarker nucleic acids, or all 60 biomarkers nucleic acids of Table 1. In some cases, the plurality of biomarker nucleic acids comprises, consists essentially of or consists of at least two biomarker nucleic acids, at least 18 biomarker nucleic acids, at least 36 biomarker nucleic acids, at least 54 biomarker nucleic acids, or all 56 biomarkers nucleic acids of Table 2. In some cases, the plurality of biomarker nucleic acids comprises, consists essentially of or consists of at least two biomarker nucleic acids, at least 10 biomarker nucleic acids, at least 20 biomarker nucleic acids, at least 30 biomarker nucleic acids, at least 40 biomarker nucleic acids, at least 50 biomarker nucleic acids, at least 55 biomarker nucleic acids, or all 56 biomarkers nucleic acids of Table 2.

Figure 8:
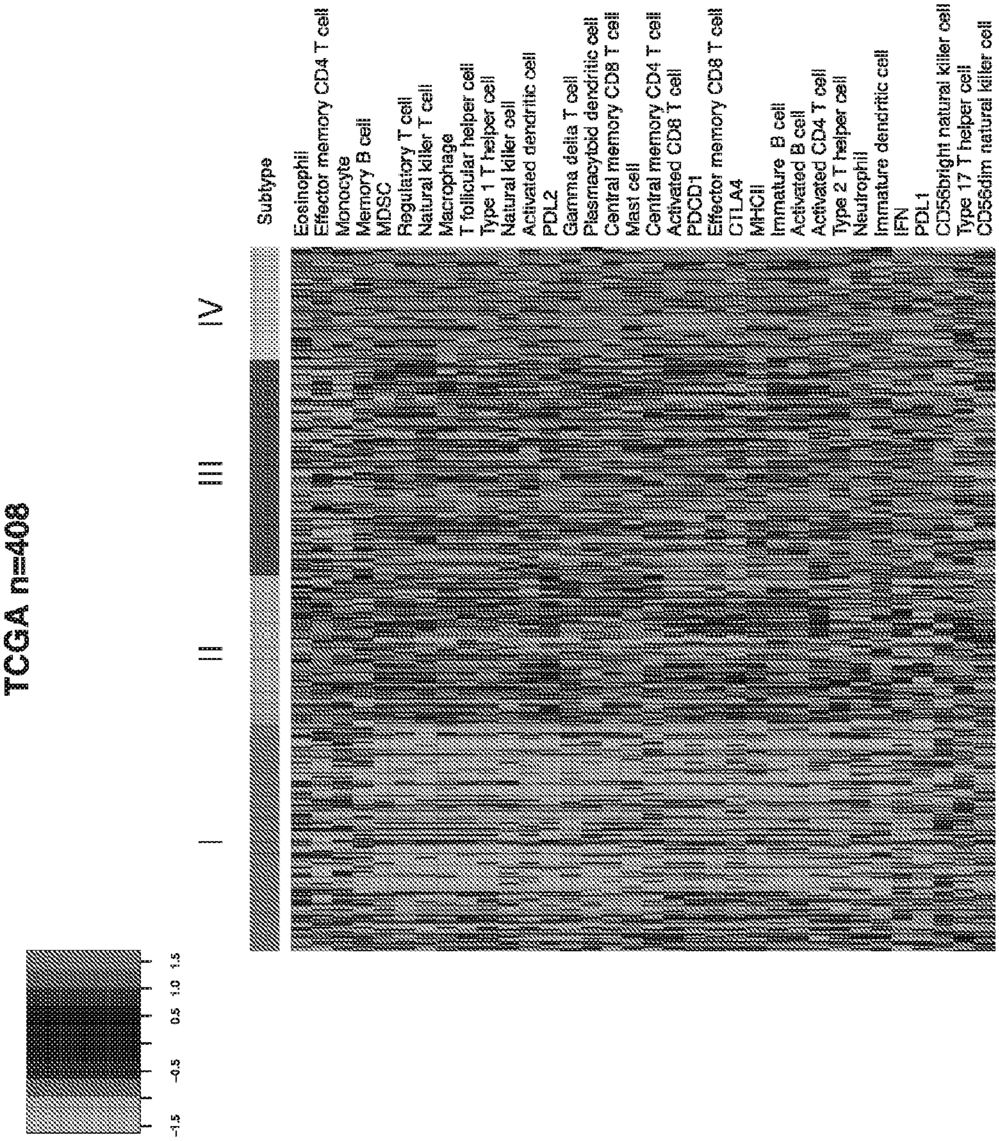
FIG. 8 illustrates a heatmap of immune signatures across defined bladder cancer subtypes (60-gene subtypes). The immune signatures used to generate this data were derived from Bindea, G, et al., Immunity, 39(4):782-95 (2013); Faruki, H, et al., J Thorac Oncol, 12(6): 943-953 (2017); and Charoentong, P., et al., Cell Reports, 18(1): 248-262 (2017), the disclosures of which are incorporated herein by reference in their entireties.

In another embodiment, the methods and compositions provided herein allow for the detection of at least one or a plurality of biomarkers in a bladder cancer sample obtained from a subject such that the at least one or the plurality of biomarkers are selected from the biomarkers listed in Table 1 or Table 2 in combination with the detection of at least one or a plurality of biomarkers from one or more additional sets of biomarkers in a bladder cancer sample obtained from the subject. The detection can be at the nucleic acid level or protein level. In one embodiment, the detection is at the nucleic acid level and the detection can be by using any amplification, hybridization and/or sequencing assay disclosed herein. The one or more additional sets of biomarkers can be selected from a set of biomarkers whose presence, absence and/or level of expression is indicative of immune activation, proliferation or a combination thereof. The set of biomarkers for indicating immune activation can be gene expression signatures of and/or Adaptive immune Cells (AIC) and/or innate immune Cells (IIC), individual immune biomarkers, interferon genes, major histocompatibility complex, class II (WIC II) genes or a combination thereof (See, FIG. 8). The gene expression signatures for IICs, AICs, IFN and MHC class II can be any known gene signatures for said cell types or genes known in the art. For example, the immune gene signatures can be those from Bindea et al. (Immunity 2013; 39(4); 782-795), Faruki H. et al., JTO, 12(6): 943-953 (2017), Charoentong P. et al., Cell reports, 18, 248-262 (2017) and/or WO2017/201165 and WO2017/201164. The individual immunomarkers can be those found in Faruki H. et al., JTO, 12(6): 943-953 (2017), Charoentong P. et al., Cell reports, 18, 248-262 (2017), WO2017/201165 or WO2017/201164. In one embodiment, the individual immunomarkers can be CTLA4 (e.g., NM_005214 (SEQ ID NO. 80), PDCD1 (e.g., NM_005018; SEQ ID NO. 81), PDL2 (e.g., AY254343; SEQ ID NO. 82) and CD274 (PD-L1; e.g., NM_014143; SEQ ID NO. 83). In one embodiment, immune subtyping or immune cell activation can be determined using the gene signatures found in Thorsson, V., Gibbs, D. L., Brown, S. D., Wolf, D., Bortone, D. S., Yang, T. H. O., Porta-Pardo, E., Gao, G. F., Plaisier, C. L., Eddy, J. A. and Ziv, E., 2018, The immune landscape of cancer. *Immunity,* 48(4), pp. 812-830. The additional set of biomarkers for indicating proliferation can be gene expression signatures that include the 11 gene signature comprising BIRC5, CCNB1, CDC20, CDCA1, CEP55, KNTC2, MKI67, PTTG1, RRM2, TYMS, and UBE2C found in Martin M. et al., Breast Cancer Res Treat, 138: 457-466 (2013), the 18 gene signature found in US 20160115551 and/or the 26 gene signature found in 62/789,668 filed Jan. 8, 2019.

Further to any of the above embodiments, the methods and compositions provided herein further comprise determining tumor mutation burden (TMB) and/or TMB rate of the tumor sample. The TMB and/or TMB rate can be determined or calculated using any method known in the art. In one embodiment, the TMB and/or TMB rate is determined from RNA as described in 62/743,257 filed on Oct. 9, 2018 and 62/771,702 filed on Nov. 27, 2018.

Further to any of the above embodiments, the methods and compositions provided herein further comprise determining a cell of origin subtype of the bladder cancer sample. In one embodiment, cell of origin subtype is determined using any method known in the art such as, for example, as provided in Hoadley et al, Cell. 2018 Apr. 5; 173(2):291-304, which is herein incorporated by reference herein.

Kits

Kits for practicing the methods provided herein can be further provided. By "kit" can encompass any manufacture (e.g., a package or a container) comprising at least one reagent, e.g., an antibody, a nucleic acid probe or primer, etc., for specifically detecting the expression of a biomarker as provided herein. The kit may be promoted, distributed, or sold as a unit for performing the methods provided herein. Additionally, the kits may contain a package insert describing the kit and methods for its use.

In one embodiment, kits for practicing the methods as provided herein are provided. Such kits are compatible with both manual and automated immunocytochemistry techniques (e.g., cell staining). These kits comprise at least one antibody directed to a biomarker of interest, chemicals for the detection of antibody binding to the biomarker, a counterstain, and, optionally, a bluing agent to facilitate identification of positive staining cells. Any chemicals that detect antigen-antibody binding may be used in the practice of the methods provided herein. The kits may comprise at least 2, at least 3, at least 4, at least 5, at least 6, at least 7, at least 8, at least 9, at least 10, or more antibodies for use in the methods provided herein.

In one embodiment, the kits for practicing the methods provided herein comprise at least one primer pair directed to a biomarker of interest, chemicals for the detection of amplification of the biomarker of interest, and, optionally, any agent necessary for quantifying the detection level of the biomarker of interest. Any chemicals that detect amplification products may be used in the practice of the methods provided herein. The kits may comprise at least 2, at least 3, at least 4, at least 5, at least 6, at least 7, at least 8, at least 9, at least 10, or more primer pairs for use in the methods provided herein.

In one embodiment, the kits for practicing the methods provided herein comprise at least one probe directed to a biomarker of interest, chemicals for the detection of hybridization of the probe to the biomarker of interest, and, optionally, any agent necessary for quantifying the level of the biomarker of interest. Any chemicals that detect hybridization products may be used in the practice of the methods provided herein. The kits may comprise at least 2, at least 3, at least 4, at least 5, at least 6, at least 7, at least 8, at least 9, at least 10, or more probes for use in the methods provided herein.

EXAMPLES

The present invention is further illustrated by reference to the following Examples. However, it should be noted that these Examples, like the embodiments described above, are illustrative and are not to be construed as restricting the scope of the invention in any way.

Example 1—Development and Validation of the 60-Gene Bladder Cancer Subtyping Signature

Background

Recent advances in cancer genomics have led to an increased understanding of mutational and gene expression profiles in bladder cancer. Bladder cancer subtypes, as defined by underlying genomic features, have shown varied cell of origin, tumor drivers, proliferation, immune responses, and prognosis.

Provided herein is a novel 60-gene expression subtype classification method which provides valuable insight into tumor biology and potential therapeutic response. Differential expression of immune infiltrating cells and biomarkers, tumor mutation burden, therapeutic targets, and overall survival were examined in Muscle Invasive Bladder Cancer (MIBC) subtypes (luminal, luminal infiltrated, basal, and basal infiltrated/neuronal).

Objective

This example was initiated to address the need for an efficient method for improved tumor classification that could inform prognosis, drug response and patient management based on underlying genomic and biologic tumor characteristics. Using multiple available public datasets, including the dataset described in Robertson, A G, et al., Cell, 171(3): 540-556 (2017) (dataset referred to herein as "Gold standard," "GS," or "TCGA-2017"); the dataset described in Cancer Genome Atlas Research Network, Nature, 507(492): 315-22 (2014) (dataset described herein as TCGA-2014); the Seiler dataset (Seiler, R., et al., Eur Urol 72(4):544-554 (2017)); and the Sjodahl dataset (Sjodahl, G., et al., Clin Cancer Res, 18(12):3377-86 (2012)), a bladder cancer subtyping method and algorithm was developed. (All datasets and dataset references are incorporated herein by reference in their entireties.) The diagnostic method developed in this example includes evaluation of gene expression subtypes and application of an algorithm for categorization of bladder cancer into one of 4 subtypes (Luminal (Type I), Luminal Infiltrated (Type II), Basal (Type III), and Basal infiltrated/neuronal (Type IV)).

Methods

Figure 4:
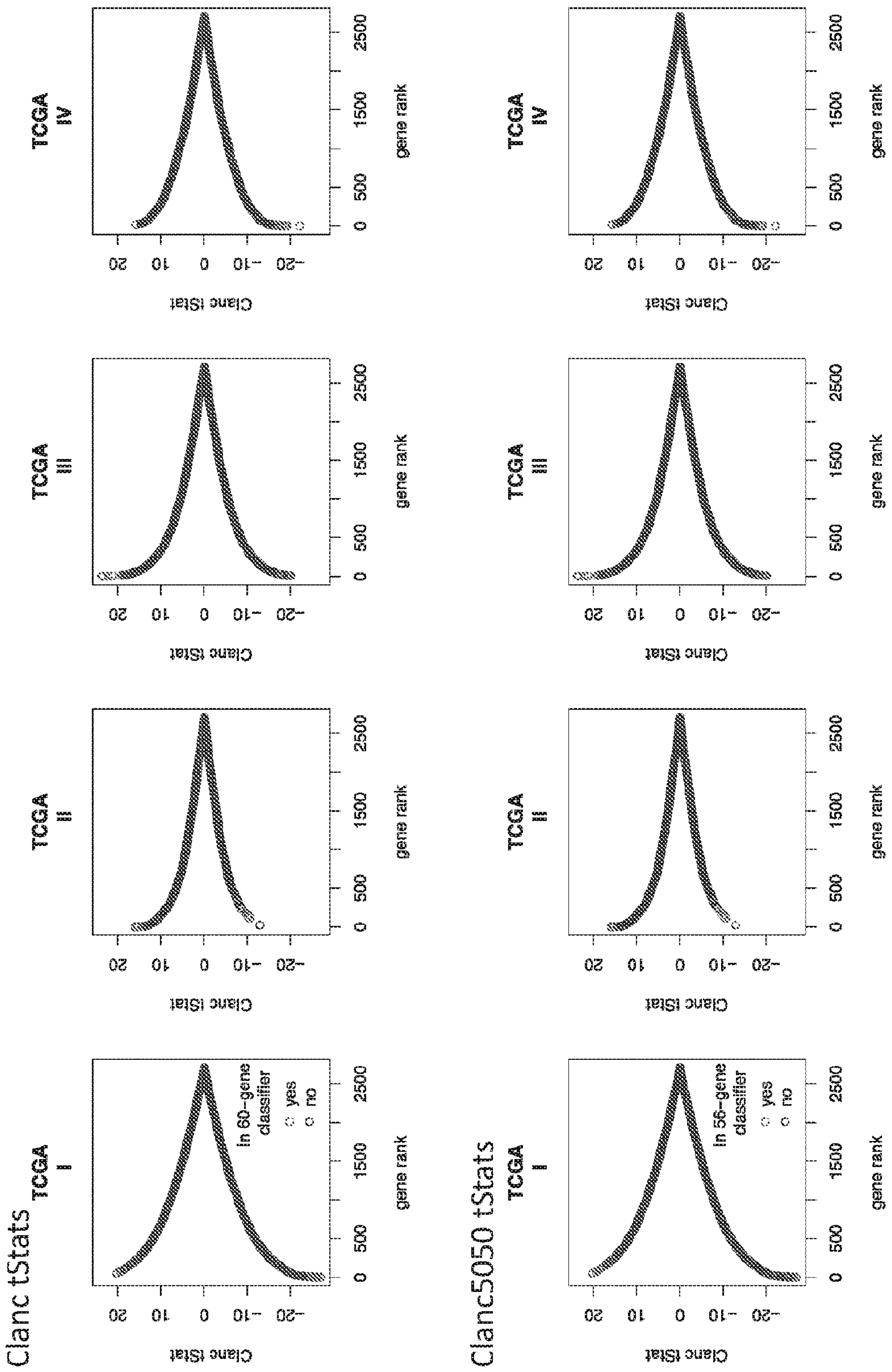
FIG. 4 illustrates Clanc tStats data used for gene selection. Shown are Clanc tStats data from the entire TCGA-2017 dataset, minus non-prototypes. The genes with a high-magnitude tStats value (shown in red) were selected for a 60-gene subtyper (top row; 50:50 high:low approach). Also shown are selected genes for a 56-gene subtyper (bottom row, 50:50 high:low approach).
Figure 5:
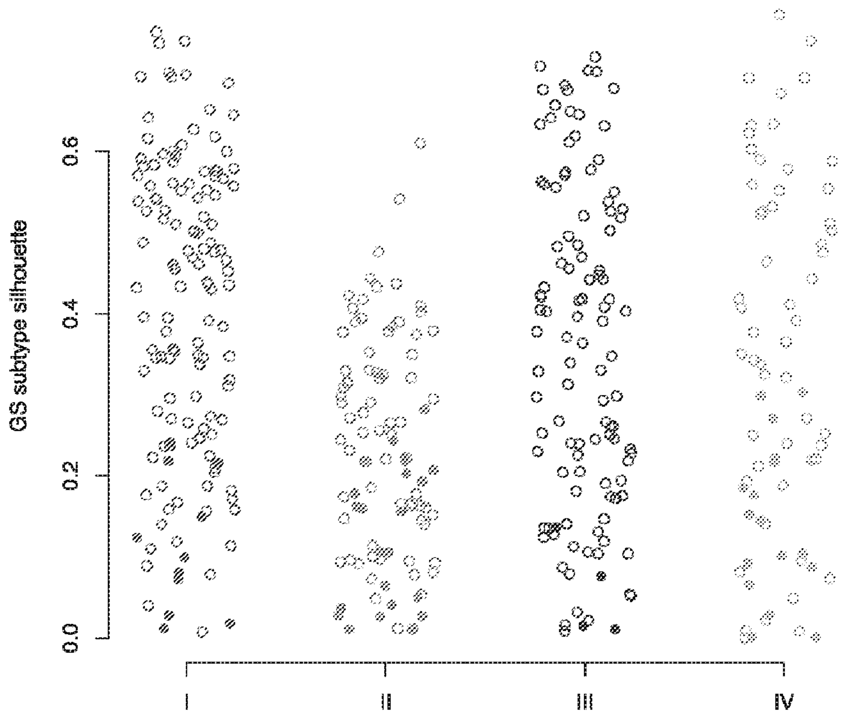
FIG. 5 illustrates agreement and disagreement between the GS subtype (rows) and the subtype based on the 60-gene subtyper (columns) (left panel). Overall agreement was 87%. The GS subtype silhouette for the TCGA-2017 dataset (n=408) is also shown (right panel), wherein a solid dot indicates that the GS subtype and the 60-gene subtype don't agree.

The TCGA-2017 bladder cancer gene expression data was examined using the 2708-gene classifier previously developed by Robertson et al. (2017) to differentiate the luminal, luminal infiltrated, basal, and basal infiltrated/neuronal subtypes. (FIG. 1) To develop a reduced and clinically applicable gene signature for evaluation of bladder cancer, a 5-fold cross-validation (CV) on the entire TCGA bladder cancer dataset (n=408) was conducted to find the number of genes that would be required to provide differentiation of the subtypes with sufficient agreement with the previously developed gold standard (i.e., aforementioned 2708-gene classifier) as shown in FIG. 2. Prototype samples were then chosen based on the gold standard silhouette (FIG. 3). A minimal gene set that optimally classified the luminal, luminal infiltrated, basal, and basal infiltrated/neuronal subtypes was identified using a modification of the software packages ClaNC. The Clanc t-statistics were calculated for all 2708 gold standard subtyping genes using the prototype samples and 60 genes were selected based on the ranks of the strongest t-statistics (i.e., select an equal number of negatively and positively correlated genes for each bladder cancer subtype) (FIG. 4). A nearest centroid classifier (FIG. 5, FIG. 6) was fit using the 60 genes and the prototypes only followed by an evaluation of the full TCGA dataset. Validation of the reduced gene signature was compared to the gold standard gene signature in TCGA datasets (FIG. 5) and in several other publicly available datasets (FIG. 16) including the Seiler, et. al. (2017), and Sjodahl, et. al. (2012), references.

Figure 7:
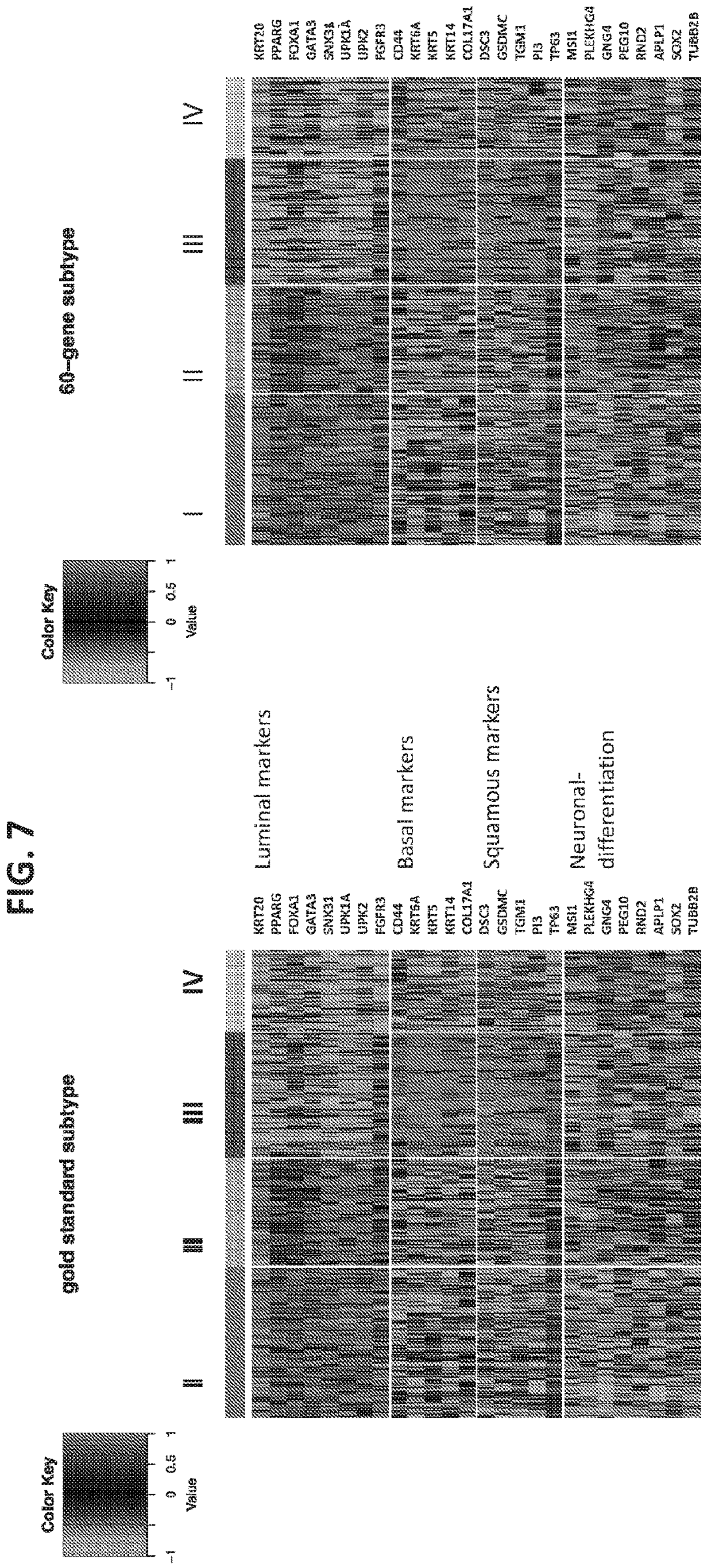
FIG. 7 illustrates heatmaps comparing various markers (luminal markers, basal markers, squamous markers, and basal infiltrated/neuronal-differentiation markers) across defined bladder cancer subtypes (GS subtype, left panel and 60-gene subtype, right panel). The heatmaps show a high degree of concordance between the GS subtype and the 60-gene subtype.
Figure 11:
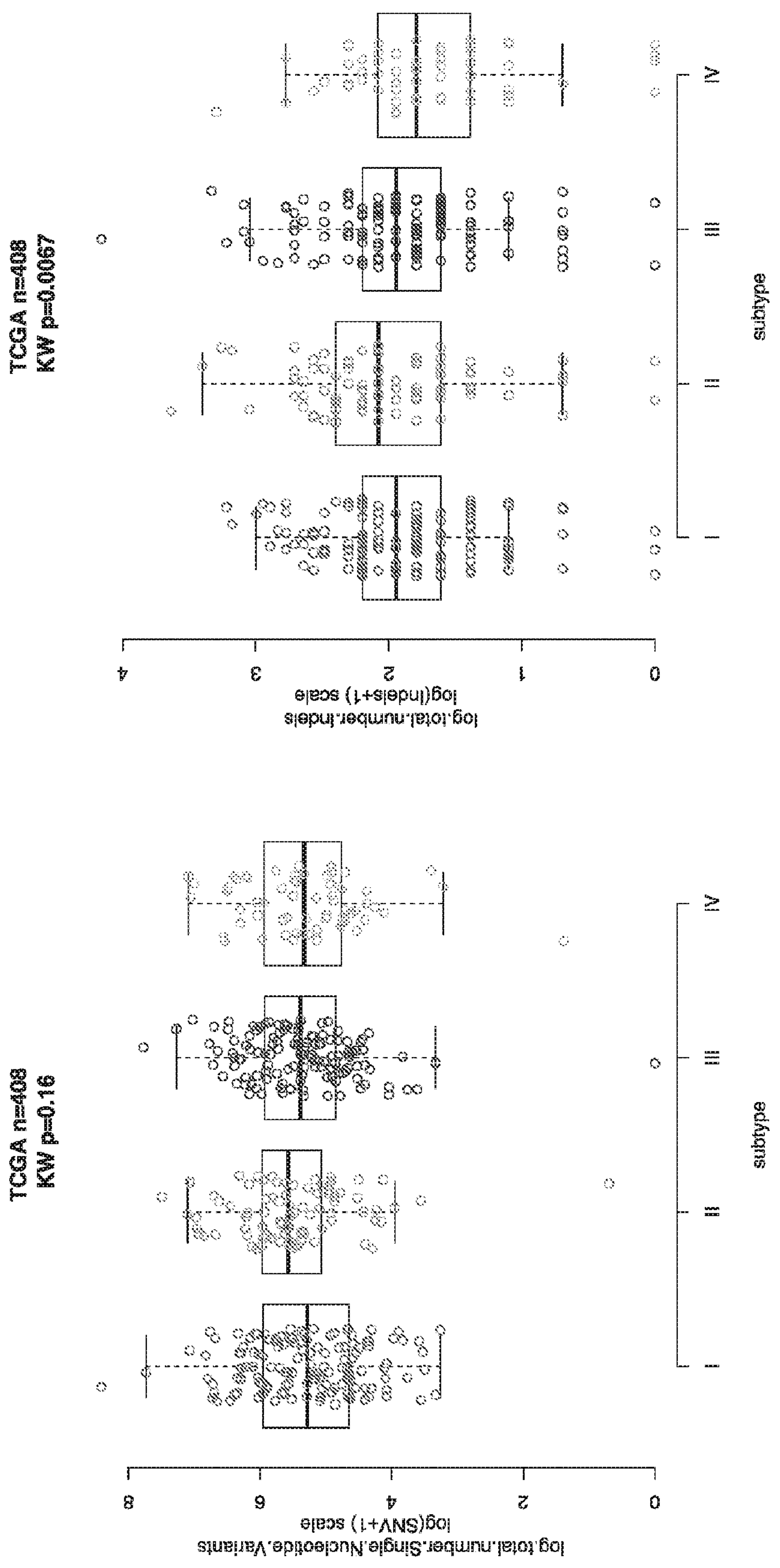
FIG. 11 provides boxplots showing tumor mutation burden across the 60-gene signature subtypes. Single nucleotide variants are shown in the left panel, and indels are shown in the right panel. No notable differences between the subtypes were observed.
Figure 12:
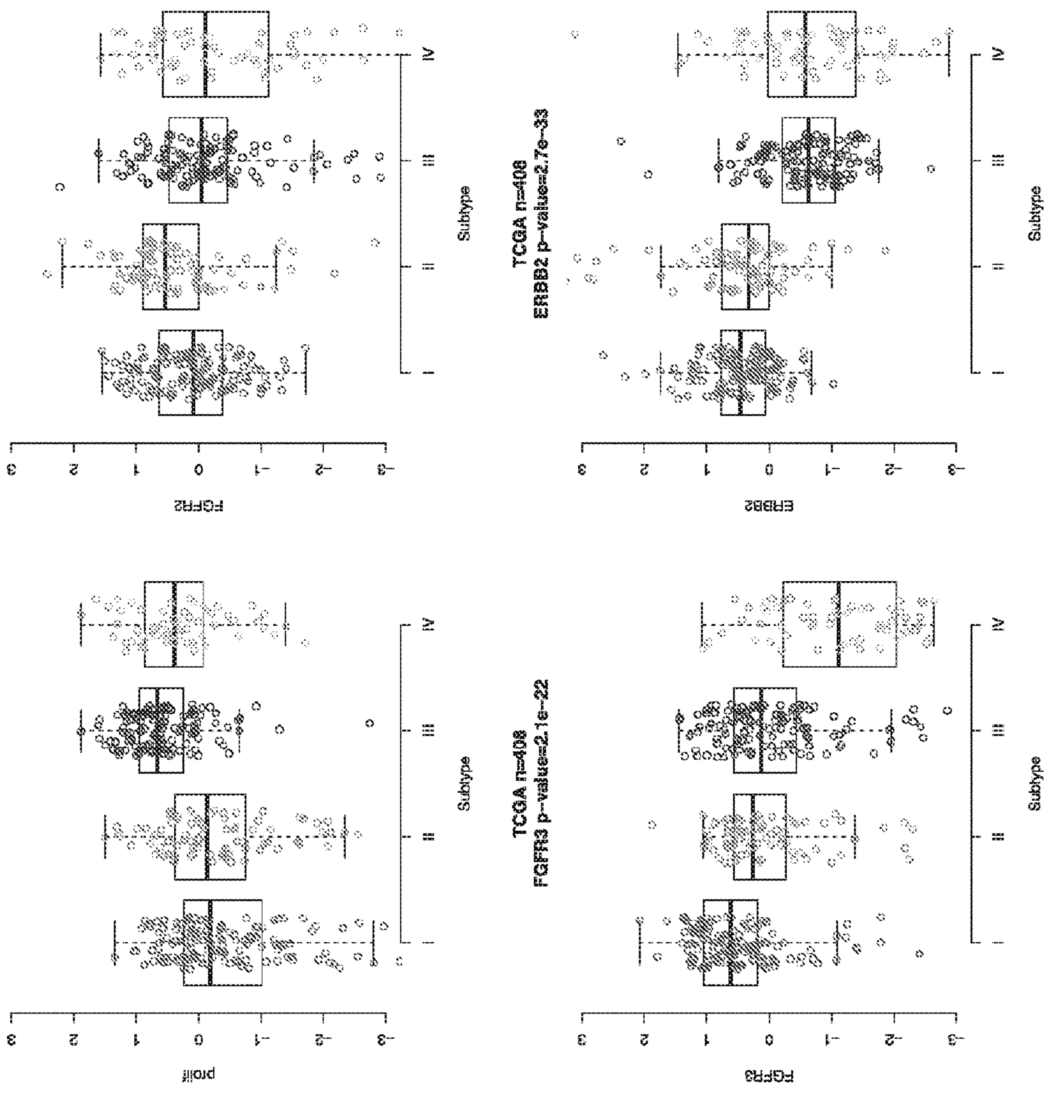
FIG. 12 provides boxplots showing proliferation by subtype (60-gene signature) (top left panel). Subtypes III (basal) and IV (basal infiltrated/neuronal) were more proliferative than subtypes I (luminal) and II (luminal infiltrated). The gene signature used to determine proliferation is described in Martin, M., et al. Breast Cancer Res Treat 138:457-466 (2013), which is incorporated by reference in its entirety.
Figure 13:
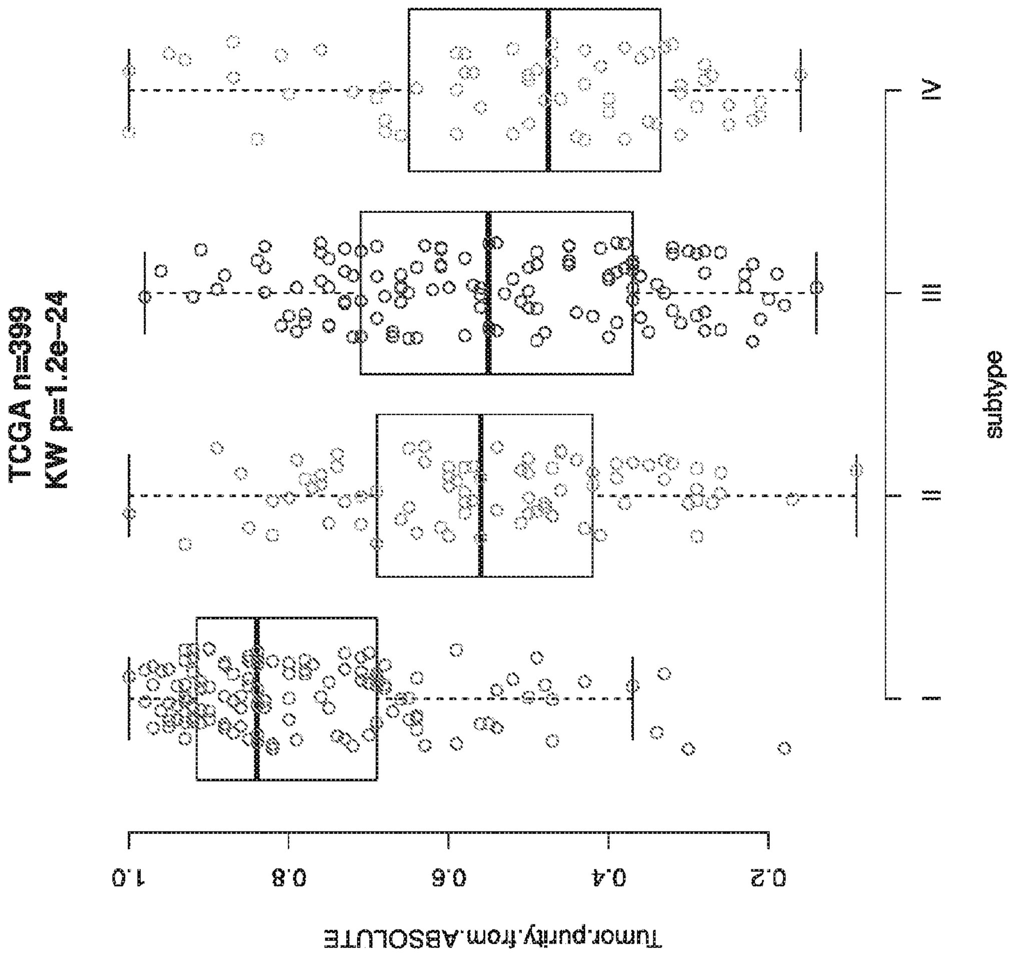
FIG. 13 illustrates tumor purity by ABSOLUTE differences across gene expression subtypes. ABSOLUTE tumor purity was measured using somatic copy number data from Robertson, A G, et al., Cell, 171(3): 540-556 (2017) (supplement). ABSOLUTE tumor purity was measured as described in Carter, S. L. et al. Absolute quantification of somatic DNA alterations in human cancer. Nat. Biotechnol. 30, 413-421 (2012), which is incorporated herein by reference in its entirety.

Signatures of multiple immune cells (FIG. 8), single immune-biomarkers (FIG. 7), drug target genes (FIG. 12), proliferation (FIG. 12), mutation burden (FIG. 11), tumor driver/suppressor mutation frequencies (FIG. 14, FIG. 15) and tumor purity (FIG. 13) were examined for differential expression. Differences in gene mutation distributions were evaluated using Fisher's exact test. Survival differences (FIG. 9, FIG. 10A-B) were assessed using stratified cox models and Kaplan Meier plots. FIG. 20 presents a comparison of the subtyping of the TCGA-2017 bladder cancer dataset (n=408) samples based on the 5-type classification system described in Roberston, et al. (2017), and the 4-type classification system based on the 60 gene subtype described herein.

Results

Development of the 60 Gene Signature

Figure 16:
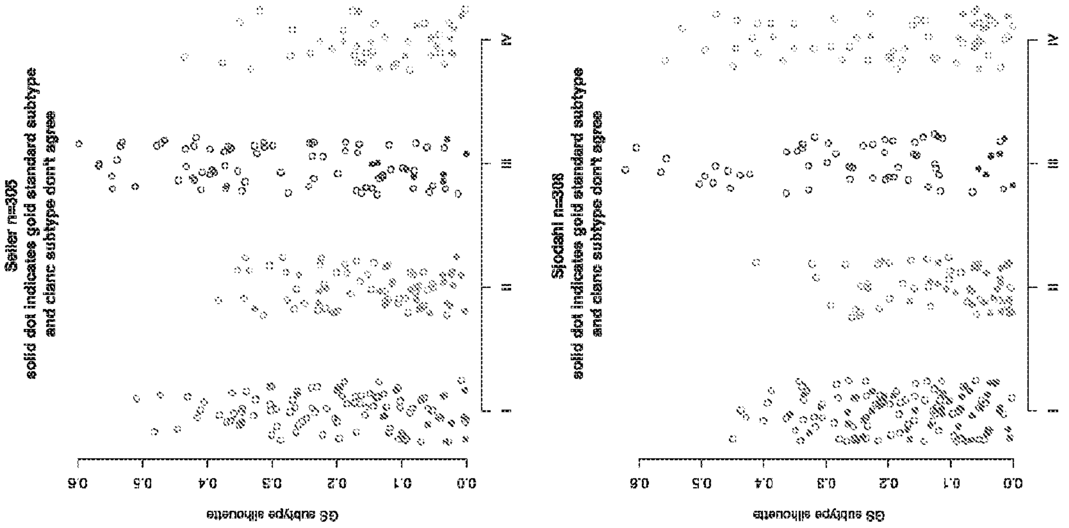
FIG. 16 illustrates the results of subtyping using the 60-gene signature in two additional datasets: the Seiler dataset (Seiler, R., et al., Eur Urol 72(4):544-554 (2017)) and the Sjodahl dataset (Sjodahl, G., et al., Clin Cancer Res, 18(12):3377-86 (2012)), both of which are incorporated by reference herein in their entireties. A comparison between the GS subtype (rows) and the 60-gene subtype (columns) was performed for the Seiler dataset (top left panel, agreement=0.81) and the Sjodahl dataset (bottom left panel, agreement=0.72). The GS subtype silhouette is shown for the Seiler dataset (top right panel) and for the Sjodahl dataset (bottom right panel). Solid dots indicate that the GS subtype and the 60-gene subtype do not agree.
Figure 17A:
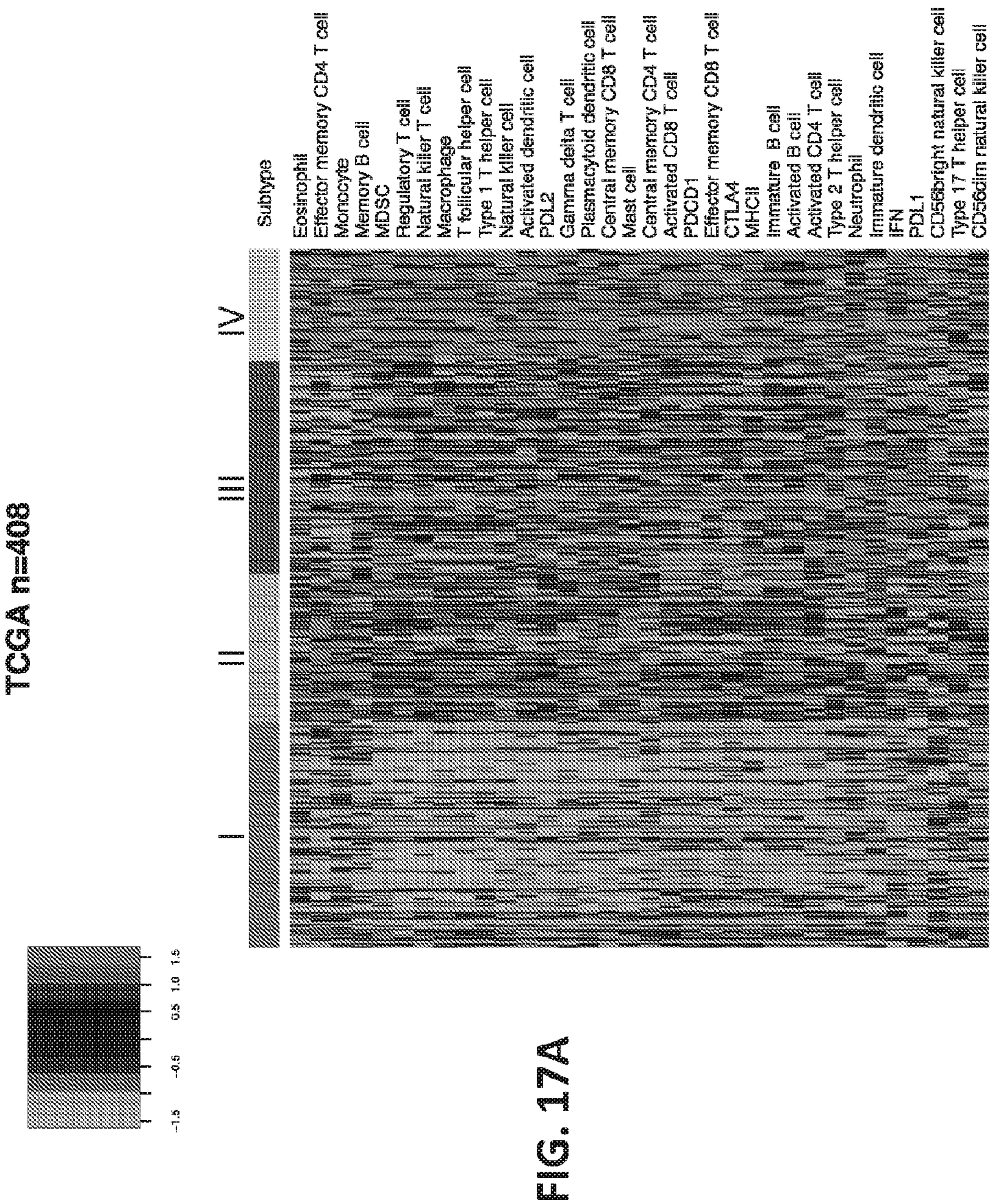
FIG. 17A-C provides heatmaps illustrating immune profiles of the four bladder cancer gene expression subtypes (defined by the 60 gene signature) across the TCGA-2017 dataset (FIG. 17A), the Seiler dataset (FIG. 17B), and the Sjodahl dataset (FIG. 17C). In general, a high concordance was observed.
Figure 17B:
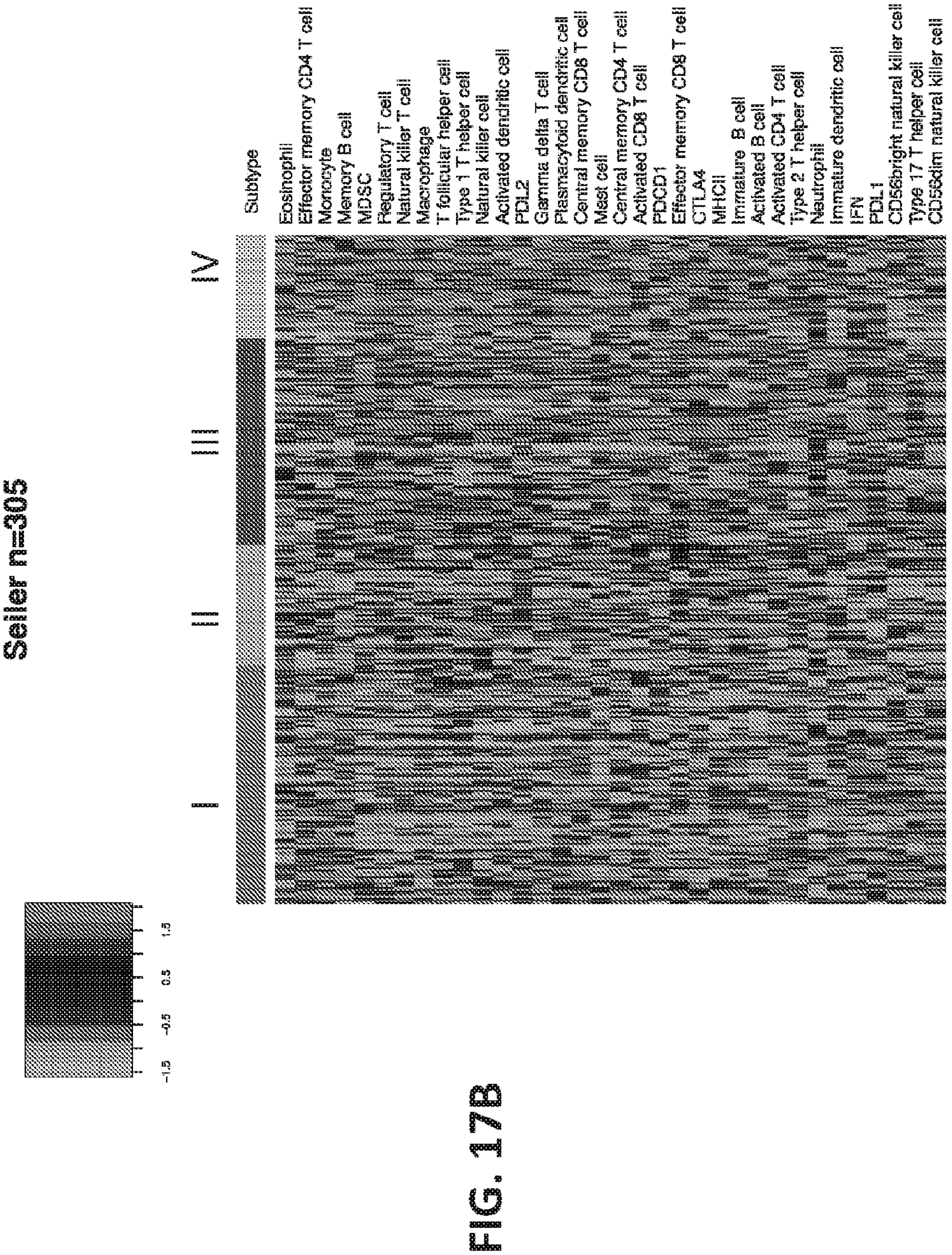
Figure 17C:
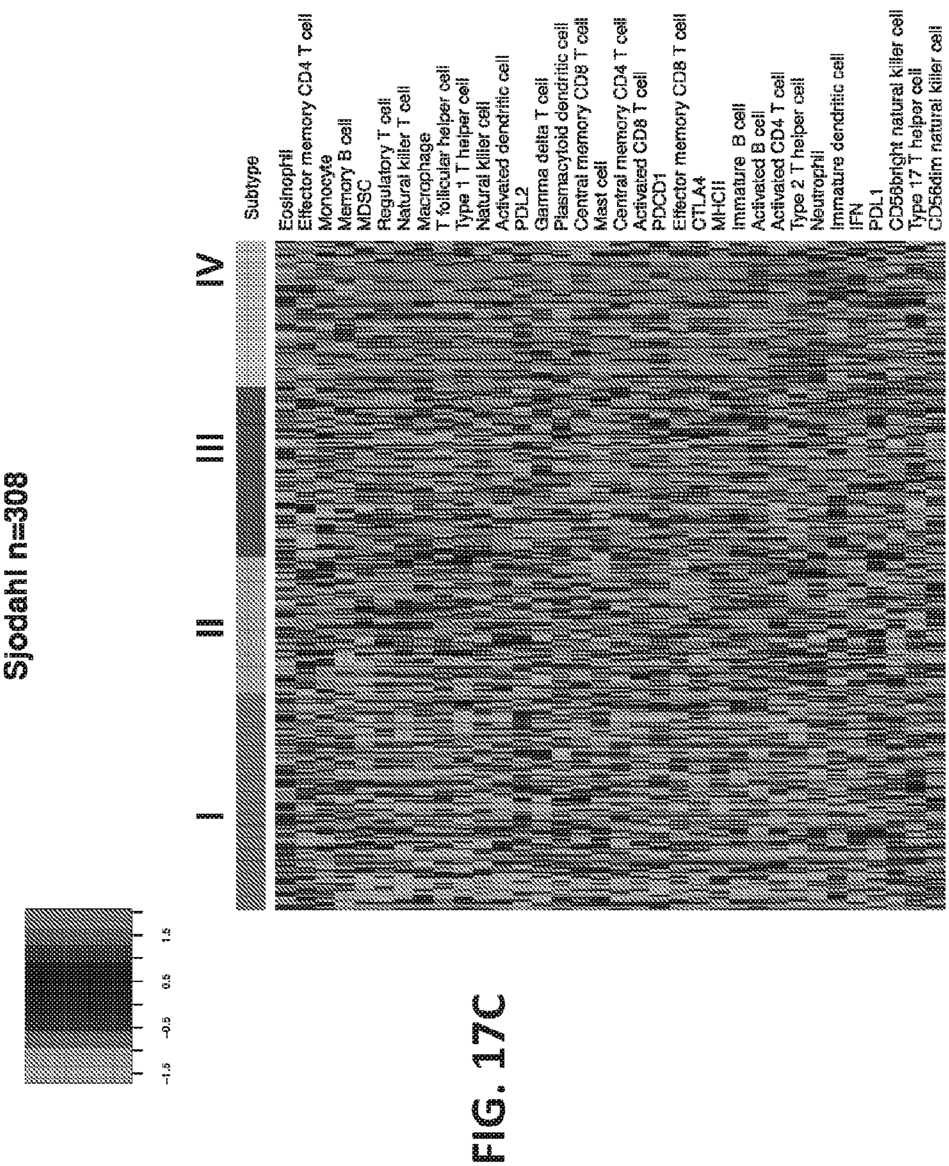
Figure 18:
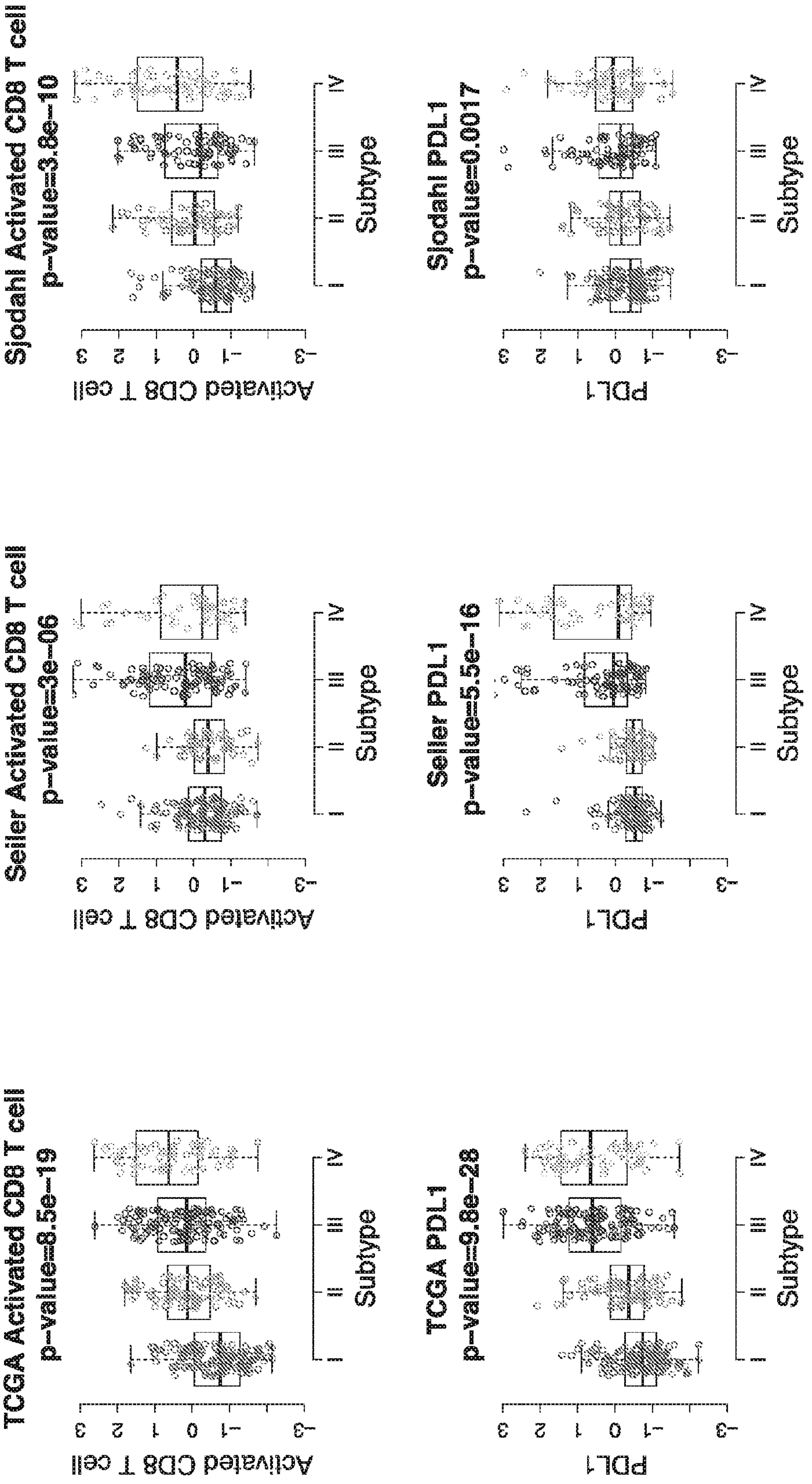
FIG. 18 provides boxplots showing t-cells and CD274 (PD-L1) by gene expression subtype in the various gene expression datasets. Similar patterns were observed in each dataset.

The 60 gene signature gene list developed in this study is shown in Table 1 and FIG. 6. Agreement of subtype calls using the 60 gene signature with the published 2708 gold standard gene signature subtype call in several different test datasets is shown in FIG. 1 and FIG. 16. The newly developed 60 gene signature demonstrated agreement of 0.87 in the TCGA-2014 dataset (FIG. 1) and 0.72 or 0.81 in the other 2 test datasets (FIG. 16).

Figure 9:
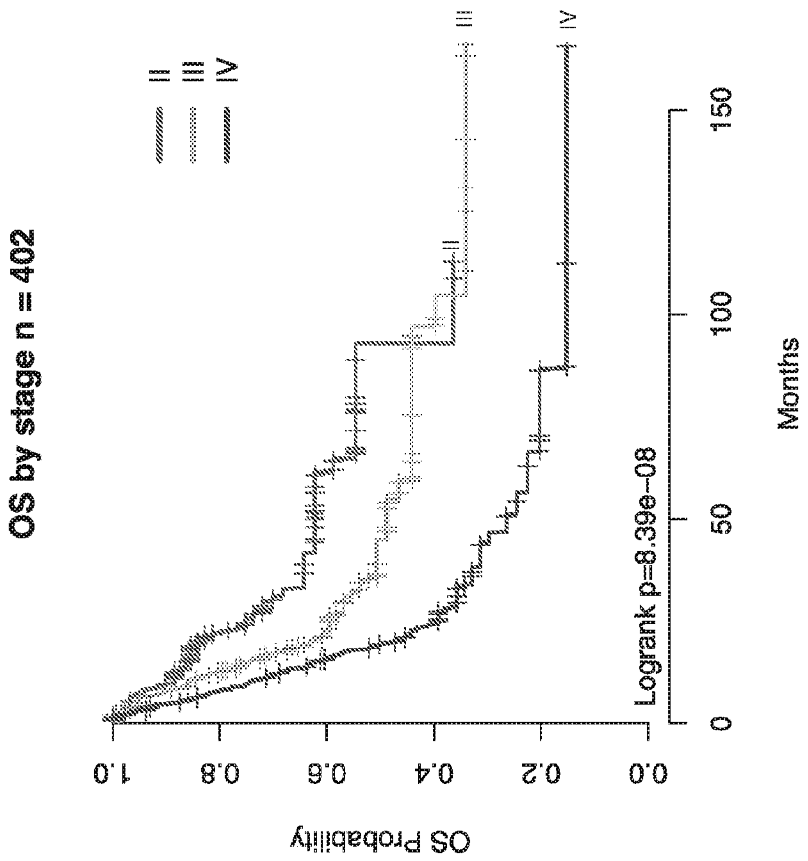
FIG. 9 provides survival curves of tumors from the TCGA-2017 dataset (n=402) based on clinical staging (stages II, III and IV in FIG. 9), showing that later-stage samples are correlated with a worse survival. Roman numerals indicate stage. Logrank p=8.39e-08.
Figure 10A:
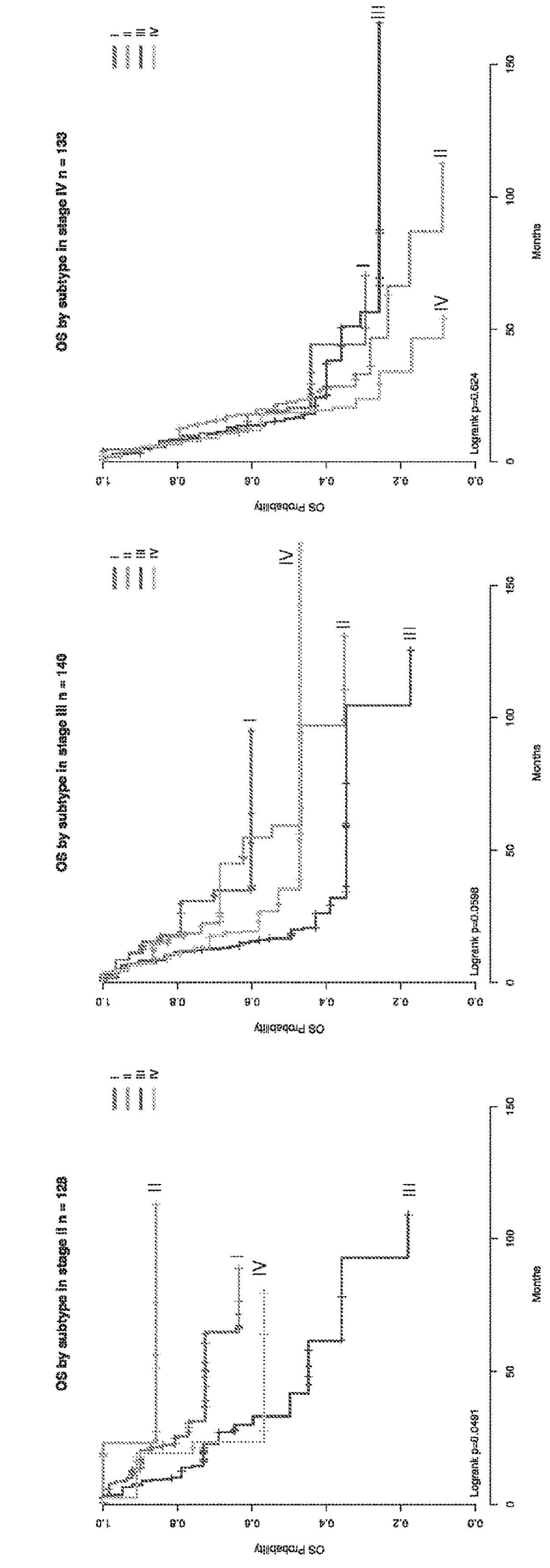
FIG. 10A-B provides survival curves by subtype in stage II, III and IV using the 60-gene subtype (FIG. 10A) and in stage II, III, and IV. Also shown are survival curves using the 60-gene subtype with the samples identified as "luminal" or "basal infiltrated/neuronal" in the TCGA-2017 data excluded (FIG. 10B). Survival differences were still evident even after "luminal" and "basal infiltrated/neuronal" TCGA-2017 subtypes were excluded (see FIG. 10B). OS-subtype association test p-value using cox model, p=0.00262; OS-subtype association test p-value using stratified (for stage) cox model, p=0.0385.
Figure 10B:
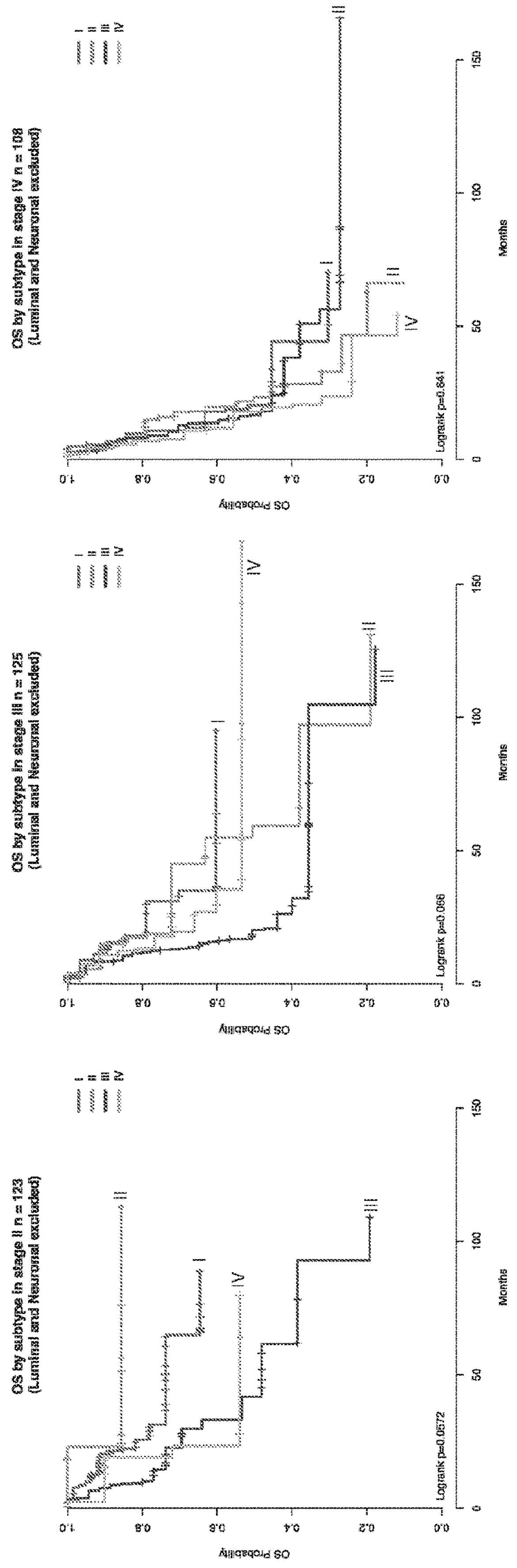
Figure 19:
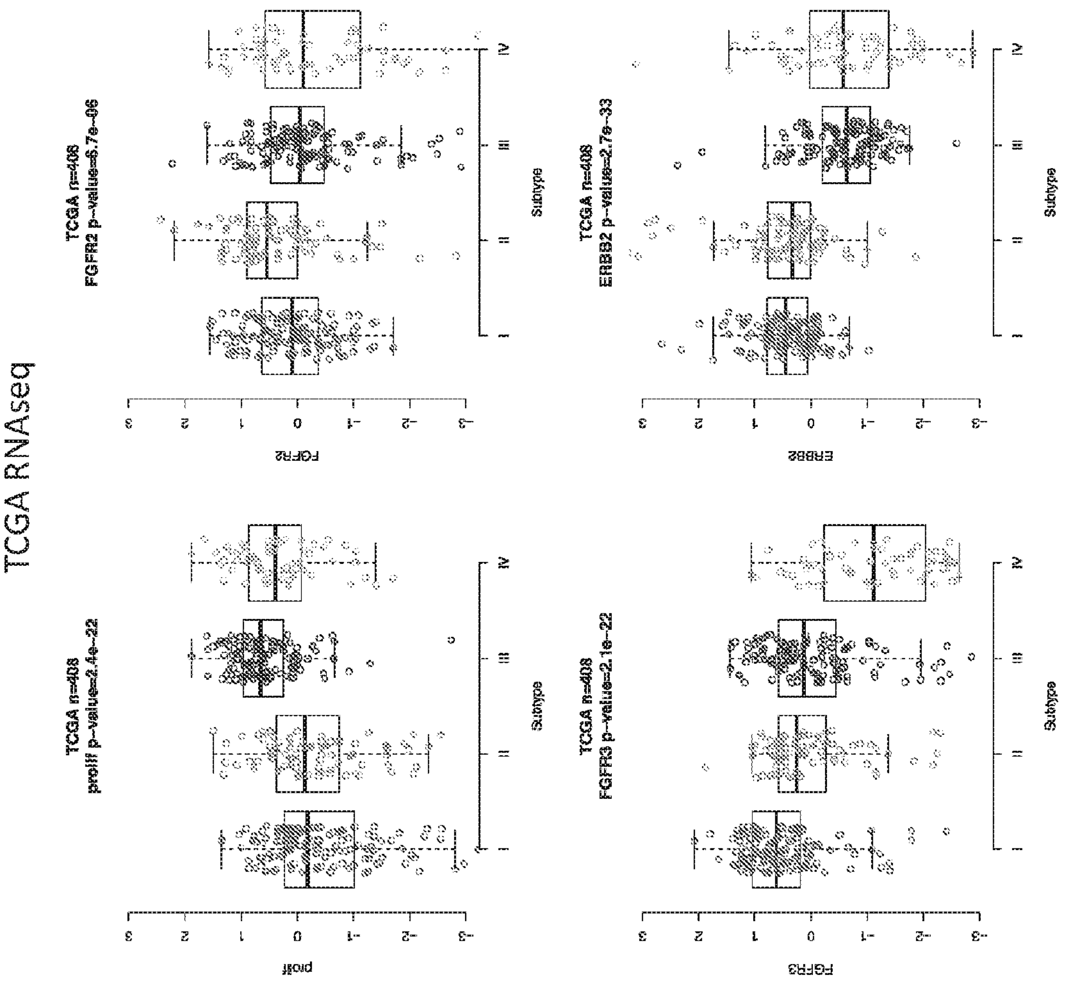
FIG. 19 provides boxplots showing proliferation and gene expression (FGFR3, FGFR2, ERBB2) across the various gene expression datasets.
Figure 19:
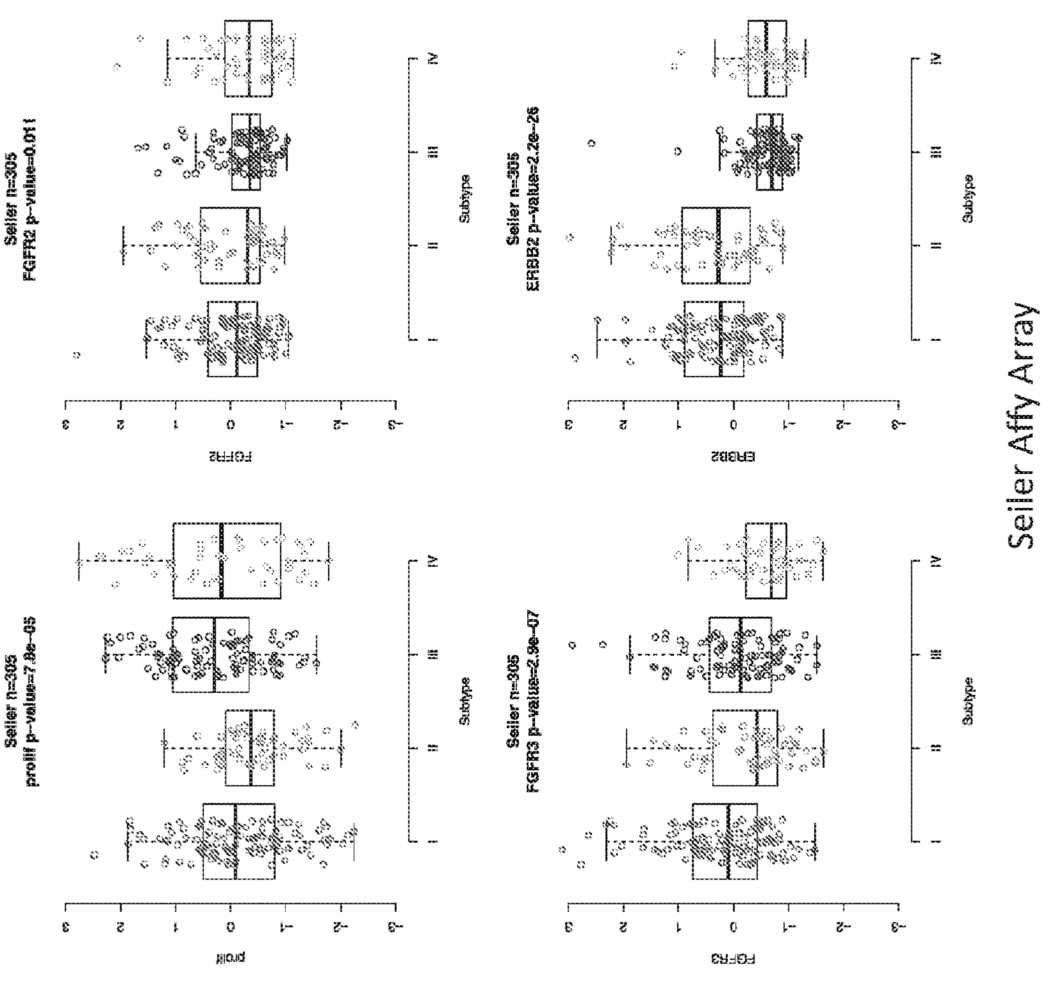
Figure 19:
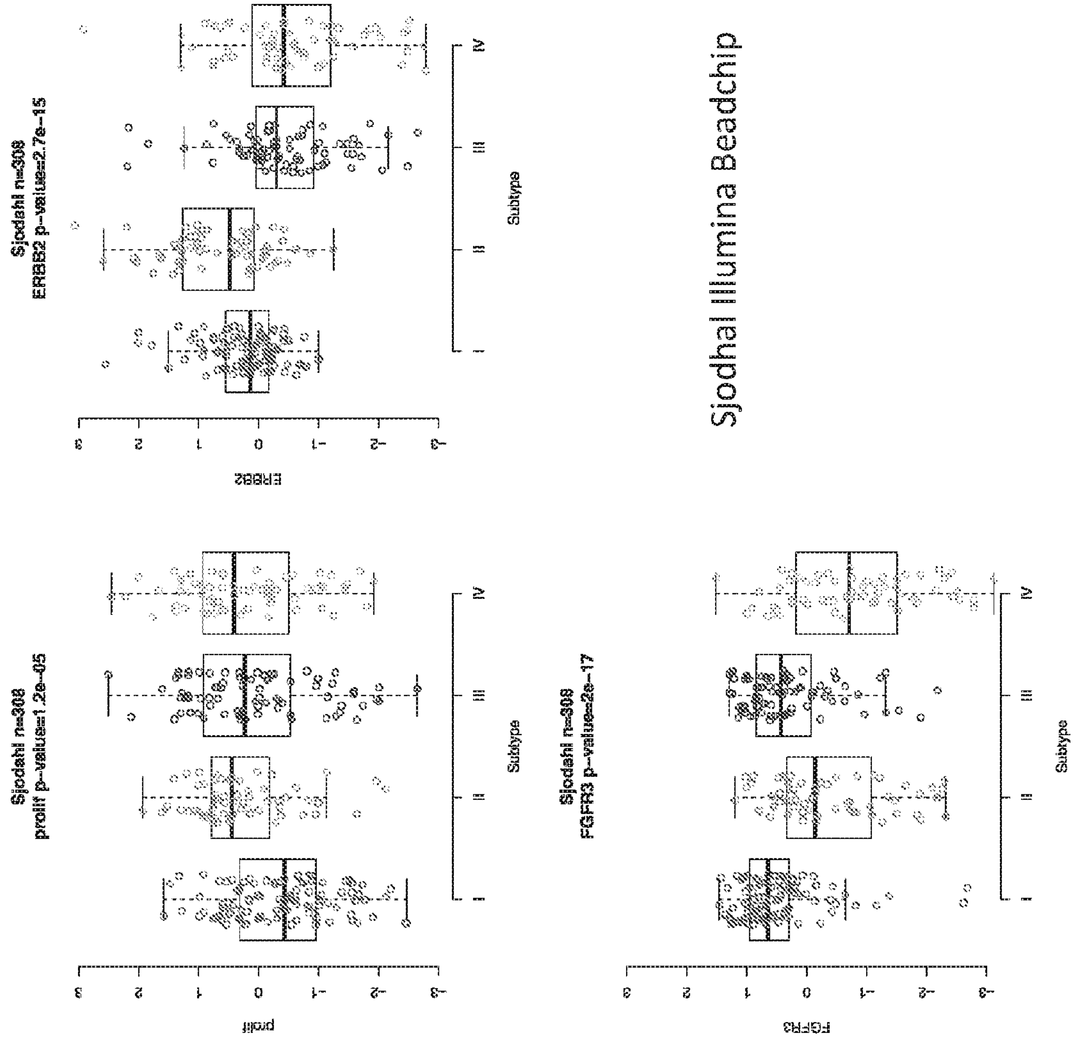

Evaluation of Assignment to Luminal, Luminal Infiltrated, Basal, or Basal Infiltrated/Neuronal Subtypes Immune cell expression was significantly different across the subtypes in multiple datasets (T cells $p<1e-05$ and CD274(PD-L1) $p<0.002$) (FIG. 17A-C, FIG. 18). The luminal subtype showed lower immune expression for most markers. Drug target genes were differentially expressed (FGFR2, FGFR3, and ERBB2 $p<1e-05$ in TCGA), as was proliferation ($p<1e-20$ in TCGA), and patterns were reproducible across datasets, with luminal and luminal-infiltrated subtypes showing higher expression of FGFR2, FGFR3, and ERBB2 and lower proliferation (FIG. 19). Mutation frequencies of FGFR3 and RB1 varied across subtypes (p=1e-05 and p=0.0005 in TCGA), whereas mutation burden did not (p=0.16), despite marked differences in immune infiltration. Significant differences in survival were observed (p=0.0385 adjusting for stage in TCGA), with luminal and luminal-infiltrated showing better survival and basal worse survival (FIG. 9, FIG. 10A-B).

Conclusions

Development and validation of a 60-gene signature for bladder cancer subtyping was described. The resulting 60 gene signature maintains high concordance rates when applied to several independent test sets. Biologic gene expression subtypes of MIBC using a reduced 60-gene signature reveal key differences in prognosis, immune cell expression, and drug targets. Subtypes provide potential biomarkers for targeted and immunotherapy response. The data demonstrate that differences in prognosis that may be meaningful to therapeutic management.

Figure 21:
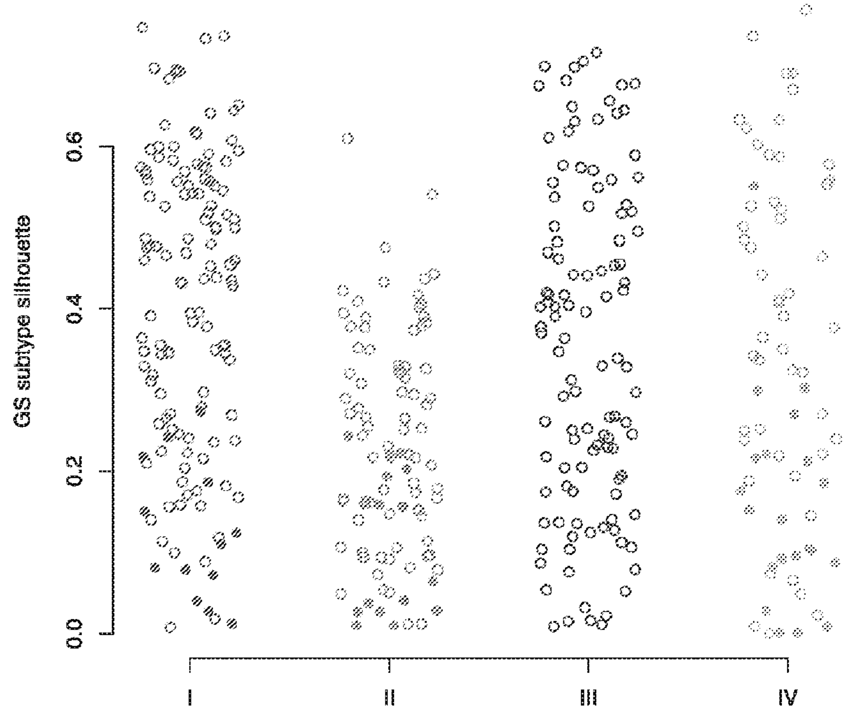
FIG. 21 illustrates agreement and disagreement between the GS subtype (rows) and the subtype based on the 56-gene subtyper (columns) (left panel). Overall agreement was 88%. The GS subtype silhouette for the TCGA-2017 dataset (n=408) is also shown (right panel), wherein a solid dot indicates that the GS subtype and the 65-gene subtype do not agree.

Example 2—Development and Validation of the 56-Gene Bladder Cancer Subtyping Signature Using a similar method as described above, a second, 56-gene subtyping signature was identified (FIG. 4, FIG. 21). A nearest centroid classifier (FIG. 22, Table 2) was fit using the 56 genes. Validation of the reduced gene signature was compared to the gold standard gene signature in TCGA datasets (FIG. 21).

INCORPORATION BY REFERENCE

The following references are incorporated by reference in their entireties for all purposes.

Carter, S. L. et al. Absolute quantification of somatic DNA alterations in human cancer. Nat. Biotechnol. 30, 413-421 (2012).

Dabney A R. ClaNC: Point-and-click software for classifying microarrays to nearest centroids. Bioinformatics. 2006; 22: 122-123. doi:10.1093/bioinformatics/bti756

Tibshirani R, Hastie T, Narasimhan B, Chu G. Diagnosis of multiple cancer types by shrunken centroids of gene expression. Proc Natl Acad Sci USA. 2002; 99: 6567-72. doi:10.1073/pnas.082099299

Martin M. et al., PAM50 proliferation score as a predictor of weekly paclitaxel benefit in breast cancer. Breast Cancer Res Treat, 138: 457-466 (2013).

Seiler R. et al., Impact of Molecular Subtypes in Muscle-invasive Bladder Cancer on Predicting Response and Survival after Neoadjuvant Chemotherapy. Eur Urol, 72(4):544-554 (2017).

Sjödahl G. et al., A molecular taxonomy for urothelial carcinoma. Clin Cancer Res, 18(12):3377-86 (2012).

The Cancer Genome Atlas Research Network. Comprehensive molecular characterization of urothelial bladder carcinoma. Nature volume 507, pages 315-322 (2014).

Robertson, A G, et al., Cell, 171(3): 540-556 (2017) Bindea G. et al., Spatiotemporal dynamics of intratumoral immune cells reveal the immune landscape in human cancer. Immunity, 39(4): 782-95 (2013).

Faruki H. et al., Lung Adenocarcinoma and Squamous Cell Carcinoma Gene Expression Subtypes Demonstrate Significant Differences in Tumor Immune Landscape. JTO, 12(6): 943-953 (2017).

Charoentong P. et al., Pan-cancer Immunogenomic Analyses Reveal Genotype-Immunophenotype Relationships and Predictors of Response to Checkpoint Blockade. Cell reports, 18, 248-262 (2017).

Further Numbered Embodiments of the Disclosure

Other subject matter contemplated by the present disclosure is set out in the following numbered embodiments:

1. A method for determining a bladder cancer subtype of a bladder cancer sample obtained from a patient, the method comprising detecting an expression level of at least one classifier biomarker of Table 1 or Table 2, wherein the detection of the expression level of the classifier biomarker specifically identifies a luminal, luminal infiltrated, basal or basal infiltrated/neuronal bladder cancer subtype.

2. The method of embodiment 1, wherein the method further comprises comparing the detected levels of expression of the at least one classifier biomarker of Table 1 or Table 2 to the expression of the at least one classifier biomarker of Table 1 or Table 2 in at least one sample training set(s), wherein the at least one sample training set(s) comprises expression data of the at least one classifier biomarker of Table 1 or Table 2 from a reference bladder cancer luminal sample, expression data of the at least one classifier biomarker of Table 1 or Table 2 from a reference bladder cancer luminal infiltrated sample, expression data of the at least one classifier biomarker of Table 1 or Table 2 from a reference bladder cancer basal sample, expression data of the at least one classifier biomarker of Table 1 or Table 2 from a reference bladder cancer basal infiltrated/neuronal sample or a combination thereof; and classifying the sample as luminal, luminal infiltrated, basal or basal infiltrated/neuronal subtype based on the results of the comparing step.

3. The method of embodiment 2, wherein the comparing step comprises applying a statistical algorithm which comprises determining a correlation between the expression data obtained from the sample and the expression data from the at least one training set(s); and classifying the sample as a luminal, luminal infiltrated, basal or basal infiltrated/neuronal subtype based on the results of the statistical algorithm.

4. The method of any one of embodiments 1-3, wherein the expression level of the classifier biomarker is detected at the nucleic acid level.

5. The method of embodiment 4, wherein the nucleic acid level is RNA or cDNA.

6. The method embodiment 4 or 5, wherein the detecting an expression level comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques.

7. The method of embodiment 6, wherein the expression level is detected by performing RNAseq.

8. The method of embodiment 7, wherein the detection of the expression level comprises using at least one pair of oligonucleotide primers specific for at least one classifier biomarker of Table 1 or Table 2.

9. The method of any one of embodiments 1-8, wherein the sample is a formalin-fixed, paraffin-embedded (FFPE) bladder tissue sample, a fresh or a frozen tissue sample, an exosome, wash fluids, cell pellets, or a bodily fluid obtained from the patient.

10. The method of embodiment 9, wherein the bodily fluid is blood or fractions thereof, urine, saliva, or sputum.

11. The method of any one embodiments 1-10, wherein the at least one classifier biomarker comprises a plurality of classifier biomarkers.

12. The method of embodiment 11, wherein the plurality of classifier biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, or at least 60 classifier biomarkers of Table 1.

13. The method of embodiment 11, wherein the plurality of classifier biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, or at least 56 classifier biomarkers of Table 2.

14. The method of any one of embodiments 1-13, wherein the at least one classifier biomarker comprises, consists essentially of or consists of all the classifier biomarkers of Table 1 or Table 2.

15. A method for determining a muscle invasive bladder cancer (MIBC) subtype of a bladder cancer sample obtained from a patient, the method comprising detecting an expression level of at least one classifier biomarker of Table 1 or Table 2, wherein the detection of the expression level of the classifier biomarker specifically identifies a luminal, luminal infiltrated, basal or basal infiltrated/neuronal bladder cancer subtype.

16. The method of embodiment 15, wherein the method further comprises comparing the detected levels of expression of the at least one classifier biomarker of Table 1 or Table 2 to the expression of the at least one classifier biomarker of Table 1 or Table 2 in at least one sample training set(s), wherein the at least one sample training set comprises expression data of the at least one classifier biomarker of Table 1 or Table 2 from a reference bladder cancer luminal sample, expression data of the at least one classifier biomarker of Table 1 or Table 2 from a reference bladder cancer luminal infiltrated sample, expression data of the at least one classifier biomarker of Table 1 or Table 2 from a reference bladder cancer basal sample, expression data of the at least one classifier biomarker of Table 1 or Table 2 from a reference bladder cancer basal infiltrated/neuronal sample or a combination thereof; and classifying the sample as luminal, luminal infiltrated, basal or basal infiltrated/neuronal subtype based on the results of the comparing step.

17. The method of embodiment 16, wherein the comparing step comprises applying a statistical algorithm which comprises determining a correlation between the expression data obtained from the sample and the expression data from the at least one training set(s); and classifying the sample as a luminal, luminal infiltrated, basal or basal infiltrated/neuronal subtype based on the results of the statistical algorithm.

18. The method of any one of embodiments 15-17, wherein the expression level of the classifier biomarker is detected at the nucleic acid level.

19. The method of embodiment 18, wherein the nucleic acid level is RNA or cDNA.

20. The method of embodiment 18 or 19, wherein the detecting an expression level comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques.

21. The method of embodiment 20, wherein the expression level is detected by performing RNAseq.

22. The method of embodiment 21, wherein the detection of the expression level comprises using at least one pair of oligonucleotide primers specific for at least one classifier biomarker of Table 1 or Table 2.

23. The method of any one of embodiments 15-22, wherein the sample is a formalin-fixed, paraffin-embedded (FFPE) bladder tissue sample, fresh or a frozen tissue sample, an exosome, wash fluids, cell pellets, or a bodily fluid obtained from the patient.

24. The method of embodiment 23, wherein the bodily fluid is blood or fractions thereof, urine, saliva, or sputum.

25. The method of any one of embodiments 15-24, wherein the at least one classifier biomarker comprises a plurality of classifier biomarkers.

26. The method of embodiment 25, wherein the plurality of classifier biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers or at least 60 classifier biomarkers of Table 1.

27. The method of embodiment 25, wherein the plurality of classifier biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, or at least 56 classifier biomarkers of Table 2.

28. The method of any one of embodiments 15-27, wherein the at least one classifier biomarker comprises, consists essentially of or consist of all the classifier biomarkers of Table 1 or Table 2.

29. A method of detecting a biomarker in a bladder cancer sample obtained from a patient, the method comprising measuring the expression level of a plurality of classifier biomarker nucleic acids selected from Table 1 or Table 2 using an amplification, hybridization and/or sequencing assay.

30. The method of embodiment 29, wherein the bladder cancer sample was previously diagnosed as being muscle invasive bladder cancer (MIBC).

31. The method of embodiment 30, wherein the previous diagnosis was by histological examination.

32. The method of any one of embodiments 29-31, wherein the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques.

33. The method of embodiment 32, wherein the expression level is detected by performing RNAseq.

34. The method of embodiment 31, wherein the detection of the expression level comprises using at least one pair of oligonucleotide primers per each of the plurality of biomarker nucleic acids selected from Table 1 or Table 2.

35. The method of any one of embodiments 29-34, wherein the sample is a formalin-fixed, paraffin-embedded (FFPE) bladder tissue sample, fresh or a frozen tissue sample, an exosome, wash fluids, cell pellets, or a bodily fluid obtained from the patient.

36. The method of embodiment 35, wherein the bodily fluid is blood or fractions thereof, urine, saliva, or sputum.

37. The method of any one of embodiments 29-36, wherein the plurality of biomarker nucleic acids comprises, consists essentially of or consists of at least two biomarker nucleic acids, at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers or at least 60 classifier biomarker nucleic acids of Table 1.

38. The method of any one of embodiments 29-36, wherein the plurality of classifier biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, or at least 56 classifier biomarkers of Table 2.

39. The method of any one of embodiments 29-36, wherein the plurality of biomarker nucleic acids comprises, consists essentially of or consists of all the classifier biomarker nucleic acids of Table 1 or Table 2.

40. A method of treating muscle invasive bladder cancer (MIBC) in a subject, the method comprising:

measuring the expression level of at least one biomarker nucleic acid in a MIBC sample obtained from the subject, wherein the at least one biomarker nucleic acid is selected from a set of biomarkers listed in Table 1 or Table 2, wherein the presence, absence and/or level of the at least one biomarker indicates a subtype of the MIBC;

and administering a therapeutic agent based on the subtype of the MIBC.

41. The method of embodiment 40, wherein the at least one biomarker nucleic acid selected from the set of biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers or at least 60 classifier biomarker nucleic acids of Table 1.

42. The method of embodiment 40, wherein the at least one biomarker nucleic acid selected from the set of biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, or at least 56 classifier biomarkers of Table 2.

43. The method of embodiment 40, wherein the at least one biomarker nucleic acid selected from the set of biomarkers comprises, consists essentially of or consists of all the classifier biomarker nucleic acids of Table 1 or Table 2.

44. The method of any one of embodiments 40-43, further comprising measuring the expression of at least one biomarker from an additional set of biomarkers.

45. The method of embodiment 44, wherein the additional set of biomarkers comprises BIRC5, CCNB1, CDC20, CDCA1, CEP55, KNTC2, MKI67, PTTG1, RRM12, TYMS, UBE2C, TP53, RB1, FGFR2, FGFR3, and ERBB2.

46. The method of embodiment 44, wherein the additional set of biomarkers comprise genes selected from Gene Expression Omnibus Dataset GSE87304, Gene Expression Omnibus Dataset GSE32894 or a combination thereof.

47. The method of embodiment 44, wherein the additional set of biomarkers comprises at least an immune cell signature, a cell proliferation signature, or drug target genes.

48. The method of any one of embodiments 40-47, wherein the measuring the expression level is conducted using an amplification, hybridization and/or sequencing assay.

49. The method of embodiment 48, wherein the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques.

50. The method of embodiment 49, wherein the expression level is detected by performing qRT-PCR.

51. The method of any one of embodiments 40-50, wherein the sample is a formalin-fixed, paraffin-embedded (FFPE) bladder tissue sample, fresh or a frozen tissue sample, an exosome, wash fluids, cell pellets, or a bodily fluid obtained from the patient.

52. The method of embodiment 51, wherein the bodily fluid is blood or fractions thereof, urine, saliva, or sputum.

53. The method of any one of embodiments 40-52, wherein the subject's MIBC subtype is selected from luminal, luminal infiltrated, basal, and basal infiltrated/neuronal.

54. The method of embodiment 40, wherein the at least one biomarker nucleic acid is a plurality of biomarker nucleic acids, wherein the plurality of biomarker nucleic acids comprises at least one biomarker nucleic acid listed in Table 1 or Table 2 in combination with one or more biomarker nucleic acids from a publically available bladder cancer dataset, wherein the presence, absence and/or level of the plurality of biomarker nucleic acids indicates a subtype of the MIBC.

55. The method of embodiment 40, wherein the at least one biomarker nucleic acid is a plurality of biomarker nucleic acids, wherein the plurality of biomarker nucleic acids comprises all of the biomarker nucleic acids listed in Table 1 or Table 2, all of the biomarker nucleic acids listed in embodiment 45 or embodiment 46, in combination with one or more biomarker nucleic acids from a publically available bladder cancer dataset, wherein the presence, absence and/or level of the plurality of biomarker nucleic acids indicates a subtype of the bladder cancer.

56. The method of embodiment 54 or 55, wherein the publically available bladder cancer dataset is TCGA bladder cancer RNAseq dataset.

57. A method of predicting overall survival in a muscularly invasive bladder cancer (MIBC) patient, the method comprising detecting an expression level of at least one classifier biomarker of Table 1 or Table 2 in a MIBC sample obtained from a patient, wherein the detection of the expression level of the at least one classifier biomarker specifically identifies a luminal, luminal infiltrated, basal, and basal infiltrated/neuronal subtype, and wherein identification of the subtype is predictive of the overall survival in the patient.

58. The method of embodiment 57, wherein the method further comprises comparing the detected levels of expression of the at least one classifier biomarker of Table 1 or Table 2 to the expression of the at least one classifier biomarker of Table 1 or Table 2 in at least one sample training set(s), wherein the at least one sample training set comprises expression data of the at least one classifier biomarker of Table 1 or Table 2 from a reference bladder cancer luminal sample, expression data of the at least one classifier biomarker of Table 1 or Table 2 from a reference bladder cancer luminal infiltrated sample, expression data of the at least one classifier biomarkers of Table 1 or Table 2 from a reference bladder cancer basal sample, expression data of the at least one classifier biomarker of Table 1 or Table 2 from a reference bladder cancer basal infiltrated/neuronal sample or a combination thereof; and classifying the sample as luminal, luminal infiltrated, basal or basal infiltrated/neuronal subtype based on the results of the comparing step.

59. The method of embodiment 58, wherein the comparing step comprises applying a statistical algorithm which comprises determining a correlation between the expression data obtained from the sample and the expression data from the at least one training set(s); and classifying the sample as a luminal, luminal infiltrated, basal or basal infiltrated/neuronal subtype based on the results of the statistical algorithm.

60. The method of any one of embodiments 57-59, wherein the expression level of the classifier biomarker is detected at the nucleic acid level.

61. The method of embodiment 60, wherein the nucleic acid level is RNA or cDNA.

62. The method of any one of embodiments 57-61, wherein the detecting an expression level comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques.

63. The method of embodiment 62, wherein the expression level is detected by performing qRT-PCR.

64. The method of embodiment 57, wherein the detection of the expression level comprises using at least one pair of oligonucleotide primers specific for at least one classifier biomarker of Table 1 or Table 2.

65. The method of any one of embodiments 57-64, wherein the sample is a formalin-fixed, paraffin-embedded (FFPE) bladder tissue sample, fresh or a frozen tissue sample, an exosome, wash fluids, cell pellets, or a bodily fluid obtained from the patient.

66. The method of embodiment 65, wherein the bodily fluid is blood or fractions thereof, urine, saliva, or sputum.

67. The method of any one of embodiments 57-66, wherein the at least one classifier biomarker comprises a plurality of classifier biomarkers.

68. The method of embodiment 67, wherein the plurality of classifier biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, or at least 60 classifier biomarkers of Table 1.

69. The method of embodiment 67, wherein the plurality of classifier biomarkers comprises, consists essentially of or consists of at least 2 classifier biomarkers, at least 5 classifier biomarkers, at least 10 classifier biomarkers, at least 20 classifier biomarkers, at least 30 classifier biomarkers, at least 40 classifier biomarkers, at least 50 classifier biomarkers, or at least 56 classifier biomarkers of Table 2.

70. The method of any of embodiments 57-69, wherein the at least one classifier biomarker comprises, consists essentially of or consists of all the classifier biomarkers of Table 1 or Table 2.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of assaying a bladder sample obtained from a human patient, the method comprising measuring a nucleic acid expression level of each and every classifier biomarker from a set of classifier biomarkers consisting of only aldehyde dehydrogenase 1 family member L2 (ALDH1L2), annexin A6 (ANXA6), arylsulfatase family member I (ARSI), breast carcinoma amplified sequence 1 (BCAS1), basonuclin 1 (BNC1), chromosome 10 open reading frame 99 (C10orf99), HID1 domain containing (C17orf28), calpain 5 (CAPN5), coiled-coil domain containing 80 (CCDC80), collagen type VI alpha 2 chain (COL6A2) carboxypeptidase X, M14 family member 2 (CPXM2), collagen triple helix repeat containing 1 (CTHRC1), desmoglein 3 (DSG3), elastin microfibril interfacer 1 (EMILIN1), epsin 3 (EPN3), envoplakin (EVPL), fibroblast activation protein alpha (FAP), fibrillin 1 (FBN1), fibroblast growth factor 7 (FGF7), flavin containing monooxygenase 9 pseudogene (FMO9P), fibronectin type III domain containing 1 (FNDC1), gamma-aminobutyric acid type B receptor subunit 2 (GABBR2), glutamine-fructose-6-phosphate transaminase 2 (GFPT2) gamma-glutamyltransferase 6 (GGT6), gremlin 1, DAN family BMP antagonist (GREM1), grainyhead like transcription factor 3 (GRHL3), interleukin 20 receptor subunit beta (IL20RB), keratin 6A (KRT6A), keratin 6B (KRT6B), keratin 6C (KRT6C), leiomodin 1 (LMOD1), HECTD2 antisense RNA 1 (LOC100188947), murine retrovirus integration site 1 homolog (MRVI1), neuropilin 2 (NRP2), PDZ and LIM domain 3 (PDLIM3), phospholipase A2 group IVF (PLA2G4F), podocan (PODN), periostin (POSTN), paired related homeobox 1 (PRRX1), adhesion molecule 4 (PVRL4), Rap guanine nucleotide exchange factor like 1 (RAPGEFL1), ras homolog family member U (RHOU), ras homolog family member V (RHOV), signal peptide, CUB domain and EGF like domain containing 2 (SCUBE2), syndecan 1 (SDC1), serpin family B member 13 (SERPINB13) secreted frizzled related protein 2 (SFRP2), secreted frizzled related protein 4 (SFRP4), solute carrier family 30 member 2 (SLC30A2), SPARC related modular calcium binding 2 (SMOC2), sorting nexin 31 (SNX31), small proline rich protein 2A (SPRR2A), scavenger receptor cysteine rich family member with 5 domains (SSC5D), T-box 3 (TBX3), transducin like enhancer of split 2 (TLE2), TOX high mobility group box family member 3 (TOX3), uroplakin 1A (UPK1A), uroplakin 2 (UPK2), uroplakin 3A (UPK3A) and zinc finger protein 750 (ZNF750), wherein the measuring is performed by an amplification, hybridization and/or sequencing assay.

2. The method of claim 1, wherein the bladder sample was previously diagnosed as being muscle invasive bladder cancer (MIBC).

3. The method of claim 1, wherein the amplification, hybridization and/or sequencing assay is selected from the group consisting of quantitative real time reverse transcriptase polymerase chain reaction (qRT-PCR), RNAseq, microarray analysis, gene chip analysis, Serial Analysis of Gene Expression (SAGE), Rapid Analysis of Gene Expression (RAGE), nuclease protection assays, and Northern blotting.

4. The method of claim 1, wherein the bladder sample is a formalin-fixed, paraffin-embedded (FFPE) bladder tissue sample, fresh or a frozen bladder tissue sample, an exosome, wash fluids, cell pellets, or a bodily fluid obtained from the bladder of the human patient.

5. A method of treating muscle invasive bladder cancer (MIBC) in a human subject, the method comprising: measuring in a bladder sample obtained from the human subject, a nucleic acid expression level of each and every classifier biomarker in a set of classifier biomarkers consisting of only ALDH1L2, ANXA6, ARSI, BCAS1, BNC1, C10orf99, C17orf28, CAPN5, CCDC80, COL6A2, CPXM2, CTHRC1, DSG3, EMILIN1, EPN3, EVPL, FAP, FBN1, FGF7, FMO9P, FNDC1, GABBR2, GFPT2, GGT6, GREM1, GRHL3, IL20RB, KRT6A, KRT6B, KRT6C, LMOD1, LOC100188947, MRVI1, NRP2, PDLIM3, PLA2G4E, PODN, POSTN, PRRX1, PVRL4, RAPGEFL1, RHOU, RHOV, SCUBE2, SDC1, SERPINB13, SFRP2, SFRP4, SLC30A2, SMOC2, SNX31, SPRR2A, SSC5D, TBX3, TLE2, TOX3, UPK1A, UPK2, UPK3A and ZNF750, and wherein the nucleic acid expression level of each and every classifier biomarker from the set of classifier biomarkers indicates a subtype of MIBC selected from the group consisting of luminal, luminal infiltrated, basal, and basal infiltrated/neuronal; and administering a therapeutic agent based on the subtype of MIBC, wherein if the subtype of MIBC is luminal then the therapeutic agent is an FGFR3 inhibitor, if the subtype of MIBC is luminal-infiltrated then the therapeutic agent is an immunotherapy, if the subtype is basal then the therapeutic is chemotherapy or immunotherapy and if the subtype of MIBC is basal infiltrated/neuronal then the therapeutic is chemotherapy.

6. The method of claim 5, further comprising a separate measuring step that comprises measuring the nucleic acid expression level of at least one biomarker from an additional set of biomarkers, wherein the additional set of biomarkers consists of only BIRC5, CCNB1, CDC20, CDCA1, CEP55, KNTC2, MKI67, PTTG1, RRM2, TYMS, UBE2C, TP53, RB1, FGFR2, FGFR3, and ERBB2.

7. The method of claim 5, wherein the measuring the expression level is conducted using an amplification, hybridization and/or sequencing assay, wherein the amplification, hybridization and/or sequencing assay is selected from the group consisting of performing quantitative real time reverse transcriptase polymerase chain reaction (qRT-PCR), RNAseq, microarray analysis, gene chip analysis, Serial Analysis of Gene Expression (SAGE), Rapid Analysis of Gene Expression (RAGE), nuclease protection assays and Northern blotting.

8. The method of claim 5, wherein the bladder sample is a formalin-fixed, paraffin-embedded (FFPE) bladder tissue sample, fresh or a frozen tissue sample, an exosome, wash fluids, cell pellets, or a bodily fluid obtained from the bladder of the human patient.

9. The method of claim 1, further comprising measuring a nucleic acid expression level of each and every classifier biomarker from the set of classifier biomarkers consisting of only ALDH1L2, ANXA6, ARSI, BCAS1, BNC1, C10orf99, C17orf28, CAPN5, CCDC80, COL6A2, CPXM2, CTHRC1, DSG3, EMILIN1, EPN3, EVPL, FAP, FBN1, FGF7, FMO9P, FNDC1, GABBR2, GFPT2, GGT6, GREM1, GRHL3, IL20RB, KRT6A, KRT6B, KRT6C, LMOD1, LOC100188947, MRVI1, NRP2, PDLIM3, PLA2G4F, PODN, POSTN, PRRX1, PVRL4, RAPGEFL1, RHOU, RHOV, SCUBE2, SDC1, SERPINB13, SFRP2 SFRP4, SLC30A2, SMOC2, SNX31, SPRR2A, SSC5D, TBX3, TLE2, TOX3, UPK1A, UPK2, UPK3A and ZNF750 in a control luminal sample, luminal infiltrated sample, basal sample or basal infiltrated/neuronal sample.

10. The method of claim 5, where further comprising comparing the measured nucleic acid expression levels of each and every classifier biomarker from the set of classifier biomarkers consisting of only ALDH1L2, ANXA6, ARSI, BCAS1, BNC1, C10orf99, C17orf28, CAPN5, CCDC80, COL6A2, CPXM2, CTHRC1, DSG3, EMILIN1, EPN3, EVPL, FAP, FBN1, FGF7, FMO9P, FNDC1, GABBR2, GFPT2, GGT6, GREM1, GRHL3, IL20RB, KRT6A, KRT6B, KRT6C, LMOD1, LOC100188947, MRVI1, NRP2, PDLIM3, PLA2G4F, PODN, POSTN, PRRX1, PVRL4, RAPGEFL1, RHOU, RHOV, SCUBE2, SDC1, SERPINB13, SFRP2, SFRP4, SLC30A2, SMOC2, SNX31, SPRR2A, SSC5D, TBX3, TLE2, TOX3, UPK1A, UPK2, UPK3A and ZNF750 in the bladder sample obtained from the human subject to the nucleic acid expression levels of each and every classifier biomarker from the set of classifier biomarkers consisting of only ALDH1L2, ANXA6, ARSI, BCAS1, BNC1, C10orf99, C17orf28, CAPN5, CCDC80, COL6A2, CPXM2, CTHRC1, DSG3, EMILIN1, EPN3, EVPL, FAP, FBN1, FGF7, FMO9P, FNDC1, GABBR2, GFPT2, GGT6, GREM1, GRHL3, IL20RB, KRT6A, KRT6B, KRT6C, LMOD1, LOC100188947, MRVI1, NRP2, PDLIM3, PLA2G4F, PODN, POSTN, PRRX1, PVRL4, RAPGEFL1, RHOU, RHOV, SCUBE2, SDC1, SERPINB13, SFRP2, SFRP4, S LC30A2, SMOC2, SNX31, SPRR2A, SSC5D, TBX3, TLE2, TOX3, UPK1A, UPK2, UPK3A and ZNF750 in at least one sample training set(s), wherein the at least one sample training set is a reference MIBC luminal sample, a reference MIBC luminal infiltrated sample, a reference MIBC basal sample, a reference MIBC basal infiltrated/neuronal sample or a combination thereof; and classifying the subtype of MIBC as luminal, luminal infiltrated, basal or basal infiltrated/neuronal based on the results of the comparing step.

11. The method of claim 10, wherein the comparing step comprises applying a statistical algorithm which comprises determining a correlation between the nucleic acid expression levels of each classifier biomarker from the plurality of classifier biomarkers obtained from the lung sample and the nucleic acid expression levels of each classifier biomarker from the plurality of classifier biomarkers from the at least one training set(s); and classifying the subtype of MIBC as luminal, luminal infiltrated, basal or basal infiltrated/neuronal subtype based on the results of the statistical algorithm.

12. The method of claim 5, wherein the chemotherapy is cisplatin-based neoadjuvant therapy if the subtype of MIBC is basal or etoposide-cisplatin therapy if the subtype of MIBC is basal-infiltrated/neuronal.

13. The method of claim 5, wherein the immunotherapy is an immune checkpoint inhibitor if the subtype of MIBC is luminal-infiltrated.

* * * * *

UNITED STATES PATENT AND TRADEMARK OFFICE

CERTIFICATE OF CORRECTION

PATENT NO. : 12,195,805 B2
APPLICATION NO. : 16/969304
DATED : January 14, 2025
INVENTOR(S) : Hawazin Faruki et al.

It is certified that error appears in the above-identified patent and that said Letters Patent is hereby corrected as shown below:

In the Claims

At Column 349, Claim number 1, Line number 32, reads:
"transaminase 2 (GFPT2) gamma-glutamyltransferase 6"
Should read:
--transaminase 2 (GFPT2), gamma-glutamyltransferase 6--

At Column 350, Claim number 5, Line number 30, reads:
"PLA2G4E, PODN, POSTN, PRRX1, PVRL4, RAPGEFL1"
Should read:
--PLA2G4F, PODN, POSTN, PRRX1, PVRL4, RAPGEFL1--

Signed and Sealed this
Nineteenth Day of August, 2025

Coke Morgan Stewart
*Acting Director of the United States Patent and Trademark Office*

SEQUENCE LISTING

```
<160> NUMBER OF SEQ ID NOS: 83

<210> SEQ ID NO 1
<211> LENGTH: 7428
<212> TYPE: DNA
<213> ORGANISM: Homo sapiens

<400> SEQUENCE: 1

agtgctagcg ctcctctcca gcatgctgcg gcggggcagc caggcgctcc ggcgcttctc     60

cactggccgg gtttatttca aaaacaagct gaagttggca ctaattggcc agagcctctt    120

tggacaagaa gtctatagcc acctccgcaa agagggccac cgagtagtag gggtgttcac    180

agttccagac aaggatggaa aagctgaccc tctggctttg gctgcagaga aagatgggac    240

ccctgtgttc aagcttccta aatggagggt caagggcaag accatcaaag aagtggcaga    300

agcctacaga tccgtgggtg cagagctaaa tgtgctccct ttctgcactc agttcattcc    360

catggatata attgatagtc caaagcacgg ctctatcatt tatcacccat ccatcctgcc    420

caggcacaga ggagcctctg ctatcaattg gactctaatt atgggagata agaaagctgg    480

gttttctgtt ttctgggctg atgatggctt ggatacagga cccatccttc ttcagagatc    540

atgtgatgtt gaacccaatg atacagtgga tgcactttat aatcggtttc tttttcctga    600

aggaatcaag gccatggtag aagctgtcca actcatagct gatggaaaag ctcctcgtat    660

accccagcca gaagaagggg caacatatga aggtatccag aaaaaggaaa atgctgagat    720

ttcttgggac cagtctgccg aagttttaca taactggatt cgaggtcatg ataaagtccc    780
```

-continued

```
tggagcttgg acagagataa atggacagat ggtcactttc tatggctcga cattactgaa    840
tagctctgtg cctcctggag aaccactgga aattaaaggt gccaagaagc ctggtctcgt    900
taccaaaaat ggacttgttc tttttggtaa cgatggaaaa gcactgacgg tgagaaatct    960
gcagtttgaa gatggaaaaa tgatccctgc ctctcagtac ttttcaacgg gtgagacgtc   1020
agtggtagaa ctgacagctg aagaggtgaa agtggcagag accatcaagg tcatctgggc   1080
tggaatttta agcaatgtcc ccattattga agactcaaca gacttcttta aatctggagc   1140
aagctcaatg gatgttgcca ggctggttga agagatcaga cagaaatgtg gtgggcttca   1200
gttgcagaat gaagatgtct atatggccac caagtttgaa ggctttatcc aaaaggtcgt   1260
gaggaaactg agaggagaag atcaagaggt ggagctggtt gtagattata tttcaaagga   1320
ggtcaatgaa atcatggtaa aaatgccata ccagtgtttc ataaatggac agttcacaga   1380
tgcagacgat ggaaagactt acgacactat caacccaaca gatggatcta caatatgcaa   1440
agtatcctac gcttctttgg cggatgttga taaagcagta gcagcagcaa aagatgcttt   1500
tgaaaacggt gaatggggaa gaatgaatgc aagagaaaga ggaagattga tgtatagact   1560
tgcagaccta ctggaagaga accaagaaga gctggcaact attgaagccc ttgattcagg   1620
ggctgtctat accttggccc tgaagacaca cattggaatg tctgtgcaaa cattcagata   1680
ttttgctggc tggtgcgaca aaattcaggg ttctactatt ccaatcaacc aggcccgtcc   1740
aaatcgcaat ctgaccttca ccaagaaaga gccactcggt gtctgtgcca ttattattcc   1800
ctggaactac ccgctgatga tgctggcatg gaagagtgct gcgtgtttgg cagcaggcaa   1860
taccttagtg ctcaagccag cacaggtcac gcccttgact gctttgaagt ttgcagaact   1920
gtctgtgaaa gcaggctttc caaagggggt catcaacatc attccaggct caggtggcat   1980
agcaggacaa cgtctgtctg aacatcctga catccgcaaa cttggtttca ctggatccac   2040
tcctattggc aaacagatca tgaagagctg tgctgttagc aacttgaaga aagtttccct   2100
tgagcttggt ggcaagtctc cacttataat atttaatgac tgtgaacttg acaaggctgt   2160
gcgaatgggc atgggagcag tatttttcaa caaaggagag aactgtattg ctgctgggcg   2220
gttgttcgtg gaagaatcca tccacgacga atttgtgaca agagtggtag aagaaattaa   2280
aaagatgaaa attggtgatc cacttgacag atccactgat catgggcccc aaaatcataa   2340
ggctcatctg gaaaagctgc tgcaatactg tgaaactgga gtgaaagaag ggccactttt   2400
ggtgtacggg ggaagacaag tccaaaggcc aggctttttc atggagccga ccgtgttcac   2460
agatgtggaa gactacatgt acctcgccaa agaggaatcc tttgggccta ttatggtcat   2520
ttctaaattc caaaatgggg acatcgatgg agtgttgcag cgagcaaata gtacagagta   2580
tggtttggcc tcaggggttt ttacaagaga cataaacaaa gctatgtatg tgagtgaaaa   2640
actggaagca ggaactgttt ttattaacac atacaacaag acagatgtgg cggcccccatt  2700
tggcggagtt aaacaatctg gctttggaaa agacttaggt gaggaagctc taaatgaata   2760
tctcaaaacc aagacggtga cactggaata ttagagcaac accatcatca ggaaagcctt   2820
gacagacagc cctttacaac tctggacaca cttaagaaga ttgggtgtgt tgaggcagga   2880
ggtgtcagcc acaaaccaaa aaatacacag atggaccatg aagagggcca ggccatgtta   2940
aagcatttac acatgtgcct gagtattttc taatacacct tccagtgatt tggagttgtt   3000
gcattttgac tatgttgtat atcatacgta tttctaaaat accaagctgt ttctccccta   3060
cctagacaaa tctattcatg gttcccatct tgaagatgtc agtaccatgc agttataata   3120
cacaaggtgc atttattgga aactttgtat aatatgtaca ggtttttaac ctctgaacta   3180
```

-continued

```
tacatagggg gttattaaaa agattttcta taagtcttct aaggaacagt ataacctgta   3240
aggaatgtga aggtagttct tttttagtat ttggaaataa gatacatctt tgtgcctttg   3300
atattccatt ttttaaccca ctgtgatggg tgatcaacct agaaacatta tcttgagtac   3360
ctactaggta ccaggtacta tattatgttc tgaggagtat agagaattta atgatatgat   3420
ggctggcccc cacatagttt aaattttagt aaatagcttt tgaagcaaat tttacatatg   3480
atatagtaga aggctgatcc tggtcgtatc ataccatctt cctatctatg taactttggg   3540
aaactctcgc aactcctctg agcctctgct tccctatgtg taaaacaggg atagtaaatg   3600
ccttcctcag gacccttaat aggagaattc attgcagtaa tgtaagtaaa gcacctcaca   3660
ttaatgcttt gctcatggta agtactcaaa tttaactctg atttcctccg tcaccattct   3720
taaaagatat tgagatagtt taattaacta gatgaattca tttcccacaa cccttttcaa   3780
tcatcaattc ctagatattt ttctcatcca ttgttctgac acaatgcctg atacagcagc   3840
actgaaaaat gccacacaat gaaaaatggc aatagtacaa ggaaaagggg tgcttttctt   3900
tgggcagctc gctcgtcctt catgggacat cttactttcc atttttctac ctattggttc   3960
tgctgttcac tggctgtgtg atcttgggca agatagtaat ctaatatctc agagcctagg   4020
ttgagtatct ataaaatgaa aatcaaatct ctatctcagt aggtgttgca aggattcagt   4080
gagataatat acataatgca cttaacaagg cgtttggacc atagcattga agaaatggaa   4140
actattaaca gcccatttcc cattggcaga cagaagtagt caggtgagta aattttcacc   4200
atctatgtgt gactagaagg cggcaaattt ctgaatcaca tgagtctcca aaagatagcc   4260
agaaagttaa attctattaa tcctccttta aaaataaaat ttcagtaaac attccttttt   4320
ctttggcttt gaagaagcct tagggaatat ttgtcatttt ggagacttgg cagaataaca   4380
tgaggggatt gtagggaatc aataaaaact aaacaacaaa atcagagtca gagaacattt   4440
tcaaaaggaa gaataggagg tttgatccca gcatgataaa cagagcgaat ttggcctgga   4500
agcacttttg attatactat agctcattta ccatcccaga gtttggcaca gctgaaattt   4560
taagttggaa tgaatattca ctgggcccaa aatgacagtt catatttgaa taaaagtgac   4620
aaaagccttt ttataagtaa tcacttttaa gtgaaatgtt ttaactgatt tcatgtgatt   4680
tagaatatga tttaatcaaa ttattttaat gatagatgga atggcagaca aaaacatgcc   4740
tgtccttcta gactgatttt actttaccct ctaatattca tctcagtagc agtgttttaa   4800
atattctctg ggctgcaaaa ctctttggga atctgataaa agctatgaac actccctgtg   4860
tcccgcttct acccccaaaa ttcatgtgca cacacacaat tctgcaagta tcttcaaagg   4920
gttcacagac ctcccaaagg ccatgcttgg gccccagatt aagaactcct ttctccatag   4980
caagttttaa acatttctta ccagcttaca tttttagatc tggctgatca gaatcaaagg   5040
ctctgtgtaa tacataaagt taccaagtga actggaattg gaacatcacc ctccccagcc   5100
tgctaggtga tttacttaac acatagagta ataaaatcat cgctgttgct ttagatcacg   5160
gattattttg ctaataatgc taaggatgaa gctgtgatct tattatcacc tgaatcggga   5220
ggtgtggaca ctttaagcag ttccactttc cttctaattc cccatcccca tgcctttgct   5280
aaagctgtcc cttttgctct aacacccttc ctggaccttc ctaccctagc tgggctaagt   5340
gtttctcctc agcgttccca cttgtttcaa acatagcact taccacttgt actaaaatta   5400
cttgccttct taattagata tgaacaaccc tccccaactc cagtatgggc cttctgtcaa   5460
taataatacg atatgacagc taccatttat taagggcctc ctgtatgaaa gaccttaggc   5520
```

-continued

```
taagcatgtt ttaaatgtta tttaatcttc acaatctctg aaaaaaatga agaaatcaac   5580

gtgcttttct tactacctct acccctaagc cattattact tttttttttt tttgagacag   5640

agttttgctc ttgttgccca ggctgcagtg cagtggtgca atcttggctc actgcaacct   5700

ctgcctcttg ggttcaagcg attgtcatgc cttagccttc caagtagctg ggattacagg   5760

tgtgtgccac tacacctggc taagtagaga tggggtttcg ccatgttggc caggctggtc   5820

ttgaactcct gacctcaagt gatccacctg cctccgcctc ccaaagtgct gggattacag   5880

gcatgaacca ctgcacctgg cctgttacct ctttcctaca attttgctca agtctcccaa   5940

ctggtcttct ggattcctct cttctgcggt cctgttcaaa gcttaagtca gacagtgtca   6000

cttcactcgt ctgtttaaaa cctttcaatg gcccccattt cacgtagacc aaagtccaac   6060

gtatttacct ggcctactga tcttgctcct agctacctct gacctcatct cctgtcaatt   6120

tccctctcat tctgttccac catcctgact gccttgactt cctcaacaga acaagcctgc   6180

tcctgcctca gggcctctgt ccttattctt cctcttccca ggggtgtgct ggtaaaatat   6240

ttaacaaata gttctccggg acgggggaga aaaccctcat ttgtagcatt tgcaggtatc   6300

tatgtgtaaa tactctcatc aaggctattt ttgagccact aatttgcctt cactgaatac   6360

agagtttggg aagagatgca tgccatcaga acaaatgcaa gccagcacca gcacaccact   6420

gcctcttcct gcaactcttg tccatacaca acctcatggc tggctggctc acttcctgca   6480

ggtctctcct caaatatcat ctgatgagag acacattccc tgactatgct ttctaaaata   6540

ggccatatgc ccccacattc ataccccatc tgctgtcatt ctttattctt tttataagtg   6600

cattattttc atagcactta tcactacctg ttgtatatta atcaatgatc ttttcccatt   6660

agaatgtaag tttcatgaac aggtacttgt tttaatactg tatctccagt cctaatgtgt   6720

aacaggagcc caataaatgt ttgctttcaa atggagaggt taagtaacct gctcaaatca   6780

cacagctatt aagtggcaga acaggttttc aagcaatgca tctggtggtt ttaactaagt   6840

cgagatagtt tttattccta atgcctaaat cagggcctag gtagtgagct gtgggcacat   6900

attaagtatt ggttaaacta aaaataataa gcaaaatgga cattatctat aaaagctttt   6960

gtggaaatgg ctagagctag ggtaaggaaa caaatttggt tccccatacc tgccctccaa   7020

gaaaataaag ctgtcaagga aaatctgggc taagagtagg atatgaggga tgatggataa   7080

ggcatgagac atgagaaata agggggatta aattattatt actattatac aaatgatgcc   7140

tgagtagatt tttaaaatga ttaaataccc aatgatgtaa aaaacattta taaaatagga   7200

aagtaagact gactcaacca taatttgttg agtcaaccca aaaatctatt tggttatttt   7260

caaacagaaa tagcctacag atgatatctg agattgttcc aaactttttc tatgaatatg   7320

tatacttttt ttacataatt aacataatac tgtatattaa tttgttacct gctttttcaa   7380

ttaacaatat atcataagca tctatgccaa taaacacaat tctgcata               7428
```

<210> SEQ ID NO 2
<211> LENGTH: 2889
<212> TYPE: DNA
<213> ORGANISM: Homo sapiens

<400> SEQUENCE: 2

```
gcggttgctg ctgggctaac gggctccgat ccagcgagcg ctgcgtcctc gagtccctgc     60

gcccgtgcgt ccgtctgcga cccgaggcct ccgctgcgcg tggattctgc tgcgaaccgg    120

agaccatggc caaaccagca cagggtgcca agtaccgggg ctccatccat gacttcccag    180

gctttgaccc caaccaggat gccgaggctc tgtacactgc catgaagggc tttggcagtg    240
```

-continued

```
acaaggaggc catactggac ataatcacct cacggagcaa caggcagagg caggaggtct    300
gccagagcta caagtccctc tacggcaagg acctcattgc tgatttaaag tatgaattga    360
cgggcaagtt tgaacggttg attgtgggcc tgatgaggcc acctgcctat tgtgatgcca    420
aagaaattaa agatgccatc tcgggcattg gcactgatga gaagtgcctc attgagatct    480
tggcttcccg gaccaatgag cagatgcacc agctggtggc agcatacaaa gatgcctacg    540
agcgggacct ggaggctgac atcatcggcg acacctctgg ccacttccag aagatgcttg    600
tggtcctgct ccagggaacc agggaggagg atgacgtagt gagcgaggac ctggtacaac    660
aggatgtcca ggacctatac gaggcagggg aactgaaatg ggaacagat gaagcccagt    720
tcatttacat cttgggaaat cgcagcaagc agcatcttcg gttggtgttc gatgagtatc    780
tgaagaccac agggaagccg attgaagcca gcatccgagg ggagctgtct ggggactttg    840
agaagctaat gctggccgta gtgaagtgta tccggagcac cccggaatat tttgctgaaa    900
ggctcttcaa ggctatgaag ggcctgggga ctcgggacaa caccctgatc cgcatcatgg    960
tctcccgtag tgagttggac atgctcgaca ttcgggagat cttccggacc aagtatgaga   1020
agtccctcta cagcatgatc aagaatgaca cctctggcga gtacaagaag actctgctga   1080
agctgtctgg gggagatgat gatgctgctg gccagttctt cccggaggca gcgcaggtgg   1140
cctatcagat gtgggaactt agtgcagtgg cccgagtaga gctgaaggga actgtgcgcc   1200
cagccaatga cttcaaccct gacgcagatg ccaaagcgct gcggaaagcc atgaagggac   1260
tcgggactga cgaagacaca atcatcgata tcatcacgca ccgcagcaat gtccagcggc   1320
agcagatccg gcagaccttc aagtctcact ttggccggga cttaatgact gacctgaagt   1380
ctgagatctc tggagacctg gcaaggctga ttctggggct catgatgcca ccggcccatt   1440
acgatgccaa gcagttgaag aaggccatgg agggagccgg cacagatgaa aaggctctta   1500
ttgaaatcct ggccactcgg accaatgctg aaatccgggc catcaatgag gcctataagg   1560
aggactatca caagtccctg gaggatgctc tgagctcaga cacatctggc cacttcagga   1620
ggatcctcat ttctctggcc acggggcatc gtgaggaggg aggagaaaac ctggaccagg   1680
cacgggaaga tgcccaggtg gctgctgaga tcttggaaat agcagacaca cctagtggag   1740
acaaaacttc cttggagaca cgtttcatga cgatcctgtg tacccggagc tatccgcacc   1800
tccggagagt cttccaggag ttcatcaaga tgaccaacta tgacgtggag cacaccatca   1860
agaaggagat gtctggggat gtcagggatg catttgtggc cattgttcaa agtgtcaaga   1920
acaagcctct cttctttgcc gacaaacttt acaaatccat gaagggtgct ggcacagatg   1980
agaagactct gaccaggatc atggtatccc gcagtgagat tgacctgctc aacatccgga   2040
gggaattcat tgagaaatat gacaagtctc tccaccaagc cattgagggt gacacctccg   2100
gagacttcct gaaggccttg ctggctctct gtggtggtga ggactagggc cacagctttg   2160
gcgggcactt ctgccaagaa atggttatca gcaccagccg ccatggccaa gcctgattgt   2220
tccagctcca gagactaagg aaggggcagg ggtgggggga ggggttgggt tgggctctta   2280
tcttcagtgg agcttaggaa acgctcccac tcccacgggc catcgagggc ccagcacggc   2340
tgagcggctg aaaaaccgta gccatagatc ctgtccacct ccactcccct ctgaccctca   2400
ggctttccca gcttcctccc cttgctacag cctctgccct ggtttgggct atgtcagatc   2460
caaaaacatc ctgaacctct gtctgtaaaa tgagtagtgt ctgtactttg aatgaggggg   2520
ttggtggcag gggccagttg aatgtgctgg gcggggtggt gggaaggata gtaaatgtgc   2580
```

-continued

```
tggggcaaac tgacaaatct tcccatccat ttcaccaccc atctccatcc aggccgcgct   2640

agagtactgg accaggaatt tggatgcctg ggttcaaatc tgcatctgcc atgcacttgt   2700

ttctgacctt aggccagccc ctttccctcc ctgagtctct attttcttat ctacaatgag   2760

acagttggac aaaaaaatct tggcttccct tctaacatta acttcctaaa gtatgcctcc   2820

gattcattcc cttgacactt tttatttcta aggaagaaat aaaaagagat acacaaacac   2880

ataaacaca                                                           2889
```

<210> SEQ ID NO 3
<211> LENGTH: 3113
<212> TYPE: DNA
<213> ORGANISM: Homo sapiens

<400> SEQUENCE: 3

```
gaattctctc ccgccgtgtc ccctcgaccc gcccaacttg tgcctccctc cccttcccct     60

ctggggtcct gcccacctcc ctgcagggag ctgggctgtt ttaaggactc cgggtggggc    120

gagaggccgg gaaagcagag gagagagaaa ttaggaggcg ggagaaatcc agggcaagaa    180

ggaagagggg agtcagagga tggtagagag cactttttgg aagctgccac gccgcgtctc    240

aggctggccg ggctgagctg gggaagaggg agcaaaggcg gcgcagggcc tgcgcttagg    300

cagcgggagg cagctcggcg cgggcctgac ctccccagag cgccccgctg cggccgagca    360

gatccggccc agccgtccgg cagccagtcc cggaccagac actggaccgt ccccgggggg    420

cgctgaactc cctcgcagca tccgagccgg cgggccggtg gtgcgccctg ggcgcgcgag    480

gtggtgaggc cccaggagcc cggcgcgccg ggacgcgcgg gccggcttgg cgatgcacac    540

cctcactggc ttctccctgg tcagcctgct cagcttcggc tacctgtcct gggactgggc    600

caagccgagc ttcgtggccg acgggcccgg ggaggctggc gagcagccct cggccgctcc    660

gccccagcct ccccacatca tcttcatcct cacggacgac caaggctacc acgacgtggg    720

ctaccatggt tcagatatcg agacccctac gctggacagg ctggcggcca agggggtcaa    780

gttggagaat tattacatcc agcccatctg cacgccttcg cggagccagc tcctcactgg    840

caggtaccag atccacacag gactccagca ttccatcatc cgcccacagc agcccaactg    900

cctgcccctg gaccaggtga cactgccaca gaagctgcag gaggcaggtt attccaccca    960

tatggtgggc aagtggcacc tgggcttcta ccggaaggag tgtctgccca cccgtcgggg   1020

cttcgacacc ttcctgggct cgctcacggg caatgtggac tattacacct atgacaactg   1080

tgatggccca ggcgtgtgcg gcttcgacct gcacgagggt gagaatgtgg cctgggggct   1140

cagcggccag tactccacta tgctttatgc ccagcgcgcc agccatatcc tggccagcca   1200

cagccctcag cgtcccctct tcctctatgt ggccttccag gcagtacaca cacccctgca   1260

gtcccctcgt gagtacctgt accgctaccg caccatgggc aatgtggccc ggcggaagta   1320

cgcggccatg gtgacctgca tggatgaggc tgtgcgcaac atcacctggg ccctcaagcg   1380

ctacggtttc tacaacaaca gtgtcatcat cttctccagt gacaatggtg gccagacttt   1440

ctcgggggc agcaactggc cgctccgagg acgcaagggc acttattggg aaggtggcgt   1500

gcggggccta ggctttgtcc acagtcccct gctcaagcga aagcaacgga caagccgggc   1560

actgatgcac atcactgact ggtacccgac cctggtgggt ctggcaggtg gtaccacctc   1620

agcagccgat gggctagatg gctacgacgt gtggccggcc atcagcgagg gccgggcctc   1680

accacgcacg gagatcctgc acaacattga cccactctac aaccatgccc agcatggctc   1740

cctggagggc ggctttggca tctggaacac cgccgtgcag gctgccatcc gcgtgggtga   1800
```

```
gtggaagctg ctgacaggag accccggcta tggcgattgg atcccaccgc agacactggc   1860
caccttcccg ggtagctggt ggaacctgga acgaatggcc agtgtccgcc aggccgtgtg   1920
gctcttcaac atcagtgctg acccttatga acgggaggac ctggctggcc agcggcctga   1980
tgtggtccgc accctgctgg ctcgcctggc cgaatataac cgcacagcca tcccggtacg   2040
ctacccagct gagaaccccc gggctcatcc tgactttaat gggggtgctt gggggccctg   2100
ggccagtgat gaggaagagg aggaagagga agggagggct cgaagcttct cccggggtcg   2160
tcgcaagaaa aaatgcaaga tttgcaagct tcgatccttt ttccgtaaac tcaacaccag   2220
gctaatgtcc caacggatct gatggtgggg agggagaaaa ctgtccttta gaggatcttc   2280
cccactccgg cttggccctg ctgtttctca gggagaagcc tgtcacatct ccatctacag   2340
ggagttggag ggtgtagagt cccttggttg aacagggtag ggagcctgga taggagtggg   2400
tgggaataaa ccagactggg atgcctgtgt ctcagtcctg cctcctcacg gacttgctct   2460
gtgacctcag gtgacccaca tgagctttta gcctcagttt cctcatctgt aaaatgagct   2520
ctaatgactt tgtgactctt tggtgtggcc ctggagcctg gggccacggt ggagttcctg   2580
gccggccttg ccacttgaca actcctttaa ggcttccccc ttaacacggg atccctgtgg   2640
tggtgtttgg gagttgcctg gaggcaactc caagcctggc cccagctga agcatggcaa   2700
tctggctgct ctctacaggg acccccaagc gctgtgggtg gagggcaggg gtcggggggg   2760
ttgaccttct tgggtcttca catggcctag gccagtcctc cggtcagact ggtgtcaggc   2820
accgtggtgc aaaattcctc ttctggcccc tccagtaccc agagaaactg gctgggccat   2880
taactgctgc agcaccaagg gtggtagaaa gagctgtgaa gagcccccaa accagtacca   2940
ggacacctgg gttctcctgt gacctggggc acagttcttg ccctctaggc cttgatttcc   3000
ccacctgcaa gtggggatgc cagccctggc tctgcctcct tcatgaggct ctggaagact   3060
ggccaaggtt gtggaggagc ttgtgaactt gattaaagtg tcgtaacatg gaa          3113
```

<210> SEQ ID NO 4
<211> LENGTH: 3490
<212> TYPE: DNA
<213> ORGANISM: Homo sapiens

<400> SEQUENCE: 4

```
actgggtaga atacttgggg tgccagggag gcattaatgc gagaggagtc aggtgctcag     60
tttttattgg agttgggagg gcagccccac atcaggaaga gaacctgttt ctgcaggatg    120
gtccggggag aagggaggac tccacccagg cttgtgtttg ccctgctctg tgtattcagc    180
cagcaggctc tgcacaagga agcaaagtgc agggagccag gctccaccga cagccaggca    240
ctgggcagca cgcactggag acccaggacc ctgtgcagga gcagctccgg gtgacacgag    300
gggactgaag atactcccac aggggctcag caggagcaat gggtaaccaa atgagtgttc    360
cccaaagagt tgaagaccaa gagaatgaac cagaagcaga gacttaccag gacaacgcgt    420
ctgctctgaa cggggttcca gtggtggtgt cgacccacac agttcagcac ttagaggaag    480
tcgacttggg aataagtgtc aagacggata atgtggccac ttcttccccc gagacaacgg    540
agataagtgc tgttgcggat gccaacggaa agaatcttgg gaaagaggcc aaacccgagg    600
caccagctgc taaatctcgt tttttcttga tgctctctcg gcctgtacca ggacgtaccg    660
gagaccaagc cgcagattca tcccttggat cagtgaagct tgatgtcagc tccaataaag    720
ctccagcgaa caaagaccca agtgagagct ggacacttcc ggtggcagct ggaccggggc    780
```

-continued

```
aggacacaga taaaacccca gggcacgccc cggcccaaga caaggtcctc tctgccgcca    840
gggatcccac gcttctccca cctgagacag ggggagcagg aggagaagct ccctccaagc    900
ccaaggactc cagctttttt gacaaattct tcaagctgga caagggacag gaaaaggtgc    960
caggtgacag ccaacaggaa gccaagaggg cagagcatca agacaaggtg gatgaggttc   1020
ctggcttatc agggcagtcc gatgatgtcc ctgcagggaa ggacatagtt gacggcaagg   1080
aaaaagaagg acaagaactt ggaactgcgg attgctctgt ccctggggac ccagaaggac   1140
tggagactgc aaaggacgat tcccaggcag cagctatagc agagaataat aattccatca   1200
tgagtttctt taaaactctg gtttcaccta acaaagctga aacaaaaaag gacccagaag   1260
acacgggtgc tgaaaagtca cccaccactt cagctgacct taagtcagac aaagccaact   1320
ttacatccca ggagacccaa ggggctggca agaattccaa aggatgcaac ccatcggggc   1380
acacacagtc cgtgacaacc cctgaacctg cgaaggaagg caccaaggag aaatcaggac   1440
ccacctctct gcctctgggc aaactgtttt ggaaaaagtc agttaaagag gactcagtcc   1500
ccacaggtgc ggaggagaat gtggtgtgtg agtcaccagt agagattata aagtccaagg   1560
aagtagaatc agccttacaa acagtggacc tcaacgaagg agatgctgca cctgaaccca   1620
cagaagcgaa actcaaaaga gaagaaagca aaccaagaac ctctctgatg gcgtttctca   1680
gacaaatgtc agtgaaaggg gatggaggga tcacccactc agaagaaata aatgggaaag   1740
actccagctg ccaaacatca gactccacag aaaagactat cacaccgcca gagcctgaac   1800
caacaggagc accacagaag ggtaaagagg gctcctcgaa ggacaagaag tcagcagccg   1860
agatgaacaa gcagaagagc aacaagcagg aagccaaaga accagcccag tgcacagagc   1920
aggccacggt ggacacgaac tcactgcaga atggggacaa gctccaaaag agacctgaga   1980
agcggcagca gtcccttggg ggcttcttta aaggcctggg accaaagcgg atgttggatg   2040
ctcaagtgca aacagaccca gtatccatcg gaccagttgg caaatccaag taaacaaatc   2100
agcacggttc ccaccaggtt ctcctgccac caagatgtgt tctccttact ccatctcctc   2160
cccaaacacg ctccatgtat atattcttct gatggccagc aaatgaaatt ctgcctagaa   2220
attaagcccg agctgttgta tattgaggtg tattatttac gtctctggtc cagtcttttc   2280
tggcaaataa cagtaaagat ggtttagcag gtcacctagt tgggtcagaa gagtcgatga   2340
tcaccaagca ggaaagggag ggaatagagg aatgtgttcg ggttaagtga tgaaaatggc   2400
agtggtggcc gggcgtggtg gctctcgcct gtaatctcag cactttggga ggccgaggca   2460
ggtggatcac ctgaggtcag gagttcaaga ctagcctggc caacatcatg aaaccccgtc   2520
tctactaaaa atacaaaaat tagccaggca tggtggcaca cacctgtagt cccagctact   2580
cgggagccca acgcacgaga accgcttgta cccaggaggt ggaggttgca gtgagccgaa   2640
gttgcaccat tgcactccac cctgggcgac agagcaagat tctatcaaaa aaaaaaaaag   2700
gcagtggcaa gtaagttata gaagagaaat gctgctagaa ggaattaagc gttgtagtaa   2760
atgcgtgctt atcctctaag cttgaagaag ggagacgaaa atccatttgt ttaaattcac   2820
atctcaagga gggagaaccc gggctgtgtt gggtggttgc caatttccta gaacggaatg   2880
tgtggggtat agaaaaagga atgaataagc gttgtttttc aaatagggtc cttgtaagtt   2940
attgatgaga gggaaaagat tgactgggga gggcttaaaa tgatttggga aaacaattgc   3000
ttttgaggct cagtgacaac ggcaaagatt acaacttaaa aaaaaaaaat aaataaaaaa   3060
taaaggaagt tgcacggtta ttttgcaaca caagggggcg gcaaggtccc cattttttatc   3120
ctgtaatact gtatccctaa caaagatttg gtctctgcta tcttacatta ttaatgtttc   3180
```

tcagatggct gaggggctcg cttcatctgt tccgtctgac acttatctca agtgtgtctg 3240
tcattcctaa tgttctcagg atgtgctctg ataaaaccct ccccataacc tcagttaata 3300
aaaatttaca gaagacttct caaatacctg agttgttttt aatacctgta caaaggagta 3360
aataggaccc tgagtctatt aaaatgtaat tcaaagtagc atatgattga ctgacagtca 3420
tgtaaactgt atctttcttt ttctgattta ataaaaaata catttacttc taaagtaaaa 3480
aaaaaaaaaa 3490

<210> SEQ ID NO 5
<211> LENGTH: 4627
<212> TYPE: DNA
<213> ORGANISM: Homo sapiens

<400> SEQUENCE: 5
gcggcggggg cggccatcgt gctgcgcagc ctgggcgctt ggggagccgc ccacttcgcc 60
gggtcgcgcc ccgacggccg gagcgtggat gcggcggcgc ccgccgagcc ggggcggacg 120
cggggcggcc cgggcccggg agacgcgccg gcagccccgg caccgcagcg gtcgcaggat 180
ggccgaggct atcagctgta ctctgaactg tagttgccaa agtttcaaac ccgggaaaat 240
aaaccaccgt cagtgtgacc aatgcaagca tggatgggtg gcccacgctc taagtaagct 300
aaggatcccc cccatgtatc caacaagcca ggtggagatt gtccagtcca atgtagtgtt 360
tgatattagc agcctcatgc tctatgggac ccaggccatc cccgttcgcc taaaaatcct 420
actggaccgg ctcttcagtg tgttgaagca agatgaggtt ctccagatcc tccatgcctt 480
ggactggaca cttcaggatt atatccgtgg atacgtactg caggatgcat caggaaaggt 540
gttggatcac tggagcatca tgaccagtga ggaagaagtg gccaccttgc agcagttcct 600
tcgttttgga gagaccaaat ctatagttga actcatggca attcaagaga aagaagagca 660
atccatcatc ataccacctt ccacagcaaa tgtagatatc agggctttca tcgagagctg 720
cagtcacagg agttctagcc tccccactcc tgtggacaaa ggaaacccca gcagtataca 780 ccccttgag aacctcataa gcaacatgac tttcatgctg cctttccagt tcttcaaccc 840
tctgcctcct gcactgatag ggtcattgcc cgaacaatat atgttggagc agggtcatga 900
ccaaagtcag gaccccaaac aggaagtcca tgggcccttc cctgacagca gcttcttaac 960
ttccagttcc acaccatttc aggttgaaaa agatcagtgt ttaaactgtc cggatgctat 1020
tactaaaaaa gaagacagca cccatttaag tgactccagc tcatacaaca ttgtcactaa 1080
gtttgaaagg acacagttat cccctgaggc caaagtgaag cctgagagga atagccttgg 1140
tacaaagaag ggccgggtgt tctgcactgc atgtgagaag accttctatg acaaaggcac 1200
cctcaaaatc cactacaatg ccgtccactt gaagatcaag cataagtgca ccatcgaagg 1260
gtgtaacatg gtgttcagct ccctaaggag ccggaatcgc catagcgcca accccaaccc 1320
tcggctgcac atgccaatga acagaaataa ccgggacaaa gacctcagga acagcctgaa 1380
cctggccagc tctgagaact acaagtgccc aggtttcaca gtgacgtccc cagactgtag 1440
gcctcctccc agctaccctg gttcaggaga ggattccaaa ggccaaccag ccttcccaaa 1500
cattgggcaa aatggtgtgc tttttcccaa cctaaagaca gtccagccag tccttccttt 1560
ctaccgcagt ccagccacgc ctgccgaggt agcaaacacg cctgggatac tcccttccct 1620
cccgctgttg tcctcttcaa tcccagaaca gctcatttca aacgaaatgc catttgatgc 1680
ccttcccaag aagaaatcca ggaagtccag tatgcctatc aaaatagaga aagaagctgt 1740

-continued

```
ggaaatagct aatgagaaaa gacacaacct cagctcagat gaagacatgc cctacaggt   1800
ggtcagtgaa gatgagcagg aggcctgcag tcctcagtca cacagagtat ctgaggagca   1860
gcatgtacag tcaggaggct tagggaagcc tttccctgaa ggggagaggc cctgccatcg   1920
tgaatcagta attgagtcca gtggagccat cagccaaacc cctgagcagg ccacacacaa   1980
ttcagagagg gagactgagc agacaccagc attgatcatg gtgccaaggg aggtcgagga   2040
tggtggccat gaacactact tcacacctgg gatggaaccc caagttcctt tttctgacta   2100
catggaactg cagcagcgcc tgctggctgg gggactcttc agtgctttgt ccaacagggg   2160
aatggctttt ccttgtcttg aagattctaa agaactggag cacgtgggtc agcatgcatt   2220
agcaaggcag atagaagaaa atcgcttcca gtgtgacatc tgcaagaaga cctttaaaaa   2280
tgcttgtagt gtgaaaattc atcacaagaa tatgcatgtc aaagaaatgc acacatgcac   2340
agtggagggc tgtaatgcta cctttccctc ccgcaggagc agagacagac acagctcaaa   2400
cctaaacctc caccaaaaag cattgagcca ggaagcattg gagagtagtg aagatcattt   2460
ccgtgcagct accttctga aagatgtggc taaggaagcc tatcaggatg tggcttttac    2520
acagcaagcc tcccagacat ctgtcatctt caaaggaaca agtcgaatgg gcagtctggt   2580
ttacccaata acgcaagtcc acagtgccag cctggagagc tacaactctg gccccttgag   2640
cgagggcacc atcctggatt tgagcactac ctcgagcatg aagtcagaga gtagcagcca   2700
ttcttcctgg gactctgacg gggtgagtga ggaaggcact gtgcttatgg aggacagtga   2760
tgggaactgt gaagggtcga gccttgtccc tggggaagat gagtacccca tctgtgtcct   2820
gatggagaag gctgaccaga gccttgctag cctgccttct gggttgccca taacctgtca   2880
tctctgccaa aagacataca gtaacaaagg gacctttagg gcccactaca aaactgtgca   2940
cctccggcag ctccacaaat gcaaagtacc aggctgcaac accatgtttt cgtctgttcg   3000
cagtcgaaac agacacagcc agaatcccaa cctgcacaaa agcctggcct catctccaag   3060
tcacctccag taacaagatg gcaaaccaag tatgctcaga taagcttttt tcataattca   3120
ggaataaagt agtccataga aatgtttctg tttcatatca tttggggcga gtcaggcaaa   3180
agtatttgat ttgactttat agttttccac agcacaatga gcaaaagaca aacctcgtgg   3240
gaagatgaca ctggggcagc ccttcctatt atttttctta gcccaagagg tctttcactg   3300
atacaaggaa aacttgcaga aatgtgattt ttcccagatt tgtttacatg ttccctggga   3360
cagatccagg tctgcagatc gacaccagtg ggcccaggac ctgggggtgg ctttaaatga   3420
ggcttgcagt gttaaaggtc ttggataaga agggtcctgg ggaagaagac tctgtggaca   3480
agataccagt ccccaaaaca gcattttcag ttccttcttc aattagtttg aaatccagac   3540
ctgagtttgg aagactgatt ttttgagacc atccctgtgt ttggagtgga taattgtccc   3600
tcccctcagc cctgcaccag aggtctcata tgttacccca gggagttctc agaggattgg   3660
gttggcctct aacatgttcc ttgttaattc ttgttctgta acatgcattc aagaagctag   3720
gggaaaaata tctcatgcac ttaaataatg gtcttcaatt taatttaaaa atattttgac   3780
aatatttaat ttgtgcttat gtggtgtttg gtgtgagtgc agatattgca ctgtgtcacc   3840
tctggatctc tgctcagaag cagaacaagt gatgacctaa atgtcaaaat cactgctcgt   3900
tttcatttgg tgaacttcaa actctgttct ttttggtcac ctgtggaatg aatgcaagca   3960
tgattttggc aggaacattt gtacatattc tgccgtagat aatgtggttc tgatggttgt   4020
tgtgtatttt cagtatcact ggatccctca gtcttcaccg ttttataaac gtataagatt   4080
aggatgaact tttgaattta cttggtagga aaaaaagtag gacattattg ccatattgta   4140
```

-continued tgtcttaata tttaacttat tcggaaatat attccacact gttacataca ttttccatgg 4200
tagaaaggaa gttcagtcag tcctgtggaa tgaaaccatc tcctaaaatt cagcatttgc 4260
agcattctaa aagcctgtgt aggtacaagg acattgattt tgtattcaga attcaagtta 4320
actatctttt aaattcgtgg ttgatgtaag taataaaaaa cattcttaaa gttgagggtt 4380
ataagagaga ttatttctgt ggtctaaagg ttaaaaagcc aacaacctgt taccaattat 4440
ttcagctttt tttgttttaa taagtgtgac aacttaaaac ttgtttctat ttaaagtgaa 4500
atgtatcttt caactgttta gttacccagc tgtttaatat tccagtcttc ccaaagtgaa 4560
aagatttgta tacaaatgtt ttctatgatt taataaaaat atatggcaca ccaaaaaaaa 4620
aaaaaaa 4627

<210> SEQ ID NO 6
<211> LENGTH: 825
<212> TYPE: DNA
<213> ORGANISM: Homo sapiens

<400> SEQUENCE: 6
acttctgcag cacagctccc ttcccaggac gtgaaaatct gccttctcac catgaggctt 60
ctagtccttt ccagcctgct ctgtatcctg cttctctgct tctccatctt ctccacagaa 120
gggaagaggc gtcctgccaa ggcctggtca ggcaggagaa ccaggctctg ctgccaccga 180
gtccctagcc ccaactcaac aaacctgaaa ggacatcatg tgaggctctg taaaccatgc 240
aagcttgagc cagagccccg cctttgggtg gtgcctgggg cactcccaca ggtgtagcac 300
tcccaaagca agactccaga cagcggagaa cctcatgcct ggcacctgag gtacccagca 360
gcctcctgtc tccccttca gccttcacag cagtgagctg caatgttgga gggcttcatc 420
tcgggctgca aggaccctgg gaaagttcca gaactccacg tccttgtctc aattgtgcca 480
tcaactttca gagctatcat gagccaacct caccccacag ggcctcagtc gccaccatgt 540
gggcctctcc agtgcaaacc accgagcatt ccaccatgac cggtcacagc tacaaatcca 600
gagaccatca atcctgctag agtgcagggt ggcaagcacc caagggtggc tgaccaagac 660
tgcagagtct cctccatctt caggtccatt cagcctcctg gcatttaact accagcatcc 720
agtggtcccc aaggaatccc ttcctagcct cctgacatga gtctgctgga aagagcatcc 780
aaacaaacaa gtaataaata aataaataaa ctcaatgcag acaca 825

<210> SEQ ID NO 7
<211> LENGTH: 3298
<212> TYPE: DNA
<213> ORGANISM: Homo sapiens

<400> SEQUENCE: 7
gtctcctgcg agagccgcgg gggccgcgga gctggagccg gagctgaagc cggagccggg 60
ttggagtctg ggcgggggcc gggccggagc gggctccaga gacatggggt cgaccgactc 120
caagctgaac ttccggaagg cggtgatcca gctcaccacc aagacgcagc ccgtggaagc 180
caccgatgat gccttttggg accagttctg ggcagacaca gccacctcgg tgcaggatgt 240
gtttgcactg gtgccggcag cagagatccg ggccgtgcgg gaagagtcac cctccaactt 300
ggccaccctg tgctacaagg ccgttgagaa gctggtgcag ggagctgaga gtggctgcca 360
ctcggagaag gagaagcaga tcgtcctgaa ctgcagccgg ctgctcaccc gcgtgctgcc 420
ctacatcttt gaggaccccg actggagggg cttcttctgg tccacagtgc ccggggcagg 480

-continued

```
gcgaggaggg cagggagaag aggatgatga gcatgccagg cccctggccg agtccctgct    540
cctggccatt gctgacctgc tcttctgccc ggacttcacg gttcagagcc accggaggag    600
cactgtggac tcggcagagg acgtccactc cctggacagc tgtgaataca tctgggaggc    660
tggtgtgggc ttcgctcact ccccccagcc taactacatc cacgatatga accggatgga    720
gctgctgaaa ctgctgctga catgcttctc cgaggccatg tacctgcccc cagctccgga    780
aagtggcagc accaacccat gggttcagtt cttttgttcc acggagaaca gacatgccct    840
gcccctcttc acctccctcc tcaacaccgt gtgtgcctat gaccctgtgg gctacgggat    900
cccctacaac cacctgctct tctctgacta ccgggaaccc ctggtggagg aggctgccca    960
ggtgctcatt gtcactttgg accacgacag tgccagcagt gccagcccca ctgtggacgg   1020
caccaccact ggcaccgcca tggatgatgc cgatcctcca ggccctgaga acctgtttgt   1080
gaactacctg tcccgcatcc atcgtgagga ggacttccag ttcatcctca agggtatagc   1140
ccggctgctg tccaaccccc tgctccagac ctacctgcct aactccacca agaagatcca   1200
gttccaccag gagctgctag ttctcttctg gaagctctgc gacttcaaca agaaattcct   1260
cttcttcgtg ctgaagagca gcgacgtcct agacatcctt gtccccatcc tcttcttcct   1320
caacgatgcc cgggccgatc agtctcgggt gggcctgatg cacattggtg tcttcatctt   1380
gctgcttctg agcggggagc ggaacttcgg ggtgcggctg aacaaaccct actcaatccg   1440
cgtgcccatg gacatcccag tcttcacagg gacccacgcc gacctgctca ttgtggtgtt   1500
ccacaagatc atcaccagcg ggcaccagcg gttgcagccc ctcttcgact gcctgctcac   1560
catcgtggtc aacgtgtccc cctacctcaa gagcctgtcc atggtgactg ccaacaagtt   1620
gctgcacctg ctggaggcct tctccaccac ctggttcctc ttctctgccg cccagaacca   1680
ccacctggtc ttcttcctcc tggaggtctt caacaacatc atccagtacc agtttgatgg   1740
caactccaac ctggtctacg ccatcatccg caagcgcagc atcttccacc agctggccaa   1800
cctgcccacg gacccgccca ccattcacaa ggccctgcag cggcgccggc ggacacctga   1860
gcccttgtct cgcaccggct cccaggaggg cacctccatg gagggctccc gccccgctgc   1920
ccctgcagag ccaggcaccc tcaagaccag tctggtggct actccaggca ttgacaagct   1980
gaccgagaag tcccaggtgt cagaggatgg caccttgcgg tccctggaac ctgagcccca   2040
gcagagcttg gaggatggca gcccggctaa gggggagccc agccaggcat ggagggagca   2100
gcggcgaccg tccacctcat cagccagtgg gcagtggagc ccaacgccag agtgggtcct   2160
ctcctggaag tcgaagctgc cgctgcagac catcatgagg ctgctgcagg tgctggttcc   2220
gcaggtggag aagatctgca ttgacaaggg cctgacggat gagtctgaga tcctgcggtt   2280
cctgcagcat ggcaccctgg tggggctgct gcccgtgccc caccccatcc tcatccgcaa   2340
gtaccaggcc aactcgggca ctgccatgtg gttccgcacc tacatgtggg gcgtcatcta   2400
tctgaggaat gtggaccccc ctgtctggta cgacaccgac gtgaagctgt ttgagataca   2460
gcgggtgtga ggatgaagcc gacgaggggc tcagtctagg ggaaggcagg gccttggtcc   2520
ctgaggcttc ccccatccac cattctgagc tttaaattac cacgatcagg gcctggaaca   2580
ggcagagtgg ccctgagtgt catgccctag agacccctgt ggccaggaca atgtgaactg   2640
gctcagatcc ccctcaaccc ctaggctgga ctcacaggag ccccatctct ggggctatgc   2700
ccccaccaga gaccactgcc cccaacactc ggactccctc tttaagacct ggctcagtgc   2760
tggcccctca gtgcccaccc actcctgtgc tacccagccc cagaggcaga agccaatggg   2820
tcactgtgcc ctaaggggtt tgaccaggga accacgggct gtcccttgag gtgcctggac   2880
```

-continued agggtaaggg ggtgcttcca gcctcctaac ccaaagccag ctgttccagg ctccagggga 2940
aaaaggtgtg gccaggctgc tcctcgagga ggctgggagc tggccgactg caaaagccag 3000
actggggcac ctcccgtatc cttggggcat ggtgtggggt ggtgagggtc tcctgctata 3060
ttctcctgga tccatggaaa tagcctggct ccctcttacc cagtaatgag gggcagggaa 3120
gggaactggg aggcagccgt ttagtcctcc ctgccctgcc cactgcctgg atggggcgat 3180
gccacccctc atccttcacc cagctctggc ctctgggtcc caccacccag ccccccgtgt 3240
cagaacaatc tttgctctgt acaatcggcc tctttacaat aaaacctcct gctccaca 3298

<210> SEQ ID NO 8
<211> LENGTH: 4367
<212> TYPE: DNA
<213> ORGANISM: Homo sapiens

<400> SEQUENCE: 8
agtcccagct ggatctccgg ccagagcccg aggctgctgc gccgggcggc tgcagcctcc 60
gctccagcgc ccgcgccgtg ccctgcatcc cgggagcccg gctggacccg cggcggctcg 120
gccggtgttc cccctcccct ccctggggca gcagccacca tgttctcgtg tgtgaagccc 180
tatgaggacc agaactactc agccctgagg cgggactgcc ggcgcaggaa ggtgctcttc 240
gaggaccccc tcttccccgc cactgacgac tcactctact ataagggcac gccggggccc 300
gccgtcaggt ggaagcgacc caagggcatc tgcgaggacc cccgcctctt tgtggatggc 360
atcagctccc acgacctgca ccagggccag gtgggcaact gctggtttgt ggcagcctgc 420
tcgtcacttg cctcccggga gtcgctgtgg caaaaggtca tcccagactg gaaggagcag 480
gaatgggacc ccgaaaagcc caacgcctac gcgggcatct tccacttcca cttctggcgc 540
ttcggggaat gggtggacgt ggtcatcgat gaccggctgc ccacagtcaa caaccagctc 600
atctactgcc actccaactc ccgcaatgag ttttggtgcg ccctagtgga gaaggcctat 660
gccaaactgg caggctgtta ccaggccctg gatggaggca acacagcaga cgcactggtg 720
gacttcacgg gtggtgtttc tgagcccatc gacctgaccg agggtgactt tgccaacgat 780
gagactaaga ggaaccagct ctttgagcgc atgttaaagg tgcacagccg gggcggcctc 840
atcagtgcct ccatcaaggc agtgacagca gctgacatgg aggcccgcct ggcgtgcggc 900
ctggtaaagg gccacgcata cgccgtcact gatgtgcgca aggtgcgcct gggccacggc 960
ctactggcct tcttcaagtc agagaagttg gacatgatcc gcctgcgcaa cccctggggc 1020
gagcgggagt ggaacgggcc ctggagtgac acctcggagg agtggcagaa agtgagcaag 1080
agtgagcggg agaagatggg tgtgaccgtg caggacgacg gtgagttctg gatgaccttc 1140
gaggacgtgt gccggtactt cacggacatc atcaagtgcc gcgtgatcaa cacatcccac 1200
ctgagcatcc acaagacgtg ggaggaggcc cggctgcatg gcgcctggac gctgcatgag 1260
gacccgcgac agaaccgcgg tggcggctgc atcaaccaca aggacacctt cttccagaac 1320
ccacagtaca tcttcgaagt caagaagcca gaagatgaag tcctgatctg catccagcag 1380
cggccaaagc ggtctacgcg ccgggagggc aagggtgaga acctggccat tggctttgac 1440
atctacaagg tggaggagaa ccgccagtac cgcatgcaca gcctgcagca caaggccgcc 1500
agctccatct acatcaactc acgcagcgtc ttcctgcgca ccgaccagcc cgagggccgc 1560
tatgtcatca tccccacaac cttcgagcca ggccacactg gcgagttcct gctccgagtc 1620
ttcactgatg tgccctccaa ctgccgggag ctgcgcctgg atgagccccc acacacctgc 1680

-continued

```
tggagctccc tctgtggcta cccccagctg gtgacccagg tacatgtcct gggagctgct   1740
ggcctcaagg actccccaac aggggctaac tcttatgtga tcatcaagtg tgagggagac   1800
aaagtccgct cggctgtgca gaagggcacc tccacaccag agtacaatgt gaaaggcatc   1860
ttctaccgca agaagctgag ccagcccatc actgtacagg tctggaacca ccgagtgctg   1920
aaggatgaat ttctgggcca ggtgcaccta aaggctgacc cggacaacct ccaggccctg   1980
cataccctcc acctccggga ccgaaatagc cggcagccca gcaacctgcc aggcactgtg   2040
gccgtgcaca ttctcagcag cacctccctc atggctgtct gacacctgcc cacctacctg   2100
gctctgaccg ttcccaccac catctgcatg tccccactgg gcctgagtct agcctgggag   2160
ccaggatact ggggtccttt tcccactctt ccactgactt gctgtgtgac cttaggaagt   2220
ctctgcccct ctctcagcct cagtgtcccg agggccccga agcattccat tctcgtggag   2280
gagtttcctt gctgagattt caaatagtcc tccccacctc aactgtcacc actgctaagg   2340
gactctatcc attgagcaca ttttcctaag gccctgctgt ctgccgagga gcgccaagaa   2400
gatgtcactt gtttacacac gaactgccac atccccaagc tccgttcttg cccctcgtgt   2460
cctaggccca acccagcctc ccagacctca ctttccccat cagcaatacc tggtgttctc   2520
ccaccttgaa aggactcttg gctcctgccg ggttcctgct caggctggaa ttgggaaaat   2580
atgcaggtga catttgttca ttctctaatc ccatcctctc acccatccat ttcctcactc   2640
agtggagatt tgccaaatga ataaacgaca cctttgaggc cccaggtgaa gcggggccct   2700
actccggcct ctgccttggg cctcgcctct gtcctcaggt cctctcagag gcagatacct   2760
aggggagctg ctgctgcctg ctcattctag cttccgattc cattcccagc ccctgcgtta   2820
aggtccctgg agaggtggcg tcagtggggg tgaggaaggg catcttcctg actcctctgc   2880
ccagtgctgg aaggagcatg cctgggttag tgggccaggg gccaggcagc tgggggcctt   2940
tggggaccag aaggggagat gtgctcccag agcctctctg ctgtaagacc ccagcttttc   3000
ctggaagatg ggactctggg gtgtgtggtg ctcaccagag tcaggccacc cactgggctc   3060
ggcaggagat agggagcccc atcacctgac cacagccccc caccaacatt cccccaaaat   3120
gcagcctagg aggccgcagt gctcttcttc ctgcccagac caaaatgttc cttttagtcc   3180
tcaatgtttt atattctttt tgttttgaaa atctcaattt taatcagggg ttttaaaaga   3240
aaattgaaag cctgaacctc catttttctt cttggctcca gttttgctgg tcctctggag   3300
aactcttcgt gagcactggt gccgtgaccc acttgggatc tctgctgtgc ccttctcggg   3360
cttccagacc aggtgtagca aatgaaaaag tgcagttaat tcaagaacag gaatccctgt   3420
gtccttgctg ggatttcctt ttgggaacct gactttccga ctccagatcc tgctgtctgg   3480
atcagtgttc tggctggagg tgctggattc tctgattttg cctcctcact ctgtgtctgg   3540
ctttgctcct gggtcttggc cctgggccat atgaggggcc aggaaatgaa cgacaaggag   3600
gataagagtg ttctttcttg aaagccggga cttcccctca agaacctggg cctggggccg   3660
ggactctgca tgactgggag caagtcactt aaacctcctg tgcctcgatt tccccccttct  3720
acaaagtggg gccaatgatt cttgtgtgtc agcactgtta ctaccgagtg ctgagtaagg   3780
gcaaaataat accccttttct ctatgtatct ctgtatgcac acgcactata tatatatata  3840
tatatatata tacattcatg taatcaccac ttctcgatgt ctatttcaaa tcaaggctcc   3900
tgagtagggg gtgaagtgag ccagcttgca cctcaggcta acacatagga ctttgctcag   3960
ccatgtcccc tgggatacag gggcacacca ggaccaagtg gcagacctgt gggcttcagc   4020
ctcggggccg gggcatgcct gccacccccct gacaaaaaca ggttccacag tgctaccctt  4080
```

-continued gcttcctgcc ccttgaggtg ggccaggctg gctcctggct atgcagggat ctctggtccc 4140
caggagacct tgggggccag gcaggtaagg atcaggggtg ataggggaga gcaattactt 4200
tgttcactgt atgcacccgc gggggcctgg gagtccccat ttgcaggtgg gtagggcctc 4260
cagcccacac cacccagacc taggcttccc tcttctcagg atccaccaca gggttagggg 4320
acaggaagcc tgttctattc tcaataaatc ttacaaaatt ccaaaaa 4367

<210> SEQ ID NO 9
<211> LENGTH: 4712
<212> TYPE: DNA
<213> ORGANISM: Homo sapiens

<400> SEQUENCE: 9
agccttctca ctcctcactg agtccactct gaacgtgcta aaatgggaag gaggcggtgt 60
tttgctgatc tgttaaattc ttagtgaagt ttccttgatt tccagtggct gctgttgttt 120
gagtttggtt tggagcaaaa ctgaggtagt cctaacattt ctgggactga atccaggcaa 180
gagaaagaag aaaaagaaga agaaaaagag gaggaaaaag gtagggagaa ataaagggag 240
gagagaagca cagtgaaaga aaaaaaaagt cccttttcga catcacattc ctgtgttttc 300
cctcagcctg gaaaacatat taatcccagt gcttttacgc ccggaaacaa agagactaag 360
ccagactatg gggaaaggg agataagaag gatcctggaa ctttaaagag ggaaagagtg 420
agattcagaa atcgccagga ctggacttta agggacgtcc tgtgtcagca caagggactg 480
gcacacacag acacacgaga ccgaggagaa actgcagaca aatggagata caaagactta 540
gaaggacagc tcctttcacc tcatcctact tgtccagaag gtaaaaagac acagccagaa 600
agaaaaggca tcggctcagc tctcagatca ggacaggctg tggatctgtg gcggtactct 660
gaaagctgga gctgcagcac acccctttttg tattgctcac cctcggtaaa gagagagagg 720
gctgggagga aaagtagttc atctaggaaa ctgtcctggg aaccaaactt ctgatttctt 780
ttgcaaccct ctgcattcca tctctatgag ccaccattgg attacacaat gacatggaga 840
atgggacccc gtttcactat gctgttggcc atgtggctag tgtgtggatc agaaccccac 900
ccccatgcca ctattagagg cagccacgga ggacggaaag tgcctttggt ttctccggac 960
agcagtaggc cagctcggtt tctgaggcac actgggaggt ctcgcggaat tgagagatcc 1020
actctggagg aaccaaacct tcagcctctc cagagaagga ggagtgtgcc cgtgttgaga 1080
ctagctcgcc caacagagcc gccagcccgc tcggacatca atggggccgc cgtgagacct 1140
gagcaaagac cagcagccag gggctctccg cgtgagatga tcagagatga ggggtcctca 1200
gctcggtcaa gaatgttgcg tttcccttcg gggtccagct ctcccaacat ccttgccagc 1260
tttgcaggga agaacagagt atgggtcatc tcagcccctc atgcctcgga aggctactac 1320
cgcctcatga tgagcctgct gaaggacgat gtgtactgtg agctggcgga gaggcacatc 1380
caacagattg tgctcttcca ccaggcaggt gaggaaggag gcaaggtgag aaggatcacc 1440
agcgagggcc agatcctgga gcagcccctg gaccctagcc tcatccctaa gctgatgagc 1500
ttcctgaagc tggagaaggg caagtttggc atggtgctgc tgaagaagac gctgcaggtg 1560
gaggagcgct atccatatcc cgttaggctg gaagccatgt acgaggtcat cgaccaaggc 1620
cccatccgta ggatcgagaa gatcaggcag aagggctttg tccagaaatg taaggcctct 1680
ggtgtagagg gccaggtggt ggcggagggg aatgacggtg gagggggagc aggaaggcca 1740
agcctgggca gcgagaagaa gaaagaggac ccaaggagag cacaagtccc accaaccaga 1800

-continued

```
gagagtcggg tgaaggtcct gagaaaactg gccgccactg caccagcttt gccccaacct   1860
ccctcaaccc ccagagccac caccccttcct cctgccccag ccacaacagt gactcggtcc   1920
acgtcccggg cggtaacagt tgctgcaaga cctatgacca ccactgcctt tcccaccacg   1980
cagaggccct ggaccccctc accctcccac aggcccccta caaccactga ggtgatcact   2040
gccaggagac cctcagtttc agagaatctt taccctccat cccggaagga tcagcacagg   2100
gagaggccac agacaaccag gaggcccagc aaggccacca gcttggagag cttcacaaat   2160
gcccctccca ccaccatctc agaacccagc acaagggctg ctggcccagg ccgtttccgg   2220
gacaaccgca tggacaggcg ggaacatggc caccgagacc caaatgtggt gccaggtcct   2280
cccaagccag caaaggagaa acctcccaaa aagaaggccc aggacaaaat tcttagtaat   2340
gagtatgagg agaagtatga cctcagccgg cctactgcct ctcagctgga ggacgagctg   2400
caggtgggga atgttcccct taaaaaagca aaggagtcta aaaagcatga aaagcttgag   2460
aaaccagaga aggagaagaa aaaaaagatg aagaatgaga acgcagacaa gttacttaag   2520
agtgaaaagc aaatgaagaa gtctgagaaa aagagcaagc aagagaaaga gaagagcaag   2580
aagaaaaaag gaggtaaaac agaacaggat ggctatcaga aacccaccaa caaacacttc   2640
acgcagagtc ccaagaagtc agtggccgac ctgctggggt cctttgaagg caaacgaaga   2700
ctccttctga tcactgctcc caaggctgag aacaatatgt atgtgcaaca acgtgatgaa   2760
tatctggaaa gtttctgcaa gatggctacc aggaaaatct ctgtgatcac catcttcggc   2820
cctgtcaaca acagcaccat gaaaatcgac cactttcagc tagataatga gaagcccatg   2880
cgagtggtgg atgatgaaga cttggtagac cagcgtctca tcagcgagct gaggaaagag   2940
tacggaatga cctacaatga cttcttcatg gtgctaacag atgtggatct gagagtcaag   3000
caatactatg aggtaccaat aacaatgaag tctgtgtttg atctgatcga tactttccag   3060
tcccgaatca aagatatgga gaagcagaag aaggagggca ttgtttgcaa agaggacaaa   3120
aagcagtccc tggagaactt cctatccagg ttccggtgga ggaggaggtt gctggtgatc   3180
tctgctccta acgatgaaga ctgggcctat tcacagcagc tctctgccct cagtggtcag   3240
gcgtgcaatt ttggtctgcg ccacataacc attctgaagc ttttaggcgt tggagaggaa   3300
gttgggggag tgttagaact gttcccaatt aatgggagct ctgttgttga gcgagaagac   3360
gtaccagccc atttggtgaa agacattcgt aactattttc aagtgagccc ggagtacttc   3420
tccatgcttc tagtcggaaa agacggaaat gtcaaatcct ggtatccttc cccaatgtgg   3480
tccatggtga ttgtgtacga tttaattgat tcgatgcaac ttcggagaca ggaaatggcg   3540
attcagcagt cactggggat gcgctgccca gaagatgagt atgcaggcta tggttaccat   3600
agttaccacc aaggatacca ggatggttac caggatgact accgtcatca tgagagttat   3660
caccatggat acccttactg agcagaaata tgtaacctta gactcagcca gtttcctctg   3720
cagctgctaa aactacatgt ggccagctcc attcttccac actgcgtact acatttcctg   3780
ccttttttctt tcagtgtttt tctaagacta aataaatagc aaactttcac ctattcatga   3840
gttattattg aaacctcaaa tcataaagac atttaaaaga attgtttttc taactggagg   3900
ggctctagtg ctaaataata gtactgaaaa ttgatattat tttcctttttc ttatatgaag   3960
gaccttattt ggcatataaa attttataaa atatgtattt aaagcttttt cttatttttt   4020
gtattaattg gtaagtgaaa actctgttaa agatcacacc acaatgtttt caagaaacat   4080
ctgaaaagat aaaacaaaga acaaataact tataatactt acttaaattg acacttttttg   4140
aaatgccagt ctgaaaataa ttaagatatc tctgctttgt atgagtttct tttatgaaac   4200
```

ttgataccac gggagtccag taatattggc cacaaaagcc agagaaagta ccaagcccag 4260
ctttgttatc atagccactt cctgccctgc ttctgttatt tttagtgttt tttcagatat 4320
aaatcggggt ccaggaaatc ctcaccagaa tctggcactg cagccaaagg cgatacttcc 4380
agagttctag taggctgcta tggaatttct ggcatgaaaa ttcttgaccc ctcacacttt 4440
accccctgta cagcacaggc ataccatgga gatattacag gatcagttcc agaccaccat 4500
aataaagtgg atatcgcaat aaagtgagtc acacaaaatt tttggtttct cagtgcatat 4560
aaaagttatg tttacactct ttagtagtct attaagtgta taatagcttt atgtccaaaa 4620
aatgtacatg ttttatttta aaaatacttt attgctaaaa attgctaatg atcataatct 4680
ttttgcattg atgttgatgg ctgctgaatg at 4712

<210> SEQ ID NO 10
<211> LENGTH: 3168
<212> TYPE: DNA
<213> ORGANISM: Homo sapiens

<400> SEQUENCE: 10
gcttactcgg cgcccgcgcc tcgggccgtc gggagcggag cctcctcggg accaggactt 60
cagggccaca ggtgctgcca agatgctcca gggcacctgc tccgtgctcc tgctctgggg 120
aatcctgggg gccatccagg cccagcagca ggaggtcatc tcgccggaca ctaccgagag 180
aaacaacaac tgcccagaga agaccgactg ccccatccac gtgtacttcg tgctggacac 240
ctcggagagc gtcaccatgc agtcccccac ggacatcctg ctcttccaca tgaagcagtt 300
cgtgccgcag ttcatcagcc agctgcagaa cgagttctac ctggaccagg tggcgctgag 360
ctggcgctac ggcggcctgc acttctctga ccaggtggag gtgttcagcc caccgggcag 420
cgaccgggcc tccttcatca agaacctgca gggcatcagc tccttccgcc gcggcacctt 480
caccgactgc gcgctggcca acatgacgga gcagatccgg caggaccgca gcaagggcac 540
cgtccacttc gccgtggtca tcaccgacgg ccacgtcacc ggcagcccct gcgggggcat 600
caagctgcag gccgagcggg cccgcgagga gggcatccgg ctcttcgccg tggcccccaa 660
ccagaacctg aaggagcagg gcctgcggga catcgccagc acgccgcacg agctctaccg 720
caacgactac gccaccatgc tgcccgactc caccgagatc gaccaggaca ccatcaaccg 780
catcatcaag gtcatgaaac acgaagccta cggagagtgc tacaaggtga gctgcctgga 840
aatccctggg ccctctggcc ccaagggcta ccgtggacag aagggtgcca agggcaacat 900
gggtgagccg ggagagcctg gccagaaggg aagacaggga gacccgggca tcgaaggccc 960
cattggattc ccaggaccca agggcgttcc tggcttcaaa ggagagaagg gtgaatttgg 1020
agccgacggt cgcaaggggg cccctggcct ggctggcaag aacgggaccg atggacagaa 1080
gggcaagctg gggcgcatcg gacctcctgg ctgcaaggga gaccctggaa accggggccc 1140
cgacggttac ccgggggaag cagggagtcc aggggagcga ggagaccaag gcggcaaggg 1200
ggaccctggc cgcccaggac gcagagggcc cccgggagaa atcggggcca agggaagcaa 1260
ggggtatcaa ggcaacagtg gagccccagg aagtcctggt gtgaaaggag ccaagggcgg 1320
gcctgggccc cgcggaccca aaggcgagcc ggggcgcagg ggagaccccg gcaccaaggg 1380
cagcccaggc agcgatggcc ccaaggggga gaagggggac cctggccctg aggggccccg 1440
cggcctggct ggagaggttg gcaacaaagg agccaaggga gaccgaggct tgcctggacc 1500
cagaggcccc cagggagctc ttggggagcc cggaaagcag ggatctcggg gagaccccgg 1560

-continued

```
tgatgcagga ccccgtggag actcaggaca gccaggcccc aagggagacc ccggcaggcc   1620
tggattcagc tacccaggac cccgaggagc acccggagaa aaaggcgagc ccggcccacg   1680
cggccccgag ggaggccgag gcgactttgg cttgaaagga gaacctggga ggaaaggaga   1740
gaaaggagag cctgcggatc ctggtccccc tggtgagcca ggccctcggg ggccaagagg   1800
agtcccagga cccgagggtg agcccggccc ccctggagac cccggtctca cggagtgtga   1860
cgtcatgacc tacgtgaggg agacctgcgg gtgctgcgac tgtgagaagc gctgtggcgc   1920
cctggacgtg gtcttcgtca tcgacagctc cgagagcatt gggtacacca acttcacact   1980
ggagaagaac ttcgtcatca acgtggtcaa caggctgggt gccatcgcta aggaccccaa   2040
gtccgagaca gggacgcgtg tgggcgtggt gcagtacagc cacgagggca cctttgaggc   2100
catccagctg gacgacgaac gtatcgactc cctgtcgagc ttcaaggagg ctgtcaagaa   2160
cctcgagtgg attgcgggcg gcacctggac accctcagcc ctcaagtttg cctacgaccg   2220
cctcatcaag gagagccggc gccagaagac acgtgtgttt gcggtggtca tcacggacgg   2280
gcgccacgac cctcgggacg atgacctcaa cttgcgggcg ctgtgcgacc gcgacgtcac   2340
agtgacggcc atcggcatcg gggacatgtt ccacgagaag cacgagagtg aaaacctcta   2400
ctccatcgcc tgcgacaagc cacagcaggt gcgcaacatg acgctgttct ccgacctggt   2460
cgctgagaag ttcatcgatg acatggagga cgtcctctgc ccggaccctc agatcgtgtg   2520
cccagacctt ccctgccaaa cagatgcacc gtggcctggc ggcgagcccc cggtcacctt   2580
cctccgcacg gaagaggggc cggacgccac cttccccagg accattcccc tgatccaaca   2640
gttgctaaac gccacggagc tcacgcagga cccggccgcc tactcccagc tggtggccgt   2700
gctggtctac accgccgagc gggccaagtt cgccaccggg gtagagcggc aggactggat   2760
ggagctgttc attgacacct ttaagctggt gcacagggac atcgtggggg accccgagac   2820
cgcgctggcc ctctgctaaa gcccgggcac ccgcccagcc gggctgggcc ctccctgcca   2880
cactagcttc ccagggctgc cccgacaggg ctggctctca gtggaggcca gagatctgga   2940
atcggggtca gcggggctac agtccttcca ggggctctgg ggcagctccc agcctcttcc   3000
catgctggtg gccaccgtgt cccttgctgc ggctgcatct tccagtctct cctccgtctt   3060
cctgtggccg ctctctttat aagaaccctg gtcattgaat ttaaggccca ccccaagtcc   3120
agaatgacct cgcaagaccc ttaactcact cccaaaaaaa aaaaaaaa                3168
```

<210> SEQ ID NO 11
<211> LENGTH: 3544
<212> TYPE: DNA
<213> ORGANISM: Homo sapiens

<400> SEQUENCE: 11

```
acacgcgcag ccagccggcc gcctcccgcg cccaagcgcg ccgctctgct gtgccctgcg     60
cccttgcccc gcgccagctt ctgcgcccgc agcccgcccg gcgcccccgg tgaccgtgac    120
cctgccctgg gcgcggggcg gagcaggcat gtcccgcccg gggaccgcta ccccagcgct    180
ggccctggtg ctcctggcag tgaccctggc cggggtcgga gcccagggcg cagccctcga    240
ggaccctgat tattacgggc aggagatctg gagccgggag ccctactacg cgcgcccgga    300
gcccgagctc gagaccttct ctccgccgct gcctgcgggg cccggggagg agtgggagcg    360
gcgcccgcag gagcccaggc cgcccaagag ggccaccaag cccaagaaag ctcccaagag    420
ggagaagtcg gctccggagc cgcctccacc aggtaaacac agcaacaaaa aagttatgag    480
aaccaagagc tctgagaagg ctgccaacga tgatcacagt gtccgtgtgg cccgtgaaga    540
```

-continued

```
tgtcagagag agttgcccac ctcttggtct ggaaacctta aaaatcacag acttccagct    600
ccatgcctcc acggtgaagc gctatggcct gggggcacat cgagggagac tcaacatcca    660
ggcgggcatt aatgaaaatg atttttatga cggagcgtgg tgcgcgggaa gaaatgacct    720
ccagcagtgg attgaagtgg atgctcggcg cctgaccaga ttcactggtg tcatcactca    780
agggaggaac tccctctggc tgagtgactg ggtgacatcc tataaggtca tggtgagcaa    840
tgacagccac acgtgggtca ctgttaagaa tggatctgga gacatgatat ttgagggaaa    900
cagtgagaag gagatccctg ttctcaatga gctacccgtc cccatggtgg cccgctacat    960
ccgcataaac cctcagtcct ggtttgataa tgggagcatc tgcatgagaa tggagatcct   1020
gggctgccca ctgccagatc ctaataatta ttatcaccgc cggaacgaga tgaccaccac   1080
tgatgacctg gattttaagc accacaatta taaggaaatg cgccagttga tgaaagttgt   1140
gaatgaaatg tgtcccaata tcaccagaat ttacaacatt ggaaaaagcc accagggcct   1200
gaagctgtat gctgtggaga tctcagatca ccctggggag catgaagtcg gtgagcccga   1260
gttccactac atcgcggggg cccacggcaa tgaggtgctg ggccgggagc tgctgctgct   1320
gctggtgcag ttcgtgtgtc aggagtactt ggcccggaat gcgcgcatcg tccacctggt   1380
ggaggagacg cggattcacg tcctcccctc cctcaacccc gatggctacg agaaggccta   1440
cgaagggggc tcggagctgg gaggctggtc cctgggacgc tggacccacg atggaattga   1500
catcaacaac aactttcctg atttaaacac gctgctctgg gaggcagagg atcgacagaa   1560
tgtccccagg aaagttccca atcactatat tgcaatccct gagtggtttc tgtcggaaaa   1620
tgccacggtg gctgccgaga ccagagcagt catagcctgg atggaaaaaa tcccttttgt   1680
gctgggcggc aacctgcagg gcggcgagct ggtggtggcg taccccctacg acctggtgcg   1740
gtccccctgg aagacgcagg aacacacccc cacccccgac gaccacgtgt tccgctggct   1800
ggcctactcc tatgcctcca cacaccgcct catgacagac gcccggagga gggtgtgcca   1860
cacggaggac ttccagaagg aggagggcac tgtcaatggg gcctcctggc acaccgtcgc   1920
tggaagtctg aacgatttca gctaccttca tacaaactgc ttcgaactgt ccatctacgt   1980
gggctgtgat aaatacccac atgagagcca gctgcccgag gagtgggaga ataaccggga   2040
atctctgatc gtgttcatgg agcaggttca tcgtggcatt aaaggcttgg tgagagattc   2100
acatggaaaa ggaatcccaa acgccattat ctccgtagaa ggcattaacc atgacatccg   2160
aacagccaac gatggggatt actggcgcct cctgaaccct ggagagtatg tggtcacagc   2220
aaaggccgaa ggtttcactg catccaccaa gaactgtatg gttggctatg acatgggggc   2280
cacaaggtgt gacttcacac ttagcaaaac caacatggcc aggatccgag agatcatgga   2340
gaagtttggg aagcagcccg tcagcctgcc agccaggcgg ctgaagctgc gggggcagaa   2400
gagacgacag cgtgggtgac cctcctgggc ccttgagact cgtctgggac ccatgcaaat   2460
taaaccaacc tggtagtagc tccatagtgg actcactcac tgttgtttcc tctgtaattc   2520
aagaagtgcc tggaagagag ggtgcattgt gaggcaggtc ccaaaaggga aggctggagg   2580
ctgaggctgt tttcttttct ttgttcccat ttatccaaat aacttggaca gagcagcaga   2640
gaaaagctga tgggagtgag agaactcagc aagccaacct gggaatcaga gagagaagga   2700
gaaggagggg agcctgtccg ttcagagcct ctggctgcat agaaaaggat tctggtgctt   2760
cccctgtttg cgtggcagca agggttccac gtgcatttgc aatttgcaca gctaaaattg   2820
cagcatttcc ccagctgggc tgtcccaaat gttaccattt gagatgctcc caggcgtcct   2880
```

-continued aagagaatcc accctctctg gccctgggac attgcaagct gctacaaata aattctgtgt 2940
tcttttgaca atagcgtcat tgccaagtgc acatcagtga gcctcttgaa tctgtttagt 3000
ctcctttttc aacaaaggag tgtgttcaga aaaggagaga gaggctgaga tcattcagga 3060
gtttgttggg cagcaagcat ggagcttctt gcacaaattc tgggtccata aacaaccccc 3120
aaagtccctg ctgatccagt agccctggag gttccccagg tagggagagc cagaggtgcc 3180
agccttcctg aagggccaga aaatttagcc tggatctcct cttttacctg ctaggactgg 3240
aaagagccag aagtggggtg gcctgaagcc ctctctctgc ttgaggtatt gcccctgtgt 3300
ggaattgagt gctcatgggt tggcctcata tcagcctggg agttattttt gatatgtaga 3360
atgccagatc ttccagatta ggctaaatgt aatgaaaacc tcttaggatt atctgtggag 3420
catcagtttg ggaagaatta ttgaattatc ttgcaagaaa aaagtatgtc tcactttttg 3480
ttaatgttgc tgcctcattg acctgggaaa aatgaaaaaa aaaaataaag caaatggtaa 3540
gacc 3544

<210> SEQ ID NO 12
<211> LENGTH: 1240
<212> TYPE: DNA
<213> ORGANISM: Homo sapiens

<400> SEQUENCE: 12
gaaaggcgca ttgatgcagc ctgcggcggc ctcggagcgc ggcggagcca gacgctgacc 60
acgttcctct cctcggtctc ctccgcctcc agctccgcgc tgcccggcag ccgggagcca 120
tgcgacccca gggccccgcc gcctccccgc agcggctccg cggcctcctg ctgctcctgc 180
tgctgcagct gcccgcgccg tcgagcgcct ctgagatccc caaggggaag caaaaggcgc 240
agctccggca gagggaggtg gtggacctgt ataatggaat gtgcttacaa gggccagcag 300
gagtgcctgg tcgagacggg agccctgggg ccaatggcat tccgggtaca cctgggatcc 360
caggtcggga tggattcaaa ggagaaaagg gggaatgtct gagggaaagc tttgaggagt 420
cctggacacc caactacaag cagtgttcat ggagttcatt gaattatggc atagatcttg 480
ggaaaattgc ggagtgtaca tttacaaaga tgcgttcaaa tagtgctcta agagttttgt 540
tcagtggctc acttcggcta aaatgcagaa atgcatgctg tcagcgttgg tatttcacat 600
tcaatggagc tgaatgttca ggacctcttc ccattgaagc tataatttat ttggaccaag 660
gaagccctga aatgaattca acaattaata ttcatcgcac ttcttctgtg gaaggacttt 720
gtgaaggaat tggtgctgga ttagtggatg ttgctatctg ggttggtact tgttcagatt 780
acccaaaagg agatgcttct actggatgga attcagtttc tcgcatcatt attgaagaac 840
taccaaaata aatgctttaa ttttcatttg ctacctcttt ttttattatg ccttggaatg 900
gttcacttaa atgacatttt aaataagttt atgtatacat ctgaatgaaa agcaaagcta 960
aatatgttta cagaccaaag tgtgatttca cactgttttt aaatctagca ttattcattt 1020
tgcttcaatc aaaagtggtt tcaatatttt ttttagttgg ttagaatact ttcttcatag 1080
tcacattctc tcaacctata atttggaata ttgttgtggt cttttgtttt ttctcttagt 1140
atagcatttt taaaaaaata taaaagctac caatctttgt acaatttgta aatgttaaga 1200
atttttttta tatctgttaa ataaaaatta tttccaacaa 1240

<210> SEQ ID NO 13
<211> LENGTH: 5579
<212> TYPE: DNA
<213> ORGANISM: Homo sapiens

<400> SEQUENCE: 13
ataacagacc atctgtagac tccttcggaa agcagcagag acgctgcaga gggcttttct 60
tagacatcaa ctgcagacgg ctggcaggat agaagcagcg gctcacttgg actttttcac 120
cagggaaatc agagacaatg atggggctct tccccagaac tacaggggct ctggccatct 180
tcgtggtggt catattggtt catggagaat tgcgaataga gactaaaggt caatatgatg 240
aagaagagat gactatgcaa caagctaaaa gaaggcaaaa acgtgaatgg gtgaaatttg 300
ccaaaccctg cagagaagga gaagataact caaaaagaaa cccaattgcc aagattactt 360
cagattacca agcaacccag aaaatcacct accgaatctc tggagtggga atcgatcagc 420
cgccttttgg aatctttgtt gttgacaaaa acactggaga tattaacata acagctatag 480
tcgaccggga ggaaactcca agcttcctga tcacatgtcg ggctctaaat gcccaaggac 540
tagatgtaga gaaaccactt atactaacgg ttaaaatttt ggatattaat gataatcctc 600
cagtattttc acaacaaatt ttcatgggtg aaattgaaga aaatagtgcc tcaaactcac 660
tggtgatgat actaaatgcc acagatgcag atgaaccaaa ccacttgaat tctaaaattg 720
ccttcaaaat tgtctctcag gaaccagcag gcacacccat gttcctccta agcagaaaca 780
ctggggaagt ccgtactttg accaattctc ttgaccgaga gcaagctagc agctatcgtc 840
tggttgtgag tggtgcagac aaagatggag aaggactatc aactcaatgt gaatgtaata 900
ttaaagtgaa agatgtcaac gataacttcc caatgtttag agactctcag tattcagcac 960
gtattgaaga aaatatttta agttctgaat tacttcgatt tcaagtaaca gatttggatg 1020
aagagtacac agataattgg cttgcagtat atttctttac ctctgggaat gaaggaaatt 1080
ggtttgaaat acaaactgat cctagaacta atgaaggcat cctgaaagtg gtgaaggctc 1140
tagattatga acaactacaa agcgtgaaac ttagtattgc tgtcaaaaac aaagctgaat 1200
ttcaccaatc agttatctct cgataccgag ttcagtcaac cccagtcaca attcaggtaa 1260
taaatgtaag agaaggaatt gcattccgtc ctgcttccaa gacatttact gtgcaaaaag 1320
gcataagtag caaaaaattg gtggattata tcctgggaac atatcaagcc atcgatgagg 1380
acactaacaa agctgcctca aatgtcaaat atgtcatggg acgtaacgat ggtggatacc 1440
taatgattga ttcaaaaact gctgaaatca aatttgtcaa aaatatgaac cgagattcta 1500
ctttcatagt taacaaaaca atcacagctg aggttctggc catagatgaa tacacgggta 1560
aaacttctac aggcacggta tatgttagag tacccgattt caatgacaat tgtccaacag 1620
ctgtcctcga aaaagatgca gtttgcagtt cttcaccttc cgtggttgtc tccgctagaa 1680
cactgaataa tagatacact ggcccctata catttgcact ggaagatcaa cctgtaaagt 1740
tgcctgccgt atggagtatc acaaccctca atgctacctc ggccctcctc agagcccagg 1800
aacagatacc tcctggagta taccacatct ccctggtact tacagacagt cagaacaatc 1860
ggtgtgagat gccacgcagc ttgacactgg aagtctgtca gtgtgacaac aggggcatct 1920
gtggaacttc ttacccaacc acaagccctg ggaccaggta tggcaggccg cactcaggga 1980
ggctggggcc tgccgccatc ggcctgctgc tccttggtct cctgctgctg ctgttggccc 2040
cccttctgct gttgacctgt gactgtgggg caggttctac tgggggagtg acaggtggtt 2100
ttatcccagt tcctgatggc tcagaaggaa caattcatca gtggggaatt gaaggagccc 2160
atcctgaaga caaggaaatc acaaatattt gtgtgcctcc tgtaacagcc aatggagccg 2220
atttcatgga aagttctgaa gtttgtacaa atacgtatgc cagaggcaca gcggtggaag 2280

-continued

```
gcacttcagg aatggaaatg accactaagc ttggagcagc cactgaatct ggaggtgctg   2340
caggctttgc aacagggaca gtgtcaggag ctgcttcagg attcggagca gccactggag   2400
ttggcatctg ttcctcaggg cagtctggaa ccatgagaac aaggcattcc actggaggaa   2460
ccaataagga ctacgctgat ggggcgataa gcatgaattt tctggactcc tacttttctc   2520
agaaagcatt tgcctgtgcg gaggaagacg atggccagga agcaaatgac tgcttgttga   2580
tctatgataa tgaaggcgca gatgccactg gttctcctgt gggctccgtg ggttgttgca   2640
gttttattgc tgatgacctg gatgacagct tcttggactc acttggaccc aaatttaaaa   2700
aacttgcaga gataagcctt ggtgttgatg gtgaaggcaa agaagttcag ccaccctcta   2760
aagacagcgg ttatgggatt gaatcctgtg gccatcccat agaagtccag cagacaggat   2820
ttgttaagtg ccagactttg tcaggaagtc aaggagcttc tgctttgtcc acctctgggt   2880
ctgtccagcc agctgtttcc atccctgacc ctctgcagca tggtaactat ttagtaacgg   2940
agacttactc ggcttctggt tccctcgtgc aaccttccac tgcaggcttt gatccacttc   3000
tcacacaaaa tgtgatagtg acagaaaggg tgatctgtcc catttccagt gttcctggca   3060
acctagctgg cccaacgcag ctacgagggt cacatactat gctctgtaca gaggatcctt   3120
gctcccgtct aatatgacca gaatgagctg gaataccaca ctgaccaaat ctggatcttt   3180
ggactaaagt attcaaaata gcatagcaaa gctcactgta ttgggctaat aatttggcac   3240
ttattagctt ctctcataaa ctgatcacga ttataaatta aatgtttggg ttcatacccc   3300
aaaagcaata tgttgtcact cctaattctc aagtactatt caaattgtag taaatcttaa   3360
agtttttcaa aaccctaaaa tcatattcgc caggaaattt tcctaaacat tcttaagctt   3420
ctatttttcc cctgccaaag gaaggtgttt atcattttaa aatgcaatgt gatttagtgg   3480
attaagcagg agcgctggtt cttgtctcca ttgccttttc ttatatcatt gataatgatg   3540
taagaatcac aaggggccgg gcgcggtggc tcacgcctgt aatcccagca ctttgggagg   3600
ccgaggcagg tggatcatga ggtcaggaga tcgagaccat cctggctaac aaggtgaaac   3660
cccgtctcta ctaaaaatac aaaaaattag ccgggcgcag tggcgggcgc ctgtagtccc   3720
agctactcgg gaggctgagg caggagaatg gcatgaaccc gggaagcgga gcttgcagtg   3780
agccgagatt gcgccactgc agtccgcagt ccggcctggg cgacagagcg agactccgtc   3840
tcaaaaaaaa aaaaaaaaaa agaatcacaa ggtatttgct aaagcatttt gagctgcttg   3900
gaaaaaggga agtagttgca gtagagtttc ttccatcttc ttggtgctgg gaagccatat   3960
atgtgtcttt tactcaagct aaggggtata agcttatgtg ttgaatttgc tacatctata   4020
tttcacatat tctcacaata agagaatttt gaaatagaaa tatcatagaa catttaagaa   4080
agtttagtat aaataatatt ttgtgtgttt taatcccttt gaagggatct atccaaagaa   4140
aatattttac actgagctcc ttcctacacg tctcagtaac agatcctgtg ttagtctttg   4200
aaaatagctc attttttaaa tgtcagtgag tagatgtagc atacatatga tgtataatga   4260
cgtgtattat gttaacaatg tctgcagatt ttgtaggaat acaaaaacatg gcctttttta  4320
taagcaaaac gggccaatga ctagaataac acatagggca atctgtgaat atgtattata   4380
agcagcattc cagaaaagta gttggtgaaa taattttcaa gtcaaaaagg gatatggaaa   4440
gggaattatg agtaacctct atttttaag ccttgctttt aaattaaaca gctacagcca   4500
tttaagcctt gaggataata aagcttgaga gtaataatgt taggttagca aaggtttaga   4560
tgtatcactt catgcatgct accatgatag taatgcagct cttcgagtca tttctggtca   4620
ttcaagatat tcaccctttt gcccatagaa agcaccctac ctcacctgct tactgacatt   4680
```

gtcttagctg atcacaagat cattatcagc ctccattatt ccttactgta tataaaatac 4740
agagttttat attttccttt cttcgttttt caccatattc aaaacctaaa tttgtttttg 4800
cagatggaat gcaaagtaat caagtgtttg tgctttcacc tagaagggtg tggtcctgaa 4860
ggaaagaggt cccctaaata tcccccaccc tggtgctcct ccctctccct ggtaccctga 4920
ctaccaggaa gtcaggtgct agagcagctg gagaagtgca ggcagcctgt gcttccacag 4980
atgggggtgc tgctgcaaca aggctttcaa tgtgcccatc ttaggtggga gaagctagat 5040
cctgtgcagc agcctggtaa gtcctgagga ggttccattg ctcttcctgc tgctgtcctt 5100
tgcttctcaa cggtggctcg ctctacagtc tagagcacat gcagctaact tgtgcctctg 5160
cttatgcatg agggttaaat taacaaccat aaccttcatt tgaagttcaa aggtgtattc 5220
aggatcctca aagcatttta accttgccgc ttaaaaccca atttaccgtg aaatgggaat 5280
tttgctgcat tgttaaactg tagtggaaac catgctatag taataaaggt tatataagag 5340
agaaattgaa attaaatgtg tttttaaatt tcaaaaaaaa atcaatcttt aggatgactt 5400
aaaaattgat ttgccatgta aaatgtatct gcatttttta cacaaaactt gttttaagca 5460
taaaatttta aaactgtact acttgatgta ttatacattt tgaaccatat gtattaaacc 5520
ataaacagta taatgttgtt ataataaaac aggcaataaa tttataaata aaagctgaa 5579

<210> SEQ ID NO 14
<211> LENGTH: 3959
<212> TYPE: DNA
<213> ORGANISM: Homo sapiens

<400> SEQUENCE: 14
gggaggggag ccagcaggga ggaggaggcc agggcccgcc ccacagccac tctcgcgcct 60
ccgaacagcc acaggggcaa agccctgtca cccccaggat ccggtcatca gggaaagagg 120
acagggagac cagaagaggg ccagctggga cgaggggcg gacgcccagg aggcaacttc 180
tgagacgcag ctcctgagag gggcagggac caggcgcggg aggccagagg gggcacagag 240
aacaaacccc ctcagaagtg aagaggagag cggaaggaac cgagagggga cggacaggag 300
ctgaggagga aagaggaggg gagaggggtc aggccaggca gccaaggaga agacgtgtgg 360
ccgggggcta tcagaaggaa actgggacgg acgggccggg ctcgggctgt cctgtggagc 420
agcagcatcc ccggggccgg cagaggcgcc agtggctggg cgggatgagt ctctgagggc 480
cactgtggag cgccccgcca tggccccccg caccctctgg agctgctacc tctgctgcct 540
gctgacggca gctgcagggg ccgccagcta ccctcctcga ggtttcagcc tctacacagg 600
ttccagtggg gccctcagcc ccggggggcc ccaggcccag attgcccccc ggccagccag 660
ccgccacagg aactggtgtg cctacgtggt gacccggaca gtgagctgtg tccttgagga 720
tggagtggag acatatgtca agtaccagcc ttgtgcctgg ggccagcccc agtgtcccca 780
aagcatcatg taccgccgct tcctccgccc tcgctaccgt gtggcctaca agacagtgac 840
cgacatggag tggaggtgct gtcagggtta tgggggcgat gactgtgctg agagtcccgc 900
tccagcgctg gggcctgcgt cttccacacc acggcccctg gcccggcctg cccgccccaa 960
cctctctggc tccagtgcag gcagcccccct cagtggactg gggggagaag gtcctgggga 1020
gtcagagaag gtgcagcagc tggaggaaca ggtgcagagc ctgaccaagg agctgcaagg 1080
cctgcggggc gtcctgcaag gactgagcgg gcgcctggca gaggatgtgc agagggctgt 1140
ggagacggcc ttcaacggga ggcagcagcc agctgacgcg gctgcccgcc ctggggtgca 1200

-continued

```
tgaaaccctc aatgagatcc agcaccagct gcagctcctg gacacccgcg tctccaccca   1260
cgaccaggag ctgggtcacc tcaacaacca tcatggcggc agcagcagca gtgggggcag   1320
cagggcccca gccccagcct cagcccctcc gggccccagt gaggagctgc tgcggcagct   1380
ggagcagcgg ttgcaggagt cctgctccgt gtgcctggcc gggctagatg gcttccgccg   1440
gcagcagcag gaggacaggg agcggctgcg agcgatggag aagctgctgg cctcggtgga   1500
ggagcggcaa cggcacctcg cagggctggc ggtgggccgc aggccccctc aggaatgctg   1560
ctctccagag ctgggccggc gactggcaga gctggagcgc aggctggatg tcgtggccgg   1620
ctcagtgaca gtgctgagtg ggcggcgagg cacagagctg ggaggagccg cggggcaggg   1680
aggccacccc ccaggctaca ccagcttggc ctcccgcctg tctcgcctgg aggaccgctt   1740
caactccacc ctgggccctt cggaggagca ggaggagagc tggcctgggg ctcctggggg   1800
gctgagccac tggctgcctg ctgcccgggg ccgactagag cagttggggg ggctgctggc   1860
caatgtgagc ggggagctgg gggggcggtt ggatctgttg gaggagcagg tggcaggggc   1920
catgcaggca tgcgggcagc tctgctctgg ggcccctggg gagcaggact ctcaagtcag   1980
cgagatcctc agtgccttgg agcgcagggt gctggacagt gaggggcagc tgcggctggt   2040
gggctccggc ctgcacacgg tggaagcagc gggggaggcc cggcaggcca cgctggaggg   2100
attacaagag gttgtgggcc ggctccagga tcgtgtggat gcccaggatg agacagctgc   2160
agagttcaca ctacggctga atctcactgc ggcccggcta ggccaactgg aggggctgct   2220
gcaggcccat ggggatgagg gctgtggggc ctgtggcgga gtccaagagg aactaggccg   2280
ccttcgggat ggtgtggagc gctgctcctg ccccctgttg cctcctcggg gtcctggggc   2340
tggtccaggt gttgggggcc caagccgtgg gcccctggac ggcttcagcg tgtttggggg   2400
cagctcaggc tcagccctgc aggccctgca aggagagctc tctgaggtta ttctcagctt   2460
cagctccctc aatgactcac tgaatgagct ccagaccact gtggagggcc agggcgctga   2520
tctggctgac ctgggggcaa ccaaggaccg tatcatttct gagattaaca ggctgcagca   2580
ggaggccaca gagcatgcta cagagagtga agagcgcttc cgaggcctag aggagggaca   2640
agcacaggcc ggccagtgcc ccagcttaga ggggcgattg ggccgtcttg agggtgtctg   2700
tgaacggttg gacactgtgg ctgggggact gcagggcctg cgcgagggcc tttccagaca   2760
cgtggctggg ctctgggctg ggctccggga aaccaacacc accagccaga tgcaggcagc   2820
cctgctggag aagctggtcg gggacaggc gggcctgggc aggcggctgg gtgcccttaa   2880
cagctccctg cagctcctgg aggaccgtct gcaccagctc agcctgaagg acctcactgg   2940
gcctgcagga gaggctgggc ccccagggcc tcctgggctg cagggacccc caggccctgc   3000
tggacctcca ggatcaccag gcaaggacgg gcaagagggc cccatcgggc caccaggtcc   3060
tcaaggtgaa cagggagtgg agggggcacc agcagcccct gtgccccaag tggcattttc   3120
agctgctctg agtttgcccc ggtctgaacc aggcacggtc cccttcgaca gagtcctgct   3180
caatgatgga ggctattatg atccagagac aggcgtgttc acagcgccac tggctggacg   3240
ctacttgctg agcgcggtgc tgactgggca ccggcacgag aaagtggagg ccgtgctgtc   3300
ccgctccaac cagggcgtgg cccgcgtaga ctccggtggc tacgagcctg agggcctgga   3360
gaataagccg gtggccgaga gccagcccag cccgggcacc ctgggcgtct tcagcctcat   3420
cctgccgctg caggccgggg acacggtctg cgtcgacctg gtcatggggc agctggcgca   3480
ctcggaggag ccgctcacca tcttcagcgg ggccctgctc tatggggacc cagagcttga   3540
acacgcgtag actggggtcc cgcccgacgt gtctacgtcg gctgaagaga cagcgggggc   3600
```

ggcgggctcc tggggtctcg cctgagacgg ggcacctagc cctgggcgag cgccgcaccc 3660
gggcccgcag cggcaccgcg cccagagcgg cctctcccca cgcccggggc gcgccggctc 3720
agggaggctc ggggccgccc atgcagactt ttggcctggc gcgatccccc aagaacccct 3780
ccagggccgg cctgcggagg agccgatcct cgcaccctcc gctccctcca ctggccctcc 3840
aggtcgattc cctgggctcc aggctccccc gcgcgggcgc cgcccaccgc catactaaac 3900
gatcgaggaa taaagacact tggtttttct aaaaaaaaaa aaaaaaaaaa aaaaaaaaa 3959

<210> SEQ ID NO 15
<211> LENGTH: 3879
<212> TYPE: DNA
<213> ORGANISM: Homo sapiens

<400> SEQUENCE: 15
ggagtgctgc ctggcgctgg ctaggaggca aacgcacgcg ggaagagctg ctacccattc 60
cagggaccct gccgctgccc ctctgagggg tctgcacctc ctgggagcag gtgggtctct 120
gggacgaggg tccatggtgg atggctctgg agacgctccc gaggctgtgc cgtcccgctg 180
ctgcacaggt cggagggtca ccgcagaggc tactcgggct ggggctgggg ccgagggagc 240
ccgcactgga gccccatgtg gaacccaagg atgcagctgc tctgctaaca cggcagccca 300
tccttcaaga ctgtgacctc gccacagtgg ccctcagccc tccacctccg gcgggggcga 360
gggccaccca cctccaagtc tccagccatg acgacctccg cactccggcg ccaggtgaag 420
aacatcgtgc acaactactc cgaggcagaa atcaaggtgc gcgaggccac cagcaatgac 480
ccctggggcc cccctagttc gctcatgtcc gagatcgctg acctgacctt caacacagtg 540
gccttcaccg aagtcatggg catgctgtgg cggcggctca atgacagcgg caagaactgg 600
cggcacgtgt acaaggctct aacattgctg gactacctgc tcaagacggg ctccgagcgg 660
gtggcccacc agtgccgcga gaacctctac accatccaga cactcaagga cttccagtac 720
atcgaccgcg acggcaagga ccagggcgtc aacgtgcgcg agaaggtcaa gcaggtgatg 780
gccctgctca aggatgagga gcggctgcgg caggagcgaa cccacgccct caagaccaag 840
gagcgcatgg cactggaggg catcggcatt ggcagtgggc agctgggctt cagccgccgc 900
tacggcgagg actacagccg ctcccggggc tccccgtcct cctacaactc ctcctcttcg 960
tcaccccgct atacctccga cctggagcag gcccggcctc agacgtcagg ggaagaggaa 1020
ctgcagctgc agctggccct cgccatgagc cgtgaggagg cagagaagcc tgtcccccca 1080
gcctcccaca gggacgagga cctgcagctg cagctggctc tgcgcctgag ccggcaggag 1140
cacgagaagg aggtgaggtc ctggcagggt gatggctccc ccatggccaa tggtgcaggg 1200
gccgtggtcc accatcagcg ggacagagag cctgagagag aagagagaaa ggaggaggag 1260
aagctaaaaa ccagccagtc ctccatcctg gacttggctg acatcttcgt acctgccctg 1320
gccccgccct ccacacactg ctctgctgac ccatgggaca tcccaggttt taggccgaac 1380
acagaggcca gtggatcctc ctgggggcct tctgcagacc cctggtctcc gatcccctca 1440
ggaaccgtcc tgtcccgaag ccagccctgg gatctgactc ccatgctctc ctcctctgag 1500
ccctggggca ggaccccagt gctgcctgct gggcccccca ccacagaccc ctggccctg 1560 aactctcccc accacaaact ccccagcact ggggctgacc cttggggagc ctccctggag 1620
acctccgaca cacctggtgg tgcctcgacc tttgacccat ttgccaaacc tccagaatcc 1680
acagagacca aggaggggct ggagcaggcc ctgccctctg ggaagcccag cagccctgtg 1740

-continued

```
gagctggacc tgtttggaga ccccagcccc agttccaagc aaaatggcac gaaggagcca   1800
gatgccctgg acctgggcat actaggggaa gcactaaccc agccaagcaa agaggcccga   1860
gcttgccgga ctcccgagtc cttcctgggt ccctcagctt cctccttggt caaccttgac   1920
tcgttggtca aggcacccca ggttgcaaag acccggaacc ccttcctgac aggtctcagc   1980
gctccgtccc ccaccaaccc gttcggcgcg ggcgagccgg gcaggccgac gctaaaccag   2040
atgcgcaccg gctcgccggc gctgggcctg gcaggcgggc ctgtgggggc gcccctgggc   2100
tccatgacct acagcgcctc tctgcccctc ccgctcagca gcgtgccagc tggcttgacc   2160
ctccccgcct cggttagcgt cttcccgcag gccggagcct tcgcaccgca gccgctgctg   2220
cccacgccga gctcagccgg gccgcggccc ccgccccgc agaccggcac caacccccttc   2280
ctctgagccc cgccccgtcc cataccggcc tgcgcctgcg ccggacgctc cgcggccccg   2340
cctccggacc cggggctggg cggggcgccg gtgctagtgg aacgccgagc cagtggcggc   2400
tggtatcccg cggcggctct ggaagctgga cgcggaccac ggcccgggag ctagaaactg   2460
aacgcccgca taataaagac tggaaccctc gttctcagct ctcaccaagt ggactttttg   2520
cggggtgtgg cggccgggtc tcgaccacag cgtggatcac cggctgttta ggaaactgca   2580
gctgcacaac gtggggtgca aaactgcccc gcttccttta cagctcttct caaccctcac   2640
ctccatcccc cgtcacccag gcaccttcgc ttccagatgc tgccaggctg tcactcaatt   2700
cggtcatttc attcatttat cacacatggg cactggggtt gggctaacag caagagacaa   2760
taggcctttg ttcctattta ttgggtactg cttacgtgct aagcagatca gtttatttaa   2820
tgcttgcaac gactctctga ggtagaaaat attgttaatt ccgttcagga tcccggctac   2880
ataatctgtg gggctcaata caaaataaaa atgtaggggc tccttgttca aaatcgtatg   2940
aagaatttca aaacagggac aacagagcat gaaaccaagc gcaaagccca ctgcagtgcg   3000
attgcacagg tatctcacct tgcagccggc actactccca tttttcaggc aaggaaaccg   3060
tggctcagag aggttgaatg gcatgctcaa agtcacaaag ctggcatggg gcggggctgg   3120
aactcaagag tcagacagtc tggctccaag gcctggagat cccaggctgg gccccagatt   3180
taattcagca aatattgact gactgctgtg gacaaagtgc tgggctcacc ttggagggat   3240
ccaacctcca ggagctcgag cgcagcaggg tagacaagcc aggggcacgt gatgcggctg   3300
tggcagaagc caagtgcagg agctcccagg ctcctttgtt ttactgagtc accttaaatg   3360
taactctgcc ctctcccttg cttcgccaag gctagcgaga aactcagtct tagccacaca   3420
ggaggaatcg gacccccttct ggggggtttat gtggagtctg ggaaaccaag ggtggggtga   3480
ggcctggtac tcaatccagg aggggcccct atgaccaccc tcgcctgttt ttcttctcaa   3540
tgctccctga tcactggacc actggacact gatgtgtcct cagtgcttgg ggtctggctc   3600
tgcaggcagc ctgcagccag cctccatccc cctttcaggg acaaatggcc ttccaccaga   3660
gtcggtgagt ggagaggcac aatgccactc cccttcctga ggtgggggta ggggaaggga   3720
gtcccacaat gcagttacaa acaggatgga caagaacacc tgctcaggag tcagacttac   3780
agggttcaaa gttctgctcc aaggtttgac cctaacaaga atcacttagt aataagtggt   3840
tatgctctgt gaccttgagt aaattactta ccctctcca                          3879
```

<210> SEQ ID NO 16
<211> LENGTH: 6695
<212> TYPE: DNA
<213> ORGANISM: Homo sapiens

<400> SEQUENCE: 16

-continued

```
agactggttg tgcaggagga ggcatgagtg tggccgttgt gggtgcatgc gcgtcaggcc     60
tgggacccgg ccgcccgccc gctgcctcac ctgcaaggag gggcctccca gaaactccct    120
tccccagtgc ccagccgccc cacctcgcca gacttagctg accagccagt gaggacgccc    180
gctgcctccc acctgccctc ctgccgtctt tcgccagcca agcccagcct gagccagcac    240
ttgcctttac gaccatgttc aaggggctga gcaaaggctc ccaggggaag ggtcccccca    300
agggctcccc cgccaagggg tcccccaaag gctcccccag caggcacagc cgggctgcca    360
cccaggagct ggcccttctc atctcccgca tgcaagccaa cgccgaccag gtggagcggg    420
acatcctgga gacgcagaag aggctgcagc aggaccggct gaacagtgag cagagccagg    480
ccctgcagca ccagcaggag acgggccgca gcctgaagga ggctgaggtg ctgctcaagg    540
acctcttcct ggacgtggac aaggcccggc ggctcaagca cccgcaggct gaggagattg    600
agaaggacat caagcagctg cacgagcggg tgacccagga gtgtgcggag taccgtgccc    660
tgtacgagaa gatggtgctg ccccccgacg tgggacccag ggtcgactgg gcacgcgtgc    720
tggagcagaa acagaagcag gtctgcgcag gccagtacgg gccgggcatg gcggagctgg    780
agcaacagat cgccgagcac aacatcctgc agaaggagat cgacgcctat gggcagcagc    840
tgcggagcct cgtggggccg gatgcagcca ccatccggag ccaataccga gacctactga    900
aggcggcgtc gtggcgcggg cagagcctgg gcagcctgta cacgcacctc cagggctgca    960
cgcggcagct gagcgccctg gctgagcagc agcgccgcat cctgcagcag gactggagcg   1020
acctcatggc cgaccctgcg ggcgtgcggc gggagtacga gcacttcaag cagcacgagc   1080
tgctgagcca ggagcagagc gtgaaccagc tggaggacga cggcgagcgc atggtggagc   1140
tgcggcaccc cgcggtgggg cccatccagg cccaccagga ggccctgaag atggagtggc   1200
agaacttcct gaacctgtgt atctgccagg agacccagct gcagcacgtg gaggactacc   1260
gccggttcca ggaagaggcc gactcagtca gccagaccct ggcgaagctc aactccaact   1320
tggatgccaa gtacagccct gcacctgggg gccccccctgg cgccccccaca gagctgctgc  1380
aacagctgga ggcagaggaa aaacggctgg ccgtcaccga gagggccact ggggacctgc   1440
agcggcgaag ccgggatgtg gcccctctgc cacagcgaag aaaccccccct cagcagcccc  1500
tgcacgtgga cagcatctgc gactgggact caggagaagt gcagctgctg cagggtgagc   1560
ggtataagct ggtagataac actgacccgc acgcctgggt cgtgcagggc cctggcgggg   1620
agaccaagcg tgctcccgcc gcctgcttct gcatcccagc accagaccct gatgctgtgg   1680
ccagggcctc ccggctggcc tcagagctgc aggccctgaa gcagaaattg gccacagtcc   1740
agagccgcct gaaggccagt gctgtggagt ctcttcggcc cagccagcag ggtacccagg   1800
gtggcccggg gagaggtggc tgtggggcta gaaggagtag attccgactt ccgactgctc   1860
catctggctc agacctggcc aacccacagg cccagaagct cctgacacag atgacccggc   1920
tggatggaga cctgggacag atagagaggc aggtgctggc ctgggcgcgg gccccgctga   1980
gccgccccac acccttggag gacttggagg gccgcatcca cagccatgag ggcacagccc   2040
agcgcctgca gagcctggga acggagaagg agacagccca gaaggagtgc gaggcgtttc   2100
tgtccacgcg gcccgtgggc cccgctgccc tgcagctgcc cgtagccctc aacagcgtga   2160
agaacaagtt cagtgacgtg caggttctgt gcagcctcta cggggagaaa gccaaggctg   2220
ccctggatct ggagcggcag atccaggatg cggacagggt catccgaggc ttcgaggcca   2280
ccctggtgca ggaggccccc atccctgctg aaccgggggc tctgcaggag agggtcagcg   2340
```

-continued

```
agctgcagcg ccagcggagg gagctgctgg aacagcagac ctgcgtgctg cggctacacc   2400
gcgcgctgaa ggcctcggag cacgcatgcg ctgccctgca gaacaacttc caggagttct   2460
gccaagacct gcctcgccag cagcgccagg tgcgagccct caccgaccgc taccacgccg   2520
taggggacca gctggacctg cgggagaagg tggtgcagga tgccgccctc acctaccagc   2580
agttcaagaa ctgcaaggat aacctgagct cctggctgga gcacctgccc cgcagccagg   2640
tgcggcccag cgacggcccc agccagatcg cctacaagct gcaggcgcag aagaggctga   2700
cgcaggagat ccagagccga gagcgggaca gggccacagc atcccacctc tcccaggccc   2760
tgcaggcagc gctccaggac tatgagctcc aggcagacac ctaccgctgc tctttggagc   2820
ccaccctggc agtgtcagcc cccaagagac cccgagtggc tcccctgcaa gagagcatcc   2880
aagcccagga gaagaacctt gcaaaggcct atactgaggt tgcagcagca cagcagcagc   2940
tgctccagca gctggagttt gctagaaaaa tgctggagaa gaaggagctc agtgaggaca   3000
tccgaaggac ccatgatgca aagcagggct ccgagagccc tgcccaagca gggagagagt   3060
cagaggccct gaaggcccag ctggaagagg agaggaagcg ggtggcccgg gtgcagcatg   3120
agctggaggc gcagaggagc caactgctgc agctgaggac ccagcggccc ttggagaggc   3180
tggaggagaa ggaagtggta gagttctacc gggaccccca gctggagggc agcctgtcca   3240
gggtgaaggc ccaggtggag gaggagggca agcggcgggc tggcctgcag gcagacctgg   3300
aagtggcagc ccagaaggtc gtgcagctgg aaagcaagag gaagaccatg cagcctcatc   3360
tgctgaccaa ggaggtcacc caggtggaga gggaccccgg cctggacagc caggcggccc   3420
agctcaggat ccagatccag cagctccgcg gggaggatgc cgtcatctcg gcccggctgg   3480
aagggctgaa gaaggagcta ctggcccttg agaagaggga ggtggacgtg aaggagaagg   3540
tcgtggtgaa agaggtagtc aaggtggaga agaatctgga aatggtcaag gcagcccagg   3600
ctctgaggct gcagatggag gaggatgctg cgcggaggaa gcaggcggag gaggctgtgg   3660
ccaagctaca ggctcgcatc gaagacctgg agcgggctat cagctcggtg gagcccaagg   3720
tcatcgtgaa ggaggtgaag aaggtggagc aggacccagg gctcctccag gagtcctcca   3780
ggctgaggag cctcctcgag gaggagagga ccaagaacgc gacgctggcc agggagctga   3840
gcgacctgca cagcaagtac agcgtggtgg agaagcagag gcccaaagtg cagctccagg   3900
agcgcgtcca cgagatcttc caggtggatc cggagacaga gcaggagatc actcggctca   3960
aggccaagct gcaggagatg gcgggcaaga ggagcggtgt ggagaaggag gtggagaagc   4020
tgctgcccga cctggaggtc ctgcgggccc agaagcccac ggtggagtac aaggaggtga   4080
cccaggaggt ggtgaggcat gagaggagcc ccgaggtgct gcgtgagatc gaccgcctga   4140
aggctcagct caacgagctc gtcaacagcc acgggcgctc ccaggagcag ctcatccgcc   4200
tgcagggtga gcgcgacgag tggaggcgcg agcgggccaa ggtggagacc aagacggtga   4260
gcaaggaggt ggtgcgccac gagaaggacc cggtgctgga gaaagaagca gagcggctcc   4320
gccaggaggt gcgggaggcg gcccagaaga ggcgggccgc ggaggacgcg gtgtacgagc   4380
tgcagagcaa gcgcctgctg ctggagagga ggaagcccga ggagaaggtg gtggtgcagg   4440
aggtggtggt cacccagaag gacccgaagc tgcgcgagga gcacagccgg ctgagcggga   4500
gcctggatga ggaggtgggc cggcggcgcc agctagagct tgaggtgcag cagctgcggg   4560
ccggcgtgga ggagcaggag ggcctgctca gcttccagga ggaccgcagc aagaagctgg   4620
ccgtggagag ggagctgcgg cagctgacct tgaggatcca ggagctcgag aagcggcctc   4680
ccacggtgca ggagaagatc atcatggagg aagtggtcaa gctggagaag gacccggacc   4740
```

```
tggagaagtc cacggaagcc ctgcggtggg acctggacca ggagaagacc caggtaaccg   4800
agctgaatcg ggagtgcaag aacctgcagg tccagattga cgtcctccag aaagccaaat   4860
cgcaggagaa gaccatctac aaggaagtga tccgggtgca gaaggaccgc gtcctggaag   4920
atgagcgggc ccgcgtgtgg gagatgctca acagggagcg cacggcccgg caggcccggg   4980
aggaggaggc acggcgcctg cgggagcgca ttgaccgggc cgagacgctg ggagaaacct   5040
ggtcccggga ggagtccgag ctgcagaggg cccgggacca ggccgaccag gagtgtgggc   5100
ggctgcagca ggagctgcgg gctctggaga ggcagaagca gcagcagaca ctgcagctgc   5160
aggaggagtc gaagctgctc agccagaaga cggagagcga gcgacagaag gcggcccagc   5220
ggggccagga gctctcgcgg ctggaggcgg ccatcctccg cgagaaggac cagatctacg   5280
agaaggagcg gacgctccgg gacctccacg ccaaggtgag ccgggaggag ctcagccagg   5340
agacccagac gcgagagacc aacctttcca ccaagatctc catcctggaa cccgagacgg   5400
ggaaggacat gtccccatac gaggcctaca agaggggcat catcgacagg ggccagtact   5460
tgcagctgca ggagctcgag tgtgactggg aggaggtcac cacctcgggg ccctgtgggg   5520
aggagtctgt gctcctggac cgcaagagcg ggaagcagta ctccatcgag gccgccctcc   5580
gctgccggcg catctctaag gaggagtacc atctgtacaa ggacggccac ctgcccatct   5640
ccgagtttgc gctgcttgta gctggggaga ccaagccaag ctcctcactc tccatcggct   5700
ctatcatctc caagtccccg ctcgcctccc cggcccccca gagcaccagt ttcttctctc   5760
ccagcttctc tctcgggctc ggtgatgaca gcttccctat cgccgggatc tatgacacaa   5820
ccacagacaa caagtgcagc atcaagacgg ccgtggccaa gaacatgctg gaccccatca   5880
ctgggcagaa gctactggag gcccaggcgg ccacaggggg catcgtggac ctgctcagcc   5940
gtgagcgcta ctctgtgcac aaggcgatgg agaggggcct gatcgagaac acctccacac   6000
agaggctgct taacgcccag aaggccttca ccggcatcga ggaccccgtc accaagaaga   6060
ggctctcggt gggcgaggcc gtccagaagg gctggatgcc ccgggagagc gtgctcccac   6120
acctgcaggt gcagcacctg accgggggc tcatcgaccc caagaggaca ggccgcatcc   6180
ccatccagca ggccctcctc tccgggatga tcagtgaaga gctggcccag ctcctgcagg   6240
acgagtccag ctacgagaag gatttgacag accccatctc caaggaacgg ctgagctaca   6300
aggaggccat gggccgctgc cgcaaagacc ccctgagcgg cctgctgctc ctgccagcgg   6360
cactggaggg gtaccgctgc taccgctccg cctcccccac cgtcccgcgc tcccttcgct   6420
gacacgggcc aaggagccag tggggaagtg cgtgtgttgg gccaggtagg atacgtacac   6480
ctcttgcctc agagcagcct catcccaggc agtgggtctt ccctctgtcc aaccactgtt   6540
ttattatttt actaacatgg tgatgggctc cctcccctaa ccttggtgcc tgatccatcc   6600
ccagaccagg acagcagcca ctcagttctt cctccacctc cacccagtga tcccaataaa   6660
cgaattctgt ctccccgtgc aaaaaaaaaa aaaaa                              6695
```

<210> SEQ ID NO 17
<211> LENGTH: 2696
<212> TYPE: DNA
<213> ORGANISM: Homo sapiens

<400> SEQUENCE: 17

```
gtcctggctt cagcttccaa ctacaaagac agacttggtc cttttcaacg gttttcacag     60
atccagtgac ccacgctctg aagacagaat tagctaactt tcaaaaacat ctggaaaaat    120
```

-continued

```
gaagacttgg gtaaaaatcg tatttggagt tgccacctct gctgtgcttg ccttattggt    180
gatgtgcatt gtcttacgcc cttcaagagt tcataactct gaagaaaata caatgagagc    240
actcacactg aaggatattt taaatggaac attttcttat aaaacatttt ttccaaactg    300
gatttcagga caagaatatc ttcatcaatc tgcagataac aatatagtac tttataatat    360
tgaaacagga caatcatata ccattttgag taatagaacc atgaaaagtg tgaatgcttc    420
aaattacggc ttatcacctg atcggcaatt tgtatatcta gaaagtgatt attcaaagct    480
ttggagatac tcttacacag caacatatta catctatgac cttagcaatg gagaatttgt    540
aagaggaaat gagcttcctc gtccaattca gtatttatgc tggtcgcctg ttgggagtaa    600
attagcatat gtctatcaaa acaatatcta tttgaaacaa agaccaggag atccaccttt    660
tcaaataaca tttaatggaa gagaaaataa aatatttaat ggaatcccag actgggttta    720
tgaagaggaa atgcttgcta caaaatatgc tctctggtgg tctcctaatg gaaaattttt    780
ggcatatgcg gaatttaatg atacggatat accagttatt gcctattcct attatggcga    840
tgaacaatat cctagaacaa taaatattcc atacccaaag gctggagcta agaatcccgt    900
tgttcggata tttattatcg ataccactta ccctgcgtat gtaggtcccc aggaagtgcc    960
tgttccagca atgatagcct caagtgatta ttatttcagt tggctcacgt gggttactga   1020
tgaacgagta tgtttgcagt ggctaaaaag agtccagaat gtttcggtcc tgtctatatg   1080
tgacttcagg gaagactggc agacatggga ttgtccaaag acccaggagc atatagaaga   1140
aagcagaact ggatgggctg gtggattctt tgtttcaaca ccagttttca gctatgatgc   1200
catttcgtac tacaaaatat ttagtgacaa ggatggctac aaacatattc actatatcaa   1260
agacactgtg gaaaatgcta ttcaaattac aagtggcaag tgggaggcca taaatatatt   1320
cagagtaaca caggattcac tgttttattc tagcaatgaa tttgaagaat accctggaag   1380
aagaaacatc tacagaatta gcattggaag ctatcctcca agcaagaagt gtgttacttg   1440
ccatctaagg aaagaaaggt gccaatatta cacagcaagt ttcagcgact acgccaagta   1500
ctatgcactt gtctgctacg gcccaggcat ccccatttcc acccttcatg atggacgcac   1560
tgatcaagaa attaaaatcc tggaagaaaa caaggaattg gaaaatgctt tgaaaaatat   1620
ccagctgcct aaagaggaaa ttaagaaact tgaagtagat gaaattactt tatggtacaa   1680
gatgattctt cctcctcaat ttgacagatc aaagaagtat cccttgctaa ttcaagtgta   1740
tggtggtccc tgcagtcaga gtgtaaggtc tgtatttgct gttaattgga tatcttatct   1800
tgcaagtaag gaagggatgg tcattgcctt ggtggatggt cgaggaacag ctttccaagg   1860
tgacaaactc ctctatgcag tgtatcgaaa gctgggtgtt tatgaagttg aagaccagat   1920
tacagctgtc agaaaattca tagaaatggg tttcattgat gaaaaaagaa tagccatatg   1980
gggctggtcc tatggaggat acgtttcatc actggccctt gcatctggaa ctggtctttt   2040
caaatgtggt atagcagtgg ctccagtctc cagctgggaa tattacgcgt ctgtctacac   2100
agagagattc atgggtctcc caacaaagga tgataatctt gagcactata agaattcaac   2160
tgtgatggca agagcagaat atttcagaaa tgtagactat cttctcatcc acggaacagc   2220
agatgataat gtgcactttc aaaactcagc acagattgct aaagctctgg ttaatgcaca   2280
agtggatttc caggcaatgt ggtactctga ccagaaccac ggcttatccg gcctgtccac   2340
gaaccactta tacacccaca tgacccactt cctaaagcag tgtttctctt tgtcagacta   2400
aaaacgatgc agatgcaagc ctgtatcaga atctgaaaac cttatataaa cccctcagac   2460
agtttgctta ttttattttt tatgttgtaa aatgctagta taaacaaaca aattaatgtt   2520
```

gttctaaagg ctgttaaaaa aaagatgagg actcagaagt tcaagctaaa tattgtttac 2580
attttctggt actctgtgaa agaagagaaa agggagtcat gcattttgct ttggacacag 2640
tgttttatca cctgttcatt tgaagaaaaa taataaagtc agaagttcaa gtgcta 2696

<210> SEQ ID NO 18
<211> LENGTH: 11695
<212> TYPE: DNA
<213> ORGANISM: Homo sapiens

<400> SEQUENCE: 18
agtatttctc tcgcgagaaa ccgctgcgcg gacgatactt gaagaggtgg ggaaaggagg 60
gggctgcggg agccgcggca gagactgtgg gtgccacaag cggacaggag ccacagctgg 120
gacagctgcg agcggagccg agcagtggct gtagcggcca cgactgggag cagccgccgc 180
cgcctcctcg ggagtcggag ccgccgcttc tccactggca ggggccgcct gaagtgggag 240
cagcgcctgg agaaggcggg aggagcccgg cccgggggac gggcggcggg atagcgggac 300
cccggcggcg cggtgcgctt cagggcgcag cggcggccgc agaccgagcc ccgggcgcgg 360
caagaggcgg cgggagccgg tggcggctcg gcatcatgcg tcgagggcgt ctgctggaga 420
tcgccctggg atttaccgtg cttttagcgt cctacacgag ccatggggcg gacgccaatt 480
tggaggctgg gaacgtgaag gaaaccagag ccagtcgggc caagagaaga ggcggtggag 540
gacacgacgc gcttaaagga cccaatgtct gtggatcacg ttataatgct tactgttgcc 600
ctggatggaa aaccttacct ggcggaaatc agtgtattgt ccccatttgc cggcattcct 660
gtggggatgg attttgttcg aggccaaata tgtgcacttg cccatctggt cagatagctc 720
cttcctgtgg ctccagatcc atacaacact gcaatattcg ctgtatgaat ggaggtagct 780
gcagtgacga tcactgtcta tgccagaaag gatacatagg gactcactgt ggacaacctg 840
tttgtgaaag tggctgtctc aatggaggaa ggtgtgtggc ccaaatcga tgtgcatgca 900 cttacggatt tactggaccc cagtgtgaaa gagattacag gacaggccca tgttttactg 960
tgatcagcaa ccagatgtgc cagggacaac tcagcgggat tgtctgcaca aaaacgctct 1020
gctgtgccac agtcggccga gcctggggcc acccctgtga gatgtgtcct gcccagcctc 1080
acccctgccg ccgtggcttc attccaaata tccgcacggg agcttgtcaa gatgtggatg 1140
aatgccaggc catccccggg ctctgtcagg gaggaaattg cattaatact gttgggtctt 1200
ttgagtgcaa atgccctgct ggacacaaac ttaatgaagt gtcacaaaaa tgtgaagata 1260
ttgatgaatg cagcaccatt cctggaatct gtgaaggggg tgaatgtaca aacacagtca 1320
gcagttactt ttgcaaatgt ccccctggtt tttacacctc tccagatggt accagatgca 1380
tagatgttcg cccaggatac tgttacacag ctctgacaaa cgggcgctgc tctaaccagc 1440
tgccacagtc cataaccaaa atgcagtgct gctgtgatgc cggccgatgc tggtctccag 1500
gggtcactgt cgcccctgag atgtgtccca tcagagcaac cgaggatttc aacaagctgt 1560
gctctgttcc tatggtaatt cctgggagac cagaatatcc tcccccaccc cttggcccca 1620
ttcctccagt tctccctgtt cctcctggct ttcctcctgg acctcaaatt ccggtccctc 1680
gaccaccagt ggaatatctg tatccatctc gggagccacc aagggtgctg ccagtaaacg 1740
ttactgatta ctgccagttg gtccgctatc tctgtcaaaa tggacgctgc attccaactc 1800
ctgggagtta ccggtgtgag tgcaacaaag ggttccagct ggacctccgt ggggagtgta 1860
ttgatgttga tgaatgtgag aaaaacccct gtgctggtgg tgagtgtatt aacaaccagg 1920

-continued

```
gttcgtacac ctgtcagtgc cgagctggat atcagagcac actcacgcgg acagaatgcc   1980
gagacattga tgagtgttta cagaatggcc ggatctgcaa taatggacgc tgcatcaaca   2040
cagatggcag ttttcattgc gtgtgtaatg cgggctttca tgttacacga gatgggaaga   2100
actgtgaaga tatggatgaa tgcagcataa ggaacatgtg ccttaatgga atgtgtatca   2160
atgaagatgg cagttttaaa tgtatttgca aacctggatt ccagctggca tcagatggac   2220
gttattgcaa agacattaac gagtgtgaaa cccctgggat ctgcatgaat gggcgttgcg   2280
tcaacactga tggctcctac agatgtgaat gcttccctgg actggctgtg ggtctggatg   2340
gccgtgtgtg tgttgacaca cacatgcgga gcacatgcta tggtggatac aagagaggcc   2400
agtgtatcaa acctttgttt ggtgctgtca ctaaatctga atgctgttgc gccagcactg   2460
agtatgcatt tggggaacct tgccagccgt gtcctgcaca gaattcagcg gaatatcagg   2520
cactctgcag cagtgggcca ggaatgacgt cagcaggcag tgatataaat gaatgtgcac   2580
tagatcctga tatttgccca aatggaatct gtgaaaacct tcgtgggacc tataaatgta   2640
tatgcaattc aggatatgaa gtggattcaa ctgggaaaaa ctgcgttgat attaatgaat   2700
gtgtactgaa cagtctcctt tgtgacaatg gacaatgtag aaatactcct ggaagttttg   2760
tctgtacctg ccccaaggga tttatctaca aacctgatct aaaaacatgt gaagacattg   2820
atgaatgcga atcaagtcct tgcattaatg gagtctgcaa gaacagccca ggctctttta   2880
tttgtgaatg ttcttctgaa agtactttgg atccaacaaa aaccatctgc atagaaacca   2940
tcaagggcac ttgctggcag actgtcattg atgggcgatg tgagatcaac atcaatggag   3000
ccaccttaaa gtcccagtgc tgctcctccc tcggtgctgc gtggggaagc ccgtgcaccc   3060
tatgccaagt tgatcccata tgtggtaaag ggtactcaag aattaaagga acacaatgtg   3120
aagatataga tgaatgtgaa gtgttcccag gagtgtgtaa aaatggcctg tgtgttaaca   3180
ctagggggtc attcaagtgt cagtgtccca gtggaatgac tttggatgcc acaggaagga   3240
tctgtcttga tatccgcctg gaaacctgct tcctgaggta cgaggacgag gagtgcaccc   3300
tgcctattgc tggccgccac cgcatggacg cctgctgctg ctccgtcggg gcagcctggg   3360
gtactgagga atgcgaggag tgtcccatga gaaatactcc tgagtacgag gagctgtgtc   3420
cgagaggacc cggatttgcc acaaaagaaa ttacaaatgg aaagcctttc ttcaaagata   3480
tcaatgagtg caagatgata cccagcctct gcacccacgg caagtgcaga aacaccattg   3540
gcagctttaa gtgcaggtgt gacagcggct ttgctcttga ttctgaagaa aggaactgca   3600
cagacattga cgaatgccgc atatctcctg acctctgtgg cagaggccag tgtgtgaaca   3660
cccctgggga ctttgaatgc aagtgtgacg aaggctatga aagtggattc atgatgatga   3720
agaactgcat ggatattgat gagtgtcaga gagatcctct cctatgccga ggtggtgttt   3780
gccataacac agagggaagt taccgctgtg aatgcccgcc tggccatcag ctgtccccca   3840
acatctccgc gtgtatcgac atcaatgaat gtgagctgag tgcacacctg tgccccaatg   3900
gccgttgcgt gaacctcata gggaagtatc agtgtgcctg caaccctggc taccattcaa   3960
ctcccgatag gctattttgt gttgacattg atgaatgcag cataatgaat ggtggttgtg   4020
aaaccttctg cacaaactct gaaggcagct atgaatgtag ctgtcagccg ggatttgcac   4080
taatgcctga ccagagatca tgcaccgaca tcgatgagtg tgaagataat cccaatatct   4140
gtgatggtgg tcagtgcaca aatatccctg gagagtacag gtgcttgtgt tatgatggat   4200
tcatggcatc tgaagacatg aagacttgtg tagatgtcaa tgagtgtgac ctgaatccaa   4260
atatctgcct aagtgggacc tgtgaaaaca cgaaaggctc atttatctgc cactgtgata   4320
```

```
tgggctactc cggcaaaaaa ggaaaaactg gctgtacaga catcaatgaa tgtgaaattg   4380
gagcacacaa ctgtggcaaa catgctgtat gtaccaatac agcaggaagc ttcaaatgta   4440
gctgcagtcc cgggtggatt ggagatggca ttaagtgcac tgatctggac gaatgttcca   4500
atggaaccca tatgtgcagc cagcatgcag actgcaagaa taccatggga tcttaccgct   4560
gtctgtgcaa ggaaggatac acaggtgatg gcttcacttg tacagacctt gatgagtgct   4620
ctgagaacct gaatctctgt ggcaatggcc agtgcctcaa tgcaccagga ggataccgct   4680
gtgaatgcga catgggcttc gtgcccagtg ctgacgggaa agcctgtgaa gatattgatg   4740
agtgctccct tccgaacatc tgtgtctttg gaacttgcca caacctccct ggcctgttcc   4800
gctgtgagtg tgagataggc tacgaactgg acagaagcgg cgggaactgc acagatgtga   4860
atgaatgcct ggatccaacc acgtgcatca gtgggaactg tgtcaacact ccaggcagct   4920
atatctgtga ctgcccacct gattttgaac tgaacccaac tcgagttggc tgtgttgata   4980
cccgctctgg aaattgctat ttggatattc gacctcgagg agacaatgga gatacagcct   5040
gcagcaatga aattggagtt ggtgtttcca aagcttcctg ctgctgttct ctgggtaaag   5100
cctggggtac tccttgtgag atgtgtcctg ctgtgaacac atccgagtac aaaattcttt   5160
gtcctggagg ggaaggtttc cgaccaaatc ctatcaccgt tatattggaa gatattgatg   5220
agtgccagga gctaccaggg ctgtgccaag gaggaaaatg tatcaacacc tttgggagtt   5280
tccagtgccg ctgtccaacc ggctactacc tgaatgaaga tacacgagtg tgtgatgatg   5340
tgaatgaatg tgagactcct ggaatctgtg gtccagggac atgttacaac accgttggca   5400
actacacctg tatctgtcct ccagactaca tgcaagtgaa tgggggaaat aattgcatgg   5460
atatgagaag aagtttgtgc tacagaaact actatgctga caaccagacc tgtgatggag   5520
aattgttatt caacatgacc aagaagatgt gctgctgttc ctacaacatt ggccgggcgt   5580
ggaacaagcc ctgtgaacag tgtcccatcc caagtacaga tgagtttgct acactctgtg   5640
gaagtcaaag gccaggcttt gtcatcgaca tttataccgg tttacccgtt gatattgatg   5700
agtgccggga gatcccaggg gtctgtgaaa atggagtgtg tatcaacatg gttggcagct   5760
tccgatgtga atgtccagtg ggattcttct ataatgacaa gttgttggtt tgtgaagata   5820
ttgacgagtg tcagaacggc ccagtgtgcc agcgcaacgc cgaatgcatc aacactgcag   5880
gcagctaccg ctgtgactgt aagcccggct accgcttcac ctccacagga cagtgcaatg   5940
atcgtaatga atgtcaagaa atccccaata tatgcagtca tgggcagtgc attgacacag   6000
ttggaagctt ttattgcctt tgccacactg gttttaaaac aaatgatgac caaaccatgt   6060
gcttggacat aaatgaatgt gaaagagatg cctgtgggaa tggaacttgc cggaacacaa   6120
ttggttcctt caactgccgc tgcaatcatg gtttcatcct ttctcacaac aatgactgta   6180
tagatgttga tgaatgtgca agtggaaatg ggaatctttg cagaaatggc caatgcatta   6240
atacagtggg gtctttccag tgccagtgca atgaaggcta tgaggtggct ccagatggga   6300
ggacctgtgt ggatatcaat gaatgtcttc tagaacccag aaaatgtgca ccaggtacct   6360
gtcaaaactt ggatgggtcc tacagatgca tttgcccacc tggatacagt cttcaaaatg   6420
agaagtgtga agatattgat gagtgtgtcg aagagccaga aatttgtgcc ctgggcacat   6480
gcagtaacac tgaaggcagc ttcaaatgtc tgtgtccaga agggttttcc ttgtcctcca   6540
gtggaagaag gtgccaagat ttgcgaatga gctactgtta tgcgaagttt gaaggaggaa   6600
agtgttcatc acccaaatcc agaaatcact ccaagcagga atgctgctgt gccttgaagg   6660
```

-continued

```
gagaaggctg gggagacccc tgcgagctct gccccacgga acctgatgag gccttccgcc   6720
agatatgtcc ttatggaagt gggatcatcg tgggacctga tgattcagca gttgatatgg   6780
acgaatgcaa agaacccgat gtctgtaaac atggacagtg catcaataca gatggttcct   6840
atcgctgcga gtgtcccttt ggttatattc tagcagggaa tgaatgtgta gatactgatg   6900
aatgttctgt tggcaatcct tgtggaaatg gaacctgcaa gaatgtgatt ggaggttttg   6960
aatgcacctg cgaggaggga tttgagcccg gtccaatgat gacatgtgaa gatataaatg   7020
aatgtgccca gaatcctctg ctctgtgcct tccgatgtgt gaacacttat gggtcatatg   7080
aatgcaaatg tcccgtggga tatgtgctca gagaagaccg taggatgtgc aaagatgagg   7140
atgagtgtga agagggaaaa catgactgta ctgaaaaaca aatggaatgc aagaacctca   7200
ttggcacata tatgtgcatc tgtggacccg ggtatcagcg gagacctgat ggagaaggct   7260
gtgtagatga gaatgaatgt cagacgaagc cagggatctg tgagaatggg cgctgcctca   7320
acacccgtgg gagctacacc tgtgagtgta atgatgggtt taccgccagc cccaaccagg   7380
acgagtgcct tgacaatcgg gaagggtact gcttcacaga ggtgctacaa aacatgtgtc   7440
agatcggctc cagcaacagg aaccccgtca ccaaatcgga atgctgctgt gacggaggga   7500
gaggctgggg tccccactgt gagatctgcc ctttccaggg gactgtggct ttcaagaaac   7560
tctgtcccca tggccgagga ttcatgacca atggagcaga tatcgatgaa tgcaaggtta   7620
ttcacgatgt ttgccgaaat ggggaatgtg tcaatgacag aggatcatat cattgcattt   7680
gtaaaactgg gtacactcca gatataactg ggacttcctg tgtagatctg aacgagtgca   7740
accaggctcc caaaccctgc aattttatct gcaaaaacac agaagggagt taccagtgtt   7800
catgcccgaa aggctacatt ctgcaagagg atggaaggag ctgcaaagat cttgatgagt   7860
gtgcaaccaa gcaacacaac tgccagttcc tatgtgttaa caccattggc ggcttcacat   7920
gcaaatgtcc tcccggattt acccaacacc atacgtcctg cattgataac aatgaatgca   7980
cctctgacat caatctgtgc gggtctaagg gcatttgcca gaacactcct ggaagcttca   8040
cctgtgaatg ccagcgggga ttctcacttg atcagaccgg ctccagctgt gaagacgtgg   8100
acgagtgtga gggtaaccac cgctgccagc atggctgcca gaacatcatt gggggctaca   8160
ggtgcagctg cccccagggc tacctccagc actaccagtg gaaccagtgt gttgatgaaa   8220
acgaatgcct cagcgctcac atctgcggag gagcctcctg tcacaacacc ctggggagct   8280
acaagtgcat gtgtcccgcc ggcttccagt atgaacagtt cagtggagga tgccaagaca   8340
tcaatgaatg tggctctgcg caggccccct gcagctatgg ctgttccaat accgagggcg   8400
gttacctgtg tggctgtcca cctggttact tccgcatagg ccaagggcac tgtgtttctg   8460
gaatgggcat gggccgagga aacccagagc cacctgtcag tggtgaaatg gatgacaatt   8520
cactctcccc agaggcttgt tacgagtgta agatcaatgg ctaccccaaa cggggcagga   8580
aacggagaag cacaaacgaa actgatgcct ccaatatcga ggatcagtct gagacagaag   8640
ccaatgtgag tcttgcaagt tgggatgttg agaagacagc catctttgct ttcaatattt   8700
cccacgtcag taacaaggtt cgaatcctag aactccttcc agctcttaca actctgacga   8760
atcacaacag atacttgatc gaatctggaa atgaagatgg cttctttaaa atcaaccaaa   8820
aggaagggat cagctacctc cacttcacaa agaagaagcc agtggctgga acctattcat   8880
tacaaatcag tagtactcca ctttataaaa agaaagaact taaccaacta gaagacaaat   8940
atgacaaaga ctacctcagt ggtgaactgg gtgataatct gaagatgaaa atccaggttt   9000
tgcttcatta attcaccatc cagagaccaa ataattaaaa gaaaaacaaa tatagatagg   9060
```

```
tagaactata ttttcccccca atcagaatca tcatatcata ggtacaatct ttcaccaagt   9120
aaatttgtat aaataagcac tattctttgt attaccaaag caaggtacag gtgactaccc   9180
tagttcaaaa caaccacttt ctcaggcttc tcatgtgtgt agctaagcta ccttgtcata   9240
tgtgttgatt cttgaaaact gggacgtgta tttccattgg gggttggcca tttatgctga   9300
catgccatcc ttccagcaaa cgtacgggaa tgtgctttca attgatggac tactctattt   9360
tttgcaaatt tgtaaacttt gcttctccaa atacaagtac taggttgtcc atttatggta   9420
cctatttggt gctagtaaat tttcaaacta gatttataaa tgcactgtaa tatgtacaca   9480
acttagaaac caaattacaa gtattcagtt ccaatacttc attaatttca atcaaccaaa   9540
gttagttcag tagcttatct cagttatgag tataatacat tacatgtaaa ttaagtgtgt   9600
gtatactgta atcgtgctat tttttatcat tgaaacattt ataaactaga ataataatgc   9660
ccttaatgtg agggtttgta atggtgctta ttaagaccaa agacttgtta aatgtataca   9720
ccaagtggta atgaaatttc ggtgactggc ccacacgtgc atagaggtct gggaggacca   9780
ggaaacagcc tcagtggcca gaggatcacc agtgcatcct tcatcacagc atgtgcaata   9840
tgccaagatt accctcggtc attcctgtca acaaggggtc aatgtcataa atgtcacaat   9900
aaaacaatct cttctttttt ttagtttacc ccttggcttt gtgttcttgc atggatttgg   9960
ggttggaggg gccattccgg aggctaaata aagtctcctg gatttaaatt atcctgggtc  10020
tcttacttat ggcttatgaa agtaccaaat gtataaccac tagaagaaaa tttaacatat  10080
gagtcgatcc cttgttttat ccattgaaag tagcagagtc tggtgtcatt aacctgactt  10140
gcttgtgaga aatttagatt gtagagtcat ttctgaaaca tgacctaatt catcttgtga  10200
cttttaaata gtcttaaata ccaagttcag tcattgtctt agagcacatg aatttcatta  10260
taatagattt atcatgcccc cctctcaaat atacacagtt ttggcaagcc ttaggtgttc  10320
tgttccattt tttttcccc taaacatctt tcgttagtca atgctcatct aattacaaag  10380
ggataatccc agactgtatc caattgctgt aacttttggt ttcttaatgt cataattttt  10440
aaagtctgtt ttattttaag tgcaatattg agtatttagc tgttaggctc aatccgtcga  10500
tatgaaataa ttttttaaat ccctaagggc aggaaagcat ttcgtggtag tgaaaataag  10560
aggaaataag atggcatgaa ggtggtgggc ggagaaacta ggtaggacac aggaaagtgc  10620
tctcaaaaat ctttgaagag ctcagctgaa aaaaatggag tagatttggc tcatactatt  10680
ccggaaggca aaaccagggt cagctgatgt cagccccagt ttaatacaca cggtcccaat  10740
tatagagcta ctcactgaaa gaatgggttt ccttgcattg tggtgagctc cctgtcacaa  10800
gatagaagag tttcagtcta ggcttaatgg caaccattgg acaaagatgc tttcttccac  10860
ctaacaggcc attaacatct taaaggtatt tttgtatctc taattttgtt tataataggt  10920
gctcaacaga atgagctgaa tggctgttac aaagggggtt tgtaccttgg gtaagagatt  10980
aaaatataac tcaaaatttc cttctaacgc tgcacctatg gaaccatgtg atagaggtgt  11040
attaaaattg ttatcgaaga atatatagca tatggtaaac aacagtttgc atatggaaaa  11100
tgtctttgat aatttaacca gaactgcatt atattcaata acggattttc tttataacaa  11160
acaacagggg aaaatggagt tggcacacag tggatcactt tgatattttt aatagtccaa  11220
gtctggattt tatttattcc tgagccaaca attttgaaca gcatattttc catgtttctg  11280
actgtaacaa aacattttcc tcattgttcc attgtaaata ttcctcttgt tggaactctt  11340
tttaatcctg agatttaaac ctgtaccttt caattgtctg tgacctttca atttcacttt  11400
```

-continued caatagttga agaacttggc tttgtaaatc tctcagaagc ttgaaaatat cttgtctcta 11460
ccccctcagc ccatttcatt tgccaataat tattttgtaa gtagggttga aatgaactca 11520
gctggccttg tgaaatgttt aaacttgcac aaacaactac atttttgttc aacaaatagc 11580
agtttactca gccaaaatca ctttggatat tgccattaca aatactgtta aacttcagaa 11640
atcatgtctg taaattagat gagccaaaat aaaggacaat tgggttgatg ctgca 11695

<210> SEQ ID NO 19
<211> LENGTH: 5321
<212> TYPE: DNA
<213> ORGANISM: Homo sapiens

<400> SEQUENCE: 19
acacacacac acaagcacac acgcgctcac acacagagag aaaatccttc tgcctgttga 60
tttatggaaa caattatgat tctgctggag aacttttcag ctgagaaata gtttgtagct 120
acagtagaaa ggctcaagtt gcaccaggca gacaacagac atggaattct tatatatcca 180
gctgttagca acaaaacaaa agtcaaatag caaacagcgt cacagcaact gaacttacta 240
cgaactgttt ttatgaggat ttatcaacag agttatttaa ggaggaatcc tgtgttgtta 300
tcaggaacta aaaggataag gctaacaatt tggaaagagc aactactctt tcttaaatca 360
atctacaatt cacagatagg aagaggtcaa tgacctagga gtaacaatca actcaagatt 420
cattttcatt atgttattca tgaacacccg gagcactaca ctataatgca caaatggata 480
ctgacatgga tcctgccaac tttgctctac agatcatgct ttcacattat ctgtctagtg 540
ggtactatat ctttagcttg caatgacatg actccagagc aaatggctac aaatgtgaac 600
tgttccagcc ctgagcgaca cacaagaagt tatgattaca tggaaggagg ggatataaga 660
gtgagaagac tcttctgtcg aacacagtgg tacctgagga tcgataaaag aggcaaagta 720
aaagggaccc aagagatgaa gaataattac aatatcatgg aaatcaggac agtggcagtt 780
ggaattgtgg caatcaaagg ggtggaaagt gaattctatc ttgcaatgaa caaggaagga 840
aaactctatg caaagaaaga atgcaatgaa gattgtaact tcaaagaact aattctggaa 900
aaccattaca acacatatgc atcagctaaa tggacacaca acggagggga aatgtttgtt 960
gccttaaatc aaaaggggat tcctgtaaga ggaaaaaaaa cgaagaaaga acaaaaaaca 1020
gcccactttc ttcctatggc aataacttaa ttgcatatgg tatataaaga accagttcca 1080
gcagggagat ttctttaagt ggactgtttt ctttcttctc aaaattttct ttccttttat 1140
tttttagtaa tcaagaaagg ctggaaaact actgaaaaac tgatcaagct ggacttgtgc 1200
atttatgttt gttttaagac actgcattaa agaaagattt gaaaagtata cacaaaaatc 1260
agatttagta actaaaggtt gtaaaaaatt gtaaaactgg ttgtacaatc atgatgttag 1320
taacagtaat ttttttctta aattaattta cccttaagag tatgttagat ttgattatct 1380
gataatgatt atttaaatat tcctatctgc ttataaaatg gctgctataa taataataat 1440
acagatgttg ttatataagg tatatcagac ctacaggctt ctggcaggat ttgtcagata 1500
atcaagccac actaactatg gaaaatgagc agcattttaa atgctttcta gtgaaaaatt 1560
ataatctact taaactctaa tcagaaaaaa aattctcaaa aaaactatta tgaaagtcaa 1620
taaaatagat aatttaacaa aagtacagga ttagaacatg cttataccta taaataagaa 1680
caaaatttct aatgctgctc aagtggaaag ggtattgcta aaaggatgtt tccaaaaatc 1740
ttgtatataa gatagcaaca gtgattgatg ataatactgt acttcatctt acttgccaca 1800
aaataacatt ttataaatcc tcaaagtaaa attgagaaat ctttaagttt ttttcaagta 1860

-continued acataatcta tctttgtata attcatattt gggaatatgg cttttaataa tgttcttccc 1920
acaaataatc atgctttttt cctatggtta cagcattaaa ctctatttta agttgttttt 1980
gaactttatt gttttgttat ttaagtttat gttatttata aaaaaaaaac cttaataagc 2040
tgtatctgtt tcatatgctt ttaattttaa aggaataaca aaactgtctg gctcaacggc 2100
aagtttccct cccttttctg actgacacta agtctagcac acagcacttg ggccagcaaa 2160
tcctggaagg cagacaaaaa taagagcctg aagcaatgct tacaatagat gtctcacaca 2220
gaacaataca aatatgtaaa aaatctttca ccacatattc ttgccaatta attggatcat 2280
ataagtaaaa tcattacaaa tataagtatt tacaggattt taaagttaga atatatttga 2340
atgcatgggt agaaaatatc atattttaaa actatgtata tttaaattta gtaattttct 2400
aatctctaga aatctctgct gttcaaaagg tggcagcact gaaagttgtt ttcctgttag 2460
atggcaagag cacaatgccc aaaatagaag atgcagttaa gaataagggg ccctgaatgt 2520
catgaaggct tgaggtcagc ctacagataa caggattatt acaaggatga atttccactt 2580
caaaagtctt tcattggcag atcttggtag cactttatat gttcaccaat gggaggtcaa 2640
tatttatcta atttaaaagg tatgctaacc actgtggttt taatttcaaa atatttgtca 2700
ttcaagtccc tttacataaa tagtatttgg taatacattt atagatgaga gttatatgaa 2760
aaggctaggt caacaaaaac aatagattca tttaattttc ctgtggttga cctatacgac 2820
caggatgtag aaaactagaa agaactgccc ttcctcagat atactcttgg gagagagcat 2880
gaatggtatt ctgaactatc acctgattca aggactttgc tagctaggtt ttgaggtcag 2940
gcttcagtaa ctgtagtctt gtgagcatat tgagggcaga ggaggactta gtttttcata 3000
tgtgtttcct tagtgcctag cagactatct gttcataatc agttttcagt gtgaattcac 3060
tgaatgttta tagacaaaag aaaatacaca ctaaaactaa tcttcatttt aaaagggtaa 3120
aacatgacta tacagaaatt taaatagaaa tagtgtatat acatataaaa tacaagctat 3180
gttaggacca aatgctcttt gtctatggag ttatacttcc atcaaattac atagcaatgc 3240
tgaattaggc aaaaccaaca tttagtggta aatccattcc tggtagtata agtcacctaa 3300
aaaagacttc tagaaatatg tactttaatt atttgttttt ctcctatttt taaatttatt 3360
atgcaaattt tagaaaataa aatttgctct agttacacac ctttagaatt ctagaatatt 3420
aaaactgtaa ggggcctcca tccctcttac tcatttgtag tctaggaaat tgagattttg 3480
atacacctaa ggtcacgcag ctgggtagat atacagctgt cacaagagtc tagatcagtt 3540
agcacatgct ttctactctt cgattattag tattattagc taatggtctt tggcatgttt 3600
ttgtttttta tttctgttga gatatagcct ttacatttgt acacaaatgt gactatgtct 3660
tggcaatgca cttcatacac aatgactaat ctatactgtg atgatttgac tcaaaaggag 3720
aaaagaaatt atgtagtttt caattctgat tcctattcac cttttgttta tgaatggaaa 3780
gctttgtgca aaatatacat ataagcagag taagcctttt aaaaatgttc tttgaaagat 3840
aaaattaaat acatgagttt ctaacaatta gaaaagaaaa aattaaaaca tgaaatgata 3900
acaaaagtaa acaaaagata ctttcaaagc agtgaacaaa acattttgac ataagccata 3960
atataaatta taatataaaa aataaaaacc atagtataaa ttgtcagcct ttgagttggc 4020
tacaaattca atttaatgac agaagagaag ggatgctgga ggtaaattct tagggtttct 4080
atctcataga gtttgctctt ctggttctct agactgccaa agaacataaa gatgtgcgag 4140
gggacctagc tgtagtaaaa gcaatcctat aacaagaaaa actctaaaac agtgcccctt 4200

-continued

```
acgattttct actgaaattt ctctaatagt agaggtgtaa aataagaagt tagagaataa   4260
tgcaaagggg gcccaccaca gacggaacat ttcttttctc ttaagactca tgtgattttt   4320
gcatcttact ccataatata tttgtggttg cgttaatatg acaatgtctg caattaaaca   4380
ccagtaagca aaattgatac atcagaatga cttgcagggc ttatcatgca gtttggttta   4440
catccctact ccactgccat ttacttgagc gtgaatgaga cacaaaagat tatttgcctc   4500
ccataatcca actttacaca taaataacac aaggctaaag aaaaccagaa ctcaaattca   4560
ccacgcatag gagtgataac aaaaatattt aacagtcagt atgggtgatt actggccaat   4620
cagaatacat cactgataca tcgaaatgga tgcaggccac tatgactaac ttgtgggtat   4680
catttctatg atcaccctaa aacagagttg ggaaaatatc tattaactgg tctctctggt   4740
ttgaattctc aatatgtatc ttaatatgaa atagctcatt aaaacttcat gtgtaactat   4800
ttcagcattg ttgtcagcta ctctttattc cacttctgta cagtatttat tcaaccaagc   4860
tgctgctttc aatgaaggtc acttgttcct tcagggacac atatactccc acctatcctt   4920
taattttgaa tggtttgtca ggaaaattta ctttctcttg agttgaaaaa cttgacagga   4980
agcaagaaat aatacagtcc tagcctcttt ccaataacat ctgatttctc cattctcaaa   5040
ctacacttct caaggaacca gatatttact ctcatctggg aagatgcctc ttatgttttc   5100
cttttacttc ctggttatca tgtggttgca ttttccaagt tcttatcatt gaatttatga   5160
gagcctatca aaatttattt tctttcattt atattctaat aattgaaatg tgagatgaaa   5220
ataacatttc acttatgaaa aacccttctc ttgatgaatc cttccatgtg ttagttatct   5280
attgctgtgt aacaaattaa aacttaatgg cttgaaacaa a                       5321
```

<210> SEQ ID NO 20
<211> LENGTH: 1390
<212> TYPE: DNA
<213> ORGANISM: Homo sapiens

<400> SEQUENCE: 20

```
atacggaaaa cagaatagaa gcacagaaca aggactattg tatataagag aagcaggtgt     60
taatgtaagt tgctgtggaa tgactgtttt caagaagaga gaaggagcca atatatctac    120
tttcattaag aagctgaaat taaatttgga tttccttctt tccaaagctg agacacgatg    180
gccaaaaagc gattgctgtg attggagctg gaattagcgg actgggggcc atcaagtgct    240
gcctggatga agatctggag cccacctgct ttgaaagaaa tgatgatatt ggacatctct    300
ggaaatttca aaaaaatact tcagagaaaa tgcctagtat ctacaaatct gtgaccatca    360
atacttccaa ggagatgatg tgcttcagtg acttccctgt ccctgatcat tttcccaact    420
acatgcacaa ctccaaactc atggactact tcgggatgta tgccacacac tttggcctcc    480
tgaattacat tcgttttaag actgaagtgc aaagtgtgag gaagcaccca gatttttcta    540
tcaatggaca atgggatgtt gttgtggaga ctgaagagaa acaagagact ttggtctttg    600
atggggtctt agtttgcagt ggacaccaca cagatcccta cttaccactt cagtccttcc    660
caggcattga gaaatttgaa ggctgttatt tccatagtcg ggaatacaaa agtcccgagg    720
acttttcagg gaaaagaatc atagtgatcg gcattggaaa ttctggagtg gatattgcgg    780
tggagctcag tcgtgtagca aaacagattt gaccagtagg aactgagatt caacgtcccc    840
aagactgcaa aagtacctac aatcaaacaa attaatatat ttcctaattg gatcagcatg    900
cagacaagtt tacaaatata ttacagaaag atttgaagag ggattctggt tacgttcagt    960
taagcaggac actaatcctg aacaatctga tgtattaaag tttctaatgt ttgtatcttt   1020
```

```
ggtttgatgc atacaataga gtggaagtct gtagtagtta atatgatgat aattcgcttc   1080

taaatttaaa tccttattta tatatgaagc atagctatgt caatgtccag ggaagcattt   1140

ttaaatagta aatcagaaac atgtaaacta gtgaatacaa ttttctattt ttcattcaga   1200

aatttgttgt catagatgca gcctttatct ggaaatcagt gggcagctct ggtcaagcac   1260

agcatggcga ccactgtgta gtattttacc acctaatcct tagtagccaa cactgttaaa   1320

tctgcataat gggtagcata tgaataaaat aatatcttgt aaaaaaaaaa aaaaaaaaaa   1380

aaaaaaaaaa                                                          1390


<210> SEQ ID NO 21
<211> LENGTH: 6548
<212> TYPE: DNA
<213> ORGANISM: Homo sapiens

<400> SEQUENCE: 21

agtggcggag cgcggctgcc ggtgtgcggc cgggagcgat cgccgcgggg caggggcgcg     60

gcgggcaccg cgcagagcgc gcagaacaga cggacggcgg cggggacccg acggcggcgc    120

ctcggcactc cccagactcc ggccagcgcc cccctgccag ccgcaagcac ccagccccgg    180

cccaccccgg gctctcgatg gcccccgagg ccggggcgac cctgcgcgcg ccgcgccggc    240

tgtcctgggc ggcgctgctg ctcttggccg cgctgctccc cgtcgcctcc tcggcggcgg    300

cctcagttga ccacccactg aagccaaggc atgtgaaact gctgtccact aaaatgggcc    360

tgaaagtcac gtgggaccca cccaaagatg ctaccagtag acctgtggag cattacaaca    420

ttgcctatgg gaagtcactg aaaagtctta aatacatcaa ggtgaatgcg gagacatact    480

ccttccttat tgaggatgtg gagccggggg tagtgtactt tgtgctgctt actgcagaaa    540

accacagtgg agtgagccgt cctgtttaca gagctgaaag cccacctgga ggtgaatgga    600

tcgagattga tggttttccc attaagggtc caggaccatt taatgaaacc gtcacagaaa    660

aggaagtgcc caacaagccc ttgcgtgtgc gtgtccggtc ctcagatgac aggctgtccg    720

ttgcgtggaa ggcaccacgc ctgtctggag ccaagagtcc acgcagatca cggggttttc    780

tcctgggcta cggggagagt ggccggaaga tgaattatgt tccactgaca agagatgaac    840

ggacacacga aattaaaaag ctagcctcgg aatccgtgta tgtggtctcc ctgcagtcca    900

tgaactctca gggccggagc caaccagtct acagggctgc cctaacaaag cgaaagattt    960

cagaagagga cgaattggat gtacctgacg acatcagcgt ccgggttatg tcatctcagt   1020

ctgtgcttgt gtcctgggtg gatcctgttc tggaaaaaca gaagaaagtt gttgcatcaa   1080

gacagtacac cgtgcgctat cgagagaagg gggaattggc caggtgggat tataagcaga   1140

tcgctaacag gcgtgtgctg attgagaacc tgattccaga cactgtgtat gaatttgcag   1200

tccgtatttc acagggtgaa agagatggca aatggagtac gtcagtcttc caaagaacac   1260

cagaatctgc ccctaccaca gctcctgaaa acttgaacgt ctggccagtc aatggcaaac   1320

ctacagttgt cgctgcatct tgggatgcgc taccagagac tgaggggaaa gtgaaagaat   1380

acattctttc atacgccccg gctctcaaac catttggagc aaagtccctc acctatcctg   1440

gagacactac ttctgccctg gtggatggtc tgcagcctgg ggaacgctat cttttcaaaa   1500

tccgggccac aaacaggaga ggcctgggac ctcactccaa agccttcatt gtcgctatgc   1560

caacaaccag taaggcggat gttgagcaga acacggagga caatgggaaa cccgaaaaac   1620

ctgagccttc ctcaccttct cccagagctc cagcttcctc ccaacacccc tctgtgcctg   1680
```

-continued

```
cttctcccca agggagaaat gccaaggacc ttcttcttga cttgaagaac aaaatattgg   1740
ctaatggtgg ggcgccccga aaaccccagc ttcgcgccaa gaaggcagag gagctggatc   1800
ttcagtcgac agaaatcact ggggaggagg agctgggttc ccgggaggac tcgcccatgt   1860
caccctcaga cacccaagac cagaaacgga ccctgaggcc gccaagtaga cacggccact   1920
cggtggttgc tcccggcagg actgcagtga gggcccggat gccagcgctg ccccgaaggg   1980
aaggcgtaga taagcctggc ttttccctgg ccacgcagcc ccgcccaggg gcgcccccct   2040
cggcttcggc ctctcctgcc caccacgcgt ccacccaggg cacctctcat cgtccttccc   2100
tgcctgccag cttgaatgac aacgacttgg tggactcaga cgaagatgag cgcgctgtgg   2160
gctccctcca ccccaagggc gccttcgccc agccccggcc agccctgtcc cccagccgcc   2220
agtccccgtc cagcgttctc cgcgacagaa gctctgtgca ccccggcgca aagccagcct   2280
cgccggcccg gaggaccccc cattcagggg ccgcagagga agattccagt gcctcagccc   2340
caccctcaag actttctcca ccccatgggg gatcatctcg gctgctgccc acccagccac   2400
acctgagctc tccactttcc aagggcggga aggatggtga ggacgcccca gccaccaact   2460
ccaatgcgcc atcacggtcc accatgtcct cctccgtctc ttctcatctc tcgtccagga   2520
cgcaggtctc tgagggagcg gaggcttctg atggtgaaag ccacggtgac ggcgataggg   2580
aagacggcgg aaggcaggcg gaggccacgg cccagacgct gcgggcccgg cctgcctctg   2640
gacacttcca tttgctcaga cacaaaccct ttgctgccaa cgggaggtct ccaagcaggt   2700
tcagcattgg gcggggacct cggctgcagc cctccagctc cccacagtcg actgtgccct   2760
cccgagccca ccccagggtt ccctctcact ctgattccca ccctaagctt agctcaggta   2820
tccatggaga cgaggaggat gagaagccgc ttcctgccac cgttgtcaat gaccacgtgc   2880
cttcctcctc caggcagccc atctcccggg gctgggagga cttaaggaga agcccgcaga   2940
gaggggccag cctgcatcgg aaggaaccca tcccagagaa ccccaaatcc acaggggcag   3000
atacacatcc tcagggcaag tactcctccc tggcctccaa ggctcaggat gttcaacaga   3060
gcacagacgc ggacacggag ggtcattctc ccaaagcaca gccagggtcc acagaccgcc   3120
acgcgtcccc tgctcgtccg cccgcagcac ggtcacagca gcatcccagt gttcccagaa   3180
ggatgacacc cggccgggcc ccacaacagc agccccctcc tcccgtcgcc acgtcccagc   3240
accacccggg accccagagc agagacgcgg gtcggtcacc ttcccagccc aggctctcac   3300
tgacccaggc cgggcggccc cgccccacgt cgcagggccg ctcccactcc tcctcggacc   3360
cttacacggc gagctccaga gggatgctcc ccacggccct ccagaaccag gacgaggatg   3420
cccagggcag ctacgacgac gacagcacag aagtcgaggc ccaggatgtg cgggcccccg   3480
cgcacgccgc gcgcgccaag gaggcagctg cgtcccttcc caagcaccag caggtggagt   3540
ctcccacagg cgcaggggca ggtggcgacc acaggtccca gcgcggacat gcggcctccc   3600
ccgccaggcc cagccgaccc ggcggccccc agtcccgcgc ccgggtaccc agcagggcag   3660
cgccggggaa gtcggagcct ccttccaagc ggcccctgtc ctccaagtcc cagcagtcgg   3720
tctcagccga ggacgacgag gaggaggacg cgggattttt taaaggcggg aaagaagacc   3780
ttctgtcttc ctctgtgcca aagtggccct cttcctccac tcccaggggc ggcaaagacg   3840
ccgatgggag cctcgccaag gaagagaggg agcctgccat cgcgcttgcc cctcgcggag   3900
ggagcctggc tcctgtgaag cgacctctcc ccccacctcc aggcagctcc cccagggcct   3960
cccacgtccc ttcccgactg ccgcctcgca gcgctgccac cgtgagcccc gtcgcgggca   4020
cccaccccctg gccgcagtac accacgcgcg ccccacctgg ccacttctcc accaccccga   4080
```

tgctgtcctt gcgccagagg atgatgcatg ccagattccg taaccctctc tcccgacagc 4140
ctgccagacc ctcttacaga caaggttata atggcagacc aaatgtagaa gggaaagtcc 4200
ttcctggtag taatggaaaa ccgaatggac agagaattat caatggccct caaggaacaa 4260
agtgggttgt ggaccttgat cgtgggttag tattgaatgc agaaggaagg tacctccaag 4320
attcacatgg aaatcctctt cggattaaac taggaggaga tggtcgaacc attgtagatc 4380
tggaagggac ccccgtggtg agtcctgacg gcctcccact ctttgggcag ggcgacatg 4440
gcacacctct ggccaatgcc caagataagc caattttgag tcttggagga aagccgctgg 4500
tgggcttgga ggtcatcaaa aaaaccaccc atccccctac cactaccatg cagcccacca 4560
ctactacgac gcccctgcct accactacaa ccccgaggcc caccactgcc accacccgcc 4620
gcacgaccac cacccgccgc acgaccacca ggcgtccaac aaccacagtc cgaaccacta 4680
cgcggacaac caccaccacc acccccacac ccaccactcc catccccacc tgtccccctg 4740
ggaccttgga acggcacgac gatgatggca acctgataat gagctccaat gggatcccag 4800
agtgctacgc tgaagaagat gagttctcag gcttggagac tgacactgca gtacctacgg 4860
aagaggccta cgttatatat gatgaagatt atgaatttga gacgtcaagg ccaccaacca 4920
ccactgagcc ttcgaccact gctaccacac cgagggtgat cccagaggaa ggcgccatca 4980
gttcctttcc tgaagaagaa tttgatctgg ctggaaggaa acgatttgtt gctccttacg 5040
tgacgtacct aaataaagac ccatcagccc cgtgctctct gactgatgca ctggatcact 5100
tccaagtgga cagcctggat gaaatcatcc ccaatgacct gaagaagagt gacctgcctc 5160
cccagcatgc tccccgcaac atcaccgtgg tggccgtgga aggttgccac tcatttgtca 5220
ttgtggactg ggacaaagcc accccaggag atgtggtcac aggttacttg gtttacagtg 5280
catcctatga agacttcatc aggaacaagt ggtccactca agcttcatca gtaactcact 5340
tgcccattga gaacctaaag cccaacacga ggtattattt taaagtgcaa gcacaaaatc 5400
ctcatggcta cggacctatc agcccttcgg tctcatttgt caccgaatca gataatcctc 5460
tgcttgttgt gaggccccca ggcggtgagc ctatctggat cccattcgct ttcaaacatg 5520
atcccagcta cacggactgc catggacggc aatatgtgaa gcgcacgtgg tatcgaaagt 5580
tcgtgggagt tgttctttgt aattcactga ggtataaaat ctacctcagt gacaacctga 5640
aagatacatt ctacagcatt ggagacagct ggggaagagg tgaagaccat tgccaatttg 5700
tggattcaca ccttgatgga agaacagggc ctcagtccta tgtagaagcc ctccctacta 5760
ttcaaggcta ctatcgccag tatcgtcagg agcctgtcag gtttgggaac atcggcttcg 5820
gaacccccta ctactatgtg ggctggtacg agtgtggggt ctccatccct ggaaagtggt 5880
aatcacagga ccgtcatgct gcaagcttgc cctgcccagc cccaccaact aagtcgcact 5940
aggggctgtg agcaaagaca gccagcgtgc tcagccccgc tgccctaggt gccaggaagg 6000
tcatagatgg acactggcca ttctggtcat ctcagtctgg aactcagtcc cacttcttgg 6060
cctggacaat gaacaggatt cagttttgct gttaactttg cttctctact tttttttgtt 6120
tgtttgtaat agcacatccc agagacatca gaaaccagca actgattcag tgtgatttcc 6180
agacttttta ggcatgaaat tcggacactt cagtatttcc aggaatagca tatgcacgct 6240
gttcttgctt catggaatgc tacatgcttt ctgtttttct cattttggat ttctccaaaa 6300
ctaactgaat ttaagcttca ggtccctttg tatgcagtag aaaggaatta ttaaaaacac 6360
caccaaagaa aataaatata tcctacttga aatttactct atggacttac ccactgctag 6420
aataaatgta tcaaatctta tttgtaaatt ctcaattttg atatatatat gtatatatgc 6480
atatacatat ccacacttgt ctgcaagaat attgattaaa attgctaaat ttgtacttgt 6540
tcaccaga 6548

<210> SEQ ID NO 22
<211> LENGTH: 5499
<212> TYPE: DNA
<213> ORGANISM: Homo sapiens

<400> SEQUENCE: 22
gatccgtcac gggcgccgcc gctgccgccg ccgccgccgc ggccgttctg agccgagccg 60
gaaccctagc ccgagacgga gccggggccc gggccggcgc cattgcgcgg gcgccgcggg 120
aagaccttgg cgcggggcgg cgggccgggc caggccatgc gggccgagtg agccggcgcc 180
cgcagcccgc ggcgcggcat ggcttccccg cggagctccg ggcagcccgg gccgccgccg 240
ccgccgccac cgccgcccgc gcgcctgcta ctgctactgc tgctgccgct gctgctgcct 300
ctggcgcccg gggcctgggg ctgggcgcgg ggcgcccccc ggccgccgcc cagcagcccg 360
ccgctctcca tcatgggcct catgccgctc accaaggagg tggccaaggg cagcatcggg 420
cgcggtgtgc tccccgccgt ggaactggcc atcgagcaga tccgcaacga gtcactcctg 480
cgcccctact tcctcgacct gcggctctat gacacggagt gcgacaacgc aaaagggttg 540
aaagccttct acgatgcaat aaaatacggg cctaaccact tgatggtgtt tggaggcgtc 600
tgtccatccg tcacatccat cattgcagag tccctccaag gctggaatct ggtgcagctt 660
tcttttgctg caaccacgcc tgttctagcc gataagaaaa aataccctta tttctttcgg 720
accgtcccat cagacaatgc ggtgaatcca gccattctga agttgctcaa gcactaccag 780
tggaagcgcg tgggcacgct gacgcaagac gttcagaggt tctctgaggt gcggaatgac 840
ctgactggag ttctgtatgg cgaggacatt gagatttcag acaccgagag cttctccaac 900
gatccctgta ccagtgtcaa aaagctgaag ggaatgatg tgcggatcat ccttggccag 960
tttgaccaga atatggcagc aaaagtgttc tgttgtgcat acgaggagaa catgtatggt 1020
agtaaatatc agtggatcat tccgggctgg tacgagcctt cttggtggga gcaggtgcac 1080
acggaagcca actcatcccg ctgcctccgg aagaatctgc ttgctgccat ggagggctac 1140
attggcgtgg atttcgagcc cctgagctcc aagcagatca agaccatctc aggaaagact 1200
ccacagcagt atgagagaga gtacaacaac aagcggtcag gcgtggggcc cagcaagttc 1260
cacgggtacg cctacgatgg catctgggtc atcgccaaga cactgcagag ggccatggag 1320
acactgcatg ccagcagccg gcaccagcgg atccaggact tcaactacac ggaccacacg 1380
ctgggcagga tcatcctcaa tgccatgaac gagaccaact tcttcggggt cacgggtcaa 1440
gttgtattcc ggaatgggga gagaatgggg accattaaat ttactcaatt tcaagacagc 1500
agggaggtga aggtgggaga gtacaacgct gtggccgaca cactggagat catcaatgac 1560
accatcaggt tccaaggatc cgaaccacca aaagacaaga ccatcatcct ggagcagctg 1620
cggaagatct ccctacctct ctacagcatc ctctctgccc tcaccatcct cgggatgatc 1680
atggccagtg cttttctctt cttcaacatc aagaaccgga atcagaagct cataaagatg 1740
tcgagtccat acatgaacaa ccttatcatc cttggaggga tgctctccta tgcttccata 1800
tttctctttg gccttgatgg atcctttgtc tctgaaaaga cctttgaaac actttgcacc 1860
gtcaggacct ggattctcac cgtgggctac acgaccgctt ttggggccat gtttgcaaag 1920
acctggagag tccacgccat cttcaaaaat gtgaaaatga agaagaagat catcaaggac 1980

-continued

```
cagaaactgc ttgtgatcgt ggggggcatg ctgctgatcg acctgtgtat cctgatctgc   2040
tggcaggctg tggaccccct gcgaaggaca gtggagaagt acagcatgga gccggaccca   2100
gcaggacggg atatctccat ccgccctctc ctggagcact gtgagaacac ccatatgacc   2160
atctggcttg gcatcgtcta tgcctacaag ggacttctca tgttgttcgg ttgtttctta   2220
gcttgggaga cccgcaacgt cagcatcccc gcactcaacg acagcaagta catcgggatg   2280
agtgtctaca acgtggggat catgtgcatc atcggggccg ctgtctcctt cctgacccgg   2340
gaccagccca atgtgcagtt ctgcatcgtg gctctggtca tcatcttctg cagcaccatc   2400
accctctgcc tggtattcgt gccgaagctc atcaccctga gaacaaaccc agatgcagca   2460
acgcagaaca ggcgattcca gttcactcag aatcagaaga aagaagattc taaaacgtcc   2520
acctcggtca ccagtgtgaa ccaagccagc acatcccgcc tggagggcct acagtcagaa   2580
aaccatcgcc tgcgaatgaa gatcacagag ctggataaag acttggaaga ggtcaccatg   2640
cagctgcagg acacaccaga aaagaccacc tacattaaac agaaccacta ccaagagctc   2700
aatgacatcc tcaacctggg aaacttcact gagagcacag atggaggaaa ggccatttta   2760
aaaaatcacc tcgatcaaaa tccccagcta cagtggaaca caacagagcc ctctcgaaca   2820
tgcaaagatc ctatagaaga tataaactct ccagaacaca tccagcgtcg gctgtccctc   2880
cagctcccca tcctccacca cgcctacctc ccatccatcg gaggcgtgga cgccagctgt   2940
gtcagcccct gcgtcagccc caccgccagc ccccgccaca gacatgtgcc accctccttc   3000
cgagtcatgg tctcgggcct gtaagggtgg gaggcctggg cccggggcct cccccgtgac   3060
agaaccacac tgggcagagg ggtctgctgc agaaacactg tcggctctgg ctgcggagaa   3120
gctgggcacc atggctggcc tctcaggacc actcggatgg cactcaggtg gacaggacgg   3180
ggcaggggga gacttggcac ctgacctcga gccttatttg tgaagtcctt atttcttcac   3240
aaagaagagg aacggaaatg ggacgtcttc cttaacatct gcaaacaagg aggcgctggg   3300
atatcaaact tgcaaaaaaa aaaaaaaaaa aaaaaaaaca aaaaaactag acaaggagag   3360
aggcactaga actccagctg gaagtcacgg agtggctcga gcagccttgg gaagaggcaa   3420
ggagcttctg aagaaactgc ctctgcacac acatcactgg ctgtgacccc tcaggctagc   3480
ccttctccac tctgggggag gaggtgggaa gggccaccag gcccccagct gccaggccag   3540
ctgaccccag ccttcctgga acagggagtc tgcaggagcg cagacaggca cagccctgga   3600
gcaggcaggc cgagggctgc ggcactggag caggctgact tacatgctcc acatgggacc   3660
tgtgtcaccc aatgagatgt ttgttactct ggtaaatgcc acacgttaac acaataacac   3720
ccattcctgg gaccgtgggg atttagggca cgtcactgca gacacgctct gcagcattca   3780
ccgacagtct gtcatgcacc caccacgttg gccatgtcct tgtgttccta tcggatgctc   3840
ccagtaacca gggggaccac ccgagctaat catggaatgt ctgttcccag caaacacgat   3900
aaagaaagat tgtgcacttt aacctctctc atcagggccc aagggctggc tgggattttt   3960
ttttttttt tcccactaac tttgtttctg accaaagtga attggaggca ctctgctaaa   4020
agacatcccc gtagacatag gggagagagt tgctggctga gggcttccct tggcttccag   4080
aaggcagcct tccatccaga caagccagtg agctctcccc ttgggatcac tggggtgatc   4140
agtcagcaga ttgattctca ttcataagat cattcctccc tttaaattga gcccctaaga   4200
gcactggcct gggagtcaga cagacctggg ttcaagtcct cagtcccctg cccactccct   4260
acgtgacttt gatcaggtca ctagtgtctc tctgagcctc agtttcccct ctgtaacttg   4320
```

```
gggttgaact aaaacacctg tcctgcctac ctcacaaggt cactctgagg attgaaactt   4380

gatcttgtcc aggaaagctt tgtaccaaac agtgaagccg ccctgatccg tgaggtatga   4440

gtatgactct gaccttcagc cctccctaca gccgggggtg tggcccagag aagcttccag   4500

cacagccctc tacccagaac atccgggctg gagggaggct cccagtgact tttctgacat   4560

tcctagacag gttcattctt tgctcaagaa aggcctgaat gacaatgtcc aggatgtctg   4620

cacaactgag cagctcgctc actccctaaa gaaacctatt ggcagcttca acaggcaggc   4680

aataatctct tcccagaacc actgcagtca ggaataaact gttttctcca ccaggctttg   4740

acaaaagggc ccacaggaat cttaccaatg ccaacatttc aaagcaccct atttcacgta   4800

gcatagcttt ctgctcccct tccccaaaga gaggttatgg aggtactgta gcttttaggg   4860

aaaaaaaaat gttaacacat cacaggtcaa gttgaagtca ttctctgttt aggcactaaa   4920

aatcggtgtt gtcactcact gtgtattacc agtatttact tgctttcttg atttcaccaa   4980

aaccaaattt aatttaaagg accacattaa tttttcaaag ggaaagagac aattaattgt   5040

acataatgta tacacacaca caaaaaaaaa tacctgtaga aatattattc cagcatagca   5100

ggaaaacaaa caaaagtatt ggactgtcgg aggtgagcct gtgcgtctgt aaccctttgt   5160

gactcctgag cgtgcgctgt cttctaggtt aactcacgaa gtacattctc tgtcttactg   5220

atactgtagg ttcacccatt ttttttaat ttcctcgcaa ataacaagac ccacagaagt   5280

gactctagct acttaatggt tctgttcttt tatatgcagc aaacacaccg tccatttctg   5340

aagaggcttc ggcctgaagg cattttccaa tgatgttagt gcacaaaacg ctttaaatta   5400

gactggaact gccagaatca aatgtaaatg aggaatttct cgtaccccta ctgcatggta   5460

tcgattttta ataaattgtt gcaaatttgt ttttatgaa                          5499
```

```
<210> SEQ ID NO 23
<211> LENGTH: 3034
<212> TYPE: DNA
<213> ORGANISM: Homo sapiens

<400> SEQUENCE: 23

agctggagcc cgcggagccc acggagccca cggagcccac ggaggagccc acggaggagc     60

cccagcgtcc gaacgggcag accccctcga gccgcgaagg agcccgagaa gcagccacga    120

tgtgcggaat ctttgcctac atgaactaca gagtcccccg gacgaggaag gagatcttcg    180

aaaccctcat caagggcctg cagcggctgg agtacagagg ctacgactcg gcaggtgtgg    240

cgatcgatgg gaataatcac gaagtcaaag aaagacacat tcagctggtc aagaaaaggg    300

ggaaagtcaa ggctctcgat gaagaacttt acaaacaaga cagcatggac ttaaaagtgg    360

agtttgagac acacttcggc attgcccaca cgcgctgggc cacccacggg gtccccagtg    420

ctgtcaacag ccaccctcag cgctcagaca aaggcaacga atttgttgtc atccacaatg    480

ggatcatcac aaattacaaa gatctgagga aatttctgga aagcaaaggc tacgagtttg    540

agtcagaaac agatacagag accatcgcca agctgattaa atatgtgttc gacaacagag    600

aaactgagga cattacgttt tcaacgttgg tcgagagagt cattcagcag ttggaaggtg    660

cattcgcgct ggttttcaag agtgtccact acccaggaga agccgttgcc acacggagag    720

gcagcccccct gctcatcgga gtccggagca aatacaagct ctccacagaa cagatcccta    780

tcttatacag gacgtgcact ctggagaatg tgaagaatat ctgtaagaca cggatgaaga    840

ggctggacag ctccgcctgc ctgcatgctg tgggcgacaa ggccgtggaa ttcttctttg    900

cttctgatgc aagcgctatc atagagcaca ccaaccgggt catcttcctg gaggacgatg    960
```

acatcgccgc agtggctgat gggaaactct ccattcaccg ggtcaagcgc tcggccagtg 1020
atgacccatc tcgagccatc cagaccttgc agatggaact gcagcaaatc atgaaaggta 1080
acttcagtgc gtttatgcag aaggagatct tcgaacagcc agaatcagtt ttcaatacta 1140
tgagaggtcg ggtgaatttt gaaaccaaca cagtgctcct gggtggcttg aaggaccact 1200
tgaaggagat tcgacgatgc cgacggctca tcgtgattgg ctgtggaacc agctaccacg 1260
ctgccgtggc tacgcggcaa gttttggagg aactgactga gcttcctgtg atggttgaac 1320
ttgctagtga ttttctggac aggaacacac ctgtgttcag ggatgacgtt tgctttttca 1380
tcagccagtc aggcgagacc gcggacaccc tcctggcgct gcgctactgt aaggaccgcg 1440
gcgctctcac cgtgggcgtc accaacaccg tgggcagctc catctctcgc gagaccgact 1500
gcggcgtcca catcaacgca gggccggaga tcggcgtggc cagcaccaag gcttatacca 1560
gtcagttcat ctctctggtg atgtttggtt tgatgatgtc tgaagaccga atttcactac 1620
aaaacaggag gcaagagatc atccgtggct tgagatcttt acctgagctg atcaaggaag 1680
tgctgtctct ggaggagaag atccacgact tggccctgga gctctacacg cagagatcgc 1740
tgctggtgat ggggcggggc tacaactatg ccacctgcct ggaaggagcc ctgaaaatta 1800
aagagataac ctacatgcac tcagaaggca tcctggctgg ggagctgaag cacgggcccc 1860
tggcactgat tgacaagcag atgcccgtca tcatggtcat tatgaaggat ccttgcttcg 1920
ccaaatgcca gaacgccctg cagcaagtca cggcccgcca gggtcgcccc attatactgt 1980
gctccaagga cgatactgaa agttccaagt ttgcgtataa gacaattgag ctgccccaca 2040
ctgtggactg cctccagggc atcctgagcg tgattccgct gcagctgctg tccttccacc 2100
tggctgttct ccgaggatat gacgttgact tccccagaaa tctggccaag tctgtaactg 2160
tggaatgagg ctgagaccgt gacaagacca tcaccacctt tcatctgatt ccagacctgt 2220
cccaacagca gggatgctac atgggaagag aagtggacat cccacatgtt ctgcgtgctc 2280
ctgtagagct tgacagcttc cacgtgcctt ctacccaagt gcttttgctt acagcagata 2340
ctgtttctct gtgtcctgaa gtcgccagag gagaagggaa tcattgttta cacatgggga 2400
tcagagcaga cttctccact actgtgcaat agagatacag ctctcttcag agtaactgtg 2460
aaccttttat aaccaacact agagttagtt ttaaaagaca agatatttat aatgacgact 2520
gtatagcttt taagttattt ttctagtatg tggctttctg tagccgtggt aacggccaaa 2580
ctgttcatcc tagctaccca tgctctgtgt ccaggcttgc tcctggcagg tggcattcat 2640
ctcagatgtg agcacaaggc attggccctc tggactcctt tctcctttc tttcctctct 2700 aggctgctcc tgaatcctgt tctctgacat ccgtggagcc cctcctgcat ccacctatgc 2760
ctcctataag tccagttgaa atctcagcct ccttcaacat tttcttctcg tgtgtggccc 2820
acatccctcc acttctccaa cttctgttta atctgatcac ggctcttttt aagccctggc 2880
agcattttgg tccctgctcc ttgcccatag taaaacagct tgaaatatcc catgcaagag 2940
agtagtttca agtgggcaac tctgctctct atttaaaagc gtgcacaatc aaaagtacta 3000
tgcaatttta ggacaataaa gaacatacag tttt 3034

<210> SEQ ID NO 24
<211> LENGTH: 2652
<212> TYPE: DNA
<213> ORGANISM: Homo sapiens

<400> SEQUENCE: 24

-continued

```
aggcttgggc agggcctctg agacacagcc ggaaaggctg gcaggcagga gggctggggc     60
gagcactggg gggccatgga gcgggcagaa gagcccgtgg tctatcagaa gctgctgccc    120
tgggagccaa gcttggagtc ggaggaggaa gtggaggagg aggagacatc agaggcgctg    180
gttctaaacc cccggaggca ccaggactct tccaggaaca aggctggcgg gctgcccgga    240
acctgggccc gtgtagtggc agccctgctg ctgctggctg ttggctgctc cctggctgtg    300
aggcagctcc agaatcaggg caggtcgaca ggaagcttgg gctctgtggc ccctccaccc    360
ggcggacact cccacggccc tggcgtatac caccacggtg ccatcatcag ccctgcaggc    420
cgagagctgc ttgttgccgg gggcaacgtc gtggatgctg gagttggagc tgcattgtgc    480
ctggcagtgg tgcatcctca tgccacgggg ctaggtgcca tgttttgggg cctcttccac    540
gatagctcct caggcaattc cacggccctg acatcaggcc cagcacagac cctggccccc    600
ggcctggggc tgcccgcggc tctgcccacc ctgcacctgc tgcatgcacg cttcggccgc    660
ctgccctggc cacgcctgct agtgggcccc accacgctgg ctcaggaggg cttcctggtg    720
gacacacccc tggcaagggc tctggtggct cggggcacag aaggcctctg tccactactt    780
tgccatgctg atgggacacc cctgggcgct ggggcccgag ccaccaaccc acaactggca    840
gctgtgcttc gcagcgcagc cctcgctccc acctcagacc ttgctgggga tgctctactg    900
agtctactgg cgggagacct gggggtggag gtgccctcgg ctgtgcccag gcccactttg    960
gaaccagcag agcagctacc tgtgccccag ggcatcctgt tcaccacccc cagtccctca   1020
gctggcccag aactgctggc actgttggag gcagccctgc gctccggggc gcccatccct   1080
gacccctgcc caccgttcct gcagactgct gtgagccccg agagcagtgc cctggccgcc   1140
gtggacagca gcggctctgt gctccttctc acctcctcgc tcaactgctc ctttggctct   1200
gcacacctgt ccccaagcac tggggttctg ctcagcaacc tggtggccaa gtctaccact   1260
agtgcctggg cctgccccct catcctccgt ggcagcctgg atgacacaga ggctgatgtg   1320
ttggggcttg tggcttcagg gacccctgat gtggccaggg ccatgactca caccctactc   1380
aggcatctgg cagcaaggcc ccctacccag gcccagcacc agcatcaggg tcagcaagaa   1440
ccaacagagc atcccagcac ttgtggccaa gggaccctgc tccaggtggc agcccacaca   1500
gagcacgccc atgtctccag tgtcccccat gcctgctgcc ccttccaggg gttctaacag   1560
gatgggggtg ggtctggcag aaggcagagt tatctgaagc atgggggcag gagcagagca   1620
gacacagcag caatggagtg tgcacccgca gggtgtggtg cctcacacct gtaatctcag   1680
cactttgggt ggtcaaggca ggaagatacc tcgaggccag gagtttgaaa ctagcctaga   1740
caacaaagca agatctcatc tgtactaaaa atttaaaaat ttgccagggg cggtggcaca   1800
tgcctgttgt cccagctgct tgggaggctg aggcaggaag ctcgcttgag ctcaggagtt   1860
caaggctgca gagagctagg atcacaccac tgcactccag cctggacaac agagtgagaa   1920
cctgtcttta aaataataat aataataata aaaaaatagc tgggtgcggt ggctcatgcc   1980
tgtaatccca gcactttggg aggccaaggc aggtggatca cctgaggcta ggagttcgag   2040
accagcttgg gcaacatggc gaaaccccgt ctctactaaa aatacaaaaa attagctggg   2100
catggtggcg ggcacctgta atcccagcta cttgggaggc tgaggcagga gaatcacttg   2160
aacccgagag gtggaggttg cagtgaacca agatcgcacc attgcaaccc cacctgggca   2220
acaagaggga aaccctgtct aaaaaaaaaa aaaaaaaaaa ggatttatta tgtgctcact   2280
gctggctcag gccccaacct ctggcctttt aagttaccta gacttgagtt ctggcatcca   2340
gagctaacaa tcattcttca gatcacccac accggatgga atctctagct attttatcag   2400
```

```
ctaagaaaat cagggtaata acgaaaaagc agtagggcct ggggctagca ctgagttcag   2460

atccagcttt caggaggaca gtggaaagag tgcagagcct ctgcctaggc cctgggcccc   2520

acgaagcagg acaggcagag cccagggtac tgttggcatc tctgtccttc ccttcaggac   2580

acccccttacc tatctgcctc aaccagactg ggtacaaaat aaagatcaag tctcccggaa   2640

accaaaaaaa aa                                                       2652


<210> SEQ ID NO 25
<211> LENGTH: 14575
<212> TYPE: DNA
<213> ORGANISM: Homo sapiens

<400> SEQUENCE: 25

actcggtgcg ccttccgcgg accgggcgac ccagtgcacg gccgccgcgt cactctcggt     60

cccgctgacc ccgcgccgag ccccggcggc tctggccgcg gccgcactca gcgccacgcg    120

tcgaaagcgc aggccccgag gacccgccgc actgacagta tgagccgcac agcctacacg    180

gtgggagccc tgcttctcct cttggggacc ctgctgccgg ctgctgaagg gaaaaagaaa    240

gggtcccaag gtgccatccc cccgccagac aaggcccagc acaatgactc agagcagact    300

cagtcgcccc agcagcctgg ctccaggaac cgggggcggg gccaagggcg gggcactgcc    360

atgcccgggg aggaggtgct ggagtccagc caagaggccc tgcatgtgac ggagcgcaaa    420

tacctgaagc gagactggtg caaaacccag ccgcttaagc agaccatcca cgaggaaggc    480

tgcaacagtc gcaccatcat caaccgcttc tgttacggcc agtgcaactc tttctacatc    540

cccaggcaca tccggaagga ggaaggttcc tttcagtcct gctccttctg caagcccaag    600

aaattcacta ccatgatggt cacactcaac tgccctgaac tacagccacc taccaagaag    660

aagagagtca cacgtgtgaa gcagtgtcgt tgcatatcca tcgatttgga ttaagccaaa    720

tccaggtgca cccagcatgt cctaggaatg cagccccagg aagtcccaga cctaaaacaa    780

ccagattctt acttggctta aacctagagg ccagaagaac ccccagctgc ctcctggcag    840

gagcctgctt gtgcgtagtt cgtgtgcatg agtgtggatg ggtgcctgtg ggtgttttta    900

gacaccagag aaaacacagt ctctgctaga gagcactccc tattttgtaa acatatctgc    960

tttaatgggg atgtaccaga aacccacctc accccggctc acatctaaag ggcggggcc   1020

gtggtctggt tctgactttg tgtttttgtg ccctcctggg gaccagaatc tcctttcgga   1080

atgaatgttc atggaagagg ctcctctgag ggcaagagac ctgttttagt gctgcattcg   1140

acatggaaaa gtccttttaa cctgtgcttg catcctcctt tcctcctcct cctcacaatc   1200

catctcttct taagttgata gtgactatgt cagtctaatc tcttgtttgc caaggttcct   1260

aaattaattc acttaaccat gatgcaaatg tttttcattt tgtgaagacc ctccagactc   1320

tgggagaggc tggtgtgggc aaggacaagc aggatagtgg agtgagaaag ggagggtgga   1380

gggtgaggcc aaatcaggtc cagcaaaagt cagtagggac attgcagaag cttgaaaggc   1440

caataccaga acacaggctg atgcttctga gaaagtcttt tcctagtatt taacagaacc   1500

caagtgaaca gaggagaaat gagattgcca gaaagtgatt aactttggcc gttgcaatct   1560

gctcaaacct aacaccaaac tgaaaacata aatactgacc actcctatgt tcggacccaa   1620

gcaagttagc taaaccaaac caactcctct gctttgtccc tcaggtggaa aagagaggta   1680

gtttagaact ctctgcatag ggtgggaat taatcaaaaa cctcagaggc tgaaattcct   1740

aatacctttc ctttatcgtg gttatagtca gctcatttcc attccactat ttcccataat   1800
```

-continued

```
gcttctgaga gccactaact tgattgataa agatcctgcc tctgctgagt gtacctgaca   1860
gtagtctaag atgagagagt ttagggacta ctctgtttta gcaagagata ttttgggggt   1920
ctttttgttt taactattgt caggagattg ggctaaagag aagacgacga gagtaaggaa   1980
ataaagggaa ttgcctctgg ctagagagta gttaggtgtt aatacctggt agagatgtaa   2040
gggatatgac ctccctttct ttatgtgctc actgaggatc tgaggggacc ctgttaggag   2100
agcatagcat catgatgtat tagctgttca tctgctactg gttggatgga cataactatt   2160
gtaactattc agtatttact ggtaggcact gtcctctgat taaacttggc ctactggcaa   2220
tggctactta ggattgatct aagggccaaa gtgcagggtg ggtgaacttt attgtacttt   2280
ggatttggtt aacctgtttt cttcaagcct gaggttttat atacaaactc cctgaatact   2340
ctttttgcct tgtatcttct cagcctccta gccaagtcct atgtaatatg gaaaacaaac   2400
actgcagact tgagattcag ttgccgatca aggctctggc attcagagaa cccttgcaac   2460
tcgagaagct gtttttattt cgtttttgtt ttgatccagt gctctcccat ctaacaacta   2520
aacaggagcc atttcaaggc gggagatatt ttaaacaccc aaaatgttgg gtctgatttt   2580
caaactttta aactcactac tgatgattct cacgctaggc gaatttgtcc aaacacatag   2640
tgtgtgtgtt ttgtatacac tgtatgaccc caccccaaat ctttgtattg tccacattct   2700
ccaacaataa agcacagagt ggatttaatt aagcacacaa atgctaaggc agaattttga   2760
gggtgggaga gaagaaaagg gaaagaagct gaaaatgtaa aaccacacca gggaggaaaa   2820
atgacattca gaaccagcaa acactgaatt tctcttgttg ttttaactct gccacaagaa   2880
tgcaatttcg ttaacggaga tgacttaagt tggcagcagt aatcttcttt taggagcttg   2940
taccacagtc ttgcacataa gtgcagattt ggctcaagta aagagaattt cctcaacact   3000
aacttcactg ggataatcag cagcgtaact accctaaaag catatcacta gccaaagagg   3060
gaaatatctg ttcttcttac tgtgcctata ttaagactag tacaaatgtg gtgtgtcttc   3120
caactttcat tgaaaatgcc atatctatac catattttat tcgagtcact gatgatgtaa   3180
tgatatattt tttcattatt atagtagaat atttttatgg caagatattt gtggtcttga   3240
tcatacctat taaaataatg ccaaacacca aatatgaatt ttatgatgta cactttgtgc   3300
ttggcattaa aagaaaaaaa cacacatcct ggaagtctgt aagttgtttt ttgttactgt   3360
aggtcttcaa agttaagagt gtaagtgaaa aatctggagg agaggataat ttccactgtg   3420
tggaatgtga atagttaaat gaaaagttat ggttatttaa tgtaattatt acttcaaatc   3480
ctttggtcac tgtgatttca agcatgtttt ctttttctcc tttatatgac tttctctgag   3540
ttgggcaaag aagaagctga cacaccgtat gttgttagag tcttttatct ggtcagggga   3600
aacaaaatct tgacccagct gaacatgtct tcctgagtca gtgcctgaat ctttattttt   3660
taaattgaat gttccttaaa ggttaacatt tctaaagcaa tattaagaaa gactttaaat   3720
gttattttgg aagacttacg atgcatgtat acaaacgaat agcagataat gatgactagt   3780
tcacacataa agtcctttta aggagaaaat ctaaaatgaa aagtggataa acagaacatt   3840
tataagtgat cagttaatgc ctaagagtga aagtagttct attgacattc ctcaagatat   3900
ttaatatcaa ctgcattatg tattatgtct gcttaaatca tttaaaaacg gcaaagaatt   3960
atatagacta tgaggtacct tgctgtgtag gaggatgaaa ggggagttga tagtctcata   4020
aaactaattt ggcttcaagt ttcatgaatc tgtaactaga atttaatttt caccccaata   4080
atgttctata tagcctttgc taaagagcaa ctaataaatt aaacctattc tttctgtgtg   4140
tgtgagcgtg cgtttgtgtt tggtagtgtt cctagggcag aggtggagca gggatgcact   4200
```

-continued

```
tatcatggga agggaggtag aaaagagaat tggatagcct gtgatctttg gtggaattta   4260
ttccttttgc ctaggccttt cagaccctgc ttgatttccg taggacactt caggttgtgg   4320
caagggagag ctggtctgca atcggaagta ccagcctctt ccctagagca caactagaaa   4380
gaagaactat agagtgttat aagggaggcc ctgagatgga aggaccatca cacagaaatg   4440
ataatatctt catttcaggg tgttccaggg gaaaagcagg agaaagattt ggggctcagt   4500
agaaggaaaa gcttcctagt ggtaagagtg attggcaata ccatgaggta cctttaaaag   4560
atagtgaact cctgtccttg gaaatattaa accacaggct agatatcatt taatagggat   4620
gtgaagtaga gtaagtcact gcccttggtg tgcaattgtg aacttgtcaa tttctgaggt   4680
ccctttctac ttagatatat aatacaagat ttctattagg tatgggtgct ctgatgataa   4740
tgaaaatccc agcagctatg tatgggatgg ttacaccaga cactgtgcta aggattttct   4800
ttgaattgtt tctcactcaa tcttcacggt agctcagtga ggtaggtacc attatcactg   4860
ctagaaagca gtgaacttat atggtcttac tgtggcactg ggtccttaaa cattatgcaa   4920
aactgtgagc aacttttatc ggtttgttct tttaagaaca taacacagca ctctaaaaat   4980
agatctaact agattgttca catctagcga ttaaggccac cctgagatta tagctgcatc   5040
atcaggaacc caagatctga agcattcagt caaagcctct tggccacctc tctttttgtc   5100
atggccttct tggacttgga gggggagaat ggaagcaagt accaaggaga aagtgttctc   5160
agaaaagcca cacccattag aaaaatacaa ggcctgaaag gtgtgagtgg gacttgacac   5220
ggaagagcat ttcaagctta agaaaaaaaa aaaaaagaag aatgtgggag gatgtcagca   5280
acaatgcttg agattccctg gtcccccaaa gagtctctcc tccataaaac taatgagaat   5340
gtgacaaaaa tagattcaac ttcttatagc tctggaaatt aactgaagat gtatagcaat   5400
ttgcagagca tttattcaag aaaaagacta aatctctgtg agcactgtga tattgtaact   5460
tgcactactc tcatctcccc ctctccagct ccacaatagc tttgaaacca acagcctgca   5520
attaccatga aaatcagcag tctggcagcc actgaaggtg acagaatgga gttggagttc   5580
tttcaaagtc ccattcctag acaattgtca ctatttgacc tgtttggcag gccctggaag   5640
ctccacttgc aaggctatat ttgacctgac tggaagcttc ccagggtaaa aaactttgtc   5700
aaaacaacta gaggcaattg attctctttg tggctgcctg gggtaatgta taacagttgg   5760
ggaaagcaat tggctaaata aaaagcctaa aaggagaagc tggaaaaaga gattttcata   5820
gggactttga aaagctccaa agtgttattg gcaatctaga ctgccaaatg cataaatagg   5880
actccatcca tgcccaggac tgtgcagatg ctcaggaaaa acccaagaaa gccttaagct   5940
ctcacttcaa gctgatcttg aggctctgca caagccataa gtaaagggaa tgcagagttg   6000
tcaattgcat ggcggagtgt tgagtgtgcc tcagcattca cacagagctc cttggcagag   6060
actggttgaa ttattgattc caagtgtttg aggaaatccg tgtacaacta ttagatgact   6120
actaaccaag cagagacttc agtgtccaca cacaacaaaa aatacagact ttacagaatt   6180
agttcagaaa agtcattaaa caaagaaaca acaacaaacc ctggggaaat gacagtacga   6240
tcaaaccatg catggccctg cctgcatgtg ggaatcctca tccaagtcat actttctaaa   6300
catcataaaa agcccaaacc agtctccttt cctggctctc tcaagtcatt ttcagaccag   6360
gttaggagac gtgagctgct ctccacaaaa agcctcatgt gagtaataaa tgtttcatac   6420
tctcttgggg tgtgtgtaac atcatcagtc tcagcatcta aaccaaattt tggtgacatt   6480
tcatcttgtt tatgcagatg tccaccacac ctataaataa acaaactact gaaactgatt   6540
```

-continued

```
caagaaaaaa taaaaatctg aatagagcta tcacaagtaa agagattaaa taagcaatca   6600
aataacttcc cagaaagaaa agcccaattt aggatgtctt aactgattaa tgttagcaaa   6660
tatttaaaga agaattggta caaattcttc acaaactctt ccagaaatgg aagaggagga   6720
aacactttcc accttatttt ctataactag tattaccttg ataccaaatt ctgacaaata   6780
catcaaaaat aaaaccatag accaatatct cttttaagtg taaatgcaaa aaaattcaac   6840
aaaatgctag ataactgggt ccaacaacat atggaaagga ttatatacct tgaccaagtg   6900
ggatttgccc caggaatgca agattgattt aaccatcagt gtaatgcatc atattaatag   6960
aataaagaca gaaaccacac aatcatctcg atacacgcag aaaaatcatt tggcaaaatt   7020
caacacccct ttgtaataaa atcactcaac acactaggaa gagaagggaa cttcttcaac   7080
ctcacacatg gcatctatga aaaacccaca gctggccggg tatggtggct caagcctgta   7140
atcccagcac tttgggaggc tgagccaggc ggatcacctg aggtcaggag ttcgagacca   7200
acctgaccaa catggagaaa ccctgtatct actaaaaata caaaaaatta gcccggcgtg   7260
gtggcaaatg cctgtaatcc cagctgcttg ggaggctgag gcaggagaat cggttgaacc   7320
caggaggtgg aggttctggt gagccgagat cacgccattg tactccagcc tgggcaacaa   7380
gaacaaaact ctgtctcaaa aaaaaaaaaa aaaagaaaag aaaaacccac agctaacatc   7440
atacttaaag gtgaaagact gaaagctttc ccccaagagg aactaacagg atatctgctg   7500
tcactatttt tattcaatat tatactggag gttctaccta gggtaattag gcaaaaaaaa   7560
aaaaaaaaaa aaaaaaaaaa aaaaaaaaaa aaaaaaaaaa aagaaaagaa aaaagtcatc   7620
cagattggaa aagaaataaa atgatttcaa ttttaagatg acataatatt gtatgtagaa   7680
atcctaagga atttacaaaa gaactattag agctaataca tgatttcagc aaggttgcag   7740
gatacaagat caacatacag atataaattg tattctacac acttgtaatg aaaaatctga   7800
aaataaaatt aagaaaatag caccctttga atagtatcaa aaagaataaa atacatagaa   7860
aaaatgtaac aggaagtgca agactggtac attgaaaaca ataaaacatt gttaaaaaat   7920
ttaaaatcat caaaatagat ggaaataaaa cctgtgttca tggatgaaaa aaattaacat   7980
tgctctacag attcaataca attcttatca aaatcccagg tggcttaaga aattgacaag   8040
ttaatcctaa aattcataag aaattgaaag ggatccacaa tagccaaaat aatcttaaaa   8100
aagattttaa aaagttggag aactcacact tcctggtttc ataacataca ccaggctggg   8160
catggtggtt catgcccata atcccagcac tttgggaagt tgaggcagaa ggatcacttg   8220
agcacaggag tttgagacca gcctggacga tatagtgaga ccttgtctct actaaaaatt   8280
taaaaaggaa ttagccaggt gtggtaacat gcacctgttg tcccagctac ttaggaggct   8340
gaggcatgag gatcacttga gcccagaaga ttgtaccact gcactccagc ctacatgaca   8400
gagtaagtct ctgtctcaaa aacaaaacaa acaacaaaaa tactgaaagc tttccccata   8460
caggaactaa caggatatct gctgtcacta tttttattca atattgttct ggaggttcta   8520
gctagggcaa ttaggcaaaa aaaggaaaaa gaagtcatcc agattagaaa agaaataaaa   8580
taatttcaat tttcagatga cataatattg tatgtagaaa tcctaaggaa tttacaaaag   8640
aactgctacc ctgaaagaat tgttgtaagg caaatacccc tgtaattacc attaggggaa   8700
gaaatttttc catgcttcac agaaactctc cttatacccc acctcaattt taatcttttt   8760
ctgtaccact acagttataa ttctcctaaa gcttaaagca attacctcct tgtttatatt   8820
tatagtttca tcactgaagt gtgcattcct aaactcaaca ccttagtctg gttgcaaaca   8880
gtttaaatga gaaaagataa ggcctgaatt aaggcagcag ccctaaacct ttttctataa   8940
```

```
tcctgatagt gattaccacc taggggatta taaatgtttg cttcttcctc tggcaccaac   9000
aagtttactg agcagaagtt taaaataatt ggataatggg gcaggtgaca tcagcaagat   9060
gttgtattag caaatgctgg acccttcttc aatccacaaa cacatctatt ctgcaaaaat   9120
tcatggctaa attcctttgt gaggaatcca gaaactaaaa ggctcctgca ctcccagcaa   9180
atgcaaaaac cagactcacc aaagctggta gagagatttg agataccacc ttgtccgaat   9240
ccctaacccc agcacagtgc catgtagtca gcaagagact ccctagcact cagtttctcc   9300
caggtgagag gagttggttc acatatccaa gacctccaac ttttctgagg agattcccag   9360
aggactggct tctatcttgt cagtcttgga gctctgacag aattggtact atctagctac   9420
ctggggaagg acagagacag aggtttagac cagtagatga catggcaccc tgccctctac   9480
tgcctcacct cctggctcag cacagacagg acaaaaatca tggctaccta catttccctg   9540
gagaaggaat gatttgttaa aggcccccaa atcactgggc agacttattg gtgggggtct   9600
tctcctctga ggcccagctg tgaggactgg gacaggtgac tgctttgtct aatgtgcaga   9660
caccaacaca aagagtcaag gaaaatgaat aatcatacga agatgttcca aaccaaagaa   9720
caagataaat ctctggaaac tgagctaatg aaataaactt atgtgattta cctgacagag   9780
aattcagaat agctctcata aagattctca ccagagtcaa gagaacaatg catgaaaaaa   9840
gttaagaatt ttgacaaaga gatagagtat atttaaaagt accaaaaaga aatggaactg   9900
aagaacacaa caactgaact gaaaaaattt atgacaggac atcaacagga gacaagatta   9960
atcagaagaa agaatcaatg aacttgaaga caggtcattg gaaataattc agttagagga  10020
gaaattaaaa tgaaaaagag tgaaaaaaag cccaagggtc ttatgggcaa catcaagctg  10080
aacaatatac tcattattgg catcacagaa taaaagagag aaaagaactg agaacgtatt  10140
caaagaaata atggctgaac acttcccaaa tatgaggaag aaaatgaaca ttctgatcca  10200
agaagcccaa aggtcataaa aaagtgatcc caaagcctac aggcatatta taagttgtca  10260
tcctagagaa agaaaaatat ctttctccca gcctccatat tcaaatctta aggaaaattc  10320
ttatggactt agcttgagtt tcaagttcat ttctaaaatc aatcatggtg gccaaacgga  10380
atgagcattc tgatttgcca gtgtggtctc atgttacccc tgtgcctaga aaggaaacag  10440
gagatgaaaa gcatggtgat aagaagactg gatggcacca catgggatag ggggaaagta  10500
gttgaaaaaa aatagttgta aggaaaagag atacaaggag tcaaaaataa caaatatcta  10560
cttaaaagcc ttttccacat ttaatgtttt ttgttcactg tggtgtagta ataaatgtct  10620
atacttaagg ggtgaggatt gatatattta aagtgaatgg tctggaaggc aaggaagctc  10680
attccaacag attcatgcta cattgtttag tgacaaataa ggggaacaga acagagaaag  10740
tgatttcagc tataaatata ggagataata aaatccttta gtaaacagta tctaagcctt  10800
gtttttatga tattggggaa cagtaacaga tcaaagtact gtagtcttca gtatgcagac  10860
ctttcacttt cttagtttat tccagggtct tttttttttt tgctgctatt acaaatagca  10920
ttgttttcct aatttttgtt taagatagtt catcgttggt atagaaatgc cattgatttt  10980
tgtatgttga ttttgtatcc tccaacttta ctgaatttat tagttctaac agtttttttga  11040
tggagtcttt agggttttct atgtataaga ttatgtcatc tgcaaacagc aacaatttta  11100
ccctttgttt tcaacgtgag cgtcttttat ttatttttct tgcctaattg ctttagctag  11160
gacttccagc actaaattga atagaagtga tgagagtggg catgtatgcc ttgtttctgg  11220
tcttaaagaa aaacatttca gttttccatt attcggtata atgttagtta tgggttttta  11280
```

-continued aaaatatata tgacctttat taggttgagg tacttttcct ctattcttag tttattgaat 11340
gtttttctca tgaaagtgtg ttaaattttg tcaaaacctt ttttacatcc atcaaatgat 11400
tatgtaattt ttatccttta ttctgttaat ggattatcac attaactaat tttcatatct 11460
tgaagcatac ttgcatccta ggaataaatc ccactttgtc atagtctttg atccttttaa 11520
tataatgtta aatttggttt gccagtattt tgttgaggat ttttgcatct atatattcat 11580
caaggatatt gggctgtaat tttcttttct tgtggtgtct ttgtccggct ttagtataaa 11640
ggtaattctg gcttcataaa ataagttaga aagtgttctc tcttctttga ttttttttgga 11700 agagtttgag aataattggc attagttttg ttaaatgttt ggttgaattc actagtgaaa 11760
ttatttggtc ctgggatttt ctttactggg agttttttga ttacttgttc aatctttacg 11820
ctagtcatag gtctgtccag tctttgtatt tcttcatgat ttagtcatca tgtattcatg 11880
ggttgtaaga cttaatattc ttaaaatgcc catattaccc aaagtgatct atagattcat 11940
gcaatcccca tcaaaaatcc cagtggcatt tttatttaca gaaatagaat aattctaaaa 12000
ttcatctgaa gccacaaaag acaatgaata aacaaatcaa tcttgaaaaa gaagaacaaa 12060
gctggaggca ttatacttcc tgatttcaaa atatcctgca aaggtacagt aatcaaaaca 12120
gtatgttacc agcataaaga caaacacaca gaccaataga acagaataga gagctcagca 12180
acaaatccgt gaatatacag tcaactgaca tttggcaatg gtgccaagca tactcagtgg 12240
gagaaatgat aatctcttca acaaatggtg ttgggaaaac tgaatatcca catgcaaaag 12300
aataaaattg gaccctatct tataccaaaa atcaactcaa aatggattat ttaaatgtaa 12360
gacttgaaac agtaaaactc ctagaagtaa acagaagaga aagtttcatg acattgccct 12420
tggcaatgat ttcatgtaca taacaacaaa agcacaggta ataaaaacaa aaatagacaa 12480
atgggactac ctcaaattaa aatgtttctg cacagcaaac gaccaactga atgaaaaggc 12540
aatctatgga acagaagaca cggggtgaca tgagaccact ttggcaaatc agaatgctca 12600
ttccatttgg ccaccatgat tggttttaga aatggacttg aagctcaaag aaagcccata 12660
atatattcct taagatttga atatagaggc tggaagaaag atttttttct ttctctagga 12720
tgacaagtta tatataataa gcctgtaggc caatatctgc tggcagccac ctttcccagg 12780
tatatggatg aaactatctg aaggatgaag cctccattca cagaaaatca gagctgtaaa 12840
gggaagagga tatcctgatg aatttttttc ttggattgag ccatgtctga agtcaagcca 12900
acttttgaag tatcctatag tacttatata ttgcttggta acaaattatg ccaaaattta 12960
gtagcttaaa acaacaaaca tctattatct catgcatttc tgatatagat ataggagtga 13020
ctaatctggg tggttctggg tcagaatctc tggtgagtgt gtaggcaagg tgtcagtagg 13080
gggctgcaat tatctaaagg cttgcctggg gctggagacg cactttcaat gtggtgtact 13140
cacgtggctg ttggttggag gccaaatgtg ctaggcaaag cctcatgcac atttctctgt 13200
aaggaaacaa agctggctta cttgggggca ggattttttt ttttcccagt tgttcttcaa 13260
aatgaagttt cccgctccaa gtcccagcca gatatgtgaa aaacaatcct tgcagaacaa 13320
ccctattagc agttctgcaa ggatttttag gaaccgtatt agcaagttcc tcagttcctc 13380
accatgtgaa cctctcttca cgacttagta actggcttcc tctagagtga ctaatccaag 13440
agacagcaag gattgacagc catgacagca cagtgccttt catgacttac tctccaaagt 13500
tacaaacctt tacttttgct ttatcttatt tgttagagca agtcactaaa tttgcccaca 13560
tctaagatga gggtatttgg gcttcacctc ttgaatggag aagcacccaa aaatctgtgg 13620
cctttttttt taattacact ctcagttaca tgaatcaata aattccattt ttggcttagc 13680

-continued

```
ttctattggg tttctatcac ttgcaaccaa agtgccctaa ccagtatcta catctgagtc  13740
attaagaaag tttcagacag ggctgggcgc ggtggctcac acctgttaat cccagacttt  13800
gggaggccga ggcaggcgga tcacgtggtc aggagatcga gaccatcctg gctaacacgg  13860
tgaaacctta tctctactaa aaatacaaaa aattagccgg gtgtggtggc aggtgcctga  13920
agtcccagct actcgggagg ctgaggcagg ggaatggcgt gaacccggga gacggagctt  13980
gcagtgagcc gagatcacgc cactgcgctc cagcctgggc gacagagtga gactcagctt  14040
caaaaaaaaa aaaaaaaaag aaagtttcag atattattgt ttattgcttt taatctagtg  14100
aattcataaa tcgtcactta actcaagcaa aacaatgtta ctctctttgt acattgtaca  14160
gatgcaggat aacaatgcag tgttatcctg catctgtaca atcaagcacc caaactggtt  14220
ctgtagaggc aggaccttag catatagcag agataactta tcttccagca gatccggagc  14280
tccattttgt agacagaaat gaatgctctg tgccacagaa ggagctgttg cactattcat  14340
tcccgtttcc tcccattcac tctccacatc tccaatcctg gcattgtctg ctttgttact  14400
tgttaaaaac ttgatttcgt agattgcttt aaaataagaa caaaatgtac tttgacacac  14460
atcattttgt ttggttctca ttaattttga gagaaaggca agatagatat ttaaatgacc  14520
cctattttag tggtaaacaa gctgaaatta gataaataaa atgatttgcc taatg       14575
```

<210> SEQ ID NO 26
<211> LENGTH: 2710
<212> TYPE: DNA
<213> ORGANISM: Homo sapiens

<400> SEQUENCE: 26

```
aggagatgtg ccaaactgtt aagagtggtt atttctgagc agaagaatgt ggatgaattc     60
cattcttcct atttttcttt tcaggtctgt gcggctgcta aagaacgacc cagtcaactt    120
gcagaaattc tcttacacta gtgaggatga ggcctggaag acgtacctag aaaacccgtt    180
gacagctgcc acaaaggcca tgatgagagt caatggagat gatgacagtg ttgcggcctt    240
gagcttcctc tatgattact acatgggtcc caaggagaag cggatattgt cctccagcac    300
tgggggcagg aatgaccaag gaaagaggta ctaccatggc atggaatatg agacggacct    360
cactcccctt gaaagcccca cacacctcat gaaattcctg acagagaacg tgtctggaac    420
cccagagtac ccagatttgc tcaagaagaa taacctgatg agcttggagg gggccttgcc    480
cacccctggc aaggcagctc ccctccctgc aggccccagc aagctggagg ccggctctgt    540
ggacagctac ctgttaccca ccactgatat gtatgataat ggctccctca actccttgtt    600
tgagagcatt catggggtgc cgcccacaca gcgctggcag ccagacagca ccttcaaaga    660
tgacccacag gagtcgatgc tcttcccaga tatcctgaaa acctccccgg aacccccatg    720
tccagaggac taccccagcc tcaaaagtga ctttgaatac accctgggct cccccaaagc    780
catccacatc aagtcaggcg agtcacccat ggcctacctc aacaaaggcc agttctaccc    840
cgtcaccctg cggaccccag caggtggcaa aggccttgcc ttgtcctcca acaaagtcaa    900
gagtgtggtg atggttgtct tcgacaatga gaaggtccca gtagagcagc tgcgcttctg    960
gaagcactgg cattcccggc aacccactgc caagcagcgg gtcattgacg tggctgactg   1020
caaagaaaac ttcaacactg tggagcacat tgaggaggtg gcctataatg cactgtcctt   1080
tgtgtggaac gtgaatgaag aggccaaggt gttcatcggc gtaaactgtc tgagcacaga   1140
cttttcctca caaaaggggg tgaagggtgt ccccctgaac ctgcagattg acacctatga   1200
```

-continued

```
ctgtggcttg ggcactgagc gcctggtaca ccgtgctgtc tgccagatca agatcttctg   1260

tgacaaggga gctgagagga agatgcgcga tgacgagcgg aagcagttcc ggaggaaggt   1320

caagtgccct gactccagca acagtggcgt caagggctgc ctgctgtcgg gcttcagggg   1380

caatgagacg acctaccttc ggccagagac tgacctggag acgccacccg tgctgttcat   1440

ccccaatgtg cacttctcca gcctgcagcg ctctggaggg gcagcccccct cggcaggacc   1500

cagcagctcc aacaggctgc ctctgaagcg tacctgctcg cccttcactg aggagtttga   1560

gcctctgccc tccaagcagg ccaaggaagg cgaccttcag agagttctgc tgtatgtgcg   1620

gagggagact gaggaggtgt ttgacgcgct catgttgaag accccagacc tgaaggggct   1680

gaggaatgcg atctctgaga agtatgggtt ccctgaagag aacatttaca aagtctacaa   1740

gaaatgcaag cgaggaatct tagtcaacat ggacaacaac atcattcagc attacagcaa   1800

ccacgtcgcc ttcctgctgg acatgggggga gctggacggc aaaattcaga tcatccttaa   1860

ggagctgtaa ggcctctcga gcatccaaac cctcacgacc tgcaaggggc cagcagggac   1920

gtggccccac gccacacaca acctctccac atgcctcagc gctgttactt gaatgccttc   1980

cctgagggaa gaggcccttg agtcacagac ccacagacgt cagggccagg gagagaccta   2040

gggggtcccc tggcctggat ccccatggta tgcttgaatc tgctccctga acttcctgcc   2100

agtgcctccc cgtaccccaa aacaatgtca ccatggttac cacctaccca gaagactgtt   2160

ccctcctccc aagacccttg tctgcagtgg tgctcctgca ggctgcccgt taagatggtg   2220

gcggcacacg ctccctcccg cagcaccacg ccagctggtg cggcccccac tctctgtctt   2280

ccttcaactt cagacaaagg atttctcaac ctttggtcag ttaacttgaa aactcttgat   2340

tttcagtgca aatgactttt aaaagacact atattggagt ctctttctca gacttcctca   2400

gcgcaggatg taaatagcac taacgatcga ctggaacaaa gtgaccgctg tgtaaaacta   2460

ctgccttgcc actcactgtt gtatacattt cttatttacg attttcattt gttatatata   2520

tatataaata tactgtatat atatgcaaca ttttatattt ttcatggata tgtttttatc   2580

atttcaaaaa atgtgtattt cacatttctt ggactttttt tagctgttat tcagtgatgc   2640

attttgtata ctcacgtggt atttagtaat aaaaatctat ctatgtatta cgtcacatta   2700

aaaaaaaaaa                                                           2710
```

<210> SEQ ID NO 27
<211> LENGTH: 1929
<212> TYPE: DNA
<213> ORGANISM: Homo sapiens

<400> SEQUENCE: 27

```
agaacaattc aggcttcgct gcgactcaga cctcagctcc aacatatgca ttctgaagaa     60

agatggctga gatggacaga atgctttatt ttggaaagaa acaatgttct aggtcaaact    120

gagtctacca aatgcagact ttcacaatgg ttctagaaga aatctggaca agtcttttca    180

tgtggttttt ctacgcattg attccatgtt tgctcacaga tgaagtggcc attctgcctg    240

cccctcagaa cctctctgta ctctcaacca acatgaagca tctcttgatg tggagcccag    300

tgatcgcgcc tggagaaaca gtgtactatt ctgtcgaata ccagggggag tacgagagcc    360

tgtacacgag ccacatctgg atccccagca gctggtgctc actcactgaa ggtcctgagt    420

gtgatgtcac tgatgacatc acggccactg tgccatacaa ccttcgtgtc agggccacat    480

tgggctcaca gacctcagcc tggagcatcc tgaagcatcc ctttaataga aactcaacca    540

tccttacccg acctgggatg gagatcacca aagatggctt ccacctggtt attgagctgg    600
```

aggacctggg gccccagttt gagttccttg tggcctactg gaggagggag cctggtgccg 660
aggaacatgt caaaatggtg aggagtgggg gtattccagt gcacctagaa accatggagc 720
caggggctgc atactgtgtg aaggcccaga cattcgtgaa ggccattggg aggtacagcg 780
ccttcagcca gacagaatgt gtggaggtgc aaggagaggc cattcccctg gtactggccc 840
tgtttgcctt tgttggcttc atgctgatcc ttgtggtcgt gccactgttc gtctggaaaa 900
tgggccggct gctccagtac tcctgttgcc ccgtggtggt cctcccagac accttgaaaa 960
taaccaattc accccagaag ttaatcagct gcagaaggga ggaggtggat gcctgtgcca 1020
cggctgtgat gtctcctgag gaactcctca gggcctggat ctcataggtt tgcggaaggg 1080
cccaggtgaa gccgagaacc tggtctgcat gacatggaaa ccatgagggg acaagttgtg 1140
tttctgtttt ccgccacgga caagggatga gagaagtagg aagagcctgt tgtctacaag 1200
tctagaagca accatcagag gcagggtggt ttgtctaaca gaacactgac tgaggcttag 1260
gggatgtgac ctctagactg ggggctgcca cttgctggct gagcaaccct gggaaaagtg 1320
acttcatccc ttcggtccta agttttctca tctgtaatgg gggaattacc tacacacctg 1380
ctaaacacac acacacagag tctctctcta tatatacaca cgtacacata aatacaccca 1440
gcacttgcaa ggctagaggg aaactggtga cactctacag tctgactgat tcagtgtttc 1500
tggagagcag gacataaatg tatgatgaga atgatcaagg actctacaca ctgggtggct 1560
tggagagccc actttcccag aataatcctt gagagaaaag gaatcatggg agcaatggtg 1620
ttgagttcac ttcaagccca atgccggtgc agaggggaat ggcttagcga gctctacagt 1680
aggtgacctg gaggaaggtc acagccacac tgaaaatggg atgtgcatga acacggagga 1740
tccatgaact actgtaaagt gttgacagtg tgtgcacact gcagacagca ggtgaaatgt 1800
atgtgtgcaa tgcgacgaga atgcagaagt cagtaacatg tgcatgtttg ttgtgctcct 1860
tttttctgtt ggtaaagtac agaattcagc aaataaaaag ggccaccctg gccaaaagcg 1920
gtctttaaa 1929

<210> SEQ ID NO 28
<211> LENGTH: 2308
<212> TYPE: DNA
<213> ORGANISM: Homo sapiens

<400> SEQUENCE: 28
agtcctgctt ctcttccctc tctcctccag cctctcacac tctcctcagc tctctcatct 60
cctggaacca tggccagcac atccaccacc atcaggagcc acagcagcag ccgccggggt 120
ttcagtgcca actcagccag gctccctggg gtcagccgct ctggcttcag cagcgtctcc 180
gtgtcccgct ccaggggcag tggtggcctg ggtggtgcat gtggaggagc tggctttggc 240
agccgcagtc tgtatggcct gggggctcc aagaggatct ccattggagg gggcagctgt 300
gccatcagtg gcggctatgg cagcagagcc ggaggcagct atggctttgg tggcgccggg 360
agtggatttg gtttcggtgg tggagccggc attggctttg gtctgggtgg tggagccggc 420
cttgctggtg gctttggggg ccctggcttc cctgtgtgcc cccctggagg catccaagag 480
gtcaccgtca accagagtct cctgactccc ctcaacctgc aaatcgatcc caccatccag 540
cgggtgcggg ctgaggagcg tgaacagatc aagaccctca acaacaagtt tgcctccttc 600
atcgacaagg tgcggttcct ggagcagcag aacaaggttc tggaaacaaa gtggaccctg 660
ctgcaggagc agggcaccaa gactgtgagg cagaacctgg agccgttgtt cgagcagtac 720
atcaacaacc tcaggaggca gctggacagc attgtcgggg aacggggccg cctggactca 780
gagctcagag gcatgcagga cctggtggag gacttcaaga acaaatatga ggatgaaatc 840
aacaagcgca cagcagcaga gaatgaattt gtgactctga agaaggatgt ggatgctgcc 900
tacatgaaca aggttgaact gcaagccaag gcagacactc tcacagacga gatcaacttc 960
ctgagagcct tgtatgatgc agagctgtcc cagatgcaga cccacatctc agacacatct 1020
gtggtgctgt ccatggacaa caaccgcaac ctggacctgg acagcatcat cgctgaggtc 1080
aaggcccaat atgaggagat tgctcagaga agccgggctg aggctgagtc ctggtaccag 1140
accaagtacg aggagctgca ggtcacagca ggcagacatg gggacgacct gcgcaacacc 1200
aagcaggaga ttgctgagat caaccgcatg atccagaggc tgagatctga gatcgaccac 1260
gtcaagaagc agtgcgccaa cctgcaggcc gccattgctg atgctgagca gcgtggggag 1320
atggccctca aggatgccaa gaacaagctg gaagggctgg aggatgccct gcagaaggcc 1380
aagcaggacc tggcccggct gctgaaggag taccaggagc tgatgaatgt caagctggcc 1440
ctggacgtgg agatcgccac ctaccgcaag ctgctggagg gtgaggagtg caggctgaat 1500
ggcgaaggcg ttggacaagt caacatctct gtggtgcagt ccaccgtctc cagtggctat 1560
ggcggtgcca gtggtgtcgg cagtggctta ggcctgggtg gaggaagcag ctactcctat 1620
ggcagtggtc ttggcgttgg aggtggcttc agttccagca gtggcagagc cattgggggt 1680
ggcctcagct ctgttggagg cggcagttcc accatcaagt acaccaccac ctcctcctcc 1740
agcaggaaga gctataagca ctaaagtgcg tctgctagct ctcggtccca cagtcctcag 1800
gcccctctct ggctgcagag ccctctcctc aggttgcctt tcctctcctg gcctccagtc 1860
tcccctgctg tcccaggtag agctgggtat ggatgcttag tgccctcact tcttctctct 1920
ctctctatac catctgagca cccattgctc accatcagat caacctctga ttttacatca 1980
tgatgtaatc accactggag cttcactgtt actaaattat taatttcttg cctccagtgt 2040
tctatctctg aggctgagca ttataagaaa atgacctctg ctccttttca ttgcagaaaa 2100
ttgccagggg cttatttcag aacaacttcc acttactttc cactggctct caaactctct 2160
aacttataag tgttgtgaac cccccacccag gcagtatcca tgaaagcaca agtgactagt 2220
cctatgatgt acaaagcctg tatctctgtg atgatttctg tgctcttcgc tgtttgcaat 2280
tgctaaataa agcagattta taatacaa 2308

<210> SEQ ID NO 29
<211> LENGTH: 2302
<212> TYPE: DNA
<213> ORGANISM: Homo sapiens

<400> SEQUENCE: 29
gtcctgcttc tcctccctct cgcctccagc ctctcacact ctcctaagcc ctctcatctc 60
ctggaaccat ggccagcaca tccaccacca tcaggagcca cagcagcagc cgccggggtt 120
tcagtgccaa ctcagccagg ctccctgggg tcagccgctc tggcttcagc agcatctccg 180
tgtcccgctc caggggcagt ggtggcctgg gtggcgcatg tggaggagct ggctttggca 240
gccgcagtct gtatggcctg gggggctcca agaggatctc cattggaggg ggcagctgtg 300
ccatcagtgg cggctatggc agcagagccg gaggcagcta tggctttggt ggcgccggga 360
gtggatttgg tttcggtggt ggagccggca ttggctttgg tctgggtggt ggagccggcc 420
ttgctggtgg ctttgggggc cctggcttcc ctgtgtgccc ccctggaggc atccaagagg 480
tcactgtcaa ccagagtctc ctgactcccc tcaacctgca aattgacccc gccatccagc 540
gggtgcgggc cgaggagcgt gagcagatca agaccctcaa caacaagttt gcctccttca 600
tcgacaaggt gcggttccta gagcagcaga acaaggttct ggacaccaag tggaccctgc 660
tgcaggagca gggcaccaag actgtgaggc agaacctgga gccgttgttc gagcagtaca 720
tcaacaacct caggaggcag ctggacaaca tcgtgggggga acggggtcgt ctggactcgg 780
agctgagaaa catgcaggac ctggtggagg acctcaagaa caaatatgag gatgaaatca 840
acaagcgcac agcagcagag aatgaatttg tgactctgaa gaaggatgtg gatgctgcct 900
acatgaacaa ggttgaactg caagccaagg cagacactct tacagatgag atcaacttcc 960
tgagagcctt gtatgatgca gagctgtccc agatgcagac ccacatctca gacacatccg 1020
tggtgctatc catggacaac aaccgcaacc tggacctgga cagcatcatc gctgaggtca 1080
aggcccaata tgaggagatt gctcagagga gcagggctga ggctgagtcc tggtaccaga 1140
caaagtacga ggagctgcag atcacagcag gcagacatgg ggacgacctg cgcaacacca 1200
agcaggagat tgctgagatc aaccgcatga tccagaggct gagatctgag atcgaccacg 1260
tcaagaagca gtgtgccaac ctacaggccg ccattgctga tgctgagcag cgtggggaga 1320
tggccctcaa ggatgctaag aacaagctgg aagggctgga ggatgccctg cagaaggcca 1380
agcaggacct ggcccggctg ctgaaggagt accaggagct gatgaacgtc aagctggccc 1440
tggatgtgga gatcgccacc taccgcaagc tgctggaggg cgaggagtgc aggctgaatg 1500
gcgaaggcgt tggacaagtc aacatctctg tagtgcagtc caccgtctcc agtggctatg 1560
gcggtgccag cggtgtcggc agtggcttag gcctgggtgg aggaagcagc tactcctatg 1620
gcagtggtct tggcgttgga ggcggcttta gttccagcag cggcagagcc actgggggtg 1680
gcctcagctc tgttggaggc ggcagttcca ccatcaagta caccaccacc tcctcctcca 1740
gcaggaagag ctacaagcac tgaagtgctg ccgccagctc tcagtcccac agctctcagg 1800
cccctctctg gcagcagagc cctctcctca ggttgcttgt cctcccctgg cctccagtct 1860
cccctgccct cccgggtaga gctgggatgc cctcactttt cttctcatca atacctgttc 1920
cactgagctc ctgttgctta ccatcaagtc aacagttatc agcactcaga catgcgaatg 1980
tcctttttag ttcccgtatt attacaggta tctgagtctg ccataattct gagaagaaaa 2040
tgacctatat ccccataaga actgaaactc agtctaggtc cagctgcaga tgaggagtcc 2100
tctctttaat tgctaaccat cctgcccatt atagctacac tcaggagttc tcatctgaca 2160
agtcagttgt cctgatcttc tcttgcagtg tccctgaatg gcaagtgatg taccttctga 2220
tgcagtctgc attcctgcac tgctttctct gctctctttg ccttcttttg ttctgttgaa 2280
taaagcatat tgagaatgtg aa 2302

<210> SEQ ID NO 30
<211> LENGTH: 2309
<212> TYPE: DNA
<213> ORGANISM: Homo sapiens

<400> SEQUENCE: 30
gtcctgcttc tcctgcctct cgcctccagc ctccaacgct cgccacagcc ctctcatctc 60
ctggaaccat ggccagcaca tccaccacca tcaggagcca cagcagcagc cgccggggtt 120
tcagtgccaa ctcagccagg ctccctgggg tcagccgctc tggcttcagc agcatctccg 180
tgtcccgctc caggggcagt ggtggcctgg gtggtgcatg tggaggagct ggctttggca 240
gccgcagtct gtatggcctg gggggctcca agaggatctc cattggaggg ggcagctgtg 300
ccatcagtgg cggctatggc agcagagccg gaggcagcta tggctttggt ggcgccggga 360
gtggatttgg tttcggtggt ggagccggca ttggctttgg tctgggtggt ggagccggcc 420
ttgctggtgg ctttgggggc cctggcttcc ctgtgtgccc ccctggaggc atccaagagg 480
tcaccgtcaa ccagagtctc ctgactcccc tcaacctgca aattgacccc gccatccagc 540
gggtgcgggc cgaggagcgt gagcagatca agaccctcaa caacaagttt gcctccttca 600
tcgacaaggt gcggttccta gagcagcaga acaaggttct ggacaccaag tggaccctgc 660
tgcaggagca gggcaccaag actgtgaggc agaacctgga gccgttgttc gagcagtaca 720
tcaacaacct caggaggcag ctggacagca tcgtcgggga acggggccgc ctggactcgg 780
agctgagaaa catgcaggac ctggtggagg acctcaagaa caaatatgag gatgaaatca 840
acaagcgcac agcagcagag aatgaatttg tgactctgaa gaaggatgtg gatgctgcct 900
acatgaacaa ggttgaactg caagccaagg cagacactct cacagatgag atcaacttcc 960
tgagagcctt gtatgatgca gagctgtccc agatgcagac ccacatctca gacacatccg 1020
tggtgctatc catggacaac aaccgcaacc tggacctgga cagcatcatc gctgaggtca 1080
aggcccaata cgaggagatt gctcagagga gccgggctga ggctgagtcc tggtaccaga 1140
ccaagtacga ggagctgcag gtcacagcag gcagacatgg ggacgacctg cgcaacacca 1200
agcaggagat tgctgagatc aaccgcatga tccagaggct gagatctgag atcgaccatg 1260
tcaagaagca gtgtgccagc ctgcaggctg ccattgctga tgctgagcag cgtgggggaga 1320 tggcactcaa ggatgctaag aacaagctgg aagggctgga ggatgccctg cagaaggcca 1380
agcaggacct ggcccggctg ctgaaggagt accaggagct gatgaatgtc aagctggccc 1440
tggatgtgga gatcgccacc taccgcaagc tgctggaggg cgaggagtgc aggctgaatg 1500
gcgaaggcgt tggacaagtc aacgtctctg tagtacagtc caccatctcc agtggctatg 1560
gcggtgccag cggtgtcggc agtggcttag gcctgggtgg aggaagcagc tactcctatg 1620
gcagtggtct tggcattgga ggtggcttca gttccagcag tggcagagcc attgggggtg 1680
gcctcagctc tgttggaggc ggcagttcca ccatcaagta caccaccacc tcctcctcca 1740
gcaggaagag ctacaagcac taaagtgctg cctccagctc tcggtcccac agtcctcagg 1800
cccttctctg gctgcagagc cgtctcctca ggttgcctat cctctcctgg cctctagtct 1860
tccctgctct ccgaggtaga gctgggtatg gatgcttagt gccctcactt ctctctgtct 1920
atacctgccc catctgagca cccattgctc accatcagat caacctttga ttttacatca 1980
taatgtattc accaatggag cttcactttg ttactaaatt attaatttct tgcctccaaa 2040
attgttctct ctgaggctga gcattataag aaaatgatct ctgttccttt tcattactga 2100
aaatcgcctg gggcttattt cagaacaact tccacttatt ttccattggc cccaaactc 2160 cctaagttaa aagtattgtg aaccccccgcc ccgcagtatg catggaagca caagtgacta 2220
gtcgtatgat gtacacagtc tttctccctg tgatgatttc tctgctcttt gctctttgta 2280
atttctaaat aaagcaggtt ttagaataa 2309

<210> SEQ ID NO 31
<211> LENGTH: 3927
<212> TYPE: DNA
<213> ORGANISM: Homo sapiens

<400> SEQUENCE: 31
gtccactagc cctgggcttc agggaggctg ctgcgtccag tgaacacttc agcacctgta 60
gcacagaagg gccaaggagc tgcagtcctc gaccagcagg aggtttgctc ctcagcccac 120

-continued

```
tcgctgcatc cagatcagct caccccctctc ccttccctgc ccaccaggac tctgatagcc    180
cctggcagcc acagcccatt ttgccaagat gtctagagta gccaaatatc gccggcaggt    240
gagtgaagac cccgacatcg acagcctgct ggagaccctg tctcccgagg agatggagga    300
gctggagaag gagctggacg tggtggaccc agacgggagt gttcccgtgg ggctgcggca    360
gagaaaccag acggagaaac agtccacggg tgtgtacaac cgggaggcca tgctcaactt    420
ctgtgaaaag gagaccaaga aacttatgca gagggagatg tccatggatg aaagcaagca    480
agtggagacc aagacagatg ccaagaatgg agaggaaagg ggcagagatg ccagcaaaaa    540
agccctgggc cccagacggg actcagatct ggggaaggag ccaaagaggg gtggtttaaa    600
gaaaagcttc tctagagaca gagatgaagc tggtggcaag agtggcgaga agcccaagga    660
ggagaagatc atccggggca ttgacaaggg ccgggtcagg gctgcagtgg ataagaagga    720
ggcagggaag gatgggagag gagaggagag ggcagtggcc accaagaagg aagaggagaa    780
gaaagggagt gacaggaaca caggcttgag cagggacaag gataaaaaga gagaggagat    840
gaaggaggtg gccaagaaag aggatgatga gaaggtaaaa ggggagcgta ggaacacaga    900
caccagaaaa gagggtgaga agatgaaaag agcaggtggg aacacagaca tgaaaaagga    960
ggatgagaag gtaaaaagag gaactgggaa cacagacacc aaaaaggacg atgaaaaagt   1020
caagaagaat gaacccttac atgaaaagga agccaaggat gacagcaaga ccaaaacacc   1080
cgagaaacag acgcccagtg gccccaccaa gccctctgaa ggaccggcca aggtggagga   1140
ggaggcagct cccagcatat ttgatgagcc tctggagaga gtgaagaaca atgaccccga   1200
gatgactgag gtgaacgtca acaactcaga ctgcatcaca aatgagatct tggtccggtt   1260
tactgaggct ctggagttca acactgtggt taagctgttc gccttggcca acacgcgagc   1320
cgatgaccac gtggcctttg ccattgccat catgctcaag gccaacaaga ccatcaccag   1380
cctcaacctg gactccaacc acatcacagg caaaggcatc ctggccatct tccgggccct   1440
cctccagaac aacacgctga ccgagctccg cttccacaac cagcgacaca tctgtggagg   1500
caagacggag atggagatcg ccaagctgct gaaggagaat actaccctgc tcaagctggg   1560
ctaccatttt gagctggccg ggccccgaat gactgtcacc aatctgctca gccgcaacat   1620
ggacaagcag agacaaaagc ggctgcagga gcaaaggcag gcacaggaag ccaagggaga   1680
gaagaaggat ctgctggagg tacccaaggc cggggccgtg gctaagggct ccccaaaacc   1740
ttcacctcaa ccatctccaa agccctctcc aaagaactca cccaaaaaag ggggtgctcc   1800
agctgcccca ccacccccctc cccctccctt ggctccaccc cttatcatgg agaacctgaa   1860
gaattcactc tcaccagcta cccagaggaa gatgggagac aaagtcctcc ctgcccagga   1920
gaagaactcc cgtgaccagc tattggctgc catccgctcc agcaacctca agcagctcaa   1980
gaaggtggaa gtgcccaaac tgcttcagta ggaccaggct gccaggcacc atctgccaat   2040
gccatgactg ctcaggcctc acctcccagg gctacacaga ccctgcccac cccatccctg   2100
gctgacctgc tgtggatgtc cctattctgc catgggagag tccaggcctg ggtcacgctc   2160
aaggaaggat gccttatctc ttctcacttt ccttttcttg tctctgaggc tctccaaatt   2220
ttgctttagt acatggagct caggtttctg gacaagaaga gtccttttag cacatcactg   2280
agaagatggc actgtccagg gcccatgtag ctggcaagct gcaaaaggcc tgtgatccag   2340
gaaagatgtc ccacagggac cacatccacc ccagccccac tgccctccag ggccaggatt   2400
caggcctctg aggagcccac ggggcaaagc tgctgggcca gtggcactct gtgtgggaaa   2460
```

-continued

```
atggcagaaa gatggagagg catgggggcc caaaggggag cgtggggagg ggctgaggat   2520
accccaaagt ccaggctaat tagaggatgt ggcaggggca gtggcctgga tgcacagtgc   2580
ctgatgggag taggctccag acaggaggag tgggacagac agcagctgga cttgaaggtt   2640
tgatgccaaa gcagacattt tcctcacacc cacctgctgc tgtatgaata gctgtgtatc   2700
tgtttttcca taagattttg ataatatata caaaccttta gctgtgaatg gctgtgcccc   2760
acctgttgtc ctgaactgtg agtcctgatc ctaaccctgg gctccctgga ggactctaga   2820
agctcaggtt ccctgccaca ctatttgagt tggccaagaa ataaattcac atcctcagaa   2880
agtgcagcat ggaggaaaat ctgaactcta agcagaagac tctccactga cctggttgtc   2940
caggtctaga aggccaggcc tctactaggt ctgctcctga accagtcctg ctgcctggag   3000
tcagtagcca gagttgttct caggggtgct ggggcagagt ggagcccagg gtgctgggat   3060
ggctatatta ggcatgttca gggatgctca ttccatgact ctgcctaacc atgggctcag   3120
ggccaggtcc tcacagcagt cacaggccca ggaaggcggc aggcagagaa gtggagtgac   3180
tatttggaga atagcaccca tatctgtgtg ccctagggct cagaggggcc tcatcttccc   3240
cagccctccc cacctgctca ccaattccac ttcctgcccc aactgcagga atgctgacaa   3300
tgctgccatg cccaccatcg ggtgtaggtg aaaggcatct ttctgaattt cattctcttg   3360
aaggtgctgc caccccttgg cactgtggaa ctgccacctt gggtctgtgt cacttgtagg   3420
tttctctgcc tccaggttgc ctcaacagca ggaggcacag cagtttcacc atctttgagg   3480
tgagggtggg gtgccccagc taggaagcaa gatcgctgtg ctaggtctga ccaaaaccag   3540
agggcagtct agtcctgggg gtaaagccct cagatcccag ggtacactct tctccattcc   3600
ctccacccac ttgcctgtca ccccagtcac ctaagcaatc actgggccca gaggagagga   3660
gacagacaca cactggctcc tggacctaaa gggtatgagc tggagctaag gccagctaga   3720
gcttccactg tcagccctca ctgtcagtcc cactgcaccc ccctgtgcct gctgggcact   3780
gggcactagc tagatgcttt aggttgcttc agctgatcct tcaactctgt gaggtggata   3840
ccaatattct attttgcaga tagaatttgg cccagagagg ttaactaata tatccatgat   3900
cacacagcta ataaaagtca gagctca                                       3927
```

<210> SEQ ID NO 32
<211> LENGTH: 1038
<212> TYPE: DNA
<213> ORGANISM: Homo sapiens

<400> SEQUENCE: 32

```
agagagaagg cagggctgaa atacggtgtg gccatggcac aggctccttc ccacagcttg     60
gctcagcagg atggttagat ttcccacgcg tcaaaagaat gctgaggaag gccttcacaa    120
tgaacagaaa gctgcagttt cctcctctgt attctttctc cactcccact cgcctcatgt    180
accccactga cccaggtatg agaaacccag cctgcacctt ctatagcacc acatgcctag    240
actgaggaaa gatccacaaa tgccactctt cttcgaatag cctaccttca tgaagtctca    300
ccaacccgct gaatatggac tccaacggtg ccctagggga tggtggagcc accagatgga    360
aggagcctgg tgatcccgag aaggagagat gcctcgctga cctgaacatc tttccagaac    420
tgttaaatga agcctgcagg acaccagctg acagtggaag gactgaggaa ggttgtataa    480
ttttgtgcaa ggtccaccac aaatccagct gaagaactgc tccaaagttt aggtcatggc    540
aagaacaaga ctggatcact ccatgtcagt ggaaacatgt ccaccaactt catcattgtc    600
tgttgtcatg gttcacttta gatgtaaact tgactggatt aaggattccc taaagtgtca    660
```

```
ggcctctgag cccaagctaa gccatcatat cccctgtgac ctgcatgtac acatccagat    720
ggccggttcc tgccttaact gacgacattc caccacaaaa gaagtgaaaa tggcctgttc    780
ctgccttaac tgatgacatt atcttgtgaa attccttctc ctggctcatc ctggctccaa    840
agctccccca ctgagcacct tgtgaccccc actcctgccc accagagaac aacccccttt    900
gactgtaatt ttcctttacc ttcccaaatc ttataaaatg gccccacccc atctcccttt    960
gctgactttc ttttcagact cagccctcct gcaaccagtt gattaaaagc tttattgctc   1020
acaaaaaaaa aaaaaaaa                                                 1038
```

<210> SEQ ID NO 33
<211> LENGTH: 6045
<212> TYPE: DNA
<213> ORGANISM: Homo sapiens

<400> SEQUENCE: 33

```
ctccggtgtt gatgcaaact caagccggct ctcactgtgg cttgtggctc cgggaaatgg     60
aacccagctt gggacaggga tgggaatgga tttgacttgt ccttttggca tctccccagc    120
ctgtggagcc caggcctctt ggagcatctt tggggctgac gcagcggagg ttccgggcac    180
acgtggccac tcccagcagg aggctgccat gccccacatt cccgaggacg aggagccccc    240
cggagagcca caggcagccc agagccctgc cggccaaggt cctcctgccg caggagtatc    300
ttgcagtcca actcccacga ttgtcctgac tggggatgcc acttcaccag aaggagaaac    360
cgacaaaaac ctggccaaca gagttcacag tccccacaag aggctttctc accgacactt    420
gaaggtgtcc actgcctccc tgacatctgt ggaccccgcg gggcacatca ttgacctggt    480
gaatgaccag ctgccagaca tcagcatctc agaggaggac aagaagaaaa acctggcgct    540
gctggaagaa gccaagttgg tgagtgagcg attcctgacc cgccgtggga ggaagtccag    600
gagcagcccc ggagactccc catcagctgt ttccccgaac ctcagcccca gcgcttctcc    660
tacatcctct cggagcaact cacttacagt ccccaccccg ccaggtttgg atgtgtgcag    720
tggcccgcca tcccctctgc ctggagcacc accacagcag aagggggatg aggccgacgt    780
ctcttcacct caccctggcg agcctaacgt ccccaaaggg ctagctgaca ggaagcagaa    840
tgaccagagg aaagtgtctc agggcaggct ggctcctcgt cctcctccag ttgagaagtc    900
caaagagatt gcaatagaac aaaaggaaaa cttcgatccc ctccagtacc ccgagaccac    960
acccaaaggc ctagctcctg ttacaaacag cagtgggaaa atggccctga acagccctca   1020
gcctggcccc gtggagagcg agctggggaa gcagctcttg aaaacgggct gggagggcag   1080
ccctctgccg agaagtccaa cccaggatgc ggcaggagtg ggtcccccag cctcccaggg   1140
gagaggccca gctggagagc cgatggggcc cgaggctggc tccaaagctg agcttccacc   1200
cactgtgtcc cggcccccgc tgctgcgagg gctctcctgg gacagtggcc ctgaagaacc   1260
tggcccccgg ctgcagaaag tgcttgccaa gctgccactg gcagaggaag aaaagcgttt   1320
tgcaggcaag gccggcggca agctggccaa ggcccctggt ctcaaagact ttcagataca   1380
agtgcagccc gtgcggatgc agaaactgac caagctccga gaggagcaca tcctgatgag   1440
aaatcagaac ttagtggggc tcaagcttcc agaccttagt gaagcagctg agcaggaaaa   1500
agggcttcct tctgaactct ccccagctat tgaggaagaa gagtcaaaga gtggcttaga   1560
tgtcatgcct aatatttctg atgtgctgct gcgcaaactg cgggtccaca ggagtctccc   1620
tggaagtgcc cctccactca ctgaaaagga agttgagaac gtgtttgtgc aactgtcctt   1680
```

-continued

```
ggcctttaga aatgacagct acactctgga atctagaatt aaccaggctg aaagggaacg   1740
caacctgaca gaggagaaca ctgagaaaga actggaaaac ttcaaagctt ccattacgtc   1800
ctcagcttca ctctggcacc actgtgagca ccgggaaacc taccagaagt tgctggagga   1860
catcgctgtc ctgcaccgcc tggctgcccg cctctccagc cgagctgagg tggtaggcgc   1920
cgtccgccag gaaaagcgca tgtcgaaagc aacggaagtg atgatgcagt atgtggagaa   1980
tctaaagagg acgtatgaga aggaccatgc ggagctcatg gagtttaaaa agcttgcaaa   2040
tcagaattca agccgcagct gtggcccctc tgaagatggg gtccctcgca cggcacggtc   2100
catgtccctc acgctgggaa agaatatgcc tcgccggagg gtcagcgttg ctgtggttcc   2160
taagtttaat gccctgaatc tgcctggcca aactcccagc tcatcatcca ttccctcctt   2220
accagccttg tcggaatcac ccaatgggaa aggcagccta cctgtcactt cagcactgcc   2280
tgcacttttg gaaaatggaa agacaaatgg ggacccagat tgtgaagcct ctgctcctgc   2340
gctgaccctg agctgcctgg aggagcttag tcaggagacc aaggccagga tggaggaaga   2400
agcctacagc aagggattcc aagaaggtct aaagaagacc aaagaacttc aagacctgaa   2460
ggaggaggag gaagaacaga agagtgagag tcctgaggaa cctgaagagg tagaagaaac   2520
tgaggaagag gaaaagggcc caagaagcag caaacttgaa gaattggtcc atttcttaca   2580
agtcatgtat cccaaactgt gtcagcactg gcaagtgatc tggatgatgg ctgcagtgat   2640
gctggtcttg actgttgtgc tggggctcta caattcctat aactcttgtg cagagcaggc   2700
tgatgggccc cttggaagat ccacttgctc ggcagcccag agggactcct ggtggagctc   2760
aggactccag catgagcagc ctacagagca gtaggaaacc tcacacctag ccagtgccct   2820
gctctgagac actcagacta ccaccctttc cccaagtata acgtcaggcc caagtgtgga   2880
cacactgccg cccatcccat caggtcatga ggaagggttc ttttaacact cggcacttct   2940
gtgggagcta ttcatacaca gtgacttgat gttcttggag gatcaacaaa actgccctgg   3000
gaaagcatcc agtggatgaa gaagtcacct tcaccaagga actctattgg aagggaaggt   3060
ctcctgcccc tagctcaggt ggctggggag aactaaaaca ccttcactgg tggttggggg   3120
taaggagcgg ggcacggggg aggaggaggt agggggcagt aaaaaactta ctctcttttt   3180
tcctctctgt aattggttat caggaagaat ttgcttaatg actaacaccc taagcatcag   3240
acctggaatt tggagttgca aagtgactat cttcccattt cccatctcat tttcaataac   3300
ttcagcctcc cattctttcc tttggaatga gagtttcttt ttacagaagt aggaaaggct   3360
tctcagaaaa aaaaaaaaaa gtataggctg aatttagctc agtgcttgaa atgggaagat   3420
atgaattatt atatacgcat ctgtccacac atacacacat actgttgtgt acacacacac   3480
aacatgcctg tgcacagagc caacaaccct tcaaaagtgt gctctgggtg tgtacctctg   3540
gataaataag atgcatgcca agccaaccca cagattttca ccagtgtggg gcagtcacca   3600
ggcacctgtt caatgagctg tccacatgga ttgaagatgt tttaaaaaca cagaaaactc   3660
atggcttcaa tggcagactt actagtctcc atttcaaatg ccaactctga gctgctgtac   3720
agcacaatct attccctatt ctctctttga aaacagttaa cccacctcac aggtgaatga   3780
ggagagaaga tgtgctttct gcttcagtct cttactctgt gtgtgaccac atgcaagagt   3840
aaacttgcac ctcagtgctt cagttcaaat ggggtttcca accccagtat aattaggggt   3900
gtttcagagc atccccagtt atttagcaca acactgaagg agcacatccc ctctccattt   3960
tgacttctct ccccactttt acagccactg ccttcatcag ttttgtagag gtttgatttc   4020
catgtgggtt ttgttgtcat tgttttgcat ttttgttttg ttattgatat tgtttgcttt   4080
```

```
cattgctaaa actcatatac gacttactat gagccaagca ctgttctcag tattacatag   4140

gtatgaattc atttaagtcc tgaagaaaaa gaaaaaaaaa tacgaagtgg atattaccct   4200

tcccattttc aaataaggaa actgaagcac aaaaagaaca agtaacttga caaggacacc   4260

ccggtagtaa atcatggggc tggagctcaa ccccagggta ggctggctcc agagctgtgc   4320

tctccttgac tcttctgatg gtctcctagc tggaagcctc acatttcagt ctcattcccc   4380

caagtggccc atcagctact ccatctctgg ctccccaact aaacagtttc tctcatagtg   4440

ctggacctcc actcactagt ttttttcca gctgttcttc tcttttcttc aggtcactct   4500

tctcgaccga gtgcaaaaat tatcccctcc ataccagctt tgatgacctt ccttccatac   4560

tcctcaccag acacaacata ataggtcaca cactcctctg tgctttctgg cacgttttaa   4620

acattattat tattgacctt tacctatagt ataccatggc ctatttatgt atccatctcc   4680

cctagcattt ttcctcaaag acaagaacca tgtcttaccc atctcttggg taagtgccta   4740

gcatggtggc tgacgcttgg gagggtgtca ttaaatgttg ctcaaaagaa caagcaaaca   4800

tttaaggtgg tggagagcag cctggggaca gctgacatgc tgcatgcttc tcagtaccag   4860

caccatcaca atgcaaaaag caacatcttt cttaacctca gcttattctg tttttcagtc   4920

tactctgtga gagagcagga atgagaccag actagcaaca ccattgccaa gctcaaggac   4980

tgggctcaat gcagtcactc cttcagagag accccccacc ccaagcatgc cccactttaa   5040

aatagcatgt ttattgaagg gggcatcctt tacagtagct agaaaatgac tgaggcccaa   5100

gccagggttg atcaaggatg tgccattaag gtaaagagtt acagagcagg gcagagggac   5160

tctgggggca gaagtggatg atttgcccgg cctcttccag gggtctgga tacaactgaa   5220

ggagctttag ctacatgagg ccctcagagc caaagacagg atgcaaatag agttctagag   5280

agtggccgtg gaagcagaac tccaggtggg gaatgttcaa tctctgcctc ccttaaagca   5340

gggccaggct cagctggccc cattgttcac ttggtcacaa gtttcctacc tttgtttctg   5400

gatgagtcaa aggccaggaa ggcagttatg gagagctcct gcacctccag ctgccccaca   5460

gaaaagcctg caagagtact tccaggcaca ggccctctcc caccctattc catttgtaag   5520

caagggaggt cgaggaaaag gacatctcca aaagggagca taagaatagc catatataca   5580

ggggctgaaa aagtgctcat gagtccatct tttctggaaa gcaaagacca gcctgaagca   5640

gtgggagctg ctgcccaagc ggtagtgaac tggagagaaa caggccctgg attttcagtg   5700

aggatgtgga tctgaagagt cccccaaatg cctctgaagt ctgacatctc tgcttagccc   5760

taggagtctg gttccctgcc ttcagttgca gagtgatgtg tttgtgtcat tgttgatgtc   5820

acctcctaaa aagaccttca ctttctggct gccacaaagc catatgtgtt gctccccata   5880

tacagcctga cagagtaaat ggagaggaag tgctggattt gtgtatcact ggctatcagt   5940

tcctcatgtt gttaagcctc acacaggtgt gctagcattg aactgtagag tgtcacatac   6000

ctgagtttga aaataaaagc acatttccaa acctcaaaaa aaaaa                    6045
```

<210> SEQ ID NO 34
<211> LENGTH: 6671
<212> TYPE: DNA
<213> ORGANISM: Homo sapiens

<400> SEQUENCE: 34

```
cagagatcgc gagcgaggca ccagcctgca gccggccccc agcacatcct cagccgcaca     60

gacactcggc gaggtggagg tgagggcggg cgccagcgaa ctcggagagg ggctcgctca    120
```

-continued

```
ctcccaggcg atcccagccg ccaccgccgc cgcaccagca gcagcaacag cagcagcagc    180
ttccttcctc agactcccct cgagaggctg gccaagcggg tgtagccgtt gggggaggct    240
cccgccgggg gaacccggcg aggacaagag cagggcggcc gccttccact cgggctgtcc    300
ggcggcggct gcctccgccc gtgtgtccgt caagggtgcc gcgggatgtg tgtcagttta    360
cgcctctgag atcacacagc tgcctggggg ccgtgtgatg cccaaggcaa gtcttggttt    420
taattattat tattatcatt attgttacgc ttggctttcg ggaaatactc gtgatatttg    480
taggataaag gaaatgacac tttgaggaac tggagagaac atatatgcgt tttgttttta    540
agaggaaaac cgtgttctct tcccggcttg ttccctcttt gctgatttca ggagctactc    600
tcctcctggt gaggtggaaa ttccagcaag aatagaggtg aagacaagcc accaggactc    660
aggagggaaa cgctgaccat tagaaacctc tgcataagac gttgtaagga ggaaaataaa    720
agagagaaaa acacaaagat ttaaacaaga aacctacgaa cccagctctg gaaagagcca    780
ccttctccaa aatggatatg tttcctctca cctgggtttt cttagccctc tacttttcaa    840
gacaccaagt gagaggccaa ccagacccac cgtgcggagg tcgtttgaat tccaaagatg    900
ctggctatat cacctctccc ggttaccccc aggactaccc ctcccaccag aactgcgagt    960
ggattgttta cgcccccgaa cccaaccaga agattgtcct caacttcaac cctcactttg   1020
aaatcgagaa gcacgactgc aagtatgact ttatcgagat tcgggatggg gacagtgaat   1080
ccgcagacct cctgggcaaa cactgtggga acatcgcccc gcccaccatc atctcctcgg   1140
gctccatgct ctacatcaag ttcacctccg actacgcccg gcagggggca ggcttctctc   1200
tgcgctacga gatcttcaag acaggctctg aagattgctc aaaaaacttc acaagcccca   1260
acgggaccat cgaatctcct gggtttcctg agaagtatcc acacaacttg gactgcacct   1320
ttaccatcct ggccaaaccc aagatggaga tcatcctgca gttcctgatc tttgacctgg   1380
agcatgaccc tttgcaggtg ggagaggggg actgcaagta cgattggctg gacatctggg   1440
atggcattcc acatgttggc cccctgattg gcaagtactg tgggaccaaa acaccctctg   1500
aacttcgttc atcgacgggg atcctctccc tgacctttca cacggacatg gcggtggcca   1560
aggatggctt ctctgcgcgt tactacctgg tccaccaaga gccactagag aactttcagt   1620
gcaatgttcc tctgggcatg gagtctggcc ggattgctaa tgaacagatc agtgcctcat   1680
ctacctactc tgatgggagg tggacccctc aacaaagccg gctccatggt gatgacaatg   1740
gctggacccc caacttggat tccaacaagg agtatctcca ggtggacctg cgctttttaa   1800
ccatgctcac ggccatcgca acacagggag cgatttccag ggaaacacag aatggctact   1860
atgtcaaatc ctacaagctg gaagtcagca ctaatggaga ggactggatg gtgtaccggc   1920
atggcaaaaa ccacaaggta tttcaagcca acaacgatgc aactgaggtg gttctgaaca   1980
agctccacgc tccactgctg acaaggtttg ttagaatccg ccctcagacc tggcactcag   2040
gtatcgccct ccggctggag ctcttcggct gccgggtcac agatgctccc tgctccaaca   2100
tgctggggat gctctcaggc ctcattgcag actcccagat ctccgcctct tccacccagg   2160
aatacctctg gagccccagt gcagcccgcc tggtcagcag ccgctcgggc tggttccctc   2220
gaatccctca ggcccagccc ggtgaggagt ggcttcaggt agatctggga acacccaaga   2280
cagtgaaagg tgtcatcatc cagggagccc gcggaggaga cagtatcact gctgtggaag   2340
ccagagcatt tgtgcgcaag ttcaaagtct cctacagcct aaacggcaag gactgggaat   2400
acattcagga ccccaggacc cagcagccaa agctgttcga agggaacatg cactatgaca   2460
cccctgacat ccgaaggttt gaccccattc cggcacagta tgtgcgggta tacccggaga   2520
```

```
ggtggtcgcc ggcggggatt gggatgcggc tggaggtgct gggctgtgac tggacagact   2580
ccaagcccac ggtagagacg ctgggaccca ctgtgaagag cgaagagaca accaccccct   2640
accccaccga agaggaggcc acagagtgtg gggagaactg cagctttgag gatgacaaag   2700
atttgcagct cccttcggga ttcaattgca acttcgattt cctcgaggag ccctgtggtt   2760
ggatgtatga ccatgccaag tggctccgga ccacctgggc cagcagctcc agcccaaacg   2820
accggacgtt tccagatgac aggaatttct tgcggctgca gagtgacagc cagagagagg   2880
gccagtatgc ccggctcatc agcccccctg tccacctgcc ccgaagcccg gtgtgcatgg   2940
agttccagta ccaggccacg ggcggccgcg gggtggcgct gcaggtggtg cgggaagcca   3000
gccaggagag caagttgctg tgggtcatcc gtgaggacca gggcggcgag tggaagcacg   3060
ggcggatcat cctgcccagc tacgacatgg agtaccagat tgtgttcgag ggagtgatag   3120
ggaaaggacg ttccggagag attgccattg atgacattcg gataagcact gatgtcccac   3180
tggagaactg catggaaccc atctcggctt ttgcaggtga gaattttaaa gtggacatcc   3240
cagaaataca tgagagagaa ggatatgaag atgaaattga tgatgaatac gaggtggact   3300
ggagcaattc ttcttctgca acctcagggt ctggcgcccc ctcgaccgac aaagaaaaga   3360
gctggctgta caccctggat cccatcctca tcaccatcat cgccatgagc tcactgggcg   3420
tcctcctggg ggccacctgt gcaggcctcc tgctctactg cacctgttcc tactcgggcc   3480
tgagctcccg aagctgcacc acactggaga actacaactt cgagctctac gatggcctta   3540
agcacaaggt caagatgaac caccaaaagt gctgctccga ggcatgacgg attgcacctg   3600
aatcctatct gacgtttcat tccagcaaga ggggctgggg aagattacat tttttttcc    3660
tttggaaact gaatgccata atctcgatca aaccgatcca gaataccgaa ggtatggaca   3720
ggacagaaaa gcgagtcgca ggaggaaggg agatgcagcc gcacagggga tgattaccct   3780
cctaggaccg cggtggctaa gtcattgcag gaacggggct gtgttctctg ctgggacaaa   3840
acaggagctc atctctttgg ggtcacagtt ctattttgtt tgtgagtttg tattattatt   3900
attattatta ttattattat attttatttc tttggtctgt gagcaactca aagaggcaga   3960
agaggagaat gacttttcca gaatagaagt ggagcagtga tcattattct ccgctttctc   4020
tttctaatca acacttgaaa agcaaagtgt cttttcagcc tttccatctt tacaaataaa   4080
actcaaaaaa gccgtccagc ttatcccatc ctctgattgt cttctgactt aagggattta   4140
ctgtggtgta ggttctgcca gccaacccta caagctgcca tttccagtcc tagcatttaa   4200
gtaggatgtt gttgccttta acttttctta tccaggggaa aattgccatt ttagggtcag   4260
catgaacagc tctttcttgt atgcgattta aaacaaactg gaaaggaaac ttcacacgtc   4320
aaaatccata gaagcgcctg gacgaggctt aaagtgcttt gtgagtgaat aggagccatt   4380
cgctaattct agacccacag tgtctggtgg tggggcttcc cttgtggggc ttctggtggt   4440
ggttttgcct tttcttttcc ctcctccatg ttcttctaaa acatatacat atatacatac   4500
acacatacac atattcttca ggtctctaag cccctggaag cagcattgtg tgatattctc   4560
agaggcaggg gaaaatagag ggaaaaatag agactattgg tatgttctcc ccatcagcga   4620
gttattgtaa ctggtcacca ctggacggga aggagaacag aggagaggga aagagaagcc   4680
caacctctgt gatcatatga gggccaaggc tgagcagtgt agacagagac cctttgaaat   4740
gcatttgtct ctcaaataga ctagtaaaca ccgacttctc ctttgggtta caaacaccat   4800
ttcaaccttt cgggagagtc agagctagga tgtacaagaa ctgattctaa ccagaagtcc   4860
```

-continued gcaagtactg tggacaagaa tgcttaacca tgctgcttca gccttgagag acctaggttc 4920
ttacacatat gcacacacgc atacacacat gcacgcacac acacatacac acatgcacgc 4980
acgcacgcat gcacaccaat ttatgttttt attaagtgcc ttgaaaaaat gaagaaaaat 5040
gtattttccc tttatgtaaa aattagtgaa tatcttatga attaaggcat tcctctttcc 5100
ctaaccccga tggctccatt cccaagtacc ccaactcact gctgatccta ttaaaggaat 5160
gagtcctgct acccgagtgg tagtcatagc cctagatgac tctcaactac tcttcaaagg 5220
gaggcatcag gaatagaatg aaactgtgtg aaggataaga ttgttcgcat caagatccaa 5280
atcttgattt catattaacg cctaaggatt gcctgtgtgc tggaaatata tttgaaactc 5340
aaccagtatg cccagcctat tgcatatcat tgtcagacca tttttgctgc tgtggtcacc 5400
cacgatttca tttgtcttat acccaggtga aaggggaagg gtgaatggga ctggctggtt 5460
cctttaaatg ttaacttatg gaaatgctag ttcaaatggt aatgtcacag tgttttgtat 5520
gcagagagca agagttcaac caacagctgt ttattcatgt gtgtgtgtct ttgctgcttt 5580
gagttctctg tatctactgt gtatgtgaat ggtcatgtgg gactcagtgg tggtgttgtg 5640
actttgacct agggtccgag tgtcacagct gatcttggca ctcggcactc attggcacag 5700
tggtagttag aggtgaaaag tagagctgtc aagcccaagg gcttagcttt agggctcctc 5760
ctgagttcgg cccacagtag aagcaagatt ttaactagcc ccttttcctc ttcaccctcc 5820
catgatgcgc agtgttcaga aagctggtaa gtcctaggga tttccagaag tagcctgcag 5880
aagaaggtaa gtttgaaagc cactccaggg gtcctgatgc tgtcatgctc agtgagccat 5940
tttacagttc tccaaagtct agccctgttt cggacctgca cttcacctct aagttatgta 6000
caactcaacc tgcatccctc taaaagtcct atatccatat tcaccattgg ctaatttgag 6060
gccctgagtg ggccttgaat gctaaaaaga agcagggtac gcagggctac atgtagatac 6120
cacaccaagg ctggaggctg gtctgtcata agacagaaag aaagacgctg ggcccaattt 6180
tgacttggcc aggggacacc ttggtgtgtt tgttatcttt atctgtgggt aggctagctg 6240
acccatctcc ttgagtcatt ccctttggga aaccccactg ccagtattga tctccttttt 6300
gccttgtact gaatgacaca ttacctccac actctcccgg actaggtggt caacagggcc 6360
acagggttgc tttctgtctt tggtggggca ggggagttga cagggatgag ggtccaagga 6420
ataagcatga atgacaagaa aacaagggaa agagttaacc tgtcacatag caggttaact 6480
ttttcagggt ttgcagttag aggtattcga ccattcactg gctgagccag atcacgggaa 6540
cttgagagct tttactgtga ttcttcaatg taaaaaataa acaacaatgt caaactgtgt 6600
ttatatgatt tgtataaagc ctttttaaga ttactattta aataaacatt ataccagaga 6660
taaaaaaaaa a 6671

<210> SEQ ID NO 35
<211> LENGTH: 2853
<212> TYPE: DNA
<213> ORGANISM: Homo sapiens

<400> SEQUENCE: 35
cggtgacgtc acccccagcg gggataaagc gcccccgccc gggtcggggc caggacgccg 60
cccggcgcgg agtggctgcc ctgcgcgggg acactcagag cccggtgggc gggaggaagg 120
cggcatgccc cagacggtga tcctcccggg ccctgcgccc tggggcttca ggctctcagg 180
gggcatagac ttcaaccagc ctttggtcat caccaggatt acaccaggaa gcaaggcggc 240
agctgccaac ctgtgtcctg gagatgtcat cctggctatt gacggctttg ggacagagtc 300

-continued

```
catgactcat gctgatgcgc aggacaggat taaagcagca gctcaccagc tgtgtctcaa    360
aattgacagg ggagaaactc acttatggtc tccacaagta tctgaagatg ggaaagccca    420
tcctttcaaa atcaacttag aatcagaacc acaggacggg aactactttg aacacaagca    480
taatattcgg cccaaacctt tcgtgatccc gggccgaagc agtggatgca gcactccctc    540
cgggattgac tgtggcagtg gacgcagcac cccttcttct gtcagtactg ttagtaccat    600
ttgcccaggt gacttgaaag ttgcggctaa gctggcccct aacattcctt tggaaatgga    660
acttcctggt gtgaagattg tacatgctca gtttaataca cctatgcagt tgtactcaga    720
tgacaatatt atggaaacac tccagggtca ggtttcaaca gccctagggg aaacaccttt    780
gatgagcgag cccacagcct cggtgccccc cgagtcggac gtgtaccgga tgctccacga    840
caatcggaat gagcccacac agcctcgcca gtcgggctcc ttcagagtgc tccagggaat    900
ggtggacgat ggctctgatg accgtccggc tggaacgcgg agtgtgagag ctccggtgac    960
gaaagtccat ggcggttcag gcggggcaca gaggatgccg ctctgtgaca aatgtgggag   1020
tggcatagtc ggtgctgtgg tgaaggcgcg ggataagtac cggcaccctg agtgcttcgt   1080
gtgtgccgac tgcaacctca acctcaagca aaagggctac ttcttcatag aaggggagct   1140
gtactgcgaa acccacgcaa gagcccgcac aaagccccca gagggctatg acacggtcac   1200
tctgtatccc aaagcttaag tctctgcagg cgtggcacgc acgcacgcac ccacccacgc   1260
gcacttacac gagaagacat tcatggcttt gggcagaagg attgtgcaga ttgtcaactc   1320
caaatctaaa gtcaaggctt tagaccttta tcctattgtt tattgaggaa aaggaatggg   1380
aggcaaatgc ctgctatgtg aaaaaaacat acacttagct atgttttgca actctttttg   1440
gggctagcaa taatgatatt taaagcaata attttttgta tgtcatactc cacaatttac   1500
atgtatatta cagccatcaa acacataaac atcaagatat ttgaaggact ctaattgtct   1560
ttccttgaca agttgatttt gcaattgtgg taaatagcaa ataacaatct tgtattctaa   1620
cataatctgc agttgtctgt atgtgtttta actattacag tgcatgttag ggagaaattc   1680
cctgaatttc tttagttttg tattcaaaca attatgccac tcgatgcaac aaacataata   1740
aatacataaa agatttaaaa aatacctaat gaagtggcat tcattgaatt caaataaaat   1800
caacatttca atgagagaac ccaatcatat tttaacatgt acactaacaa atattttaag   1860
ataaatgtgg cttcttcagg ttttataact cattactctt tcttatgagc acaaaatttc   1920
tgatgataga agcgttgaaa tttgctagtt aaaggtagtt cagtctcttt caaattaaaa   1980
gtttcacttg cttcaacaga gactctttca atttaaatat ctctttcaga tcaatattca   2040
gtcaaattga aggttcaaag tccatcactg ctgtttctta ggctcaatgg ttcaccacct   2100
cctcctcttc ccaagatggc atctccagga agaaacaatt tagacgactt cctaaggaag   2160
gcaggggctg ctggtctcct ggggtcctgc ttgtatccac tgttgaaatc cttggtttca   2220
cttgtgatct gtggtctgtt ttcttgacat agttgaggcc aggcaataat aacacctcca   2280
ctaccacctc caaaactctc agctcagctt tcctggagtc atggatcctc tgtctgagac   2340
atgcactctg cctggccctg gcgcaggcag cctaccttgc aggctctgca tggcgttacc   2400
ttgcctctca cccagggtgc ccatggcaat gctcctgact tgcatctctc acctactttc   2460
catgtccccc actggggacg tacaggaact tctgaaactg tcccctcagg ttcaaaccat   2520
ggggaaccag cagggtgggg accctcagac cctctgtctc accaccttgt gtcacatggt   2580
catctctacc acccctcaac ccccacagct gctaacttct ggcctgaaac aagtgttctc   2640
```

ctcccataag gtcccaaatg ggacacaagt tttattgctc tgggattctt ccaaacttaa 2700
ctgactctga ccctgacctg ttcaggattt tgagaggagc caaaacacgt gcctggcccc 2760
tgtaggcatt tgacattgca actcctgtgc caacacatgc attcactaac aaagctatta 2820
aaaaaataaa acagactttt gagatcaaag aaa 2853

<210> SEQ ID NO 36
<211> LENGTH: 3492
<212> TYPE: DNA
<213> ORGANISM: Homo sapiens

<400> SEQUENCE: 36
aactcagtgc tgcctgtcac acctgagcca gcagtttgtg caaccagagg agcgcaggca 60
gggttccctg ctggggcccg ggctgcccag ccatgctttg ggcactctgg ccaaggtggc 120
tggcagacaa gatgctgccc ctcctggggg cagtgctgct tcagaagaga gagaagaggg 180
gccctctgtg gaggcactgg cggcgggaaa cctacccata ctatgacctc caggtgaagg 240
tgctgagggc cacaaacatc cggggcacag acctgctgtc caaagccgac tgctatgtgc 300
aactgtggct gcccacggcg tccccaagcc ctgcccagac taggatagtg gccaactgca 360
gtgaccccga gtggaatgag accttccact accagatcca tggtgctgtg aagaacgtcc 420
tggagctcac cctctatgac aaggacatcc tgggcagcga ccagctctct ctgctcctgt 480
ttgacctgag aagcctcaag tgtggccaac ctcacaaaca caccttccca ctcaaccacc 540
aggattcaca agagctgcag gtggaatttg ttctggagaa gagccaggtg cctgcatctg 600
aagtcatcac caacggggtt ctggtggctc acccctgtct gagaatccag ggcacgctcc 660
ggggagatgg gacagcccca cgggaagagt acggctctag gcagctccag ctggcagtgc 720
ctggagccta cgagaagcca cagctcttgc ccctgcagcc tcccacagag ccaggcctcc 780
cacccacctt taccttccac gtgaacccag tgctgagctc caggctacac gtggagctga 840
tggagctgct ggcagctgtg cagagtggcc ccagcgcaga gttggaggct cagaccagca 900
agctgggcga ggggggcatc ctgctctcct ctctgcccct aggccaggag gaacagtgtt 960
ctgtggccct gggggagggc caggaggtgg ctctgagcat gaaggtggaa atgagctccg 1020
gggacctaga cctacgcctt ggctttgacc tctctgacgg ggagcaggag tttctggaca 1080
ggaggaagca ggtcgtgtcc aaggccctgc agcaagtgct gggattgagt gaggctctgg 1140
acagtggcca ggtgcctgta gtggctgtgt tgggttccgg gggtggaacc cgagccatgt 1200
cttctctgta cggcagcctg gcagggttgc aggagctcgg ccttctagac actgtgacct 1260
acctgagtgg ggtctctggg tctacctggt gcatctccac actctacagg gacccagcct 1320
ggtcccaggt ggccttgcag ggccccattg agcgtgccca ggttcacgtc tgcagcagta 1380
agatgggagc tttgtccacg gagcggctac agtactacac tcaggaactg ggggtccggg 1440
agcgcagtgg ccacagcgtg tccctcatcg acctctgggg cctccttgtt gagtatctcc 1500
tgtaccagga ggagaaccct gccaagctgt ctgaccaaca ggaggcggtc cgccagggtc 1560
agaaccctta ccccatttac accagtgtca acgtccgcac caacttgagt ggggaagatt 1620
ttgcagagtg gtgcgagttc acgccctatg aggttggctt ccccaagtac ggggcttatg 1680
ttcccaccga gctcttcggc tcagaactct tcatgggacg attgctgcag ctccagcctg 1740
aaccccggat ctgttacctg caaggtatgt ggggcagcgc ctttgccacc agcctggatg 1800
agatcttcct aaagaccgcc ggctcgggcc tcagcttcct ggagtggtac agaggcagtg 1860
tgaatatcac agacgactgc cagaagcctc agctgcacaa cccctcgagg ctgcgaacga 1920

-continued

```
ggctcctcac cccacagggg cccttctccc aggctgtgct ggacatattc acctcccgct   1980
tcacttccgc ccagagcttt aacttcaccc ggggtctctg cttgcacaag gactatgtgg   2040
ctggcaggga gttcgtggcc tggaaagaca cacacccgga cgccttcccc aaccagctca   2100
cccccatgcg ggactgcctg tacctggtgg acggaggctt tgccatcaac tctccgttcc   2160
cactggctct gctgcctcag agagcagtgg acctcattct gtcctttgac tattccttgg   2220
aagccccttt tgaggtcttg aagatgacag agaagtactg cctggaccga ggaatcccct   2280
tccctagcat cgaggtgggc cctgaggaca tggaggaggc ccgtgagtgc tatctgtttg   2340
ccaaggctga ggacccccgc tcccccattg tgctgcactt ccccctggtt aaccgtacct   2400
tccgcacaca cctggcccca ggtgtggagc gacaaacagc tgaggagaag gcctttgggg   2460
actttgtcat caacaggcca gacacccccct atggcatgat gaacttcacc tatgagcccc   2520
aggactttta tcggctggtg gccctcagtc gatacaacgt cctgaacaac gtggagacct   2580
tgaagtgcgc cctccagctg gctctggacc ggcaccaggc tcgggagagg gcaggggcct   2640
gaccaaggca ggaagcggag gactgtgaca gagaggagac acactgctca tggtcagggc   2700
ttgtagaggg aggagcgatg gggactctgt gcaggatctg cttcccttct ctccaggacc   2760
tgcctcgagg tgccccaggc cccggaaagc tcttgcagaa ttgcagcttg gactggggca   2820
gggctctcct tgtgtgtttt tggagaagat gggcagtaga tcgctccagg gactcttggg   2880
gatgtagggc agaagagaac agcactcatt tcacagcggg gtgtggagag aatcaggtga   2940
gccacagagc ccaccccaga cacagaagga cctcagaggg cccaagtcct cagacccaca   3000
cagaacaggg gctgagggca ctgagaagcc agctgtcctc cttacactga gatggaaagc   3060
agagatgcat ccatccacac ttcctgcaga gcggcccaag ccccaacccc acctcgagct   3120
cctggatgca ctgctatcaa gaacaatgag gggctgaggg gatggccagc ctatgttgct   3180
gactccatca tcctaaccct ccttctgcct tctggtctcc tcgtgcctcc tcccagatca   3240
cccttctctt cccagcgccc taaagcctgt ggggtgatgt cccattctgg ctgctccagg   3300
tgggagatgt gcgcgtgtct ccctgccagt tacccaggct tcactcttcg aacctggacc   3360
acagtctctg gtgatgtgtg tagtggccac atcatgcaaa tatagtctca ccattcctag   3420
gagctaaatg ggtgtgtcta gtaggggcat cagttcatcg gggagaggt gtgcacctgt   3480
atgtggggca gg                                                       3492
```

<210> SEQ ID NO 37
<211> LENGTH: 3180
<212> TYPE: DNA
<213> ORGANISM: Homo sapiens

<400> SEQUENCE: 37

```
ttctcctgcc cgcgcctggg gggaccctac gcctgtgtcc gaaggaggcc ggcgtccagc     60
agatgctccc ggggcgggtg gggagtgggg gaagggggcg ggagagaggc ggggaggaga    120
aaacccacaa caaaacttgc gtcgcggaga gcgcccagct tgacttgaat ggaaggagcc    180
cgagcccgcg gagcgcagct gagactgggg gagcgcgttc ggcctgtggg gcgccgctcg    240
gcgccggggc gcagcaggtt ccgtcagccc tggcgcccag gcgcatctga ctcggcaccc    300
cctgcaggca ccatggccca gagccgggtg ctgctgctcc tgctgctgct gccgccacag    360
ctgcacctgg gacctgtgct tgccgtgagg gccccaggat ttggccgaag tggcggccac    420
agcctgagcc ccgaagagaa cgaatttgcg gaggaggagc cggtgctggt actgagccct    480
```

-continued

```
gaggagcccg ggcctggccc agccgcggtc agctgccccc gagactgtgc ctgttcccag    540
gagggcgtcg tggactgtgg cggtattgac ctgcgtgagt tcccggggga cctgcctgag    600
cacaccaacc acctatctct gcagaacaac cagctggaaa agatctaccc tgaggagctc    660
tcccggctgc accggctgga gacgctgaac ctgcaaaaca accgcctgac ttcccgaggg    720
ctcccagaga aggcgtttga gcatctgacc aacctcaatt acctgtactt ggccaataac    780
aagctgacct tggcaccccg cttcctgcca aacgccctga tcagtgtgga ctttgctgcc    840
aactatctca ccaagatcta tgggctcacc tttggccaga agccaaactt gaggtctgtg    900
tacctgcaca acaacaagct ggcagacgcc gggctgccgg acaacatgtt caacggctcc    960
agcaacgtcg aggtcctcat cctgtccagc aacttcctgc gccacgtgcc caagcacctg   1020
ccgcctgccc tgtacaagct gcacctcaag aacaacaagc tggagaagat cccccccgggg   1080
gccttcagcg agctgagcag cctgcgcgag ctatacctgc agaacaacta cctgactgac   1140
gagggcctgg acaacgagac cttctggaag ctctccagcc tggagtacct ggatctgtcc   1200
agcaacaacc tgtctcgggt cccagctggg ctgccgcgca gcctggtgct gctgcacttg   1260
gagaagaacg ccatccggag cgtggacgcg aatgtgctga cccccatccg cagcctggag   1320
tacctgctgc tgcacagcaa ccagctgcgg gagcagggca tccacccact ggccttccag   1380
ggcctcaagc ggttgcacac ggtgcacctg tacaacaacg cgctggagcg cgtgcccagt   1440
ggcctgcctc gccgcgtgcg caccctcatg atcctgcaca accagatcac aggcattggc   1500
cgcgaagact ttgccaccac ctacttcctg gaggagctca acctcagcta caaccgcatc   1560
accagcccgc aggtgcaccg cgacgccttc cgcaagctgc gcctgctgcg ctcgctggac   1620
ctgtcgggca accggctgca cacgctgcca cctgggctgc ctcgaaatgt ccatgtgctg   1680
aaggtcaagc gcaatgagct ggctgccttg gcacgagggg cgctggtggg catggctcag   1740
ctgcgtgagc tgtacctcac cagcaaccga ctgcgcagcc gagccctggg cccccgtgcc   1800
tgggtggacc tcgcccatct gcagctgctg gacatcgccg ggaatcagct cacagagatc   1860
cccgaggggc tccccgagtc acttgagtac ctgtacctgc agaacaacaa gattagtgcg   1920
gtgcccgcca atgccttcga ctccacgccc aacctcaagg ggatctttct caggtttaac   1980
aagctggctg tgggctccgt ggtggacagt gccttccgga ggctgaagca cctgcaggtc   2040
ttggacattg aaggcaactt agagtttggt gacatttcca aggaccgtgg ccgcttgggg   2100
aaggaaaagg aggaggagga agaggaggag gaggaggaag aggaaacaag atagtgacaa   2160
ggtgatgcag atgtgaccta ggacgatgga ccgccggact cttttctgca gcacacgcct   2220
gtgtgctgtg agccccccac tctgccgtgc tcacacagac acacccagct gcacacatga   2280
ggcatcccac atgacacggg ctgacacagt ctcatatccc caccccttcc cacggcgtgt   2340
cccacggcca gacacatgca cacacatcac accctcaaac acccagctca gccacacaca   2400
actaccctcc aaaccaccac agtctctgtc acacccccac taccgctgcc acgccctctg   2460
aatcatgcag ggaagggtct gcccctgccc tggcacacac aggcacccat tccctccccc   2520
tgctgacatg tgtatgcgta tgcatacaca ccacacacac acacatgcac aagtcatgtg   2580
cgaacagccc tccaaagcct atgccacaga cagctcttgc cccagccaga atcagccata   2640
gcagctcgcc gtctgccctg tccatctgtc cgtccgttcc ctggagaaga cacaagggta   2700
tccatgctct gtggccaggt gcctgccacc ctctggaact cacaaaagct ggcttttatt   2760
cctttcccat cctatgggga caggagcctt caggactgct ggcctggcct ggcccaccct   2820
gctcctccag gtgctgggca gtcactctgc taagagtccc tccctgccac gccctggcag   2880
```

gacacaggca cttttccaat gggcaagccc agtggaggca ggatgggaga gccccctggg 2940
tgctgctggg gccttggggc aggagtgaag cagaggtgat ggggctgggc tgagccaggg 3000
aggaaggacc cagctgcacc taggagacac ctttgttctt caggcctgtg ggggaagttc 3060
cgggtgcctt tattttttat tcttttctaa ggaaaaaaat gataaaaatc tcaaagctga 3120
tttttcttgt tatagaaaaa ctaatataaa agcattatcc ctatccctgc aaaaaaaaaa 3180

<210> SEQ ID NO 38
<211> LENGTH: 3301
<212> TYPE: DNA
<213> ORGANISM: Homo sapiens

<400> SEQUENCE: 38
gccagttctc ttcggggact aactgcaacg gagagactca agatgattcc ctttttaccc 60
atgttttctc tactattgct gcttattgtt aaccctataa acgccaacaa tcattatgac 120
aagatcttgg ctcatagtcg tatcaggggt cgggaccaag gcccaaatgt ctgtgccctt 180
caacagattt tgggcaccaa aaagaaatac ttcagcactt gtaagaactg gtataaaaag 240
tccatctgtg gacagaaaac gactgtgtta tatgaatgtt gccctggtta tatgagaatg 300
gaaggaatga aaggctgccc agcagttttg cccattgacc atgtttatgg cactctgggc 360
atcgtgggag ccaccacaac gcagcgctat tctgacgcct caaaactgag ggaggagatc 420
gagggaaagg gatccttcac ttactttgca ccgagtaatg aggcttggga caacttggat 480
tctgatatcc gtagaggttt ggagagcaac gtgaatgttg aattactgaa tgctttacat 540
agtcacatga ttaataagag aatgttgacc aaggacttaa aaaatggcat gattattcct 600
tcaatgtata acaatttggg gcttttcatt aaccattatc ctaatggggt tgtcactgtt 660
aattgtgctc gaatcatcca tgggaaccag attgcaacaa atggtgttgt ccatgtcatt 720
gaccgtgtgc ttacacaaat tggtacctca attcaagact tcattgaagc agaagatgac 780
ctttcatctt ttagagcagc tgccatcaca tcggacatat tggaggccct tggaagagac 840
ggtcacttca cactctttgc tcccaccaat gaggcttttg agaaacttcc acgaggtgtc 900
ctagaaagga tcatgggaga caaagtggct tccgaagctc ttatgaagta ccacatctta 960
aatactctcc agtgttctga gtctattatg ggaggagcag tctttgagac gctggaagga 1020
aatacaattg agataggatg tgacggtgac agtataacag taaatggaat caaaatggtg 1080
aacaaaaagg atattgtgac aaataatggt gtgatccatt tgattgatca ggtcctaatt 1140
cctgattctg ccaaacaagt tattgagctg gctggaaaac agcaaaccac cttcacggat 1200
cttgtggccc aattaggctt ggcatctgct ctgaggccag atggagaata cactttgctg 1260
gcacctgtga ataatgcatt ttctgatgat actctcagca tggatcagcg cctccttaaa 1320
ttaattctgc agaatcacat attgaaagta aaagttggcc ttaatgagct ttacaacggg 1380
caaatactgg aaaccatcgg aggcaaacag ctcagagtct tcgtatatcg tacagctgtc 1440
tgcattgaaa attcatgcat ggagaaaggg agtaagcaag ggagaaacgg tgcgattcac 1500
atattccgcg agatcatcaa gccagcagag aaatccctcc atgaaaagtt aaaacaagat 1560
aagcgcttta gcaccttcct cagcctactt gaagctgcag acttgaaaga gctcctgaca 1620
caacctggag actggacatt atttgtgcca accaatgatg cttttaaggg aatgactagt 1680
gaagaaaaag aaattctgat acgggacaaa aatgctcttc aaaacatcat tctttatcac 1740
ctgacaccag gagttttcat tggaaaagga tttgaacctg gtgttactaa cattttaaag 1800
accacacaag gaagcaaaat ctttctgaaa gaagtaaatg atacacttct ggtgaatgaa 1860
ttgaaatcaa aagaatctga catcatgaca acaaatggtg taattcatgt tgtagataaa 1920
ctcctctatc cagcagacac acctgttgga aatgatcaac tgctggaaat acttaataaa 1980
ttaatcaaat acatccaaat taagtttgtt cgtggtagca ccttcaaaga aatccccgtg 2040
actgtctata caactaaaat tataaccaaa gttgtggaac caaaaattaa agtgattgaa 2100
ggcagtcttc agcctattat caaaactgaa ggacccacac taacaaaagt caaaattgaa 2160
ggtgaacctg aattcagact gattaaagaa ggtgaaacaa taactgaagt gatccatgga 2220
gagccaatta ttaaaaaata caccaaaatc attgatggag tgcctgtgga aataactgaa 2280
aaagagacac gagaagaacg aatcattaca ggtcctgaaa taaaatacac taggatttct 2340
actggaggtg gagaaacaga agaaactctg aagaaattgt tacaagaaga ggtcaccaag 2400
gtcaccaaat tcattgaagg tggtgatggt catttatttg aagatgaaga aattaaaaga 2460
ctgcttcagg gagacacacc cgtgaggaag ttgcaagcca acaaaaaagt tcaaggatct 2520
agaagacgat taagggaagg tcgttctcag tgaaaatcca aaaaccagaa aaaaatgttt 2580
atacaaccct aagtcaataa cctgacctta gaaaattgtg agagccaagt tgacttcagg 2640
aactgaaaca tcagcacaaa gaagcaatca tcaaataatt ctgaacacaa atttaatatt 2700 ttttttctg aatgagaaac atgagggaaa ttgtggagtt agcctcctgt ggtaaaggaa 2760
ttgaagaaaa tataacacct tacacccttt ttcatcttga cattaaaagt tctggctaac 2820
tttggaatcc attagagaaa aatccttgtc accagattca ttacaattca aatcgaagag 2880
ttgtgaactg ttatcccatt gaaaagaccg agccttgtat gtatgttatg gatacataaa 2940
atgcacgcaa gccattatct ctccatggga agctaagtta taaaaatagg tgcttggtgt 3000
acaaaacttt ttatatcaaa aggctttgca catttctata tgagtgggtt tactggtaaa 3060
ttatgttatt ttttacaact aattttgtac tctcagaatg tttgtcatat gcttcttgca 3120
atgcatattt tttaatctca aacgtttcaa taaaaccatt tttcagatat aaagagaatt 3180
acttcaaatt gagtaattca gaaaaactca agatttaagt taaaaagtgg tttggacttg 3240
ggaacaggac tttatacctc ttttactgta acaagtactc attaaaggaa attgaatgaa 3300
a 3301

<210> SEQ ID NO 39
<211> LENGTH: 4071
<212> TYPE: DNA
<213> ORGANISM: Homo sapiens

<400> SEQUENCE: 39
tgattcgagc gggaagaggg gggtgggtgg gatcggtggg ggagaccatg acctccagct 60
acgggcacgt tctggagcgg caaccggcgc tgggcggccg cttggacagc ccgggcaacc 120
tcgacaccct gcaggcgaaa aagaacttct ccgtcagtca cctgctagac ctggaggaag 180
ccggggacat ggtggcggca caggcggatg agaacgtggg cgaggctggc cggagcctgc 240
tggagtcgcc gggactcacc agcggcagcg acaccccgca gcaggacaat gaccagctga 300
actcagaaga aaaaaagaag agaaagcagc gaaggaatag gacaaccttc aatagcagcc 360
agctgcaggc tttggagcgt gtctttgagc ggacacacta tcctgatgct tttgtgcgag 420
aagaccttgc ccgccgggtg aacctcaccg aggcgagagt gcaggtgtgg tttcagaacc 480
gaagagccaa gttccgcagg aatgagagag ccatgctagc caataaaaac gcttccctcc 540
tcaaatccta ctcaggagac gtgactgctg tggagcagcc catcgtacct cgtcctgctc 600

```
cgagacccac cgattatctc tcctgggggga cagcgtctcc gtacagatcc tcgtccctcc    660
caagatgttg tttacacgag ggcttcata acggattcta acggaagaca ctgaaaagcg     720
ccatggctac ttattctgcc acatgtgcca acaatagccc tgcacagggc atcaacatgg    780
ccaacagcat tgccaacctg agactgaagg ccaaggaata tagtttacag aggaaccagg    840
tgccaacagt caactgagga aaaaaaataa ttaaacaggc ctaagaagaa atcaaaaacc    900
ataagacacc tatcctgctc tgttatttct tcatctgctg gggggaaaaa gtaaattaca    960
aacaaacaaa caaagcagaa ctaaaatatt gggaccatgg cagagaaaag caggagagga   1020
gcaaaatgaa aattagttaa caaatgttcc tcctccctct gggataccac caccacttgt   1080
ttctgtgtgt gtttattttg tttttctttc attcatgctt tgcttaatgt actccaggct   1140
tcttcagcta ggttcagccc acccaccccc atgattgtat gaagttttaa aaaaaactac   1200
agcagccaaa gaaactatat atatatatat atatatatat atccagaatg attgcctcta   1260
ctgtcctcat tgacttgttt gaaccttagt gccttaccct gtcctcttcc cagttctctt   1320
tatagaagct ctaggagctt tcgaaaagcc aaagtctttc tgaagaatct gtgctggaca   1380
gacataattc cctttctcat tgtctccatc tttgttggtc atggtaaggt ttttccatca   1440
gcctctgaaa aaatagttgt gcacaacatc tgctcactgg actgtctgat ccaatgtaat   1500
tggctgcgtc tggctaattc taagcactaa agtctacatc taagctatag atttaagctt   1560
gaagctacag attatatcac tatcaccacc acccctcacc ctatgcaatc aatcaatcaa   1620
tcatcttaag ttaaagatat ttgttgtctt tgaatgattt gctgtcacag actatttggt   1680
agaagaaata tttttcacct gagagaggaa gagaaatttc tctagtaaca caaagagtga   1740
gttctaaaag gcatgcccac atctctttcg tgccttaagg atagtgagat gcacacttat   1800
atatatactg tatatattta tatatttata tatatatttc atatatatat ataatattgc   1860
aagcttaagt ttgcaatttc ccaaacaata caaaaagcaa attacacacc ctcaccactg   1920
ttcttatctc tatagtgatg aaacattaat tagggatctt gctgcttttc tttttctaca   1980
cgaagttttc attaaagcca cagaataatt gatagggcag ctgtttgaga acaggtccca   2040
ttttcacatt agggctttaa atgaattaga aactatttga ggctataaaa atgtccttga   2100
gtttggagcc tgagctctgg tgaaatgctg atacatctga tctatcatgg gaattgcagt   2160
tagagagagt aaggaatacc atttagtcat ctatccgttc ttcacttagc aggaatatga   2220
aagaaaggca catgtttaag aggaatacct aaaggttttt ctaaattcca acatttaaaa   2280
ggcaattgtg ggctattttt attttttaat attttgaaat aaagtttagt gtctagggct   2340
gggagccagg actgatcttc catttctttt tctttgttcc cagccatgct tttgtaactt   2400
gccaggtgga cttgaccaac tacattacca tgctgtgcct cagtttaccc atttgtaaaa   2460
tgggattaat aatacttacc tacctcacag ggtgttgtg aggctctatt catttgctcc    2520
tttattcttt cctgtattct ctgtatgtcc agcactttgt agccatggga ggaaagggac   2580
tataaaagtg tacaatgtta atggaatgat acggtacctg aaagccttgt tttctagtaa   2640
gaaaatgcta ccttgctgta catacttata accttgtatt tggaaatgag aaataggttt   2700
atattttcag atctctcaaa aatcacatca tttgaccaaa gaataattta agacacatag   2760
aacagatttt tttaatttat attttcatcc tgaccagctt agttctaata atttttagtt   2820
gtgagtgatt aaaaaacttt ggatcaattt tggtcaaaca tgccaacttt gtagtctgag   2880
tgacaggcaa ggatttttgg gtttaagatg cacttttagc acacatttgt atttcccttg   2940
```

gcatatcaga ttgagctaat ggtgatgtta tttcaatcta acagccacca atctgaaatt 3000
gtatttcaaa tgttgattct gtagttcttt aaataataat gaagctcatc ttatacattt 3060
tgctttcacc aattgattcc ttcttctttt agcccactat taaaacattt cttactgaat 3120
ggttcatgta ggcttgctga acagcacgca ttacttgctt cctgaagagt tcccccattc 3180
atccatttgt cccattagtt gctgtggatt atcaagtttt gaaggaactg tacatcccaa 3240
cagactgaaa cattctaagt gaaatgagta taatccaagt aactggtgaa ctttggaggt 3300
ttggagcttg aagagaatgg ctaagaagat ttgaattata gggagggaac agaaatcata 3360
catgaaaagg ttttactgag aaggggaaaa ccttagatag agggacatgt gaaacaaaat 3420
catttgaaat tttgattcag acatccattt ccagtggcaa acagcaaagc ctgaacccat 3480
aaacccaaat gataggtgaa gttgggtggt tttatccaat gtctcaagca agcaatgtct 3540
gggaatatca tagagtaaca agtgctggtc agccaaagaa acattcactg ctggtgaacc 3600
aataccataa gcatgtatta tctaagcact tgatcaagaa atatacatgt tgtacaagct 3660
ctcaattttg ttcatttatt atcaaatttt taaaatacaa gtttggtatg tgatttggaa 3720
aagatgcctt ctggatctta agccagttgt cagtggaggt cctcagggct gcaaatgtca 3780
agacataacc ctgttcctca ccatcatgat accagataca ggtgaataca taggaactat 3840
ctgcctgtgt cctcaatctc ccttcaaaca agatgctgat ttgtagggta cttggcaggt 3900
taaattaaac cagaagaggt gacttaataa aaaagggaat gacatttagg gtataaagat 3960
ctcataagaa atgtaatatg taaattatat cttgctttat gttgtaaaat atacattgtt 4020
tgcgctagaa tagaaatgat ttcttttcaa taaaaagaaa gaaggactct a 4071

<210> SEQ ID NO 40
<211> LENGTH: 3458
<212> TYPE: DNA
<213> ORGANISM: Homo sapiens

<400> SEQUENCE: 40
gccgtcgttg ttggccacag cgtgggaagc agctctgggg gagctcggag ctcccgatca 60
cggcttcttg ggggtagcta cggctgggtg tgtagaacgg ggccggggct ggggctgggt 120
cccctagtgg agacccaagt gcgagaggca agaactctgc agcttcctgc cttctgggtc 180
agttccttat tcaagtctgc agccggctcc cagggagatc tcggtggaac ttcagaaacg 240
ctgggcagtc tgcctttcaa ccatgcccct gtccctggga gccgagatgt gggggcctga 300
ggcctggctg ctgctgctgc tactgctggc atcatttaca ggccggtgcc ccgcgggtga 360
gctggagacc tcagacgtgg taactgtggt gctgggccag gacgcaaaac tgccctgctt 420
ctaccgaggg gactccggcg agcaagtggg gcaagtggca tgggctcggg tggacgcggg 480
cgaaggcgcc caggaactag cgctactgca ctccaaatac gggcttcatg tgagcccggc 540
ttacgagggc cgcgtggagc agccgccgcc cccacgcaac cccctggacg gctcagtgct 600
cctgcgcaac gcagtgcagg cggatgaggg cgagtacgag tgccgggtca gcaccttccc 660
cgccggcagc ttccaggcgc ggctgcggct ccgagtgctg gtgcctcccc tgccctcact 720
gaatcctggt ccagcactag aagagggcca gggcctgacc ctggcagcct cctgcacagc 780
tgagggcagc ccagccccca gcgtgacctg ggacacggag gtcaaaggca caacgtccag 840
ccgttccttc aagcactccc gctctgctgc cgtcacctca gagttccact tggtgcctag 900
ccgcagcatg aatgggcagc cactgacttg tgtggtgtcc catcctggcc tgctccagga 960
ccaaaggatc acccacatcc tccacgtgtc cttccttgct gaggcctctg tgaggggcct 1020

-continued

```
tgaagaccaa aatctgtggc acattggcag agaaggagct atgctcaagt gcctgagtga   1080
agggcagccc cctccctcat acaactggac acggctggat gggcctctgc ccagtggggt   1140
acgagtggat ggggacactt tgggctttcc cccactgacc actgagcaca gcggcatcta   1200
cgtctgccat gtcagcaatg agttctcctc aagggattct caggtcactg tggatgttct   1260
tgacccccag gaagactctg ggaagcaggt ggacctagtg tcagcctcgg tggtggtggt   1320
gggtgtgatc gccgcactct tgttctgcct tctggtggtg gtggtggtgc tcatgtcccg   1380
ataccatcgg cgcaaggccc agcagatgac ccagaaatat gaggaggagc tgaccctgac   1440
cagggagaac tccatccgga ggctgcattc ccatcacacg gaccccagga gccagccgga   1500
ggagagtgta gggctgagag ccgagggcca ccctgatagt ctcaaggaca acagtagctg   1560
ctctgtgatg agtgaagagc ccgagggccg cagttactcc acgctgacca cggtgaggga   1620
gatagaaaca cagactgaac tgctgtctcc aggctctggg cgggccgagg aggaggaaga   1680
tcaggatgaa ggcatcaaac aggccatgaa ccattttgtt caggagaatg ggaccctacg   1740
ggccaagccc acgggcaatg gcatctacat caatgggcgg ggacacctgg tctgacccag   1800
gcctgcctcc cttccctagg cctggctcct tctgttgaca tgggagattt tagctcatct   1860
tgggggcctc cttaaacacc cccatttctt gcggaagatg ctccccatcc cactgactgc   1920
ttgaccttta cctccaaccc ttctgttcat cgggagggct ccaccaattg agtctctccc   1980
accatgcatg caggtcactg tgtgtgtgca tgtgtgcctg tgtgagtgtt gactgactgt   2040
gtgtgtgtgg aggggtgact gtccgtggag ggtgactgt gtccgtggtg tgtattatgc   2100
tgtcatatca gagtcaagtg aactgtggtg tatgtgccac gggatttgag tggttgcgtg   2160
ggcaacactg tcagggtttg gcgtgtgtgt catgtggctg tgtgtgacct ctgcctgaaa   2220
aagcaggtat tttctcagac cccagagcag tattaatgat gcagaggttg gaggagagag   2280
gtggagactg tggctcagac ccaggtgtgc gggcatagct ggagctggaa tctgcctccg   2340
gtgtgaggga acctgtctcc taccacttcg gagccatggg ggcaagtgtg aagcagccag   2400
tccctgggtc agccagaggc ttgaactgtt acagaagccc tctgccctct ggtggcctct   2460
gggcctgctg catgtacata ttttctgtaa atatacatgc gccgggagct tcttgcagga   2520
atactgctcc gaatcacttt taattttttt cttttttttt tcttgccctt tccattagtt   2580
gtatttttta tttattttta tttttatttt tttttagaga tggagtctca ctatgttgct   2640
caggctggcc ttgaactcct gggctcaagc aatcctcctg cctcagcctc cctagtagct   2700
gggactttaa gtgtacacca ctgtgcctgc tttgaatcct ttacgaagag aaaaaaaaaa   2760
ttaaagaaag cctttagatt tatccaatgt ttactactgg gattgcttaa agtgaggccc   2820
ctccaacacc agggggttaa ttcctgtgat tgtgaaaggg gctacttcca aggcatcttc   2880
atgcaggcag ccccttggga gggcacctga gagctggtag agtctgaaat tagggatgtg   2940
agcctcgtgg ttactgagta aggtaaaatt gcatccacca ttgtttgtga taccttaggg   3000
aattgcttgg acctggtgac aagggctcct gttcaatagt ggtgttgggg agagagagag   3060
cagtgattat agaccgagag agtaggagtt gaggtgaggt gaaggaggtg ctgggggtga   3120
gaatgtcgcc tttccccctg ggttttggat cactaattca aggctcttct ggatgtttct   3180
ctgggttggg gctggagttc aatgaggttt atttttagct ggcccaccca gatacactca   3240
gccagaatac ctagatttag tacccaaact cttcttagtc tgaaatctgc tggatttctg   3300
gcctaaggga gaggctccca tccttcgttc cccagccagc ctaggacttc gaatgtggag   3360
```

```
cctgaagatc taagatccta acatgtacat tttatgtaaa tatgtgcata tttgtacata   3420

aaatgatatt ctgtttttaa ataaacagac aaaacttg                           3458


<210> SEQ ID NO 41
<211> LENGTH: 3468
<212> TYPE: DNA
<213> ORGANISM: Homo sapiens

<400> SEQUENCE: 41

attgtgccct accagagagg acagatgggc accgcctcca gtggcaatgc taattcaccc     60

aagaggcctt cccagctctt ctcacagaag gaagataaac tccacatatt tctatatcct    120

gctggatgac attgtcctta cccattctct cttcctcccg acggagaaat ttctgcagga    180

gctacaccag tactttgttc gggcaggagg catggagggc cctgaagggc tgggccggaa    240

gcaagcctgt ctagccatgc ttctccattt cttggacacc taccaggggc tgcttcaaga    300

ggaagagggg gccggccaca tcatcaagga tctatacctg ctaattatga aggacgagtc    360

cctttaccag ggcctccgag aggacactct gaggctgcac cagctggtgg agacggtgga    420

actaaagatt ccagaggaga accagccacc cagcaagcag gtgaagccac tcttccgcca    480

cttccgccgg atagactcct gtctgcagac ccgggtggcc ttccggggct ctgatgagat    540

cttctgccgt gtatacatgc ctgaccactc ttatgtgacc atacgcagcc gcctttcagc    600

atctgtgcag gacattctgg gctctgtgac ggagaaactt caatattcag aggagcccgc    660

ggggcgtgag gattccctca tcctggtagc tgtgtcctcc tctggagaga aggtccttct    720

ccagcccact gaggactgtg ttttcaccgc actgggcatc aacagccacc tgtttgcctg    780

tactcgggac agctatgagg ctctggtgcc cctccccgag gagatccagg tctcccctgg    840

agacacagag atccaccgag tggagcctga ggacgttgcc aaccacctaa ctgccttcca    900

ctgggagctg ttccgatgtg tgcatgagct ggagttcgtg gactacgtgt tccacgggga    960

gcgcggccgc cgggagacgg ccaacttgga gctgctgctg cagcgctgca gcgaggtcac   1020

gcactgggtg gccaccgaag tgctgctctg cgaggccccg ggcaagcgcg cgcagctgct   1080

caagaagttc atcaagatcg cggccctctg caagcagaac caggacctgc tgtctttcta   1140

cgccgtggtc atggggctgg acaacgccgc tgtcagccgc cttcgactca cctgggagaa   1200

gctgccaggg aaattcaaga acttgtttcg caaatttgag aacctgacgg acccctgcag   1260

gaaccacaaa agctaccgag aagtgatctc caaaatgaag ccccctgtga ttcccttcgt   1320

gcctctgatc ctcaaagacc tgactttcct gcacgaaggg agtaagaccc ttgtagatgg   1380

tttggtgaac atcgagaagc tgcattcagt ggccgaaaaa gtgaggacaa tccgcaaata   1440

ccggagccgg cccctttgcc tggacatgga ggcatccccc aatcacctgc agaccaaggc   1500

ctatgtgcgc cagtttcagg tcatcgacaa ccagaacctc ctcttcgagc tctcctacaa   1560

gctggaggca aacagtcagt gagagtggag gctccagtca gacccgccag atccttgggc   1620

acctggcact caagcacttt gcacgatgtc tcaaccaaca tctgacatct ttcccgtgga   1680

gcaacttcct gctccacggg aaagaggtcg atggatttac ccctggaccc ataagtctgt   1740

tcatcctgct gaagtcccct ccccattgct ccttcaagcc aaaactacac tttgctggtt   1800

cctgtcccct ctgagaaagg ggatagaaag ctccttcctc tatgtcctcc catcgagatc   1860

tgttctgggg atggagcttc caacttcctc ttgcagcagg aaagaatgct gctcaccctt   1920

ctgtcttgca gagtgggatt gtgggaggga ttggcagcct tcttctccac cacctgtcca   1980

gcttcttcct ggtcagggct gggacccca ggaatattat gttgccgtgt gtgtgtgtgt   2040
```

gtgtgtgtgt gtgtgtgtgt gtgtgtgtgt gtgtgtgtgt gtgtcttctt ttagggagca 2100
ggagtgcatc tggtaattga gggtggatgt tgtgtgtgct ggggaggggt ccttctgttt 2160
ggtgctaccc ttgtctactc tgcccctgga tggtgcgggg tgctttctcc acccccacac 2220
tccctgctca gctcctcgtg ctgccctgca tgcccaggct tgtgagccaa gctgcttttt 2280
ggggcaggga gtagcagcag gtgggagggg ttacccatca gcccttgcaa gtcccccact 2340
caggcctctg gaaggtccag ggatgggctc tgatgagagg gtaaaagatg ctcagggaaa 2400
cacaggcctc agctgcctag aggaccctcc ccctgccttg cagtgggctc gggtagagca 2460
gtatcaggag ctagggttgt ctgctgccca cactcctgct ttttgggata tctaactgct 2520
aaggagggag ttgacatccc ccttctggct catgtgtctg acaccaacaa catggtctct 2580
gtccctctct ctttgactct ccctttgtcc tccccataga gctggggtgg ggtggatccc 2640
tatacctggg gcaggcagcc ccaaagtggg ggagggggat ggcagagact gtaaaggcgc 2700
cactggactc tggcaaggcc tttattacct ttactcccct ccctctccca tcaccagcct 2760
caaggcctga ggggtgcagg ggctcctggc agctactggg tgaggtttcc tggcacagac 2820
tcacccttct ttctggcacc acctctttcc cttttgaaga gacagcaaca gccgtagcaa 2880
aagcagctgc tgctcctgct atgagggtgt atatattttt tacccaaagc tctggaattg 2940
tacatttatt ttttaaaact caaagaggga aagagccttg tatcatatgt gaacattgta 3000
tcataggtaa tgttgtacag acccttttat acagtgatct gtcttgttcc tgcagcaaaa 3060
atcctctatg gacataggag gtgctgtgtc ccatgccctc ttgccctgac agtgtcccat 3120
gggccccctt ctgctccctg ccccctccct gctactgctg atgcactctc ctctccctgc 3180
agcccctggc ttcccagcct tcctcctgac cccttccaac agccttggaa ctccagctgc 3240
caccaccctc tgggtcggac actgggaccc actggcccag tcttggctgc tgcttacccc 3300
tagccttgat gcctgcccag ggacccccag ccccctcccg ttgccctgca gctttaacag 3360
agtgaaccat gtgtattgta caggcgcggt tgtcattgca gaaaccgctg ggtggagaag 3420
aagccgataa agtctatgaa tcaacctgcc aaaaaaaaaa aaaaaaaa 3468

<210> SEQ ID NO 42
<211> LENGTH: 3965
<212> TYPE: DNA
<213> ORGANISM: Homo sapiens

<400> SEQUENCE: 42
agagcgcttg ggatccacgg cgctcggacc gctgtcctcc aacagcgcag ggcagagcgg 60
ctggcgccgc cggagcgcgg agccacgacc ctccctggcc gcctttgtct actggccgtg 120
cggcccggaa ccgccactct ccagggccgg ggacgcgccc gcagctgtcg gtgacagctc 180
ctccctaccg caaccctccg gggcggaggg gcggtcgggc cgggccctgc tagcccgcga 240
ccgcaagccc gcgctcgcgg atcgatgccc ccgcagcagg gggaccccgc gttccccgac 300
cgctgcgagg cgcctccggt gccgccgcgt cgggagcgcg gtggacgcgg gggacgcggg 360
cctggggagc cggggggccg ggggcgtgcg gggggtgccg aggggcgcgg cgtcaagtgc 420
gtgctggtcg gcgacggcgc ggtgggcaag acgagcctgg tggtgagcta caccaccaac 480
ggctacccca ccgagtacat ccctactgcc ttcgacaact tctccgcggt ggtgtctgtg 540
gatgggcggc ccgtgagact ccaactctgt gacactgccg gacaggatga atttgacaag 600
ctgaggcctc tctgctacac caacacagac atcttcctgc tctgcttcag tgtcgtgagc 660

-continued

```
ccctcatcct tccagaacgt cagtgagaaa tgggtgccgg agattcgatg ccactgtccc    720
aaagccccca tcatcctagt tggaacgcag tcggatctca gagaagatgt caaagtcctc    780
attgagttgg acaaatgcaa agaaaagcca gtgcctgaag aggcggctaa gctgtgcgcc    840
gaggaaatca aagccgcctc ctacatcgag tgttcagcct tgactcaaaa aaacctcaaa    900
gaggtctttg atgcagccat cgtcgctggc attcaatact cggacactca gcaacagcca    960
aagaagtcta aaagcaggac tccagataaa atgaaaaacc tctccaagtc ctggtggaag   1020
aagtactgct gtttcgtatg atgctggcaa gacacccaga aaggctattt tcagatgaaa   1080
tcgatattag aagctatatt agctgaaaca actcctttta ctgcgtagaa cctatatcga   1140
gagtgtgtgt atatgtatta taggaggagc tctcaatttt atgtattctt tctgccttta   1200
attttcttgt ttgtttgagc ttagggatga gatacttatg caagatattt ttgaagtaaa   1260
ttaaacattt ttcacatctc tggaaattta gagttctaga cctctggtta atttatatct   1320
aatatgaaga agacacctct aatctggatg ttaagaatga agttctgcta cattataatg   1380
tacagaagag caaaagggag gaacactatg gttaaccctc tcttgattaa gggctactta   1440
atgcacagtg cattatgtac acaggtcaac catggtaaca atagttctta gctttgaaac   1500
tccatgcaaa ccatgccttt tttttaagga gcaaaaatct gagaaaaaaa gtgagagacc   1560
tctgcctaca aaacctcaaa ccagtcactt ttgtcaattg ctaataccca gttacttatg   1620
atttaaaaac aaccaacaga aaacatccca ctgactgtat ggcactctgt agtcaaaaaa   1680
ggaaacttcc ttattgggac ttttctttct tagtccagtt gtgttgacac atatgaacac   1740
agacaaagtg ctatgcggag gaaagcaagt gttggtcagt agtttcatgt tttagggagt   1800
ggttcctgtg gagatcagaa agtgacattt gctttcggta ctgtaatacg tgcaccaaac   1860
tgcctcaatc ctaggtaacg agggcaacag ggagcacctg tctggattgt ttttaaacct   1920
ccatactcaa gctgtctctt cggcagggag gtgaatactc ttgaaaggcc aacagcaagt   1980
gtttgtggga cacaacacag ataatttttt cttaagtcgg ccaagatgta cttctctgtg   2040
tgcacaccca tgcacactca tgcacacaga tacataggtc tgtatggctg tatttgctgt   2100
tgattcagac tttcacacca ttaatgggga aaagcgtggc cacaaaaaca gatgctagga   2160
agcttggctt cctcttcttg ttgacccttt tttgaaccaa catctttttt attatattca   2220
gagtatgttt ttaagtgtat cttaatatat acatttttta ggacatctta aatctaaaca   2280
aaaaataaaa tgaacatctc ttgaaacctg ttaaaacaac cagttaaagc cacagatggc   2340
tttcagggca gtagcagcag aggccagtgg actctgagga ctcctgaggg gcggggcgtg   2400
tagccagcca ggtgcatgcc gggaccatgg cccccatact tggctgcttc ctgtgacagt   2460
gaaatacatc cttcaaggtg gcagctgtta gggctgaatc ttctggagaa aaaggtgcca   2520
tctcaggaga atagctttta ctctggtagg aatgcttccg agacaccaca aggcagcctg   2580
aacactcagt tgcagggtcg ggcttgcggt gggtgaccca gagccaccaa agtcacatcc   2640
acaactaatg agggaaatct gtaaagccag ttagatagaa gaattttatt tttctgtggg   2700
ttttgtgttg tctttttttat gttaaaaaga aatccagttt gtgtttttct atagaaaaag   2760
taaaagatca ggttatactt taggttaggg gttctattta ttcctgttag taaataaaat   2820
taacaaattt ctttgtttaa caaaagatta atctttaaac cactaaaata catagactga   2880
ttgattattc aacacattgg aattgatgtc ggtcatagtt tcctgaagca tttagttaca   2940
acctgaagga ataaaatgat ttgtggaaat gcttaaaata gacctaactg aatacagtct   3000
catcttgccg cgcctggctt acctatctgt ggaaagctag gcttcccagg ctgggctctg   3060
```

```
cctgtctggt gcctggaggt gtgggaggga agatgagtta tttaactggt aagcgatttg   3120

aaacactatt tttatattaa agtaaatggc atggagtata gtgcaaattc atttttaaga   3180

tagaacacaa aacttgaaag aagttttatg cgtgtgacag tgtatggggc tgcagttggt   3240

ctccctggag gggacttcca cacctcctgc ctttaggcca tgggtggaaa gtgctcagtg   3300

aagtacacct gtgtggccca gttctgaaag ctttatacag ttgaatttta agtggggttg   3360

ataacacctt ggactgttag tgttaaaaat ctagtgggtt gacctttaaa tgcaacagtt   3420

tttaaaatat attgctgcat tttatagaat agtaaaggta cgattatact tgagattttc   3480

ctccattttt atttcttcgt gaacatagag tttggggccg aaaatgtttt taaagtatgt   3540

gtttgagtta aatataaagt tggttcactt caaagctaaa aaattgttaa acttgcagct   3600

tggtattgca gagaagattt tataagaatt ttgctttaga gaatgccact ttggctgaac   3660

tacaagtgta ggccaccatt ataatttata aatacagcat acttcaaaac tgtttgttat   3720

ctcttgttac catgtatgta taaatggacc ttttataacc ttgttctctg cttgacagac   3780

tcaagagaaa ctacccaggt attacacaag ccaaaatggg agcaaggcct tctctccaga   3840

ctatcgtaac ctggtgcctt accaagttgt gcttttctgt tttcaagtgt aaatgatgtt   3900

gagcagaatg ttgtacttga aaatgctata agtgagatgg tatgaaataa attctgactt   3960

atgaa                                                               3965
```

<210> SEQ ID NO 43
<211> LENGTH: 1650
<212> TYPE: DNA
<213> ORGANISM: Homo sapiens

<400> SEQUENCE: 43

```
acccattcag tcagaggcag ccagcgggac ctgcttcacc gagcgcagcg aagccgagac     60

ccgggctggc ccctctgctg cccccggagc gggccatgcc gccgcgggag ctgagcgagg    120

ccgagccgcc cccgctccgg gccccgaccc ctcccccgcg gcggcgtagc gcgcccccag    180

agctgggcat caagtgcgtg ctggtgggcg acggcgccgt gggcaagagc agcctcatcg    240

tcagctacac ctgcaatggg taccccgcgc gctaccggcc cactgcgctg gacaccttct    300

ctgtgcaagt cctggtggat ggagctccgg tgcgcattga gctctgggac acagcgggac    360

aggaggattt tgaccgactt cgttcccttt gctacccgga taccgatgtc ttcctggcgt    420

gcttcagcgt ggtgcagccc agctcctttc aaaacatcac agagaaatgg ctgcccgaga    480

tccgcacgca caacccccag gcgcctgtgc tgctggtggg cacccaggcc gacctgaggg    540

acgatgtcaa cgtactaatt cagctggacc agggggggccg ggagggcccc gtgccccaac    600

cccaggctca gggtctggcc gagaagatcc gagcctgctg ctaccttgag tgctcagcct    660

tgacgcagaa gaacttgaag gaagtatttg actcggctat tctcagtgcc attgagcaca    720

aagcccggct ggagaagaaa ctgaatgcca aaggtgtgcg caccctctcc cgctgccgct    780

ggaagaagtt cttctgcttc gtttgagcag ctatggctgc atagcaagta gtaggcagga    840

ggccaaagac ttctgagacc tggggcaccc gggcctttgc ggcagctact ggcagggcct    900

ggccacctca taggactcag ttcccttctg aacactcggg ggacatgggc ctctaactgc    960

ccactctgat atgcctgggt gagcctagga gggaaggctc tgatttggat ttctccagtc   1020

aaagctcaca gaaaaaaacc tggcactttg attttcatgg gatggtccta acagggtcag   1080

tcacctccga gcagtttggg aacccagttt cttgtcctgg gccctcaggt cagcctggct   1140
```

-continued

```
gaattaggac ccttccttgg cacaggggtg agaaagagct tggggaacgc ttggcattat   1200

ggagggctgg aaggggctca accccgattt ggagagaagt ttgggatgga gtgggcgaga   1260

gattgagaga gcgagcagga aaagaggtct tggagcctgg gactgatggt ggataaggcc   1320

tggaaagaag atgacgagga ggaggagaga gggaagtggg gtggatgagg agcaggctga   1380

cacctgggct gccctcaatc cccaaggcca gggagggcgg ggctggcccc tgggaagaac   1440

tgggtctctg ggctccctag gcactgccca aactggctga gccaggagtg gggcaggaag   1500

tgagagtcaa ggcccagcaa aaggaggggg aggagctgca aattagaacc tgaaggagga   1560

ccgggttggg gatcatccct ttcctcaagg tcacacagcc tagaagctag agcagtgcag   1620

agtctgcaaa taaaacctta agtctgtgaa                                    1650
```

<210> SEQ ID NO 44
<211> LENGTH: 4550
<212> TYPE: DNA
<213> ORGANISM: Homo sapiens

<400> SEQUENCE: 44

```
ccgcgcacac ctccccgcgc cgccgccgcc accgcccgca ctccgccgcc tctgcccgca     60

accgctgagc catccatggg ggtcgcgggc cgcaaccgtc ccggggcggc ctgggcggtg    120

ctgctgctgc tgctgctgct gccgccactg ctgctgctgg cgggggccgt cccgccgggt    180

cggggccgtg ccgcggggcc gcaggaggat gtagatgagt gtgcccaagg gctagatgac    240

tgccatgccg acgccctgtg tcagaacaca cccacctcct acaagtgctc ctgcaagcct    300

ggctaccaag gggaaggcag gcagtgtgag gacatcgatg aatgtggaaa tgagctcaat    360

ggaggctgtg tccatgactg tttgaatatt ccaggcaatt atcgttgcac ttgttttgat    420

ggcttcatgt tggctcatga cggtcataat tgtcttgatg tggacgagtg cctggagaac    480

aatggcggct gccagcatac ctgtgtcaac gtcatgggga gctatgagtg ctgctgcaag    540

gaggggtttt tcctgagtga caatcagcac acctgcattc accgctcgga agagggcctg    600

agctgcatga ataaggatca cggctgtagt cacatctgca aggaggcccc aaggggcagc    660

gtcgcctgtg agtgcaggcc tggttttgag ctggccaaga accagagaga ctgcatcttg    720

acctgtaacc atgggaacgg tgggtgccag cactcctgtg acgatacagc cgatggccca    780

gagtgcagct gccatccaca gtacaagatg cacacagatg ggaggagctg ccttgagcga    840

gaggacactg tcctggaggt gacagagagc aacaccacat cagtggtgga tggggataaa    900

cgggtgaaac ggcggctgct catggaaacg tgtgctgtca acaatggagg ctgtgaccgc    960

acctgtaagg atacttcgac aggtgtccac tgcagttgtc ctgttggatt cactctccag   1020

ttggatggga agacatgtaa agatattgat gagtgccaga cccgcaatgg aggttgtgat   1080

catttctgca aaaacatcgt gggcagtttt gactgcggct gcaagaaagg atttaaatta   1140

ttaacagatg agaagtcttg ccaagatgtg gatgagtgct ctttggatag gacctgtgac   1200

cacagctgca tcaaccaccc tggcacattt gcttgtgctt gcaaccgagg gtacaccctg   1260

tatggcttca cccactgtgg agacaccaat gagtgcagca tcaacaacgg aggctgtcag   1320

caggtctgtg tgaacacagt gggcagctat gaatgccagt gccaccctgg gtacaagctc   1380

cactggaata aaaaagactg tgtggaagtg aaggggctcc tgcccacaag tgtgtcaccc   1440

cgtgtgtccc tgcactgcgg taagagtggt ggaggagacg ggtgcttcct cagatgtcac   1500

tctggcattc acctctcttc aggactgcaa ggggcctact ctgtcacctg tggctcttcc   1560

tctcctctca ggaacaaaca acaaaaatca aatgactctg cttttgggga tgtcaccacc   1620
```

-continued

```
atcaggacaa gtgtaacctt taagctaaat gaaggcaagt gtagtttgaa aaatgctgag   1680
ctgtttcccg agggtctgcg accagcacta ccagagaagc acagctcagt aaaagagagc   1740
ttccgctacg taaaccttac atgcagctct ggcaagcaag tcccaggagc cctggccga    1800
ccaagcaccc ctaaggaaat gtttatcact gttgagtttg agcttgaaac taaccaaaag   1860
gaggtgacag cttcttgtga cctgagctgc atcgtaaagc gaaccgagaa gcggctccgt   1920
aaagccatcc gcacgctcag aaaggccgtc cacagggagc agtttcacct ccagctctca   1980
ggcatgaacc tcgacgtggc taaaaagcct cccagaacat ctgaacgcca ggcagagtcc   2040
tgtggagtgg gccagggtca tgcagaaaac caatgtggtc tgtgtcaacc tggtgaatat   2100
tctgcagatg gctttgcacc ttgccagctc tgtgccctgg gcacgttcca gcctgaagct   2160
ggtcgaactt cctgcttccc ctgtggagga ggccttgcca ccaaacatca gggagctact   2220
tcctttcagg actgtgaaac cagagttcaa tgttcacctg gacatttcta caacaccacc   2280
actcaccgat gtattcgttg cccagtggga acataccagc ctgaatttgg aaaaaataat   2340
tgtgtttctt gcccaggaaa tactacgact gactttgatg gctccacaaa cataacccag   2400
tgtaaaaaca gaagatgtgg aggggagctg ggagatttca ctgggtacat tgaatcccca   2460
aactacccag gcaattaccc agccaacacc gagtgtacgt ggaccatcaa cccaccccc    2520
aagcgccgca tcctgatcgt ggtccctgag atcttcctgc ccatagagga cgactgtggg   2580
gactatctgg tgatgcggaa aacctcttca tccaattctg tgacaacata tgaaacctgc   2640
cagacctacg aacgccccat cgccttcacc tccaggtcaa agaagctgtg gattcagttc   2700
aagtccaatg aagggaacag cgctagaggg ttccaggtcc catacgtgac atatgatgag   2760
gactaccagg aactcattga agacatagtt cgagatggca ggctctatgc atctgagaac   2820
catcaggaaa tacttaagga taagaaactt atcaaggctc tgtttgatgt cctggcccat   2880
ccccagaact atttcaagta cacagcccag gagtcccgag agatgtttcc aagatcgttc   2940
atccgattgc tacgttccaa agtgtccagg tttttgagac cttacaaatg actcagccca   3000
cgtgccactc aatacaaatg ttctgctata gggttggtgg gacagagctg tcttccttct   3060
gcatgtcagc acagtcgggt attgctgcct cccgtatcag tgactcatta gagttcaatt   3120
tttatagata atacagatat tttggtaaat tgaacttggt ttttctttcc cagcatcgtg   3180
gatgtagact gagaatggct ttgagtggca tcagcttctc actgctgtgg gcggatgtct   3240
tggatagatc acgggctggc tgagctggac tttggtcagc ctaggtgaga ctcacctgtc   3300
cttctggggt cttactcctc ctcaaggagt ctgtagtgga aaggaggcca cagaataagc   3360
tgcttattct gaaacttcag cttcctctag cccggccctc tctaagggag ccctctgcac   3420
tcgtgtgcag gctctgacca ggcagaacag gcaagagggg agggaaggag acccctgcag   3480
gctccctcca cccaccttga gacctgggag gactcagttt ctccacagcc ttctccagcc   3540
tgtgtgatac aagtttgatc ccaggaactt gagttctaag cagtgctcgt gaaaaaaaaa   3600
agcagaaaga attagaaata aataaaaact aagcacttct ggagacataa taatgtacat   3660
ttattgccag ccttcctcgt tgcaagcttc caccctgcag caaatgcact atgctgactc   3720
tcgcaccttc agctgtgccc tctgacactc tgctggccat tgcctgaggg actggggagt   3780
tcaggtgaaa tgtaatttcc tcagtggatg agaatcatca attgtcatga aaaggcgatt   3840
tcaccaaccc tgagtcggta ttgccaaggg ttctactccc caagtgggct tcccatcaca   3900
agggatctga ggtccaggtg ggtgtggtga ggcccagcct gtcatgtatg ccttccttcc   3960
```

ccagtctcaa atgtgagaga cggactctgc tccgtggaca tgagcagccc cttgaagggt 4020
ggtctcattc tctaacagta acagcactgc cagaaacacc ccctgaatgc cacacgatca 4080
tctcactttg ggtcaggcca gcagggcctc acgatcattt cttgaacttg aattttcagt 4140
gttattgaat ctttaaacat ttaaatcccc aagcaaaaat ctcattacag tgaataaaaa 4200
ggaatccaat caaacaagcc accacttccc taatggatgg actacctaca actatagtgt 4260
tttgttattt caataacaat tctatgcaca gccaattctc cataccaaag tactaaaaaa 4320
atgtttaaca agcatttttg aagaaaacaa agagaacttc attatggtta aacttgcttt 4380
tcatctcagt gttgcttttt ttaacctgtt aataacattg attcttaaaa agtcctaatc 4440
aaacttcttt atttggatgg gccctaaata ttcattttca gatttctctt caaaagtttg 4500
aacatcatca ttaaaaaaaa aatagcatta aaacaaaaaa aaaaaaaaaa 4550

<210> SEQ ID NO 45
<211> LENGTH: 3309
<212> TYPE: DNA
<213> ORGANISM: Homo sapiens

<400> SEQUENCE: 45
ttcagcccct ctcccgggct gcgcctccgc actccgggcc cgggcagaag ggggtgcgcc 60
tcggccccac cacccaggga gcagccgagc tgaaaggccg ggaaccgcgg cttgcgggga 120
ccacagctcc cgaaagcgac gttcggccac cggaggagcg ggagccaagc aggcggagct 180
cggcgggaga ggtgcgggcc gaatccgagc cgagcggaga ggaatccggc agtagagagc 240
ggactccagc cggcggaccc tgcagccctc gcctgggaca gcggcgcgct gggcaggcgc 300
ccaagagagc atcgagcagc ggaacccgcg aagccggccc gcagccgcga cccgcgcagc 360
ctgccgctct cccgccgccg gtccgggcag catgaggcgc gcggcgctct ggctctggct 420
gtgcgcgctg gcgctgagcc tgcagccggc cctgccgcaa attgtggcta ctaatttgcc 480
ccctgaagat caagatggct ctggggatga ctctgacaac ttctccggct caggtgcagg 540
tgctttgcaa gatatcacct tgtcacagca gaccccctcc acttggaagg acacgcagct 600
cctgacggct attcccacgt ctccagaacc caccggcctg gaggctacag ctgcctccac 660
ctccaccctg ccggctggag aggggcccaa ggagggagag gctgtagtcc tgccagaagt 720
ggagcctggc ctcaccgccc gggagcagga ggccaccccc cgacccaggg agaccacaca 780
gctcccgacc actcatcagg cctcaacgac cacagccacc acggcccagg agcccgccac 840
ctcccacccc cacagggaca tgcagcctgg ccaccatgag acctcaaccc ctgcaggacc 900
cagccaagct gaccttcaca ctccccacac agaggatgga ggtccttctg ccaccgagag 960
ggctgctgag gatggagcct ccagtcagct cccagcagca gagggctctg gggagcagga 1020
cttcaccttt gaaacctcgg gggagaatac ggctgtagtg gccgtggagc ctgaccgccg 1080
gaaccagtcc ccagtggatc agggggccac gggggcctca cagggcctcc tggacaggaa 1140
agaggtgctg ggaggggtca ttgccggagg cctcgtgggg ctcatctttg ctgtgtgcct 1200
ggtgggtttc atgctgtacc gcatgaagaa gaaggacgaa ggcagctact ccttggagga 1260
gccgaaacaa gccaacggcg gggcctacca gaagcccacc aaacaggagg aattctatgc 1320
ctgacgcggg agccatgcgc cccctccgcc ctgccactca ctaggccccc acttgcctct 1380
tccttgaaga actgcaggcc ctggcctccc ctgccaccag gccacctccc cagcattcca 1440
gcccctctgg tcgctcctgc ccacggagtc gtggggtgtg ctgggagctc cactctgctt 1500
ctctgacttc tgcctggaga cttagggcac caggggtttc tcgcatagga cctttccacc 1560
acagccagca cctggcatcg caccattctg actcggtttc tccaaactga agcagcctct 1620
ccccaggtcc agctctggag gggaggggga tccgactgct ttggacctaa atggcctcat 1680
gtggctggaa gatcctgcgg gtggggcttg gggctcacac acctgtagca cttactggta 1740
ggaccaagca tcttgggggg gtggccgctg agtggcaggg gacaggagtc cactttgttt 1800
cgtggggagg tctaatctag atatcgactt gtttttgcac atgtttcctc tagttctttg 1860
ttcatagccc agtagacctt gttacttctg aggtaagtta agtaagttga ttcggtatcc 1920
ccccatcttg cttccctaat ctatggtcgg gagacagcat cagggttaag aagacttttt 1980 ttttttttt ttaaactagg agaaccaaat ctggaagcca aaatgtaggc ttagtttgtg 2040
tgttgtctct tgagtttgtc gctcatgtgt gcaacagggt atggactatc tgtctggtgg 2100
ccccgtttct ggtggtctgt tggcaggctg gccagtccag gctgccgtgg ggccgccgcc 2160
tctttcaagc agtcgtgcct gtgtccatgc gctcagggcc atgctgaggc ctgggccgct 2220
gccacgttgg agaagcccgt gtgagaagtg aatgctggga ctcagccttc agacagagag 2280
gactgtaggg agggcggcag gggcctggag atcctcctgc agaccacgcc cgtcctgcct 2340
gtggcgccgt ctccaggggc tgcttcctcc tggaaattga cgaggggtgt cttgggcaga 2400
gctggctctg agcgcctcca tccaaggcca ggttctccgt tagctcctgt ggccccaccc 2460
tgggccctgg gctggaatca ggaatatttt ccaaagagtg atagtctttt gcttttggca 2520
aaactctact taatccaatg ggtttttccc tgtacagtag attttccaaa tgtaataaac 2580
tttaatataa agtagtcctg tgaatgccac tgccttcgct tcttgcctct gtgctgtgtg 2640
tgacgtgacc ggacttttct gcaaacacca acatgttggg aaacttggct cgaatctctg 2700
tgccttcgtc tttcccatgg ggagggattc tggttccagg gtccctctgt gtatttgctt 2760
ttttgttttg gctgaaattc tcctggaggt cggtaggttc agccaaggtt ttataaggct 2820
gatgtcaatt tctgtgttgc caagctccaa gccccatctt ctaaatggca aaggaaggtg 2880
gatggcccca gcacagcttg acctgaggct gtggtcacag cggaggtgtg gagccgaggc 2940
ctaccccgca gacaccttgg acatcctcct cccacccggc tgcagaggcc agaggccccc 3000
agcccagggc tcctgcactt acttgcttat ttgacaacgt ttcagcgact ccgttggcca 3060
ctccgagagg tgggccagtc tgtggatcag agatgcacca ccaagccaag ggaacctgtg 3120
tccggtattc gatactgcga ctttctgcct ggagtgtatg actgcacatg actcgggggt 3180
ggggaaaggg gtcggctgac catgctcatc tgctggtccg tgggacggtg cccaagccag 3240
aggctgggtt catttgtgta acgacaataa acggtacttg tcatttcggg caaaaaaaaa 3300
aaaaaaaaa 3309

<210> SEQ ID NO 46
<211> LENGTH: 3224
<212> TYPE: DNA
<213> ORGANISM: Homo sapiens

<400> SEQUENCE: 46
aaagttccaa ggagatttta aggtgcacgc aaggtggaaa accactgctg aagcagatgt 60
ggagaactat aaattaagga tcccagctac ttaattgact tatgcttcct agttcgttgc 120
ccagccacca ccgtctctcc aaaaaacccga ggtctcgcta aaatcatcat ggattcactt 180
ggcgccgtca gcactcgact tgggtttgat cttttcaaag agctgaagaa aacaaatgat 240
ggcaacatct tcttttcccc tgtgggcatc ttgactgcaa ttggcatggt cctcctgggg 300

```
acccgaggag ccaccgcttc ccagttggag gaggtgtttc actctgaaaa agagacgaag    360
agctcaagaa taaaggctga agaaaaagag gtggtaagaa taaaggctga aggaaaagag    420
attgagaaca cagaagcagt acatcaacaa ttccaaaagt ttttgactga aataagcaaa    480
ctcactaatg attatgaact gaacataacc aacaggctgt ttggagaaaa aacatacctc    540
ttccttcaaa aatacttaga ttatgttgaa aaatattatc atgcatctct ggaacctgtt    600
gattttgtaa atgcagccga tgaaagtcga aagaagatta attcctgggt tgaaagcaaa    660
acaaatgaaa aaatcaagga cttgttccca gatggctcta ttagtagctc taccaagctg    720
gtgctggtga acatggttta ttttaaaggg caatgggaca gggagtttaa gaaagaaaat    780
actaaggaag agaaattttg gatgaataag agcacaagta aatctgtaca gatgatgaca    840
cagagccatt cctttagctt cactttcctg gaggacttgc aggccaaaat tctagggatt    900
ccatataaaa acaacgacct aagcatgttt gtgcttctgc ccaacgacat cgatggcctg    960
gagaagataa tagataaaat aagtcctgag aaattggtag agtggactag tccagggcat   1020
atggaagaaa gaaaggtgaa tctgcacttg ccccggtttg aggtggagga cggttacgat   1080
ctagaggcgg tcctggctgc catggggatg ggcgatgcct tcagtgagca caaagccgac   1140
tactcgggaa tgtcgtcagg ctccgggttg tacgcccaga agttcctgca cagttccttt   1200
gtggcagtaa ctgaggaagg caccgaggct gcagctgcca ccggcatagg ctttactgtc   1260
acatccgccc caggtcatga aaatgttcac tgcaatcatc ccttcctgtt cttcatcagg   1320
cacaatgaat ccaacagcat cctcttcttc ggcagatttt cttctcctta agatgatcgt   1380
tgccatggca ttgctgcttt tagcaaaaaa caactaccag tgttactcat atgattatga   1440
aaatcgtcca ttcttttaaa tgttgtctca cttgcatttc cagtcttggc catcaaatca   1500
atgatttaat gactccaata atgtgtgtgt ttataaccat cctcgaaagt gaaatgtcct   1560
tttctttgtg ccatgcgtaa ggtgagtcaa accaaacctc attgataatc tccctttggt   1620
ttcctttgaa agtaaattgg tatcttgtag ttttgtgcac acgaaaggag agaaagtctc   1680
tccagtaaag agtacgaact agtaattttg gggggtctct ctaattctgg tattttgaca   1740
tgttataata cgcaagtaaa ataaaacaat agtttactca gctcatgtta ctattcccca   1800
acagatattg tggcaaatca cacataggaa agagaatttg ggaatacagt agcaaaacat   1860
aaattaaaac tcaaatgcca ggacaaaata aaacaatata ccagatggag aggatgcccg   1920
tattttcatc ttccattcta acattatcca ttgttagatg cataagcatt ttgatattgt   1980
gtaataaatg tggtatttga gaagataaat gatgtagttg atcagtattc ctcctctatc   2040
accttttag actttgtaag gtaaatattt ggactaactt ttagaaaagt ttcccttttt   2100
ttctccattt acatttttct ggtttttttt tttttttgag tgaggtacga gtattaccaa   2160
atgatatttt ctgaagatgc tttttggaaa gctctgaatc tatacctaat gctcttaatt   2220
attggcttgt ttcatttttt tcctccagtt tttaacaaga tcacataact ggcttatttt   2280
taacagcttt gtcaaactac aatttacatg ccgtaaaatg tacacactgt aattttataa   2340
ttcattgact tttagtaaat ttctagcgtt atgcatcgcc acaatccagt tttagaatat   2400
ttccatgacc ctaagaagtt tcctcatgtc tattaatatt cccaatccta ggcaccactg   2460
agttgttttc tgtctttata agtttttctt tctacatctt atataaatgg aatcataata   2520
catgtagtat tttgtgtctg gcgtcttgca cttagcatgg tgttcttgag gttcatctgt   2580
tgtagtatgt attgatactt aatttttta ttgccgaata ctattccatt gcatggaaaa   2640
gacctatttt atttctaggt tcaccagttg agggacattt ggattgttcc cacttcttgg   2700
```

```
ctgttaggaa taatgttgct ctgaacatgt aaataaagat ctttgtgttc acatatgttt   2760

tcatttctgt tggggagatt cctaggctag aaattgctgg gccatatgaa aaatcaatag   2820

ttagctttgt aagaaacagt caaactgttt tccaacgtga cattttatat tcccaccagg   2880

aatgtttaaa actagtgtct tcaaatcctc accaacatcc aggattgtgt ctttatgatt   2940

atagccattt ttgtaggtac aaagtggcat ctcatggtgg ttttaatttg catttccata   3000

atatctaatt aggttgagct ttttttatgt gcttattggc catttgtttg actttgtttg   3060

gtgaaatgta tacaaatcat ttgctcattt ttaatttggg ttgtctgtct tgtcttctca   3120

ttttattgag ttaaatgagt tcttaataat ctctggctta caagtcctta atttatcaaa   3180

tatatgatac gtggacattt cctcataaaa aaaaaaaaaa aaaa                    3224
```

<210> SEQ ID NO 47
<211> LENGTH: 1996
<212> TYPE: DNA
<213> ORGANISM: Homo sapiens

<400> SEQUENCE: 47

```
gccccagcaa cggctcattc tgctccccg ggtcggagcc ccccggagct gcgcgcgggc     60

ttgcagcgcc tcgcccgcgc tgtcctcccg gtgtcccgct tctccgcgcc ccagccgccg    120

gctgccagct tttcggggcc ccgagtcgca cccagcgaag agagcgggcc cgggacaagc    180

tcgaactccg gccgcctcgc ccttccccgg ctccgctccc tctgccccct cggggtcgcg    240

cgcccacgat gctgcagggc cctggctcgc tgctgctgct cttcctcgcc tcgcactgct    300

gcctgggctc ggcgcgcggg ctcttcctct ttggccagcc cgacttctcc tacaagcgca    360

gcaattgcaa gcccatccct gccaacctgc agctgtgcca cggcatcgaa taccagaaca    420

tgcggctgcc caacctgctg ggccacgaga ccatgaagga ggtgctggag caggccggcg    480

cttggatccc gctggtcatg aagcagtgcc acccggacac caagaagttc ctgtgctcgc    540

tcttcgcccc cgtctgcctc gatgacctag acgagaccat ccagccatgc cactcgctct    600

gcgtgcaggt gaaggaccgc tgcgccccgg tcatgtccgc cttcggcttc ccctggcccg    660

acatgcttga gtgcgaccgt ttcccccagg acaacgacct ttgcatcccc ctcgctagca    720

gcgaccacct cctgccagcc accgaggaag ctccaaaggt atgtgaagcc tgcaaaaata    780

aaaatgatga tgacaacgac ataatggaaa cgctttgtaa aaatgatttt gcactgaaaa    840

taaaagtgaa ggagataacc tacatcaacc gagataccaa aatcatcctg gagaccaaga    900

gcaagaccat ttacaagctg aacggtgtgt ccgaaaggga cctgaagaaa tcggtgctgt    960

ggctcaaaga cagcttgcag tgcacctgtg aggagatgaa cgacatcaac gcgccctatc   1020

tggtcatggg acagaaacag ggtggggagc tggtgatcac ctcggtgaag cggtggcaga   1080

aggggcagag agagttcaag cgcatctccc gcagcatccg caagctgcag tgctagtccc   1140

ggcatcctga tggctccgac aggcctgctc cagagcacgg ctgaccattt ctgctccggg   1200

atctcagctc ccgttcccca agcacactcc tagctgctcc agtctcagcc tgggcagctt   1260

ccccctgcct tttgcacgtt tgcatcccca gcatttcctg agttataagg ccacaggagt   1320

ggatagctgt tttcacctaa aggaaaagcc cacccgaatc ttgtagaaat attcaaacta   1380

ataaaatcat gaatattttt atgaagttta aaaatagctc actttaaagc tagttttgaa   1440

taggtgcaac tgtgacttgg gtctggttgg ttgttgtttg ttgttttgag tcagctgatt   1500

ttcacttccc actgaggttg tcataacatg caaattgctt caattttctc tgtggcccaa   1560
```

```
acttgtgggt cacaaaccct gttgagataa agctggctgt tatctcaaca tcttcatcag   1620

ctccagactg agactcagtg tctaagtctt acaacaattc atcattttat accttcaatg   1680

ggaacttaaa ctgttacatg tatcacattc cagctacaat acttccattt attagaagca   1740

cattaaccat ttctatagca tgatttcttc aagtaaaagg caaaagatat aaattttata   1800

attgacttga gtactttaag ccttgtttaa aacatttctt acttaacttt tgcaaattaa   1860

acccattgta gcttacctgt aatatacata gtagtttacc tttaaaagtt gtaaaaatat   1920

tgctttaacc aacactgtaa atatttcaga taaacattat attcttgtat ataaacttta   1980

catcctgttt taccta                                                   1996
```

<210> SEQ ID NO 48
<211> LENGTH: 2868
<212> TYPE: DNA
<213> ORGANISM: Homo sapiens

<400> SEQUENCE: 48

```
ggctgcgctc cgagctgcgg agtccgggac tggagctgcc cgggcgggtt cgcgccccga     60

aggctgagag ctggcgctgc tcgtgccctg tgtgccagac ggcggagctc cgcggccgga    120

ccccgcggcc ccgctttgct gccgactgga gtttgggggga agaaactctc ctgcgcccca   180

gaggatttct tcctcggcga agggacagcg aaagatgagg gtggcaggaa gagaagggcg    240

ctttctgtct gccggggtcg cagcgcgaga gggcagtgcc atgttcctct ccatcctagt    300

ggcgctgtgc ctgtggctgc acctggcgct gggcgtgcgc ggcgcgccct gcgaggcggt    360

gcgcatccct atgtgccggc acatgccctg gaacatcacg cggatgccca accacctgca    420

ccacagcacg caggagaacg ccatcctggc catcgagcag tacgaggagc tggtggacgt    480

gaactgcagc gccgtgctgc gcttcttcct ctgtgccatg tacgcgccca tttgcaccct    540

ggagttcctg cacgacccta tcaagccgtg caagtcggtg tgccaacgcg cgcgcgacga    600

ctgcgagccc ctcatgaaga tgtacaacca cagctggccc gaaagcctgg cctgcgacga    660

gctgcctgtc tatgaccgtg gcgtgtgcat ctcgcctgaa gccatcgtca cggacctccc    720

ggaggatgtt aagtggatag acatcacacc agacatgatg gtacaggaaa ggcctcttga    780

tgttgactgt aaacgcctaa gccccgatcg gtgcaagtgt aaaaaggtga agccaacttt    840

ggcaacgtat ctcagcaaaa actacagcta tgttattcat gccaaaataa aagctgtgca    900

gaggagtggc tgcaatgagg tcacaacggt ggtggatgta aaagagatct tcaagtcctc    960

atcacccatc cctcgaactc aagtcccgct cattacaaat tcttcttgcc agtgtccaca   1020

catcctgccc catcaagatg ttctcatcat gtgttacgag tggcgctcaa ggatgatgct   1080

tcttgaaaat tgcttagttg aaaaatggag agatcagctt agtaaaagat ccatacagtg   1140

ggaagagagg ctgcaggaac agcggagaac agttcaggac aagaagaaaa cagccgggcg   1200

caccagtcgt agtaatcccc ccaaaccaaa gggaaagcct cctgctccca aaccagccag   1260

tcccaagaag aacattaaaa ctaggagtgc ccagaagaga acaaacccga aaagagtgtg   1320

agctaactag tttccaaagc ggagacttcc gacttcctta caggatgagg ctgggcattg   1380

cctgggacag cctatgtaag gccatgtgcc ccttgcccta acaactcact gcagtgctct   1440

tcatagacac atcttgcagc atttttctta aggctatgct tcagtttttc tttgtaagcc   1500

atcacaagcc atagtggtag gtttgccctt tggtacagaa ggtgagttaa agctggtgga   1560

aaaggcttat tgcattgcat tcagagtaac ctgtgtgcat actctagaag agtagggaaa   1620

ataatgcttg ttacaattcg acctaatatg tgcattgtaa aataaatgcc atatttcaaa   1680
```

-continued caaaacacgt aattttttta cagtatgttt tattaccttt tgatatctgt tgttgcaatg 1740
ttagtgatgt tttaaaatgt gatcgaaaat ataatgcttc taagaaggaa cagtagtgga 1800
atgaatgtct aaaagatctt tatgtgttta tggtctgcag aaggattttt gtgatgaaag 1860
gggatttttt gaaaaatcta gagaagtagc atatggaaaa ctataatgtg tctttttac 1920 aatgacttca gctctgtttt tagctagaaa ctctaaaaac aaaaataata ataaagaaaa 1980
ataaataaaa aggagaggca gacaatgtct ggattcctgt tttttggtta cctgatttca 2040
tgatcatgat gcttcttgtc aacaccctct taagcagcac cagaaacagt gagtttgtct 2100
gtaccattag gagttaggta ctaattagtt ggctaatgct caagtatttt atacccacaa 2160
gagaggtatg tcactcatct tacttcccag gacatccacc ctgagaataa tttgacaagc 2220
ttaaaaatgg ccttcatgtg agtgccaaat tttgttttct tcatttaaat attttctttg 2280
cctaaataca tgtgagagga gttaaatata aatgtacaga gaggaaagtt gaggttccac 2340
ctctgaaatg agaattactt gacagttggg atactttaat cagaaaaaaa gaacttatct 2400
tgcagcattt tatcaacaaa tttcataatt gtggacaatt ggaggcattt attttaaaaa 2460
acaattttat tggccttttg ctaacacagt aagcatgtat tctctataag gcattcaata 2520
aatgcacaac gcccaaagga aataaaatcc tatctaatcc tactctccac tacacagagg 2580
taatcactat tagtattttg gcatattatt ctccaggtgt ttcttatgca cttataaaat 2640
gatttgaaca aataaaacta ggaacctgct atacatgtgt ttcataacct gcctcctttg 2700
cttggccctt tattgagata agttttcctg tcaagaaagc agaaaccatc tcatttctaa 2760
cagctgtgtt atattccata gtatgcatta ctcaacaaac tgttgtgcta ttggatactt 2820
aggtggtttc ttcactgaca atactgaata aacatctcaa tagtcaaa 2868

<210> SEQ ID NO 49
<211> LENGTH: 2506
<212> TYPE: DNA
<213> ORGANISM: Homo sapiens

<400> SEQUENCE: 49
ggccgcgggg cgcagcggct gacccgagac acgggagcgc ttggcacgcg gagccagagc 60
cggagctgca gccgcagcgg gagccggggg agctcagggg ccgcaggagc cgggccggag 120
tgagcgcacc tcgcggggcc ctcggggcag gtgggtgagc gccacccgga gtcccgcgcg 180
caactttcag ggcgcactcg gcggggcggc tgcgcggctg ccgggactcg gcgcgggact 240
gcatggaggc caaggagaag cagcatctgt tggacgccag gccggcaatc cggtcataca 300
cgggatctct gtggcaggaa ggggctggct ggattcctct gccccgacct ggcctggact 360
tgcaggccat tgagctggct gcccagagca accatcactg ccatgctcag aagggtcctg 420
acagtcactg tgaccccaag aaggggaagg cccagcgcca gctgtatgta gcctctgcca 480
tctgcctgtt gttcatgatc ggagaagtcg ttggtgggta cctggcacac agcttggctg 540
tcatgactga cgcagcacac ctgctcactg actttgccag catgctcatc agcctcttct 600
ccctctggat gtcctcccgg ccagccacca agaccatgaa ctttggctgg cagagagctg 660
agatcttggg agccctggtc tctgtactgt ccatctgggt cgtgacgggg gtactggtgt 720
acctggctgt ggagcggctg atctctgggg actatgaaat tgacgggggg accatgctga 780
tcacgtcggg ctgcgctgtg gctgtgaaca tcataatggg gttgaccctt caccagtctg 840
gccatgggca cagccacggc accaccaacc agcaggagga gaaccccagc gtccgagctg 900

```
ccttcatcca tgtgatcggc gactttatgc agagcatggg tgtcctagtg gcagcctata    960
ttttatactt caagccagaa tacaagtatg tagaccccat ctgcaccttc gtcttctcca   1020
tcctggtcct ggggacaacc ttgaccatcc tgagagatgt gatcctggtg ttgatggaag   1080
ggacccccaa gggcgttgac ttcacagctg ttcgtgatct gctgctgtcg gtggaggggg   1140
tagaagccct gcacagcctg catatctggg cactgacggt ggcccagcct gttctgtctg   1200
tccacatcgc cattgctcag aatacagacg cccaggctgt gctgaagaca gccagcagcc   1260
gcctccaagg gaagttccac ttccacaccg tgaccatcca gatcgaggac tactcggagg   1320
acatgaagga ctgtcaggca tgccagggcc cctcagactg actgctcagc caggcaccaa   1380
ctggggcatg aacaggacct gcaggtggct ggactgagtg tcccccaggc ccagccagga   1440
ctttgcctac cccagctgtg ttgtaaacca ggtccccctc ctgacctctg ccccactcca   1500
ggaatggagc tcttcccagc ctcccatctg actacagcca gggtggggac tcagcgggta   1560
taaagctagt gtgaccctgc tcttccagct cctgggccag ctctggaagg gctgtatttg   1620
ggcctaatcc tcagcaaatg ttctaccact cgcaggggca aaggtggtga gccacgggac   1680
gtccaagggg aggctggccc cagcgcgccc atactgcctg cctcatgccc cattctcagc   1740
ctggctggcc tttgccttta tgaatctgag cccctccatc tgcctatagc aataggcacg   1800
ggggtgagga ccctcacact ctcatttgag cctccctgag gcagggagcc aggaggcacc   1860
tgaggcctat ctgtgcctta gtcacttcag ctatgagcca aatgttccct ttcctggagg   1920
ggagaggctt cttactaggt aagagacagg tttcctcttt ccttatttcc tcagctgtgc   1980
caacacaaaa aacaactttg gcacaggtgg tgggcagggg gtagagagat ttcagcttgg   2040
gttctgcact aacagcctcc aagcccccctg gcacttctgt tgccctgaga gtgtcccagg   2100
ggattcagag tctccagaaa gatatggctg ggccaactct gttgcctacc tggcctgacc   2160
cagtcggagc ctgacatggt ggagggaaag ggagacaagt ggggctgcac tcggtccaga   2220
ggccagctag gagggaaacc gcagcttcct ggggcttgtg tgtgaagatt cctgacttag   2280
gggtggcttt tgtttacaag atgcaagagg ggaaacctgt ccccgactca tcgagacaac   2340
atgcccagtt atcagggagt cctgtgtcac aaggtctgtc tctgccattg taagcaagtg   2400
ccttgggcga gctggcctct gccccacagt ctcatctgta caccgacagg gttgatgcct   2460
ccctcacagg gttgagaaca agagccagtt ggccaagtaa aaaaaa                  2506
```

<210> SEQ ID NO 50
<211> LENGTH: 3150
<212> TYPE: DNA
<213> ORGANISM: Homo sapiens

<400> SEQUENCE: 50

```
gggtatttga caggagcgag ggcggacgca aagaacgcgg aggacctctg ggtgcctgca     60
ggggagctgc tccagccggg ccgccgggag cggtggggag agcatcgcgg agccgcccct    120
ccacgcgccc gcccagccgc gctcgcccac tgggctctcc cggctgcagt gccagggcgc    180
aggacgcggc cgatctcccg ctcccgccac ctccgccacc atgctgctcc cccagctctg    240
ctggctgccg ctgctcgctg ggctgctccc gccggtgccc gctcagaagt tctcggcgct    300
cacgtttttg agagtggatc aagataaaga caaggattgt agcttggact gtgcgggttc    360
gccccagaaa cctctctgcg catctgacgg aaggaccttc ctttcccgtt gtgaatttca    420
acgtgccaag tgcaaagatc cccagctaga gattgcatat cgaggaaact gcaaagacgt    480
gtccaggtgt gtggccgaaa ggaagtatac ccaggagcaa gcccggaagg agtttcagca    540
```

-continued

```
agtgttcatt cctgagtgca atgacgacgg cacctacagt caggtccagt gtcacagcta    600
cacgggatac tgctggtgcg tcacgcccaa cgggaggccc atcagcggca ctgccgtggc    660
ccacaagacg ccccggtgcc cgggttccgt aaatgaaaag ttaccccaac gcgaaggcac    720
aggaaaaaca gtctccttgc aaatcttttc cgttctgaat tcagatgatg ccgcagctcc    780
agcgttggag actcagcctc aaggagatga agaagatatt gcatcacgtt accctaccct    840
ttggactgaa caggttaaaa gtcggcagaa caaaaccaat aagaattcag tgtcatcctg    900
tgaccaagag caccagtctg ccctggagga agccaagcag cccaagaacg acaatgtggt    960
gatccctgag tgtgcgcacg gcggcctcta caagccagtg cagtgccacc cctccacggg   1020
gtactgctgg tgcgtcctgg tggacacggg gcgccccatt cccggcacat ccacaaggta   1080
cgagcagccg aaatgtgaca acacggccag ggcccaccca gccaaagccc gggacctgta   1140
caagggccgc cagctacaag gttgtccggg tgccaaaaag catgagtttc tgaccagcgt   1200
tctggacgcg ctgtccacgg acatggtcca cgccgcctcc gacccctcct cctcgtcagg   1260
caggctctca gaacccgacc ccagccatac cctagaggag cgggtggtgc actggtactt   1320
caaactactg gataaaaact ccagtggaga catcggcaaa aaggaaatca aacccttcaa   1380
gaggttcctt cgcaaaaaat caaagcccaa aaaatgtgtg aagaagtttg ttgaatactg   1440
tgacgtgaat aatgacaaat ccatctccgt acaagaactg atgggctgcc tgggcgtggc   1500
gaaagaggac ggcaaagcgg acaccaagaa acgccacacc cccagaggtc atgctgaaag   1560
tacgtctaat agacagccaa ggaaacaagg ataaatggct cataccccga aggcagttcc   1620
tagacacatg ggaaatttcc ctcaccaaag agcaattaag aaaacaaaaa cagaaacaca   1680
tagtatttgc actttgtact ttaaatgtaa attcactttg tagaaatgag ctatttaaac   1740
agactgtttt aatctgtgaa aatggagagc tggcttcaga aaattaatca catacaatgt   1800
atgtgtcctc ttttgacctt ggaaatctgt atgtggtgga gaagtatttg aatgcattta   1860
ggcttaattt cttcgccttc cacatgttaa cagtagagct ctatgcactc cggctgcaat   1920
cgtatggctt tctctaaccc ctgcagtcac ttccagatgc ctgtgcttac agcattgtgg   1980
aatcatgttg gaagctccac atgtccatgg aagtttgtga tgtacggccg accctacagg   2040
cagttaacat gcatgggctg gtttgtttct tgggattttc tgttagtttg tcttgttttg   2100
ctttccagag atcttgctca tacaatgaat cacgcaacca ctaaagctat ccagttaagt   2160
gcaggtagtt cccctggagg aaataatatt ttcaaactgt cgttggtgtg atactttggc   2220
tcaaaggatc tttgcttttc cattttaagc ttctgttttg agttttgccc tggggcttga   2280
atgagtccca gagagtcgtt cggatggtgg gaggctgcct aggaggcagt aaatccagtc   2340
acagtgcctg ggaggggccc atccttccaa aatgtaaatc cagtcgcggt gtgaccgagc   2400
tggctaacag gcttgtctgc ctggttttcc tcctacacgt ggacattatt ctcctgatcc   2460
tcctacctgg tccaccccag ggctaccgga aggtaaaatc ttcacctgaa ccaattatga   2520
gcagtctcct tactgaaggt acagccggat acgtggtgcc cccggggctg gtgttggcag   2580
ccggggggag gtgcctgagg gtccccacgg ttcctttctg cttttctgaa tgcatcaagg   2640
gtacgagaac ttgccaatgg gaaattcatc cgagtggcac tggcagagaa ggataggagt   2700
ggaatgccca cacagtgacc aacagaactg gtctgcgtgc ataaccagct gccaccctca   2760
ggcctgggcc ccagagctca gggcacccag tgtcttaagg aaccatttgg aggacagtct   2820
gagagcagga acttcaagct gtgattctat ctcggctcag acttttggtt ggaaaaagat   2880
```

cttcatggcc ccaaatcccc tgagacatgc cttgtagaat gattttgtga tgttgtgatg 2940
cttgtggagc atcgcgtaag gcttcttgct tatttaaact gtgcaaggta aaaatcaagc 3000
ctttggagcc acagaaccag ctcaagtaca tgccaatgtt gtttaagaaa cagttatgat 3060
cctaaacttt ttggataatc ttttatattt ctgacctttg aatttaatca ttgttcttag 3120
attaaaataa aatatgctat tgaaactata 3150

<210> SEQ ID NO 51
<211> LENGTH: 2450
<212> TYPE: DNA
<213> ORGANISM: Homo sapiens

<400> SEQUENCE: 51
agatgtcccc ggccggcgag agcgggcgcc ggggttcgct ctgagtcgcg tggcaggccg 60
cgctgcgtcc accgctgccg agttcagagc cgcgcaccgc ccgccgccgc aggtcgggtt 120
cccagcgcta ctcccaagac accgctcagc catgaagatg catttctgta tcccggtgtc 180
ccagcagcgg tccgacgcgc tgggggggccg ctacgtgctg tactccgtgc acctggacgg 240
gttcctcttc tgcagggtgc gctacagcca gctgcacggt tggaacgaac agctaaggcg 300
ggtctttgga aattgcctgc caccccttccc accaaagtac tatctggcaa tgaccacagc 360
tatggctgat gagaggaggg accaactgga acaatatttg caaaatgtaa ccatggaccc 420
aaacgtgttg agaagtgatg tcttcgttga gtttttaaaa ctggcgcagc tgaatacatt 480
tgacatcgcc accaagaaag cttatctgga catatttctg cccaatgaac agagtattag 540
aatcgaaatt ataacatcag acactgctga aagagtccta gaggtggtgt cacacaaaat 600
tggactgtgt cgagagctct tgggctactt cggcctcttt ctcattcggt ttggcaagga 660
gggcaagctc tctgttgtga aaaaattggc tgactttgaa ctcccttatg ttagtcttgg 720
aagttctgag gtggaaaact gtaaggttgg actccgaaag tggtatatgg ctccatccct 780
cgactccgtg ctgatggact gcagggtggc ggtagatttg ctctacatgc aggcaataca 840
ggacattgaa aaaggatggg ccaaacccac acaggcacag aggcagaaat tagaagcttt 900
ccagaaagaa gacagtcaaa caaagttttt ggagctggcc cgggaggtac ggcactatgg 960
atacctgcag ctggatcctt gtacctgtga ctacccagaa tcaggctctg gagctgttct 1020
ttctgttggc aataatgaga tcagctgctg catcaccctg cctgacagcc agacccagga 1080
catcgttttc cagatgagca gggtgaagtg ctggcaggtc actttccttg gaactctgct 1140
ggatacggat gggccccaga gaactctcaa ccagaactta gagctcagat ttcaatacag 1200
tgaggatagt tgctggcagt ggtttgttat ttacaccaaa caggcttttt tgctgagtag 1260
ctgcttgaaa aagatgatct cagaaaagat ggtaaagcta gctgctgaga atacagaaat 1320
gcagattgaa gttccggaac aaagcaaaag taaaaaatac cacattcaac aaagccagca 1380
gaaagactat tctagttttc tatcaagaaa aagcaagatt aagatagcta aagatgactg 1440
cgtttttggg aacataaagg aagaagatct ctgaagaaag ctctcatatt ttaaaatatc 1500
cttggaggct atctcaagac agtgaaagaa cttggggatt caggtgggct acctaccatc 1560
agtggaggaa atttgacctc ttcccatttt tttggcatta acatggactg tattcatcaa 1620
ggtattatac cacagcactc tatggaaatc tcaagattag aaaaaaaaaa agaaccaagt 1680
tatagagtta gtttttattt tatttttgca cttcgtcatg acagtataga gtttgttttt 1740
aatgtctcat aaatgacaag tggcaaattc aaatcaactc atataaaact cattctattt 1800
tttctctaaa atagatcttt atatggcttc atgaagtctt ttatgtgttt tgaatttaca 1860
taaatgaaag tctcataaaa tatcataaag atattttgga tcgatttcta aagatgtgac 1920
tcttcaacgg aggagaatag ggctctgaga aatggaatca ctgaaaaaga aacctgggtt 1980
ctctgatcta tccacacaga actagagcaa ggaggtgatg aaatactgat ctctttcctc 2040
acataagtct gagcctacca atatggatgt actcaaagtg aaacgctgcc ctgttctctg 2100
cttgaccatt gttataattt tattctgtcc ttagagtact gaaggcagtt caataatcaa 2160
catgctattt ggaatgtttt aatttggaaa gcaataaggc tctgcacctg atatcagata 2220
ccttataatt ctcttagctt taaaaatatg tatactttct cacaaggttt ttccttatct 2280
agcttcattt ctctcatggt aattaatgta attatgtata gaattaagac cacaataagg 2340
gagatgatca gaggaatctg tatagtgtaa ttagaaaaag tacaatattc taatgttcta 2400
actgggttgt atacctaatt atataataaa tacaaaataa ttccagtgaa 2450

<210> SEQ ID NO 52
<211> LENGTH: 677
<212> TYPE: DNA
<213> ORGANISM: Homo sapiens

<400> SEQUENCE: 52
aaacccctgg tacctgagca ctgatctgcc ttggagaacc tgatcctgag actccagcag 60
gatgtcttat caacagcagc agtgcaagca gccctgccag ccacctcctg tgtgccccac 120
gccaaagtgc ccagagccat gtccaccccc gaagtgccct gagccctgcc caccaccaaa 180
gtgtccacag ccctgcccac ctcagcagtg ccagcagaaa tatcctcctg tgacaccttc 240
cccaccctgc cagtcaaagt atccaccgaa gagcaagtaa cagcttcaga attcatcagg 300
accaagaaag gataaggata tttggctcac ctcgttccac agctccacct tcatcttctc 360
atcaaagcct accatggata cacagggagc ttctttctcc ttagccagta atctgcccat 420
gatgatccct gacagcaaaa agtttctttt ctgaggctgc catactgcca ctgtccaggt 480
ggagactgag caaaggaagt cctgggctgt gccagctccc agagcttcgg aagaaagagc 540
agcagctctc tccctgggaa ccatcagaga attctgttga tgtgttctgt gtctgtctgt 600
cacctggtca cgagcttcta ccacctttgc aattgtcact tatctttcac tccctgaata 660
aagtatctat gcatata 677

<210> SEQ ID NO 53
<211> LENGTH: 4977
<212> TYPE: DNA
<213> ORGANISM: Homo sapiens

<400> SEQUENCE: 53
cctcctggca aagcgtccag ccctgcctgc tcctcctcgg gcctgggcgc ctccagcagg 60
cacttccctc cctccctctc tccccagctg cctcctcctc ttctctcccc gctctccttc 120
ccctttcacc ccatcccctg ccctggctgc aaccatgagg gtcttggcct gcctccttgc 180
ggccctggtg gggatccagg ctgttgagcg cctgcgcctg gccgatggcc cccatgggtg 240
cgctggccgc ctggaggtct ggcatggcgg gcgctggggc accgtgtgtg atgacggctg 300
ggacctgcgc gatgccgccg tggcctgccg gcagctgggc tgcggagggg cactggccgc 360
cccgggaggc gccttcttcg gggagggggc agggcctgtg tggctcagcg agctggcttg 420
ccggggcaac gaggggcagc tgggcctctg ccaccaccgg ggctggaagg cccacatctg 480
ctcccacgag gaggacgcgg gcgtcgtctg cgcaggtcag cgtgtggcta actccaggga 540

-continued

```
cgactcaaca tctcccctgg atggggctcc ctggccaggg ctgttgctgg agctgagccc    600
cagcacggag gagcccctgg tgacacatgc cccccgccca gctgggaacc cccagaacgc    660
ctcccggaag aagagccccc ggcccaagca ggccaagtcc acccgggccc ctctgctgac    720
gacaggagcc ccccgccaag agcggctgcg cctggtctct ggcccccaca ggtgcgccgg    780
acgcctggag gtctggcacg gcgggcgctg gggcaccgta tgtgacgatg gctgggacct    840
gcgcgacgct gctgtagcct gccgggaact gggctgtggg ggggcgctgg ctgccccggg    900
cggtgccaga ttcgggcctg gtgcagggcc cgtgtggatg gacgatgtgg ggtgtggagg    960
aggagaacag gccctccgag actgccccg aagcccctgg ggccggagca actgtgacca   1020
cagcgaggat gcggggctgg tctgcaccgg cccagcacct cggctgcgcc tggccgatgg   1080
cccccacggg tgcgccggcc gcctggaggt ctggcacggg ggtcgctggg ggtcggtgtg   1140
tgacgacgcc tgggacctgc gagacgccgc tgtggcctgc cgagagctgg gctgcggagg   1200
ggcgctggcc gcccccgggg gcgccttctt tggggagggg tctggaccca tcatcctgga   1260
cgaccttcgg tgtcggggaa acgagacggc cttacgattc tgcccagctc ggccctgggg   1320
ccagcatgac tgtcaccacc gcgaggacgc cggggccgtg tgtgacggca tgcccctggg   1380
ctacgtccct cccacggccc ccacggacag caacaactcc acgcccaggg aggctgcctc   1440
caggcccccg tccaccatga cgagccaggc tccagggacg gcaggcgttt cacctcctcc   1500
agcctcccct actgtccttt gggagcctgg accggaagcc gggtccccccc agctgcgcct   1560
ggtggctggg cccagcaagt gctcaggtcg actggaggtg tggcatgacc agcgctgggg   1620
gaccgtgtgt gacgatagct gggacatgcg ggattcagct gtggtctgcc gggagctggg   1680
ctgtggtgga cctcagcagc cagaccctgc tgctggccgc tttggctggg gtgcgggccc   1740
catctggcta gatgatgtgg gctgtgtggg gaccgaggct tcactgtccg actgccctgc   1800
tgctccctgg ggaaagcaca actgcgctca caatgaggat gttggggtca cctgcactgg   1860
gcccccaggc ctggactcca tctcagaccc cttcagctgg agctggattc ctggactggg   1920
gagagatcgg gatgcctggc tcccgggaga gctggccacc aagccctctg caagtgtgac   1980
tgccagtgtt ctggagaaaa caaccacgaa ggccccaggg aaaatgccta agagtactaa   2040
gaagtgggtg acaaaaaatg caaagagacc aaccactcaa cccccagtga tgccaaccac   2100
gaaacactcc agggcccaaa gccccccaga cctaacctca cagaccactg cagcactgac   2160
cactgaggcc tcccgaagac ctacctctga gtttaccaga aggccgacca cggaggcccc   2220
ccagagatgg acctctcaca ccactgccac gctgacccct caggcccccc gagaacggac   2280
cactaagacc atggcaatgc tgaccactca aggcccccaa gaaatgacct ctgagtccac   2340
tatcaagagt atccctcagg cctccctgga gccatctgct gagatcccag aagggtctcc   2400
agagtcaccc aaagacccgg ccccctctcc cagtgttagc accactgggg aatcaggcct   2460
gttccgggtt cgtctggccg atgggcccaa ccgctgtgct ggccggctgg aagtgtggca   2520
tgccggacgc tggggaacag tgtgtgatga caactgggac ctgcgggacg ccactgtggc   2580
ctgctgggaa ctgggctgtg gaaaggtccg gcctcgagta ggcaaaaccc attacggccc   2640
tgggactggg cccatctggc tggatgacat gggctgtaag ggaagcgagg cctcactgag   2700
cgactgcccc tcgggggctt gggggaagca caactgtgac cacgaggaag acgtggggct   2760
cacctgcact ggctacacag actatgacga ttatcccccc tggacctggg accccacctc   2820
aagagaggac ctggccaagg ggactaccac agcgggggta cctggacaca ctctcccctg   2880
gaggaccacc cggcgcccgg gtagctcctc cccagcaata aggcgcctgc cggacacagg   2940
```

cagcaaagat ggttacaagc ttccctggac gtgggacaca ccatcaggaa ggggcctggc 3000
tgaggggacc cctaccgcag gcaaactagg accaactctt ggggctggca ccaccaggag 3060
cccaggcagt cctccaactc tgagagtcca tggagacaca ggttccccga ggaaaccgtg 3120
gcccgagcgc cggccaccgc ggcccgctgc gaccaggaca gcgcccccaa ccccgtcccc 3180
aggtccctcc gcctctccgg gacccccagg cccagcgctg acctctgact ccagtcgaga 3240
gctcactccc cactcagcct tgacgtccga ggcgacctct gacgctccgg acacttcacc 3300
acccacccca gacccggcct cccggacgaa ccccgacctc atcttgacaa gccctgactt 3360
tgctttgtcc acccctgact ccagtgtggt tcccgcgttg accccggagc cctcacccac 3420
gcccttaccc accttgccca aagagctgac ctctgaccct tctacaccgt cggaggtgac 3480
cagcctttcc cctacctcag agcaggtccc agaatctgac acaaccccag atttggacac 3540
aactccatac tccagtacag tctcagaata ttctagatcc ccagacccct ccccaagccc 3600
tcaccccact actaccccctg atcccaccat ggcccctgac cccatcacaa cccttaaccc 3660
tactgtgacc cctcacttcc ctaccacccc tcaccccacc acgacccctc accccaccac 3720
catcactcac tccaccatga ttcctgaccc caccacaacc cctcaaccct tcaccaccat 3780
cactcactcc accatgattc ctgaccccac cacaacccct caacccttca ccaccatgca 3840
gcccaccaca acccctcact ccacaacccc tcaccccacc acgacccctc atcccaccac 3900
catcactcac tccaccatga ttcctgaccc caccacaacc cctcaaccct tcaccaccat 3960
gcagcccacc acgatgcctc atcccaccac gacccctcac cccaccacga ctcctcaccc 4020
caccacaacc cctcacccca ccacaacccc tcaccccacc atgactcctg accccaccac 4080
gaccccttac cccaccacta ctcctgatcc caccacgacc cctcacccca caactcctga 4140
cccttcctca accccctgtca tcactactgt gtcccttcca acctccttgg ggacagaact 4200
ctcctctccc actctagcac caacagtcaa gcccagtctg cacccccagt tgaccttcac 4260
agcacctgcc cctcacacct ccacatccca gatacccacc ttagagccct ctccagcctt 4320
ggagtccagc ccctccaggt cctccacagc cacaagcatg gacccactgt ccactgagga 4380
cttcaagcca cccagaagcc agagccccaa cctaacccct ccacccaccc ataccccaca 4440
ctcagcctct gaccttactg tgtcccctga cccccctcctt tcccccacag cccacccctt 4500
ggatcatcct ccccttgacc ccctcaccct agggccaact cctggtcaga gcccaggccc 4560
ccatggtcca tgtgtggccc caacaccacc tgtaagggtc atggcttgtg agccacctgc 4620
cctggtggag ctggtggctg ctgtgaggga tgtgggtggt cagctgcaga gactgaccca 4680
ggtcgtggaa caggagcggc aggagcgcca agccctgctg ctggggctga cgcagctggt 4740
agaagctgcc cggggtctgg ggcagctggg tgaggctgtg aagagactgg cagagatggc 4800
ctggaccacc agcatgcctg caccaaccac cactacccca gaggaagaag aaagacccct 4860
gaggggagac gtgtgaccct ctccaggatt tgaggggctt aagacacccc caaccaaaaa 4920
aaacaaaaac aaaaaaaacc cccaaagtat ctaattaaaa acaaggtgtg aatggta 4977

<210> SEQ ID NO 54
<211> LENGTH: 4733
<212> TYPE: DNA
<213> ORGANISM: Homo sapiens

<400> SEQUENCE: 54
agacgcccgg tgaattctag aggcggcgga gggtggcgag gagctctcgc tttctctcgc 60

-continued

```
tccctccctc tccgactccg tctctctctc tctctctctc tctcccctcc ctctctttcc    120
ctctgttcca ttttttcccc ctctaaatcc tccctgccct gcgcgcctgg acacagattt    180
aggaagcgaa ttcgctcacg ttttaggaca aggaagagag agaggcacgg gagaagagcc    240
cagcaagatt tggattgaaa ccgagacacc ctccggaggc tcggagcaga ggaaggagga    300
ggagggcggc gaacggaagc cagtttgcaa ttcaagtttt gatagcgctg gtagaagggg    360
gtttaaatca gatttttttt tttttaaagg agagagactt tttccgctct ctcgctccct    420
gttaaagccg ggtctagcac agctgcagac gccaccagcg agaaagaggg agaggaagac    480
agatagggg cgggggaaga agaaaaagaa aggtaaaaag tcttctagga gaacctttca    540
catttgcaac aaaagaccta ggggctggag agagattcct gggacgcagg gctggagtgt    600
ctatttcgag ctcagcggca gggctcgggc gcgagtcgag accctgctcg ctcctctcgc    660
ttctgaaacc gacgttcagg agcggctttt taaaaacgca aggcacaagg acggtcaccc    720
gcgcgactat gtttgctgat ttttcgcctt gccctcttta aaagcggcct cccattctcc    780
aaaagacact tcccctcctc cctttgaagt gcattagttg tgatttctgc ctccttttct    840
tttttctttc ttttttgttt tgctttttcc cccttttga attatgtgct gctgttaaac    900
aacaacaaaa aaacaacaaa acacagcagc tgcggacttg tccccggctg gagcccagcg    960
ccccgcctgg agtggatgag cctctccatg agagatccgg tcattcctgg gacaagcatg   1020
gcctaccatc cgttcctacc tcaccgggcg ccggacttcg ccatgagcgc ggtgctgggt   1080
caccagccgc cgttcttccc cgcgctgacg ctgcctccca acggcgcggc ggcgctctcg   1140
ctgccgggcg ccctggccaa gccgatcatg gatcaattgg tgggggcggc cgagaccggc   1200
atcccgttct cctccctggg gccccaggcg catctgaggc ctttgaagac catggagccc   1260
gaagaagagg tggaggacga ccccaaggtg cacctggagg ctaaagaact ttgggatcag   1320
tttcacaagc ggggcaccga gatggtcatt accaagtcgg gaaggcgaat gtttcctcca   1380
tttaaagtga gatgttctgg gctggataaa aaagccaaat acattttatt gatggacatt   1440
atagctgctg atgactgtcg ttataaattt cacaattctc ggtggatggt ggctggtaag   1500
gccgaccccg aaatgccaaa gaggatgtac attcacccgg acagccccgc tactggggaa   1560
cagtggatgt ccaaagtcgt cactttccac aaactgaaac tcaccaacaa catttcagac   1620
aaacatggat ttactatatt gaactccatg cacaaatacc agccccggtt ccacattgta   1680
agagccaatg acatcttgaa actcccttat agtacatttc ggacatactt gttccccgaa   1740
actgaattca tcgctgtgac tgcataccag aatgataaga taacccagtt aaaaatagac   1800
aacaaccctt ttgcaaaagg tttccgggac actggaaatg gccgaagaga aaaaagaaaa   1860
cagctcaccc tgcagtccat gagggtgttt gatgaaagac acaaaaagga gaatgggacc   1920
tctgatgagt cctccagtga acaagcagct ttcaactgct tcgcccaggc ttcttctcca   1980
gccgcctcca ctgtagggac atcgaacctc aaagatttat gtcccagcga gggtgagagc   2040
gacgccgagg ccgagagcaa agaggagcat ggccccgagg cctgcgacgc ggccaagatc   2100
tccaccacca cgtcggagga gccctgccgt gacaagggca gccccgcggt caaggctcac   2160
cttttcgctg ctgagcggcc ccgggacagc gggcggctgg acaaagcgtc gcccgactca   2220
cgccatagcc ccgccaccat ctcgtccagc actcgcggcc tgggcgcgga ggagcgcagg   2280
agcccggttc gcgagggcac agcgccggcc aaggtggaag aggcgcgcgc gctcccgggc   2340
aaggaggcct tcgcgccgct cacggtgcag acggacgcgg ccgccgcgca cctggcccag   2400
ggcccccctgc ctggcctcgg cttcgccccg ggcctggcgg gccaacagtt cttcaacggg   2460
```

```
cacccgctct tcctgcaccc cagccagttt gccatggggg gcgccttctc cagcatggcg   2520
gccgctggca tgggtcccct cctggccacg gtttctgggg cctccaccgg tgtctcgggc   2580
ctggattcca cggccatggc ctctgccgct gcggcgcagg gactgtccgg ggcgtccgcg   2640
gccaccctgc ccttccacct ccagcagcac gtcctggcct ctcagggcct ggccatgtcc   2700
cctttcggaa gcctgttccc ttacccctac acgtacatgg ccgcagcggc ggccgcctcc   2760
tctgcggcag cctccagctc ggtgcaccgc cacccettcc tcaatctgaa caccatgcgc   2820
ccgcggctgc gctacagccc ctactccatc ccggtgccgg tcccggacgg cagcagtctg   2880
ctcaccaccg ccctgccctc catggcggcg gccgcggggc ccctggacgg caaagtcgcc   2940
gccctggccg ccagcccggc ctcggtggca gtggactcgg gctctgaact caacagccgc   3000
tcctccacgc tctcctccag ctccatgtcc ttgtcgccca aactctgcgc ggagaaagag   3060
gcggccacca gcgaactgca gagcatccag cggttggtta gcggcttgga agccaagccg   3120
gacaggtccc gcagcgcgtc cccgtagacc cgtcccagac acgtcttttc attccagtcc   3180
agttcaggct gccgtgcact ttgtcggata taaaataaac cacgggcccg ccatggcgtt   3240
agcccttcct tttgcagttg cgtctgggaa ggggccccgg actccctcga gagaatgtgc   3300
tagagacagc ccctgtcttc ttggcgtggt ttatatgtcc gggatctgga tcagattctg   3360
ggggctcaga aacgtcggtt gcattgagct actgggggta ggagttccaa catttatgtc   3420
cagagcaact tccagcaagg ctggtctggg tctctgccca ccaggcgggg aggtgttcaa   3480
agacatctcc ctcagtgcgg atttatatat atatttttcc ttcactgtgt caagtggaaa   3540
caaaaacaaa atctttcaaa aaaaaaatcg ggacaagtga acacattaac atgattctgt   3600
ttgtgcagat taaaaacttt atagggactt gcattatcgg ttctcaataa attactgagc   3660
agctttgttt ggggagggaa gtccctacca tccttgttta gtctatatta agaaaatctg   3720
tgtcttttta atattcttgt gatgttttca gagccgctgt aggtctcttc ttgcatgtcc   3780
acagtaatgt atttgtggtt tttattttga acgcttgctt ttagagagaa aacaatatag   3840
cccccctaccc ttttcccaat cctttgccct caaatcagtg acccaaggga ggggggggatt   3900
taaagggaag gagtgggcaa aacacataaa atgaatttat tatatctaag ctctgtagca   3960
ggattcatgt cgttctttga cagttctttc tctttcctgt atatgcaata acaaggtttt   4020
aaaaaaataa taaagaagtg agactattag acaaagtatt tatgtaatta tttgataact   4080
cttgtaaata ggtggaatat gaatgcttgg aaaattaaac tttaatttat tgacattgta   4140
catagctctg tgtaaataga attgcaactg tcaggttttg tgttcttgtt ttcctttagt   4200
tgggtttatt tccaggtcac agaattgctg ttaacactag aaaacacact tcctgcacca   4260
acaccaatac cctttcaaaa gagttgtctg caacattttt gttttctttt ttaatgtcca   4320
aaagtggggg aaagtgctat ttcctatttt caccaaaatt ggggaaggag tgccactttc   4380
cagctccact tcaaattcct taaaatataa ctgagattgc tgtggggagg gaggagggca   4440
gaggctgcgg tttgactttt taatttttct tttgttattt gtatttgcta gtctctgatt   4500
tcctcaaaac gaagtggaat ttactactgt tgtcagtatc ggtgttttga attggtgcct   4560
gcctatagag atatattcac agttcaaaag tcaggtgctg agagatggtt taaagacaaa   4620
ttcatgaagg tatattttgt gttatagttg ttgatgagtt ctttggtttt ctgtattttt   4680
ccccctctct ttaaaacatc actgaaattt caataaattt ttattgaaat gtc          4733
```

<210> SEQ ID NO 55

<211> LENGTH: 2812
<212> TYPE: DNA
<213> ORGANISM: Homo sapiens

<400> SEQUENCE: 55
gccgagcccc gccggaggga ggcggctccg cgcggggccc gccgcccgcg ccgccgccac 60
cgaaacccgg ccgcggcgcg cccgaccttc tgcgccggct gccgcggccg ccctcgccgc 120
gctcccgccc cggccgctgc ccctgcccgc cccgctcgcc ccgcgcaccc caacccgggg 180
aggggctccc acgaccccgg gcgcgcgcgc ttgggggcgc gccagggact ccagggtccc 240
ttgccccgcg ccgcttctcc ctcctccctc tttcttcggg cagcctcccc accaccccac 300
ttcagcctcc cccactcttg ccgcctccat atcatcaagc tctggtggcg cctgggggc 360
ttttcggatc ggcaggatgt acccccaggg aaggcacccg accccgctcc agtccggcca 420
gcccttcaag ttctcgatct tggagatctg cgaccgcatc aaagaagaat tccagtttct 480
tcaggctcaa taccacagcc tcaagctaga atgtgagaag ctggccagcg agaagacgga 540
aatgcagcga cattatgtca tgtattatga gatgtcgtac gggctcaaca ttgaaatgca 600
taagcaggcg gagattgtga agcgtctgag cggtatctgc gctcagatta tccccttcct 660
gacccaggag catcagcagc aggtgctcca ggccgtagaa cgcgccaagc aggtcaccgt 720
gggggagctg aacagcctca tcgggcagca gctccagccg ctgtcccacc acgcaccccc 780
tgtgcccctc accccccgcc cagccgggct ggtgggcggc agtgctacgg ggctgcttgc 840
tctgtctgga gccctggctg cccaggctca gctggcggcg gctgtcaagg aggaccgtgc 900
gggcgtggag gccgaggggt ccagagtgga gagagccccg agcaggagtg catctccctc 960
gccccctgag agtctcgtgg aggaggagcg accgagtggc cctggtggtg gcgggaagca 1020
gagagcagat gagaaggagc catcaggacc ttatgaaagc gacgaagaca agagtgatta 1080
caatctggtg gtggacgagg accaaccctc agagcccccc agcccggcta ccacccccctg 1140
cggaaaggta cccatctgca ttcctgcccg tcgggacctg gtggacagtc cagcctcctt 1200
ggcctctagc cttggctcac cgctgcctag agccaaggag ctcatcctga atgaccttcc 1260
cgccagcact cctgcctcca aatcctgtga ctcctccccg ccccaggacg cttccacccc 1320
cgggcccagc tcggccagtc acctctgcca gcttgctgcc aagccagcac cttccacgga 1380
cagcgtcgcc ctgaggagcc ccctgactct gtccagtccc ttcaccacgt ccttcagcct 1440
gggctcccac agcactctca acggagacct ctccgtgccc agctcctacg tcagcctcca 1500
cctgtccccc caggtcagca gctctgtggt gtacggacgc tcccccgtga tggcatttga 1560
gtctcatccc catctccgag ggtcatccgt ctcttcctcc ctacccagca tccctggggg 1620
aaagccggcc tactccttcc acgtgtctgc ggacgggcag atgcagccgg ttcccttccc 1680
ctcggatgca ctggtaggcg cgggcatccc gcggcacgcc cggcagctgc acacgctggc 1740
ccatggcgag gtggtctgcg cggtcaccat cagcggctcc acacagcatg tgtacacggg 1800
cggcaagggc tgtgtgaagg tgtgggacgt gggccagcct ggggccaaga cgcccgtggc 1860
ccagctcgac tgcctgaacc gagacaacta cattcgttcc tgcaagttgc tgccggatgg 1920
ccggagtctg atcgtgggcg gtgaggccag caccttgtcc atttgggacc tggcggcgcc 1980
cacccccccgt atcaaggccg agctgacttc ctcagcccca gcctgctacg ccctggccgt 2040
cagccccgac gccaaggttt gcttctcctg ctgcagcgat ggcaacattg tggtctggga 2100
cctgcagaat cagactatgg tcaggcagtt ccagggccac acggacggcg ccagctgcat 2160
tgatatttcc gattacggca ctcggctctg gacagggggc ctggacaaca cggtgcgctg 2220

```
ctgggacctg cgggagggcc gccagctgca gcagcatgac ttcagctccc agattttctc   2280

cctgggccac tgccctaacc aggactggct ggcggtcgga atggagagta gcaacgtgga   2340

gatcctgcac gtccgcaagc cggagaaata ccagctgcac ctccacgaga gctgcgtgct   2400

gtccctgaag tttgcctcct gcggacggtg gtttgtgagc accgggaagg acaacctgct   2460

caacgcctgg aggacgccgt acggggccag cattttccag tccaaggagt cgtcctcagt   2520

cctgagttgt gacatctcca gaaataacaa atacatcgtg acaggctcgg gggacaagaa   2580

ggccaccgtg tatgaggtgg tctactgaga catgaccccc cttcctgtac ccgaagtcca   2640

gactcccagg ggaatcagca gccaggacag acatcctagc agccgcctcc cagccctgcc   2700

taggaaccgt acatcccatc tgctctctgg ccaacggctt cacaccttcc cctgctgcat   2760

gtgggggccg atgggcaggg gacctcggtg gaaataaaat gtatctatca ca            2812
```

```
<210> SEQ ID NO 56
<211> LENGTH: 4959
<212> TYPE: DNA
<213> ORGANISM: Homo sapiens

<400> SEQUENCE: 56

gtctccgcgg ctcgtctcct cagtccgccc ggggaggagg aggaggagcg gggccagccg     60

ccgccgccgc cgccgtccca gcctcgccca gcgcacctga actcgcctcg ccgacccggg    120

ccccagcgcc gcgccccgcg cccccggcgc ccggcccgcg cgcagcgctg cctcggtgcc    180

ccggcggggc gcgtccccccc ggccgcctcc cgctctcccg cggctcgcgt ggccgcgcct    240

ttgtgtgcgg cggccgcggc tcccgagctc ctcgggctct gggtcccggc gcccctccgg    300

ccgcgagtcc cacgcgccac ccccgggcgc cctcgacggt ggatctagcg gcggcgagga    360

ggcgggtccc ggccccggcg aaccccagtc ccggcccccg gccccgggcc cagcttcggc    420

atggatgtga ggttctaccc cgcggcggcc ggggaccctg ccagcctgga cttcgcgcag    480

tgcctggggt actacggcta cagcaagttt ggaaataata ataactatat gaatatggct    540

gaggcgaaca atgcgttctt cgctgccagt gagcagacat tccacacacc aagccttggg    600

gacgaggaat tcgaaattcc accaatcacg cctcctccag agtcagaccc tgccctaggc    660

atgccggatg tactgctacc ctttcaagcc ctcagcgatc cattgccttc ccagggaagt    720

gaattcacac cccagtttcc ccctcaaagc ctggacctcc cttccattac aatctcaaga    780

aatctcgtgg aacaagatgg cgtgcttcat agcagtgggt tgcatatgga tcagagccac    840

acacaagtgt cccagtaccg gcaggatccc tccctgatca tgcggtccat cgtccacatg    900

accgatgctg cgcgttctgg ggtcatgcct cctgcccagc tcaccaccat caaccagtct    960

cagctcagcg cccagttggg gttgaatttg ggaggtgcca gtatgcctca cacatctcct   1020

tcacctccag caagcaaatc agccactccc tccccttcca gctccatcaa tgaagaggat   1080

gctgatgaag ccaacagagc cattggagag aaaagagctg ctccagactc tggcaagaag   1140

cccaagactc caaagaaaaa gaaaaagaaa gatcccaatg agccacagaa gccagtgtca   1200

gcatatgccc tgtttttcag agacacacag gctgcaatta aaggtcaaaa ccccaatgca   1260

acctttggag aggtctcaaa aattgtagca tctatgtggg acagccttgg agaagaacaa   1320

aagcaggtat ataaaaggaa aacagaagct gccaaaaaag aatacctgaa ggccctggcg   1380

gcatacaggg ccagcctcgt ttctaaggct gctgctgagt cagcagaagc ccagaccatc   1440

cgttctgttc agcagaccct ggcgtcgacc aatctaacat cctctctcct tctcaacact   1500
```

-continued

```
ccactgtctc aacatggaac agtgtcagca tcacctcaga ctctccagca atccctccct   1560
aggtcaatcg ctcccaaacc cttaaccatg agactcccca tgaaccagat tgtcacatca   1620
gtcaccattg cagccaacat gccctcgaac attggggctc cactgataag ctccatggga   1680
acgaccatgg ttggctcagc accctccacc caagtgagtc cttcggtgca aacccagcag   1740
catcagatgc aattgcagca gcagcagcag cagcaacaac aacagatgca acagatgcag   1800
cagcagcaac tccagcagca ccaaatgcat cagcaaatcc agcagcagat gcagcagcag   1860
catttccagc accacatgca gcagcacctg cagcagcagc agcagcatct ccagcagcaa   1920
attaatcaac agcagctgca gcagcagctg cagcagcgcc tccagctgca gcagctgcaa   1980
cacatgcagc accagtctca gccttctcct cggcagcact cccctgtcgc ctctcagata   2040
acatccccca tccctgccat cgggagcccc cagccagcct ctcagcagca ccagtcgcaa   2100
atacagtctc agacacagac tcaagtatta tcgcaggtca gtattttctg aagacgcata   2160
tggcagacgg atttgcgtat accaaggaga gtggcatagg agggaaaagc atatgtggct   2220
gaaacctgta agttggtgtt ggttatgcag aaatgtgtaa cagatcaaac ggtcctctca   2280
agtgtctatt agataggcaa taagaactgc agtgtagctg agtaacatct tttagctgac   2340
tataaatcac tttgttttta aacaagaaaa gctgtgctct tttatgtgat gccttttta    2400
tttattcagg ctatacctac aatatgtgaa tcaaactgtt taatgaatcc tgggacatac   2460
tgatgactat aaactggcct ctctgagtca tagaaaaatg gccttatttc tccagaagtg   2520
agtaaaccac acttccaggc tatctgaact cctgaagccc taaaaataaa aagcacagtt   2580
gtaactacct gaaatatgaa gatccagttt catacaaaca tttgtatgac gtgaatagtt   2640
gatggcattt ttttgtcatg aaaaaaataa tgtaaatcac agacttttgc caaagctctt   2700
atttttttc ctaaatctct ccagaaaaaa aatgcaagtg actaaattca attattgact    2760
aatttccact ttttatccat gacttctcca aatcaaacca cagtatatgt tgtaacaata   2820
tctatgacca ctgttagccc attatattca ttccaattag aagaaatgtg aatactatat   2880
tccgtgtttt gagtgacaag tttcgaaaaa taaaaacact gtatttttaa aagggaaatg   2940
cacttaaatg aaaacagtta ttacaaaagt taagatttaa aaagaaaaag caagagtttt   3000
tattatgatg taataccagt agaatattta aaaggcacac cacatctgaa taatcaatgt   3060
aaatatttc tttcaaagtt gtaagttttc atatcatgtg ctgtaaagtt ttcctaaatg    3120
aggctttaac gtaaacactg gtgacataaa ccattcattg ctacgttgct tattgtgttt   3180
ttatgctgtt ttatactttt ttatgagtta tgatagcagc aattaagttg tttgtatttt   3240
gcttaactaa aacaaaaatg cttttatctt gctatagaat aaacacattt cagtaaaaac   3300
tgtggactgt attttgatgc aacaacaaag aaactgttca cttttcaaat aaaatgatat   3360
gtcagatttc atttttggtt ccttgaatac atgtaagatg gggaaatatg ccacatacca   3420
agtttcgttt tagcccaaac atcatcttcc atttttcaat tggaaatatg atatttatgg   3480
ccaagaatat gcattgcata gcctgaaatg aagatccttg aaaaaaccaa aacaacgcat   3540
tggaaatatt tgtgtaattg tcttttttt tttttttttt tttttaaga tgcaagtaca    3600
aggtaagtat agagaaaaaa gtaatcgctt ttttgagggg gctagaacta gctgggtatt   3660
gtaatgttat tgcgattaaa atagatggtg aatgctaatt cttaagccaa aataattatt   3720
tcggtgccca tttattcccc ccttttcttg ctctgtagcg gttcctcttt gagagcagtg   3780
tgaccactat ccccagttgt cttgcatgat taattacagc atctgtcctg tcagaagcta   3840
taatgaagag gtcttgataa aaattgcaaa ttaccactgg caacagtctt aaactgctta   3900
```

tgataaaatg aaaattaaaa acagcaagtg tcaaccctga ccagaatcct aatctggaaa 3960
gaatgagggt gtgcgtggtg cgctccacag ctactatgtg caagacattc aaaaataatg 4020
gaatatggat ccctcaaagt tgttgtattt cagagattat ttactgtatg ttgtgggtta 4080
tgaataatga attcagcttt caatatttca taatcctctc ctactctgta ttatgtacaa 4140
atattgaaca gcaagagatt ctaattataa atttatggat ttcttgctgt agaaaaattt 4200
atgtctaaat tgaagctttt cataagatgt attagttgac aggtatcagt gttcaaacag 4260
ccttagaatg atgcctaatt acatctacaa gggagtgatt gtattccaca aagaaatgat 4320
gtgctagcat cagatccttc agaagtagag ctcgaatggt aaaagatttt ctgtgaattg 4380
aaactaacat tacataacaa taaccatttt atattctgtt gtgaaacctt tagacagatg 4440
tcttcaaaat taattgctaa actacatgtg acagtaattg tgtattagtt ctgtaattgt 4500
cattttgaaa acccatgaag tattgcttgg aaaaaaatgt cactagtgat aagacttaat 4560
tgcaagtgaa gtctgttttc aactgtttgc agttagaagc aggtgttgta acatctatta 4620
aatgatttta taaatcttgg gttttatcac atttgattaa atgctgctaa gccactgatg 4680
gtcaattcca gaggaaaaaa aaagtttaat gactacagtt tataaaatta atcaccaggc 4740
aaaactacat atttaaaatg tcaaaaggct tgaatcatga aaagaattcc tcaaccttgt 4800
taccaaatta ttgttttcag gattcacaaa gcatgttata tatccattta tatttcagtt 4860
tatacatatg actggtttct attcctgaga cttaagtaag tacttggtgc gctttttctt 4920
ttgttacagg tcagaaataa atcaggataa tgaaaaata 4959

<210> SEQ ID NO 57
<211> LENGTH: 1284
<212> TYPE: DNA
<213> ORGANISM: Homo sapiens

<400> SEQUENCE: 57
cagagaggct gcagacagag aaggatgatg gcgtctgcgg cagcagcgga ggccgagaag 60
ggatctccag ttgtggtggg cctgctagtt gtgggcaata tcattattct gctgtcaggc 120
ctgtccctgt ttgctgagac catatgggtg acagccgacc agtaccgtgt atacccactg 180
atgggagtct caggcaagga tgacgtcttc gctggtgcct ggattgccat cttctgcggc 240
ttctccttct tcatggtagc cagttttggt gtgggtgccg cactctgccg ccgccggtcc 300
atggtcctca cgtacctggt gctcatgctc atcgtctaca tcttcgagtg cgcctcctgc 360
atcacgtcct acacccaccg tgactacatg gtgtccaacc catccctgat caccaagcag 420
atgctgacct tctacagcgc ggacaccgac cagggccagg agctgacccg cctctgggac 480
cgcgtcatga ttgagcaaga atgctgtggc acatctggtc ccatggactg ggtgaacttc 540
acgtcagcct tccgggcggc cactccggag gtggtgttcc cctggccccc actgtgctgt 600
cgccggacgg gaaacttcat ccccctcaac gaggagggct gccgcctggg gcacatggac 660
tacctgttca ccaagggctg cttcgaacac atcggccacg ccatcgacag ctacacgtgg 720
ggtatctcgt ggtttgggtt tgccatcctg atgtggacgc tcccggtcat gctgatagcc 780
atgtatttct acaccatgct ctgagggaca ggaggggaag gcaacataca caccccggac 840
tcctccgcat cctcctcctg cttcctccgc tgggcctgga tggctgcctc acctctcacc 900
tcccaacgtc cctagccctt acgtccttcc acttccaaga tctttttcca ggttcctgag 960
ccctactgtg tctcaggtgt gccctgaaac cccagggctt gtgtgcacat atccttagcc 1020

```
catctttcaa gggacctctc catgatccca cctcccattc acagatacct ctcttgtagc   1080

tctctgacct cctccttcat ggcaggcatc gccattcttg ctgaaccgtt tgtgattgcc   1140

atttgagctc tggaagcctc tattgccatg agagttctgt cacggtcact ttactgtccc   1200

catcatcacc cagcacgggg ctaagcatat actagatagt caataaataa ataaataatg   1260

aatgaatgaa aaaaaaaaaa aaaa                                          1284
```

<210> SEQ ID NO 58
<211> LENGTH: 934
<212> TYPE: DNA
<213> ORGANISM: Homo sapiens

<400> SEQUENCE: 58

```
acttgcctca ggaaccccag cctgccagca cctattccac ctcccagccc agcatggcac     60

ccctgctgcc catccggacc ttgcccttga tcctgattct gctggctctg ctgtccccag    120

gggctgcaga cttcaacatc tcaagcctct ctggtctgct gtccccggcg ctaacggaga    180

gcctgctggt tgccttgccc ccctgtcacc tcacaggagg caatgccaca ctgatggtcc    240

ggagagccaa tgacagcaaa gtggtgacgt ccagctttgt ggtgcctccg tgccgtgggc    300

gcagggaact ggtgagtgtg gtggacagtg gtgctggctt cacagtcact cggctcagtg    360

cataccaggt gacaaacctc gtgccaggaa ccaaattcta catttcctac ctagtgaaga    420

aggggacagc cactgagtcc agcagagaga tcccaatgtc cacactccct cgaaggaaca    480

tggaatccat tgggctgggt atggcccgca caggggggcat ggtggtcatc acggtgctgc    540

tctctgtcgc catgttcctg ctggtgctgg gcttcatcat tgccctggca ctgggctccc    600

gcaagtaagg aggtctgccc ggagcagcag cttctccagg aagcccaggg caccatccag    660

ctccccagcc cacctgctcc caggccccag gcctgtggct cccttggtgc cctcgcctcc    720

tcctcctgcc ctcctctccc ctagagccct ctcctccctc tgtccctctc cttgcccccca    780

gtgcctcacc ttccaacact ccattattcc tctcacccca ctcctgtcag agttgacttt    840

cctcccattt taccacttta aacaccccca taacaattcc cccatccttc agtgaactaa    900

gtccctataa taaaggctga ggctgcatct gcca                                934
```

<210> SEQ ID NO 59
<211> LENGTH: 1084
<212> TYPE: DNA
<213> ORGANISM: Homo sapiens

<400> SEQUENCE: 59

```
aggtctggtg cccgcgcctg ctcgctggac cgcccgcccc gcgctctggc ggctcctccc     60

gggcgatgcc tccgctctgg gccctgctgg ccctcggctg cctgcggttc ggctcggctg    120

tgaacctgca gccccaactg gccagtgtga ctttcgccac caacaacccc acacttacca    180

ctgtggcctt ggaaaagcct ctctgcatgt ttgacagcaa agaggccctc actggcaccc    240

acgaggtcta cctgtatgtc ctggtcgact cagccatttc caggaatgcc tcagtgcaag    300

acagcaccaa caccccactg ggctcaacgt tcctacaaac agagggtggg aggacaggtc    360

cctacaaagc tgtggccttt gacctgatcc cctgcagtga cctgcccagc ctggatgcca    420

ttggggatgt gtccaaggcc tcacagatcc tgaatgccta cctggtcagg gtgggtgcca    480

acgggacctg cctgtgggat cccaacttcc agggcctctg taacgcaccc ctgtcggcag    540

ccacggagta caggttcaag tatgtcctgg tcaatatgtc cacgggcttg gtagaggacc    600

agaccctgtg gtcagacccc atccgcacca accagctcac ccccatactcg acgatcgaca    660
```

```
cgtggccagg ccggcggagc ggaggcatga tcgtcatcac ttccatcctg ggctccctgc    720

ccttctttct acttgtgggt tttgctggcg ccattgccct cagcctcgtg gacatgggga    780

gttctgatgg ggaaacgact cacgactccc aaatcactca ggaggctgtt cccaagtcgc    840

tgggggcctc ggagtcttcc tacacgtccg tgaaccgggg gccgccactg gacagggctg    900

aggtgtattc cagcaagctc caagactgag cccagcacca cccctgggca gcagcatcct    960

cctctctggc cttgccccag gccctgcagc ggtggttgtc acaccctgac ttcagggaag   1020

gtgaaacagg gcttgtccct ccaactgcag gaaaaccctt aataaaatct tctgatgagt   1080

tcta                                                                1084
```

<210> SEQ ID NO 60
<211> LENGTH: 3158
<212> TYPE: DNA
<213> ORGANISM: Homo sapiens

<400> SEQUENCE: 60

```
agtttcaccc agcaagcgtg agaacaggta ctgcttcctg agcaccgcca gccaccggca     60

ccaagaccgg ccacatccca gcactgccca cctctgctcc cagccgccag atgacggagg    120

ctctcgccag accctcagca cgcagagctg gcttctgata gaagtgatcg ggaaagaaag    180

caaagcggga ggtgcctctt tagaaaccac gaagtgcacg cggcgtcgac agtgatcacg    240

ccacctggac agccagagtc caaggcataa ggaggaaaat gagtctcctc aaagagcgga    300

agccaaaaaa gccacattac atccccaggc ctccaggaaa gcccttcaag tataaatgtt    360

tccaatgtcc ctttacttgc aatgagaagt cacatctttt taatcacatg aagtatggtc    420

tttgtaaaaa ctcgattact ttagtatcag agcaggatcg agttcccaag tgccctaaat    480

ctaactcact agaccccaag caaaccaacc agcccgatgc cacggcgaag ccagcctctt    540

ccaagtctgt cgcaaatgga ctctctgcct tcgactcgaa gcttcagcac agctctgcca    600

gggaagacat caaggaaaac ctggagctgc aagcccgggg aacccacagg tgcctgggac    660

agaagccagc cctccacagg gcatcaccct gcaagagccc agctccggaa gccgccctcg    720

gtgcccagcc tgctctggaa ggcgcagctc ggccttctgc atttgttcca gtcggcgagc    780

acagactcaa ggggccagac aacgccgagg cgcccgagac actggcttta cacaacccca    840

ctgccaaggc cgtgtctttc cacaccaagt cggccttcca cactcctggc taccccctgga    900

aagccggctc acctttcctt ccaccagagt ttccacataa aatctcatct acaaaggggc    960

ttggggccat ttccccttac atgcacccca caatcccaga gtacccgcct cacttttaca   1020

cagagcacgg gctggccacc atctactcgc cttacctgct ggctgggagc tcgcctgagt   1080

gtgacgcacc cctgctgtca gtctacggaa cccaagaccc gagacacttc ctgcctcacc   1140

cggggccgat ccctaagcac ctggctccat ctccagccac atacgatcac tacaggtttt   1200

tccagcaata tccctctaac ctgccgattc cttacggatt ttacaggcca gagtctgcat   1260

tttcctccta tggtctcaga ctcccacctg tcactggcct cacccgagat cagagctctc   1320

acctgcttga agaagccacc ctggtctatc cagcctcgag tccttccagg ttaaaccctt   1380

cggaccccaa cagaaaacac gtcgagttcg aaagtccaat tcctgaggct aaagactcct   1440

ccaaggctgg gcagagagac acggaagggt ccaaaatgag cccccgcgca gggagtgcag   1500

ccacgggctc cccagggagg ccgagcccca ccgacttcat gcagacgagc cagacctgcg   1560

aaggcctgta cgacctctcc aacaaggcag cctccagcgc actgggaaga ctctacccgc   1620
```

cagagcaaag cctcacagcc ttcaggcctg ttaagaaaag cacagaatgc ctacctgccc 1680
aggctgctga gaccacagca gagtctccag taagcctcaa tgttgtgaac ggagaccctc 1740
ctgctccgac cggaagcgcc tctctcgtct cggaggccgc gccttccagt ccggacgaca 1800
gctccgggat gggccccctc aacctctcca agaaatcaga gataaacctg gcagccaccc 1860
acgaacccac gtaccaaggc agcccccagg cggaaaccgc cagcttctca gagctgcagg 1920
accttccact caatctctcg gtgaaggacc cctgtaacac ccaggctccg aggcctgcct 1980
tccccggtcg accacgagct gcagaacctg ctgctgctgt tccacagaag actgggacag 2040
aaggttctga ggatgggccc agccaccctg agaccaagcc aggcagcctc gacggtgacg 2100
gggccccacc cacaggcccc ggcgaggagg ctccagacgc atgcgcggtg gacagcagcg 2160
aggagcagaa gcagacggca gccgtggccc tgtgccagct ggcggcctac agccccagga 2220
acatccgggt gggcgatggg gatgctgcgg ccccggaacc tgcctgccgg caagacacac 2280
ccacactgag ctccatggag agccaagagg cccagtgtga cctcagaccc aaaggacaaa 2340
agaggacaag tctaagggat gctggaaaat cccagcaagg agctaagaag gcgaagctgc 2400
aggacacggc cagagtgttc acactacgaa ggagggcccg ggtgtcctaa cgccgggttc 2460
acacgtgtgt tcacagagct acggccacac acacgccttc caaggtggca agctacaaca 2520
cctctgaact ggcactttca catttttaca aatgcagctg ctgcttctca aaaaaacaaa 2580
caaacaaaca aacaaaaaac cctccaattc agtttttata aatattaagc atgaatatta 2640
aaaggtgctt ctacttttgg ttgtaaaaac acctgaatga ctctaagact gatatgtatt 2700
ttcaagtcta agctgtctta cagaagatct tttataaatg tttccttata aatatctcac 2760
cattacaaca aattgtttta actgtttttc tattagctct agctgcatat ttgatgtaaa 2820
tgacaattac tgaaaaaatg tcagaaaaaa cattttcagt actaacatta aagtgccata 2880
tgtaaaaaag aaaaatgtga tttgtataac taaataacac acaaacatca agaggctatt 2940
tatacaaata atttatttcc actagggaaa gtgcattact ggtgaaggta ttatcaattt 3000
attctacttg cttataatgt tacagtgaat gttctggctt actctgcctc actttccatt 3060
ccccaaaatg atgtgtatgt tgctaatttt ccaataaact catatgaacc ataaggaaac 3120
ataaaatgca aataaacata aatctatgtt atccttta 3158

<210> SEQ ID NO 61
<211> LENGTH: 6979
<212> TYPE: DNA
<213> ORGANISM: Homo sapiens

<400> SEQUENCE: 61
aaaataggct gcaatcaagt tcacttccaa aggcggaatt catgggtaca tatggtgtcc 60
acgtgtgtac acctgcagag ttgtaacatg cgggcatttc tcccctcagc ccgccattct 120
ggcttcttaa cttgcaccct aacagctcga cagaaccttg gcgtccacaa aaaggacttg 180
aggtgggaca tggaagaaca gggacccctc ctggtttgtc cacccagccc acacctccat 240
tcctcaccca acctaccact tcagagccgg gaaaagacct cagagaacat ccgctccgac 300
tctaccgagg ctcagacagg acaacaagag tgtgctggac actgggaaat gtggtccagg 360
agcagtcaca gtccctatag acctcccaca aattaccgta atgcaaagag tgctcagccc 420
ctgccgacat gagcaatggg cagcgcgtcc agctgggttc ctgccccatg agaagcacac 480
agcctggttt ggtaggtggg gctccatcag ggctgtttgg atacctgggt ggagcccaca 540
gaccagcccc caccttgtgt ggttagggct ttgctaggaa ggcccatctg tgcgccatga 600

-continued

```
ccttggaact cgatgtgaga tccctggacc ggcagcagca cctggaagct tgttggaaat    660
gctgatctca ggtgggactc cagaattccc gcatctgcac ctgcactccc aaaatacctc    720
cccaccaggt gatccgaggc catggggcgg tctgaagggc actgtgctgg ggcgtcccac    780
cactagaaat ccagtccggt aatctgaaga tgtaagtgcc cccaggagga gtgacggagt    840
gacacaaatg acacaagggg aggggacttg tcaggtgtcc actcctgact gcaagttccc    900
agggcagaag gcaatgcccc cacagggact tttccagaca ctccgagtgc acctgaattg    960
cattttgagt gatgctgcct gctaagcagg aagagccctc cggagcctcg aaaagcagag   1020
tggaagtggt ggtgcccagg acgcatgggc tctgatggga agagggaggt gggcctgagc   1080
atgggccttc ttctccccag gtcagagggg cctggatgcc cctggaggga acactgaggt   1140
cacctctggc caaatcttcc tgttctgcca gtacccagcc ctgttcagtg acgtcaagct   1200
tttgggtccc tgtcctgggg ccctccacgc tggccgggct gtgtagagac gcccttctct   1260
ccactttatt gggtccagat tgttgtgtgg cttctcccct cctctgcagc ctggggtctg   1320
aaaacagcga tgccaacaga cagacagatt tccaaaagaa aggtccggct cagccaagga   1380
caaaggggcc tcgcagaggc tcctgggggt cagaaagctg agagtctacc aggcaggtgc   1440
cttctccacc cacaggcaca agctacaaca gctttccaag aagtgcatcc acatcgtccc   1500
caggtccaga tgcccacatt gccctgcagg gaccaagacc acactcgggc tgcttggaca   1560
ggatgtagct ggtcactgtt ctggagctgg cccctctgta gcctgtgaca atcagcttga   1620
gtctctctgc caagtctccg ccttctgttc ttcttgccga ccttgaagca gagttgacgt   1680
ttcaggtttt tccagcagac aaagctcact caatctgata ctgtggaggt tgttaattta   1740
acaaccaacc catcctcatg ttgagaaacc agctccaaat gctcacctgg ctgtcaggga   1800
tggggagcct catgggtgaa agagggttgt gatggcataa tttaaaccaa aagaggcatt   1860
cgcggttgcc cgtgttgcct caggcctgct ggcctcctgc tgtgaacatt ttgggcaata   1920
ctgtctctgc cagtgacccc caattgtcca cttgtctcca gcaagatcga accatgtaag   1980
tgccatttct gacaagttgg gtgaacgttg gtttcaaatc atcagctctg cattcaagtg   2040
ccctgctaca attctggctc actctgtggg aataactgcc tgcctgggca cgttgctgtt   2100
gctgcctccc aaacggcagt ttctggggtc ccaggtcatc caggctggat gtggcttggg   2160
agagacctgt ggcaccaggt tggagggagg tctcacctct cctttctgag ctgtggactg   2220
cagcttcagg accctatgga tgaggccgaa tgtcatgaag ataatggaat ttggagtctc   2280
aacaaagcca agccacatgc cagagattca ccacctgggg cccaggatca gaagtgtgcc   2340
cttaggaggc caaacatcca cctgtctacc aactagacat ttggtctcag acagcaagaa   2400
aggctgcgtt tatgtcatta gggggaacac cacggtcttc ggcatgagag aggtgtaatt   2460
ctcaagttca tcagagctcg gcttccccca tgagaggaaa caatttgcca ggttgaagaa   2520
cacacgcttt gagggttctc agaggctgac acctgttgtg aatcttggaa actcaagccc   2580
cagtgcaaac ggccttgaag gaggtcgagc atcatggttc caacaagtga ctcgctttga   2640
taacccgatg tgtaagcaga atcgcaatgc atccgtcctt ccctaatcat cacgtggctg   2700
tcatctggtc aatgaactga ggcccgaagg cttgagtcaa actggttttc aaggctgtgc   2760
tcatgggatt tatatgtttc ttgagccctg ttggaggctc ttggcaggtc tgaacattaa   2820
acatttcttt tcttcctttt gcacactgct tcaacctaaa gagttggagc gaactagctc   2880
tatatcattt ctgtgttgta aatgggaaat tagctacccc ataacttccc attgtctcct   2940
```

-continued

```
gagaggttac aaattgtgtt acagatatta gcaagtgtta atcctcacga tgtccctggg   3000
agggaaccag aagtatcgta gatgaagaca tcgaggcaca gagaggtgag gccactggga   3060
agaagccaca cagcataaca gtggcaggtc aagaaaaggg ctggggttct ccccaccaat   3120
accaaatgat tttgctctgt ggagtttgtg tctcggttag gacattggtg agctatgtca   3180
cctatgtttc aggtgacagg gacatcacaa caaaggtttg ttgggttaac aatgtcaagc   3240
atttccctgc cccagacccc aaactcattg ccacactcca taccactgtc acggagtgca   3300
gatagtgggg tttggaatct cagtaaagcc aaaccacagg ccagagattc accatatggg   3360
gccgtcggtc atccccgatc ctgttgtccc aatagctttc attctggtga taggatatct   3420
gcatctccta gaaatgtggc tgctaagccc cactcctgca cggatcattc accggctccc   3480
cactcagcgt agccactcct gggtggatcg gcaaacagct cttcaatacg tccacccccca   3540
tgtgtcacag agcttttcag gtggaaggat tttgcattct cccaagagag attcagtgag   3600
ccaagtcagg acccaagttc tcagtcaagg gtaagatgct gtagccgaga gttccccaac   3660
ccccgccctg tccgacgtct cggcaagagg cagcacttcc tgcacccggc tctgccaatg   3720
cactgggcgc tggggtgtgg ggttggggtc ccccctgctc ccgccggaag ggtgttttag   3780
ggaactgtgg gcctcctccc accttggcag ctccgtttaa ggctccaggg actgcttggc   3840
tgctccacag tgacggtcac tctgaggtgg agcctgtgta tcctggatgg aggcagggcc   3900
ggacactgtg acaggtcctc tgggcccatc tccagctgaa caggaaagtc catggcccac   3960
ccaagacagg tgggctggtg tcttctctct cctgggcgct gtggagctga aaccgcagag   4020
tccatcggga ttttgcccag gagcaaggga catcctcagc ctgcggccgc tatgtacagt   4080
gagaacgaca cctggggcca tctggcttct cttccttcct gggtctctca cgttgggtct   4140
ggtggagcca ccagttcctt acacgttggt gacctccagg ctgttgtagc cttccagacg   4200
gcactgttcc agcctgctct gggggtcatc gtctccgcaa tcttcgtttt gaagagagcc   4260
atagtcatca tggaaatcgg gatctttgct gctgaagccc cttcctatct tccccagggg   4320
cagctgagaa gagaagaata tgatcaaagg acaggaagaa gagaaacaag aattaagaat   4380
gaaggtctgg gaaatgtctc caattctaat tgctctgtga ttgagtaact tacttaacct   4440
ctgtgtgctc ctcctattag taataatact ccctgctcag ggaggttgag gggagtttgt   4500
gaatgaccat taggggagag ctttgtgtcc ccctgccccc ggaaggattc agttggttac   4560
caagggtgag gacaaatatc gttagtctga ttattcctga ttcacaaaag cctccttctt   4620
ccctccttgg tgggtggaga gttgaggaag tgtgtcctgg agactacctg tgagaatgtc   4680
tgagcaggcc catgaggtct gactgcactc ccaagtcaag gaggaatatt ctagacggcc   4740
tggtgtggca gaaagaatgc gagttttgga gactcacaga cccaggttca gatccctgct   4800
ctgccacttc ccagctgtgt gaccttggac aagtcacttc ccctctctga gcccattttt   4860
ctcagctaca aaatgggaat agtagtttct aactcccagg tttgttgtaa aaagtaaagt   4920
cccaccagtc tggccaacat ggtgaaaccc cgcctctcct aaaaatacaa aaattagccg   4980
ggcgtggtgg cgagctcctg tagtccctgc tactcaggag gccgaggcat gagaatcact   5040
tgaacccagg aatcagaggt tgcagtgagc tgagatcgtg caactgcact ccagcctgac   5100
agagaccctg tctcaaaaaa aaaaaagtca agtcccatct gcaaagcaca tagcaagtgc   5160
ttgcaccgag taagtccttg atgtacttga tgaatagtga ctattattat cacacatagt   5220
aggccttcaa aaatacttct ctcttactgc acacatctct gtgttaaagt agtcacatta   5280
gtgctttgta actatttatt tgactgcctt tctttccaga ccagtgtttc cagatcttct   5340
```

tttttatta ttattattgc tccctaagga gactttttag acagtttttt cctaattgca 5400
cccctgctgt gaaattgtaa tgccacagac atactacgcc tctgcttccg taccatatgt 5460
acatttgtgc ttttacatag aaagaataag aatttttgcc accgccccca ccccccacca 5520
gcgccaaaac aaattttcac tcctttgggg ggcaatatca gccccaatta ctagaatgca 5580
cgttctagaa tggagcttct taagggtaaa gtggcaatgt attcatgttt atgaatgaat 5640
ggggatcatg ccttcttcaa atggaagaca ttttggatta cccagttctg ccgtctctgt 5700
ctgtgcattt ccattgagga atctgtgtca gttggagtct gtgcaatcag acctgaactg 5760
cacatgtttt catactgttt ggttggagtc accagagggt tcatctttgc tattggtcag 5820
gtcactgaag tcgcaaattg aaatcagtga ttggggctca gagtttgggg ctgcgccgga 5880
accctctggg cagcctagct gaatgcagga tccccctcgc cccagagaac tccttttcca 5940
ggagaccaag gtgggtccca gaatctgcaa gttcagtaat agccccaggt gattctcatg 6000
caggcaggtg agacctgcac tttgagatcc aggtgctact cgaagccctg cgggggcttt 6060
gtgcactgta cccaaagcat cgtgaaggtt ccttgaaggt acatccaggg catctgtcct 6120
ggatgccccc gtgacccggc ctggcactcc accttcacag gccagcacag gagccacaga 6180
gctcccggga ggagaaaaaa agacctttcc cgggtctgca ggactcacag gtaaatccat 6240
tgagagactt acccggccag ccttgtactt gagaccgctg ctgttctcct cctttcctgc 6300
ccgcgtgacg ctggaggccc tgccaggggg cgttccaaaa cgctcagcct cccggatgcc 6360
tgtggagctg aagagaggac cattttgagt cagcagggga ggctcagtca gctccccaga 6420
cacacacaca cacacacaca cacacacaca cacacacaca cacattggtg acaatgacca 6480
cagctgctga gaccgactga ttacctccca cgtgccatcc ttgtgctcag cactttataa 6540
gcgtgattct cacaacatgc ctggggcttg ggactgccag cccagcatta cagggaaagg 6600
aggccagaga cagcaagcaa tttgcccaag acgacacagc tgttagcggc agaatcaaga 6660
tctgaactca ggcttctgac actccaaagt cttgatctta actcttcagt gtactgtgaa 6720
ccttactgca acagactcca gatgagaatc tcagcatggt agctaattag ttgtgcttgg 6780
agaagcatga ggagtctccc ctgctctgaa tttgcaatct gtgtccccca cctggctttc 6840
tgcctgaagc tgcccccatg actcccttct ttgtgcaaaa gcatggaagc ttctgttagg 6900
atttggccaa ctacagcctg cctgcaggtc aaatccagct ggccgactga ttttataaat 6960
aaagttttat tggaactca 6979

<210> SEQ ID NO 62
<211> LENGTH: 1546
<212> TYPE: DNA
<213> ORGANISM: Homo sapiens

<400> SEQUENCE: 62
accgtgtgct gggacacccc acagtcagcc gcatggctcc cctgtgcccc agcccctggc 60
tccctctgtt gatcccggcc cctgctccag gcctcactgt gcaactgctg ctgtcactgc 120
tgcttctggt gcctgtccat ccccagaggt tgccccggat gcaggaggat tccccccttgg 180 gaggaggctc ttctggggaa gatgacccac tgggcgagga ggatctgccc agtgaagagg 240
attcacccag agaggaggat ccacccggag aggaggatct acctggagag gaggatctac 300
ctggagagga ggatctacct gaagttaagc ctaaatcaga agaagagggc tccctgaagt 360
tagaggatct acctactgtt gaggctcctg gagatcctca agaaccccag aataatgccc 420
acagggacaa agaaggggat gaccagagtc attggcgcta tggaggcgac ccgccctggc 480
cccgggtgtc cccagcctgc gcgggccgct tccagtcccc ggtggatatc cgcccccagc 540
tcgccgcctt ctgcccggcc ctgcgccccc tggaactcct gggcttccag ctcccgccgc 600
tcccagaact gcgcctgcgc aacaatggcc acagtgtgca actgaccctg cctcctgggc 660
tagagatggc tctgggtccc gggcgggagt accgggctct gcagctgcat ctgcactggg 720
gggctgcagg tcgtccgggc tcggagcaca ctgtggaagg ccaccgtttc cctgccgaga 780
tccacgtggt tcacctcagc accgcctttg ccagagttga cgaggccttg gggcgcccgg 840
gaggcctggc cgtgttggcc gcctttctgg aggagggccc ggaagaaaac agtgcctatg 900
agcagttgct gtctcgcttg gaagaaatcg ctgaggaagg ctcagagact caggtcccag 960
gactggacat atctgcactc ctgccctctg acttcagccg ctacttccaa tatgaggggt 1020
ctctgactac accgccctgt gcccagggtg tcatctggac tgtgtttaac cagacagtga 1080
tgctgagtgc taagcagctc cacaccctct ctgacaccct gtggggacct ggtgactctc 1140
ggctacagct gaacttccga gcgacgcagc ctttgaatgg gcgagtgatt gaggcctcct 1200
tccctgctgg agtggacagc agtcctcggg ctgctgagcc agtccagctg aattcctgcc 1260
tggctgctgg tgacatccta gccctggttt ttggcctcct tttgctgtc accagcgtcg 1320 cgttccttgt gcagatgaga aggcagcaca gaaggggaac caaagggggt gtgagctacc 1380
gcccagcaga ggtagccgag actggagcct agaggctgga tcttggagaa tgtgagaagc 1440
cagccagagg catctgaggg ggagccggta actgtcctgt cctgctcatt atgccacttc 1500
cttttaactg ccaagaaatt ttttaaaata aatatttata ataaaa 1546

<210> SEQ ID NO 63
<211> LENGTH: 9031
<212> TYPE: DNA
<213> ORGANISM: Homo sapiens

<400> SEQUENCE: 63
agacgccgtc gagatgcagg gcccaccgct cctgaccgcc gcccacctcc tctgcgtgtg 60
caccgccgcg ctggccgtgg ctcccgggcc tcggtttctg gtgacagccc cagggatcat 120
caggcccgga ggaaatgtga ctattggggt ggagcttctg gaacactgcc cttcacaggt 180
gactgtgaag gcggagctgc tcaagacagc atcaaacctc actgtctctg tcctggaagc 240
agaaggagtc tttgaaaaag gctcttttaa gacacttact cttccatcac tacctctgaa 300
cagtgcagat gagatttatg agctacgtgt aaccggacgt acccaggatg agattttatt 360
ctctaatagt acccgcttat catttgagac caagagaata tctgtcttca ttcaaacaga 420
caaggcctta tacaagccaa agcaagaagt gaagtttcgc attgttacac tcttctcaga 480
ttttaagcct tacaaaacct ctttaaacat tctcattaag gaccccaaat caaatttgat 540
ccaacagtgg ttgtcacaac aaagtgatct tggagtcatt tccaaaactt ttcagctatc 600
ttcccatcca atacttggtg actggtctat tcaagttcaa gtgaatgacc agacatacta 660
tcaatcattt caggtttcag aatatgtatt accaaaattt gaagtgactt tgcagacacc 720
attatattgt tctatgaatt ctaagcattt aaatggtacc atcacggcaa agtatacata 780
tgggaagcca gtgaaaggag acgtaacgct tacattttta cctttatcct tttggggaaa 840
gaagaaaaat attacaaaaa catttaagat aaatggatct gcaaacttct cttttaatga 900
tgaagagatg aaaaatgtaa tggattcttc aaatggactt tctgaatacc tggatctatc 960
ttcccctgga ccagtagaaa ttttaaccac agtgacagaa tcagttacag gtatttcaag 1020

-continued

```
aaatgtaagc actaatgtgt tcttcaagca acatgattac atcattgagt tttttgatta   1080
tactactgtc ttgaagccat ctctcaactt cacagccact gtgaaggtaa ctcgtgctga   1140
tggcaaccaa ctgactcttg aagaaagaag aaataatgta gtcataacag tgacacagag   1200
aaactatact gagtactgga gcggatctaa cagtggaaat cagaaaatgg aagctgttca   1260
gaaaataaat tatactgtcc cccaaagtgg aacttttaag attgaattcc caatcctgga   1320
ggattccagt gagctacagt tgaaggccta tttccttggt agtaaaagta gcatggcagt   1380
tcatagtctg tttaagtctc ctagtaagac atacatccaa ctaaaaacaa gagatgaaaa   1440
tataaaggtg ggatcgcctt ttgagttggt ggttagtggc aacaaacgat tgaaggagtt   1500
aagctatatg gtagtatcca ggggacagtt ggtggctgta ggaaaacaaa attcaacaat   1560
gttctcttta acaccagaaa attcttggac tccaaaagcc tgtgtaattg tgtattatat   1620
tgaagatgat ggggaaatta taagtgatgt tctaaaaatt cctgttcagc ttgtttttaa   1680
aaataagata aagctatatt ggagtaaagt gaaagctgaa ccatctgaga aagtctctct   1740
taggatctct gtgacacagc ctgactccat agttgggatt gtagctgttg acaaaagtgt   1800
gaatctgatg aatgcctcta atgatattac aatggaaaat gtggtccatg agttggaact   1860
ttataacaca ggatattatt taggcatgtt catgaattct tttgcagtct ttcaggaatg   1920
tggactctgg gtattgacag atgcaaacct cacgaaggat tatattgatg gtgtttatga   1980
caatgcagaa tatgctgaga ggtttatgga ggaaaatgaa ggacatattg tagatattca   2040
tgacttttct ttgggtagca gtccacatgt ccgaaagcat tttccagaga cttggatttg   2100
gctagacacc aacatgggtt acaggattta ccaagaattt gaagtaactg tacctgattc   2160
tatcacttct tgggtggcta ctggttttgt gatctctgag gacctgggtc ttggactaac   2220
aactactcca gtggagctcc aagccttcca accatttttc attttttga atcttcccta   2280
ctctgttatc agaggtgaag aatttgcttt ggaaataact atattcaatt atttgaaaga   2340
tgccactgag gttaaggtaa tcattgagaa aagtgacaaa tttgatattc taatgacttc   2400
aaatgaaata aatgccacag gccaccagca gacccttctg gttcccagtg aggatggggc   2460
aactgttctt tttcccatca ggccaacaca tctgggagaa attcctatca cagtcacagc   2520
tctttcaccc actgcttctg atgctgtcac ccagatgatt ttagtaaagg ctgaaggaat   2580
agaaaaatca tattcacaat ccatcttatt agacttgact gacaataggc tacagagtac   2640
cctgaaaact ttgagtttct catttcctcc taatacagtg actggcagtg aaagagttca   2700
gatcactgca attggagatg ttcttggtcc ttccatcaat ggcttagcct cattgattcg   2760
gatgccttat ggctgtggtg aacagaacat gataaatttt gctccaaata tttacatttt   2820
ggattatctg actaaaaaga aacaactgac agataatttg aaagaaaaag ctctttcatt   2880
tatgaggcaa ggttaccaga gagaacttct ctatcagagg gaagatggct ctttcagtgc   2940
ttttgggaat tatgaccctt ctgggagcac ttggttgtca gcttttgttt taagatgttt   3000
ccttgaagcc gatccttaca tagatattga tcagaatgtg ttacacagaa catacacttg   3060
gcttaaagga catcagaaat ccaacggtga attttgggat ccaggaagag tgattcatag   3120
tgagcttcaa ggtggcaata aaagtccagt aacacttaca gcctatattg taacttctct   3180
cctgggatat agaaagtatc agcctaacat tgatgtgcaa gagtctatcc atttttgga    3240
gtctgaattc agtagaggaa tttcagacaa ttatactcta gcccttataa cttatgcatt   3300
gtcatcagtg gggagtccta aagcgaagga agctttgaat atgctgactt ggagagcaga   3360
```

-continued

```
acaagaaggt ggcatgcaat tctgggtgtc atcagagtcc aaactttctg actcctggca   3420
gccacgctcc ctggatattg aagttgcagc ctatgcactg ctctcacact tcttacaatt   3480
tcagacttct gagggaatcc caattatgag gtggctaagc aggcaaagaa atagcttggg   3540
tggttttgca tctactcagg ataccactgt ggctttaaag gctctgtctg aatttgcagc   3600
cctaatgaat acagaaagga caaatatcca agtgaccgtg acggggccta gctcaccaag   3660
tcctgtaaag tttctgattg acacacacaa ccgcttactc cttcagacag cagagcttgc   3720
tgtggtacag ccaacggcag ttaatatttc cgcaaatggt tttggatttg ctatttgtca   3780
gctcaatgtt gtatataatg tgaaggcttc tgggtcttct agaagacgaa gatctatcca   3840
aaatcaagaa gcctttgatt tagatgttgc tgtaaaagaa aataaagatg atctcaatca   3900
tgtggatttg aatgtgtgta caagcttttc gggcccgggt aggagtggca tggctcttat   3960
ggaagttaac ctattaagtg gctttatggt gccttcagaa gcaatttctc tgagcgagac   4020
agtgaagaaa gtggaatatg atcatggaaa actcaacctc tatttagatt ctgtaaatga   4080
aacccagttt tgtgttaata ttcctgctgt gagaaacttt aaagtttcaa atacccaaga   4140
tgcttcagtg tccatagtgg attactatga gccaaggaga caggcggtga gaagttacaa   4200
ctctgaagtg aagctgtcct cctgtgacct ttgcagtgat gtccagggct gccgtccttg   4260
tgaggatgga gcttcaggct cccatcatca ctcttcagtc atttttattt tctgtttcaa   4320
gcttctgtac tttatggaac tttggctgtg atttattttt aaaggactct gtgtaacact   4380
aacatttcca gtagtcacat gtgattgttt tgttttcgta gaagaatact gcttctattt   4440
tgaaaaaaga gttttttttc tttctatggg gttgcaggga tggtgtacaa caggtcctag   4500
catgtatagc tgcatagatt tcttcacctg atctttgtgt ggaagatcag aatgaatgca   4560
gttgtgtgtc tatattttcc cctctcaaaa tcttttagaa ttttttttgga ggtgtttgtt   4620
ttctccagaa taaaggtatt actttagaat aggtattctc ctcattttgt gaaagaaatg   4680
aacctagatt cttaagcatt attacacatc catgtttgct taaagatgga tttccctggg   4740
aatgggagaa aacagccagc aggaggagct tcatctgttc ccttcccacc tccaacctag   4800
ccctactgcc caccccaccc caacccaccc catgcccagt ggtctcagta gatacttctt   4860
aactggaaat tctttctttt cagaatctag gtggtgaatt ttttttaagt ggcacggtct   4920
ttttctgctt gaaatctgat cacacccccc agccattgcc ctccctctct ttttcctctg   4980
tagagaaatg tgaggggcag tacatttact gtgcttttca caccatctca gaggttgagg   5040
agcatactga aaattgccct ggggggtgct gggtgtgctg tctccttccc acatcctcag   5100
ccccacacca gctctatttc aggggtgaga gtcagagagc actgcaatat gtgcttcatg   5160
ggatttcgat tcgaagatcc tagaccaggg agacactgtg agccagggat acaacaaaat   5220
actaggtaag tcactgcaga ccgacctccc tgcagtttgg gaaagaagct gggtttgtgg   5280
agaatcagag catcttgaca tgactgctga cctaaagatc cctggcattg gccagggatc   5340
ctgtggaacc tcttctagtt caggggtgtg agcattagac tgccagttgt ctagtgacat   5400
ctgatgcttg ctgtgaactt ttaagatccc cgaatcctga gcacctcaat ctttaattgc   5460
cctgtattcc gaagggtaat ataatttatc tggatggaaa ttttaaagat gaatccccct   5520
tttttctttt cttctctctt ttctttcctt ctccctttct tctttgcctt ctaaatatac   5580
tgaaatgatt tagatatgtg tcaacaatta atgatctttt attcaatcta agaaatggtt   5640
tagtttttct ctttagctct atggcatttc actcaagtgg acaggggaaa aagtaattgc   5700
catgggctcc aaagaatttg ctttatgttt ttagctattt aaaaataaat ccatcaaaaa   5760
```

taaagtatgc aaatgtatct tttaaagtta atttttaaaa atgctcttat tttagtgaat 5820
tttcagaaat tatagtggaa tggatgctca tatattgctt atggatattt tggataccaa 5880
agtaggaata actgacattc agtattttaa agctggcaaa cctgtacata gaaaatagat 5940
ccccagacag tggtctatga agagggcagt taagtatcaa atacttaatt ttcttgcctt 6000
tttttcttaa gtggggaaaa gtttctagat ctcttacacc tctgacacaa tctgttctaa 6060
aacaggcact tgtaatgttg gggcctcctt gtaaacgtgt tttgcccttt tactctctgg 6120
gagttcttta aaggtgaaat catcttacaa agaaattggg ggagggtctt ggcaaaggac 6180
tttcccctcc tctttcctgg cctgggaacc ttatactgac aatcaatact ttatatttta 6240
aagtatataa tttatagtta acttctagtg taatatatta ggaaacacta gaatggaaag 6300
gccattggaa gacaggttgt atcttttttta gaccatattt ccttgtttaa aaactatcat 6360
ttgaatactt ttttggtgaa gaactccatg ttttcaagtt aaaggtcacc tcgtaggcca 6420
ggcgcagtgg ctcatgcctg taatcccagc actctgggag gctgaggcgg gtgaatcaca 6480
aggttaggag tttgagacca gcctggccaa tatggtgaaa ccccgtccct actaaaaata 6540
caaaatttag ccaggcgtgg tggcatgcac ctgtagtccc acctactcgg gaggctgagg 6600
caggagaatc acttgaacct gagagacaga ggttgcagtg agccgagatc acgccactgc 6660
actccagcct gggggacaga gtgagattct gtctcaaaaa acaaaaaaca aaaaagtcac 6720
cttgtaactc atctcttttt attgtaagtt tattaaaaat gaagaggaca acaatgagaa 6780
ggaacataaa gggttagcta gcactgtctc ctggtgcatg gggctgtgca gatgtcccgg 6840
ccacttcttc cttcatactt cccttagaga acttgctctg ctacaagcag tgggcttgga 6900
ctaaaagtga ttaaaatacc acaggcataa ggagaaaagg agtatatgta gtagtaataa 6960
ttactagtat aaattatttt cttcacatgc tatgagtaat aatattaaaa aactcatttt 7020
accattaaga ttccttatgc tgaagctctt ccatttagaa tactgtcaat gtcatttact 7080
ggtatgaact aaagtccccc ttcttttcca ctcactggga accttagtaa aacaccagca 7140
tatcttacct ctctttctga ctggccgatg cttccagaga ctgaatgttg ggaaaaccta 7200
gtagccaaac aattctagga cagaataaca tttttatatt tggttccacc atcttattac 7260
atttagttat agttttaaaa aagaaattca agcccattaa aatatgtctg gtcaatgaaa 7320
tgcttccttt tattgtgttg tgctattgta ctttgttttt caaaacattg taaaaatagt 7380
atctttggtt tagtattttg gattatatat tataatctga ggagtgtttt gcttatgtag 7440
aatccagata tatttctgtt acctaggaga tgttacttac atatgtaata ctgtatcctg 7500
cacgtggaaa tattcagaat tgtagatagc ataactctcc ctgctcctat tcttttgagc 7560
ctaggtataa tttttttttt ttttttagaa aaagacatat ttagctttaa tttctattta 7620
tgctaaacat atttataagt agtctgtcaa tataatacca actattttta tttttacata 7680
attcaattat ttcatttgac atgtctggca gactcaagac attaagtaaa aaattggaac 7740
tatgattttt ctttgtcatt ttttaaaaaa gaattatttt attaacctgc tggcatataa 7800
tctggagttc ttttcacaac cttacttttt ctgatttgct ttattgaatg attgaatact 7860
catttctttc taaaaatatg ttgtaaattc tcccttggca agatttctcc ctatgagggt 7920
agttattatt tgagtctgcc aagtggttac catggggcaa ggtgccatga tgtattcttg 7980
ggtgcattgg ttttttgcgc attgtaaatt taagacactt atagtaagtg gactcattca 8040
tagatgagtt tcagaacctt ttacgttctc ggtagaggct tctgtcggac aggcagaaga 8100
gtgtattcct cactttttt tttgtcttca aattccagta aggcatagca cttttaagaa 8160
attagaattt ttctatcatc tatgcaaatg atatttatgt taatattaaa tatcttatgt 8220
tacactggga gtaatttgag gtgcaattat ttttattact actttgaata gaggaccatt 8280
atccttcttt cttcagaaaa ctaagaagta agtgtaactt ttaaagtaag tatatatcag 8340
tgagagtagg cttgttttac aactatttct agccagtgag ttgtgttttc atgtctcatc 8400
aaaagacaat accacattgc atcattttac aaaatatgtt gtcattttca tttcagttgt 8460
aacataggaa aatagatatt tcctagatga tttctgagtt tcttactgca aagaacagtt 8520
ataaattggt atacatgtgt ctctgtaata gggataaatat tgatatatct gttgctacat 8580
atttaagaat cattctatct tatgttgtct tgaggccaag atttaccacg tttgcccagt 8640
gtattgaatt ggtggtagaa ggtagttcca tgttccattt gtagatcttt aagattttat 8700
ctttgataac tttaatagaa tgtggctcag ttctggtcct tcaagcctgt atggtttgga 8760
ttttcagtag gggacagttg atgtggagtc aatctctttg gtacacagga agctttataa 8820
aatttcattc acgaatctct tattttggga agctgttttg catatgagaa gaacactgtt 8880
gaaataagga actaaagctt tatatattga tcaaggtgat tctgaaagtt ttaattttta 8940
atgttgtaat gttatgttat tgttaattgt actttattat gtattcaata gaaaatcatg 9000
atttattaat aaaagcttaa attctcatct a 9031

<210> SEQ ID NO 64
<211> LENGTH: 4190
<212> TYPE: DNA
<213> ORGANISM: Homo sapiens

<400> SEQUENCE: 64
atatgtagcc ttttcatttt catgaaagtg aagtgatttt tagaattctt agttgttttc 60
tttagaagaa catttctagg gaataataca agaagattta ggaatcattg aagttataaa 120
tctttggaat gagcaaactc agaatggtgc tacttgaaga ctctggatct gctgacttca 180
gaagacattt tgtcaacttg agtcccttca ccattactgt ggtcttactt ctcagtgcct 240
gttttgtcac cagttctctt ggaggaacag acaaggagct gaggctagtg gatggtgaaa 300
acaagtgtag cgggagagtg gaagtgaaag tccaggagga gtggggaacg gtgtgtaata 360
atggctggag catggaagcg gtctctgtga tttgtaacca gctgggatgt ccaactgcta 420
tcaaagcccc tggatgggct aattccagtg caggttctgg acgcatttgg atggatcatg 480
tttcttgtcg tgggaatgag tcagctcttt gggattgcaa acatgatgga tggggaaagc 540
atagtaactg tactcaccaa caagatgctg gagtgacctg ctcagatgga tccaatttgg 600
aaatgaggct gacgcgtgga gggaatatgt gttctggaag aatagagatc aaattccaag 660
gacggtgggg aacagtgtgt gatgataact tcaacataga tcatgcatct gtcatttgta 720
gacaacttga atgtggaagt gctgtcagtt tctctggttc atctaatttt ggagaaggct 780
ctggaccaat ctggtttgat gatcttatat gcaacggaaa tgagtcagct ctctggaact 840
gcaaacatca aggatgggga aagcataact gtgatcatgc tgaggatgct ggagtgattt 900
gctcaaaggg agcagatctg agcctgagac tggtagatgg agtcactgaa tgttcaggaa 960
gattagaagt gagattccaa ggagaatggg ggacaatatg tgatgacggc tgggacagtt 1020
acgatgctgc tgtggcatgc aagcaactgg gatgtccaac tgccgtcaca gccattggtc 1080
gagttaacgc cagtaaggga tttggacaca tctggcttga cagcgtttct tgccagggac 1140
atgaacctgc tatctggcaa tgtaaacacc atgaatgggg aaagcattat tgcaatcaca 1200

-continued

```
atgaagatgc tggcgtgaca tgttctgatg gatcagatct ggagctaaga cttagaggtg   1260
gaggcagccg ctgtgctggg acagttgagg tggagattca gagactgtta gggaaggtgt   1320
gtgacagagg ctggggactg aaagaagctg atgtggtttg caggcagctg ggatgtggat   1380
ctgcactcaa aacatcttat caagtgtact ccaaaatcca ggcaacaaac acatggctgt   1440
ttctaagtag ctgtaacgga aatgaaactt ctctttggga ctgcaagaac tggcaatggg   1500
gtggacttac ctgtgatcac tatgaagaag ccaaaattac ctgctcagcc cacagggaac   1560
ccagactggt tggaggggac attccctgtt ctggacgtgt tgaagtgaag catggtgaca   1620
cgtggggctc catctgtgat tcggacttct ctctggaagc tgccagcgtt ctatgcaggg   1680
aattacagtg tggcacagtt gtctctatcc tgggggggagc tcactttgga gagggaaatg  1740
gacagatctg ggctgaagaa ttccagtgtg agggacatga gtcccatctt tcactctgcc   1800
cagtagcacc ccgcccagaa ggaacttgta gccacagcag ggatgttgga gtagtctgct   1860
caagatacac agaaattcgc ttggtgaatg gcaagacccc gtgtgagggc agagtggagc   1920
tcaaaacgct tggtgcctgg ggatccctct gtaactctca ctgggacata gaagatgccc   1980
atgttctttg ccagcagctt aaatgtggag ttgccctttc taccccagga ggagcacgtt   2040
ttggaaaagg aaatggtcag atctggaggc atatgtttca ctgcactggg actgagcagc   2100
acatgggaga ttgtcctgta actgctctag gtgcttcatt atgtccttca gagcaagtgg   2160
cctctgtaat ctgctcagga aaccagtccc aaacactgtc ctcgtgcaat tcatcgtctt   2220
tgggcccaac aaggcctacc attccagaag aaagtgctgt ggcctgcata gagagtggtc   2280
aacttcgcct ggtaaatgga ggaggtcgct gtgctgggag agtagagatc tatcatgagg   2340
gctcctgggg caccatctgt gatgacagct gggacctgag tgatgcccac gtggtttgca   2400
gacagctggg ctgtggagag gccattaatg ccactggttc tgctcatttt ggggaaggaa   2460
cagggcccat ctggctggat gagatgaaat gcaatggaaa agaatcccgc atttggcagt   2520
gccattcaca cggctggggg cagcaaaatt gcaggcacaa ggaggatgcg ggagttatct   2580
gctcagaatt catgtctctg agactgacca gtgaagccag cagagaggcc tgtgcagggc   2640
gtctggaagt tttttacaat ggagcttggg gcactgttgg caagagtagc atgtctgaaa   2700
ccactgtggg tgtggtgtgc aggcagctgg gctgtgcaga caaagggaaa atcaaccctg   2760
catctttaga caaggccatg tccattccca tgtgggtgga caatgttcag tgtccaaaag   2820
gacctgacac gctgtggcag tgcccatcat ctccatggga gaagagactg gccagcccct   2880
cggaggagac ctggatcaca tgtgacaaca agataagact tcaggaagga cccacttcct   2940
gttctggacg tgtggagatc tggcatggag gttcctgggg gacagtgtgt gatgactctt   3000
gggacttgga cgatgctcag gtggtgtgtc aacaacttgg ctgtggtcca gctttgaaag   3060
cattcaaaga agcagagttt ggtcagggga ctggaccgat atggctcaat gaagtgaagt   3120
gcaaagggaa tgagtcttcc ttgtgggatt gtcctgccag acgctggggc catagtgagt   3180
gtgggcacaa ggaagacgct gcagtgaatt gcacagatat ttcagtgcag aaaaccccac   3240
aaaaagccac aacaggtcgc tcatcccgtc agtcatcctt tattgcagtc gggatccttg   3300
gggttgttct gttggccatt ttcgtcgcat tattcttctt gactaaaaag cgaagacaga   3360
gacagcggct tgcagtttcc tcaagaggag agaacttagt ccaccaaatt caataccggg   3420
agatgaattc ttgcctgaat gcagatgatc tggacctaat gaattcctca gaaaattccc   3480
atgagtcagc tgatttcagt gctgctgaac taatttctgt gtctaaattt cttcctattt   3540
```

```
ctggaatgga aaaggaggcc attctgagcc acactgaaaa ggaaaatggg aatttataac   3600

ccagtgagtt cagcctttaa gataccttga tgaagacctg gactattgaa tggagcagaa   3660

attcacctct ctcactgact attacagttg catttttatg gagttcttct tctcctagga   3720

ttcctaagac tgctgctgaa tttataaaaa ttaagtttgt gaatgtgact acttagtggt   3780

gtatatgaga ctttcaaggg aattaaataa ataaataaga atgttattga tttgagtttg   3840

ctttaattac ttgtccttaa ttctattaat ttctaaatgg gcttcctaat tttttgtaga   3900

gtttcctaga tgtattataa tgtgttttat ttgacagtgt ttcaatttgc atatacagta   3960

ctgtatattt tttcttattt ggtttgaata attttcctat taccaaataa aaataaattt   4020

atttttactt tagtttttct aagacaggaa aagttaatga tattgaaggg tctgtaaata   4080

atatatggct aactttataa ggcatgactc acaacgattc tttaactgct ttttgttact   4140

gtaattctgt tcactagaat aaaatgcaga gccacacctg gtgagggcac              4190


<210> SEQ ID NO 65
<211> LENGTH: 5488
<212> TYPE: DNA
<213> ORGANISM: Homo sapiens

<400> SEQUENCE: 65

attcagggaa gcagccccgg cggccagcag ggagctcagg acagagcagg ctccctggga     60

agcctccggg tgataggggt gttccagctg cggcgctctg gggggttcaga gggggatctt   120

gaatgaacaa atgaatgaac tgctttctgg gcaaacagcc acagccagag gagcctgtga    180

ttggcagaaa gaagccaggg tgtgcaagtc tccccaacag cctcgagtgg cctgcagtca    240

cagggaaccc tcaggaagac cttccgggca gagaccagag ggaagcccat ctctccagca    300

gaactgcttg gatttttcta ccaggaggct cagggctctg caacaatgat agcagaagct    360

gatggcatct agagatctag gctgggacta gcacagcatc acttctacca ctttctgttg    420

gtcacagcaa ctcaccatgc cagtgcagat tcaaggggag gagaaataga gtccacttct    480

tgatgggagg cgtgacatgt gtttctagct gtgtacaggg actgattggc tgaggactca    540

cattggagag ctgcagacaa cataacggtg aatgagaatg gaggatgaag attacaacac    600

ttccatcagt tacggtgatg aataccctga ttatttagac tccattgtgg ttttggagga    660

cttatccccc ttggaagcca gggtgaccag gatcttcctg gtggtggtct acagcatcgt    720

ctgcttcctc gggattctgg gcaatggtct ggtgatcatc attgccacct tcaagatgaa    780

gaagacagtg aacatggtct ggttcctcaa cctggcagtg gcagatttcc tgttcaacgt    840

cttcctccca atccatatca cctatgccgc catggactac cactgggttt tcgggacagc    900

catgtgcaag atcagcaact tccttctcat ccacaacatg ttcaccagcg tcttcctgct    960

gaccatcatc agctctgacc gctgcatctc tgtgctcctc cctgtctggt cccagaacca   1020

ccgcagcgtt cgcctggctt acatggcctg catggtcatc tgggtcctgg ctttcttctt   1080

gagttcccca tctctcgtct tccgggacac agccaacctg catgggaaaa tatcctgctt   1140

caacaacttc agcctgtcca cacctgggtc ttcctcgtgg cccactcact cccaaatgga   1200

ccctgtgggg tatagccggc acatggtggt gactgtcacc cgcttcctct gtggcttcct   1260

ggtcccagtc ctcatcatca cagcttgcta cctcaccatc gtgtgcaaac tgcagcgcaa   1320

ccgcctggcc aagaccaaga agcccttcaa gattattgtg accatcatca ttaccttctt   1380

cctctgctgg tgcccctacc acacactcaa cctcctagag ctccaccaca ctgccatgcc   1440

tggctctgtc ttcagcctgg gtttgcccct ggccactgcc cttgccattg ccaacagctg   1500
```

-continued

```
catgaacccc attctgtatg ttttcatggg tcaggacttc aagaagttca aggtggccct   1560
cttctctcgc ctggtcaatg ctctaagtga agatacaggc cactcttcct accccagcca   1620
tagaagcttt accaagatgt catcaatgaa tgagaggact tctatgaatg agagggagac   1680
cggcatgctt tgatcctcac tgtggaaccc ctcaatggac tctctcaacc cagggacacc   1740
caaggatatg tcttctgaag atcaaggcaa gaacctcttt agcatccacc aattttcact   1800
gcattttgca tgggatgaac agtgttttat gctgggaatc tagggcctgg aaccccttc    1860
ttctagtgga cagaacatgc tgtgttccat acagccttgg actagcaatt tatgcttctt   1920
gggaggccag ccttgactga ctcaaagcaa aaaaggaaga attctcaaaa gcattgccat   1980
gaactgggat tggcataggg cggtgggatt aagctgccta ttgtgtgtgc cccagaaatg   2040
acactctcca aggtccattc ctggtgtgag cagtgagggg gtcagagcaa acccagtgtg   2100
atgcagatca cacttggccc ttgtatatat attatcagta gctggccaga aaaccctacc   2160
ttcaagtcac tgctctgtgt taaagtatgt ggaaatgcat aggtgatctg ggagaggaag   2220
gtgacatatc agcccatgaa ctccataggc catgaatttg gctttcggat cagctaggaa   2280
gacagagaac tggtcctgag aggtcctgtg ggctctttgc aagggcaaga caagtgaggg   2340
atgcaacgag gacttgagat ttggcaaaga aatgagaaag gagaaaagaa cctttaaagg   2400
atgcaggcat ggagcagctc accctagaac atcgcaggct gatggtgctt taggctggag   2460
ctatttgggg cgtcagggtg gtgccagccc ctgatctcac cttgcccctc ttacctgggg   2520
gtggggttgt ggcaggcatc ttcaccagca gccctcaccc catcacaggg atttttttct   2580
gcctttccta atccactcag ctctggctgg aggtgcttag aataaaacac tggtggtggg   2640
gcttctcatt ctggttaatt tcctcaacgc ctttggagac aggtccaaaa tgcagctttg   2700
ggaagcaact ccggagagtc ccctgggaag aagagtatgt ccgaggactc agtcacttga   2760
gacagagtct ggagctggac tccttgaact gtgtttctga gctgcagaca ccaaatacct   2820
cctggataca ggtgcctggc atggcttttc tcatctaata ctgacacgtc cctgtggcca   2880
cagagtgtca tagccccatt tacaaatgac atagctgagg cccagatggg gaaagtaact   2940
tgcccagcat cacacagcta atcagtggca gagttaagat ctgaacctgg ctccgtctgg   3000
ctccagaaac tctgttcttc tatttggaat ttatctgtgg agattattct agtatattga   3060
tagcctacat ttatttagca ctttttatat tatgcacttt acatatgttt tctcatttaa   3120
tcattacagc aaccctgagt taggtatggt tataacttcc cttttacata ggaggaatct   3180
gaggcttaga gaggttaagt aacttgccca aaggtaccca gctagtctct gccggagctt   3240
ggatttgaac ttcagtttgc ctggctcaaa tgaggctgca gagttgggaa ggacttaaaa   3300
agtttggaga tttttgccat aaatattgat ttttctgcaa atgaggatga acatcttaat   3360
ggcctttaag aaactttgca aatagttttc aaaaatgatg caacatggca gagaaaatgc   3420
acttggcttc cagctccctc aacagccatt aacagcctcc taccgtggct cccacctcct   3480
atgtctccag agatcaaggc aatggggagg gaaagctggc aggaggcagt cccttgtggg   3540
cctgaggccc tttggctcct aagtgtccac attctgttct cttccaagtc ccttcattgt   3600
taagctgatt ctccaacaag atgcaatgaa cagatgcaat gtctaccccg cgctgggcga   3660
gttcccgagg ccatgggctg tttggaatca cacttcatta agagacaaac tgttccttcc   3720
cttattgtgc cttaatgctt atgacaaggc agctctgaat tgatcccaag ctggagcctc   3780
tgaatgcttt aaagagtttg aatatagacg gtttgagagc aaaaagggag ctttaaatat   3840
```

```
tgctcagtgg cccccatctc ccctcttccc acatttactg aggcacgaga tgggatggga   3900

cctgtcccgg gtcacagcag cagtcgtcag cgccttggcc ctcctggctt gtaggatgct   3960

gcttttcctg ggcttctggc agtccaggcc aggatggggg agccaggaat tcatgttgtc   4020

attggaaaag ctgataaaca ggagcacaat tcaaaccggc tgttttcctc cttagagtct   4080

ggcctccctc tttctggctg ctctgtgggt cttcctgttc tgacttaggt tcctgtcaag   4140

tacttaaatg cagccttaac atcccataca gtcttgtccc cacagcttca tgtgaacatc   4200

tccatgggtc atgcatatat cgtccctgca gtgtgcaaag tgtgctcacc tgcactgctg   4260

cacaggcaac caacatactt agtgcccaga gccttctctc tgggcccagg actcagtgat   4320

ggggccttac ttagccctgc ctcctgggtg gggtggggga gctgagggat cgtgaggaca   4380

agaggtagag ggaaaagaaa agaagatggt gtttgaggat aggggaggga caggagaggg   4440

gacagaaagg tcccagagca tgatgatgaa ggaaagggat ctggcattca tgaagcacct   4500

acgatggttc aggcacaaac actgaaacct caaattggcc ctggcagaag gggaccatca   4560

tagcaaggtg gggggggggt gcagaaagtg agtttctgtt tcaagaacag acttcactag   4620

ttcagagttg cacagctagt gaggtatgga gctgggcttt gaatcaggtc agctgcctga   4680

atgcccaact tcttcagccc ttggaaggag agggtgggga gaagaagaag gaaaagacaa   4740

ggaagaaaga aagaagagag aaggggagag gaatggaagt ccaaagagtg ggaggaattt   4800

gatttcagaa ccatctccag ctgacccttg agccagcaag gacagggaga agggaagagc   4860

aagaacacga agggcctcaa gcaccgggat gcctttgcca gccttagata attcccagag   4920

cgcacagagc cctgcaggtt cctgggtcct tctccagaga agaggcacag agattctggc   4980

agcaaggttc agaaggggtg aggaaactgg gcactgacaa aggggagggga ttggctcaaa   5040

ttcgacccca gagtcagctc tggtggggtt gggagcctgg atgggtggga gaagatagaa   5100

tccaatcgtg aaaaccataa gggaccttca aactcatctt gcccagatgt ctcccatttc   5160

acagatgagg gaactgaggt tttgagagct tcccctgagg actctgcaaa acgaggtggt   5220

gtctggtttg gatgaaagtg gtcggtgatt cctcaactcc tgccctgcct ccctctctcg   5280

ttcctcccta acatgttatg ctcttgttgg ggctgggatg ccctaggccc aaggttacca   5340

aatcctgggt ttggaaaatt gctgctgggg gtggtatcta ggaccagaga ggaatctact   5400

atttctactg tgaaataatt cagcaggggg tcttcttact tcttcccttt gaggacaaag   5460

tttctctcga ataaagagac tgaagcaa                                      5488
```

<210> SEQ ID NO 66
<211> LENGTH: 5725
<212> TYPE: DNA
<213> ORGANISM: Homo sapiens

<400> SEQUENCE: 66

```
gactacgatc caggctggag ttgcgctcgg ccggtctgag cgctggcgct gcccggacgc     60

cgcggggtcc ccgccagccc agggcactcg gcgcggggat ctgcgcgcct cgctctccct    120

tcccgatgcc gccgcccggc tgctgatcgc cgcaccacct tccctcatcg gcttgggtcc    180

gtggaggtcc ctgcagaggc aggaagcctc cttaggaaag cagggatgga ggtaaattgt    240

ttaacactaa aagacctgat cagccccagg cagcccagac tagattttgc agttgaagat    300

ggggaaaatg cacaaaagga aaatatattt gttgatcgat caaggatggc cccgaagact    360

ccaataaaaa atgaaccaat tgatttatcg aagcaaaaaa aatttactcc agaaagaaat    420

cccattactc cagttaagtt tgttgacaga cagcaagcgg aaccatggac acccacagct    480
```

-continued

```
aacctgaaga tgctcattag tgctgccagc ccagatataa gggaccggga gaagaaaaag    540
ggactattcc gacccattga aaacaaggac gatgcattta cagattctct acagcttgat    600
gttgttgggg acagtgctgt ggacgaattt gaaaagcaaa ggccaagcag aaaacagaaa    660
agtttaggac tcctgtgcca gaagtttcta gctcgctatc caagttatcc cttgtcaact    720
gagaaaacta ccatctccct agatgaagtt gctgtcagtc ttggtgtgga aaggagacgc    780
atctatgaca ttgtaaatgt gctggagtcg ctgcatctgg tcagccgggt ggctaagaat    840
cagtatggct ggcatggacg gcacagcctg ccaaaaaccc tgaggaacct ccagagacta    900
ggagaggagc agaaatatga agagcaaatg gcctacctcc aacagaaaga gctggacctg    960
atagattata aatttggaga acgtaaaaaa gatggtgatc cagattccca ggaacaacag   1020
ttactggatt tctctgaacc cgactgtccc tcttcatctg caaacagtag aaaagacaag   1080
tctctgagaa ttatgagcca gaagtttgtc atgctgttcc tcgtctccaa aaccaagatt   1140
gtcactctgg atgtggctgc caaaatactg atagaagaaa gccaagatgc cccagaccat   1200
agtaaattta aaacaaaggt acgacgcctc tatgacatag ccaatgttct gaccagcttg   1260
gctctgataa agaaagtgca tgtaacagaa gagcgaggtc gtaaaccagc cttcaagtgg   1320
atcgggcctg tggacttcag ctcaagtgat gaagaactgg tggatgtttc tgcatctgtc   1380
ttaccagaat tgaaaagaga aacatatggc cagattcaag tctgtgcaaa acagaagctg   1440
gctcgccatg gttcttttaa cacagttcag gcttctgaga ggatccagag gaaagtgaac   1500
tcagaaccga gcagcccgta cagagaagaa caaggatcag gtggctactc tttagaaatt   1560
ggaagcctgg cagctgtcta tagacagaaa atagaagaca attcacaggg aaaagccttt   1620
gccagtaaga gagtggtgcc tccatcaagc agcttggacc ctgttgctcc tttccctgtc   1680
ctctctgttg acccagaata ttgtgttaat cctttagccc acccagtatt ttctgttgct   1740
cagacggacc tgcaggcatt ctccatgcag aacggtctga atggacaagt ggatgtctca   1800
cttgcttctg cagcctctgc tgtggagagc ctgaagccag cactccttgc tggccagcct   1860
ctagtgtatg tgccctctgc ctcactgttc atgctgtatg gaagtctgca ggagggacca   1920
gcgtcagggt cagggtcaga gagggatgac agaagctcag aagccccagc cacagtagag   1980
ctgtcatctg caccctcagc tcagaagcgc ctctgtgagg agaggaaacc tcaggaggag   2040
gatgagccag ccactaaaag gcaaagtagg gaatatgaag acggcccgct gtcgcttgtc   2100
atgcccaaga aaccctcaga ttccacagac cttgcctctc ccaagactat gggtaacagg   2160
gcatctatac cctcaaaga cattcatgtg aatggccaac tccctgctgc agaagagatt   2220
tcaggaaagg caacagcaaa ctctcttgtt tcttctgagt ggggaaatcc ttcaagaaat   2280
acagatgttg aaaagccttc aaaagaaaat gaaagcacca aagagccttc tttgctacaa   2340
tatctttgtg tgcagtctcc tgcaggatta aatggtttca atgtactttt atctggcagt   2400
caaacccccc ctactgtggg cccgtcctca ggtcagctgc cgtctttcag tgtcccttgc   2460
atggtcttac catctccacc tctgggccct tttcctgttc tctattctcc tgcaatgccg   2520
ggcccggttt cttctactct tggtgctctc ccaaacacag gacctgtgaa tttcagcttg   2580
cctggccttg gatcaatagc ccagcttctc gtcggcccca cagctgtggt taatccaaag   2640
tcgtccacac tcccttctgc agaccctcag cttcagagtc agccctcact aaacctaagt   2700
ccagtgatgt caaggtcaca cagtgtcgtc caacaacctg agtcccccgt ttacgtggga   2760
catccagtct cagtagtaaa attacatcag tcaccagttc cagtgacccc caagagcatc   2820
```

-continued

```
caacgcacac atcgtgagac gtttttcaag acacccggca gccttggaga ccctgtcctg   2880
aagagaagag aaaggaacca gtcacgaaac accagctcgg cccagaggag actagaaatc   2940
cccagcggcg gcgctgacta acctgccgct ttgccaggtg ggggtgggat caaacgccct   3000
gagagtcccg gatgtccgag gcgggatgca aaccatcccg tcctgagcac gggtccttcc   3060
tctctctttc atccacactt ctgttaactt cccaccacca tcaatcatct gatttcctga   3120
aagtaattaa ttgtgcattt aataccagtt agagttccga ctctgcatgg tgtcacagtg   3180
aaagcgccga ctgacttatg gttttgattc aagaatcgtc ttattctgga agtagatctg   3240
aataggctac cggagccttg tttttctaaa ggggggcgct gtctagcact taactagggt   3300
aagcattctt aacatgtatt tccacttgcc ctgagtaaat ctgtggtgag agaagcttcc   3360
tttctgcagt ttaaaaaagc tactgcttcc ttaggcttca tcaggaagcc accttcagtt   3420
gtgaatccta tggtgttatt tattttgttc ctgaaatggg atttagtgca aaaagtttac   3480
aactacagtc tttaacacat tttttcagg gtatgacgac ttgaatgttt atacttttat   3540
tctataattt gccctgcact tattttacaa cctagtaata atgtggataa atgtatctac   3600
atgacacatg tcaagaccaa aataactgtg aatgacacac cttgctgtaa atgaactgtg   3660
ctaaccctga ctgtgggctt gagaacaaag atgaactcta gaactctagc agcctaactg   3720
ctgcttctca aataactgtg tgaacagtga gatattactg tttgtttcta aaaatcctac   3780
tgtgcccagt ttccttcact acatgccctg catttttat ttaaatattt agctgtagcg   3840
ccatcagata tggatgcctt ctaacaattg ctgtttgtaa aataaatcag gatggtagaa   3900
agtgattata tggaaaattg gaacctggat gagacctttt cgttgaattc tgaagagtaa   3960
tgatgtgaaa attgatacag ggcaagagat gattcttttg tttttcttct acttcatgtc   4020
cagaagagta agagggaaaa tggacatatg tttcatatcc aagggtattc aaactgtagt   4080
tagttggtac ctctgaaaaa tgagaatggt gagcgcacgg gttggttgtt ctagcatgaa   4140
tacaattctg gaaactgtta tgcaatttcc cttttttaac ccacattact ttaggggtgc   4200
attaagtcgc caaactatac tagttctttg tattcctaga cttgctgata tttacctctc   4260
tcttgtctct tcagagtaaa tggttccctt ctttccttcc tactttcctt cattctctct   4320
tccttccctc cttcctactt cttttcttcc ttcctcttcc tctcttaaaa ctatcttaga   4380
tgtagaatcc tggtgtaggg ttttatttta tttttatttt ttgacccaat aaaatgttat   4440
atgaaagaat gaaaatatta atttaagaga ctctgggagt ctgaataaag tagctttata   4500
ttaactacag gataatatta gccttattac ccccacaaga ttttttaaaa cttgaggtag   4560
gtagctacat taaataaatt tgctacttat ataaaaattt ttatcaacac taaactttta   4620
aagtttacaa gttttttttt tctttttttac agtcttctat agagttaggt taaaaatgtg   4680
gttctaacca tcaacaattg catggttaaa tgaccctgaa ctaaaactga tgggttccct   4740
atcaaaacaa ataaaaatat accttttca ggtttcaatc tgtgcagggt atatgcatgt   4800
taattctacc atgcttaaga acttccacaa aatatttcat ggagaggtct gcatttagac   4860
ggaaacagaa attgcttttc ccctcactgt tcctgaatgc tctatacttg ttttaacatt   4920
tttgctatct tttttatta ttctgatcat gatatgacca tttaacctca gaattcataa   4980
ttcctgaggg gtgttaagaa gcagtcccat tggtgaggat attatgactt ggtgaccatt   5040
cttaggagta gaaaaccaag gacaattgct tctgtattca gtatccactt cttaatgtgg   5100
ctttatatgt aaaaataata atgcagtggt tgtttctgtc aggaaaataa atcttacaga   5160
acaactggtg gaattgaagc tgctgcgcta gacttggata ttttgggtag tgaagaagca   5220
```

atggcaatct tgagtctatt attgtataat ttagtaaaag aaaaaaataa tcgttggtgg 5280
tcctactaag agaatgcagc ttttttgagt tgtcacagag gctgtgtgtg ccctacactg 5340
accagggttt gtaaaaccct ttcattctgg tacaagagtc gggggtataa cttttatact 5400
tgaatctacc taccaagttt acatttctca attccttttt gtaaggtgct atttctgtat 5460
ttaaataact ttcttttaac gtaaagctgc tttctgctta tcttattgca ctgctagttg 5520
tatgtaggta ttaattttat tgctgcttac tgcttttgtt ttcttattat ttagctctgc 5580
tctttttcct aatggctata ttatctatag ctatttactt gtaactgtac tacatgtaaa 5640
ctgatttttt gttctgattt tttttctaat atttttagga aaatattaag ctttataaaa 5700
tagcaataaa aaataattca tttaa 5725

<210> SEQ ID NO 67
<211> LENGTH: 649
<212> TYPE: DNA
<213> ORGANISM: Homo sapiens

<400> SEQUENCE: 67
ggaggcccga gcgagggaca agactccgac tccagctctg actttttcg cggctctcgg 60 cttccactgc agccatgtca ctcctcttgc tggtggtctc agcccttcac atcctcattc 120
ttatactgct tttcgtggcc actttggaca agtcctggtg gactctccct gggaaagagt 180
ccctgaatct ctggtacgac tgcacgtgga acaacgacac caaaacatgg gcctgcagta 240
atgtcagcga gaatggctgg ctgaaggcgg tgcaggtcct catggtgctc tccctcattc 300
tctgctgtct ctccttcatc ctgttcatgt tccagctcta caccatgcga cgaggaggtc 360
tcttctatgc caccggcctc tgccagcttt gcaccagcgt ggcggtgttt actggcgcct 420
tgatctatgc cattcacgcc gaggagatcc tggagaagca cccgcgaggg ggcagcttcg 480
gatactgctt cgccctggcc tgggtggcct tccccctcgc cctggtcagc ggcatcatct 540
acatccacct acggaagcgg gagtgagcgc cccgcctcgc tcggctgccc ccgccccttc 600
ccggcccccc tcgccgcgcg tcctccaaaa aataaaacct taaccgcgg 649

<210> SEQ ID NO 68
<211> LENGTH: 2604
<212> TYPE: DNA
<213> ORGANISM: Homo sapiens

<400> SEQUENCE: 68
aagcaccgcg cagccgcctc cgccgcagga tcccccggtg caggcctccg tgctggtgcg 60
gatcctggag ctcagccgcg cgcgccctgc ccgatcctgt gccgacccac cgcactatgc 120
gcgccgtgcc gctgcccgcc ccgctcctgc cgctgctgct gctcgcgctc ctggccgctc 180
ccgccgcccg cgccagcaga gccgagtccg tctccgcgcc gtggcccgaa cccgagcgcg 240
agtcgcggcc accgcccggc ccggggcccg ggaacaccac ccggtttggg tctggggcgg 300
cgggcggcag cggcagctcc agctccaaca gcagtggcga cgccttggtg acccgcattt 360
ccatcctcct ccgcgaccta cccaccctca aggcagccgt gatcgtggcg ttcgccttta 420
ccaccctcct catcgcctgc ctgctgctgc gcgtcttcag gtcgggaaag aggttaaaga 480
agacacgcaa gtatgatatc atcaccactc cagcagagcg agtggaaatg gcgccactaa 540
atgaagagga tgatgaagat gaggactcca cagtattcga catcaaatac aggtaaaacc 600
tgtttcccag cctggtggca tcctgtggaa agttggtcag ctgcaacctg gggtgtgaag 660

```
gactggacct ggaagccctc ttgcgtcgga ggtgttgaaa ccaaaacgaa cgttatgtat    720

aaaaccccag ctccatcgtg cgtgtcaggc atctgctcag actgtcactg gcaagctcgt    780

ttccacgtca ccacaatgga gttgcttctg ccacccttg ggcatccctt taaagtgccc     840

cctacttcta ctccccatgt aagaggcttt gtgccttgct aaggagcaaa gggtagaaac    900

atgttgattt taaagaagtt tttttaagac aattgttgac aatagtaaaa gagatcagga    960

ggatcaagaa tctaaaacaa gcctgaagga tgtccaactg tgtatttaga atttccgaca   1020

ttcttctcta ctggatctac acattggacc ccatctgatc ctttgctgct tttttggctt   1080

ggtcaggtcc tggcctcatt ttggcgttac ctgtgtcaga gttcaaggtg gatgtgctta   1140

gagctggtca gccccttcca gacctggaca cgtctgtggc tccttttctt tcttcctttt   1200

tttttttttt taaaaaaaaa aaaggttcag cagaaatcag cgtggctagt tcacaaagaa   1260

tttccagtat cagggaaaaa ctgtgcgtgt gtgtgtgtgt gtgtgtgcac gtgtgtgcgt   1320

gtgcacgtgt gtgataccta taaaacagtt tctccttctc tgaagggaaa ggaaagtgct   1380

aggcagcctg tgattagcaa cattctttgt gctttttttgt tgttcctctg ctctgtcaca  1440

gttctacgtt gtttgcctta gaaatgtaat ttttaaaaac cattttaaaa atgaacggtg   1500

atttggctgg ctggaaaaaa tcacactgtc aggggactat atttgaagtc agtctagacg   1560

gggctggact aggaacccac ctggacccag gagaccccac aggacccagg aggtccctgc   1620

cggaaggcag aggttcaggt gagagtggct cacctctgag ctggtgaagt gaggacttgc   1680

ctgtgacatg acccagggat ctgctgctgg cttctggaga cagggccttg ggctgacttc   1740

tcaggttgat tgaggcctcc tgactagcgg tgttcccagg ctagaggtga ttggctgcaa   1800

caaagatgct tctattagtc tattagcagt gccttcggga ccctgggatt ttgctctctc   1860

tagaaaggtg ttttttattt ttttattttt tatctccccc ttttttcctg gctttgctcc   1920

agggtttgtg tatttgcctg tttattgtcc tgctcttttt ttttttggat gaaaactcca   1980

gcctttcctg actcacctcc atcttcggtt cttcagtttt ctgagaagag ttgggatatg   2040

tgggaagggg catgggagct cggcagcctc cgcctgccag gaaggcagtt tcgcctctgc   2100

aggaaagagc agagcccgtg ggaagccctg ggtgagggtg gcgcagccgg cccagcacgc   2160

atggtattgc cagccacggg gggcctgcgt gtagtctctg ctccctgcat ttcaccttct   2220

ttgttgactt tccttctctg ttttccccca tctgtttgcc agaggggtgg gactggcaac   2280

agaacagccg tggctgcttt atctctcctc tccacggtgt actcaggcct gagtggtgac   2340

tcacgggagc ctggccacct cgcagctgtt cgcccccctca acctttgaac tggaactgct  2400

ggctcacaca gggttttcga caactgcagc tgaatctcat ggaaaagctg gattcctctg   2460

ccttacgcag aaacacccgg gctccatctg ccaggtgctt gccactggtc ctggcagaaa   2520

tggcggctgc tgaaagtgac cttccaaatc cttggtggca cttcagcgcc acaggctctc   2580

caataaaaac cctttacaca caaa                                          2604
```

<210> SEQ ID NO 69
<211> LENGTH: 6717
<212> TYPE: DNA
<213> ORGANISM: Homo sapiens

<400> SEQUENCE: 69

```
gattcaggtg ggcgggctgg tgggcagaag ggcagacggg cagaggaagt gccagtgcca     60

ctgggaccat ggctctgacg gtaacgcgtg caacgactaa cagggctgac cggcacccac    120

gaccgacaag tgaagctcac ctttcgaggc tttacccaga aaacaagaaa aattcactgt    180
```

-continued

```
ggtccagaag cagatatcgg tgagctgttc cgatggcccc actatggggc tccactggct    240
ggggagtgtc tgtctgtgca ggtggtcaac tgcagccgtg tattcagcct taggcctcta    300
gggaccctgg tgatctccct gcagcagcta cagaatgctg ggcatttggt gctacgggaa    360
gccctagtgg atgagaatct tcaagtgtcc ccgatccagg tggagcttga cctgaagtac    420
cagcccccag agggcgctac tggagcctgg tcagaggagg actttggggc acccatccag    480
gacagcttcg agttaatcat ccccaatgtg ggcttccagg aactggagcc tggggaggcc    540
cagctggagc ggcgggcagt ggctctaggc cgcaggctag ctcgaagtct aggccagcag    600
gacgatgaag agaatgagct ggagcttgag ctggagcagg acctggatga tgagcctgac    660
gtggaacttt ctggtgttat gttcagcccc ctcaagagcc gcgccagggc cctggcccat    720
ggggatccct tccaggtgtc cagagctcaa gacttccagg tgggagtcac tgtgctggaa    780
gcccagaaac tggtgggagt caacattaac ccctatgtgg ccgtgcaagt ggggggggcag    840
cgccgtgtga ccgccacaca gcgtgggacc agttgcccct tctacaatga gtacttcttg    900
ttcgaatttc atgacacgcg gcttcgtctc caagacttgc tgctggagat cacggctttc    960
cattcgcaga ccctcccctt tatggccacc cggataggca ccttcaggat ggacctgggc   1020
atcatcttgg accagccaga tggccagttc taccaaagat gggttccgct gcatgatccc   1080
cgagacaccc gcgccgggac caagggtttc attaaggtca ccttgtccgt gagggcgcgc   1140
ggggacctgc cccctccaat gctacccccg gccccagggc actgttcgga catcgagaag   1200
aacctgctcc tgccgcgcgg ggtgcccgcc gagaggccat gggcgcggct ccgcgtgcgc   1260
ctgtaccgcg ccgaggggct tcccgcgctg cgcctggggc tgctgggcag cctggtccgc   1320
gccctgcacg accagcgcgt cctggtggag ccctatgtgc gggtgtcttt cctggggcag   1380
gagggcgaga cgtcggtgag cgccgaggcg gcggcgcccg aatggaacga gcagctgagc   1440
ttcgtggagc tcttcccgcc gctgacgcgc agcctccgcc tgcagctgcg ggacgacgcg   1500
cccctggtcg acgcggcact cgctacgcac gtgccggacc tgaggcggat ctcccatccg   1560
ggccgcgcgg cggggtttaa ccctaccttc ggcccggcct gggtgcccct ctatggctcg   1620
ccccccggcg cggggctccg ggatagtctt caaggtctca acgaaggcgt tggccaaggc   1680
atttggttcc gcggccgcct tctgctggct gtgtccatgc aggtgttgga agggagagct   1740
gaacctgagc ctccccaggc ccagcagggg tccacgttgt cccggctcac ccgaaagaag   1800
aaaaagaaag ccagaaggga tcagacccca aaggcggttc cgcagcactt ggacgccagc   1860
cccggtgccg aggggcctga gatcccccgt gccatggagg tggaggtgga ggagctgctg   1920
ccgctgccag agaatgtcct ggcgccctgt gaagatttcc tgcttttcgg tgtgctcttc   1980
gaggccacca tgatcgaccc caccgtggcc tcccagccca tcagcttcga gatctccatt   2040
ggtcgcgcag gccgtctgga ggagcaattg ggccgagggt ccagggctgg ggagggaact   2100
gagggtgcag ccgtggaggc tcagcctctg ctgggagcca ggccagagga ggagaaagag   2160
gaggaagaac tggggaccca tgctcagcgg cctgagccca tggacggcag tgggccatac   2220
ttctgcttgc ccctctgtca ctgcaagcca tgcatgcatg tgtggagttg ctgggaggac   2280
cacacctggc gcctgcagag cagcaactgc gtgcgcaaag tggccgagag gctggaccag   2340
gggctgcagg aggttgagag actgcagcgc aagccggggc ctggcgcctg tgcacagctc   2400
aagcaggcac tggaagtact ggtggctggg agcagacagt tttgccacgg tgccgagcgc   2460
aggacgatga cccggcccaa tgccctggat cgatgccgag ggaaactcct ggtgcacagc   2520
```

-continued

```
ctgaaccttt tggctaagca aggactgcga cttctacgcg gcctgagacg gcgcaatgtg   2580
caaaagaagg tggcactggc caagaagctc ctggcaaaac tgcgctttct ggctgaggag   2640
ccccagccac ccctccccga tgtgctggtc tggatgctca gcgggcagcg ccgtgtggcc   2700
tgggcccgga tccctgccca ggatgtgctg ttctctgtgg ttgaggagga acggggccga   2760
gactgtggga agatccagag tctaatgctc acggcacccg gggcagcccc tggtgaggtc   2820
tgtgccaagc tggagctctt cctgcggctg ggcctgggca agcaagccaa ggcctgcacc   2880
tctgagctgc cccggattt gctgcccgag ccctcagccg ggctgccctc cagcctacac   2940
cgggacgact ttagctactt ccaactccgg gctcacttgt accaggcccg gggtgtgttg   3000
gctgcagatg acagtggcct ctcggacccc tttgctcgag tcctcatctc tacccagtgt   3060
cagaccacac gggtcctgga gcagacgctg agccctctgt gggatgaact cctggtattt   3120
gagcagttga tcgtggatgg gaggagggag cacctgcagg aggagcctcc attagtgatc   3180
atcaatgtat ttgaccacaa taagtttggc ccccccgtgt tcctgggcag ggcactggcc   3240
gccccaaggg taaagctgat ggaggaccca taccaacgcc cagagttgca gttcttcccc   3300
ctgaggaagg gaccctgggc agccggagag ctcattgccg cctttcaact cattgaacta   3360
gactacagtg gccgacttga gccctcagtg cccagtgagg tggagcccca ggatctggca   3420
cccctggttg agccccactc tggacgcctg tcccttccac ccaacgtgtg cccagtgctc   3480
agggagttcc gtgttgaggt gctgttctgg ggtcttaggg gacttggtcg tgtgcatctg   3540
ctcgaggtgg agcagcccca ggttgtactg gaggtggctg ggcaaggtgt ggagtctgag   3600
gtcctggcca gctaccgtga gagccccaat ttcactgagc ttgtcaggca tctgacagtg   3660
gacttgccgg agcagcctta cttgcagcct ccactcagca tcttggtgat tgagcgccgg   3720
gcctttggcc acacagtcct tgtgggttcc cacattgtcc cccacatgct gcgattcaca   3780
tttcggggtc atgaggatcc tcctgaggag gaaggagaga tggaggagac aggggatatg   3840
atgcccaagg gacctcaagg acagaagtcc ctggatccct tcttggctga agcgggtata   3900
tccagacagc tcctgaagcc tcctctgaag aagctcccac taggaggcct cctaaatcaa   3960
ggccctgggc tggaggaaga catcccagat ccagaggagc tcgactgggg gtccaagtac   4020
tatgcgtcgc tgcaggagct ccaggggcag cacaactttg atgaagatga aatggatgat   4080
cctggagatt cagatggggt caacctcatt tctatggttg gggagatcca agaccaggat   4140
ctacaacagg tccctgaagg aagaatttaa ccactttgaa gactggctga atgtgtttcc   4200
tctgtaccga gggcaagggg gccaggatgg aggtggagaa gaggaaggat ctggacacct   4260
tgtgggcaag ttcaagggct ccttcctcat ttaccctgaa tcagaggcag tgttgttctc   4320
tgagccccag atctcccggg ggatcccaca gaaccggccc atcaagctcc tggtcagagt   4380
gtatgttgta aaggctacca acctggctcc tgcagacccc aatggcaaag cagaccctta   4440
cgtggtggtg agcgctggcc gggagcggca ggacaccaag gaacgctaca tccccaagca   4500
gctcaacccc atctttggag agatcctgga gctaagcatc tctctcccag ctgagacgga   4560
gctgacggtc gccgtatttg atcatgacct cgtgggttct gacgacctca tcggggagac   4620
ccacattgat ctggaaaacc gattctatag ccaccacaga gcaaactgtg ggctggcctc   4680
ccagtatgaa gtgtgggtcc agcagggccc acaggagcca ttctgagttt ctggccaaac   4740
acattcaagc tcacattccc ttttgtgttc tccagatcct atgatttcat ggaaggggac   4800
cctcccaccc accgccactg ccaaccaaga catagctcag tggtcaagac ttgggcttgg   4860
gagtcgggat cctgtaacga atgtcacttg accgctttct tttttatga aacagtctcg    4920
```

```
ctctgtctcc caggttggag tgcagtggca cgatctcggc tgactgcaac ctccacctcc   4980

tgggttcaag cgattctcct gcctcagcct ccccagtagc tgggattaca ggcgtgggcc   5040

cccatgtcca gctaattttt atatttttag tagagacagg gtttcaccat gttgtccagg   5100

ctggtcttga acccctgacc tcaagtgatc cacccacctc tgcctcccaa agtgctggga   5160

ttacaggtgt gagccaccat gccaggccca cttaacctct tcaagtctgt tttctcatct   5220

gcaaaacaga ggtaataaga tcagtatctt cttaatggaa gcacctggac tacatttttt   5280

tcattcattg ttatcataaa tgaggactaa cctgtctccc gttgggagtt ttgaacctag   5340

acctcatgtc ttcatgacgt catcactgcc ccaggcccag ctgtgtccct acaccagccc   5400

cagctgacgc atcttctttt tctgcctgta gagatggtta caatgcctgg cgtgatgcat   5460

tctggccttc gcagatcctg gcggggctgt gccaacgctg tggcctccct gcccctgaat   5520

accgagccgg tgctgtcaag gtgggcagca aagtcttcct gacaccaccg gagaccctgc   5580

ccccagggat ctcttcacat gtggattgac atctttcctc aagatgtgcc tgctccaccc   5640

ccagttgaca tcaagcctcg gcagccaatc agctatgagc tcagagttgt catctggaac   5700

acggaggatg tggttctgga cgacgagaat ccactcaccg gagagatgtc gagtgacatc   5760

tatgtgaaga gctgggtgaa ggggttggag catgacaagc aggagacaga cgttcacttc   5820

aactccctga ctggggaggg gaacttcaat tggcgctttg tgttccgctt tgactacctg   5880

cccacggagc gggaggtgag cgtccggcgc aggtctggac cctttgccct ggaggaggcg   5940

gagttccggc agcctgcagt gctggtcctg caggtctggg actatgaccg catctctgcc   6000

aatgacttcc ttggatccct ggagttgcag ctaccagaca tggtgcgtgg ggcccggggc   6060

cccgagctct gctctgtgca gctggcccgc aatggggccg ggccgaggtg caatctgttt   6120

cgctgctgcc gccgcctgag ggctggtgg ccggtagtga agctgaagga ggcagaggac    6180

gtggagcggg aggcgcagga ggctcaggct ggcaagaaga agcgaaagca gaggaggagg   6240

aagggccggc cagaagacct ggagttcaca gacatgggtg gcaatgtgta catcctcacg   6300

ggcaaggtgg aggcagagtt tgagctgctg actgtggagg aggccgagaa acggccagtg   6360

gggaaggggc ggaagcagcc agagcctctg gagaaaccca gccgccccaa aacttccttc   6420

aactggtttg tgaacccgct gaagaccttt gtcttcttca tctggcgccg gtactggcgc   6480

accctggtgc tgctgctact ggtgctgctc accgtcttcc tcctcctggt cttctacacc   6540

atccctggcc agatcagcca ggtcatcttc cgtcccctcc acaagtgact ctcgctgacc   6600

ttggacactc acccagggtg ccaacccttc aatgcctgct cctggaagtc tttcttaccc   6660

atgtgagcta ccccagagtc tagtgcttcc tctgaataaa cctatcacag ccactga      6717
```

<210> SEQ ID NO 70
<211> LENGTH: 2477
<212> TYPE: DNA
<213> ORGANISM: Homo sapiens

<400> SEQUENCE: 70

```
ataaagtcct gccgggcacc actgggcatc tctttcaagg tttctgctgg gtttctgaac     60

tgctgggttt ctgcttgctc ctctggagat gcagcgtctg ttgactccag tgaagcgcat    120

tctgcaactg acaagagcgg tgcaggaaac ctccctcaca cctgctcgcc tgctcccagt    180

agcccaccaa aggttttcta cagcctctgc tgtccccctg gccaaaacag atacttggcc    240

aaaggacgtg ggcatcctgg ccctggaggt ctacttccca gcccaatatg tggaccaaac    300
```

-continued

```
tgacctggag aagtataaca atgtggaagc aggaaagtat acagtgggct tgggccagac    360
ccgtatgggc ttctgctcag tccaagagga catcaactcc ctgtgcctga cggtggtgca    420
acggctgatg gagcgcatac agctcccatg ggactctgtg ggcaggctgg aagtaggcac    480
tgagaccatc attgacaagt ccaaagctgt caaaaacagtg ctcatggaac tcttccagga   540
ttcaggcaat actgatattg agggcataga taccaccaat gcctgctacg gtggtactgc    600
ctccctcttc aatgctgcca actggatgga gtccagttcc tgggatggtc gttatgccat    660
ggtggtctgt ggagacattg ccgtctatcc cagtggtaat gctcgtccca caggtggggc    720
cggagctgtg gctatgctga ttgggcccaa ggcccctctg gccctggagc gagggctgag    780
gggaacccat atggagaatg tgtatgactt ctacaaacca aatttggcct cggagtaccc    840
aatagtggat gggaagcttt ccatccagtg ctacttgcgg gccttggatc gatgttacac    900
atcataccgt aaaaaaatcc agaatcagtg gaagcaagct ggcagcgatc gacccttcac    960
ccttgacgat ttacagtaca tgatctttca tacacccttt tgcaagatgg tccagaagtc   1020
tctggctcgc ctgatgttca atgacttcct gtcagccagc agtgacacac aaaccagctt   1080
atataagggg ctggaggctt tcggggggct aaagctggaa gacacctaca ccaacaagga   1140
cctggataaa gcacttctaa aggcctctca ggacatgttc gacaagaaaa ccaaggcttc   1200
cctttacctc tccactcaca atgggaacat gtacacctca tccctgtacg ggtgcctggc   1260
ctcgcttctg tcccaccact ctgcccaaga actggctggc tccaggattg gtgccttctc   1320
ttatggctct ggtttagcag caagtttctt ttcatttcga gtatcccagg atgctgctcc   1380
aggctctccc ctggacaagt tggtgtccag cacatcagac ctgccaaaac gcctagcctc   1440
ccgaaagtgt gtgtctcctg aggagttcac agaaataatg aaccaaagag agcaattcta   1500
ccataaggtg aatttctccc cacctggtga cacaaacagc cttttcccag gtacttggta   1560
cctggagcga gtggacgagc agcatcgccg aaagtatgcc cggcgtcccg tctaaaggtg   1620
ttctgcagat ccatggaaag cttcctggga aacgtatgct agcagagctt ctccccgtga   1680
atcatatttt taagatccca ctcttagctg gtaaatgaat ttgaatcgac atagtagccc   1740
cataagcatc agccctgtag agtgaggagc catctctagc gggcccttca ttcctctcca   1800
tgctgcaatc actgtcctgg gcttatggtg ctatggacta ggggtccttt gtgaaagagc   1860
aagatggagc aatggagaga agacctcttc ctgaatcact ggactccaga aatgtgcatg   1920
cagatcagct gttgccttca agatccagat aaactttcct gtcatgtgtt agaactttat   1980
tattattaat attgttaaac ttctgtgctg ttcctgtgaa tctccaaatt ttgtaccttg   2040
ttctaagcta atatatagca attaaaaaga gagaaagagg aaatgattcc tgcgtttctt   2100
ggaacccaga atacaaaccc agcctaacat gcagcaagcc tgctagacct tgtgggtcag   2160
agggctgggt ccttgcctca caggctgcct ctgtcccctt gcaattccat tctatttctg   2220
ccacatgcca agtgctatga caggtacaag gcaaataaga acggtagaac acagcttccc   2280
ccagcccact tccctgttct aaagacacca catagacaga gagcagcaga caggggccag   2340
caggagctgt agttcagatc ttcttggtca ttccttgccg ctgttatttg aacaaataaa   2400
cacagcgcaa aggttaacaa gtttttgcct tctatagcca aaaataaaaa aataaataaa   2460
ttttgaaaaa aaaaaaa                                                  2477
```

<210> SEQ ID NO 71
<211> LENGTH: 4800
<212> TYPE: DNA
<213> ORGANISM: Homo sapiens

<400> SEQUENCE: 71
agagcggcgg ccggtcccgc gcggagcccg gcgcccctcc agcccgagcc aggacgccgc 60
cggccccggt cccggccccg ggcacgcagc gagccaggga tgtgagcggc gccccgcggc 120
atggcagcct caggggtgcc cagaggatgc gacatcctca tcgtctacag cccggatgcc 180
gaggaatggt gccagtacct gcagaccctg ttcctgtcca gtcggcaggt ccgcagccag 240
aagatactga ctcacaggct gggccccgag gcctccttct cggcagagga cctaagcctt 300
ttcctcagca cccgctgtgt cgtggtgctg ctgtccgcgg agctggtgca gcacttccac 360
aagcccgcct tgctgcccct gctgcagaga gctttccatc ctccgcaccg cgtggtcagg 420
ctgctctgcg gcgtgcggga cagcgaggag ttcctagact tctttccaga ttgggcccat 480
tggcaggagc tcacctgtga cgatgagcca gagacctacg tggcagctgt gaaaaaagcc 540
atttccgaag attctggctg tgactcagtc actgacactg agcctgagga cgagaaggtt 600
gtttcctact cgaagcagca gaacctgccg acggtgactt cacctgggaa cctgatggtg 660
gtgcagccgg accgcattcg ctgtggggca gaaaccactg tctatgttat tgtgagatgt 720
aagctggatg acagggtggc gacagaagca gagttttctc ctgaggattc tccctctgta 780
aggatggaag ccaaggtgga gaatgagtac accatttcag tgaaggctcc caacctttca 840
tctgggaacg tttctctgaa gatatattct ggagacttag tggtgtgtga aaccgttatc 900
agctattata ctgacatgga agaaattggg aatttattgt ccaatgccgc gaatcctgtg 960
gaattcatgt gtcaggcctt taaaattgtg ccctacaaca cagagaccct tgataaactg 1020
ctaaccgaat ccctgaagaa caatatccct gcaagcggac tgcacctctt tggaatcaac 1080
cagctggaag aagaagatat gatgacaaat cagagggatg aagagctgcc caccctgttg 1140
cattttgctg cgaagtatgg actgaagaac ctcactgcct tgttgctcac ctgcccagga 1200
gccctgcagg cgtacagcgt ggccaacaag catggccact accccaacac catcgctgag 1260
aaacacggct tcagggacct gcggcagttc atcgacgagt atgtggaaac ggtggacatg 1320
ctcaagagtc acattaaaga ggaactgatg cacggggagg aggctgatgc tgtgtacgag 1380
tccatggccc acctttccac agacctgctt atgaaatgct cgctcaaccc cggctgtgac 1440
gaggatctct atgagtccat ggctgccttt gtcccagctg ccactgaaga cctctatgtt 1500
gaaatgcttc aggccagtac atctaaccca atccctggag atggtttctc tcgggccact 1560
aaggactcta tgatccgcaa gtttttagaa ggcaacagca tgggaatgac caatctggag 1620
agagatcagt gccatcttgg tcaggaagaa gatgtttatc acacggtgga tgacgatgag 1680
gccttttctg tggacctggc cagcaggccc cctgtcccag tgcccagacc agagaccact 1740
gctcctggtg ctcaccagct gcctgacaac gaaccataca tttttaaagt ttttgcagaa 1800
aaaagtcaag agcggcctgg gaatttctac gtttcctcag agagcatcag gaaagggccg 1860
cccgtcagac catggaggga caggccccag tcgagtatat atgacccttt tgcgggaatg 1920
aaaacgccag gccagcggca gcttatcacc ctccaggagc aggtgaagct gggcattgtc 1980
aacgtggatg aggctgtgct ccacttcaaa gagtggcagc tcaaccagaa gaaacgatcg 2040
gagtcctttc gtttccagca ggaaaatctt aaacggctaa gagacagcat cacccgaaga 2100
cagagagaga agcaaaaatc aggaaagcag acagacttgg agatcacggt cccaattcgg 2160
cactcacagc acctgcctgc aaaagtggag tttggagtct atgagagtgg ccccaggaaa 2220
agtgtcattc cccctaggac ggagctgaga cgaggagact ggaaaacaga cagcacctcc 2280
agcacagcaa gtagcacaag taaccgctcc agcacccgga gcctcctcag tgtgagcagc 2340
gggatggaag gggacaacga ggataatgaa gtccctgagg ttaccagaag tcgcagtcca 2400
ggcccccac aagtggatgg gacacccacc atgtccctcg agagaccccc cagggtgcct 2460
ccgagagctg cctcacagag gcctccgacc agggagacct tccatcctcc tccacctgtt 2520
ccacccagag gacgctgatt ccacctccta aaacctgcct acttcaggac tttaagactc 2580
acagtcttca gcctgttaat gatgtcttca tgttgagttt tatagcatga ctgttgacct 2640
taagatccat tctcattgct gataatgctg cagccctgct ggtttgggct tgcctcgaag 2700
attttattaa ggcacgaaga agtgaaaaac taagggcttc attcaccatc accaagtata 2760
tcgaaccata tacttgtttg ccaaaaggat gaagacttaa tcgaaatact tacctctaat 2820
ttgccatatc agaagcctaa aaagaatgat cataaatgta cttcaccagt gattttactg 2880
aaatgcactt atattagtct ttatgtattt gctagttcag cctgatttct agaagaggtt 2940
atagtgtgag acttgtagta ttcaagtaag ataagtgacc taattttaaa ataattcttc 3000
tacttttctg tatattcagc agggtattta agtgctaggg ctggtcacac acaaccaact 3060
gaaaaagact agagggatta gtacaaactc ctcttataca gaaggcaaat ctgaggttcc 3120
acagaagtct ggaaccaaga ctattcagtt ggttaaataa agaggttagt ctagactggg 3180
cctgctcatt ctaggtcacc acattttcca tctccaaata gccaggccct ctctccctca 3240
agaaatgccc agatgtagaa attcatcagt gcctattggt cttccagaat tttccatctt 3300
ccgtatctcc caggcatgag actaccaagt ttgtttgttt tctttccaat ttgggaattt 3360
atacttcagt atggtttcaa cgcagttatg tttccagaga acatctagaa gtggctggaa 3420
accagaagct ggggattcca gggaccccac ttagtgctct atttccttta taggttttat 3480
ttctggtcat agagagagaa ggacctttga ctttttcttc gttgaggctt ctgaggagga 3540
aaaacaaacc taaaatagaa atacagtcag cctttcaaat ccatgggttc tgtgtccgtg 3600
gattcaacca accttggatc aaaaatattt gaaaaaaaat ctacaaagtt tcaaaaagca 3660
aaacttgaat ttgctgcatg ccaagaagta tgttgaattc atgtaaatga agtgatgtgt 3720
aggcattgta ttagatatta taagaaatct agaaatgatt taaagcatac aggaggatgt 3780
gcataggtta tatgcaaata ctatgctatt ttatatatgg gacttgagca tttgtggatt 3840
ttgatactgg gggatcctgg aaccaatccc ccatggatac caaagtacga ctgtagttat 3900
ctatttttta catacttatt attaccacca tgctcagtaa gtccattttt gcatggaata 3960
tggagcctta aaacatgtca tgaatttgga gtccctggca cataaatcta ccttcaaatc 4020
agaggtcctt aatgatgcct aaacatacag taaaattaga atcagaaata cttctttaaa 4080
aaatattcaa aatgtgtttg tttcccatgg gattattctc tatcccacac gaatgtaaaa 4140
aaatccacat taatgatcca tttaagtata gttttattgg gtccttttct aatgattaaa 4200
ggttctttct caatttcatt cctcagtcct gcaagtaagg actcatactg aagagtactg 4260
aaacaaggac ttcttgtcag aaacagcttc tggaatcttg ggttttgttt ttgtttttg 4320
acaaaataca ctattggcca tgtccatcac gagagtgttt gtagtaatta attaccttgt 4380
acaggacctg gcacttagta gcattcttca aatgttccct cagtgatcct tttactctcc 4440
ttgtcactta tttgggagaa ataggggcac gtgagataag aagaagaata attttgatgt 4500
tggtatgctt gccctgttac ttatagacag tctttgtcat aggcaaactt gaatttgatt 4560
taaaataggg ctgggaaaaa tattcaataa ctgtaagccc ccttttggat gccaaactta 4620
gaattttgta cattctctga tgaacaagca tttagatcgt aacatggtaa agcctattac 4680
cagccaatgt tgttagcatc tttgtatgca catcactgtt tgtgcaatat atgaatattt 4740
tgttgcattg tattcttata taaaaataag tagaaaacat aaaattgaaa ttgctgatga 4800

<210> SEQ ID NO 72
<211> LENGTH: 3328
<212> TYPE: DNA
<213> ORGANISM: Homo sapiens

<400> SEQUENCE: 72
agttggtcgg tgggccagtg gcccgtcgct cgcttctggg ctctcatgtt tgaaggtggg 60
agggacacgg gagcggcccg cacacctgag ccgcccggag aggagcctcg gccccgtacc 120
cagtaagaag aggaggaggc caggcaggca aaaggagtca tggcttctga tgctagtcat 180
gcgctggaag ctgccctgga gcaaatggac gggatcattg caggcactaa aacaggtgca 240
gatcttagtg atggtacttg tgagcctgga ctggcttccc cggcctccta catgaacccc 300
ttcccggtgc tccatctcat cgaggacttg aggctggcct tggagatgct ggagcttcct 360
caggagagag cagccctcct gagccagatc cctggcccaa cagctgccta cataaaggaa 420
tggtttgaag agagcttgtc ccaggtaaac caccacagtg ctgctagtaa tgaaacctac 480
caggaacgct tggcacgtct agaaggggat aaggagtccc tcatattgca ggtgagtgtc 540
ctcacagacc aagtagaagc ccagggagaa aagattcgag acctggaagt gtgtctggaa 600
ggacaccagg tgaaactcaa tgctgctgaa gagatgcttc aacaggagct gctaagccgc 660
acatctcttg agacccagaa gctcgatctg atgactgaag tgtctgagct gaagctcaag 720
ctggttggca tggagaagga gcagagagag caggaggaga agcagagaaa agcagaggag 780
ttactgcaag agctcaggca cctcaaaatc aaagtggaag agttggaaaa tgaaaggaat 840
cagtatgaat ggaagctaaa ggccactaag gctgaagtcg cccagctgca agaacaggtg 900
gccctgaaag atgcagaaat tgagcgtctg cacagccagc tctcccggac agcagctctc 960
cacagtgaga gtcacacaga gagagaccaa gaaattcaac gtctgaaaat ggggatggaa 1020
actttgctgc ttgccaatga agataaggac cgtcggatag aggagcttac ggggctgtta 1080
aaccagtacc ggaaggtaaa ggagattgtg atggtcactc aagggccttc ggagagaact 1140
ctctcaatca atgaagaaga accggaggga ggtttcagca agtggaacgc tacaaataag 1200
gaccctgaag aattatttaa acaagagatg cctccaagat gtagctctcc tacagtgggg 1260
ccacctccat tgccacagaa atcactggaa accagggctc agaaaaagct ctcttgtagt 1320
ctagaagact tgagaagtga atctgtggat aagtgtatgg atgggaacca gcccttcccg 1380
gtgttagaac ccaaggacag ccctttcttg gcggagcaca aatatcccac tttacctggg 1440
aagctttcag gagccacgcc caatggagag gctgccaaat ctcctcccac catctgccag 1500
cctgacgcca cggggagcag cctgctgagg ctgagagaca cagaaagtgg ctgggacgac 1560
actgctgtgg tcaatgacct ctcatccaca tcatcgggca ctgaatcagg tcctcagtct 1620
cctctgacac cagatggtaa acggaatccc aaaggcatta agaagttctg ggggaaaatc 1680
cgaagaactc agtcaggaaa tttctacact gacacgctgg ggatggcaga gtttcgacga 1740
ggtgggctcc gggcaaccgc agggccaaga ctctctagga ccagggactc caagggacag 1800
aaaagtgacg ccaatgcccc ctttgcccag tggagcacag agcgtgtgtg tgcatggctg 1860
gaggactttg gcctggctca gtatgtgatc tttgccaggc agtgggtatc ttctggccac 1920
accttattga cagccacccc tcaggacatg gaaaaggagc taggaattaa gcacccactc 1980

```
cacaggaaga agcttgtttt agcagtgaaa gccatcaaca ccaaacagga ggagaagtct   2040
gcactgctag accacatttg ggtgacaagg tggcttgatg atattggctt accccagtac   2100
aaagaccagt ttcatgaatc tagagttgac ggacgaatgc tgcaatacct aactgtgaac   2160
gatttactct tcttaaaagt caccagccaa ctacatcatc tcagcatcaa atgtgccatt   2220
cacgtgctgc atgtcaacaa gttcaacccc cactgcctgc accggcggcc agctgatgag   2280
agtaaccttt ctccttcaga agttgtacag tggtccaacc acagggtgat ggagtggtta   2340
cgatctgtgg acctggcaga gtatgcaccc aatcttcgag ggagtggagt ccatggaggc   2400
ctcattatcc tggagccacg cttcactggg gacaccctgg ctatgcttct caacatcccc   2460
ccacaaaaga cgctcctcag gcgccacctg accaccaagt tcaatgcctt gattggtccg   2520
gaggctgaac aggagaagcg agagaaaatg gcctcaccag cttacacacc actgaccacc   2580
acagccaaag tccggccaag gaaactagga ttttcacact tcggaaacat aagaaaaaag   2640
aagttcgatg aatcgacgga ctacatttgc ccaatggagc ccagtgacgg tgtcagtgat   2700
agtcacaggg tctacagtgg ctaccggggc ctcagccccc ttgatgcccc tgaactggat   2760
gggctggacc aggtgggaca gattagctga tgcccttgtc acctgccctc tgtgcaccct   2820
gagagctcac agtaacactg tgtgtgtcac catataactg cacctcaccc ccgcacgtgt   2880
gcatgactcg cagagaatat tccagcaatt gtgtacccct gggccagtct ctttgaaccc   2940
tgagggtggc caggatctgg agctgcatct ctaaggggcc aggctttggg gaccattgcc   3000
aaaggtggac tcaggaggaa agacacttaa agacactttt acatgtctag taattcttga   3060
tgttcatctt cagcaccagt ggaaacacat gaacttcgat gcaggtccag agaccatgga   3120
cactcccacg aggctcagct ctcaggcacc ccctacactt cagttgaggg aaaagctcaa   3180
gtgccttagg cccgtggacc acagtcttgg ctgagatcaa agggatgagc aacagggact   3240
tctgccacag tgacaatgga attgtgttgt gccttacttc agaggtggtc tcttctttct   3300
tgtaataaaa gcaatattta tgcggaaa                                      3328
```

<210> SEQ ID NO 73
<211> LENGTH: 10277
<212> TYPE: DNA
<213> ORGANISM: Homo sapiens

<400> SEQUENCE: 73

```
atctcccagc tcagccgagc ccgtgcccag gccacgcttt gttccagccg ccgcctcctc     60
taccctacgg cgtccggagc catccctcgc ctgctcgctc tctcctttcg cccactccct    120
gcatctgggc ctgcatcacc tttgccaacc gctcccccga tcctgccgac actcctcccc    180
caaacttctg accggcaccc ttgcctggta cccttctctc cattcctccc cctccatctt    240
ctttccccga cccctctcgg gtccctcttt tcccaaaacc cgggtctctc cgcgtggccc    300
cgcctccagg ccggggatgt cccccgcggc cccgcgccca tggtcctgac gctgcttctc    360
tccgcctaca agctgtgtcg cttcttcgcc atgtcgggcc cacggccggg cgccgagcgg    420
ctggcggtgc ctgggccaga tgggggcggt ggcacgggcc catggtgggc tgcgggtggc    480
cgcgggcccc gcgaagtgtc gccgggggca ggcaccgagg tgcaggacgc cctggagcgc    540
gcgctgccgg agctgcagca ggccttgtcc gcgctgaagc aggcgggcgg cgcgcgggcc    600
gtgggcgccg gcctggccga ggtcttccaa ctggtggagg aggcctggct gctgccggcc    660
gtgggccgcg aggtagccca gggtctgtgc gacgccatcc gcctcgatgg cggcctcgac    720
ctgctgttgc ggctgctgca ggcgccggag ttggagacgc gtgtgcaggc cgcgcgcctg    780
```

```
ctggagcaga tcctggtggc tgagaaccga gaccgcgtgg cgcgcattgg gctgggcgtg    840
atcctgaacc tggcgaagga acgcgaaccc gtagagctgg cgcggagcgt ggcaggcatc    900
ttggagcaca tgttcaagca ttcggaggag acatgccaga ggctggtggc ggccggcggc    960
ctggacgcgg tgctgtattg gtgccgccgc acggaccccg cgctgctgcg ccactgcgcg   1020
ctggcgctgg gcaactgcgc gctgcacggg ggccaggcgg tgcagcgacg catggtagag   1080
aagcgcgcag ccgagtggct cttcccgctc gccttctcca aggaggacga gctgcttcgg   1140
ctgcacgcct gcctcgcagt agcggtgttg gcgactaaca aggaggtgga gcgcgaggtg   1200
gagcgctcgg gcacgctggc gctcgtggag ccgcttgtgg cctcgctgga ccctggccgc   1260
ttcgcccgct gtctggtgga cgccagcgac acaagccagg gccgcgggcc cgacgacctg   1320
cagcgcctcg tgccgttgct cgactctaac cgcttggagg cgcagtgcat cggggctttc   1380
tacctctgcg ccgaggctgc catcaagagc ctgcaaggca agaccaaggt gttcagcgac   1440
atcggcgcca tccagagcct gaaacgcctg gtttcctact ctaccaatgg cactaagtcg   1500
gcgctggcca agcgcgcgct gcgcctgctg ggcgaggagg tgccacggcc catcctgccc   1560
tccgtgccca gctggaagga ggccgaggtt cagacgtggc tgcagcagat cggtttctcc   1620
aagtactgcg agagcttccg ggagcagcag gtggatggcg acctgcttct gcggctcacg   1680
gaggaggaac tccagaccga cctgggcatg aaatcgggca tcacccgcaa gaggttcttt   1740
agggagctca cggagctcaa gaccttcgcc aactattcta cgtgcgaccg cagcaacctg   1800
gcggactggc tgggcagcct ggacccgcgc ttccgccagt acacctacgg cctggtcagc   1860
tgcggcctgg accgctccct gctgcaccgc gtgtctgagc agcagctgct ggaagactgc   1920
ggcatccacc tgggcgtgca ccgcgcccgc atcctcacgg cggccagaga aatgctacac   1980
tccccgctgc cctgtactgg tggcaaaccc agtggggaca ctccagatgt cttcatcagc   2040
taccgccgga actcaggttc ccagctggcc agtctcctga aggtgcacct gcagctgcat   2100
ggcttcagtg tcttcattga tgtggagaag ctggaagcag gcaagttcga ggacaaactc   2160
atccagagtg tcatgggtgc ccgcaacttt gtgttggtgc tatcacctgg agcactggac   2220
aagtgcatgc aagaccatga ctgcaaggat tgggtgcata aggagattgt gactgcttta   2280
agctgcggca agaacattgt gcccatcatt gatggcttcg agtggcctga gccccaggtc   2340
ctgcctgagg acatgcaggc tgtgcttact ttcaacggta tcaagtggtc ccacgaatac   2400
caggaggcca ccattgagaa gatcatccgc ttcctgcagg gccgctcctc ccgggactca   2460
tctgcaggct ctgacaccag tttggagggt gctgcaccca tgggtccaac ctaaccagtc   2520
cccagttccc cagccctgct gtgacttcca tttccatcgt cctttctgaa ggaacagctc   2580
ctgaaaccag tctccctggg ctgagacaac ctgggctctt cttaggaaat ggctctccct   2640
cccccctgtcc cccaccctca tggcccacct ccaacccact ttcctcagta tctggagagg   2700
gaagggaagt caggcttggg cacgggaggt tagaactccc ccaggccctg ccattgggtt   2760
gtctgtctcc gtcatgggga gggtccctgc tcagttctgg agacactgga gttggggtgg   2820
gggtggttct gcattccctt ctcctgctga tagcagtcag cttgaggagg atgacggaag   2880
gcagcctcag acaggaatta aggcaatgcc caggcgggcc tgggcactgt attctgagca   2940
agggcctggg cccaggagcc agccagggat gagtgccatc atggctctcc actcagactg   3000
tgcctggccc ctgcacttac aacttcctgc cgctctgtgg ccttgccctg taatcactca   3060
gtgcccttag ctagcctgac taagtcccag atcccctaca gcttccttcg gtgtggtatc   3120
```

-continued

```
ttttgccaca tccagggcga gggttgaggc aaaccagccc tccctctgac ttccttgtca   3180
ctgcagccag ctttgctgca cttgctggtg cacaggagcc tcctgtttgg gcctgggtct   3240
gggcatgggg aggccgtgcc tcaaagccca ccctacccca tgccttggtg ctgtgcctca   3300
ggctccttcc tggtctggcc cagctggctt ccccagcccc tcagccatcc agggctaccc   3360
actgcttact cagggaccag gcagccccca tggcagtaaa agcagcctag acagaacctg   3420
cagctctgtg gaaagaggca aagtcctgaa aaggcaaagg gttgtcactt agggcagctt   3480
ctccaacttt aacatgcatc caagtcacct gggaatgttg ttaaaatcag gagatctggg   3540
gtggggccta ggactctgca tttcttacag attcccaggt gagctgatgc tggtggttaa   3600
gggtagcaaa tctctaaagc acgaagccct cacaaatctt tgccatttcc caaacactcc   3660
gctccatggt ctccagtcat cagagcaact ctacctggta ttatcatccc cattttacag   3720
ataatgacac tgaggctcag aaaggttgag gataagccca ctttcctgtc attagtggca   3780
gccccagatc cagacctagg cctcctggca cccagtccac tggcagtgga attgctttcc   3840
tgagaatcat tctgaggctg ggctattgct tctcccttgc ttcaaagaat ctagcagcgg   3900
gggataggat tttgcaacaa aaagctgacc cagaggccat acagagcagg aatatcccat   3960
tgccccctcc tccactgggt tcagagggta agaaaagcacc ctccaataaa cccaggctcc   4020
aggccgtggg ggctgctgaa ggctctttcc ccgcaagggc caggtgttga caccttaaag   4080
ctggctgcgc ccccagcccc actcttggct gtgctggcca ggtgactcct agttcttggc   4140
cacatcatca gaaagtcaaa ggtctcactc caggtttggg gctccttcct tccactcccc   4200
tccctgccag agtctgtctt ggccagtgcc agcctcgatg ctttggtttt gaccccacct   4260
gatcctcctt tcctcatgca gcacaagtgc tcaccggggc cagagccagg gcatggatat   4320
gacaagcagg gcagcctgga cactgccctc acaggacagc gccaataaca atacagtgtc   4380
tgagtatctc caggggatga tttctggctc tttgtctcca atcagtccca ctccctcctg   4440
aggtccccaa gggcagtatt cagagaggtt tcctgcgttt tatttctatt tggtataccc   4500
tccactgttg tccactgccc tgtgtggcct tctggttgac ctctgcccga tcttctgtct   4560
ctctgaggga atcagagtcc agcatccagc cccagctgga acagctgaag tcacaagcct   4620
cctctaagcc aaggccagtg tgttcagagg tgactgccac ccatactagg acaaacacag   4680
ctcagatcac caggtcaagc acctaggcct ggcttctcct gagacagagg actcagaagt   4740
ggcctttcct ccaaagcctg ctcagacaca ggtctgtagg gccagggtgt tctgcttggc   4800
tgggctgcag ctgctacccc tcggttgggg ctgagtcagc cagatcctcc ccctacttct   4860
ccccaagggc caagaactgc tcagggacat taaaggtcaa aagtccagcc acactcattc   4920
atcctttccc caggcccatg aagagaggca tctcattgta gaatgtatga ggaagtggga   4980
agtatctcag agaatcagct aagtttccta acttgtccat ccaaatgtga tcaccacgat   5040
tcaacaattt ggggcattgc tgatctagcc gttcctagtg gggcttgctc aaggttgcac   5100
agcgagtcag tagaagccct ggctggcccc acttggtacc aatccaccag gcagctcagg   5160
gctcctgccc agcccagcag cttctgttgt ctaacgtatg gcaggcagac tgggagcagg   5220
aaaacagagg gccccaaagc ccaaggcacc agaaggtttg tttcagtttg ctgaagctga   5280
tttgtaatga ttggcactct tcagccaggg gagtgggtag gccatagcca aggatcgatt   5340
ccccaaccac agcaaaggca acactcttcc tccagagatc accaagcccc tcttacctcc   5400
ctccctcctt cccaaggctg gcactaacca ggtaccacat tcattgttaa ggaatggctg   5460
atgactgcta cacgtgttgg gaacctggtt ggggctgtgc agtttgggct ggaaggagag   5520
```

```
atgccagccc tcgtgctgcc tctggtccct gaagtgtcac ctctctcagg acctctcctc   5580
tggcctgtgg ggttataagt gatggatagc agaaagggag aactgactcc tgtcccaaat   5640
agctcctctg ccacctgtcc tgcagtgggc ctgtgtgggt tatgattcta gatcctagac   5700
agaggctggg tcagctgtgg atggggtggt gccttggtct ctcttgacta cctcgtccaa   5760
agagagcact gcccttagac aagagttgct tgtcctgctg tgggctgggc ttccagctgc   5820
agacctccag ttgcttggtg ttcactttgc tcctcttgcc ctctgtcttc tggtccaggc   5880
agatcagggg ctctggggaa actgctggaa ctcgaggtga ggatcagcct tttccagcat   5940
cctgtgagag accagagaga gagtttggat ttcatgtggg gaaccctcaa ggcctgtctg   6000
gagaagtgac acaggattta ctggggtggg ctggtccagg tagctctcct gaacctcctc   6060
cttccccaag ctgagaagct gagagctgga ggacaatatc cagggacatg gctctggaaa   6120
ataacttttt ttttttaag agacagggtc ttgctctgtt gtccaggctg gagggcagtg   6180
acataatcat agctcactgt acccttgaac tcctgggctc aagtgatcct cctgcctcag   6240
cctccttagt agctgggact accagtgcat accaccatgc ctgggtgatt ttttaaattt   6300
tttatacaga caaggtcttg ctatgttgcc caggctgatc ttgaattccc gggctcaagt   6360
ggtcctcctg cctcagcctc ccacaggatc gggattacag gcaagagcct ccacgcccgg   6420
ccatgaaata taattcttaa tatcatacag gaaaaagtca gcgggtcaag ctagcctgtg   6480
gcccagccac aactagctga caaagcttcc tggccttccc tttaacacag ttctgctgcc   6540
atagttccat ctataaaatg ggaatggagg gaaatagggg aactgggaga gagaacacag   6600
ccttgccaag cagcaatgtt agcctgatcc ttcctccacc tagctcgcca tctcgccctt   6660
ggaaaatggc tcctggagga ttaggcagcc atctgcaagg agaggggcaa cctgggacaa   6720
gacacccaga gggtaaggat tccaggaatg aagctgccat ttctggttgg gaggagaaga   6780
ggaaactttt aagagaaagg gctccattat gagcatgggt tcagggccct gcattaccca   6840
atcagaacag ccgggatgag caggaggcca gctcccagga ggaaggggaa ccccttcata   6900
aagttcagag tggctgggta gagtgagttg aagatgccgg aggccgtcag catggccagg   6960
ctattcacac aggccacagc agaaaagaga gcacctgtga agaaataaat accatactct   7020
ggagtccgaa agggccatat tccaactctg gcaccaccac ctcacagctg tgtgaccggg   7080
agtagtcact taacctatgt ctccccttcc tcaccagtaa atcctgctac atcatgtact   7140
gtgacaagga ttcagtaagg tcatatgtgg acagtagctg gcacagaggg gctactaaac   7200
aaatggctgc tattaaatcc acattaaaag tacatgtgat ctgacagaac ccagcacata   7260
aaagaaaaaa aaagtacatg tgatattgtc tgatgaaagc ttgatggaaa tggctttttt   7320
ctggtttatc ctctttggaa tcatctcctg tttgggatta actgctggtc tgatcagttc   7380
caatattcat agcggtgtca ccactgaata gcttcttatc ctttgggttc ctgttcctcc   7440
ttctgctaaa taaggataat acctatttcc tagattgtga gcaacattaa gttcacatgg   7500
aaatcaccca tcactgggcc tggtcccctg gaagtagcta gttagtaagg gctgttcttt   7560
tctcctgttt ctcttgacat ctctgggcac agagaaagtg ctgggaaaaa aagtttaggt   7620
gaatgaatga agacacatgg attctgggga caccagaacc cacagtgggc tctgtatggc   7680
accagagtct ctgtcatcat cagatcctca ttccaggaca gatggaaaaa gatgaatgtt   7740
tccagactgg ggcataaaga cccagaggct ggagaagctg ttctttatag atataccagg   7800
agaacccaca gtttacaaaa tgtgcaacaa cccaacagaa gttgagatta aattctgtca   7860
```

-continued catctagagg ggtctgtgat gtcatcaaaa gcaaaccacc cacatcacag atgaagaaac 7920
aggcctgtgg cagggctcgg actaaaaccc agatcctgag accagctgct tttaaacaca 7980
gacgtaggtt tgcatcctag ctccaccatt tactgagtaa ccttgggtga gccaatgtaa 8040
ccccctgggt ctctgtttct ttatctgtca actgtggaaa atgaaaccca tgtcacaagg 8100
ttgttcactt ctgggcttgt acacgctgac cccagagaaa cagggaactc tggcatcacc 8160
acacccatct tacagacgga aaagctgagg tctgcagaga gtaaatcctc tgctctggtt 8220
atctagaaag aacataattg tgctctgctg actgcaaatc ccaactctgc ggtttgaaaa 8280
tccaaggtgg catgatcctc tgcccattgt gggcaatttc acagaaatgt gtttgttttg 8340
gccacttact tctccagggt gagagggggg aaggcaagct gttcccccag ccatggctgc 8400
ccatcagccc gtttcgggca gcactggaca tgaggaacca gacacaggtg ggttctgaca 8460
ctcaccctgc tctgtctctc tcaccagctt ggagagttta gcccggatga caggtgtgat 8520
gactaatgac aggaaaagca acccatatcc tgtggagaaa caaacactca tcaggaaaat 8580
ggggctgggg agaggggcgt ccaagggaaa ggcagcagag ctcctatcca taccccacgt 8640
ggggcttagg ttagacccag gaagaacttc cttgatggtg agggtgggaa gacagtagtc 8700
aaggaggaat ggagactgcc cttgtctggg cttggccacc tgctagctct catgaatgaa 8760
tgctaattcc cattgattgc tttcttgtct gaacctcttg tggtcacagc aggcatcacc 8820
cacccacttg gcacttagta gggatatggc agggcacaga aaacaagcat gggctttgga 8880
gtcagccctg agttcaaaac ctgatgccat tacatattat ctgtgtggcc tggggtactt 8940
accctctctg atcctgactc cctgtatgag gaagataata aggccttcat cacaggatgg 9000
ttctgaggca taggaggctg aataatggtg cccaatggca tcagattcat agccctggaa 9060
cctgtaaata ctaccttatt tggaaaatga gtctatgcag gtgtgcagtt aagcctcctg 9120
agagagcaga gttatcctgg attaggttgg gccctaaatg ccgtcacaca tatctttata 9180
agaggaaagc agacggagat ttggcaccga cagaattgag aaggcacaaa gaggaggaga 9240
gtcaatgtga gcacagaggc agagactggt gatggccgcc ccaagccaag gaatgccagc 9300
agccccagaa gctggaagaa atgagaaaca cgttctctcc tggaggcttg caagggagca 9360
ctgcctgctg actgcttcca ttcagcccgg tggtactgac tttggacttc tggcctccag 9420
aactgtgaga gaatatgttt ctgttgtgtt aagcccccaa gtttgtggta tgtcattaca 9480
gcaatctcag ggaaccaata catgaggtaa aaaggtaaca tctatgaaga gcatggcata 9540
gggacacagc aaatgggagt tccttttccc tttgcattca gttacttaca ggcttcctgt 9600
tttcttcata accatttctc tccctgtgcg actgctgact cctcagcaaa actgcaaact 9660
cctacaggac agtggatcct ccaaagaagg tatacgatga ggcatccagg gaccctagca 9720
gtgtcaggcc cctcaaatcc cactctgttg agacctcccc ccgacccaga gcaatgacag 9780
catctttatc atctctgcat cccccagggc catcagcagg agggaaaggt tcccttctgc 9840
ttaattgtca gacaagcagt tgagttaaga aatctgtgat tattgtattg ttgactatac 9900
acagcacatt ttagggctct atcaaaataa atctgtccct ttaaaaaaag ttaactaaag 9960
ccgggcacgg tggctcatgc ctgtaatccc aacactttgg gaggctgagg caggcggatc 10020
cttgagctca ggagttagag acctggactg ggcaaaatgg tgaggacccc atctctataa 10080
aaaatacaaa aattagcaag gtgtggtaat gtgcaccagt ggtcccagct actagagagg 10140
ccaaggtggg aggatcatct gggcccgggg gatgaggctg cagtgagcca tgatcgtgcc 10200
actgcactct agcctgggta acaaagcgag accctgtctc taaatacatc aatcaaataa 10260
aaattttaaa aagttaa 10277

<210> SEQ ID NO 74
<211> LENGTH: 1707
<212> TYPE: DNA
<213> ORGANISM: Homo sapiens

<400> SEQUENCE: 74
agacacacat agcctctctg cccacctctg cttcctctag gaacacagga gttccagatc 60
acatcgagtt caccatgaat tcactcagtg aagccaacac caagttcatg ttcgacctgt 120
tccaacagtt cagaaaatca aaagagaaca acatcttcta ttcccctatc agcatcacat 180
cagcattagg gatggtcctc ttaggagcca aagacaacac tgcacaacag attaagaagg 240
ttcttcactt tgatcaagtc acagagaaca ccacaggaaa agctgcaaca tatcatgttg 300
ataggtcagg aaatgttcat caccagtttc aaaagcttct gactgaattc aacaaatcca 360
ctgatgcata tgagctgaag atcgccaaca agctcttcgg agaaaaaacg tatctatttt 420
tacaggaata tttagatgcc atcaagaaat tttaccagac cagtgtggaa tctgttgatt 480
ttgcaaatgc tccagaagaa agtcgaaaga agattaactc ctgggtggaa agtcaaacga 540
atgaaaaaat taaaaaccta attcctgaag gtaatattgg cagcaatacc acattggttc 600
ttgtgaacgc aatctatttc aaagggcagt gggagaagaa atttaataaa gaagatacta 660
aagaggaaaa attttggcca aacaagaata catacaagtc catacagatg atgaggcaat 720
acacatcttt tcattttgcc tcgctggagg atgtacaggc caaggtcctg gaaataccat 780
acaaaggcaa agatctaagc atgattgtgt tgctgccaaa tgaaatcgat ggtctccaga 840
agcttgaaga gaaactcact gctgagaaat tgatggaatg gacaagtttg cagaatatga 900
gagagacacg tgtcgattta cacttacctc ggttcaaagt ggaagagagc tatgacctca 960
aggacacgtt gagaaccatg ggaatggtgg atatcttcaa tggggatgca gacctctcag 1020
gcatgaccgg gagccgcggt ctcgtgctat ctggagtcct acacaaggcc tttgtggagg 1080
ttacagagga gggagcagaa gctgcagctg ccaccgctgt agtaggattc ggatcatcac 1140
ctacttcaac taatgaagag ttccattgta atcacccttt cctattcttc ataaggcaaa 1200
ataagaccaa cagcatcctc ttctatggca gattctcatc cccgtagatg caattagtct 1260
gtcactccat ttggaaaatg ttcacctgca gatgttctgg taaactgatt gctggcaaca 1320
acagattctc ttggctcata tttcttttct ttctcatctt gatgatgatc gtcatcatca 1380
agaatttaat gattaaaata gcatgccttt ctctctttct cttaataagc ccacatataa 1440
atgtactttt tcttccagaa aaattctcct tgaggaaaaa tgtccaaaat aagatgaatc 1500
acttaatacc gtatcttcta aatttgaaat ataattctgt ttgtgacctg ttttaaatga 1560
accaaaccaa atcatacttt ttctttgaat ttagcaacct agaaacacac atttctttga 1620
atttaggtga tacctaaatc cttcttatgt ttctaaattt tgtgattcta taaaacacat 1680
catcaataaa atagtgacat aaaatca 1707

<210> SEQ ID NO 75
<211> LENGTH: 1787
<212> TYPE: DNA
<213> ORGANISM: Homo sapiens

<400> SEQUENCE: 75
aaccacagag ggaaaggcag caagaggaga ggcataaatt taggatctca cccttcattc 60

```
cacagacaca cacagcctct ctgcccacct ctgcttcctc taggaacaca ggagttccag    120

atcacatcga gttcaccatg aattcactca gtgaagccaa caccaagttc atgttcgatc    180

tgttccaaca gttcagaaaa tcaaaagaga acaacatctt ctattcccct atcagcatca    240

catcagcatt agggatggtc ctcttaggag ccaaagacaa cactgcacaa caaattagca    300

aggttcttca ctttgatcaa gtcacagaga acaccacaga aaaagctgca acatatcatg    360

ttgataggtc aggaaatgtt catcaccagt ttcaaaagct tctgactgaa ttcaacaaat    420

ccactgatgc atatgagctg aagatcgcca acaagctctt cggagaaaag acgtatcaat    480

ttttacagga atatttagat gccatcaaga aattttacca gaccagtgtg gaatctactg    540

attttgcaaa tgctccagaa gaaagtcgaa agaagattaa ctcctgggtg gaaagtcaaa    600

cgaatgaaaa aattaaaaac ctatttcctg atgggactat tggcaatgat acgacactgg    660

ttcttgtgaa cgcaatctat ttcaaagggc agtgggagaa taaatttaaa aaagaaaaca    720

ctaaagagga aaaattttgg ccaaacaaga atacatacaa atctgtacag atgatgaggc    780

aatacaattc ctttaatttt gccttgctgg aggatgtaca ggccaaggtc ctggaaatac    840

catacaaagg caaagatcta agcatgattg tgctgctgcc aaatgaaatc gatggtctgc    900

agaagcttga agagaaactc actgctgaga aattgatgga atggacaagt ttgcagaata    960

tgagagagac atgtgtcgat ttacacttac ctcggttcaa aatggaagag agctatgacc   1020

tcaaggacac gttgagaacc atgggaatgg tgaatatctt caatggggat gcagacctct   1080

caggcatgac ctggagccac ggtctctcag tatctaaagt cctacacaag gcctttgtgg   1140

aggtcactga ggagggagtg gaagctgcag ctgccaccgc tgtagtagta gtcgaattat   1200

catctccttc aactaatgaa gagttctgtt gtaatcaccc tttcctattc ttcataaggc   1260

aaaataagac caacagcatc ctcttctatg gcagattctc atccccatag atgcaattag   1320

tctgtcactc catttagaaa atgttcacct agaggtgttc tggtaaactg attgctggca   1380

acaacagatt ctcttggctc atatttcttt tctatctcat cttgatgatg atagtcatca   1440

tcaagaattt aatgattaaa atagcatgcc tttctctctt tctcttaata agcccacata   1500

taaatgtact tttccttcca gaaaaatttc ccttgaggaa aaatgtccaa gataagatga   1560

atcatttaat accgtgtctt ctaaatttga aatataattc tgtttctgac ctgttttaaa   1620

tgaaccaaac caaatcatac tttctcttca aatttagcaa cctagaaaca cacatttctt   1680

tgaatttagg tgatacctaa atccttctta tgtttctaaa ttttgtgatt ctataaaaca   1740

catcatcaat aaaataatga cataaaatca aaaaaaaaaa aaaaaaa                 1787
```

<210> SEQ ID NO 76
<211> LENGTH: 2566
<212> TYPE: DNA
<213> ORGANISM: Homo sapiens

<400> SEQUENCE: 76

```
agcatgggaa caagcctttg tgtcacactg tgcaaccttc ctccctttct taaatgcttg     60

gggtgagaga gaagagaggc tagggtgggg catggaggac acagagagag agagtgctgt    120

gtattccttc cccgctactg tcctgtcctc agctaacttg ctctgggaca gcttccccag    180

ggctacagat actgcactca gctgactgtc ctttcttctg ggcccctggt cccagagcag    240

agctgacaaa ggagattcct gagagagcac cttcttatca cagaaagtgc tgagccaaga    300

gctcctagct gccccttttg cagatgtgaa gggccagtga accttggacc cagatggttg    360

cttaatactc ctttcccccct ccctcactcc ttcctttgcg ggctgcctca cctcctccac    420
```

-continued

```
ccttcttgct taaatccata ggcatttgtc tggccttccc ttttactgct ggctgggaag    480
gaggagcatc agaccacaga tcctggaagg cacttctctc cctgactgct gctcacactg    540
ccgtgagaac ctgcttatat ccaggaccaa ggaggcaatg ccaggaagct ggtgaagggt    600
ttcctctcct ccaccatggt tgacagcact gagtatgaag tggcctccca gcctgaggtg    660
gaaacctccc ctttgggtga tggggccagc ccagggccgg agcaggtgaa gctgaagaag    720
gagatctcac tgcttaacgg cgtgtgcctg attgtgggga acatgatcgg ctcgggcatc    780
tttgtttccc ccaagggtgt gctcatatac agtgcctcct ttggtctctc tctggtcatc    840
tgggctgtcg gggcctcttt ctccgtcttt ggggcccttt gttatgcgga actgggcacc    900
accattaaga aatctggggc cagctatgcc tatatcctgg aggcctttgg aggattcctt    960
gctttcatca gactctggac ctccctgctc atcattgagc ccaccagcca ggccatcatt   1020
gccatcacct ttgccaacta catggtacag cctctcttcc cgagctgctt cgccccttat   1080
gctgccagcc gcctgctggc tgctgcctgc atttgtctct taaccttcat taactgtgcc   1140
tatgtcaaat ggggaaccct ggtacaagat attttcacct atgctaaagt attggcactg   1200
atcgcggtca tcgttgcagg cattgttaga cttggccagg gagcctctac tcattttgag   1260
aattcctttg agggttcatc atttgcagtg ggtgacattg ccctggcact gtactcagct   1320
ctgttctcct actcaggctg ggacaccctc aactatgtca ctgaagagat caagaatcct   1380
gagaggaacc tgcccctctc cattggcatc tccatgccca ttgtcaccat catctatatc   1440
ttgaccaatg tggcctatta tactgtgcta gacatgagag acatcttggc cagtgatgct   1500
gttgctgtga cttttgcaga tcagatattt ggaatattta actggataat tccactgtca   1560
gttgcattat cctgttttgg tggcctcaat gcctccattg tggctgcttc taggcttttc   1620
tttgtgggct caagagaagg ccatctccct gatgccatct gcatgatcca tgttgagcgg   1680
ttcacaccag tgccttctct gctcttcaat ggtatcatgg cattgatcta cttgtgcgtg   1740
gaagacatct tccagctcat taactactac agcttcagct actggttctt tgtggggctt   1800
tctattgtgg gtcagcttta tctgcgctgg aaggagcctg atcgacctcg tcccctcaag   1860
ctcagcgttt tcttcccgat tgtcttctgc ctctgcacca tcttcctggt ggctgttcca   1920
ctttacagtg atactatcaa ctccctcatc ggcattgcca ttgccctctc aggcctgccc   1980
ttttacttcc tcatcatcag agtgccagaa cataagcgac cgctttacct ccgaaggatc   2040
gtggggtctg ccacaaggta cctccaggtc ctgtgtatgt cagttgctgc agaaatggat   2100
ttggaagatg gaggagagat gcccaagcaa cgggatccca aatctaacta aacaccatct   2160
ggaatcctga tgtggaaagc aggggtttct ggtctactgg ctagagctaa ggaagttgaa   2220
aaggaaagct cacttctttg gaggcacctg tccagaagcc tggcctaggc agcttcaacc   2280
tttgaactta ctttttgaaa tgaaaagtaa tttatttgtt ttgctacata ctgttccaga   2340
cttttaaagg ggacaatgaa ggtgactgtg gggaggagca tgtcaggttt gggcttggtt   2400
gttttagaag cacctgggtg tgcctaccta ctcctctttt cttttaaaag ggcccacaat   2460
gctccaattt cctgtctcct ttagagagac atgaaactat cacaggtgct ggatgacaat   2520
aaaagtttat gttcctaaaa aaaaaaaaaa aaaaaaaaaa aaaaaa                  2566
```

<210> SEQ ID NO 77
<211> LENGTH: 3433
<212> TYPE: DNA
<213> ORGANISM: Homo sapiens

<400> SEQUENCE: 77

```
gttagcgcag gggatccgag ctgggcagga catgtgagat agtcacagtt ttccagagat     60
cacgacaaga tctaaccagt cgcgcgtggt ccccggcgcc ggagcgggcc agctcagccc    120
ggcccagccc ggccccgcgc agagcccccg ccgcccccgc gcacagagcc gggtgcccct    180
tgcggtgcgc cggacgggaa gccccgagga gcagctgctg cgcccgccac ccgggtcgtc    240
cgtccaccgc gcgcgccgcc gcccgggccg ggggtccgag ccgcgcgccc ccggccccgg    300
ccccggcccc cgggcgcctg ggccggatgt cccgatgaga gagccggcgc tggcggccag    360
cgccatggct taccacccgt tccacgcgcc acggcccgcc gacttcccca tgtccgcctt    420
tctggcggcg gcgcagccct ccttcttccc ggcactcgcg ctgccgcccg gcgcgctggc    480
caagccgctg cccgacccgg gcctggcggg ggcggcggcc gcggcggcgg cggcggcagc    540
agcggccgag gcggggctgc acgtctcggc actgggcccg cacccgcccg ccgcgcatct    600
gcgctccctc aagagcctgg agcccgagga cgaggtggag gacgacccca aggtgacgct    660
ggaggccaag gagctgtggg accagttcca caagctaggc acggagatgg tcatcaccaa    720
gtccgggagg cggatgttcc ccccttcaa ggtgcgagtc agcggcctgg acaagaaggc    780
caagtatatc ctgctgatgg acattgtagc cgctgacgat tgccgctata agttccacaa    840
ctcgcgctgg atggtggcgg gcaaggccga ccctgagatg cccaaacgca tgtacatcca    900
cccagacagc ccagccacgg gggagcagtg gatggctaag cctgtggcct tccacaagct    960
gaagctgacc aacaacatct ctgacaagca cggcttcacc atcctaaact ccatgcacaa   1020
gtaccagccg cgcttccaca tagtgcgagc caacgacatc ctgaagctgc cttacagcac   1080
cttccgcacc tacgtgttcc cggagaccga cttcatcgcc gtcactgcct accagaatga   1140
caagatcaca cagctgaaga tcgacaacaa cccgtttgcc aagggcttcc gggacaccgg   1200
gaacggccgg cgggagaaaa ggaagcagct gacgctgccg tctctacgct tgtacgagga   1260
gcactgcaaa cccgagcgcg atggcgcgga gtcagacgcc tcgtcgtgcg accctccccc   1320
cgcgcgggaa ccacccacct ccccgggcgc agcgcccagt ccgctgcgcc tgcaccgggc   1380
ccgagctgag gagaagtcgt gcgccgcgga cagcgacccg gagcctgagc ggttgagcga   1440
ggagcgtgcg ggggcgccgc taggccgcag cccggctcca gacagcgcca gccccactcg   1500
cttgaccgaa cccgagcgcg cccgggagcg gcgtagtccc gagaggggca aggagccggc   1560
cgagagcggc ggggacggcc cgttcggcct gaggagcctg gagaaggagc gcgccgaagc   1620
tcggaggaag gacgaggggc gcaaggaggc ggccgagggc aaggagcagg gcctggcgcc   1680
gctggtggtg cagacagaca gtgcgtcccc cctgggcgcc ggacacctgc ccggcctggc   1740
cttttccagc cacttgcacg ggcagcagtt ctttgggccg ctgggagccg gccagccgct   1800
cttcctgcac cctggacagt tcaccatggg ccctggcgcc ttctccgcca tgggcatggg   1860
tcacctactg gcctcggtgg caggcggcgg caacggcgga ggtggcgggc ctgggaccgc   1920
cgcggggctg gacgcaggcg ggctgggtcc cgcggccagc gcagcaagca ccgccgcgcc   1980
cttcccgttc cacctctccc agcacatgct ggcatctcag ggaattccaa tgcccacttt   2040
cggaggcctc ttcccctacc cctacaccta catggcagca gcagccgcag ccgcctcggc   2100
tttgcccgcc actagtgctg cagctgccgc cgccgcagcc gccggctccc tctcccggag   2160
ccccttcctg ggcagtgccc ggccccgact gcgtttcagc ccctatcaga tcccggtcac   2220
catcccgcct agcactagcc tcctcaccac cgggctggcc tctgagggct ccaaggccgc   2280
tggtggaaac agccgggagc ctagccccct gcccgagctg gctctccgca aagtaggggc   2340
```

cccatcccgc ggtgccctgt cgcccagtgg ctcggccaag gaggcggcca atgaactgca 2400
gagcatccag agactggtga gtgggctgga gagccagcga gccctctccc caggccggga 2460
gtcgcccaag tgaggggctg cccagctgct cccctgccac gcaggccacc cgggctgcct 2520
gcccctgctg cttgggacgt gtacagcaca gaatgagtat ttatttaaat aaaggagaaa 2580
agtgggctgc agcagccgga atagagcctc gtctggcaag tcggggcctg ggacacttcc 2640
ctgggcctca acaaggatca ggctgctgga aacacagtca cttgggagct gctgggctag 2700
gtccagatcc gctccagcgt caaggtggca tccgaaggtg tctctggtct tccagcgagg 2760
tgggagaggc ctcatccagg gcccagcggt ccctgcagaa gccagaaggt gcaggggcca 2820
ggggtgggag catcggaggg agtcccagag ccctggacct tgggcctaga ccgcgtgata 2880
aaactgggtt gagggatgct ggaaccagtt acgactgaag tcagtgtaga cctgagctgg 2940
gagggaacct gttagtctcc ccacctcttc cctgaagaga caggcacccc tcccagccgt 3000
ggtcaacgga gggagtggca cttctgcctt gagtccccag gggaaaaaaa aaaaagatat 3060
ttatgaaata aatggtaatt tgtgtaaata agctttaagg ttcccagaat atgcaaattg 3120
gtattaattt attcaaaggt gtacattgct gtgtacatat atttagagat taactcatac 3180
atttaaagtt tttttcattt tacgtgagca tctatattgt acagggctgg gggggccctt 3240
ggctgcggga gaaggcccag agccctggag gagccaccac cccgccggcc cctcgacccc 3300 tcggccccctc ggcccctccg cccgggtttg gctcgcccgg cccgcgggct ccacctcagg 3360
ttttcacttt tcgctccgga gcgagaacga aacgacaaaa acgcaagaaa acaataaaac 3420
gctagaaagc gaa 3433

<210> SEQ ID NO 78
<211> LENGTH: 1315
<212> TYPE: DNA
<213> ORGANISM: Homo sapiens

<400> SEQUENCE: 78
agacgcctcc ggtagtgtaa atgaggacaa tgcctgctgg cccacatgac ggggggatgt 60
agacggcagc ggcgccagtc gctcctggca ccatggacga tgccacagtc ctaaggaaga 120
agggttacat cgtaggcatc aatcttggca agggttccta cgcaaaagtc aaatctgcct 180
actctgagcg cctcaagttc aatgtggctg tcaagatcat cgaccgcaag aaaacaccta 240
ctgactttgt ggagagattc cttcctcggg agatggacat cctggcaact gtcaaccacg 300
gctccatcat caagacttac gagatctttg agacctctga cggacggatc tacatcatca 360
tggagcttgg cgtccagggc gacctcctcg agttcatcaa gtgccaggga gccctgcatg 420
aggacgtggc acgcaagatg ttccgacagc tctcctccgc cgtcaagtac tgccacgacc 480
tggacatcgt ccaccgggac ctcaagtgcg agaaccttct cctcgacaag gacttcaaca 540
tcaagctgtc tgactttggc ttctccaagc gctgcctgcg ggacagcaat gggcgcatca 600
tcctcagcaa gaccttctgc gggtcggcag catatgcagc ccccgaggtg ctgcagagca 660
tcccctacca gcccaaggtg tatgacatct ggagcctggg cgtgatcctg tacatcatgg 720
tctgcggctc catgccctat gacgactccg acatcaggaa gatgctgcgt atccagaagg 780
agcaccgtgt ggacttcccg cgctccaaga acctgacctg cgagtgcaag gacctcatct 840
accgcatgct gcagcccgac gtcagccagc ggctccacat cgatgagatc ctcagccact 900
cgtggctgca gccccccaag cccaaagcca cgtcttctgc ctccttcaag agggaggggg 960

```
agggcaagta ccgcgctgag tgcaaactgg acaccaagac aggcttgagg cccgaccacc   1020

ggcccgacca caagcttgga gccaaaaccc agcaccggct gctggtggtg cccgagaacg   1080

agaacaggat ggaggacagg ctggccgaga cctccagggc caaagaccat cacatctccg   1140

gagctgaggt ggggaaagca agcacctagc atgacaatgg ccccgttgtg tgtggtgggg   1200

gtcggggttg gggggcatgg tgcagtcggc cttcacgtaa actaagtagg caggtaggat   1260

ctgaagaagg cacaggtgca agtaaaattc gtcaattaaa ccactatttt gatta        1315
```

<210> SEQ ID NO 79
<211> LENGTH: 1807
<212> TYPE: DNA
<213> ORGANISM: Homo sapiens

<400> SEQUENCE: 79

```
acagacgctg gcggccacca gaagtttgag cctctttggt agcaggaggc tggaagaaag     60

gacagaagta gctctggctg tgatggggat cttactgggc ctgctactcc tggggcacct    120

aacagtggac acttatggcc gtcccatcct ggaagtgcca gagagtgtaa caggaccttg    180

gaaaggggat gtgaatcttc cctgcaccta tgacccccctg caaggctaca cccaagtctt    240

ggtgaagtgg ctggtacaac gtggctcaga ccctgtcacc atctttctac gtgactcttc    300

tggagaccat atccagcagg caaagtacca gggccgcctg catgtgagcc acaaggttcc    360

aggagatgta tccctccaat tgagcaccct ggagatggat gaccggagcc actacacgtg    420

tgaagtcacc tggcagactc ctgatggcaa ccaagtcgtg agagataaga ttactgagct    480

ccgtgtccag aaactctctg tctccaagcc cacagtgaca actggcagcg gttatggctt    540

cacggtgccc cagggaatga ggattagcct tcaatgccag gctcggggtt ctcctcccat    600

cagttatatt tggtataagc aacagactaa taaccaggaa cccatcaaag tagcaaccct    660

aagtacctta ctcttcaagc ctgcggtgat agccgactca ggctcctatt tctgcactgc    720

caagggccag gttggctctg agcagcacag cgacattgtg aagtttgtgg tcaaagactc    780

ctcaaagcta ctcaagacca agactgaggc acctacaacc atgacatacc ccttgaaagc    840

aacatctaca gtgaagcagt cctgggactg gaccactgac atggatggct accttggaga    900

gaccagtgct gggccaggaa agagcctgcc tgtctttgcc atcatcctca tcatctcctt    960

gtgctgtatg gtggttttta ccatggccta tatcatgctc tgtcggaaga catcccaaca   1020

agagcatgtc tacgaagcag ccagggcaca tgccagagag gccaacgact ctggagaaac   1080

catgagggtg gccatcttcg caagtggctg ctccagtgat gagccaactt cccagaatct   1140

gggcaacaac tactctgatg agccctgcat aggacaggag taccagatca tcgcccagat   1200

caatggcaac tacgcccgcc tgctggacac agttcctctg gattatgagt ttctggccac   1260

tgagggcaaa agtgtctgtt aaaaatgccc cattaggcca ggatctgctg acataattgc   1320

ctagtcagtc cttgccttct gcatggcctt cttccctgct acctctcttc ctggatagcc   1380

caaagtgtcc gcctaccaac actggagccg ctgggagtca ctggctttgc cctggaattt   1440

gccagatgca tctcaagtaa gccagctgct ggatttggct ctgggccctt ctagtatctc   1500

tgccgggggc ttctggtact cctctctaaa taccagaggg aagatgccca tagcactagg   1560

acttggtcat catgcctaca gacactattc aactttggca tcttgccacc agaagacccg   1620

agggaggctc agctctgcca gctcagagga ccagctatat ccaggatcat ttctctttct   1680

tcagggccag acagctttta attgaaattg ttatttcaca ggccagggtt cagttctgct   1740

cctccactat aagtctaatg ttctgactct ctcctggtgc tcaataaata tctaatcata   1800
```

acagcaa 1807

<210> SEQ ID NO 80
<211> LENGTH: 1997
<212> TYPE: DNA
<213> ORGANISM: Homo sapiens

<400> SEQUENCE: 80
gctttctatt caagtgcctt ctgtgtgtgc acatgtgtaa tacatatctg ggatcaaagc 60
tatctatata aagtccttga ttctgtgtgg gttcaaacac atttcaaagc ttcaggatcc 120
tgaaaggttt tgctctactt cctgaagacc tgaacaccgc tcccataaag ccatggcttg 180
ccttggattt cagcggcaca aggctcagct gaacctggct accaggacct ggccctgcac 240
tctcctgttt tttcttctct tcatccctgt cttctgcaaa gcaatgcacg tggcccagcc 300
tgctgtggta ctggccagca gccgaggcat cgccagcttt gtgtgtgagt atgcatctcc 360
aggcaaagcc actgaggtcc gggtgacagt gcttcggcag gctgacagcc aggtgactga 420
agtctgtgcg gcaacctaca tgatggggaa tgagttgacc ttcctagatg attccatctg 480
cacgggcacc tccagtggaa atcaagtgaa cctcactatc caaggactga gggccatgga 540
cacgggactc tacatctgca aggtggagct catgtaccca ccgccatact acctgggcat 600
aggcaacgga acccagattt atgtaattga tccagaaccg tgcccagatt ctgacttcct 660
cctctggatc cttgcagcag ttagttcggg gttgtttttt tatagctttc tcctcacagc 720
tgtttctttg agcaaaatgc taaagaaaag aagccctctt acaacagggg tctatgtgaa 780
aatgccccca acagagccag aatgtgaaaa gcaatttcag ccttatttta ttcccatcaa 840
ttgagaaacc attatgaaga agagagtcca tatttcaatt tccaagagct gaggcaattc 900
taactttttt gctatccagc tatttttatt tgtttgtgca tttgggggga attcatctct 960
ctttaatata aagttggatg cggaacccaa attacgtgta ctacaattta aagcaaagga 1020
gtagaaagac agagctggga tgtttctgtc acatcagctc cactttcagt gaaagcatca 1080
cttgggatta atatggggat gcagcattat gatgtgggtc aaggaattaa gttagggaat 1140
ggcacagccc aaagaaggaa aaggcaggga gcgagggaga agactatatt gtacacacct 1200
tatatttacg tatgagacgt ttatagccga aatgatcttt tcaagttaaa ttttatgcct 1260
tttatttctt aaacaaatgt atgattacat caaggcttca aaaatactca catggctatg 1320
ttttagccag tgatgctaaa ggttgtattg catatataca tatatatata tatatatata 1380
tatatatata tatatatata tatatatata tatattttaa tttgatagta ttgtgcatag 1440
agccacgtat gtttttgtgt atttgttaat ggtttgaata taaacactat atggcagtgt 1500
ctttccacct tgggtcccag ggaagttttg tggaggagct caggacacta atacaccagg 1560
tagaacacaa ggtcatttgc taactagctt ggaaactgga tgaggtcata gcagtgcttg 1620
attgcgtgga attgtgctga gttggtgttg acatgtgctt tggggctttt acaccagttc 1680
ctttcaatgg tttgcaagga agccacagct ggtggtatct gagttgactt gacagaacac 1740
tgtcttgaag acaatggctt actccaggag acccacaggt atgaccttct aggaagctcc 1800
agttcgatgg gcccaattct tacaaacatg tggttaatgc catggacaga agaaggcagc 1860
aggtggcaga atggggtgca tgaaggtttc tgaaaattaa cactgcttgt gtttttaact 1920
caatattttc catgaaaatg caacaacatg tataatattt ttaattaaat aaaaatctgt 1980
ggtggtcgtt ttccgga 1997

<210> SEQ ID NO 81
<211> LENGTH: 2097
<212> TYPE: DNA
<213> ORGANISM: Homo sapiens

<400> SEQUENCE: 81

```
gctcacctcc gcctgagcag tggagaaggc ggcactctgg tggggctgct ccaggcatgc     60
agatcccaca ggcgccctgg ccagtcgtct gggcggtgct acaactgggc tggcggccag    120
gatggttctt agactcccca gacaggccct ggaacccccc caccttctcc ccagccctgc    180
tcgtggtgac cgaaggggac aacgccacct tcacctgcag cttctccaac acatcggaga    240
gcttcgtgct aaactggtac cgcatgagcc ccagcaacca gacggacaag ctggccgcct    300
tccccgagga ccgcagccag cccggccagg actgccgctt ccgtgtcaca caactgccca    360
acgggcgtga cttccacatg agcgtggtca gggcccggcg caatgacagc ggcacctacc    420
tctgtggggc catctccctg gcccccaagg cgcagatcaa agagagcctg cgggcagagc    480
tcagggtgac agagagaagg gcagaagtgc ccacagccca ccccagcccc tcacccaggc    540
cagccggcca gttccaaacc ctggtggttg gtgtcgtggg cggcctgctg ggcagcctgg    600
tgctgctagt ctgggtcctg gccgtcatct gctcccgggc cgcacgaggg acaataggag    660
ccaggcgcac cggccagccc ctgaaggagg acccctcagc cgtgcctgtg ttctctgtgg    720
actatgggga gctggatttc cagtggcgag agaagacccc ggagcccccc gtgccctgtg    780
tccctgagca gacggagtat gccaccattg tctttcctag cggaatgggc acctcatccc    840
ccgcccgcag ggctcagct gacggccctc ggagtgccca gccactgagg cctgaggatg    900
gacactgctc ttggcccctc tgaccggctt ccttggccac cagtgttctg cagaccctcc    960
accatgagcc cgggtcagcg catttcctca ggagaagcag gcagggtgca ggccattgca   1020
ggccgtccag ggctgagct gcctgggggc gaccggggct ccagcctgca cctgcaccag   1080
gcacagcccc accacaggac tcatgtctca atgcccacag tgagcccagg cagcaggtgt   1140
caccgtcccc tacagggagg gccagatgca gtcactgctt caggtcctgc cagcacagag   1200
ctgcctgcgt ccagctccct gaatctctgc tgctgctgct gctgctgctg ctgctgcctg   1260
cggcccgggg ctgaaggcgc cgtggccctg cctgacgccc cggagcctcc tgcctgaact   1320
tgggggctgg ttggagatgg ccttggagca gccaaggtgc ccctggcagt ggcatcccga   1380
aacgccctgg acgcagggcc caagactggg cacaggagtg ggaggtacat ggggctgggg   1440
actccccagg agttatctgc tccctgcagg cctagagaag tttcagggaa ggtcagaaga   1500
gctcctggct gtggtgggca gggcaggaaa cccctccacc tttacacatg cccaggcagc   1560
acctcaggcc ctttgtgggg cagggaagct gaggcagtaa gcgggcaggc agagctggag   1620
gcctttcagg cccagccagc actctggcct cctgccgccg cattccaccc cagcccctca   1680
caccactcgg gagagggaca tcctacggtc ccaaggtcag gagggcaggg ctggggttga   1740
ctcaggcccc tcccagctgt ggccacctgg gtgttgggag ggcagaagtg caggcaccta   1800
gggcccccca tgtgcccacc ctgggagctc tccttggaac ccattcctga aattatttaa   1860
aggggttggc cgggctccca ccagggcctg ggtgggaagg tacaggcgtt cccccggggc   1920
ctagtacccc cgccgtggcc tatccactcc tcacatccac acactgcacc cccactcctg   1980
gggcagggcc accagcatcc aggcggccag caggcacctg agtggctggg acaagggatc   2040
ccccttccct gtggttctat tatattataa ttataattaa atatgagagc atgctaa      2097
```

<210> SEQ ID NO 82
<211> LENGTH: 822
<212> TYPE: DNA
<213> ORGANISM: Homo sapiens

<400> SEQUENCE: 82
atgatcttcc tcctgctaat gttgagcctg gaattgcagc ttcaccagat agcagcttta 60
ttcacagtga cagtccctaa ggaactgtac ataatagagc atggcagcaa tgtgaccctg 120
gaatgcaact ttgacactgg aagtcatgtg aaccttggag caataacagc cagtttgcaa 180
aaggtggaaa atgatacatc ccccacaccgt gaaagagcca ctttgctgga ggagcagctg 240
cccctaggga aggcctcgtt ccacatacct caagtccaag tgagggacga aggacagtac 300
caatgcataa tcatctatgg ggtcgcctgg gactacaagt acctgactct gaaagtcaaa 360
gcttcctaca ggaaaataaa cactcacatc ctaaaggttc cagaaacaga tgaggtagag 420
ctcacctgcc aggctacagg ttatcctctg gcagaagtat cctggccaaa cgtcagcgtt 480
cctgccaaca ccagccactc caggacccct gaaggcctct accaggtcac cagtgttctg 540
cgcctaaagc cacccccctgg cagaaacttc agctgtgtgt tctggaatac tcacgtgagg 600
gaacttactt tggccagcat tgaccttcaa agtcagatgg aacccaggac ccatccaact 660
tggctgcttc acattttcat cccctcctgc atcattgctt tcattttcat agccacagtg 720
atagccctaa gaaaacaact ctgtcaaaag ctgtattctt caaaagacac aacaaaaaga 780
cctgtcacca caacaaagag ggaagtgaac agtgctatct ga 822

<210> SEQ ID NO 83
<211> LENGTH: 3634
<212> TYPE: DNA
<213> ORGANISM: Homo sapiens

<400> SEQUENCE: 83
agttctgcgc agcttcccga ggctccgcac cagccgcgct tctgtccgcc tgcagggcat 60
tccagaaaga tgaggatatt tgctgtcttt atattcatga cctactggca tttgctgaac 120
gcatttactg tcacggttcc caaggaccta tatgtggtag agtatggtag caatatgaca 180
attgaatgca aattcccagt agaaaaacaa ttagacctgg ctgcactaat tgtctattgg 240
gaaatggagg ataagaacat tattcaattt gtgcatggag aggaagacct gaaggttcag 300
catagtagct acagacagag ggcccggctg ttgaaggacc agctctccct gggaaatgct 360
gcacttcaga tcacagatgt gaaattgcag gatgcagggg tgtaccgctg catgatcagc 420
tatggtggtg ccgactacaa gcgaattact gtgaaagtca atgccccata caacaaaatc 480
aaccaaagaa ttttggttgt ggatccagtc acctctgaac atgaactgac atgtcaggct 540
gagggctacc ccaaggccga agtcatctgg acaagcagtg accatcaagt cctgagtggt 600
aagaccacca ccaccaattc caagagagag gagaagcttt tcaatgtgac cagcacactg 660
agaatcaaca caacaactaa tgagattttc tactgcactt ttaggagatt agatcctgag 720
gaaaaccata cagctgaatt ggtcatccca gaactacctc tggcacatcc tccaaatgaa 780
aggactcact tggtaattct gggagccatc ttattatgcc ttggtgtagc actgacattc 840
atcttccgtt taagaaaagg gagaatgatg gatgtgaaaa aatgtggcat ccaagataca 900
aactcaaaga agcaaagtga tacacatttg gaggagacgt aatccagcat tggaacttct 960
gatcttcaag cagggattct caacctgtgg tttaggggtt catcggggct gagcgtgaca 1020
agaggaagga atgggcccgt gggatgcagg caatgtggga cttaaaaggc ccaagcactg 1080

-continued

```
aaaatggaac ctggcgaaag cagaggagga gaatgaagaa agatggagtc aaacagggag   1140
cctggaggga gaccttgata ctttcaaatg cctgaggggc tcatcgacgc ctgtgacagg   1200
gagaaaggat acttctgaac aaggagcctc caagcaaatc atccattgct catcctagga   1260
agacgggttg agaatcccta atttgagggt cagttcctgc agaagtgccc tttgcctcca   1320
ctcaatgcct caatttgttt tctgcatgac tgagagtctc agtgttggaa cgggacagta   1380
tttatgtatg agtttttcct atttattttg agtctgtgag gtcttcttgt catgtgagtg   1440
tggttgtgaa tgatttcttt tgaagatata ttgtagtaga tgttacaatt ttgtcgccaa   1500
actaaacttg ctgcttaatg atttgctcac atctagtaaa acatggagta tttgtaaggt   1560
gcttggtctc ctctataact acaagtatac attggaagca taaagatcaa accgttggtt   1620
gcataggatg tcacctttat ttaacccatt aatactctgg ttgacctaat cttattctca   1680
gacctcaagt gtctgtgcag tatctgttcc atttaaatat cagctttaca attatgtggt   1740
agcctacaca cataatctca tttcatcgct gtaaccaccc tgttgtgata accactatta   1800
ttttacccat cgtacagctg aggaagcaaa cagattaagt aacttgccca aaccagtaaa   1860
tagcagacct cagactgcca cccactgtcc ttttataata caatttacag ctatatttta   1920
ctttaagcaa ttcttttatt caaaaaccat ttattaagtg cccttgcaat atcaatcgct   1980
gtgccaggca ttgaatctac agatgtgagc aagacaaagt acctgtcctc aaggagctca   2040
tagtataatg aggagattaa caagaaaatg tattattaca atttagtcca gtgtcatagc   2100
ataaggatga tgcgagggga aaacccgagc agtgttgcca agaggaggaa ataggccaat   2160
gtggtctggg acggttggat atacttaaac atcttaataa tcagagtaat tttcatttac   2220
aaagagaggt cggtacttaa aataaccctg aaaaataaca ctggaattcc ttttctagca   2280
ttatatttat tcctgatttg cctttgccat ataatctaat gcttgtttat atagtgtctg   2340
gtattgttta acagttctgt cttttctatt taaatgccac taaattttaa attcatacct   2400
ttccatgatt caaaattcaa aagatcccat gggagatggt tggaaaatct ccacttcatc   2460
ctccaagcca ttcaagtttc ctttccagaa gcaactgcta ctgcctttca ttcatatgtt   2520
cttctaaaga tagtctacat ttggaaatgt atgttaaaag cacgtatttt taaaattttt   2580
ttcctaaata gtaacacatt gtatgtctgc tgtgtacttt gctattttta tttattttag   2640
tgtttcttat atagcagatg gaatgaattt gaagttccca gggctgagga tccatgcctt   2700
ctttgtttct aagttatctt tcccatagct tttcattatc tttcatatga tccagtatat   2760
gttaaatatg tcctacatat acatttagac aaccaccatt tgttaagtat ttgctctagg   2820
acagagtttg gatttgttta tgtttgctca aaaggagacc catgggctct ccagggtgca   2880
ctgagtcaat ctagtcctaa aaagcaatct tattattaac tctgtatgac agaatcatgt   2940
ctggaacttt tgttttctgc tttctgtcaa gtataaactt cactttgatg ctgtacttgc   3000
aaaatcacat tttctttctg gaaattccgg cagtgtacct tgactgctag ctaccctgtg   3060
ccagaaaagc ctcattcgtt gtgcttgaac ccttgaatgc caccagctgt catcactaca   3120
cagccctcct aagaggcttc ctggaggttt cgagattcag atgccctggg agatcccaga   3180
gtttcctttc cctcttggcc atattctggt gtcaatgaca aggagtacct tggctttgcc   3240
acatgtcaag gctgaagaaa cagtgtctcc aacagagctc cttgtgttat ctgtttgtac   3300
atgtgcattt gtacagtaat tggtgtgaca gtgttctttg tgtgaattac aggcaagaat   3360
tgtggctgag caaggcacat agtctactca gtctattcct aagtcctaac tcctccttgt   3420
ggtgttggat ttgtaaggca ctttatccct tttgtctcat gtttcatcgt aaatggcata   3480
```

-continued

```
ggcagagatg atacctaatt ctgcatttga ttgtcacttt ttgtacctgc attaatttaa   3540

taaaatattc ttatttattt tgttacttgg tacaccagca tgtccatttt cttgtttatt   3600

ttgtgtttaa taaaatgttc agtttaacat ccca                                3634
```